US006239131B1

(12) United States Patent
Shinozaki et al.

(10) Patent No.: US 6,239,131 B1
(45) Date of Patent: May 29, 2001

(54) 1,5 BENZODIAZEPINE DERIVATIVES

(75) Inventors: Katsuo Shinozaki; Tomoyuki Yoneta, both of Osato-gun; Masakazu Murata, Konan-machi; Naoyoshi Miura, Konan-machi; Kiyoto Maeda, Konan-machi, all of (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/319,249

(22) PCT Filed: Dec. 10, 1997

(86) PCT No.: PCT/JP97/04534

§ 371 Date: Jun. 8, 1999

§ 102(e) Date: Jun. 8, 1999

(30) Foreign Application Priority Data

Dec. 10, 1996 (JP) .................................................. 8-344498
May 30, 1997 (JP) .................................................. 9-156132

(51) Int. Cl.[7] ........................ A61K 31/55; C07D 243/12; A61P 1/04

(52) U.S. Cl. ............................................ 514/221; 540/517

(58) Field of Search .............................. 540/517; 514/221

(56) References Cited

U.S. PATENT DOCUMENTS 5,585,376 * 12/1996 Finch et al. .......................... 514/221
5,691,332 * 11/1997 Claremon et al. ................... 514/221
5,726,171 * 3/1998 Claremon et al. ................... 514/221
5,739,129 * 4/1998 Aquino et al. ........................ 514/221
5,776,929 * 7/1998 Hagishita et al. ................... 514/221

FOREIGN PATENT DOCUMENTS

2272439 * 5/1994 (GB) .
WO 95/16675 * 6/1995 (WO) .

* cited by examiner

*Primary Examiner*—Richard L. Raymond
*Assistant Examiner*—Brenda Coleman
(74) *Attorney, Agent, or Firm*—Oblon, Spivak, McClelland, Maier & Neustadt, P.C.

(57) ABSTRACT

1,5-Benzodiazepine derivatives represented by formula (I), salts thereof, and medicines containing the same as the active ingredient:

(I)

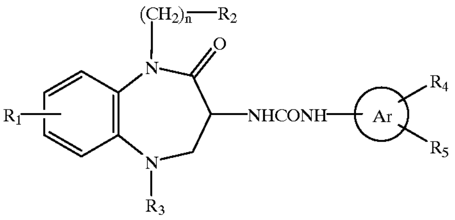

The compounds exhibit excellent gastrin and/or CCK-B receptor antagonism and are useful as remedies for gastric ulcer and gastrointestinal movement disorder.

16 Claims, No Drawings

1,5 BENZODIAZEPINE DERIVATIVES

This application is a national stage entry under 35 U.S.C. 371 of PCT/JP97/04534 filed Dec. 10, 1997.

TECHNICAL FIELD

The present invention relates to 1,5-benzodiazepine derivatives, which are important in the medical field. More specifically, the present invention relates to novel 1,5-benzodiazepine derivatives which have gastrin and/or CCK-B (cholecystokinin-B) receptor antagonism, and to preventive and therapeutic remedies for disorders in which the receptors participate.

BACKGROUND ART

Cholecystokinin (CCK) is a gastrointestinal hormone which is produced by and released from duodenal and jejunal mucous membranes, and is known to have actions such as secretion of pancreatic juice, gallbladder constriction, and stimulation of insulin secretion. CCK is also known to be present at high concentration in the cerebral cortex, hypothalamus, and hippocampus. CCK is also known to exhibit various actions, including inhibition of eating and hunger, augmentation of memory, and generation of anxiety. Meanwhile, gastrin is a gastrointestinal hormone which is produced by and released from G-cells distributed in the pylorus. Gastrin is also known to exhibit actions such as secretion of gastric acid and constriction of the pylorus and gallbladder. CCK and gastrin, having the same five amino acids in their C-terminals, exert the aforementioned actions via receptors. The receptors of CCK are classified into CCK-A receptors, which are of the peripheral-type and are distributed in the pancreas, the gallbladder, and the intestines; and CCK-B receptors, which are of the central-type and are distributed within the brain. Since gastrin receptors and CCK-B receptors show similar properties in receptor-binding experiments, and thus are proven to have high homology, they are often called CCK-B/gastrin receptors. Compounds having antagonism to these receptors, i.e., gastrin or CCK-B receptor, are expected to be useful for prevention and treatment of the following diseases and disorders: gastric ulcer, duodenal ulcer, gastritis, reflux esophagitis, pancreatitis, Zollinger-Ellison syndrome, vacuolating G-cell hyperplasia, basal-mucous-membrane hyperplasia, inflammation of the gallbladder, attack of biliary colic, motor disorders of alimentary canal, irritable bowel syndrome, certain types of tumors, eating disorders, anxiety, panic disorder, depression, schizophrenia, Parkinson's disease, tardive dyskinesia, Gilles de la Tourette syndrome, drug dependence, and drug-withdrawal symptoms. Moreover, the compounds are expected to induce pain relief or to augment the pain-relieving effect of opioid analgesics (Folia Pharmacologica Japonica, Vol. 106, 171–180 (1995), Drugs of the Future, Vol. 18. 919–931 (1993), American Journal of Physiology, Vol. 269, G628–G646 (1995), American Journal of Physiology, Vol. 259, G184–G190 (1990), European Journal of Pharmacology, 261, 257– 263 (1994), Trends in Pharmacological Science, Vol. 15, 65–66 (1994)).

Proglumide, which is a drug having gastrin receptor antagonism, has conventionally been known as a remedy for gastric ulcer and gastritis. However, proglumide has a very weak affinity with gastrin or CCK-B receptors, and has a low curative effect. It is described that some 1,4-benzodiazepine derivatives—such as L-364,718 (Dibazepaido, Japanese Patent Application Laid-Open (kokai) No. 63666/1986) and L-365,260 (Japanese Patent Application Laid-Open (kokai) No. 238069/1988)—exhibit CCK-A receptor antagonism or CCK-B receptor antagonism. It is also known that compounds having strong CCK-B receptor antagonism suppress secretion of gastric acid stimulated by pentagastrin (WO 94/438 and WO 95/18110). However, these compounds do not provide satisfactory effects when administered in vivo. Drugs which exhibit gastrin or CCK-B receptor antagonism and are clinically useful have not yet been provided.

Compounds that can be strongly bound to gastrin or cholecystokinin receptors are expected to be useful as remedies and for prevention of diseases associated with respective receptors and found in the alimentary canal and the central nervous system.

DISCLOSURE OF THE INVENTION

In view of the foregoing, in order to solve the above-mentioned problems, the present inventors have conducted earnest studies, and have found that some 1,5-benzodiazepine derivatives exhibit gastrin and/or CCK-B receptor antagonism and strong effect in suppressing the secretion of gastric acid, and that the derivatives are useful as medicines, leading to completion of the invention.

Accordingly, the present invention provides a 1,5-benzodiazepine derivative represented by the following formula (I) and salts thereof:

(I)

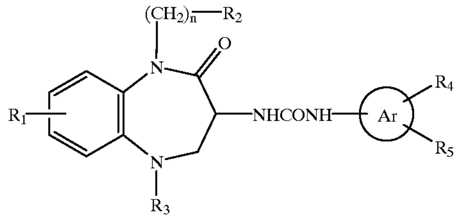

[wherein $R_1$ represents a hydrogen atom, a lower alkyl group, a lower alkoxyl group, or a halogen atom;

each of $R_2$ and $R_3$, which may be the same or different, represents a hydrogen atom, a lower alkenyl group, a lower alkyl group which may be substituted by a halogen atom, a lower alkylsulfonyl group, a mono- or di-lower alkoxyalkyl group, a phenyl group which may have a substituent, a group represented by —$CH(R_6)R_7$ (wherein $R_6$ represents a lower alkyl group, a lower alkoxyl group, a mono- or di-lower alkoxyalkyl group, a saturated or unsaturated hydrocarbon group having a C7–C10 condensed ring, or a phenyl or heterocyclic group which may have a substituent; and $R_7$ represents a hydrogen atom or a lower alkyl group), or a group represented by —CO—$R_8$ (wherein $R_8$ represents a lower alkyl group which may be substituted by a halogen atom; a lower alkenyl group; a lower alkoxyl group; a mono- or di-lower alkoxyalkyl group; an adamantyl group; a hydroxyl group; a benzyloxy group; a phenyl or heterocyclic group which may have a substituent; or a group represented by —$N(R_9)R_{10}$ (wherein $R_9$ and $R_{10}$ may be the same or different, and each represents a hydrogen atom, a lower alkyl group, a hydroxyalkyl group, a mono- or di-lower alkylaminoalkyl group, a phenyl group, or a heterocyclic group which may have a substituent));

each of $R_4$ and $R_5$, which may be identical to or different from each other, represents a hydrogen atom, a lower alkyl group which may be substituted by a halogen atom, a lower alkoxyl group, a halogen atom, a hydroxyalkyl group, an amino group, a nitro group, a mono- or di-lower alkylamino group, a lower alkylsulfonylaminocarbonyl group, a hydroxyaminocarbonyl group, a benzyloxyaminocarbonyl group, a tetrazolyl group, a 4-oxoxadiazolinyl group, a group represented by the following formula:

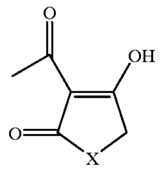

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R^{11}$ represents a hydrogen atom, a lower alkyl group or a benzyl group);

Ar represents an aromatic hydrocarbon or an aromatic heterocyclic ring; and n represents an integer between 0 and 2 inclusive].

The present invention also provides a medicine containing the above-described compound (I) as an active ingredient.

The present invention also provides a pharmaceutical composition containing the above-described compound (I) and a pharmaceutically acceptable carrier.

The present invention also provides use of the above-described compound (I) as a medicine.

The present invention also provides a method for prevention and treatment of a disease in which a gastrin receptor and/or cholecystokinin (CCK)-B receptor participates, which comprises administration of an effective amount of the above-described compound (I) to mammals, including humans.

BEST MODE FOR CARRYING OUT THE INVENTION

As used herein, "lower" refers to a straight, branched, or cyclic carbon chain having 1–8 carbon atoms, and "lower cyclic" refers to C3–C8 monocyclic.

Therefore, examples of a "lower alkyl group" include methyl, ethyl, propyl, isopropyl, cyclopropyl, butyl, isobutyl, sec-butyl, tert-butyl, cyclobutyl, cyclopropylmethyl, 1-methylcyclopropyl, 2-methylcyclopropyl, pentyl, 1-methylbutyl, 2-methylbutyl, isopentyl, tert-pentyl, 1,2-dimethylpropyl, neopentyl, 1-ethylpropyl, cyclopentyl, 1-methylcyclobutyl, 2-methylcyclobutyl, 3-methylcyclobutyl, cyclobutylmethyl, 1-cyclopropylethyl, 2-cyclopropylethyl, (1-methylcyclopropyl)methyl, (2-methylpropyl)methyl, hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methyl-1-ethylpropyl, 1-ethyl-2-methylpropyl, 1,1,2-trimethylpropyl, 1,2,2-trimethylpropyl, cyclohexyl, heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, cycloheptyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-propylpentyl, 2-propylpentyl, 3,3,4-trimethylpentyl, 3,4,4-trimethylpentyl, 1,1,2,2-tetramethylbutyl, 2,2,3,3-tetramethylbutyl, 1,1,3,3-tetramethylbutyl, and cyclooctyl.

As used herein, a "lower alkoxyl group" refers to a straight, branched, or cyclic alkoxyl group having 1–8 carbon atoms, and examples thereof include methoxy, ethoxy, propoxy, isopropoxy, cyclopropoxy, butoxy, isobutoxy, sec-butoxy, tert-butoxy, cyclobutoxy, cyclopropylmethoxy, 1-methylcyclopropoxy, 2-methylcyclopropoxy, pentyloxy, 1-methylbutoxy, 2-methylbutoxy, isopentyloxy, tert-pentyloxy, 1,2-dimethylpropoxy, neopentyloxy, 1-ethylpropoxy, cyclopentyloxy, 1-methylcyclobutoxy, 2-methylcyclobutoxy, 3-methylcyclobutoxy, cyclobutylmethoxy, 1-cyclopropylethoxy, 2-cyclopropylethoxy, (1-methylcyclopropyl)methoxy, (2-methylpropyl)methoxy, hexyloxy, 1-methylpentyloxy, 2-methylpentyloxy, 3-methylpentyloxy, isohexyloxy, 1-ethylbutoxy, 2-ethylbutoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-methyl-1-ethylpropoxy, 1-ethyl-2-methylpropoxy, 1,1,2-trimethylpropoxy, 1,2,2-trimethylpropoxy, cyclohexyloxy, heptyloxy, 1-methylhexyloxy, 2-methylhexyloxy, 2-methylhexyloxy, 4-methylhexyloxy, 5-methylhexyloxy, 1-ethylpentyloxy, 2-ethylpentyloxy, 3-ethylpentyloxy, 1-propylbutyloxy, cycloheptyloxy, 1-methylheptyloxy, 2-methylheptyloxy, 3-methylheptyloxy, 4-methylheptyloxy, 5-methylheptyloxy, 6-methylheptyloxy, 1-ethylhexyloxy, 2-ethylhexyloxy, 3-ethylhexyloxy, 4-ethylhexyloxy, 1-propylpentyloxy, 2-propylpentyloxy, 3,3,4-trimethylpentyloxy, 3,4,4-trimethylpentyloxy, 1,1,2,2-tetramethylbutyloxy, 2,2,3,3-tetramethylbutyloxy, 1,1,3,3-tetramethylbutyloxy, and cyclooctyloxy.

As used herein, a "halogen atom" refers to fluorine, chlorine, bromine, or iodine.

As used herein, a "lower alkenyl group" refers to a straight, branched, or cyclic carbon chain having one double bond and 2–8 carbon atoms.

Therefore, examples of a "lower alkenyl group" include vinyl, 1-propenyl, allyl, isopropenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-ethyl-1-propenyl, 1,2-dimethyl-1-propenyl, 1-ethyl-2-propenyl, 1,2-dimethyl-2-propenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-ethyl-2-methyl-1-propenyl, 1-ethyl-2-methyl-2-propenyl, 1,2-dimethyl-1-butenyl, 1,3-dimethyl-1-butenyl, 2,3-dimethyl-1-butenyl, 1,2-dimethyl-2-butenyl, 1,3-dimethyl-2-butenyl, 2,3-dimethyl-2-butenyl, 1,2-dimethyl-3-butenyl, 1,3-dimethyl-3-butenyl, 2,3-dimethyl-3-butenyl, 2-cyclohexen-1-yl, 3-cyclohexen-1-yl, 2-cyclohexen-1-yl, 2-cyclohepten-1-yl, 2-cycloocten-1-yl, and 2-cyclopenten-1-yl.

As used herein, a "lower alkyl group which may be substituted by a halogen atom" refers to a lower alkyl group which has no halogen atom bonded thereto or which has one to three halogen atoms bonded thereto. A "halogen atom" and a "lower alkyl atom" refers to the above-defined "halogen atom" and "lower alkyl atom," respectively A "lower alkylsulfonyl group" refers to a group in which a lower alkyl group is bonded to a sulfonyl group. A "lower alkylsulfonylaminocarbonyl group" refers to an aminocarbonyl group to which a "lower alkylsulfonyl group" mentioned above is bonded. A "mono- or di-lower alkoxyalkyl group" refers to a lower alkyl group substituted by one or two "lower alkoxy groups" described above. Therefore, examples of a "mono- or di-lower alkoxyalkyl group" include methoxymethyl, ethoxymethyl, propoxymethyl, isopropoxymethyl, cyclopropoxymethyl, butoxymethyl, isobutoxymethyl, sec-butoxymethyl, tert-butoxymethyl, cyclobutoxymethyl, cyclopropylmethoxymethyl, 1-methylcyclopropoxymethyl, 2-methylcyclopropoxymethyl, pentyloxymethyl, 1-methylbutoxymethyl, 2-methylbutoxymethyl, isopentyloxymethyl, tert-pentyloxymethyl, 1,2-dimethylpropoxymethyl, neopentyloxymethyl, 1-ethylpropoxymethyl, cyclopentyloxymethyl, 1-methylcyclobutoxymethyl, 2-methylcyclobutoxymethyl, 3-methylcyclobutoxymethyl, cyclobutylmethoxymethyl, 1-cyclopropylethoxymethyl, 2-cyclopropylethoxymethyl, (1-methylcyclopropyl)methoxymethyl, (2-methylpropyl) methoxymethyl, hexyloxymethyl, 1-methylpentyloxymethyl, 2-methylpentyloxymethyl, 3-methylpentyloxymethyl, isohexyloxymethyl, 1-ethylbutoxymethyl, 2-ethylbutoxymethyl, 1,1-dimethylbutoxymethyl, 1,2-dimethylbutoxymethyl, 1,3-diethylbutoxymethyl, 2,2-dimethylbutoxymethyl, 2,3-dimethylbutoxymethyl, 3,3-dimethylbutoxymethyl, 1-methyl-1-ethylpropoxymethyl, 1-ethyl-2-methylpropoxymethyl, 1,1,2-trimethylpropoxymethyl, 1,2,2-trimethylpropoxymethyl, cyclohexyloxymethyl, dimethoxymethyl, diethoxymethyl, dipropoxymethyl, diisopropoxymethyl, dicyclopropoxymethyl, dibutoxymethyl, diisobutoxymethyl, di-sec-butoxymethyl, di-tert-butoxymethyl, dicyclobutoxymethyl, di(cyclopropylmethoxy)methyl, di(1-methylcyclopropoxy) methyl, di(2-methylcyclopropoxy)methyl, dipentyloxymethyl, di(1 -methylbutoxy)methyl, di(2-methylbutoxy)methyl, diisopentyloxymethyl, di-tert-pentyloxymethyl, di(1,2-dimethylpropoxy)methyl, dineopentyloxymethyl, di(1-ethylpropoxy)methyl, dicyclopentyloxymethyl, di(1-methylcyclobutoxy)methyl, di(2-methylcyclobutoxy)methyl, di(3-methylcyclobutoxy) methyl, di(cyclobutylmethoxy)methyl, di(1-cyclopropylethoxy)methyl, di(2-cyclopropylethoxy)methyl, di[(1-methylcyclopropyl)methoxy]methyl, di[(2-methylpropyl)methoxy]methyl, dihexyloxymethyl, 1-methylpentyloxymethyl, 2-methylpentyloxymethyl, di(3-methylpentyloxy)methyl, diisohexyloxymethyl, di(1-ethylbutoxy)methyl, di(2-ethylbutoxy)methyl, di(1,1-dimethylbutoxy)methyl, di(1,2-dimethylbutoxy)methyl, di(1,3-dimethylbutoxy)methyl, di(2,2-dimethylbutoxy) methyl, di(2,3-dimethylbutoxy)methyl, di(3,3-dimethylbutoxy)methyl, di(1-methyl-1-ethylpropoxy) methyl, di(1-ethyl-2-methylpropoxy)methyl, di(1,1,2-trimethylpropoxy)methyl, di(1,2,2-trimethylpropoxy) methyl, dicyclohexyloxymethyl, methoxyethoxymethyl, methoxypropoxymethyl, methoxyisopropoxymethyl, methoxycyclopropoxymethyl, methoxybutoxymethyl, methoxyisobutoxymethyl, methoxy-sec-butoxymethyl, methoxy-tert-butoxymethyl, ethoxypropoxymethyl, ethoxyisopropoxymethyl, ethoxycyclopropoxymethyl, ethoxybutoxymethyl, ethoxyisobutoxymethyl, ethoxy-sec-butoxymethyl, ethoxy-tert-butoxymethyl, propoxyisopropoxymethyl, propoxycyclopropoxymethyl, propoxybutoxymethyl, propoxyisobutoxymethyl, propoxy-sec-butoxymethyl, propoxy-tert-butoxymethyl, isopropoxycyclopropoxymethyl, isopropoxybutoxymethyl, isopropoxyisobutoxymethyl, isopropoxy-sec-butoxymethyl, isopropoxy-tert-butoxymethyl, cyclopropoxybutoxymethyl, cyclopropoxyisobutoxymethyl, cyclopropoxy-sec-butoxymethyl, cyclopropoxy-tert-butoxymethyl, butoxy-sec-butoxymethyl, butoxy-tert-butoxymethyl, isobutoxy-sec-butoxymethyl, isobutoxy-tert-butoxymethyl, sec-butoxy-tert-butoxymethyl, methoxyethyl, ethoxyethyl, propoxyethyl, isopropoxyethyl, cyclopropoxyethyl, butoxyethyl, isobutoxyethyl, sec-butoxyethyl, tert-butoxyethyl, cyclobutoxyethyl, cyclopropylmethoxyethyl, 1-methylcyclopropoxyethyl, 2-methylcyclopropoxyethyl, pentyloxyethyl, 1-methylbutoxyethyl, 2-methylbutoxyethyl, isopentyloxyethyl, tert-pentyloxyethyl, 1,2-dimethylpropoxyethyl, neopentyloxyethyl, 1-ethylpropoxyethyl, cyclopentyloxyethyl, 1-methylcyclobutoxyethyl, 2-methylcyclobutoxyethyl, 3-methylcyclobutoxyethyl, cyclobutylmethoxyethyl, 1-cyclopropylethoxyethyl, 2-cyclopropylethoxyethyl, (1-methylcyclopropyl)methoxyethyl, (2-methylpropyl) methoxyethyl, hexyloxyethyl, 1-methylpentyloxyethyl, 2-methylpentyloxyethyl, 3-methylpentyloxyethyl, isohexyloxyethyl, 1-ethylbutoxyethyl, 2-ethylbutoxyethyl, 1,1-dimethylbutoxyethyl, 1,2-dimethylbutoxyethyl, 1,3-dimethylbutoxyethyl, 2,2-dimethylbutoxyethyl, 2,3-dimethylbutoxyethyl, 3,3-dimethylbutoxyethyl, 1-methyl-1-ethylpropoxyethyl, 1-ethyl-2-methylpropoxyethyl, 1,1,2-trimethylpropoxyethyl, 1,2,2 -trimethylpropoxyethyl, cyclohexyloxyethyl, dimethoxyethyl, diethoxyethyl, dipropoxyethyl, diisopropoxyethyl, dicyclopropoxyethyl, dibutoxyethyl, diisobutoxyethyl, di-sec-butoxyethyl, di-tert-butoxyethyl, dicyclobutoxyethyl, di(cyclopropylmethoxy) ethyl, di(1-methylcyclopropoxy)ethyl, di(2-methylcyclopropoxy)ethyl, dipentyloxyethyl, di(1-methylbutoxy)ethyl, di(2-methylbutoxy)ethyl, diisopentyloxyethyl, di-tert-pentyloxyethyl, di(1,2-dimethylpropoxy)ethyl, dineopentyloxyethyl, di(1-ethylpropoxy)ethyl, dicyclopentyloxyethyl, di(1-methylcyclobutoxy)ethyl, di(2-methylcyclobutoxy)ethyl, di(3-methylcyclobutoxy)ethyl, di(cyclobutylmethoxy)ethyl, di(1-cyclopropylethoxy)ethyl, di(2-cyclopropylethoxy) ethyl, di[(1-methylcyclopropyl)methoxylethyl, di[(2-methylpropyl)methoxy]ethyl, dihexyloxyethyl, 1-methylpentyloxyethyl, 2-methylpentyloxyethyl, di(3-methylpentyloxy)ethyl, diisohexyloxyethyl, di(1-ethylbutoxy)ethyl, di(2-ethylbutoxy)ethyl, di(1,1-dimethylbutoxy)ethyl, di(1,2-dimethylbutoxy)ethyl, di(1,3-dimethylbutoxy)ethyl, di(2,2-dimethylbutoxy)ethyl, di(2,3-dimethylbutoxy)ethyl, di(3,3-dimethylbutoxy)ethyl, di(1-methyl-1-ethylpropoxy)ethyl, di(1-ethyl-2-methylpropoxy) ethyl, di(1,1,2-trimethylpropoxy)ethyl, di(1,2,2-trimethylpropoxy)ethyl, dicyclohexyloxyethyl, methoxyethoxyethyl, methoxypropoxyethyl, methoxyisopropoxyethyl, methoxycyclopropoxyethyl, methoxybutoxyethyl, methoxyisobutoxyethyl, methoxy-sec-butoxyethyl, methoxy-tert-butoxyethyl, methoxypentyloxyethyl, methoxyhexyloxyethyl, ethoxypropoxyethyl, ethoxyisopropoxyethyl, ethoxycyclopropoxyethyl, ethoxybutoxyethyl, ethoxyisobutoxyethyl, ethoxy-sec-butoxyethyl, ethoxy-tert-butoxyethyl, ethoxypentyloxyethyl, ethoxyhexyloxyethyl, propoxyisopropoxyethyl, propoxycyclopropoxyethyl, propoxybutoxyethyl, propoxyisobutoxyethyl, propoxy-sec-butoxyethyl, propoxy-tert-butoxyethyl, propoxypentyloxyethyl, propoxyhexyloxyethyl, isopropoxycyclopropoxyethyl, isopropoxybutoxyethyl, isopropoxyisobutoxyethyl, isopropoxy-sec-butoxyethyl, isopropoxy-tert-butoxyethyl, isopropoxypentyloxyethyl, isopropoxyhexyloxyethyl, cyclopropoxybutoxyethyl, cyclopropoxyisobutoxyethyl, cyclopropoxy-sec-butoxyethyl, cyclopropoxy-tert-butoxyethyl, cyclopropoxypentyloxyethyl, cyclopropoxyhexyloxyethyl, butoxy-sec-butoxyethyl, butoxy-tert-butoxyethyl, butoxypentyloxyethyl, butoxyhexyloxyethyl, isobutoxy-sec-butoxyethyl, isobutoxy-tert-butoxyethyl, isobutoxypentyloxyethyl, isobutoxyhexyloxyethyl, and sec-butoxy-tert-butoxyethyl.

As used herein, a "phenyl group which may have a substituent" refers to a phenyl group which has no substituent or a phenyl group which has one or two substituents. A "heterocyclic group which may have a substituent" refers to a heterocyclic group which has no substituent, or a 5- or 6-membered heterocyclic group which has one or two substituents. As used herein, a "substituent" represents the above-mentioned "lower alkyl group," the above-mentioned "lower alkoxyl group," the above-mentioned "halogen atom," an amino group, or a nitro group. Examples of a "heterocyclic group" include pyridyl, piperidyl, pyrrolidinyl, furyl, or thienyl.

Examples of a "saturated or unsaturated hydrocarbon having a C7–C10 condensed ring" include bicyclic or tricyclic hydrocarbons, and specific examples thereof include adamantyl, bicyclo[3.1.1]heptanyl, bicyclo[3.1.1]heptenyl, 6,6-dimethyl-bicyclo[3.1.1]heptan-2-yl, or 6,6-dimethyl-bicyclo[3.1.1]hepta-2-en-2-yl.

As used herein, a "hydroxyalkyl group" refers to any of the above-described lower alkyl groups substituted by one hydroxy group.

As used herein, a "mono- or di-lower alkylamino group" refers to an amino group substituted by one or two lower alkyl groups, and specific examples thereof include methylamino, ethylamino, propylamino, isopropylamino, cyclopropylamino, butylamino, isobutylamino, sec-butylamino, tert-butylamino, cyclobutylamino, cyclopropylmethylamino, 1-methylcyclopropylamino, 2-methylcyclopropylamino, pentylamino, 1-methylbutylamino, 2-methylbutylamino, isopentylamino, tert-pentylamino, 1,2-dimethylpropylamino, neopentylamino, 1-ethylpropylamino, cyclopentylamino, 1-methylcyclobutylamino, 2-methylcyclobutylamino, 3-methylcyclobutylamino, cyclobutylmethylamino, 1-cyclopropylethylamino, 2-cyclopropylethylamino, (1-methylcyclopropyl)methylamino, (2 -methylpropyl) methylamino, hexylamino, 1-methylpentylamino, 2-methylpentylamino, 3-methylpentylamino, isohexylamino, 1-ethylbutylamino, 2-ethylbutylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-methyl-1-ethylpropylamino, 1-ethyl-2-methylpropylamino, 1,1,2-trimethylpropylamino, 1,2,2-trimethylpropylamino, cyclohexylamino, dimethylamino, diethylamino, dipropylamino, diisopropylamino, dicyclopropylamino, dibutylamino, diisobutylamino, di-sec-butylamino, di-tert-butylamino, dicyclobutylamino, di(cyclopropylmethyl) amino, di(1-methylcyclopropyl)amino, di(2-methylcyclopropyl)amino, dipentylamino, di(1-methylbutyl)amino, di(2-methylbutyl)amino, diisopentylamino, di-tert-pentylamino, di(1,2-dimethylpropyl)amino, dineopentylamino, di(1-ethylpropyl)amino, dicyclopentylamino, di(1-methylcyclobutyl)amino, di(2-methylcyclobutyl)amino, di(3-methylcyclobutyl)amino, di(cyclobutylmethyl)amino, di(1-cyclopropylethyl)amino, di(2-cyclopropylethyl)amino, di(1-methylcyclopropyl)methyl]amino, di[(2-methylpropyl) methyl]amino, dihexylamino, di(1-methylpentyl)amino, di(2-methylpentyl)amino, di(3-methylpentyl)amino, diisohexylamino, di(1-ethylbutyl)amino, di(2-ethylbutyl) amino, di(1,1-dimethylbutyl)amino, di(1,2-dimethylbutyl) amino, di(1,3-dimethylbutyl)amino, di(2,2-dimethylbutyl) amino, di(2,3-dimethylbutyl)amino, di(3,3-dimethylbutyl) amino, di(1-methyl-1-ethylpropyl)amino, di(1 -ethyl-2-methylpropyl)amino, di(1,1,2-trimethylpropyl)amino, di(1,2,2-trimethylpropyl)amino, dicyclohexylamino, methylethylamino, methylpropylamino, methylisopropylamino, methylcyclopropylamino, methylbutylamino, methylisobutylamino, methyl-sec-butylamino, methyl-tert-butylamino, methylpentylamino, methylhexylamino, ethylpropylamino, ethylisopropylamino, ethylcyclopropylamino, ethylbutylamino, ethylisobutylamino, ethyl-sec-butylamino, ethyl-tert-butylamino, ethylpentylamino, ethylhexylamino, propylisopropylamino, propylcyclopropylamino, propylbutylamino, propylisobutylamino, propyl-sec-butylamino, propyl-tert-butylamino, propylpentylamino, propylhexylamino, isopropylcyclopropylamino, isopropylbutylamino, isopropylisobutylamino, isopropyl-sec-butylamino, isopropyl-tert-butylamino, isopropylpentylamino, isopropylhexylamino, cyclopropylbutylamino, cyclopropylisobutylamino, cyclopropyl-sec-butylamino, cyclopropyl-tert-butylamino, cyclopropylpentylamino, cyclopropylhexylamino, butylisobutylamino, butyl-sec-butylamino, butyl-tert-butylamino, butylpentylamino, butylhexylamino, isobutyl-sec-butylamino, isobutylpentylamino, isobutylhexylamino, sec-butylpentylamino, sec-butylhexylamino, tert-butylpentylamino, and tert-butylhexylamino. A "mono- or di-lower alkylaminoalkyl group" refers to a lower alkyl group substituted by one "mono- or di-lower alkylamino group" described above.

A "hydroxyaminocarbonyl group" refers to an aminocarbonyl group substituted by a hydroxyl group.

A "carboxyalkylsulfinyl group" refers to a sulfinyl group to which a "carboxyalkyl group" is bonded. A "lower alkoxycarbonylalkylsulfinyl group" refers to a group in which —OH of the carboxyl group of a "carboxyalkyl-sulfiny group" is substituted by a lower alkoxy group as described above.

As used herein, "alkylene" refers to a C1–C8 straight or branched alkylene group, and examples thereof include methylene, ethylene, propylene, methylmethylene, butylene, dimethylmethylene, and pentamethylene.

An "aromatic hydrocarbon" refers to a C6–C14 aromatic hydrocarbon, and examples thereof include benzene and naphthalene. An "aromatic heterocyclic ring" refers to a 5- to 14-membered monocyclic or condensed ring having one to three nitrogen atoms, oxygen atoms, or sulfur atoms as hetero atoms, and examples thereof include pyridine, furan, and thiophene.

Preferably, $R_1$ in formula (I) is a hydrogen atom, a C1–C8 straight or branched alkyl group, a C1–C8 straight or branched alkoxyl group, or a halogen atom. More preferably, $R_1$ is a hydrogen atom, a C1–C5 straight or branched alkyl group, a C1–C5 straight or branched alkoxyl group, or a halogen atom. Most preferably, $R_1$ is a hydrogen atom, a methyl group, a methoxyl group, or a halogen atom.

Preferably, n is 0 or 1, and more preferably, n is 1.

Preferably, $R_2$ is a group represented by —CO—$R_8$ ($R_8$ is the same as described above). Preferably, $R_8$ is C1–C8 straight, branched, or cyclic alkyl which may be substituted by a halogen atom, C2–C8 alkenyl, C1–C8 alkoxyl, mono- or di-(C1–C8)alkoxy-(C1–C8)alkyl, adamantyl, bicyclo[3.1.1]heptanyl, bicyclo[3.1.1]heptenyl, 6,6-dimethyl-bicyclo[3.1.1]heptan-2-yl, 6,6-dimethyl-bicyclo[3.1.1]hepta-2-en-2-yl, benzyloxyl, phenyl, pyridyl, piperazinyl, pyrrolydinyl, furyl, thienyl (wherein any one of phenylpyridyl, piperidinyl, pyrrolydinyl, furyl, and thienyl groups may be substituted by one or two substituents selected from the group consisting of a C1–C8 alkyl group, a C1–C8 alkoxyl group, a halogen atom, an amino group, and a nitro group), or —N($R_9$ )$R_{10}$ (wherein each of $R_9$ and $R_{10}$ represents a hydrogen atom, C1–C8 alkyl, hydroxy-C1–C8 alkyl, mono- or di-(C1–C8)alkylamino-(C1–C8) alkyl, phenyl, pyridyl, piperidinyl, pyrrolydinyl, furyl, or thienyl). More preferably, R, is C1–C8 alkyl which may be substituted by a halogen atom, C1–C8 alkoxyl, C2–C3 alkenyl, phenyl, pyridyl, furyl, thienyl (wherein the phenyl, pyridyl, furyl, or thienyl may each be substituted by a C1–C8 alkyl group, a C1–C8 alkoxyl group, or a halogen atom).

Preferably, $R_3$ is a hydrogen atom; C2–C8 alkenyl; straight, branched, or cyclic C1–C8 alkyl which may be substituted by a halogen atom; C1–C8 alkylsulfonyl; mono- or di-(C1–C8)alkoxy-(C1–C8)alkyl; phenyl which may have a substituent; —CH($R_6$)$R_7$; or —$COR_8$ ($R_6$, $R_7$, and $R_8$ are the same as described above). More preferably, $R_3$ is C2–C8 alkenyl, straight, branched, or cyclic C1–C8 alkyl which may be substituted by a halogen atom, phenyl (which may be substituted by C1–C8 alkyl, C1–C8 alkoxyl, a halogen atom, an amino group, or a nitro group), or a —$COR_8$ ($R_8$ is the same as described above).

Preferably, Ar is a benzene ring.

Preferably, at least one of $R_4$ and $R_5$ is a group represented by —Y—$COOR_{11}$ (Y and $R_{11}$ are the same as described above).

More preferably, $R_4$ is a hydrogen atom, C1–C8 alkyl, halogen, C1–C8 alkoxyl, and $R^5$ is preferably —Y—$COOR_{11}$.

Examples of the group represented by —Y—$COOR_{11}$ include carboxyl, alkoxycarbonyl, benzyloxycarbonyl, carboxylalkyl, alkoxycarbonylalkyl, benzyloxycarbonylalkyl, carboxyalkyloxyl, alkoxycarbonylalkyloxyl, benzyloxycarbonylalkyloxyl, carboxyalkylthio, alkoxycarbonylalkylthio, benzyloxycarbonylalkylthio, carboxyalkylsulphinyl, alkoxycarbonylalkylsulphinyl, benzyloxycarbonylalkylsulphinyl, hydroxyaminocarbonyl, alkoxyaminocarbonyl, benzyloxyaminocarbonyl, carboxyalkylcarbamoyl, alkoxycarbonylalkylcarbamoyl, and benzyloxycarbonylalkylcarbamoyl. Among these groups, “alkyl” and “alkoxyl” are preferably those of C1–C8 straight or branched, more preferably C1–C6 straight or branched.

Examples of an alkoxycarbonyl group include a carbonyl group having a “lower alkoxyl group” as described above.

Examples of a “carboxyalkyl group” include carboxymethyl, 1-carboxyethyl, 2-carboxyethyl, 1-carboxypropyl, 2-carboxypropyl, 3-carboxypropyl, 1-carboxy-1-methylethyl, 2-carboxy-1-methylethyl, 1-carboxycyclopropyl, 2-carboxycyclopropyl, 1-carboxybutyl, 2-carboxybutyl, 3-carboxybutyl, 4-carboxybutyl, 1-carboxy-2-methylpropyl, 2-carboxy-2-methylpropyl, 3-carboxy-2-methylpropyl, 1-carboxy-1-methylpropyl, 2-carboxy-1-methylpropyl, 3-carboxy-1-methylpropyl, 2-carboxy-1,1-dimethylethyl, 1-carboxycyclobutyl, 2-carboxycyclobutyl, 1-carboxy-1-cyclopropylmethyl, (1-carboxycyclopropyl)methyl, (2-carboxycyclopropyl)methyl, 1-carboxymethylcyclopropyl, 1-methyl-2-carboxycyclopropyl, 2-carboxymethylcyclopropyl, 2-carboxy-2-methylcyclopropyl, 2-carboxy-3-methylcyclopropyl, 1-carboxypentyl, 2-carboxypentyl, 3-carboxypentyl, 4-carboxypentyl, 5-carboxypentyl, 1-carboxymethylbutyl, 1-carboxy-1-methylbutyl, 2-carboxy-1-methylbutyl, 3-carboxy-1-methylbutyl, 4-carboxy-1-methylbutyl, 2-carboxymethylbutyl, 1-carboxy-2-methylbutyl, 2-carboxy-2-methylbutyl, 3-carboxy-2-methylbutyl, 4-carboxy-2-methylbutyl, 3-carboxy-3-methylbutyl, 2-carboxy-3-methylbutyl, 3-carboxy-3-methylbutyl, 4-carboxy-3-methylbutyl, 1-carboxyhexyl, 2-carboxyhexyl, 3-carboxyhexyl, 4-carboxyhexyl, 5-carboxyhexyl, 6-carboxyhexyl, 1-carboxycyclohexyl, 2-carboxycyclohexyl, 3-carboxycyclohexyl, and 4-carboxycyclohexyl. Examples of a “carboxyalkylthio” include a sulfur atom having a “carboxyalkyl group” described above bonded thereto.

Examples of an “alkoxycarbonylalkyl group” include a lower alkyl group substituted by one “lower alkoxycarbonyl” as described above. Examples of a “benzyloxycarbonylalkyl group” include a lower alkyl group substituted by one benzyloxycarbonyl group. Therefore, an “alkoxycarbonylalkylthio group” refers to a group formed of a sulfur and a “lower alkoxycarbonylalkyl group” described above bonded thereto. A “benzyloxycarbonylalkylthio group” refers to a group formed of a sulfur atom and a “benzyloxycarbonylalkyl group” described above bonded thereto; an “alkoxycarbonylalkylcarbamoyl group” refers to a group formed of a carbamoyl group and a “lower alkoxycarbonylalkyl group” described above bonded thereto; and a “carboxyalkylcarbamoyl group” refers to a group formed of a carbamoyl group and a “carboxyalkyl group” described above bonded thereto.

A “carboxyalkyloxyl group” refers to a group formed of an oxygen atom and a “carboxyalkyl group” described above bonded thereto; an “alkoxycarbonylalkoxyl group” refers to a group formed of a lower alkoxyl group and one “lower alkoxycarbonyl group” described above bonded thereto; and a benzyloxycarbonylalkoxyl group refers to a group formed of one of the above-described alkoxyl groups and a benzyloxycarbonyl group bonded thereto.

Among these groups represented by —Y—$COOR_{11}$, $R_5$ is preferably carboxyl, C1–C8 alkoxycarbonyl, benzyloxycarbonyl, carboxy-(C1–C8)alkyl, (C1–C8) alkoxycarbonyl-(C1–C8)alkyl, benzyloxycarbonyl-(C1–C8) alkyl, carboxy-(C1–C8)alkylthio, (C1–C8)alkoxycarbonyl-(C1–C8)alkylthio, or benzyloxycarbonyl-(C1–C8)alkylthio, more preferably, carboxyl or carboxymethylthio.

The compounds (I) of the present invention can be converted into salts according to conventional methods. Examples of the salts include those formed by addition of inorganic acids, such as hydrochlorides, sulfates, nitrates, phosphates, hydrobromides, or hydroiodides; those formed by addition of organic acids, such as acetates, oxalates, malonates, succinates, maleates, fumarates, hibenzates, lactates, malates, citrates, tartrates, methanesulfonate, and ethanesulfonates; inorganic salts such as sodium salts, potassium salts, calcium salts, and magnesium salts; and organic salts such as ammonium salts, pyridine salts, triethylamine salts, ethanolamine salts, (R) or (S) isomeric α-phenethylamine salts, benzylamine salts, and 4-methylbenzylamine salts.

The present invention encompasses not only the compounds (I) of the present invention and salts thereof, but also a variety of solvates such as hydrates, and compounds having a variety of crystal structures. Further, the present invention encompasses racemates, diastereomers, mixtures of diastereomers, and optical isomers of compounds (I).

The compounds (I) of the present invention can be produced through a variety of synthetic methods in consideration of characteristics of the fundamental structure and radicals thereof. Typical production methods will be described below.

Process A

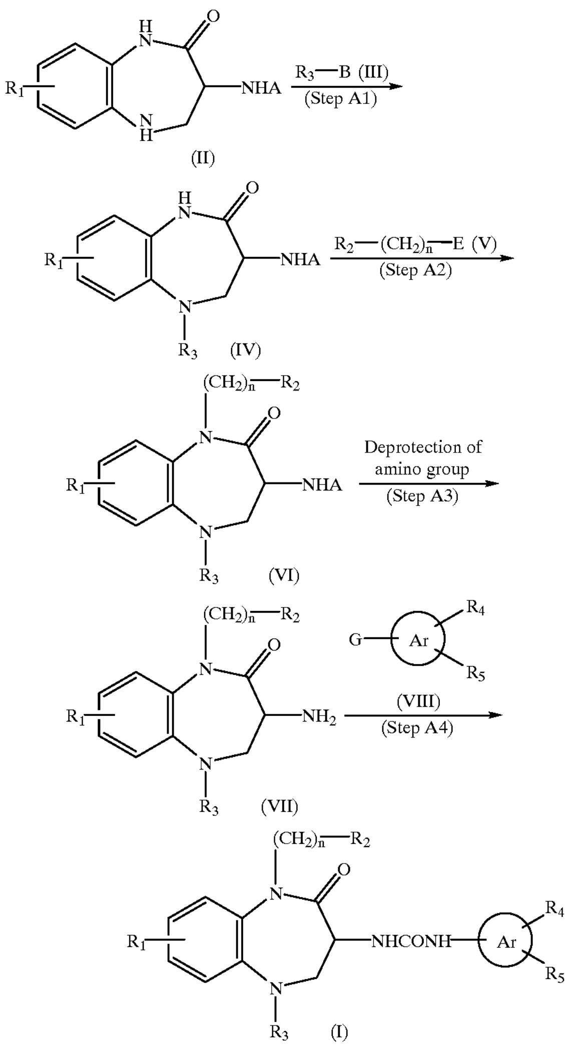

(wherein A represents a tert-butoxycarbonyl group or a benzyloxycarbonyl group; B represents a halogen atom; E represents a halogen atom; G represents an amino group, an isocyanato group, or a carboxyl group; and $R_1$, $R_2$, $R_3$, $R_4$, $R_5$, Ar, and n represent the same as defined above).

Step A1

Compound (III) is reacted with 1,5-benzodiazepine compound (II), to thereby obtain 5-substituted compound (IV). The reaction may be performed in the presence or in the absence of a base. Examples of the base include organic bases such as pyridine and triethylamine, and if necessary inorganic bases such as potassium carbonate, potassium bicarbonate, sodium carbonate, and sodium bicarbonate may optionally be used. No particular limitation is imposed on the solvents which are used for the reaction so long as they do not affect the reaction, and halogenated solvents such as 1,2-dichloroethane and methylene chloride are used. When $R_3$ is a lower alkyl group, a lower alkenyl group, or a group represented by —$CHR_6R_7$, alcoholic solvents such as methanol and ethanol and polar solvents such as N,N-dimethylformamide and dimethylsulfoxide may also be used. The reaction may be performed within the temperature range of 0° C. to reflux temperature. In this step, an isocyanato compound ($R_3$-NCO) may be used as compound (III). In this case, a compound having an amido bond at the 5-position of the benzodiazepine ring is obtained.

Step A2

Compound (V) is reacted with 5-substituted compound (IV), to thereby obtain 1,5-substituted compound (VI). The reaction is typically performed by successively adding to 5-substituted compound (IV) a base such as sodium hydride, sodium hydroxide, or sodium carbonate; compound (V); and an optional phase-transfer catalyst such as tetrabutylammonium bromide. No particular limitation is imposed on the solvents which are used for the reaction so long as they do not affect the reaction, and there may typically be used etheric solvents such as tetrahydrofuran and dioxane; toluene; N,N-dimethylformamide; and dimethylsulfoxide. The reaction may also be performed in a dual-phase system such as a water-toluene system by use of a phase-transfer catalyst such as tetrabutylammonium. The reaction may be performed at 0–150° C.

This step is performed after Step A1, and may alternatively be performed after completion of Steps A1, A3 and A4.

Step A3

When A of 1,5-substituted compound (VI) is a benzyloxycarbonyl group, compound (VI) is hydrocracked, to thereby obtain amine compound (VII). The reaction is typically performed by adding palladium carbon or palladium hydroxide in a hydrogen atmosphere at ambient pressure and 0° C.–100° C. No particular limitation is imposed on the solvents which are used for the reaction so long as they do not affect the reaction, and alcoholic solvents such as methanol and ethanol and ethyl acetate may be used. Alternatively, adding to compound (VI) an acid such as a hydrobromic acid-acetic acid solution produces amine compound (VII). The reaction is performed at 0° C.–100° C. When A of compound (VI) is a tert-butoxycarbonyl group, addition of an acid such as hydrochloric acid or trifluoroacetic acid produces amine compound (VII). The reaction is typically performed at 0° C.–100° C. Alcoholic solvents such as methanol and ethanol; halogenated solvents such as chloroform; and etheric solvents such as dioxane and diethyl ether are used as a solvent.

Step A4

Compound (VIII) is reacted with amine compound (VII), to thereby derive the compound of the present invention (I). When G of compound (VIII) is an isocyanato group, no particular limitation is imposed on the solvents which are used for the reaction so long as they do not affect the reaction, and there may typically be used etheric solvents such as tetrahydrofuran; hydrocarbon solvents such as toluene and benzene; halogenated solvents such as methylene chloride, 1,2-dichloroethane, and chloroform; and polar solvents such as N,N-dimethylformamide and acetonitrile. The reaction is performed within the temperature range of 0° C. to reflux temperature. When G of compound (VIII) is an amino group, the reaction is performed by treating amine compound (VII) with 1,1'-carbonyldiimidazole and, subsequently adding triethylamine and compound (VIII). Alternatively, the reaction is performed by adding 1,1'- carbonyldiimidazole and triethylamine to compound (VIII), and subsequently adding compound (VII). Alternatively, the reaction is performed by converting compound (VIII) to an isocyanato derivative in the presence of triphosgene and an organic base such as triethylamine, and subsequently adding amine compound (VII). When G of compound (VIII) is a carboxyl group, the reaction is performed by adding diphenylphosphoryl azide and an organic base such as triethylamine to induce Curtius rearrangement reaction to thereby derive to an isocyanato derivative, and subsequently adding compound (VII). No particular limitation is imposed on the solvents which are used for the reaction so long as they do not affect the reaction, and there may typically be used etheric solvents such as tetrahydrofuran and dioxane; halogenated solvents such as methylene chloride; and hydrocarbon solvents such as toluene and benzene. The reaction is performed within the temperature range of 0° C. to reflux temperature, while Curtius rearrangement reaction is preferably performed within the temperature range of 50° C. to reflux temperature so as to obtain a satisfactory result.

Process B

Among the compounds (I) of the present invention, compounds in which $R_2$ is an optionally substituted phenyl group and n is 0 can be produced through the following process:

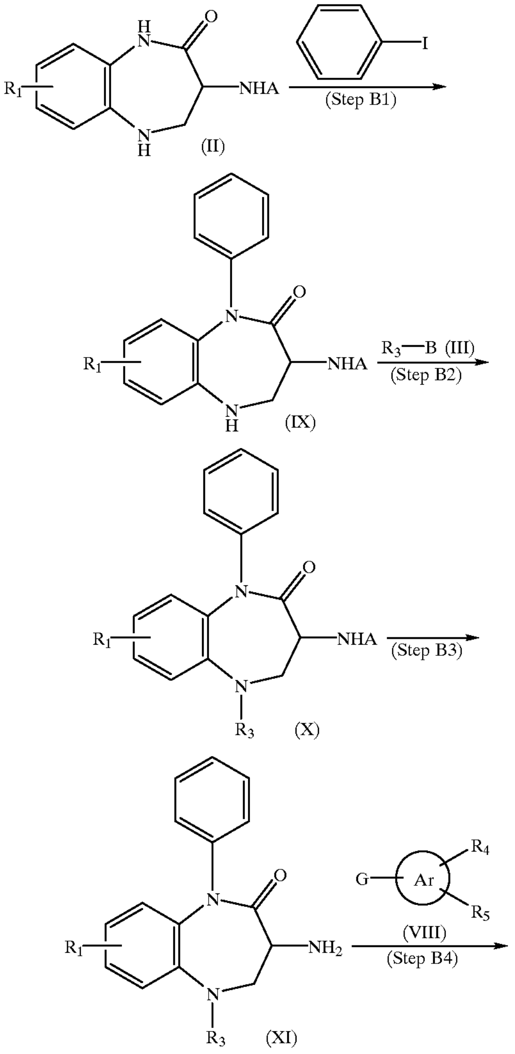

(II) (IX) (X) (XI)

-continued

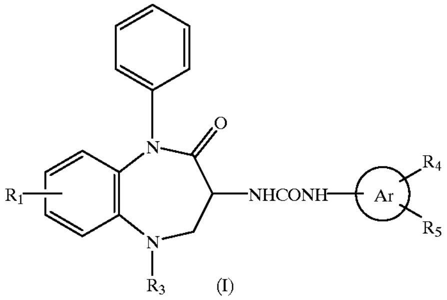
(I)

(wherein A, B, G, $R_1$, $R_3$, $R_4$, $R_5$, and Ar represent the same as defined above).

Step B1

Iodobenzene is reacted with compound (II), to thereby obtain 1-phenyl compound (IX). The reaction is typically performed by adding a base such as potassium carbonate in the presence of copper and copper iodide within the temperature range of 0° C. to reflux temperature. A solvent such as N,N-dimethylformamide is used for the reaction.

Step B2

Compound (III) is reacted with 1-phenyl compound (IX), to thereby obtain 1-phenyl-5-substituted compound (X). The reaction is performed in a manner similar to Step A1.

Step B3

When A of 1-phenyl-5-substituted compound (X) is a benzyloxycarbonyl group, compound (X) is hydrogenated to thereby obtain 1-phenylamine compound (XI). Alternatively, an acid such a hydrobromic acid-acetic acid solution is added to compound (X), to thereby obtain 1-phenylamine compound (XI). Furthermore, when A of compound (X) is a tert-butoxycarbonyl group, an acid such a hydrochloric acid-dioxane solution is added, to thereby obtain 1-phenylamine compound (XI). All the reactions are performed similarly to Step A3.

Step B4

Compound (VIII) is reacted with 1-phenylamine compound (XI), to thereby derive compound (I) of the present invention. The reaction is performed similarly to Step A4.

Process C

Among the compounds (I) of the present invention, compounds in which $R_3$ is an optionally substituted phenyl group can be produced by producing compound (Iva) through the following process; performing Step A2 of Process A using compound (Iva) instead of compound (IV); and subsequently performing Steps A3 and A4, or performing Step B1 of Process B using compound (IVa) instead of compound (II); and subsequently performing Steps B3 and B4.

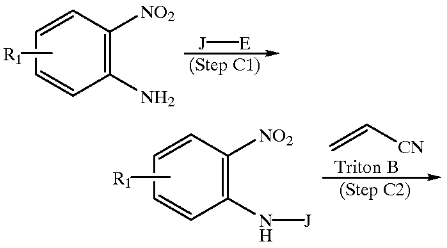

-continued

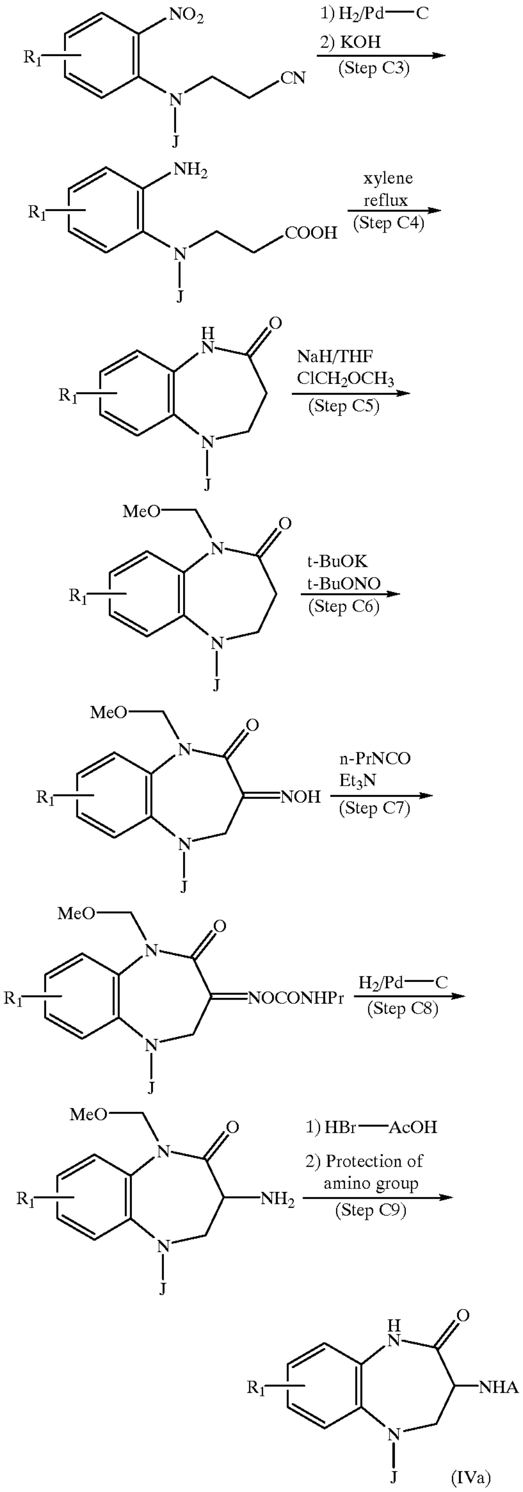

(wherein A, E, and $R_1$ represent the same as defined above and J represents a phenyl group which may be substituted).

In Step C9; i.e., protection reaction of an amino group, when A is a tert-butoxycarbonyl group, the protection reaction is performed by adding di-tert-butyl dicarbonate to thereby obtain compound (IVa), whereas when A is a benzyloxycarbonyl group, the protection reaction is performed by adding benzyloxycarbonyl chloride to thereby obtain compound (IVa).

Process D

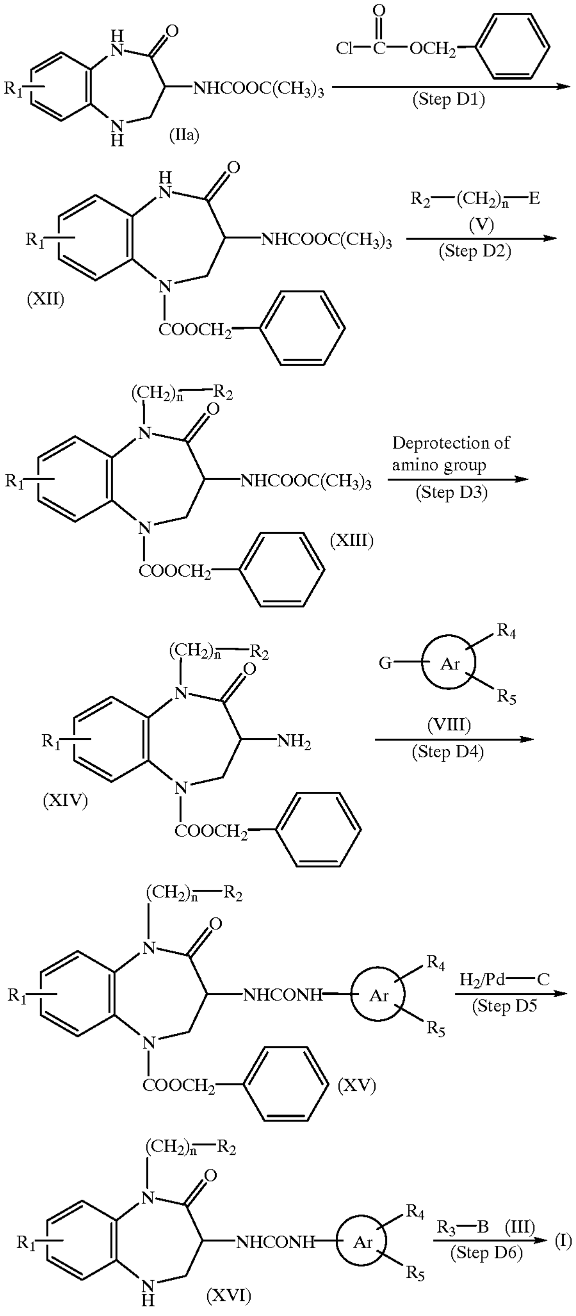

(wherein B, E, G, $R_1$, $R_2$, $R_3$, $R_4$, $R_5$, and Ar represent the same as defined above).

Step D1

Compound (IIa) is reacted with benzyloxycarbonyl chloride, to thereby obtain a 5-benzyloxycarbonyl compound (XII). The reaction is performed typically in the presence or in the absence of a base. Examples of the base include organic bases such as pyridine and triethylamine, and inorganic bases such as potassium carbonate, potassium bicarbonate, sodium carbonate, and sodium bicarbonate may optionally be used as desired. No particular limitation is imposed on the solvents which may be used for the reaction so long as they do not affect the reaction, and halogenated solvents such as 1,2-dichloroethane and methylene chloride are used. The reaction may be performed in the range of 0° C. to reflux temperature.

Step D2

Compound (V) is reacted with 5-benzyloxycarbonyl compound (XII), to thereby obtain a 1,5-substituted compound (XIII). The reaction is performed similarly to Step A2.

a cyclopentyl group, a cycloheptyl group, or a cyclooctyl group can be produced through the following process: compound (IIa) is converted to (IVb) or (IVc) by the process shown below; reaction is allowed to proceed by use of (IVb) or (IVc), instead of (IV) used in Step A2 of Process A; and a similar reaction is carried out as in Steps A3 and A4.

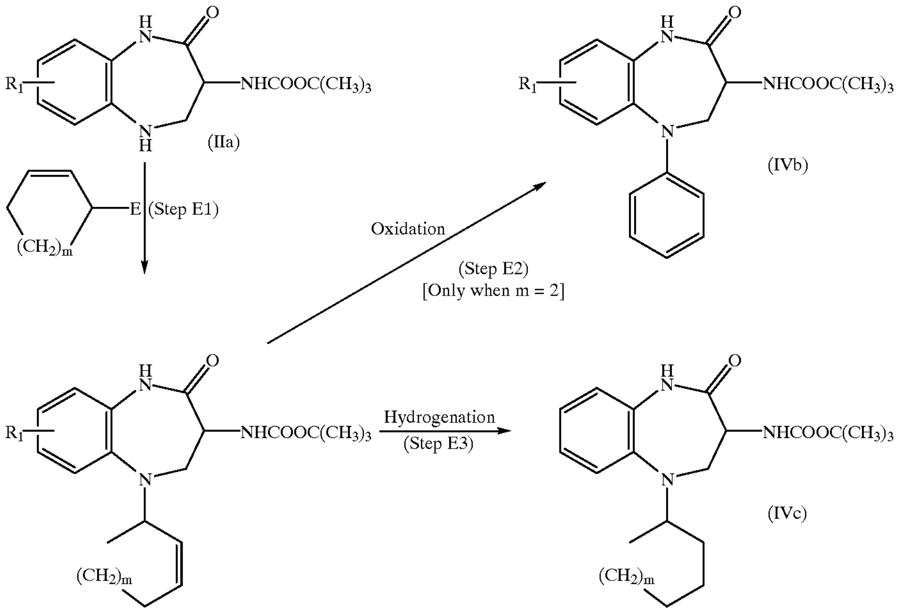

Step D3

Acid such as hydrochloric acid or trifluoroacetic acid is added to 1,5-substituted compound (XIII), to thereby obtain amine compound (VIV). The reaction is typically performed in the range of 0° C. to 100° C. Examples of the solvent include alcohol such as methanol and ethanol, halogenated solvents such as chloroform, and etheric solvents such as dioxane and diethyl ether.

Step D4

Amine compound (XV) is reacted with compound (VIII), to thereby derive to urea compound (XV). The reaction is performed similar to Step A4.

Step D5

Urea compound (XV) is hydrocracked, to thereby obtain a 5-amine compound (XVI). The reaction is typically performed by adding palladium carbon or palladium hydroxide in a hydrogen atmosphere at ambient pressure and 0° C.–100° C. No particular limitation is imposed on the solvents which may be used for the reaction so long as they do not affect the reaction, and alcoholic solvents such as methanol and ethanol and ethyl acetate may be used. Alternatively, addition of an acid such as a hydrobromic acid-acetic acid solution to (XV) produces 5-amine compound (XVI). The reaction is typically performed at 0° C.–100° C.

Step D6

5-Amine compound (XVI) is reacted with compound (III), to thereby obtain compound (I) of the present invention. The reaction is typically performed similarly to Step A1.

Process E

Among the compounds (I) of the present invention, compounds in which $R_3$ is a phenyl group, a cyclohexyl group, (wherein m represents a number of 1 to 4; and $R_1$ and E represent the same as defined above).

One type of compound (I) of the present invention can be transformed to another type of compound (I) of the present invention through additional hydrolysis, solvolysis, hydrocracking, or hydrogenation. When $R_4$ or $R_5$ is a group having a carboxyl group, a desired type of compound (I) of the present invention can be obtained through reaction with a condensing agent (such as 1-ethyl-3-(3-dimethylamino) carbodiimide, dicyclohexylcarbodiimide, or 2-chloro-1,3-dimethylimidazolium chloride) and a reagent (such as tetronic acid, thiotetronic acid, primary or secondary amine, amino acid ester, or alcohol).

The thus-produced compound (I) of the present invention is isolated in its free form or as a salt, and then purified. Isolation and purification are suitably performed by choosing from among routine procedures such as extraction, condensation, evaporation, crystallization, filtration, recrystallization, pulverization, and chromatography. Also, compound (I) of the present invention or an optically active intermediate can be produced by use of suitable starting material compounds, or through generally-employed racemic resolution. Examples of racemic resolution include a method in which the compound is transformed to a diastereomer salt through reaction with a typical optically active compound such as dibenzoyl tartarate, pyroglutamic acid, or α-phenethylamine, and subjected to optical resolution; or a method in which the compound is transformed to diastereomer compound, followed by separation and performance of Edman decomposition reaction.

The compound (I) of the present invention or salts thereof can be administered orally or parenterally. For oral administration, the compound of the present invention may be formed into solid preparations such as tablets, powder, and capsules, or into liquid preparations such as solutions, suspensions, and emulsions by use of proper additives incorporated thereto. Examples of the additives include excipients such as lactose, mannitol, corn starch, and crystalline cellulose; binders such as cellulose derivatives, acacia, and gelatin; disintegrators such as carboxymethylcellurose-Ca; lubricants such as talc, magnesium stearate.

For parenteral administration, the compound of the present invention may be formed into a liquid formulation for injection through incorporation of liquid such as water, ethanol, or glycerin.

The dose of the compound (I) of the present invention or salts thereof which is needed for the prevention or treatment of the aforementioned diseases varies depending on the dosage form, manner of administration, age, and pathological conditions. In the case of oral administration, the dose is typically 1–1,000 mg, preferably 5–500 mg, per day for an adult, which dose is preferably divided 2–3 times a day.

As described hereinbelow, compounds (I) of the present invention or salts thereof exhibit strong gastrin and/or CCK-B receptor antagonism as well as strong action of suppressing secretion of gastric acid, and therefore, they are useful for treatment, amelioration, and prevention of the diseases and disorders in which such actions are involved, which include gastric ulcer, duodenal ulcer, gastritis, reflux esophagitis, pancreatitis, Zollinger-Ellison syndrome, vacuolating G-cell hyperplasia, basal-mucous-membrane hyperplasia, inflammation of the gallbladder, attack of biliary colic, motor disorders of alimentary canal, irritable bowel syndrome, certain types of tumors, eating disorders, anxiety, panic disorder, depression, schizophrenia, Parkinson's disease, tardive dyskinesia, Gilles de la Tourette syndrome, drug dependence, and drug-withdrawal symptoms; and induction of pain relief or facilitation of induction of pain relief by use of an opioid drug.

EXAMPLES

The present invention will next be described in more detail by way of examples, which should not be construed as limiting the invention thereto.

Examples of producing intermediates of compound (I) of the present invention are provided as Referential Examples.

Referential Example 1

Preparation of 2-oxo-3-tert-butoxycarbonylamino-1,3,4,5-tetrahydro-2H-1,5-benzodiazepine Step 1

Preparation of 2-tert-butoxycarbonylamino-3-benzyloxycarbonylaminopropionic acid 2-Amino-3-benzyloxycarbonylaminopropionic acid (4.6 g) prepared according to a known method (Chem. Pharm. Bull., Vol. 7, 616 (1959)) was added to an aqueous solution (100 ml) of sodium carbonate (2.05 g). Di-tert-butyldicarbonate (4.68 g) in tetrahydrofuran (100 ml) was added thereto and the resultant mixture was stirred overnight at room temperature. The mixture was washed with ethyl acetate, and 1N hydrochloric acid was added to the aqueous layer to adjust pH to 3. The resultant mixture was extracted with methylene chloride. The organic layer was dried over anhydrous sodium sulfate and the solvent was evaporated under reduced pressure, to thereby obtain 6.51 g of the title compound.

$^1$H-NMR($CDCl_3$) δ: 1.43(9H, S), 3.45~3.70(2H, m), 4.20~4.42(1H, m), 5.08(2H, s), 5.50(1H, brs), 5.73(1H, brs), 7.32(5H, s), 8.27(1H, brs)

Step 2

Preparation of 2-tert-butoxycarbonylamino-3-(2-nitrophenyl)aminopropionic acid 2-tert-Butoxycarbonylamino-3-benzyloxycarbonylaminopropionic acid (1.06 g) was dissolved in methanol (50 ml). 10% Palladium carbon (100 mg) was added thereto, and the mixture was stirred at room temperature for two hours under hydrogen atmosphere. The resultant mixture was filtered, and the filtrate was concentrated under reduced pressure to thereby obtain 540 mg of 3-amino-2-tert-butoxycarbonylaminopropionic acid, which was dissolved in ethanol (50 ml). Potassium carbonate (365 mg) and 2-fluoronitrobenzene (377 mg) were added thereto, and the mixture was refluxed with heat for 3 hours. The resultant mixture was concentrated under reduced pressure. Water was added to the residue, and the residue was washed with diethyl ether. 1N Hydrochloric acid was added to the aqueous layer to adjust pH to 3. The resultant mixture was extracted with methylene chloride. The organic layer was dried over anhydrous sodium sulfate and the solvent was evaporated under reduced pressure, to thereby obtain 530 mg of the title compound.

$^1$H-NMR($CDCl_3$) δ: 1.44(9H, s), 3.60~3.95(2H, m), 4.50~4.70(1H, m), 5.37(1H, brs), 6.67~6.73(1H, m), 6.96~7.03(1H, m), 7.43~7.49(1H, m), 8.13~8.19(1H, m), 8.26(1H, brs), 11.50(1H, brs)

Step 3

Preparation of 2-oxo-3-tert-butoxycarbonylamino-1,3,4,5-tetrahydro-2H-1,5-benzodiazepine 2-tert-Butoxycarbonylamino-3-(2-nitrophenyl)aminopropionic acid (325 mg) was dissolved in methanol (50 ml). 10% Palladium carbon (50 mg) was added thereto, and the mixture was stirred at room temperature for one hour under hydrogen atmosphere. The resultant mixture was filtrated, and the filtrate was concentrated under reduced pressure to thereby obtain 2-tert-butoxycarbonylamino-3-(2-aminophenyl)aminopropionic acid, which was suspended in toluene (30 ml), and the mixture was refluxed with heat by use of a Dean-Stark so as to remove water for 3 hours. The resultant mixture was concentrated under reduced pressure, and the residue was purified by silica gel column chromatography (chloroform:methanol=20:1). Diisopropyl ether was added thereto for crystallization, and the mixture was filtrated to thereby obtain 210 mg of the title compound (yield: 76%).

$^1$H-NMR($CDCl_3$) δ: 1.44(9H, s), 3.39~3.47(1H, m), 3.80~3.98(2H, m), 4.44~4.55(1H, m), 5.73(1H, brs), 6.71~6.88(3H, m), 6.97~7.03(1H, m), 7.82(1H, brs)

Referential Example 2

Preparation of 2-oxo-benzyloxycarbonylamino-1,3,4,5-tetrahydro-2H-1,5-benzodiazepine 2-Oxo-3-tert-butoxycarbonylamino-1,3,4,5-tetrahydro-2H-1,5-benzodiazepine (2 g) obtained from Referential Example 1 was dissolved in chloroform (50 ml). 4N HCl-dioxane solution (20 ml) was added thereto, and the mixture was stirred at 50° C. for one hour. After the reaction mixture was allowed to cool, crystals so precipitated were collected by filtration. The crystals were dissolved in water (50 ml), and benzyloxycarbonylchloride (1.29 g) in tetrahydrofuran (30 ml) was added thereto. The mixture was cooled on ice, and 1N aqueous sodium hydroxide (22 ml) was added dropwise. The mixture was stirred for one hour. After completion of reaction, ethyl acetate was added thereto, and the resultant mixture was extracted, washed with saturated brine, and dried over anhydrous sodium sulfate. Ethanol was added for crystallization, to thereby obtain 1.49 g of the title compound.

$^1$H-NMR($CDCl_3$) δ: 3.44(1H, t), 3.81~4.02(2H, m), 4.55~4.62(1H, m), 5.10(2H, s), 6.00(1H, d), 6.72~6.89(3H, m), 6.97~7.05(1H, m), 7.26~7.39(5H, m), 7.74(1H, s)

Referential Example 3

Preparation of 2-oxo-benzyloxycarbonylamino-5-phenyl-1,3,4,5-tetrahydro-2H-1,5-benzodiazepine Step 1

Preparation of N-(2-nitrophenyl)-N-(2-cyanoethyl)aniline

Acrylonitrile (210 ml) and 40% benzyltrimethylammonium hydroxide in methanol (1.5 ml) were added to 2-nitrodiphenylamine (100 g), and the mixture was refluxed with heat for one hour. The reaction mixture was concentrated under reduced pressure, and the residue was purified by silica gel column chromatography (n-hexane:ethyl acetate=2:1) to thereby obtain 47.7 g of the titled compound as a red solid.

$^1$H-NMR($CDCl_3$) δ: 2.80(2H, t), 4.08(2H, t), 6.63(2H, dq), 6.89(1H, tt), 7.16~7.28(2H, m), 7.40(1H, dt), 7.53(1H, dd), 7.68(1H, dt), 7.87(1H, dd)

Step 2

Preparation of 3-[N-(2-aminophenyl)-N-phenyl]aminopropionic acid

10% palladium carbon (4.7 g) was added to N-(2-nitrophenyl)-N-(2-cyanoethyl)aniline (47.1 g) suspended in ethanol (500 ml), and the resultant mixture was stirred for one hour and 30 minutes under hydrogen atmosphere, under ambient pressure, at room temperature. The reaction mixture was filtered, and the filtrate was concentrated under reduced pressure. The residue was dissolved in ethanol (400 ml). An aqueous solution (700 ml) of potassium hydroxide (79.1 g) was added thereto, and the resultant mixture was refluxed for four hours with heat. After completion of reaction, the reaction mixture was allowed to cool. Concentrated hydrochloric acid and 1N hydrochloric acid were added thereto so as to adjust pH to 4. Crystals so precipitated were collected by filtration, to thereby obtain 39.9 g of the title compound as a gray solid (yield: 88.5%).

$^1$H-NMR(DMSO-$d_6$) δ: 2.40~2.56(2H, m), 3.67~3.80 (2H, m), 4.69~5.02(2H, br), 6.48~6.66(4H, m), 6.79(1H, dd), 6.90(1H, dd), 6.98~7.15(3H, m)

Step 3

Preparation of 2-oxo-5-phenyl-1,3,4,5-tetrahydro-2H-1,5-benzodiazepine o-Xylene (1 litter) was added to 3-[N-(2-aminophenyl)-N-phenyl]aminopropionic acid (108.6 g), and the resultant mixture was refluxed with heat by use of a reflux condenser equipped with a Dean-Stark water separator. The reaction mixture was allowed to cool, and crystals so precipitated were collected by filtration, to thereby obtain 93.0 g of the title compound as a gray solid (yield: 92.1%).

$^1$H-NMR($CDCl_3$) δ: 2.67(2H, t), 4.04(2H, t), 6.76(2H, d), 7.07(1H, t), 7.15~7.28(6H, m), 7.67(1H, brs)

Step 4

Preparation of 1-methoxymethyl-2-oxo-5-phenyl-1,3,4,5-tetrahydro-2H-1,5-benzodiazepine In an argon stream, 2-oxo-5-phenyl-1,3,4,5-tetrahydro-2H-1,5-benzodiazepine (40.4 g) was added to 60% sodium hydride (8.84 g) suspended in absolute tetrahydrofuran (500 ml) at 0° C. The mixture was stirred for one hour at 0° C., and chloromethyl methyl ether (20.5 g) was added thereto, followed by stirring for two hours and 30 minutes at room temperature. The reaction mixture was concentrated under reduced pressure, and ice-water was added thereto, followed by extraction with chloroform. The organic layer was washed with saturated brine, and dried over anhydrous sodium sulfate. The solvent was evaporated under reduced pressure, to thereby obtain 47.4 g of the title compound as a yellow oil (yield: 98.8%).

$^1$H-NMR($CDCl_3$) δ: 2.64(2H, t), 3.34(3H, s), 3.96(2H, t), 5.21(2H, s), 6.79(2H, d), 6.86(1H, t), 7.15~7.28(5H, m), 7.44~7.50(1H, m)

Step 5

Preparation of 1-methoxymethyl-2-oxo-3-hydroxyamino-5-phenyl-1,3,4,5-tetrahydro-2H-1,5-benzodiazepine Potassium tert-butoxide (57.8 g) was added to 1-methoxymethyl-2-oxo-5-phenyl-1,3,4,5-tetrahydro-2H-1,5-benzodiazepine (29.1 g) in absolute toluene (1 litter) at 0° C. The resultant mixture was stirred for 30 minutes at 0° C., and tert-butyl nitrite (31.9 g) was added thereto, followed by stirring for 18 hours at room temperature. Ice-water was added to the reaction mixture for separation of layers, and the aqueous layer was extracted with ethyl acetate. The organic layers were combined, washed with saturated brine, and dried over anhydrous sodium sulfate. The solvent was evaporated under reduced pressure, and the residue was purified by silica gel column chromatography (chloroform:methanol=25:1), to thereby obtain 22.8 g of the title compound as a light brown oily substance (yield: 71.1%).

$^1$H-NMR($CDCl_3$) δ: 3.42 and 3.44(3H, each s), 4.58 and 4.78(1H, each br, brs), 5.25 and 5.28(2H, each s), 6.78~7.00 (3H, m), 7.10~7.65(6H, m), 7.91(1H, brs)

Step 6

Preparation of 1-methoxymethyl-2-oxo-3-propylaminocarbonyloxyimino-5-phenyl-1,3,4,5-tetrahydro-2H-1,5-benzodiazepine To 1-methoxymethyl-2-oxo-3-hydroxyamino-5-phenyl-1,3,4,5-tetrahydro-2H-1,5-benzodiazepine (41.4 g) in absolute tetrahydrofuran (500 ml) were added n-propyl isocyanate (28.3 g) and triethylamine (33.7 g). The resultant mixture was refluxed for three hours with heat. The reaction mixture was concentrated under reduced pressure, and the residue was crushed in isopropyl ether and collected by filtration, to thereby obtain 33.4 g of the title compound (yield: 63.3%).

$^1$H-NMR($CDCl_3$) δ: 0.90(3H, t), 1.45~1.60(2H, m), 3.10~3.23(2H, m), 3.43(3H, s), 4.20~5.10(2H, m), 5.28(2H, brs), 5.53~5.64(1H, m), 6.80(2H, d), 6.95(1H, t), 7.12~7.33 (5H, m), 7.52(1H, dd)

Step 7

Preparation of 1-methoxymethyl-2-oxo-3-amino-5-phenyl-1,3,4,5-tetrahydro-2H-1,5-benzodiazepine hydrochloride 10% Palladium carbon (2.0 g) was added to 1-methoxymethyl-2-oxo-3-propylaminocarbonyloxyimino-5-phenyl-1,3,4,5-tetrahydro-2H-1,5-benzodiazepine (14.2 g) suspended in methanol (200 ml), and the resultant mixture was stirred for two hours under hydrogen atmosphere (3 kg/$cm^2$) at room temperature. The reaction mixture was filtered, and the filtrate was concentrated under reduced pressure. The residue was purified by silica gel column chromatography (chloroform:methanol=20:1), to thereby obtain a yellow oily substance. The substance was dissolved in ether, and 4N hydrochloric acid-dioxane (10 ml) was added thereto. Crystals so precipitated were collected by filtration, to thereby obtain 8.28 g of the title compound as a white solid (yield: 69.3%).

$^1$H-NMR($CDCl_3$) δ: 3.16(3H, s), 4.21~4.49(3H, m), 5.10 (2H, s); 6.80(2H, d), 6.87(1H, t), 7.15~7.27(5H, m), 7.40~7.47(1H, m), 8.99(2H, br)

Step 8

Preparation of 2-oxo-3-benzyloxycarbonylamino-5-phenyl-1,3,4,5-tetrahydro-2H-1,5-benzodiazepine 25% Hydrobromic acid-acetic acid (150 ml) was added to 1-methoxymethyl-2-oxo-3-amino-5-phenyl-1,3,4,5- tetrahydro-2H-1,5-benzodiazepine hydrochloride (12.2 g). The resultant mixture was stirred for 30 minutes at room temperature. Ether was added thereto, and solid matter so precipitated was collected by filtration, to thereby obtain 2-oxo-3-amino-5-phenyl-1,3,4,5-tetrahydro-2H-1,5-benzodiazepine hydrobromide. Water (100 ml) was added thereto so as to obtain a suspension. Benzyl chloroformate (6.23 g) in tetrahydrofuran (100 ml) and 1N aqueous sodium hydroxide (75 ml) were added to the suspension under cooling on ice, followed by stirring for one hour at room temperature. The reaction mixture was concentrated under reduced pressure, and water was added thereto, followed by extraction with methylene chloride. The organic layer was washed with saturated brine, and dried over anhydrous sodium sulfate. The solvent was evaporated under reduced pressure. The residue was purified by silica gel column chromatography (n-hexane:ethyl acetate=2:1), to thereby obtain 9.6 g of the title compound (yield: 67.9 %).

$^1$H-NMR($CDCl_3$) δ: 3.69(1H, dd), 4.32(1H, dd), 4.65(1H, dt), 5.09(2H, s), 5.87(1H, d), 6.72(2H, d), 6.86(1H, t), 7.08~7.40(11H, m), 7.75(1H, brs)

Referential Example 4

Preparation of 2-oxo-3-tert-butoxycarbonylamino-8-methyl-1,3,4,5-tetrahydro-2H-1,5-benzodiazepine Potassium carbonate (6.91 g) was added to a solution prepared by dissolving 3-amino-2-(tert-butoxycarbonyl) aminopropionic acid (5.11 g) and 4-fluoro-3-nitrotoluene (3.88 g) in ethanol (100 ml), and the resultant mixture was refluxed overnight. The reaction mixture was allowed to cool, and filtrated. The filtrated mixture was concentrated under reduced pressure. The residue was dissolved in water (200 ml), and washed with ether. 1N Hydrochloric acid was added thereto so as to adjust pH to 3, followed by extraction with methylene chloride. The organic layer was washed with saturated brine, and dried over anhydrous sodium sulfate so as to evaporate the solvent, to thereby obtain 3-(2-nitro-4-methyl)anilino-2-tert-butoxycabonylaminopropionic acid.

$^1$H-NMR($CDCl_3$) δ: 1.43(9H, s), 2.26(3H, s), 3.55~3.89 (2H, m), 4.45~4.63(1H, m), 5.44(1H, d), 6.91(1H, d), 7.27 (1H, d), 7.94(1H, s), 8.14(1H, brs), 1.50(1H, brs)

The thus-obtained compound was dissolved in ethanol (200 ml), and 10% palladium carbon (1 g) was added thereto. The resultant mixture was stirred for five hours under hydrogen atmosphere, under ambient pressure. The mixture was filtrated, and the filtrate was concentrated under reduced pressure. Toluene was added thereto, and crystals so precipitated were collected by filtration, to thereby obtain 3-(2-amino-4-methyl)anilino-2-tert-butoxycabonylaminopropionic acid. The acid was suspended in toluene (100 ml), and the suspension was refluxed overnight while water was removed by use of a Dean-Stark condenser. After reaction, the system was allowed to cool, and crystals so precipitated were collected by filtration. The precipitated crystals were washed with isopropyl ether, and dried in air, to thereby obtain 1.66 g of the title compound (yield: 40%).

$^1$H-NMR(DMSO-$d_6$) δ: 1.36(9H, s), 2.17(3H, s), 3.25~3.32(1H, m), 3.43~3.49(1H, m), 4.07~4.18(1H, m) 5.30(1H d), 6.70~6.76(3H, m), 6.83(1H, d), 9.61(1H s)

Referential Example 5

Preparation of 2-oxo-3-tert-butoxycarbonylamino-$^8$-fluoro-1,3,4,5-tetrahydro-2H-1,5-benzodiazepine The procedure of Referential Example 4 was repeated except that 1,4-difluoro-2-nitrobenzene was used instead of 4-fluoro-3-nitrotoluene, to thereby obtain the title compound.

$^1$H-NMR($CDCl_3$) δ: 1.43(9H, s), 3.40(1H, t), 3.70(1H, brs), 3.90(1H, dd), 4.46~4.58(1H, m), 5.64(1H, brd), 6.66~6.77(3H, m), 7.99(1H, s)

Referential Example 6

Preparation of (+)-2-oxo-3-benzyloxycarbonylamino-1,3,4,5-tetrahydro-2H-1,5-benzodiazepine The procedure of Steps 1 to 3 of Referential Example 1 was repeated by use of (R)-3-amino-2-benzyloxycarbonylaminopropionic acid [α]D (C=1.20, MeOH): +28.7°) produced according to a known method (Synthesis, 542 (1989) and Chem. Pharm. Bull. vol. 7, 616 (1959)), to thereby obtain the title compound (optical purity: 96%ee, [α]D (C=1.0, $CHCl_3$): +5.9°)

Production examples of the compound (I) of the present invention will next be described as Examples 1 to 176.

Example 1

Preparation of 1-[1-(2-toluoylmethyl)-2-oxo-5-pivaloyl-1,3,4,5-tetrahydro-2H-1,5-benzodiazepin-3-yl]-3-(3-methylphenyl)urea Step 1

Preparation of 2-oxo-3-tert-butoxycarbonylamino-5-pivaloyl-1,3,4,5-tetrahydro-2H-1,5-benzodiazepine 2-Oxo-3-tert-butoxycarbonylamino-1,3,4,5-tetrahydro-2H-1,5-benzodiazepine (700 mg) obtained from Reference Example 1 was suspended in 1,2-dichloroethane (20 ml). Pyridine (237 mg) and pivaloyl chloride (362 mg) were added thereto, and the mixture was refluxed for two hours. After the reaction mixture was allowed to cool, crystals that precipitated were collected by filtration, to thereby obtain 650 mg of the title compound (yield: 71%).

$^1$H-NMR(DMSO-$d_6$) δ: 0.88(9H, s), 1.34(9H, s), 3.39~3.59(1H, m), 3.98~4.17(1H, m), 4.30~4.58(1H, m), 7.10~7.51(5H, m), 10.02(1H, s)

Step 2

Preparation of 1-(2-toluoylmethyl)-2-oxo-3-tert-butoxycarbonylamino-5-pivaloyl-1,3,4,5-tetrahydro-2H-1,5-benzodiazepine 60% Sodium hydride (1.6 g) was suspended in tetrahydrofuran (100 ml), 2-Oxo-3-tert-butoxycarbonylamino-5-pivaloyl-1,3,4,5-tetrahydro-2H-1,5-benzodiazepine (7.23 g) was added thereto under ice-cooling, and the resultant mixture was stirred for one hour. Subsequently, 2-bromo-2'-methylacetophenone (4.88 g) was added thereto, and the mixture was stirred at room temperature for one hour. The reaction mixture was concentrated under reduced pressure. Ice-water was added to the residue. The resultant mixture was extracted with methylene chloride. The organic layer was washed with saturated brine, dried over anhydrous sodium sulfate, and purified by silica gel column chromatography (n-hexane:ethyl acetate=2:1), to thereby obtain 7.8 g of the title compound (yield: 79%)

$^1$H-NMR($CDCl_3$) δ: 1.03(9H, s), 1.40(9H, s), 2.57(3H, s), 4.05(1H, dd), 4.27(1H, t), 4.46(1H, d), 4.48~4.63(1H, m), 5.51(1H, brs), 5.55(1H, d), 7.24~7.77(8H, m)

Step 3

Preparation of 1-(2-toluoylmethyl)-2-oxo-3-amino-5-pivaloyl-1,3,4,5-tetrahydro-2H-1,5-benzodiazepine 4N HCl-dioxane solution (5 ml) was added to 1-(2-toluoylmethyl)-2-oxo-3-tert-butoxycarbonylamino-5-pivaloyl-1,3,4,5-tetrahydro-2H-1,5-benzodiazepine (540 mg) in ethanol (5 ml), and the mixture was stirred at 50° C. for 30 minutes. The reaction mixture was concentrated under reduced pressure, and saturated aqueous sodium bicarbonate solution was added to the residue, followed by extraction with methylene chloride. The extract was dried over anhydrous sodium sulfate, to thereby obtain 411 mg of the titled compound.

$^1$H-NMR($CDCl_3$) δ: 1.03(9H, s), 1.64(2H, brs), 2.58(3H, s), 3.66~3.83(2H, m), 4.26(1H, t), 4.37(1H, d), 5.68(1H, d), 7.20~7.49(7H, m), 7.76~7.82(1H, m)

Step 4

Preparation of 1-[1-(2-toluoylmethyl)-2-oxo-5-pivaloyl-1,3,4,5-tetrahydro-2H-1,5-benzodiazepin-3-yl]-3-(3-methylphenyl)urea 1-(2-Toluoylmethyl)-2-oxo-3-amino-5-pivaloyl-1,3,4,5-tetrahydro-2H-1,5-benzodiazepine (411 mg) was dissolved in tetrahydrofuran. m-Tolyl isocyanate (146 mg) was added thereto, and the resultant mixture was stirred at room temperature for 30 minutes. The solution was concentrated under reduced pressure, and the residue was purified by silica gel column chromatography (n-hexane:ethyl acetate=1:1), to thereby obtain 300 mg of the title compound.

$^1$H-NMR($CDCl_3$) δ: 1.03(9H, s), 2.25(3H, s), 2.50(3H, s), 4.02(1H, dd), 4.35(1H, d), 4.43(1H, d) 4.75~4.95(1H, m), 5.49(1H, d), 6.13(1H, d), 6.80(1H, d), 7.00~7.50(11H, m), 7.66(1H, d)

MS(FAB)m/z: 527($MH^+$)

Example 2

Preparation of 1-[1-[1-(2-toluoyl)ethyl)-2-oxo-5-pivaloyl-1,3,4,5-tetrahydro-2H-1,5-benzodiazepin-3-yl]-3-(3-methylphenyl)urea Step 2 of Example 1 was repeated except that 2-bromo-2'-methylpropiophenone was used instead of 2-bromo-2'-methylacetophenone. Subsequently, procedures of Step 3 and 4 of Example 1 were performed, to thereby obtain the title compound.

$^1$H-NMR($CDCl_3$) δ: 1.15(9H, s), 1.31(3H, d), 2.23(3H, s), 2.47(3H, s), 4.01~4.22(2H, m), 4.62~4.71(1H, m), 5.71(1H, q), 6.15(1H, d), 6.77~7.83(13H, m)

MS(FAB)m/z: 541($MH^+$)

Example 3

Preparation of 1-[1-(2-toluoylmethyl)-2-oxo-5-(adamantan-1-yl)carbonyl-1,3,4,5-tetrahydro-2H-1,5-benzodiazepine-3-yl]-3-(3-methylphenyl)urea Step 1

Preparation of 2-oxo-3-tert-butoxycarbonylamino-5-(adamantan-1-yl)carbonyl-1,3,4,5-tetrahydro-2H-1,5-benzodiazepine 1-Adamantylcarbonyl chloride (795 mg) and pyridine (0.33 ml) were added to 2-oxo-3-tert-butoxycarbonylamino-1,3,4,5-tetrahydro-2H-1,5-benzodiazepine (1 g) in anhydrous 1,2-dichloroethane (20 ml). The mixture was refluxed with heat for one hour. After the reaction mixture was allowed to cool, crystals so precipitated were collected by filtration, to thereby obtain 1.58 g of the titled compound as a white solid (yield: 99.8%).

$^1$H-NMR(DMSO-$d_6$) δ: 1.20~1.84(24H, m), 3.25~3.60 (1H, m), 4.02~4.17(1H, m), 4.30~4.46(1H, m), 7.10~7.35 (4H, m), 7.40~7.50(1H, m), 9.98(1H brs)

Step 2

Preparation of 1-(2-toluoylmethyl)-2-oxo-3-tert-butoxycarbonylamino-5-(adamantan-1-yl)carbonyl-1,3,4,5-tetrahydro-2H-1,5-benzodiazepine To 60% sodium hydride (128 mg) suspended in anhydrous tetrahydrofuran (30 ml), 2-oxo-3-tert-butoxycarbonylamino-5-(adamantan-1-yl)carbonyl-1,3,4,5-tetrahydro-2H-1,5-benzodiazepine was added at room temperature under argon atmosphere. The mixture was stirred at room temperature for 30 minutes. Subsequently, 2-bromo-2'-methylacetophenone (375 mg) in anhydrous tetrahydrofuran (10 ml) was added thereto, and the mixture was stirred at room temperature for 2 hours. The reaction mixture was concentrated under reduced pressure. Ice-water (50 ml) was added to the residue, followed by extraction with chloroform. The organic layer was washed with saturated brine, and dried over anhydrous sodium sulfate. The solvent was evaporated under reduced pressure. Ethanol was added to the residue for solidification and collection by filtration, to thereby obtain 426 mg of the title compound as a white solid (yield: 46.6%).

$^1$H-NMR($CDCl_3$) δ: 1.40(9H, s), 1.44~1.91(15H, m), 2.57(3H, s), 3.97(1H, dd), 4.21(1H, t), 4.41(1H, d), 4.48~4.62(1H, m), 5.49(1H, d), 5.56(1H, d), 7.21~7.51(8H, m), 7.75~7.81(1H, m)

Step 3

Preparation of 1-[1-(2-toluoylmethyl)-2-oxo-5-(adamantan-1-yl)carbonyl-1,3,4,5-tetrahydro-2H-1,5-benzodiazepin-3-yl]-3-(3-methylphenyl)urea 4N HCl-dioxane (5.0 ml) was added to 1-(2-toluoylmethyl)-2-oxo-3-tert-butoxycarbonylamino-5-(adamantan-1-yl)carbonyl-1,3,4,5-tetrahydro-2H-1,5-benzodiazepine (400 mg) in anhydrous ethanol (15 ml), and the mixture was stirred at 50° C. for 15 minutes. The reaction mixture was concentrated under reduced pressure, and saturated aqueous sodium bicarbonate was added to the residue, followed by extraction with methylene chloride. The organic layer was dried over anhydrous sodium sulfate, and the solvent was evaporated under reduced pressure, to thereby obtain 1-(2-toluoylmethyl)-2-oxo-3-amino-5-(adamantan-1-yl)carbonyl-1,3,4,5-tetrahydro-2H-1,5-benzodiazepine. Subsequently, this compound was dissolved in anhydrous tetrahydrofuran (10 ml), and m-tolyl isocyanate (0.10 ml) was added to thereto. The mixture was stirred at room temperature for 15 minutes. The solvent was evaporated under reduced pressure. A solvent mixture of isopropyl ether and ethanol was added thereto for solidification and collection by filtration, to thereby obtain 394 mg of the title compound (yield: 93.1%).

Melting point: 263–265° C. (decomposition)

$^1$H-NMR($CDCl_3$) δ: 1.40~1.70(9H, m), 1.80~1.93(6H, m), 2.25(3H, s), 2.53(3H, s), 4.01(1H, dd), 4.30(1H, t), 4.43(1H, d), 4.76~4.90(1H m), 5.57(1H, d), 6.06(1H, d), 6.78~7.50(12H, m), 7.68~7.80(1H, d)

MS(FAB)m/z: 605$(MH)^+$

Example 4

Preparation of 1-[1-(2-toluoylmethyl)-2-oxo-5-pivaloyl-8-methyl-1,3,4,5-tetrahydro-2H-1,5-benzodiazepin-3-yl]-3-(3-methylphenyl)urea Step 1

Preparation of 2-oxo-3-tert-butoxycarbonylamino-5-pivaloyl-8-methyl-1,3,4,5-tetrahydro-2H-1,5-benzodiazepine Step 1 of Example 1 was repeated except that 2-oxo-3-tert-butoxycarbonylamino-8-methyl-1,3,4,5-tetrahydro-2H-1,5-benzodiazepine that obtained from Referential Example 4 was used instead of 2-oxo-3-tert-butoxycarbonylamino-1,3,4,5-tetrahydro-2H-1,5-benzodiazepine, to thereby obtain the title compound.

$^1$H-NMR($CDCl_3$) δ: 0.97(9H, s), 1.40(9H, s), 2.39(3H, s), 3.87(1H, dd), 4.35(1H, t), 4.43–4.50(1H, m), 5.40(1H, d), 6.95(1H, s), 7.06(1H, d), 7.14(1H, d), 7.93(1H, s)

Step 2

Preparation of 1-(2-toluoylmethyl)-2-oxo-3-tert-butoxycarbonylamino-5-pivaloyl-8-methyl-1,3,4,5-tetrahydro-2H-1,5-benzodiazepine Step 2 of Example 1 was repeated except that 2-oxo-3-tert-butoxycarbonylamino-5-pivaloyl-8-methyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.03(9H, s), 1.40(9H, s), 2.37(3H, s), 2.57(3H, s), 3.93(1H, dd), 4.26(1H, t), 4.45(1H, d), 4.53–4.59(1H, m), 5.49(1H, d), 5.51(1H, d), 7.04–7.15(3H, m), 7.28–7.34(2H, m), 7.42–7.48(1H, m), 7.75–7.78(1H, m)

Step 3

Preparation of 1-(2-toluoylmethyl)-2-oxo-3-amino-5-pivaloyl-8-methyl-1,3,4,5-tetrahydro-2H-1,5-benzodiazepine Step 3 of Example 1 was repeated except that 1-(2-toluoylmethyl)-2-oxo-3-tert-butoxycarbonylamino-5-pivaloyl-8-methyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.02(9H, s), 1.66(2H, br), 2.38(3H, s), 2.59(3H, s), 3.66–3.78(2H, m), 4.19– 4.28(1H, m), 4.36(1H, d), 5.65(1H, d), 7.01(1H, s), 7.07–7.12(2H, m), 7.29–7.49(3H, m), 7.81(1H, m)

Step 4

Preparation of 1-[1-(2-toluoylmethyl)-2-oxo-5-pivaloyl-8-methyl-1,3,4,5-tetrahydro-2H-1,5-benzodiazepin-3-yl]-3-(3-methylphenyl)urea Step 4 of Example 1 was repeated except that 1-(2-toluoylmethyl)-2-oxo-3-amino-5-pivaloyl-8-methyl-1,3,4,5-tetrahydro-2H-1,5-benzodiazepine was used instead of 1-(2-toluoylmethyl)-2-oxo-3-amino-5-pivaloyl-1,3,4,5-tetrahydro-2H-1,5-benzodiazepine, to thereby obtain the title compound.

Melting point: 217.5–219.5° C.

$^1$H-NMR($CDCl_3$) δ: 1.04(9H, s), 2.25(3H, s), 2.38(3H, s), 2.51(3H, s), 3.82(1H, dd), 4.33(1H, t), 4.41(1H, d), 4.77–4.88(1H, m), 5.47(1H, d), 6.11(1H, d), 6.80(1H, d), 6.98–7.67(11H, m)

MS(FAB)m/z: 541($MH^+$)

Example 5

Preparation of 1-[1-(2-toluoylmethyl)-2-oxo-5-pivaloyl-8-fluoro-1,3,4,5-tetrahydro-2H-1,5-benzodiazepin-3-yl]-3-(3-methylphenyl)urea Step 1

Preparation of 2-oxo-3-tert-butoxycarbonylamino-5-pivaloyl-8-fluoro-1,3,4,5-tetrahydro-2H-1,5-benzodiazepine Step 1 of Example 1 was repeated except that 2-oxo-3-tert-butoxycarbonylamino-8-fluoro-1,3,4,5-tetrahydro-2H-1,5-benzodiazepine was used instead of 2-oxo-3-tert-butoxycarbonylamino-1,3,4,5-tetrahydro-2H-1,5-benzodiazepine, to thereby obtain the title compound.

$^1$H-NMR($CDCl_3$) δ: 1.00(9H, s), 1.41(9H, s), 3.89(1H, dd), 4.37(1H, t), 4.45–4.52(1H, m), 5.40(1H, d), 6.68–6.92 (1H, m), 6.96–7.03(1H, m), 7.22–7.27(1H, m), 8.08(1H, s)

Step 2

Preparation of 1-(2-toluoylmethyl)-2-oxo-3-tert-butoxycarbonylamino-5-pivaloyl-8-fluoro-1,3,4,5-tetrahydro-2H-1,5-benzodiazepine Step 2 of Example 1 was repeated except that 2-oxo-3-tert-butoxycarbonylamino-5-pivaloyl-8-fluoro-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.05(9H, s), 1.41(9H, s), 2.57(3H, s), 3.97(1H, dd), 4.28(1H, t), 4.42(1H, d), 4.54– 4.60(1H, m), 5.50(1H, d), 5.55(1H, d), 6.99–7.07(2H, m), 7.21–7.34(3H, m), 7.42–7.49(1H, m), 7.75–7.79(1H, m)

Step 3

Preparation of 1-[1-(2-toluoylmethyl)-2-oxo-5-pivaloyl-8-fluoro-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-pivaloyl-8-fluoro-1,3,4,5-tetrahydro -2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

$^1$H-NMR($CDCl_3$) δ: 1.05(9H, s), 2.28(3H, s), 2.52(3H, s), 4.01(1H, dd), 4.35(1H, t), 4.40(1H, d), 4.77–4.89(1H, m), 5.51(1H, d), 5.96(1H, d), 6.80–7.71(12H, m)

MS(FAB)m/z: 545($MH^+$)

Example 6

Preparation of 1-(1-isobutyl-2-oxo-5-pivaloyl-1,3,4,5-tetrahydro-2H-1,5-benzodiazepin-3-yl)-3-(3-methylphenyl) urea Step 1

Preparation of 1-isobutyl-2-oxo-3-tert-butoxycarbonylamino-5-pivaloyl-1,3,4,5-tetrahydro-2H-1,5-benzodiazepine Step 2 of Example 1 was repeated except that 1-bromo-2-methylpropane was used instead of 2-bromo-2'-methylacetophenone, to thereby obtain the title compound.

$^1$H-NMR($CDCl_3$) δ: 0.94(3H, d), 0.97(3H, d), 1.07(9H, s), 1.40(9H, s), 1.97–2.12(1H, m), 3.59–3.77(2H, m), 3.87–3.96(1H, m), 4.07–4.17(1H, m), 4.33–4.45(1H, m), 5.50(1H, d), 7.15–7.44(4H, m)

Step 2

Preparation of 1-(1-isobutyl-2-oxo-5-pivaloyl-1,3,4,5-tetrahydro-2H-1,5-benzodiazepin-3-yl)-3-(3-methylphenyl) urea Step 3 of Example 1 was repeated except that 1-isobutyl-2-oxo-3-tert-butoxycarbonylamino-5-pivaloyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 151.5–152.5° C.

$^1$H-NMR($CDCl_3$) δ: 0.93(3H, d), 0.98(3H, d), 1.08(9H, s), 1.99–2.16(1H, m), 2.29(3H, s), 3.58(1H, dd), 3.79(1H, dd), 3.98(1H, dd), 4.20(1H, t), 4.62–4.75(1H, m), 6.19(1H, d), 6.85(1H, d), 6.98–7.47(8H, m)

MS(FAB)m/z: 451($MH^+$)

Example 7

Preparation of 1-(1-cyclopropylcarbonylmethyl-2-oxo-5-pivaloyl-1,3,4,5-tetrahydro-2H-1,5-benzodiazepin-3-yl)-3-(3-methylphenyl)urea Step 1

Preparation of 1-cyclopropylcarbonylmethyl-2-oxo-3-tert-butoxycarbonylamino-5-pivaloyl-1,3,4,5-tetrahydro-2H-1,5-benzodiazepine Step 2 of Example 1 was repeated except that bromomethyl cyclopropylketone was used instead of 2-bromo-2'-methylacetophenone, to thereby obtain the title compound.

$^1$H-NMR($CDCl_3$) δ: 0.96–1.07(11H, m), 1.17–1.24(2H, m), 1.39(9H, s), 1.98–2.06(1H, m), 3.92(1H, dd), 4.11(1H, d), 4.24(1H, t), 4.44–4.52(1H, m), 5.20(1H, d), 5.47(1H, d), 7.14–7.44(4H, m)

Step 2

Preparation of 1-(1-cyclopropylcarbonylmethyl-2-oxo-5-pivaloyl-1,3,4,5-tetrahydro-2H-1,5-benzodiazepin-3-yl)-3-(3-methylphenyl)urea Step 3 of Example 1 was repeated except that 1-cyclopropylcarbonylmethyl-2-oxo-3-tert-butoxycarbonylamino-5-pivaloyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1 were performed, to thereby obtain the title compound.

Melting point: 184–186° C.

$^1$H-NMR($CDCl_3$) δ: 0.91–1.20(13H, m), 2.07–2.17(1H, m), 2.27(3H, s), 3.96(1H, dd), 4.06(1H, d), 4.36(1H, t), 4.70–4.81(1H, m), 5.27(1H, d), 6.23(1H, d), 6.78(1H, d), 7.03–7.50(7H, m), 7.53(1H, s)

MS(FAB)m/z: 477($MH^+$)

Example 8

Preparation of 1-[1-(2-toluoylmethyl)-2-oxo-5-methoxymethylcarbonyl-1,3,4,5-tetrahydro-2H-1,5-benzodiazepin-3-yl]-3-(3-methylphenyl)urea Step 1

Preparation of $^2$-oxo-3-tert-butoxycarbonylamino-5-methoxymethylcarbonyl-1,3,4,5-tetrahydro-2H-1,5-benzodiazepine Step 1 of Example 1 was repeated except that methoxyacetyl chloride was used instead of pivaloyl chloride, to thereby obtain the title compound.

$^1$H-NMR($CDCl_3$) δ: 1.41(9H, s), 3.29(3H, s), 3.52(1H, d), 3.85(1H, d), 3.86–3.93(1H, m), 4.45–4.71(2H, m), 5.55(1H, brd), 7.17–7.44(4H, m), 8.34(1H, brs)

Step 2

Preparation of 1-(2-toluoylmethyl)-2-oxo-3-tert-butoxycarbonylamino-5-methoxymethylcarbonyl-1,3,4,5-tetrahydro-2H-1,5-benzodiazepine Step 2 of Example 1 was repeated except that 2-oxo-3-tert-butoxycarbonylamino-5-methoxymethylcarbonyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.40(9H, s), 2.46(3H, s), 3.36(3H, s), 3.80(1H, d), 3.89(1H, d), 4.00(1H, d), 4.57–4.64(2H, m), 5.13(2H, ABq), 5.49(1H, d), 7.25–7.36(5H, m), 7.39–7.48 (2H, m), 7.71–7.76(1H, m)

Step 3

Preparation of 1-[1-(2-toluoylmethyl)-2-oxo-5-methoxymethylcarbonyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-methoxymethylcarbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 250–252° C. (decomposition)

$^1$H-NMR($CDCl_3$) δ: 2.27(3H, s), 2.43(3H, s), 3.78(3H, s), 3.80–3.92(2H, m), 4.02(1H, d), 4.69(1H, t), 4.81–4.91(1H, m), 4.96(1H, d), 5.34(1H, d), 6.65(1H, d), 6.76(1H, brs), 7.07–7.13(2H, m), 7.25–7.75(8H, m), 7.74(1H, d), 8.18(1H, s)

MS(FAB)m/z: 515($MH^+$)

Example 9

Preparation of 1-[1-(2-toluoylmethyl)-2-oxo-5-cyclopropylcarbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-cyclopropylcarbonyl-1,3,4,5-tetrahydro-2H-1,5-benzodiazepine Step 1 of Example 1 was repeated except that cyclopropylcarbonyl chloride was used instead of pivaloyl chloride, to thereby obtain the title compound.

$^1$H-NMR($CDCl_3$) δ: 0.52–0.77(2H, m), 0.88–1.00(1H, m), 1.03–1.19(2H, m), 1.41(9H, s), 3.82–3.95(1H, m), 4.43–4.65(2H, m), 5.52(1H, brd), 7.17–7.39(4H, m), 8.38 (1H, s)

Step 2

Preparation of 1-(2-toluoylmethyl)-2-oxo-3-tert-butoxycarbonylamino-5-cyclopropylcarbonyl-1,3,4,5-tetrahydro-2H-1,5-benzodiazepine Step 2 of Example 1 was repeated except that 2-oxo-3-tert-butoxycarbonylamino-5-cyclopropylcarbonyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 0.58–0.75(2H, m), 0.90–1.03(1H, m), 1.13–1.35(2H, m), 1.41(9H, s), 2.49(3H, s), 3.88(1H, dd), 4.46(1H, t), 4.50(1H, d), 4.58–4.69(1H, m), 5.11(2H, ABq), 7.22–7.45(7H, m), 7.74(1H, d)

Step 3

Preparation of 1-[1-(2-toluoylmethyl)-2-oxo-5-cyclopropylcarbonyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-cyclopropylcarbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 207–209° C.

$^1$H-NMR($CDCl_3$) δ: 0.57–0.78(2H, m), 0.95–1.04(1H, m), 1.12–1.36(2H, m), 2.26(3H, s), 2.42(3H, s), 3.91(1H, dd), 4.57(1H, t), 4.85–4.98(1H, m), 5.12(2H, s), 6.12(1H, d), 6.82(1H, d), 6.98–7.46(11H, m), 7.70(1H, d)

MS(FAB)m/z: 511($MH^+$)

Example 10

Preparation of 3-[3-(1-tert-butylcarbonylmethyl)-2-oxo-5-pivaloyl-1,3,4,5 -tetrahydro-2H-1,5-benzodiazepin-3-yl) ureido]benzoic acid Step 1

Preparation of 1-tert-butylcarbonylmethyl-2-oxo-3-tert-butoxycarbonylamino-5-pivaloyl-1,3,4,5-tetrahydro-2H-1,5-benzodiazepine Step 2 of Example 1 was repeated except that bromomethyl-tert-butylketone was used instead of 2-bromo-2'-methylacetophenone, to thereby obtain the title compound.

$^1$H-NMR($CDCl_3$) δ: 1.01(9H, s), 1.28(9H, s), 1.39(9H, s), 3.95(1H, dd), 4.05(1H, d), 4.21(1H, t), 4.43–4.53(1H, m), 5.23(1H, d), 5.49(1H, d), 7.08–7.43(4H, m)

Step 2

Preparation of 1-tert-butylcarbonylmethyl-2-oxo-3-amino-5-pivaloyl-1,3,4,5-tetrahydro-2H-1,5-benzodiazepine 1-tert-Butylcarbonylmethyl-2-oxo-3-tert-butoxycarbonylamino-5-pivaloyl-1,3,4,5-tetrahydro-2H-1,5-benzodiazepine (1 g) was dissolved in chloroform (10 ml), 4N HCl-dioxane (5 ml) was added to the solution, and the mixture was stirred at 50° C. for one hour. After the reaction mixture was allowed to cool, crystals so precipitated were collected by filtration. The crystals were neutralized with saturated aqueous sodium bicarbonate, and extracted with methylene chloride, dried over anhydrous sodium sulfate, to thereby obtain 720 mg of the titled compound (Yield: 92%).

Step 3

Preparation of 1-(tert-butylcarbonylmethyl-2-oxo-5-pivaloyl-1,3,4,5-tetrahydro-2H-1,5-benzodiazepin-3-yl)-3-(3-ethoxycarbonylphenyl)urea Ethyl 3-aminobenzoate (340 mg) was dissolved in anhydrous tetrahydrofuran (50 ml), triphosgene (228 mg) was added, triethylamine (0.9 ml) was added thereto five times after divided into five portions over 15 minutes at 0° C., and the mixture was stirred at room temperature for 5 minutes. To this solution was added a solution of 1-tert-butylcarbonylmethyl-2-oxo-3-amino-5-pivaloyl-1,3,4,5-tetrahydro-2H-1,5-benzodiazepine that obtained from Step 2 in tetrahydrofuran (10 ml), the resultant mixture was stirred at room temperature for 30 minutes. The reaction mixture was concentrated under reduced pressure, water was added, and the mixture was extracted with methylene chloride. The organic layer was washed with saturated brine, dried over anhydrous sodium sulfate, the residue was purified by silica gel column chromatography (n-hexane:ethyl acetate=2:1), to thereby obtain 870 mg of the titled compound (Yield: 79%).

$^1$H-NMR($CDCl_3$) δ: 1.04(9H, s), 1.26(9H, s), 1.34(3H, t), 3.94(1H, dd), 4.09(1H, d), 4.32(2H, q), 4.36(1H, t), 4.77–4.88(1H, m), 5.32(1H, d), 6.29(1H, d), 7.11–7.52(7H, m), 7.61(1H, d), 7.92(1H, s)

Step 4

Preparation of 3-[3-(1-tert-butylcarbonylmethyl-2-oxo-5-pivaloyl-1,3,4,5-tetrahydro-2H-1,5-benzodiazepin-3-yl) ureido]benzoic acid 1-(tert-butylcarbonylmethyl-2-oxo-5-pivaloyl-1,3,4,5-tetrahydro-2H-1,5-benzodiazepin-3-yl)-3-(3-ethoxycarbonylphenyl)urea (500 mg) was dissolved in methanol (20 ml), the solution of lithium hydroxide monohydrate (191 mg) in water (10 ml) was added, the mixture was stirred at 50° C. for 2 hours. The reaction mixture was concentrated under reduced pressure, after acidification with 1N hydrochloric acid, the mixture was extracted with chloroform. The organic layer was dried over anhydrous sodium sulfate, and recrystallized from ethanol and isopropyl ether, to thereby obtain 380 mg of the titled compound (Yield: 73%).

Melting point: 231–233° C.

$^1$H-NMR($CDCl_3$) δ: 1.06(9H, s), 1.29(9H, s), 4.06–4.18 (2H, m), 4.39(1H, t), 4.67–4.78(1H, m), 5.23(1H, d), 7.13–8.32(11H, m)

MS(FAB)m/z: 523(MH$^+$)

Example 11

Preparation of 1-[1-(2-toluoylmethyl)-2-oxo-5-(4-chlorophenyl)carbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-(4-chlorophenyl)carbonyl-1,3,4,5-tetrahydro-2H-1,5-benzodiazepine Step 1 of Example 1 was repeated except that 4-chlorobenzoyl chloride was used instead of pivaloyl chloride, to thereby obtain the title compound.

$^1$H-NMR($CDCl_3$) δ: 1.43(9H, s), 4.16–4.23(1H, m), 4.35–4.49(1H, m), 4.62–4.76(1H, m), 5.54(1H, brd), 6.76–7.27(8H, m), 8.18(1H, s)

Step 2

Preparation of 1-(2-toluoylmethyl)-2-oxo-3-tert-butoxycarbonylamino-5-(4-chlorophenyl)carbonyl-1,3,4,5-tetrahydro-2H-1,5-benzodiazepine Step 2 of Example 1 was repeated except that 2-oxo-3-tert-butoxycarbonylamino-5-(4-chlorophenyl)carbonyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.42(9H, s), 2.55(3H, s), 4.20(1H, dd), 4.25–4.45(1H, m), 4.64–4.79(1H, m), 4.95(1H, d), 5.39(1H, d), 5.59(1H, d), 6.72–7.50(11H, m), 7.81(1H, d)

Step 3

Preparation of 1-[1-(2-toluoylmethyl)-2-oxo-5-(4-chlorophenyl)carbonyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-(4-chlorophenyl)carbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 212–214° C.

$^1$H-NMR($CDCl_3$) δ: 2.21(3H, s), 2.47(3H, s), 4.20(1H, dd), 4.40–4.58(1H, m), 4.90–5.10(2H, m), 5.29(1H, d), 6.26(1H, d), 6.79(1H, d), 6.95–7.50(19H, m), 7.77(1H, d)

MS(FAB)m/z: 581(MH$^+$)

Example 12

Preparation of 1-[1-(2-toluoylmethyl)-2-oxo-5-acetyl-1,3,4,5-tetrahydro-2H-1,5-benzodiazepin-3-yl]-3-(3-methylphenyl)urea Step 1

Preparation of 2-oxo-3-tert-butoxycarbonylamino-5-acetyl-1,3,4,5-tetrahydro-2H-1,5-benzodiazepine Step 1 of Example 1 was repeated except that acetyl chloride was used instead of pivaloyl chloride, to thereby obtain the title compound.

$^1$H-NMR($CDCl_3$) δ: 1.41(9H, s), 1.80(3H, s), 3.78–3.91 (1H, m), 4.43–4.68(2H, m), 5.49(1H, brs), 7.10–7.44(4H, m), 8.05(1H, s)

Step 2

Preparation of 1-(2-toluoylmethyl)-2-oxo-3-tert-butoxycarbonylamino-5-acetyl-1,3,4,5-tetrahydro-2H-1,5-benzodiazepine Step 2 of Example 1 was repeated except that 2-oxo-3-tert-butoxycarbonylamino-5-acetyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.40(9H, s), 1.90(3H, s), 2.46(3H, s), 3.84(1H, dt), 4.59(2H, d), 5.12(2H, q), 5.49(1H, d), 7.72–7.46(7H, m), 7.72(1H, d)

Step 3

Preparation of 1-[1-(2-toluoylmethyl)-2-oxo-5-acetyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5- acetyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 215–217° C.

$^{1}$H-NMR($CDCl_3$) δ: 1.94(3H, s), 2.25(3H, s), 2.35(3H, s), 4.37(1H, dd), 4.72(1H, t), 4.82–4.97(2H, m), 5.38(1H, d), 6.33(1H, d), 6.79(1H, d), 7.06–7.69(12H, m)

MS(FAB)m/z: 485($MH^+$)

Example 13

Preparation of 3-[3-[1-(2-toluoylmethyl)-2-oxo-5-pivaloyl-8-methyl-1,3,4,5-tetrahydro-2H-1,5-benzodiazepin-3-yl]ureido]benzoic acid Step 1

Preparation of 1-[1-(2-toluoylmethyl)-2-oxo-5-pivaloyl-8-methyl-1,3,4,5-tetrahydro-2H-1,5-benzodiazepin-3-yl]-3-(3-ethoxycarbonylphenyl)urea Step 3 of Example 10 was repeated except that 1-(2-toluoylmethyl)-2-oxo-3-amino-5-pivaloyl-8-methyl-1,3,4,5-tetrahydro-2H-1,5-benzodiazepine obtained from Step 3 of Example 4 was used instead of 1-tert-butylcarbonylmethyl-2-oxo-3-amino-5-pivaloyl-1,3,4,5-tetrahydro-2H-1,5-benzodiazepine, to thereby obtain the title compound.

$^{1}$H-NMR($CDCl_3$) δ: 1.05(9H, s), 1.35(3H, t), 2.39(3H, s), 2.49(3H, s), 3.96(1H, dd), 4.29–4.42(4H, m), 4.80–4.87(1H, m), 5.49(1H, d), 6.26(1H, d), 7.04–7.94(12H, m)

Step 2

Preparation of 3-[3-[1-(2-toluoylmethyl)-2-oxo-5-pivaloyl-8-methyl-1,3,4,5-tetrahydro-2H-1,5-benzodiazepin-3-yl]ureido]benzoic acid Step 4 of Example 10 was repeated except that 1-[1-(2-toluoylmethyl)-2-oxo-5-pivaloyl-8-methyl-1,3,4,5-tetrahydro-2H-1,5-benzodiazepin-3-yl]-3-(3-ethoxycarbonylphenyl)urea was used instead of 1-(1-tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

Melting point: 246–248° C. (decomposition)

$^{1}$H-NMR($CDCl_3$) δ: 1.08(9H, s), 2.39(3H, s), 2.56(3H, s), 4.11(1H, dd), 4.43(1H, dd), 4.58(1H, d), 4.76–4.86(1H, m), 5.48(1H, d), 7.06–7.74(11H, m), 8.18(1H, s), 8.35(1H, d), 10.50(1H, br)

MS(FAB)m/z: 571$(MH)^+$

Step 3

Preparation of (+)-1-(2-toluoylmethyl)-2-oxo-3-amino-5-pivaloyl-8-methyl-1,3,4,5-tetrahydro-2H-1,5-benzodiazepine and (−)-1-(2-toluoylmethyl)-2-oxo-3-amino-5-pivaloyl-8-methyl-1,3,4,5-tetrahydro-2H-1,5-benzodiazepine 1-(2-Toluoylmethyl)-2-oxo-3-amino-5-pivaloyl-8-methyl-1,3,4,5-tetrahydro-2H-1,5-benzodiazepine (5.60 g) that obtained from Step 3 of Example 4 was dissolved in ethyl acetate (150 ml), (+)-dibenzoyl-D-tartaric acid monohydrate (4.43 g) was added, and the mixture was stirred at room temperature. Crystals so precipitated were collected by filtration, and washed with ethyl acetate, to thereby obtain the dibenzoyl tartaric acid salt (4.24 g, Melting point: 167–168° C.). The filtrate and the washings were stored elsewhere. The salt was suspended in saturated aqueous sodium bicarbonate, the mixture was extracted with chloroform. The organic layer was washed with saturated brine, dried over anhydrous sodium sulfate, and the solvent was evaporated under reduced pressure, to thereby obtain (+)-1-(2-toluoylmethyl)-2-oxo-3-amino-5-pivaloyl-8-methyl-1,3,4,5-tetrahydro-2H-1,5-benzodiazepine. Optical purity: 99%ee (the ee value was determined by High Performance Liquid Chromatography).

[α] $D^{25}$ (C=1, MeOH): +45.2°

The above filtrate and the washings were concentrated under reduced pressure, the residue was dissolved in chloroform, and successively washed with saturated aqueous sodium bicarbonate, water, and saturated brine, and dried over anhydrous sodium sulfate. The solvent was evaporated under reduced pressure, the residue was dissolved in ethyl acetate (80 ml), and the solution, after addition of (−)-dibenzoyl-L-tartaric acid monohydrate (2.45 g), was stirred at room temperature. White crystals so precipitated were collected by filtration, washed with ethyl acetate, to thereby obtain the dibenzoyl tartaric acid salt (4.26 g, Melting point: 166–167° C.). This salt was suspended in saturated aqueous sodium bicarbonate, and the suspension was extracted with chloroform. The organic layer was washed with saturated brine, dried over anhydrous sodium sulfate, and the solvent was evaporated under reduced pressure, to thereby obtain (−)-1-(2-toluoylmethyl)-2-oxo-3-amino-5-pivaloyl-8-methyl-1,3,4,5-tetrahydro-2H-1,5-benzodiazepine. Optical purity: 99%ee (the ee value was determined by High Performance Liquid Chromatography).

[α] $D^{25}$ (C=1, MeOH): −45.5°

Step 4

Preparation of (+)-3-[3-[1-(2-toluoylmethyl)-2-oxo-5-pivaloyl-8-methyl-1,3,4,5-tetrahydro-2H-1,5-benzodiazepin-3-yl]ureido]benzoic acid Isophthalic acid monobenzyl ester (2.06 g) was dissolved in anhydrous 1,4-dioxane (15 ml), diphenylphosphoryl azide (2.43 g) and triethylamine (0.97 g) were added, and the mixture was stirred at 75–80° C. for 2 hours and 30 minutes. After allowed to cool, a solution of (+)-1-(2-toluoylmethyl)-2-oxo-3-amino-5-pivaloyl-8-methyl-1,3,4,5-tetrahydro-2H-1,5-benzodiazepine (2.18 g) that obtained from Step 3 in anhydrous 1,4-dioxane (10 ml) was added dropwise, and the mixture was stirred at room temperature for one hour. The reaction mixture was concentrated under reduced pressure. The residue, after addition of saturated aqueous sodium bicarbonate, was extracted with chloroform. The organic layer was washed with saturated brine, dried over anhydrous sodium sulfate. The solvent was evaporated under reduced pressure, and purified by silica gel column chromatography (n-hexane:ethyl acetate=2:1), to thereby obtain 2.91 g of (+)-1-[1-(2-toluoylmethyl)-2-oxo-5-pivaloyl-8-methyl-1,3,4,5-tetrahydro-2H-1,5-benzodiazepin-3-yl]-3-(3-benzyloxycarbonylpheny)urea (Yield: 82.6%) as white amorphous.

$^{1}$H-NMR($CDCl_3$) δ: 1.04(9H, s), 2.38(3H, s), 2.46(3H, s), 3.94(1H, dd), 4.31–4.40(2H, m), 4.82–4.86(1H, m), 5.31 (2H, s), 5.39(1H, d), 6.41(1H, br), 7.02–7.41(12H, m), 7.57–7.66(3H, m), 7.74(1H, br), 7.95(1H, s)

The above compound was dissolved in methanol (50 ml) and tetrahydrofuran (10 ml), 10% palladium carbon (300 mg) was added, the mixture was stirred under hydrogen atmosphere at room temperature for 2 hours. The reaction mixture was filtered, and the filtrate was concentrated under reduced pressure. The residue was dissolved in ethyl acetate, isopropyl ether was added for crystallization, and crystals were collected by filtration, to thereby obtain 2.05 g of the titled compound.

[α] $D^{25}$ (C=1, MeOH): +21.7°

Melting point: 160–161° C. (contraction)

Step 5

Preparation of (−)-3-[3-[1-(2-toluoylmethyl)-2-oxo-5-pivaloyl-8-methyl-1,3,4,5-tetrahydro-2H-1,5-benzodiazepin-3-yl]ureido]benzoic acid Step 4 was repeated except that (−)-1-(2-toluoylmethyl)-2-oxo-3-amino-5-pivaloyl-8-methyl-1,3,4,5-tetrahydro-2H-1,5-benzodiazepine was used instead of (+)-1-(2-toluoylmethyl)-2-oxo-3-amino-5-pivaloyl-8-methyl-1,3,4,5-tetrahydro-2H-1,5-benzodiazepine, to thereby obtain the title compound.

[α] $D^{25}$ (C=1, MeOH): −20.2°

Melting point: 160–161° C. (contraction)

Example 14

Preparation of 1-[1-(2-toluoylmethyl)-2-oxo-5-cyclohexylcarbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-cyclohexylcarbonyl-1,3,4,5-tetrahydro-2H-1,5-benzodiazepine Step 1 of Example 1 was repeated except that cyclohexylcarbonyl chloride was used instead of pivaloyl chloride, to thereby obtain the title compound.

$^1$H-NMR($CDCl_3$) δ: 0.80–1.26(2H, m), 1.35–1.69(17H, m), 1.93–2.07(1H, m), 3.78–3.85(1H, m), 4.46–4.63(2H, m), 5.42(1H, brd), 7.15–7.42(4H, m), 7.89(1H, s)

Step 2

Preparation of 1-(2-toluoylmethyl)-2-oxo-3-tert-butoxycarbonylamino-5-cyclohexylcarbonyl-1,3,4,5-tetrahydro-2H-1,5-benzodiazepine Step 2 of Example 1 was repeated except that 2-oxo-3-tert-butoxycarbonylamino-5-cyclohexylcarbonyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 0.84–1.89(19H, m), 2.05–2.22(1H, m), 2.50(3H, s), 3.84(1H, dd), 4.54(1H, t), 4.55–4.65(1H, m), 4.82(1H, d), 5.30(1H, d), 5.49(1H, d), 7.21–7.45(7H, m), 7.75(1H, d)

Step 3

Preparation of 1-[1-(2-toluoylmethyl)-2-oxo-5-cyclohexylcarbonyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-cyclohexylcarbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 148–151° C.

$^1$H-NMR($CDCl_3$) δ: 0.80–1.95(10H, m), 2.10–2.25(1H, m), 2.26(3H, s), 2.43(3H, s), 3.87(1H, dd), 4.56(1H, t), 4.80–5.00(2H, m), 5.24(1H, d), 6.13(1H, d), 6.81(1H, d), 7.00–7.50(11H, m), 7.68(1H, d)

MS(FAB)m/z: 553($MH^+$)

Example 15

Preparation of 1-[1-(N-phenyl-N-methyl)carbamoylmethyl-2-oxo-5-phenyl-1,3,4,5-tetrahydro-2H-1,5-benzodiazepin-3-yl]-3-(3-methylsulfonylaminocarbonylphenyl)urea Step 1

Preparation of 1-(N-phenyl-N-methyl)carbamoylmethyl-2-oxo-3-benzyloxycarbonylamino-5-phenyl-1,3,4,5-tetrahydro-2H-1,5-benzodiazepine 2-Bromo-N-methyl-N-phenylacetamide (661 mg), 1N aqueous sodium hydroxide (10 ml) and tetra n-butylammonium bromide (77 mg) were added to a solution of 2-oxo-3-benzyloxycarbonylamino-5-phenyl-1,3,4,5-tetrahydro-2H-1,5-benzodiazepine (930 mg) that obtained from Referential Example 3 in toluene (25 ml), the mixture was stirred at room temperature for one hour. Water (125 ml) was added to the reaction mixture and extracted with ethyl acetate. The organic layer was washed with saturated brine, dried over anhydrous sodium sulfate. The solvent was evaporated under reduced pressure, the residue was purified by silica gel column chromatography (n-hexane:ethyl acetate=2:1), to thereby obtain 1.09 g of the title compound (Yield: 85.0%) as colorless oil.

$^1$H-NMR($CDCl_3$) δ: 3.34(3H, s), 3.56(1H, dd), 3.79(1H, d), 4.21(1H, dd), 4.57–4.72(2H, m), 5.07(2H, s), 5.91(1H, d), 6.69(2H, d), 6.81(1H, t), 7.10–7.50(16H, m)

Step 2

Preparation of 1-(N-phenyl-N-methyl)carbamoylmethyl-2-oxo-3-amino-5-phenyl-1,3,4,5-tetrahydro-2H-1,5-benzodiazepine 25% Hydrogen bromide solution in acetic acid (10 ml) was added to 1-(N-phenyl-N-methyl)carbamoylmethyl-2-oxo-3-benzyloxycarbonylamino-5-phenyl-1,3,4,5-tetrahydro-2H-1,5-benzodiazepine (1.10 g), the mixture was stirred at room temperature for one hour. Ether was added to the reaction mixture, crystals so precipitated were collected by filtration. Water and saturated aqueous sodium bicarbonate were added to the crystals, extracted with methylenechloride. The organic layer was washed with saturated brine, dried over anhydrous sodium sulfate. The solvent was evaporated under reduced pressure, to thereby obtain 710 mg of the title compound (Yield: 86.1%) as colorless oil.

$^1$H-NMR($CDCl_3$) δ: 1.68(2H, brs), 3.36(3H, s), 3.52(1H, dd), 3.64–3.82(2H, m), 3.94(1H, dd), 4.74(1H, d), 6.69(2H, d), 6.80(1H, t), 7.10–7.52(11H, m)

Step 3

Preparation of 1-[1-(N-phenyl-N-methyl)carbamoylmethyl-2-oxo-5-phenyl-1,3,4,5-tetrahydro-2H-1,5-benzodiazepin-3-yl]-3-(3-methylsulfonylaminocarbonylphenyl)urea.1.5 hydrate 1,1'-Carbonyldiimidazole (243 mg) was added to a solution of 1-(N-phenyl-N-methyl)carbamoylmethyl-2-oxo-3-amino-5-phenyl-1,3,4,5-tetrahydro-2H-1,5-benzodiazepine (500 mg) in anhydrous methylene chloride (10 ml), the mixture was stirred at room temperature for 30 minutes. The reaction mixture was concentrated under reduced pressure, the residue was dissolved in anhydrous tetrahydrofuran (15 ml), and the solution, after addition of 3-(methylsulfonylaminocarbonyl)aniline (321 mg) and triethylamine (0.21 ml), was refluxed overnight. The resultant mixture was concentrated under reduced pressure, the residue was purified by silica gel column chromatography (chloroform:methanol=10:1), to thereby obtain 240 mg of the title compound as a white solid.

Melting point: 242–244° C. (decomposition)

$^1$H-NMR(DMSO-$d_6$, 100° C.) δ: 2.87(3H, s), 3.21(3H, s), 3.54(1H, dd), 4.02(1H, dd), 4.23(1H, d), 4.49(1H, d), 4.50–4.64(1H, m), 6.44(1H, d), 6.71–6.83(3H, m), 7.05–7.54(15H, m), 7.83(1H, t), 8.68(1H, brs)

IR(KBr)$cm^{-}$:3346, 1653, 1593, 1549, 1497

MS(FAB)m/z: 641$(MH)^+$

Example 16

Preparation of 1-(1-tert-butoxycarbonylmethyl-2-oxo-5-phenyl-1,3,4,5-tetrahydro-2H-1,5-benzodiazepin-3-yl)-3-(3-methylsulfonylaminocarbonylphenyl)urea Step 1

Preparation of 1-tert-butoxycarbonylmethyl-2-oxo-3-benzyloxycarbonylamino-5-phenyl-1,3,4,5-tetrahydro-2H-1,5-benzodiazepine Under argon atmosphere a solution of 2-oxo-3-benzyloxycarbonylamino-5-phenyl-1,3,4,5-tetrahydro-2H-1,5-benzodiazepine (1.94 g) that obtained from Referential Example 3 in anhydrous tetrahydrofuran (30 ml) was added to a suspension of 60% sodium hydride (400 mg) in anhydrous tetrahydrofuran (30 ml) at 0° C., the mixture was stirred at room temperature for one hour. Tert-butyl bromoacetate (1.46 g) in anhydrous tetrahydrofuran (15 ml) to this solution, the resultant mixture was stirred at room temperature for one hour. Water (300 ml) was added to the reaction mixture, extracted with ethyl acetate. The organic layer was washed with saturated brine, dried over anhydrous sodium sulfate, and the solvent was evaporated under reduced pressure. Isopropyl ether was added for trituration to the residue, filtered, to thereby obtain 1.74 g of the titled compound (Yield: 69.4%) as a white solid.

$^1$H-NMR($CDCl_3$) δ: 1.44(9H, s), 3.62(1H, dd), 4.11(1H, d), 4.18–4.28(1H, m), 4.57–4.70(2H, m), 5.08(2H, s), 5.89 (1H, d), 6.74(2H, d), 6.86(1H, t), 7.14–7.38(11H, m)

Step 2

Preparation of 1-tert-butoxycarbonylmethyl-2-oxo-3-amino-5-phenyl-1,3,4,5-tetrahydro-2H-1,5-benzodiazepine 10% Palladium carbon (150 mg) was added to a suspension of 1-tert-butoxycarbonylmethyl-2-oxo-3-benzytoxycarbonylamino-5-phenyl-1,3,4,5-tetrahydro-2H-1,5-benzodiazepine (1.50 g) in methanol (50 ml), the mixture was stirred under hydrogen atmosphere at room temperature for 4 hours. The reaction mixture was filtered, the filtrate was concentrated under reduced pressure, and the residue was purified by silica gel column chromatography (chloroform:methanol=20:1), to thereby obtain 920 mg of the title compound (Yield: 83.5%) as colorless oil.

$^1$H-NMR($CDCl_3$) δ: 1.48(9H, s), 1.65(2H, brs), 3.52–3.63 (1H, m), 3.68–3.77(1H, m), 3.93–4.01(1H, m), 4.02(1H, d), 4.76(1H, d), 6.75(2H, d), 6.85(1H, t), 7.14–7.30(6H, m)

Step 3

Preparation of 1-(1-tert-butoxycarbonylmethyl-2-oxo-5-phenyl-1,3,4,5-tetrahydro-2H-1,5-benzodiazepin-3-yl)-3-(3-methylsulfonylaminocarbonylphenyl)urea Step 3 of Example 15 was repeated except that 1-tert-butoxycarbonylmethyl-2-oxo-3-amino-5-phenyl-1,3,4,5-tetrahydro-2H-1,5-benzodiazepine was used instead of 1-(N-phenyl-N-methyl)carbamoylmethyl-2-oxo-3-amino-5-phenyl-1,3,4,5-tetrahydro-2H-1,5-benzodiazepine, to thereby obtain the title compound.

$^1$H-NMR(DMSO-$d_6$) δ: 1.36(9H, s), 2.95(3H, s), 3.61 (1H, dd), 4.01(1H, dd), 4.48–4.73(3H, m), 6.60–6.92(4H, m), 7.13–7.58(10H, m), 7.81(1H, brs), 8.96(1H, brs)

IR(KBr)$cm^{-1}$:3368, 1746, 1668, 1593

MS(FAB)m/z: 612($MH^+$)

Example 17

Preparation of 1-[1-(2,2,2-trifluoro)ethyl-2-oxo-5-phenyl-1,3,4,5-tetrahydro-2H-1,5-benzodiazepin-3-yl]-3-(3-methylsulfonylaminocarbonylphenyl)urea Step 1

Preparation of 1-(2,2,2-trifluoro)ethyl-2-oxo-3-benzyloxycarbonylamino-5-phenyl-1,3,4,5-tetrahydro-2H-1,5-benzodiazepine Under argon atmosphere potassium carbonate (464 mg) and 1-iodo-2,2,2-trifluoroethane (0.50 ml) were added to a suspension of 2-oxo-3-benzyloxycarbonylamino-5-phenyl-1,3,4,5-tetrahydro-2H-1,5-benzodiazepine (650 mg) that obtained from Referential Example 3 in anhydrous N,N-dimethylformamide (30 ml), the mixture was stirred internal temperature at 85° C. overnight. Water was added to the reaction mixture, extracted with ethyl acetate. The organic layer was washed with saturated brine, dried over anhydrous sodium sulfate, and the solvent was evaporated under reduced pressure. The residue was purified by silica gel column chromatography (n-hexane:ethyl acetate=2:1), to thereby obtain 374 mg of the title compound (Yield: 47.4%) as a white solid.

$^1$H-NMR($CDCl_3$) δ: 3.63(1H, dd), 4.00–4.20(2H, m), 4.53–4.71(1H, m), 4.88–5.10(3H, m), 5.79(1H, d), 6.76(2H, d), 6.90(1H, t), 7.03–7.40(11H, m)

MS(EI)m/z: 469($M^+$)

Step 2

Preparation of 1-(2,2,2-trifluoro)ethyl-2-oxo-3-amino-5-phenyl-1,3,4,5-tetrahydro-2H-1,5-benzodiazepine 10% Palladium carbon (48 mg) was added to a suspension of 1-(2,2,2-trifluoro)ethyl-2-oxo-3-benzyloxycarbonylamino-5-phenyl-1,3,4,5-tetrahydro-2H-1,5-benzodiazepine (480mg) in methanol (15 ml), the mixture was stirred under hydrogen atmosphere at 50° C. for 2 hours. The reaction mixture was filtrated, the filtrate was evaporated under reduced pressure, to thereby obtain 334 mg of the title compound (Yield: 97.7%) as colorless oil.

Step 3

Preparation of 1-[1-(2,2,2-trifluoro)ethyl-2-oxo-5-phenyl-1,3,4,5-tetrahydro-2H-1,5-benzodiazepin-3-yl]-3-(3-methylsulfonylaminocarbonylphenyl)urea Step 3 of Example 15 was repeated except that 1-(2,2,2-trifluoro)ethyl-2-oxo-3-amino-5-phenyl-1,3,4,5-tetrahydro-2H-1,5-benzodiazepine was used instead of 1-(N-phenyl-N-methyl)carbamoylmethyl-2-oxo-3-amino-5-phenyl-1,3,4,5 -tetrahydro-2H-1,5-benzodiazepine, to thereby obtain the title compound.

$^1$H-NMR(DMSO-$d_6$) δ: 2.99(3H, s), 3.60–3.75(1H, m), 3.88–4.04(1H, m), 4.47–4.68(2H, m), 4.96–5.18(1H, m), 6.63–6.90(4H, m), 7.08–7.56(9H, m), 7.69–7.85(2H, m), 8.99(1H, brs)

MS(FAB)m/z: 576$(MH)^+$

Example 18

Preparation of 1-[1-(2-toluoylmethyl)-2-oxo-5-phenyl-1,3,4,5-tetrahydro-2H-1,5-benzodiazepin-3-yl]-3-(3-methylsulfonylaminocarbonylphenyl)urea Step 1

Preparation of 1-(2-toluoylmethyl)-2-oxo-3-benzyloxycarbonylamino-5-phenyl-1,3,4,5-tetrahydro-2H-1,5-benzodiazepine Step 1 of Example 15 was repeated except that 2-bromo-2'-methylacetophenone was used instead of 2-bromo-N-methyl-N-phenylacetamide, to thereby obtain the title compound.

$^1$H-NMR($CDCl_3$) δ: 2.51(3H, s), 3.64(1H, dd), 4.26(1H, dd), 4.65–4.75(1H, m), 4.80(1H, d), 5.09(2H, s), 5.36(1H, d), 5.91(1H, d), 6.74(2H, d), 6.87(1H, t), 7.14–7.42(14H, m), 7.70(1H, d)

Step 2

Preparation of 1-(2-toluoylmethyl)-2-oxo-3-amino-5-phenyl-1,3,4,5-tetrahydro-2H-1,5-benzodiazepine Step 2 of Example 17 was repeated except that 1-(2-toluoylmethyl)-2-oxo-3-benzyloxycarbonylamino-5-phenyl-1,3,4,5-tetrahydro-2H-1,5-benzodiazepine was used instead of 1-(2,2,2-trifluoro)ethyl-2-oxo-3-benzyloxycarbonylamino-5-phenyl-1,3,4,5-tetrahydro-2H-1,5-benzodiazepine, to thereby obtain the title compound.

Step 3

Preparation of 1-[1-(2-toluoylmethyl)-2-oxo-5-phenyl-1,3,4,5-tetrahydro-2H-1,5-benzodiazepin-3-yl]-3-(3-methylsulfonylaminocarbonylphenyl)urea Step 3 of Example 15 was repeated except that 1-(2-toluoylmethyl)-2-oxo-3-amino-5-phenyl-1,3,4,5- tetrahydro-2H-1,5-benzodiazepine was used instead of 1-(N-phenyl-N-methyl)carbamoylmethyl-2-oxo-3-amino-5-phenyl-1,3,4,5-tetrahydro-2H-1,5-benzodiazepine, to thereby obtain the title compound.

Melting point: 210–220° C.

$^1$H-NMR(DMSO-$d_6$) δ: 2.40(3H, s), 2.94(3H, s), 3.60 (1H, dd), 4.04(1H, dd), 4.58– 4.63(1H, m), 5.17(1H, d), 5.38(1H, d), 6.68(1H, d), 6.77–6.98(3H, s), 7.15–7.58(13H, m), 7.83(1H, brs), 7.89(1H, d), 8.99(1H, s)

MS(FAB) m/z: 626(MH$^+$)

Example 19

Preparation of 1-(1-methoxymethyl-2-oxo-5-phenyl-1,3,4,5-tetrahydro-2H-1,5-benzodiazepin-3-yl)-3-(3-methylsulfonylaminocarbonylphenyl)urea Step 3 of Example 15 was repeated except that 1-methoxymethyl-2-oxo-3-amino-5-phenyl-1,3,4,5-tetrahydro-2H-1,5-benzodiazepine that obtained from Step 7 of Referential Example 3 was used instead of 1-(N-phenyl-N-methyl)carbamoylmethyl-2-oxo-3-amino-5-phenyl-1,3,4,5-tetrahydro-2H-1,5-benzodiazepine, to thereby obtain the title compound.

Melting point: 199–205° C.

$^1$H-NMR(DMSO-$d_6$) δ: 2.91(3H, s), 3.16(3H, s), 3.66 (1H, dd), 3.97(1H, dd), 4.52–4.57(1H, m), 5.20(1H, d), 5.30(1H, d), 6.66(1H, d), 6.76–6.87(3H, m), 7.13–7.84(11H, m), 8.96(1H, brs)

MS(FAB)m/z: 576(M+K)$^+$

Example 20

Preparation of 1-[2-oxo-5-(4-methylpiperazin-1-yl)methylcarbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-chloroacetyl-1,3,4,5-tetrahydro-2H-1,5-benzodiazepine Step 1 of Example 1 was repeated except that chloroacetyl chloride was used instead of pivaloyl chloride, to thereby obtain the title compound.

$^1$H-NMR($CDCl_3$) δ: 1.41(9H, s), 3.77(2H, ABq), 3.90–3.96(1H, m), 4.50–4.65(2H, m), 5.58(1H, brs), 7.16–7.52(4H, m), 8.16(1H, s)

Step 2

Preparation of 2-oxo-3-tert-butoxycarbonylamino-5-[4-(1-methyl)piperazino]methylcarbonyl-1,3,4,5-tetrahydro-2H-1,5-benzodiazepine N-Methylpiperazine (612 mg), potassium carbonate (845 mg), and potassium iodide (100 mg) were added to a solution of 2-oxo-3-tert-butoxycarbonylamino-5-chloroacetyl-1,3,4,5-tetrahydro-2H-1,5-benzodiazepine (2.16 g) in acetone (100 ml), the mixture was refluxed for 3hours. After allowed to cool, the in soluble material was removed by filtration, and the filtrate was concentrated under reduced pressure. The residue was purified by silica gel column chromatography (silica gel NH-DM1020, produced by Fujisilicia Co. Ltd., chloroform:methanol=50:1), to thereby obtain 2.35 g of the title compound (Yield: 92%).

$^1$H-NMR($CDCl_3$) δ: 1.41(9H, s), 2.16–2.50(11H, m), 2.75(1H, d), 2.90(1H, d), 3.80–3.88(1H, m), 4.48–4.65(2H, m), 5.50(1H, d), 7.13–7.43(4H, m), 8.29(1H, brs)

Step 3

Preparation of 1-[2-oxo-5-(4-methylpiperazin-1-yl)methylcarbonyl-1,3,4,5-tetrahydro-2H-1,5-benzodiazepin-3-yl]-3-(3-methylphenyl)urea Step 3 of Example 1 was repeated except that 2-oxo-3-tert-butoxycarbonylamino-5-(4-methylpiperazin-1-yl)methylcarbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

$^1$H-NMR(DMSO-$d_6$) δ: 2.00–2.25(14H, m), 2.77(1H, s), 3.55–3.70(1H, m), 4.38–4.50(2H, m), 6.62–6.75(2H, m), 7.04–7.55(8H, m), 8.70(1H, s), 10.17(1H, s)

MS(FAB)m/z: 451(MH$^+$)

Example 21

Preparation of 1-[1-(2-toluoylmethyl)-2-oxo-5-(4-methylpiperazin-1-yl)methylcarbonyl-1,3,4,5-tetrahydro-2H-1,5-benzodiazepin-3-yl]-3-(3-methylphenyl)urea Step 1

Preparation of 1-(2-toluoylmethyl)-2-oxo-3-tert-butoxycarbonylamino-5-(4-methylpiperazin-1-yl)methylcarbonyl-1,3,4,5-tetrahydro-2H-1,5-benzodiazepine Step 2 of Example 1 was repeated except that 2-oxo-3-tert-butoxycarbonylamino-5-(4-methylpiperazin-1-yl)methylcarbonyl-1,3,4,5-tetrahydro-2H-1,5-benzodiazepine that obtained from Step 2 of Example 20 was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.40(9H, s), 2.27(3H, s), 2.32–2.65 (11H, m), 2.97(2H, ABq), 3.78–3.90(1H, m), 4.51–4.63(2H, m), 5.10(2H, s), 5.49(1H, d), 7.22–7.47(7H, m), 7.73(1H, d)

Step 2

Preparation of 1-[1-(2-toluoylmethyl)-2-oxo-5-(4-methylpiperazin-1 -yl)methylcarbonyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-(4-methylpiperazin-1-yl)methylcarbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 245–247° C.

$^1$H-NMR($CDCl_3$) δ: 2.20(3H, s), 2.26(3H, s), 2.30–2.62 (11H, m), 2.93(1H, d), 3.04(1H, d), 3.88(1H, dd), 4.70(1H, t), 4.84–4.92(1H, m), 4.95(1H, d), 5.17(1H, d), 6.21(1H, d), 6.82(1H, d), 7.00–7.67(11H, m), 7.67(1H, d)

MS(FAB)m/z: 583(MH$^+$)

Example 22

Preparation of 1-[1-(2-toluoylmethyl)-2-oxo-5-benzoyl-1,3,4,5-tetrahydro-2H-1,5-benzodiazepin-3-yl]-3-(3-methylphenyl)urea Step 1

Preparation of 2-oxo-3-tert-butoxycarbonylamino-5-benzoyl-1,3,4,5-tetrahydro-2H-1,5-benzodiazepine Step 1 of Example 1 was repeated except that benzoyl chloride was used instead of pivaloyl chloride, to thereby obtain the title compound.

$^1$H-NMR($CDCl_3$) δ: 1.43(9H, s), 4.17(1H, dd), 4.43(1H, t), 4.63–4.73(1H, m), 5.55(1H, brd), 6.70–7.27(9H, m), 8.16(1H, s)

Step 2

Preparation of 1-(2-toluoylmethyl)-2-oxo-3-tert-butoxycarbonylamino-5-benzoyl-1,3,4,5-tetrahydro-2H-1,5-benzodiazepine Step 2 of Example 1 was repeated except that 2-oxo-3-tert-butoxycarbonylamino-5-benzoyl-1,3,4,5-tetrahydro- 2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.42(9H, s), 2.57(3H, s), 4.21–4.49 (2H, m), 4.70–4.90(2H, m), 5.47–5.69(2H, m), 6.76–7.54 (12H, m), 7.83(1H, d)

Step 3

Preparation of 1-[1-(2-toluoylmethyl)-2-oxo-5-benzoyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-benzoyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

$^1$H-NMR($CDCl_3$) δ: 2.19(3H, s), 2.50(3H, s), 4.21(1H, dd), 4.42–4.60(1H, m), 4.92(1H, d), 4.92–5.10(1H, m), 5.43(1H, d), 6.34(1H, d), 6.74–6.85(2H, m), 6.90–7.08(4H, m), 7.10–7.45(11H, m), 7.79(1H, d)

MS(FAB)m/z: 547($MH^+$)

Example 23

Preparation of 1-[1-(2-toluoylmethyl)-2-oxo-5-benzoyl-1,3,4,5-tetrahydro-2H-1,5-benzodiazepin-3-yl]-3-(3-methylsulfonylaminocarbonylphenyl)urea Step 1

Preparation of 1-(2-toluoylmethyl)-2-oxo-3-amino-5-benzoyl-1,3,4,5-tetrahydro-2H-1,5-benzodiazepine Step 2 of Example 10 was repeated except that 1-(2-toluoylmethyl)-2-oxo-3-tert-butoxycarbonylamino-5-benzoyl-1,3,4,5-tetrahydro-2H-1,5-benzodiazepine that obtained from Step 2 of Example 22 was used instead of 1-tert-butylcarbonylmethyl-2-oxo-3-tert-butoxycarbonylamino-5-pivaloyl-1,3,4,5-tetrahydro-2H-1,5-benzodiazepine, to thereby obtain the title compound.

Step 2

Preparation of 1-[1-(2-toluoylmethyl)-2-oxo-5-benzoyl-1,3,4,5-tetrahydro-2H-1,5-benzodiazepin-3-yl]-3-(3-methylsulfonylaminocarbonylphenyl)urea Step 3 of Example 15 was repeated except that 1-(2-toluoylmethyl)-2-oxo-3-amino-5-benzoyl-1,3,4,5-tetrahydro-2H-1,5-benzodiazepine was used instead of 1-(N-phenyl-N-methyl)carbamoylmethyl-2-oxo-3-amino-5-phenyl-1,3,4,5-tetrahydro-2H-1,5-benzodiazepine, to thereby obtain the title compound.

$^1$H-NMR(DMSO-$d_6$) δ: 2.45(3H, s), 2.92(3H, m), 3.85–4.05(1H, m), 4.20–4.40(1H, m), 4.65–4.72(1H, m), 5.20(1H, d), 5.53(1H, d), 6.75(1H, d), 6.85– 7.58(16H, m), 7.83(1H, s), 8.03(1H, d), 8.93(1H, s)

MS(FAB)m/z: 654($MH^+$)

Example 24

Preparation of 1-[1-(2-toluoylmethyl)-2-oxo-5-benzyl-1,3,4,5-tetrahydro-2H-1,5-benzodiazepin-3-yl]-3-(3-methylphenyl)urea Step 1

Preparation of 2-oxo-3-tert-butoxycarbonylamino-5-benzyl-1,3,4,5-tetrahydro-2H-1,5-benzodiazepine 2-Oxo-3-tert-butoxycarbonylamino-1,3,4,5-tetrahydro-2H-1,5-benzodiazepine (832 mg) was dissolved in methanol (20 ml), sodium bicarbonate (445 mg) and benzyl bromide (906 mg) were added, the mixture was stirred overnight. The reaction mixture was concentrated under reduced pressure, the residue, after addition of water, was extracted with chloroform. The organic layer was dried over anhydrous sodium sulfate, the solvent was concentrated under reduced pressure, the crystals were washed with isopropyl ether, to thereby obtain 980 mg of the titled compound (Yield: 86.9%).

$^1$H-NMR($CDCl_3$) δ: 1.37(9H, s), 3.21(1H, t), 3.45–3.52 (1H, m), 4.09(1H, d), 4.44(1H, d), 4.45–4.58(1H, m), 5.44 (1H, brd), 6.98–7.31(9H, m), 7.68(1H, s)

Step 2

Preparation of 1-(2-toluoylmethyl)-2-oxo-3-tert-butoxycarbonylamino-5-benzyl-1,3,4,5-tetrahydro-2H-1,5-benzodiazepine Step 2 of Example 1 was repeated except that 2-oxo-3-tert-butoxycarbonylamino-5-benzyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.37(9H, s), 2.54(3H, s), 3.21(1H, t), 3.43(1H, t), 4.05(1H, d), 4.40(1H, d), 4.49–4.54(1H, m), 4.71(1H, d), 5.44(1H, d), 5.48(1H, brs), 7.03–7.43(12H, m), 7.74(1H, d)

Step 3

Preparation of 1-[1-(2-toluoylmethyl)-2-oxo-5-benzyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-benzyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 169–172° C.

$^1$H-NMR($CDCl_3$) δ: 2.22(3H, s), 2.48(3H, s), 3.18(1H, dd), 3.50(1H, dd), 4.02(1H, d), 4.38(1H, d), 4.73–4.90(2H, m), 5.37(1H, d), 6.06(1H, d), 6.75–7.40(17H, m), 7.66(1H, d)

MS(FAB)m/z: 533($MH^+$)

Example 25

Preparation of 1-[1-(2-toluoylmethyl)-2-oxo-5-benzyl-1,3,4,5-tetrahydro-2H-1,5-benzodiazepin-3-yl]-3-(3-methylsulfonylaminocarbonylphenyl)urea Step 1

Preparation of 1-(2-toluoylmethyl)-2-oxo-3-amino-5-benzyl-1,3,4,5-tetrahydro-2H-1,5-benzodiazepine Step 2 of Example 10 was repeated except that 1-(2-toluoylmethyl)-2-oxo-3-tert-butoxycarbonylamino-5-benzyl-1,3,4,5-tetrahydro-2H-1,5-benzodiazepine that obtained from Step 2 of Example 24 was used instead of 1-tert-butylcarbonylmethyl-2-oxo-3-tert-butoxycarbonylamino-5-pivaloyl-1,3,4,5-tetrahydro-2H-1,5-benzodiazepine, to thereby obtain the title compound.

Step 2

Preparation of 1-[1-(2-toluoylmethyl)-2-oxo-3-amino-5-benzyl-1,3,4,5-tetrahydro-2H-1,5-benzodiazepin-3-yl]-3-(3-methylsulfonylaminocarbonylphenyl)urea Step 3 of Example 15 was repeated except that 1-(2-toluoylmethyl)-2-oxo-3-amino-5-benzyl-1,3,4,5-tetrahydro-2H-1,5-benzodiazepine was used instead of 1-(N-phenyl-N-methyl)carbamoylmethyl-2-oxo-3-amino-5-phenyl-1,3,4,5-tetrahydro-2H-1,5-benzodiazepine, to thereby obtain the title compound.

$^1$H-NMR(DMSO-$d_6$) δ: 2.45(3H, s), 3.03(3H, s), 3.07–3.15(1H, m), 3.30–3.36(1H, m), 4.16(1H, d), 4.39(1H, d), 4.44–4.59(1H, m), 4.99(1H, d), 5.39(1H, d), 6.56(1H, d), 7.14–7.51(16H, m), 7.78(1H, s), 7.92(1H, d), 8.78(1H, s)

MS(FAB)m/z: 640($MH^+$)

Example 26

Preparation of 1-[1-(2-toluoylmethyl)-2-oxo-5-(N-cyclohexylcarbamoyl)-1,3,4,5-tetrahydro-2H-1,5-benzodiazepin-3-yl]-3-(3-methylphenyl)urea Step 1

Preparation of 2-oxo-3-tert-butoxycarbonylamino-5-(N-cyclohexylcarbamoyl)-1,3,4,5-tetrahydro-2H-1,5-benzodiazepine Cyclohexyl isocyanate (363 mg) was added to a solution of 2-oxo-3-tert-butoxycarbonylamino-1,3,4,5-tetrahydro-2H-1,5-benzodiazepine (800 mg) in tetrahydrofuran (50 ml), the mixture was refluxed for 2 days. The reaction mixture was concentrated under reduced pressure, the residue was purified by silica gel column chromatography (n-hexane:ethyl acetate=1:1), to thereby obtain 790 mg of the title compound (Yield: 68%).

$^1$H-NMR($CDCl_3$) δ: 0.80–2.02(19H, m), 3.51–3.73(1H, m), 3.80–4.07(2H, m), 4.33–4.55(2H, m), 5.43(1H, brd), 7.15–7.37(4H, m), 7.90(1H, s)

Step 2

Preparation of 1-(2-toluoylmethyl)-2-oxo-3-tert-butoxycarbonylamino-5-(N-cyclohexylcarbamoyl)-1,3,4,5-tetrahydro-2H-1,5-benzodiazepine Step 2 of Example 1 was repeated except that 2-oxo-3-tert-butoxycarbonylamino-5-(N-cyclohexylcarbamoyl)-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 0.95–1.76(17H, m ), 1.81–1.99(2H, m), 2.42(3H, s), 3.57–3.77(1H, m), 3.90(1H, dd), 4.27(1H, t), 4.49–4.61(1H, m), 4.65(1H, d), 5.02(1H, d), 5.39–5.49 (2H, m), 7.20–7.44(7H, m), 7.75(1H, d)

Step 3

Preparation of 1-[1-(2-toluoylmethyl)-2-oxo-5-(N-cyclohexylcarbamoyl)-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-(N-cyclohexylcarbamoyl)-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 117–119° C.

$^1$H-NMR($CDCl_3$) δ: 0.96–1.67(8H, m), 1.82–1.96(2H, m), 2.27(3H, s), 2.37(3H, s), 3.60–3.75(1H, m), 3.94(1H, dd), 4.36(1H, t), 4.80–4.90(2H, m), 4.96(1H, d), 5.54(1H, d), 6.27(1H, d), 6.81(1H, brs), 7.04–7.44(10H, m), 7.64(1H, s), 7.69(1H, d)

MS(FAB)m/z: 568($MH^+$)

Example 27

Preparation of 1-[1-(2-toluoylmethyl)-2-oxo-5-(N,N-dimethylcarbamoyl)-1,3,4,5-tetrahydro-2H-1,5-benzodiazepin-3-yl]-3-(3-methylphenyl)urea Step 1

Preparation of 2-oxo-3-tert-butoxycarbonylamino-5-(N,N-dimethylcarbamoyl)-1,3,4,5-tetrahydro-2H-1,5-benzodiazepine Step 1 of Example 1 was repeated except that N,N-dimethylcarbamoyl chloride was used instead of pivaloyl chloride, to thereby obtain the title compound.

$^1$H-NMR($CDCl_3$) δ: 1.41(9H, s), 2.52(6H, s), 3.69(1H, t), 4.17(1H, dd), 4.47–4.58(1H, m), 5.38(1H, d), 7.08–7.13(2H, m), 7.22–7.29(2H, m), 7.90(1H, s)

Step 2

Preparation of 1-(2-toluoylmethyl)-2-oxo-3-tert-butoxycarbonylamino-5-(N,N-dimethylcarbamoyl)-1,3,4,5-tetrahydro-2H-1,5-benzodiazepine Step 2 of Example 1 was repeated except that 2-oxo-3-tert-butoxycarbonylamino-5-(N,N-dimethyl)carbamoyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.40(9H, s), 2.54(3H, s), 2.59(6H, s), 3.62–3.71(1H, m), 4.17–4.24(1H, m), 4.55–4.66(2H, m), 5.38–5.48(2H, m), 7.08–7.46(7H, m), 7.75(1H, d)

Step 3

Preparation of 1-[1-(2-toluoylmethyl)-2-oxo-5-(N,N-dimethylcarbamoyl)-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-(N,N-dimethylcarbamoyl)-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 199–201° C.

$^1$H-NMR($CDCl_3$) δ: 2.21(3H, s), 2.50(3H, s), 2.61(6H, s), 3.79(1H, t), 4.19(1H, dd), 4.68(1H, d), 4.88–4.96(1H, m), 5.43(1H, d), 6.24(1H, d), 6.71–7.76(13H, m)

MS(FAB)m/z: 514($MH^+$)

Example 28

Preparation of 1-[1-(2-toluoylmethyl)-2-oxo-5-cyclopentylcarbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-cyclopentylcarbonyl-1,3,4,5-tetrahydro-2H-1,5-benzodiazepine Step 1 of Example 1 was repeated except that cyclopentylcarbonyl chloride was used instead of pivaloyl chloride, to thereby obtain the title compound.

$^1$H-NMR($CDCl_3$) δ: 1.24–1.47(11H, m), 1.53–1.78(5H, m), 1.82–1.97(1H, m), 2.32–2.43(1H, m), 3.80–3.87(1H, m), 4.50–4.66(2H, m), 5.42(1H, brd), 7.14–7.41(4H, m), 7.72(1H, s)

Step 2

Preparation of 1-(2-toluoylmethyl)-2-oxo-3-tert-butoxycarbonylamino-5-cyclopentylcarbonyl-1,3,4,5-tetrahydro-2H-1,5-benzodiazepine Step 2 of Example 1 was repeated except that 2-oxo-3-tert-butoxycarbonylamino-5-cyclopentylcarbonyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.26–1.98(17H, m), 2.44–2.59(4H, m), 3.77–3.92(1H, m), 4.55–4.66(2H, m), 4.87(1H, d), 5.24 (1H, d), 5.50(1H, d), 7.22–7.45(7H, m), 7.74(1H, d)

Step 3

Preparation of 1-[1-(2-toluoylmethyl)-2-oxo-5-cyclopentylcarbonyl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5- cyclopentylcarbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 186–188° C.

$^1$H-NMR($CDCl_3$) δ: 1.28–1.56(2H, m), 1.58–2.94(6H, m), 2.26(3H, s), 2.44(3H, s), 2.54(1H, t), 3.88(1H, dd), 4.63(1H, t), 4.84–4.95(1H, m), 4.96(1H, d), 5.18(1H, d), 6.19(1H, d), 6.81(1H, d), 7.02–7.48(11H, m), 7.68(1H, d)

MS(FAB)m/z: 539($MH^+$)

Example 29

Preparation of 1-[1-(2-toluoylmethyl)-2-oxo-5-isobutyryl-1,3,4,5-tetrahydro-2H-1,5-benzodiazepin-3-yl]-3-(3-methylphenyl)urea Step 1

Preparation of 2-oxo-3-tert-butoxycarbonylamino-5-isobutyryl-1,3,4,5-tetrahydro-2H-1,5-benzodiazepine Step 1 of Example 1 was repeated except that isobutyryl chloride was used instead of pivaloyl chloride, to thereby obtain the title compound.

$^1$H-NMR($CDCl_3$) δ: 0.87(3H, d), 1.08(3H, d), 1.41(9H, s), 2.32(1H, q), 3.78–3.87(1H, m), 4.47–4.70(2H, m), 5.43 (1H, d), 7.13–7.45(4H, m), 7.62(1H, s)

Step 2

Preparation of 1-(2-toluoylmethyl)-2-oxo-3-tert-butoxycarbonylamino-5-isobutyryl-1,3,4,5-tetrahydro-2H-1,5-benzodiazepine Step 2 of Example 1 was repeated except that 2-oxo-3-tert-butoxycarbonylamino-5-isobutyryl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 0.99(3H, d), 1.13(3H, d), 2.46(1H, q), 2.52(3H, s), 3.86(1H, dd), 4.26–4.64(2H, m), 4.74(1H, d), 5.35(1H, d), 5.51(1H, d), 7.23–7.49(7H, m), 7.74(1H, d)

Step 3

Preparation of 1-[1-(2-toluoylmethyl)-2-oxo-5-isobutyryl-1,3,4,5-tetrahydro-2H-1,5-benzodiazepin-3-yl]-3-(3-methylphenyl)urea Step 3 of Example 1 was repeated except that 1-(2-toluoylmethyl)-2-oxo-3-tert-butoxycarbonylamino-5-isobutyryl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 174.5–175.5° C.

$^1$H-NMR($CDCl_3$) δ: 1.03(3H, d), 1.15(3H, d), 2.26(3H, s), 2.42–2.54(4H, m), 3.90(1H, dd), 4.63(1H, dd), 4.79(1H, d), 4.81–4.95(1H, m), 5.31(1H, d), 6.14(1H, d), 6.82(1H, d), 7.00–7.45(11H, m), 7.67(1H, d)

MS(FAB)m/z: 513($MH^+$)

Example 30

Preparation of 3-[3-[1-[N-phenyl-N-(2-hydroxyethyl) carbamoylmethyl]-2-oxo-5-pivaloyl-1,3,4,5-tetrahydro-2H-1,5-benzodiazepin-3-yl]ureido]benzoic acid Step 1

Preparation of 1-[N-phenyl-N-(2-benzyloxyethyl) carbamoylmethyl]-2-oxo-3-tert-butoxycarbonylamino-5-pivaloyl-1,3,4,5-tetrahydro-2H-1,5-benzodiazepine Step 2 of Example 1 was repeated except that 2-bromo-[N-phenyl-N-(2-benzyloxyethyl)acetamide was used instead of 2-bromo-2'-methylacetophenone, to thereby obtain the title compound.

$^1$H-NMR($CDCl_3$) δ: 0.89(9H, s), 1.39(9H, s), 3.53–3.97 (5H, m), 4.09–4.31(2H, m), 4.42–4.70(4H, m), 5.54(1H, d), 7.14–7.49(14H, m)

Step 2

Preparation of 1-[1-[N-phenyl-N-(2-benzyloxyethyl) carbamoylmethyl]-2-oxo-5-pivaloyl-1,3,4,5-tetrahydro-2H-1,5-benzodiazepin-3-yl]-3-(3-ethoxycarbonylphenyl)urea Step 2 of Example 10 was repeated except that 1-[N-phenyl-N-(2-benzyloxyethyl)carbamoylmethyl]-2-oxo-3-tert-butoxycarbonylamino-5-pivaloyl-1,3,4,5-tetrahydro-2H-1,5-benzodiazepine was used instead of 1-tert-butylcarbonylmethyl-2-oxo-3-tert-butoxycarbonylamino-5-pivaloyl-1,3,4,5-tetrahydro-2H-1,5-benzodiazepine. Subsequently, in a similar manner to Step 3 of Example 10, to thereby obtain the title compound.

$^1$H-NMR($CDCl_3$) δ: 0.92(9H, s), 1.33(3H, t), 3.50–3.77 (4H, m), 3.9(11H, dd), 4.16–4.48(6H, m), 4.68–4.87(2H, m), 6.41(1H, d), 7.16–7.60(18H, m), 7.95(1H, s)

Step 3

Preparation of 3-[3-[1-[N-phenyl-N-(2-benzyloxyethyl) carbamoylmethyl]-2-oxo-5-pivaloyl-1,3,4,5-tetrahydro-2H-1,5-benzodiazepin-3-yl]ureido]benzoic acid 1-[1-[N-Phenyl-N-(2-benzyloxyethyl)carbamoylmethyl]-2-oxo-5-pivaloyl-1,3,4,5-tetrahydro-2H-1,5-benzodiazepin-3-yl]-3-(3-ethoxycarbonylphenyl)urea (1.01 g) was dissolved in methanol (30 ml), lithium hydroxide (294 mg) in water (30 ml) was added, the mixture was stirred at room temperature overnight. The reaction mixture was concentrated under reduced pressure, acidified with 1N hydrochloric acid, and crystals so precipitated were collected by filtration, to thereby obtain 770 mg of the title compound (Yield: 79%).

$^1$H-NMR($CDCl_3$) δ: 0.94(9H, s), 3.64–3.72(3H, m), 3.83–3.92(1H, m), 4.06–4.20(2H, m), 4.34(1H, t), 4.45–4.72(4H, m), 7.22–7.73(18H, m), 8.21(1H, s), 8.33(1H, d), 10.50(1H, brs)

Step 4

Preparation of 3-[3-[1-[N-phenyl-N-(2-hydroxyethyl) carbamoylmethyl]-2-oxo-5-pivaloyl-1,3,4,5-tetrahydro-2H-1,5-benzodiazepin-3-yl]ureido]benzoic acid 3-[3-[1-[N-Phenyl-N-(2-benzyloxyethyl) carbamoylmethyl]-2-oxo-5-pivaloyl-1,3,4,5-tetrahydro-2H-1,5-benzodiazepin-3-yl]ureido]benzoic acid (770 mg) was dissolved in ethanol (50 ml), 10% Palladium carbon (100 mg) was added, under hydrogen atmosphere the mixture was stirred at 50° C. for 2 hours. The reaction mixture was filtrated, the filtrate was evaporated under reduced pressure, to thereby obtain 580 mg of the title compound (Yield: 87%).

$^1$H-NMR($CDCl_3$) δ: 0.95(9H, s), 3.71–4.12(7H, m), 4.30–4.79(3H, m), 7.03(1H, d), 7.21–7.75(13H, m), 8.10 (2H, brs)

MS(FAB)m/z: 602($MH^+$)

Example 31

Preparation of 3-[3-[1-[N-(1-methylpiperidin-4-yl) carbamoylmethyl]-2-oxo-5-pivaloyl-1,3,4,5-tetrahydro-2H-1,5-benzodiazepin-3-yl]ureido]benzoic acid hydrochloride Step 1

Preparation of 1-[N-(1-benzylpiperidin-4-yl) carbamoylmethyl]-2-oxo-3-tert-butoxycarbonylamino-5-pivaloyl-1,3,4,5-tetrahydro-2H-1,5-benzodiazepine Step 2 of Example 1 was repeated except that 2-bromo-N-(1-benzylpiperidin-4-yl)acetamide was used instead of 2-bromo-2'-methylacetophenone, to thereby obtain the title compound.

$^1$H-NMR($CDCl_3$) δ: 0.97(9H, s), 1.42(9H, s), 1.44–1.59 (2H, m), 1.91–1.97(2H, m), 2.05–2.19(2H, m) 2.74–2.83 (2H, m), 3.48(2H, s), 3.76(1H, d), 3.77–3.89(2H, m), 4.25–4.46(2H, m), 4.92(1H, d), 5.35(1H, d), 6.35(1H, d), 7.18–7.49(9H, m)

Step 2

Preparation of 1-[N-(piperidin-4-yl)carbamoylmethyl]-2-oxo-3-tert-butoxycarbonylamino-5-pivaloyl-1,3,4,5-tetrahydro-2H-1,5-benzodiazepine Ammonium formate (1.92 g) and 10% palladium carbon (300 mg) was added to a solution of 1-[N-(1-benzylpiperidin-4-yl)carbamoylmethyl]-2-oxo-3-tert-butoxycarbonylamino-5-pivaloyl-1,3,4,5-tetrahydro-2H-1,5-benzodiazepine (2.0 g) in etanol (100 ml), the mixture was refluxed for 5 hours. The reaction mixture was filtrated, the filtrate was concentrated under reduced pressure, and the residue was purified by silica gel column chromatography (chloroform:methanol=30:1), to thereby obtain 1.1 g of the title compound (Yield: 62%).

$^1$H-NMR($CDCl_3$) δ: 0.98(9H, s), 1.31–1.44(11H, m), 1.59(1H, brs), 1.86–2.00(2H, m), 2.63–2.74(2H, m), 3.01–3.12(2H, m), 3.76–3.93(3H, m), 4.32(1H, t), 4.39–4.73 (11H, m), 4.91(1H, d), 5.42(1H, d), 6.37(1H, d), 7.21–7.35 (2H, m), 7.42–7.52(2H, m)

Step 3

Preparation of 1-[N-(1-methylpiperidin-4-yl) carbamoylmethyl]-2-oxo-3-tert-butoxycarbonylamino-5-pivaloyl-1,3,4,5-tetrahydro-2H-1,5-benzodiazepine 1-N-(Piperidin-4-yl)carbamoylmethyl]-2-oxo-3-tert-butoxycarbonylamino-5-pivaloyl-1,3,4,5-tetrahydro-2H-1,5-benzodiazepine (1.0 g) was dissolved in the mixed solvent (100 ml) of acetonitrile and methanol (1:1), 37% formalin (2ml) and sodium cyanoborohydride (377 mg) was added, and acetic acid (1 ml) was added thereto dropwise, the mixture was stirred at 50° C. for one hour. After the reaction mixture was concentrated under reduced pressure, water was added to the residue, and extracted with chloroform. The organic layer was washed with saturated aqueous sodium bicarbonate, dried over anhydrous sodium sulfate, and purified by silica gel column chromatography (chloroform), to thereby obtain 640 mg of the title compound (Yield: 52%).

$^1$H-NMR($CDCl_3$) δ: 0.98(9H, s), 1.41(9H, s), 1.43–1.58 (2H, m), 1.84–1.97(2H, m), 2.03–2.16(2H, m), 2.26(3H, s), 2.66–2.78(2H, m), 3.78(1H, d), 3.79–3.88(2H, m), 4.30(1H, t), 4.38–4.57(1H, m), 4.89(1H, d), 5.41(1H, d), 6.32(1H, d), 7.19–7.35(2H, m), 7.41–7.55(2H, m)

Step 4

Preparation of 1-[1-[N-(1-methylpiperidin-4-yl) carbamoylmethyl]-2-oxo-3-amino-5-pivaloyl-1,3,4,5-tetrahydro-2H-1,5-benzodiazepin-3-yl]-3-(3-benzyloxycarbonylphenyl)urea hydrochloride Step 2 of Example 10 was repeated except that 1-[N-(1-methylpiperidin-4-yl)carbamoylmethyl]-2-oxo-3-tert-butoxycarbonylamino-5-pivaloyl-1,3,4,5-tetrahydro-2H-1,5-benzodiazepine was used instead of 1-tert butylcarbonylmethyl-2-oxo-3-tert-butoxycarbonylamino-5-pivaloyl-1,3,4,5-tetrahydro-2H-1,5-benzodiazepine, to thereby obtain 1-[N-(1-methylpiperidin-4-yl) carbamoylmethyl]-2-oxo-3-amino-5-pivaloyl-1,3,4,5-tetrahydro-2H-1,5-benzodiazepine.

Diphenylphosphoryl azide (391 mg) and triethylamine (152 mg) were added to a solution of isophthalic acid monobenzylester (364 mg) in dioxane (50 ml), the mixture was stirred at 80° C. until bubbling was finished. After the reaction mixture was allowed to cool, a solution of 1-[N-(1-methylpiperidin-4-yl)carbamoylmethyl]-2-oxo-3-amino-5-pivaloyl-1,3,4,5-tetrahydro-2H-1,5-benzodiazepine (490 mg) in dioxane (10 ml) was added and then stirred at room temperature for 30 minutes. The resultant mixture was concentrated under reduced pressure, methylene chloride was added to the residue, and washed with saturated aqueous sodium bicarbonate and saturated brine. After dried over anhydrous sodiun sulfate, the solvent was evaporated under reduced pressure, the residue was purified by silica gel column chromatography (chloroform:methanol=5:1), and 4N HCl-dioxane was added to the residue in a manner known per se in the art, to thereby obtain 300 mg of the title compound.

$^1$H-NMR($CDCl_3$) δ: 1.01(9H, s), 1.45–2.19(6H, m), 2.26 (3H, s), 2.73–2.85(2H, m), 3.75–3.90(2H, m), 3.93(1H, dd), 4.39(1H, t), 4.68–4.75(1H, m), 5.07(1H, d), 5.33(2H, s), 6.28(1H, d), 7.07(1H, d), 7.24–7.95(13H, m), 8.31(1H, s)

Step 5

Preparation of 3-[3-[1-[N-(1-methylpiperidin-4-yl) carbamoylmethyl]-2-oxo-5-pivaloyl-1,3,4,5-tetrahydro-2H-1,5-benzodiazepin-3-yl]ureido]benzoic acid hydrochloride 10% Palladium carbon (100 mg) was added to a solution of 1-[1-[N-(1-methylpiperidin-4-yl)carbamoylmethyl]-2-oxo-5-pivaloyl-1,3,4,5-tetrahydro-2H-1,5-benzodiazepin-3-yl]-3-(3-benzyloxycarbonylphenyl)urea hydrochloride (300 mg) in ethanol (50 ml), under hydrogen atmosphere the mixture was stirred at 50° C. for one hour. The reaction mixture was filtrated, the filtrate was evaporated under reduced pressure. Ethanol was added to the residue, crystals so precipitated were collected by filtration, to thereby obtain the title compound (Yield: 92%).

$^1$H-NMR(DMSO-$d_6$) δ: 0.92(9H, s), 1.65–2.05(4H, m), 2.70(3H, s), 2.91–3.52(4H, m), 3.66(1H, dd), 3.73–4.03(2H, m), 4.22(1H, t), 4.35–4.49(1H, m), 4.67(1H, d), 6.73(1H, d), 7.27–7.61(7H, m), 7.99(1H, t), 8.34(1H, d), 9.16(1H, s), 10.40(1H, brs), 12.50(1H, brs)

MS(FAB)m/z: 579($MH^+$)

Example 32

Preparation of 1-(1-tert-butylcarbonylmethyl-2-oxo-5-pivaloyl-1,3,4,5-tetrahydro-2H-1,5-benzodiazepin-3-yl)-3-(3-methylphenyl)urea Step 3 of Example 1 was repeated except that 1-tert-butylcarbonylmethyl-2-oxo-3-tert-butoxycarbonylamino-5-pivaloyl-1,3,4,5-tetrahydro-2H-1,5 -benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 252–255° C. (decomposition)

$^1$H-NMR($CDCl_3$) δ: 1.03(9H, s), 1.26(9H, s), 2.24(3H, s), 3.95(1H, dd), 4.31(1H, t), 4.08(1H, d), 4.70–4.87(1H, m), 5.27(1H, d), 6.10(1H, d), 6.73–6.82(2H, m), 6.92–7.18(4H, m), 7.22–7.48(3H, m)

MS(FAB)m/z: 493$(MH)^+$

Example 33

Preparation of 3-[3-(1-tert-butylcarbonylmethyl-2-oxo-5-phenyl-1,3,4,5-tetrahydro-2H-1,5-benzodiazepin-3-yl)] ureido]phenylthioacetic acid Step 1

Preparation of 1-tert-butylcarbonylmethyl-2-oxo-3-amino-5-phenyl-1,3,4,5-tetrahydro-2H-1,5-benzodiazepine Step 1 of Example 15 was repeated except that bromomethyl-tert-butylketone was used instead of 2-bromo-N-methyl-N-phenylacetamide, to thereby obtain 1-tert-butylcarbonylmethyl-2-oxo-3-benzyloxycarbonylamino-5-phenyl-1,3,4,5-tetrahydro-2H-1,5-benzodiazepine.

$^1$H-NMR($CDCl_3$) δ: 1.26(9H, s), 3.62(1H, dd), 4.14–4.43 (2H, m), 4.56–4.74(1H, m), 5.07(2H, s), 5.14(1H, d), 5.80–5.95(1H, m), 6.77(2H, d), 6.86(1H, t), 7.06–7.46(11H, m)

In a similar manner to Step 2 of Example 17, the title compound was obtained.

$^1$H-NMR($CDCl_3$) δ: 1.28(9H, s), 1.67(2H, brs), 3.57(1H, dd), 3.77(1H, dd), 3.98(1H, dd), 4.19(1H, d), 5.26(1H, d), 6.77(2H, d), 6.85(1H, t), 7.05–7.30(6H, m)

Step 2

Preparation of 1-(1-tert-butylcarbonylmethyl-2-oxo-5-phenyl-1,3,4,5-tetrahydro-2H-1,5-benzodiazepin-3-yl)-3-(3-ethoxycarbonylmethylthiophenyl)urea Triphosgene (138 mg) was added under ice-cooling to a solution of ethyl 3-aminophenylthioacetate (262 mg) in tetrahydrofuran (50 ml), triethylamine (0.55 ml) was added five times each 0.11 ml over 15 minutes. After the reaction mixture was stirred at room temperature for 5 minutes, a solution of 1-tert-butylcarbonylmethyl-2-oxo-3-amino-5-phenyl-1,3,4,5-tetrahydro-2H-1,5-benzodiazepine (500 mg) in tetrahydrofuran (10 ml) was added thereto, stirred at room temperature for one hour. Water was added to the reaction mixture, extracted with ethyl acetate. The organic layer was washed with saturated brine, dried over anhydrous sodiun sulfate, the residue was purified by silica gel column chromatography (n-hexane:ethyl acetate=2:1), to thereby obtain 330 mg of the title compound.

$^1$H-NMR($CDCl_3$) δ: 1.20(3H, t), 1.24(9H, s), 3.62(2H, s), 3.65–3.76(1H, m), 4.14(2H, q), 4.15–4.21(1H, m), 4.45(1H, d), 4.84–4.95(1H, m), 5.11(1H, d), 6.29(1H, d), 6.76–6.87 (3H, m), 6.96–7.45(11H, m)

Step 3

Preparation of 3-[3-(1-tert-butylcarbonylmethyl-2-oxo-5-phenyl-1,3,4,5-tetrahydro-2H-1,5-benzodiazepin-3-yl) ureido]phenylthioacetic acid A solution of lithium hydroxide monohydrate (104 mg) in water (5 ml) was added to a solution of 1-(1-tert-butylcarbonylmethyl-2-oxo-5-phenyl-1,3,4,5-tetrahydro-2H-1,5-benzodiazepin-3-yl)-3-(3-ethoxycarbonylmethyl-thiophenyl)urea (290 mg) in methanol (10 ml), the mixture was stirred overnight at room temperature. The reaction mixture was concentrated under reduced pressure. Water was added and acidified with 1N hydrochloric acid. Crystals so precipitated were collected by filtration, to thereby obtain 260 mg of the title compound (Yield: 94%).

$^1$H-NMR($CDCl_3$) δ: 1.24(9H, s), 3.62(2H, s), 3.70(1H, dd), 4.16(1H, dd), 4.43(1H, d), 4.85–4.93(1H, m), 5.10(1H, d), 5.50(1H, brs), 6.65(1H, d), 6.75–7.33(13H, m), 7.39(1H, s)

MS(FAB)m/z: 561($MH^+$)

Example 34

Preparation of 3-[3-(1-tert-butylcarbonylmethyl-2-oxo-5-phenyl-1,3,4,5-tetrahydro-2H-1,5-benzodiazepin-3-yl) ureido]phenylsulfinylacetic acid Step 1

Preparation of 1-(1-tert-butylcarbonylmethyl-2-oxo-5-phenyl-1,3,4,5-tetrahydro-2H-1,5-benzodiazepin-3-yl)-3-(3-ethoxycarbonylmethylsulfinylphenyl)urea 1-(1-tert-Butylcarbonylmethyl-2-oxo-5-phenyl-1,3,4,5-tetrahydro-2H-1,5-benzodiazepin-3-yl)-3-(3-ethoxycarbonylmethylthiophenyl)urea (460 mg) obtained from Step 2 of Example 33 was dissolved in methylene chloride (20 ml), m-chloroperbenzoic acid (170mg) was added under ice-cooling, stirred for 30 minutes. The reaction mixture was washed subsequently with saturated aqueous sodium bicarbonate and saturated brine, dried over anhydrous sodiun sulfate, and the residue was purified by silica gel column chromatography (n-hexane:ethyl acetate=1:2), to thereby obtain 320 mg of the title compound (Yield: 68%).

$^1$H-NMR($CDCl_3$) δ: 1.58 and 1.70(3H, each t), 1.25(9H, s), 3.70–3.89(3H, m), 4.10(1H, q), 4.1(1H, q), 4.15–4.23 (1H, m), 4.45(1H, dd), 4.83–4.94(1H, m), 5.16(1H, d), 6.65–6.88(4H, m), 7.13–7.35(8H, m), 7.54–7.59(1H, m), 7.67–7.73(1H, m), 7.90(1H, d)

Step 2

Preparation of 3-[3-(1-tert-butylcarbonylmethyl-2-oxo-5-phenyl-1,3,4,5-tetrahydro-2H-1,5-benzodiazepin-3-yl) ureido]phenylsulfinylacetic acid Step 3 of Example 33 was repeated except that 1-(1-tert-butylcarbonylmethyl-2-oxo-5-phenyl-1,3,4,5-tetrahydro-2H-1,5-benzodiazepin-3-yl)-3-(3-ethoxycarbonylmethyl-sulfinylphenyl)urea was used instead of 1-(1-tert-butylcarbonylmethyl-2-oxo-5-phenyl-1,3,4,5-tetrahydro-2H-1,5-benzodiazepin-3-yl)-3-(3-ethoxycarbonylmethyl-thiophenyl)urea, to thereby obtain the title compound.

$^1$H-NMR(DMSO-d6) δ: 1.17(9H, s), 3.54–3.79(3H, m), 3.96–4.05(1H, m), 4.53–4.63(1H, m), 4.75(1H, d), 5.11(1H, d), 6.77–6.89(4H, m), 7.11–7.49(10H, m), 7.77(1H, s), 9.29 (1H, s)

MS(FAB)m/z: 599($MH^+$)

Example 35

Preparation of 3-[3-(1-tert-butylcarbonylmethyl-2-oxo-5-phenyl-1,3,4,5-tetrahydro-2H-1,5-benzodiazepin-3-yl) ureido]phenoxyacetic acid Step 1

Preparation of 1-(1-tert-butylcarbonylmethyl-2-oxo-5-phenyl-1,3,4,5-tetrahydro-2H-1,5-benzodiazepin-3-yl)-3-(3-ethoxycarbonylmetoxyphenyl)urea Step 2 of Example 33 was repeated except that ethyl 3-aminophenoxyacetate was used instead of ethyl 3-aminophenylthioacetate, to thereby obtain the title compound.

$^1$H-NMR($CDCl_3$) δ: 1.24(9H, s), 1.27(3H, t), 3.67(1H, dd), 4.18–4.23(1H, m), 4.24(2H, q), 4.42(1H, d), 4.55(2H, s), 4.83–4.91(1H, m), 5.12(1H, d), 6.23(1H, d), 6.57(1H, dd), 6.76–6.92(5H, m), 7.03–7.23(8H, m)

Step 2

Preparation of 3-[3-(1-tert-butylcarbonylmethyl-2-oxo-5-phenyl-1,3,4,5-tetrahydro-2H-1,5-benzodiazepin-3-yl) ureido]phenoxyacetic acid Step 3 of Example 33 was repeated except that 1-(1-tert-butylcarbonylmethyl-2-oxo-5-phenyl-1,3,4,5-tetrahydro-2H-1,5-benzodiazepin-3-yl)-3-(3-ethoxycarbonyl-methoxyphenyl)urea was used instead of 1-(1-tert-butylcarbonylmethyl-2-oxo-5-phenyl-1,3,4,5-tetrahydro-2H-1,5-benzodiazepin-3-yl)-3-(3-ethoxycarbonylmethyl-thiophenyl)urea, to thereby obtain title compound.

$^1$H-NMR($CDCl_3$) δ: 1.22(9H, s), 3.67(1H, dd), 4.29(1H, dd), 4.35(1H, d), 4.62(2H, s), 4.85–4.94(1H, m), 5.14(1H, d), 6.45–6.94(6H, m), 7.11–7.24(8H, m), 7.39–7.45(1H, m), 7.57(1H, s)

MS(FAB) m/z: 545($MH^+$)

Example 36

Preparation of 1-(1-tert-butylcarbonylmethyl-2-oxo-5-phenyl-1,3,4,5-tetrahydro-2H-1,5-benzodiazepin-3-yl)-3-(3-methylaminophenyl)urea 3-(N-tert-Butoxycarbonyl-N-methylamino) phenylisocyanate (209 mg) was added to a solution of 1-tert-butylcarbonylmethyl-2-oxo-3-amino-5-phenyl-1,3,4,5-tetrahydro-2H-1,5-benzodiazepin (350 mg) obtained from Step 1 of Example 33 in methylene chloride (10 ml)under ice-cooling, stirred at room temperature for 30 minutes. The reaction mixture was concentrated under reduced pressure, and the residue was recrystallized from the mixed solvent of n-hexane and ethyl acetate, to thereby obtain 1-(1-tert-butylcarbonylmethyl-2-oxo-5-phenyl-1,3,4,5-tetrahydro-2H-1,5-benzodiazepin-3-yl)-3-(3-N-tert-butoxycarbonyl-N-methylaminophenyl)urea.

This compound was dissolved in methylene chloride (10 ml), trifluoroacetic acid (5 ml) was added, and the mixture was stirred at room temperature for 30 minutes. The reaction mixture was concentrated under reduced pressure, saturated aqueous sodium bicarbonate was added to the residue, and extracted with methylene chloride. The organic layer was washed with saturated brine, dried over anhydrous sodiunsulfate, and the residue was recrystallized from ethanol, to thereby obtain 300 mg of the title compound (Yield: 73%).

Melting point: 224–225° C.

$^1$H-NMR($CDCl_3$) δ: 1.22(9H, s), 2.77(3H, s), 3.64(1H, dd), 3.70(1H, brs), 4.25(1H, dd), 4.41(1H, d), 4.83–4.92(1H, m), 5.08(1H, d), 6.20–6.30(2H, m), 6.43–6.49(1H, m), 6.67–7.25(12H, m)

MS(FAB)m/z: 522(M+Na)$^+$

Example 37

Preparation of 3-[3-[1-(2-toluoylmethyl)-2-oxo-5-pivaloyl-1,3,4,5-tetrahydro-2H-1,5-benzodiazepin-3-yl] ureido]benzoic acid Step 2 of Example 10 was repeated except that 1-(2-toluoylmethyl)-2-oxo-3-tert-butoxycarbonylamino-5-pivaloyl-1,3,4,5-tetrahydro-2H-1,5-benzodiazepine obtained from Step 2 of Example 1 was used instead of 1-tert-butylcarbonylmethyl-2-oxo-3-tert-butoxycarbonylamino-5-pivaloyl-1,3,4,5-tetrahydro-2H-1,5-benzodiazepine. In a similar manner to Step 3 of Example 10 and subsequently Step 4 of Example 10, the title compound was obtained.

$^1$H-NMR($CDCl_3$) δ: 1.08(9H, s), 2.55(3H, s), 4.16(1H, dd), 4.44(1H, t), 4.59(1H, d), 4.75–4.87(1H, m), 5.51(1H, d), 7.24–7.59(11H, m), 7.66–7.75(2H, m), 8.16–8.37(2H, m)

MS(FAB)m/z: 557(MH)$^+$

Example 38

Preparation of 1-(1-phenyl-2-oxo-5-isobutyryl-1,3,4,5-tetrahydro-2H-1,5-benzodiazepin-3-yl)-3-(3-methylphenyl) urea Step 1

Preparation of 1-phenyl-2-oxo-3-benzyloxycarbonyl-amino-1,3,4,5-tetrahydro-2H-1,5-benzodiazepine 2-Oxo-3-benzyloxycarbonylamino-1,3,4,5-tetrahydro-2H-1,5-benzodiazepine (1.38 g) was dissolved in N,N-dimethylformamide (20 ml), iodobenzene (1.36 g), copper powder (286 mg), copper iodide (446 mg) and potassium carbonate (622 mg) were added, the mixture was stirred at 150° C. for 2 hours. The insoluble material was removed by filtration, the filtrate was concentrated under reduced pressure, and the residue was purified by silica gel column chromatography (n-hexane:ethyl acetate=2:1), to thereby obtain 1.00 g of the title compound.

$^1$H-NMR($CDCl_3$) δ: 3.43–3.52(2H, m), 3.99–4.10(1H, m), 4.73–4.83(1H, m), 5.08(2H, s), 5.88(1H, d), 6.80–7.39 (14H, m)

Step 2

Preparation of 1-phenyl-2-oxo-3-benzyloxycarbonylamino-5-isobutyryl-1,3,4,5-tetrahydro-2H-1,5-benzodiazepine 1-Phenyl-2-oxo-3-benzyloxycarbonylamino-1,3,4,5-tetrahydro-2H-1,5-benzodiazepine (300 mg) was dissolved in methylene chloride (15 ml), isobutyryl chloride (107 mg), pyridine (79 mg) and 4-(N,N-dimethyl)aminopyridine (1 mg) were added, the mixture was refluxed for 2 hours. The reaction mixture was washed with 1N hydrochloric acid, saturated aqueous sodium bicarbonate and saturated brine, dried over anhydrous sodium sulfate. The residue was purified by silica gel column chromatography (n-hexane:ethyl acetate=2:1), to thereby obtain 300 mg of the title compound (Yield: 85%).

$^1$H-NMR($CDCl_3$) δ: 1.08(3H, d), 1.19(3H, d), 2.57(1H, q), 3.85(1H, dd), 4.55(1H, t), 4.63–4.72(1H, m), 5.08(2H, s), 5.78(1H, d), 6.98–7.42(14H, m)

Step 3

Preparation of 1-(1-phenyl-2-oxo-5-isobutyryl-1,3,4,5-tetrahydro-2H-1,5-benzodiazepin-3-yl)-3-(3-methylphenyl) urea 10% Palladium carbon (30 mg) was added to a solution of 1-phenyl-2-oxo-3-benzyloxycarbonylamino-5-isobutyryl-1,3,4,5-tetrahydro-2H-1,5-benzodiazepine (290 mg) in ethanol (20 ml), under hydrogen atmosphere the mixture was stirred for 2 hours. The reaction mixture was filtrated, the filtrate was concentrated under reduced pressure. The residue was dissolved in tetrahydrofuran (20 ml), m-tolyl isocyanate (85 mg) was added to the solution, and then stirred at room temperature for 30 minutes. The resultant mixture was concentrated under reduced pressure, the residue was purified by silica gel column chromatography (n-hexane:ethyl acetate=1:1), to thereby obtain 150 mg of the title compound (Yield: 52%).

$^1$H-NMR($CDCl_3$) δ: 1.07(3H, d), 1.20(3H, d), 2.28(3H, s), 2.54–2.63(1H, m), 3.88(1H, dd), 4.64(1H, t), 4.95–5.02 (1H, m), 6.06(1H, d), 6.80–7.42(14H, m)

MS(FAB)m/z: 457(MH$^+$)

Example 39

Preparation of 1-(1-phenyl-2-oxo-5-cyclohexylcarbonyl-1,3,4,5-tetrahydro-2H-1,5-benzodiazepin-3-yl)-3-(3-methylphenyl)urea Step 1

Preparation of 1-phenyl-2-oxo-3-benzyloxycarbonylamino-5-cyclohexylcarbonyl-1,3,4,5-tetrahydro-2H-1,5-benzodiazepine Step 2 of Example 38 was repeated except that cyclohexylcarbonyl chloride was used instead of isobutyryl chloride, to thereby obtain the title compound.

$^1$H-NMR($CDCl_3$) δ: 0.95–1.30(2H, m), 1.43–1.88(8H, m), 2.16–2.28(1H, m), 3.83(1H, dd), 4.53(1H, t), 4.60–4.74 (1H, m), 5.08(2H, s), 5.77(1H, d), 7.01–7.41(14H, m)

Step 2

Preparation of 1-(1-phenyl-2-oxo-5-cyclohexylcarbonyl-1,3,4,5-tetrahydro-2H-1,5-benzodiazepin-3-yl)-3-(3-methylphenyl)urea Step 3 of Example 38 was repeated except that 1-phenyl-2-oxo-3-benzyloxycarbonylamino-5-cyclohexylcarbonyl-1,3,4,5-tetrahydro-2H-1,5 -benzodiazepine was used instead of 1-phenyl-2-oxo-3-benzyloxycarbonylamino-5-isobutyryl-1,3,4,5-tetrahydro-2H-1,5-benzodiazepine, to thereby obtain the title compound.

Melting point: 165–168° C.

$^1$H-NMR(DMSO-$d_6$) δ: 0.95–1.95(10H, m), 2.10–2.23 (1H, m), 2.30(3H, s), 3.62(1H, dd), 4.40–4.70(2H, m), 6.72(1H, d), 6.78(1H, d), 7.00–7.60(12H, m), 8.68(1H, s)

MS(FAB)m/z: 497(MH$^+$)

Example 40

Preparation of 1-[1-(N-tert-butylcarbamoylmethyl)-2-oxo-5-phenyl-1,3,4,5-tetrahydro-2H-1,5-benzodiazepin-3-yl]-3-(3-methylsulfonylaminocarbonylphenyl)urea Step 1

Preparation of 1-(N-tert-butylcarbamoylmethyl)-2-oxo-3-amino-5-phenyl-1,3,4,5-tetrahydro-2H-1,5-benzodiazepine Step 1 of Example 15 was repeated except that N-tert-butyl-2-iodoacetamide was used instead of 2-bromo-N-methyl-N-phenylacetamide, subsequently in a similar manner to Step 2 of Example 15, the title compound was obtained.

$^1$H-NMR($CDCl_3$) δ: 1.07(9H, s), 1.67(2H, brs), 3.52–3.75 (2H, m), 3.95(1H, dd), 4.24(1H, d), 4.54(1H, d), 6.16(1H, brs), 6.81(2H, d), 6.90(1H, t), 7.17–7.41(6H, m)

Step 2

Preparation of 1-[1-(N-tert-butylcarbamoylmethyl)-2-oxo-3-amino-5-phenyl-1,3,4,5-tetrahydro-2H-1,5-benzodiazepin-3-yl]-3-(3-methylsulfonylaminocarbonylphenyl)urea Step 3 of Example 15 was repeated except that 1-(N-tert-butylcarbamoylmethyl)-2-oxo-3-amino-5-phenyl-1,3,4,5-tetrahydro-2H-1,5-benzodiazepine was used instead of 1-(N-phenyl-N-methylcarbamoylmethyl)-2-oxo-3-amino-5-phenyl-1,3,4,5-tetrahydro-2H-1,5-benzodiazepine, to thereby obtain the title compound.

$^1$H-NMR(DMSO-$d_6$) δ: 1.20(9H, s), 2.87(3H, s), 3.25–3.66(1H, m), 3.93–4.05(1H, m), 4.19(1H, d), 4.49(1H, d), 4.50–4.65(1H, m), 6.64(1H, d), 6.76–6.88(3H, m), 7.12–7.58(11H, m), 7.78(1H, brs), 8.94(1H, brs)

IR(KBr)cm$^{-1}$:3346, 2969

MS(FAB)m/z: 607(MH)$^+$

Example 41

Preparation of 1-[1-(2,2-diethoxyethyl)-2-oxo-5-phenyl-1,3,4,5-tetrahydro-2H-1,5-benzodiazepin-3-yl]-3-(3-methylsulfonylaminocarbonylphenyl)urea Step 1

Preparation of 1-(2,2-diethoxyethyl)-2-oxo-3-benzyloxycarbonylamino-5-phenyl-1,3,4,5-tetrahydro-2H-1,5-benzodiazepine Under argon atmosphere, 2-oxo-3-benzyloxycarbonylamino-5-phenyl-1,3,4,5-tetrahydro-2H-1,5-benzodiazepine (930 mg) in anhydrous N,N-dimethylformamide (20 ml) was added to a suspension of 60% sodium hydride (192 mg) in anhydrous N,N-dimethylformamide (20 ml), then stirred at room temperature for one hour. After bromoacetaldehyde diethylacetal (946 mg) in anhydrous N,N-dimethylformamide (10 ml) was added to the mixture, the resultant mixture was stirred overnight internal temperature at 70–75° C. Ice-water was added to the reaction mixture, extracted with ethyl acetate. The organic layer was washed with saturated brine, dried over anhydrous sodium sulfate, and the solvent was evaporated under reduced pressure. The residue was purified by silica gel column chromatography (n-hexane:ethyl acetate=3:1), to thereby obtain 468 mg of the title compound as a white solid.

$^1$H-NMR($CDCl_3$) δ: 1.06(3H, t), 1.14(3H, t), 3.40–4.20 (8H, m), 4.47–4.62(1H, m), 4.80(1H, t), 5.08(2H, s), 5.84 (1H, d), 6.74(2H, d), 6.85(1H, t), 7.10–7.40(10H, m), 7.56 (1H, d)

Step 2

Preparation of 1-(2,2-diethoxyethyl)-2-oxo-3-amino-5-phenyl-1,3,4,5-tetrahydro-2H-1,5-benzodiazepine Step 2 of Example 16 was repeated except that 1-(2,2-diethoxyethyl)-2-oxo-3-benzyloxycarbonylamino-5-phenyl-1,3,4,5-tetrahydro-2H-1,5-benzodiazepine was used instead of 1-tert-butoxycarbonylmethyl-2-oxo-3-benzyloxycarbonylamino-5-phenyl-1,3,4,5-tetrahydro-2H-1,5-benzodiazepine, to thereby obtain the title compound.

$^1$H-NMR($CDCl_3$) δ: 1.06(3H, t), 1.16(3H, t), 3.40–4.00 (9H, m), 4.83(1H, t), 6.77(2H, d), 6.84(1H, t), 7.10–7.40 (7H, m), 7.55(1H, d)

Step 3

Preparation of 1-[1-(2,2-diethoxyethyl)-2-oxo-5-phenyl-1,3,4,5 -tetrahydro-2H-1,5-benzodiazepin-3-yl]-3-(3-methylsulfonylaminocarbonylphenyl)urea Step 3 of Example 15 was repeated except that 1-(2,2-diethoxyethyl)-2-oxo-3-amino-5-benzoyl-1,3,4,5-tetrahydro-2H-1,5-benzodiazepine was used instead of 1-(N-phenyl-N-methylcarbamoylmethyl)-2-oxo-3-amino-5-phenyl-1,3,4,5-tetrahydro-2H-1,5-benzodiazepine, to thereby obtain the title compound.

$^1$H-NMR(DMSO-$d_6$) δ: 0.91(3H, t), 0.98(3H, t), 3.00(3H, s), 3.20-3.67(5H, m), 3.80(1H, dd), 3.87–4.00(1H, m), 4.09 (1H, dd), 4.43–4.67(2H, m), 6.65(1H, d), 6.70–6.90(3H, m), 7.10–7.40(7H, m), 7.40–7.73(3H, m), 7.83(1H, brs), 8.98 (1H, brs)

IR(KBr)cm$^{-1}$:3337, 1651

MS(FAB)m/z: 648(M+K)$^+$

Example 42

Preparation of 3-[3-(3-methylsulfonylaminocarbonylphenyl)ureido]-2-oxo-5-phenyl-1,3,4,5-tetrahydro-2H-1,5-benzodiazepin-1-yl acetic acid Trifluoroacetic acid (0.32 ml) was added to a solution of 1-(1-tert-butoxycarbonylmethyl-2-oxo-5-phenyl-1,3,4,5-tetrahydro-2H-1,5-benzodiazepin-3-yl)-3-(3-methylsulfonylaminocarbonylphenyl)urea (400 mg) obtained from example 16 in anhydrous 1,2-dichloroethane (10 ml), the mixture was refluxed for 5 hours. Methylene chloride (30 ml) and saturated aqueous sodium bicarbonate were added to the reaction mixture and separated into organic layer and aqueous layer, the aqueous layer was adjusted to pH 2 with 1N hydrochloric acid, and extracted with ethyl acetate. The extraction was washed with saturated brine and dried over anhydrous sodium sulfate, and the solvent was evaporated under reduced pressure. Isopropyl ether was added to the residue for trituration and filtrated, to thereby obtain 226 mg of the title compound as a yellow solid (Yield: 64.0%).

$^1$H-NMR(DMSO-$d_6$) δ: 3.34(3H, s), 3.55–3.69(1H, m), 3.95–4.08(1H, m), 4.47–4.65(3H, m), 6.73–6.88(4H, m), 7.10–7.62(9H, m), 7.91(1H, br s), 9.13(1H, brs), 12.04(1H, br), 12.83(1H, br)

IR(KBr)cm$^{-1}$:3364, 1654, 1593, 1559

MS(FAB)m/z: 552(MH)$^+$

Example 43

Preparation of 1-[1-(2-toluoylmethyl)-2-oxo-5-phenyl-1,3,4,5-tetrahydro-2H-1,5-benzodiazepin-3-yl]-3-(3-methylphenyl)urea m-Tolyl isocyanate (34 mg) was added to a solution of 1-(2-toluoylmethyl)-2-oxo-3-amino-5-phenyl-1,3,4,5-tetrahydro-2H-1,5 -benzodiazepine (90 mg) obtained from Step 2 of Example 18 in tetrahydrofuran (10 ml), the mixture was stirred for 10 minutes at room temperature. The reaction mixture was concentrated under reduced pressure, the residue was purified by silica gel column chromatography (n-hexane:ethyl acetate=3:1), to thereby obtain 100 mg of the title compound (Yield: 83%).

Melting point: 196.5–197.5° C.

$^1$H-NMR($CDCl_3$) δ: 2.19(3H, s), 2.45(3H, s), 3.68(1H, dd), 4.23(1H, dd), 4.92(1H, d), 4.93–5.02(1H, m), 5.31(1H, d), 6.50(1H, d), 6.721–7.66(18H, m)

MS(FAB)m/z: 519($MH^+$)

Example 44

Preparation of 1-[1-(N-phenyl-N-methylcarbamoylmethyl)-2-oxo-5-methyl-1,3,4,5-tetrahydro-2H-1,5-benzodiazepin-3-yl]-3-(3-methylsulfonylaminocarbonylphenyl)urea Step 1

Preparation of 2-oxo-3-tert-butoxycarbonylamino-5-methyl-1,3,4,5-tetrahydro-2H-1,5-benzodiazepine Methyl iodide (1.4 ml) and sodium bicarbonate (630 mg) were added to a solution of 2-oxo-3-tert-butoxycarbonylamino-1,3,4,5-tetrahydro-2H-1,5-benzodiazepine (832 mg) in methanol (20 ml), the mixture was refluxed for 2 days. The reaction mixture was concentrated under reduced pressure, Water (30 ml) was added to the residue and extracted with methylene chloride. The organic layer was washed with saturated brine, dried over anhydrous sodiun sulfate, and the solvent was evaporated under reduced pressure. The residue was purified by silica gel column chromatography (chloroform:methanol=50:1), to thereby obtain 585 mg of the title compound (Yield: 66.9%) as brown amorphous.

$^1$H-NMR($CDCl_3$) δ: 1.41(9H, s), 2.81(3H, s), 3.29–3.42 (1H, m), 3.59(1H, dd), 4.37–4.50(1H, m), 5.46–5.60(1H, m), 6.90–7.22(4H, m), 7.52(1H, brs)

Step 2

Preparation of 1-(N-phenyl-N-methylcarbamoylmethyl)-2-oxo-3-tert-butoxycarbonylamino-5-methyl-1,3,4,5-tetrahydro-2H-1,5-benzodiazepine 2-Bromo-N-methyl-N-phenylacetamide (602 mg), 1N aqueous sodium hydroxide (10 ml) and tetra n-butylammonium bromide (58 mg) were added to a solution of 2-oxo-3-tert-butoxycarbonylamino-5-methyl-1,3,4,5-tetrahydro-2H-1,5-benzodiazepine (514 g) in toluene (15 ml), the mixture was stirred overnight at room temperature. Water (100 ml) was added to the reaction mixture and extracted with ethyl acetate. The organic layer was washed with saturated brine, dried over anhydrous sodiun sulfate, and the solvent was evaporated under reduced pressure. The residue was purified by silica gel column chromatography (n-hexane:ethyl acetate=1:1), to thereby obtain 553 mg of the title compound (71.6%) as a white solid.

$^1$H-NMR($CDCl_3$) δ: 1.38(9H, s), 2.69(3H, s), 3.22(1H, dd), 3.35(3H, s), 3.49(1H, t), 3.62(1H, d), 4.36–4.49(1H, m), 4.73(1H, d), 5.55–5.66(1H, m), 6.93–7.48(9H, m)

Step 3

Preparation of 1-(N-phenyl-N-methylcarbamoylmethyl)-2-oxo-3-amino-5-methyl-1,3,4,5-tetrahydro-2H-1,5-benzodiazepine 4N-HCl dioxane (5.0 ml) was added to a suspension of 1-(N-phenyl-N-methylcarbamoylmethyl)-2-oxo-3-tert-butoxycarbonylamino-5-methyl-1,3,4,5-tetrahydro-2H-1,5-benzodiazepine (550 mg) in ethanol (25 ml), the mixture was stirred at 50° C. for one hour. The reaction mixture was concentrated under reduced pressure, methylene chloride (50 ml) was added to the residue. The mixture was washed with saturated aqueous sodium bicarbonate, dried over anhydrous sodiun sulfate, and the solvent was evaporated under reduced pressure, to thereby obtain 414 mg of the title compound (Yield: 97.9%) as amorphous.

$^1$H-NMR($CDCl_3$) δ: 1.62(2H, brs), 2.69(3H, s), 3.07–3.30 (2H, m), 3.36(3H, s), 3.46–3.69(2H, m), 4.83(1H, d), 6.96–7.48(9H, m)

Step 4

Preparation of 1-[1-(N-phenyl-N-methylcarbamoylmethyl)-2-oxo-5-methyl-1,3,4,5-tetrahydro-2H-1,5-benzodiazepin-3-yl]-3-(3-methylsulfonylaminocarbonylphenyl)urea Step 3 of Example 15 was repeated except that 1-(N-phenyl-N-methylcarbamoylmethyl)-2-oxo-3-amino-5-methyl-1,3,4,5-tetrahydro-2H-1,5-benzodiazepine was used instead of 1-(N-phenyl-N-methylcarbamoylmethyl)-2-oxo-3-amino-5-phenyl-1,3,4,5-tetrahydro-2H-1,5-benzodiazepine, to thereby obtain the title compound.

$^1$H-NMR(DMSO-$d_6$, 100° C.) δ: 2.69(3H, s), 3.20(1H, dd), 3.24(3H, s), 3.32(1H, dd), 3.85(1H, d), 4.40(1H, ddd), 4.58(1H, d), 6.36(1H, d), 7.03–7.52(14H, m), 7.80(1H, t), 8.68(1H, brs)

IR(KBr)$cm^{-1}$:3368, 1654, 1559, 1541, 1499

MS(FAB)m/z: 579$(MH)^+$

Example 45

Preparation of 1-[1-(2,2-diethoxyethyl)-2-oxo-5-pivaloyl-1,3,4,5-tetrahydro-2H-1,5-benzodiazepin-3-yl]-3-(3-methylphenyl)urea Step 1

Preparation of 2-oxo-3-benzyloxycarbonylamino-5-pivaloyl-1,3,4,5-tetrahydro-2H-1,5-benzodiazepine Step 1 of Example 1 was repeated except that 2-oxo-3-benzyloxycarbonylamino-1,3,4,5-tetrahydro-2H-1,5-benzodiazepine was used instead of 2-oxo-3-tert-butoxycarbonylamino-1,3,4,5-tetrahydro-2H-1,5-benzodiazepine, to thereby obtain the title compound.

$^1$H-NMR($CDCl_3$) δ: 0.97(9H, s), 3.94(1H, dd), 4.38(1H, t), 4.45–4.58(1H, m), 5.07(2H, s), 5.70(1H, d), 7.14(1H, d), 7.24–7.45(8H, m), 7.92(1H, s)

Step 2

Preparation of 1-(2,2-diethoxyethyl)-2-oxo-3-benzyloxycarbonylamino-5-pivaloyl-1,3,4,5-tetrahydro-2H-1,5-benzodiazepine Step 2 of Example 1 was repeated except that 2-oxo-3-benzyloxycarbonylamino-5-pivaloyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, and that bromoacetaldehyde diethylacetal was used instead of 2-bromo-2'-methylacetophenone, to thereby obtain the title compound.

$^1$H-NMR($CDCl_3$) δ: 0.96(9H, s), 1.24(3H, t), 1.25(3H, t), 3.24(1H, dd), 3.50–3.90(5H, m), 4.23–4.32(2H, m), 4.45–4.49(1H, m), 4.96(1H, dd), 5.06(2H, s), 5.68(1H, d), 7.17–7.47(8H, m), 7.91(1H, dd)

Step 3

Preparation of 1-[1-(2,2-diethoxyethyl)-2-oxo-5-pivaloyl-1,3,4,5-tetrahydro-2H-1,5-benzodiazepin-3-yl]-3-(3-methylphenyl)urea Step 3 of Example 38 was repeated except that 1-(2,2-diethoxyethyl)-2-oxo-3-benzyloxycarbonylamino-5-pivaloyl-1,3,4,5-tetrahydro-2H-1,5-benzodiazepine was used instead of 1-phenyl-2-oxo-3-benzyloxycarbonylamino-5-isobutyryl-1,3,4,5-tetrahydro-2H-1,5-benzodiazepine, to thereby obtain the title compound.

Melting point: 167–169° C.

$^1$H-NMR($CDCl_3$) δ: 1.03(9H, s), 1.22(3H, t), 1.25(3H, t), 2.30(3H, s), 3.22(1H, dd), 3.48–3.96(5H, m), 4. 32(1H, t), 442(1H, dd), 4.64– 4.76(1H, m), 4.94(1H, dd), 6.16(1H, d), 6.83(1H, d), 7.06–7.53(7H, m), 7.94(1H, dd)

MS(FAB) m/z: 465(M-$OC_2H^5$)$^+$

Example 46

Preparation of 1-(1-tert-butylcarbonylmethyl-2-oxo-5-phenyl-1,3,4,5-tetrahydro-2H-1,5-benzodiazepin-3-yl)-3-(3-methylsulfonylaminocarbonylphenyl)urea Step 3 of Example 15 was repeated except that 1-tert-butylcarbonylmethyl-2-oxo-3-amino-5-phenyl-1,3,4,5-tetrahydro-2H-1,5-benzodiazepine obtained from Step 1 of Example 33 was used instead of 1-(N-phenyl-N-methylcarbamoylmethyl)-2-oxo-3-amino-5-phenyl-1,3,4,5-tetrahydro-2H-1,5-benzodiazepine, to thereby obtain the title compound.

Melting point: 229–233° C.

$^1$H-NMR(DMSO-$d_6$) δ: 1.17(9H, s), 2.97(3H, s), 3.50–3.66(1H, m), 3.90–4.11(1H, m), 4.50–4.65(1H, m), 4.76(1H, d), 5.12(1H, d), 6.66(1H, d), 6.73–6.88(3H, m), 7.09–7.34(7H, m), 7.42–7.59(2H, m), 7.81(1H, brs), 8.97 (1H, brs), 12.07(1H, br)

MS(FAB)m/z: 592(MH)$^+$

Example 47

Preparation of 1-[1-(2-toluoylmethyl)-2-oxo-5-methylsulfonyl-1,3,4,5-tetrahydro-2H-1,5-benzodiazepin-3-yl]-3-(3-methylphenyl)urea Step 1

Preparation of 2-oxo-3-tert-butoxycarbonylamino-5-methylsulfonyl-1,3,4,5-tetrahydro-2H-1,5-benzodiazepine Step 1 of Example 3 was repeated except that methanesulfonyl chloride was used instead of 1-adamantylcarbonyl chloride, to thereby obtain the title compound.

$^1$H-NMR(DMSO-$d_6$) δ: 1.34(9H, s), 3.02(3H, s), 3.77–3.87(1H, m), 4.07–4.28(2H, m), 7.17(1H, d), 7.21–7.31(2H, m), 7.38–7.48(2H, m), 10.00(1H, brs)

Step 2

Preparation of 1-(2-toluoylmethyl)-2-oxo-3-tert-butoxycarbonylamino-5-methylsulfonyl-1,3,4,5-tetrahydro-2H-1,5-benzodiazepine Step 2 of Example 3 was repeated except that 2-oxo-3-tert-butoxycarbonylamino-5-methylsulfonyl-1,3,4,5-tetrahydro-2H-1,5-benzodiazepine was used instead of 2-oxo-3-tert-butoxycarbonylamino-5-(adamantan-1-yl) carbonyl-1,3,4,5-tetrahydro-2H-1,5-benzodiazepine, to thereby obtain the title compound.

$^1$H-NMR($CDCl_3$) δ: 1.40(9H, s), 2.55(3H, s), 3.03(3H, s), 4.00–4.23(2H, m), 4.53–4.69(2H, m), 5.48(1H, d), 5.59(1H, d), 7.22–7.55(7H, m) ), 7.75(1H, d)

Step 3

Preparation of 1-[1-(2-toluoylmethyl)-2-oxo-5-methylsulfonyl-1,3,4,5-tetrahydro-2H-1,5-benzodiazepin-3-yl]-3-(3-methylphenyl)urea Step 3 of Example 3 was repeated except that 1-(2-toluoylmethyl)-2-oxo-3-tert-butoxycarbonylamino-5-methylsulfonyl-1,3,4,5-tetrahydro-2H-1,5-benzodiazepine was used instead of 1-(2-toluoylmethyl)-2-oxo-3-tert-butoxycarbonylamino-5-(adamantan-1-yl)carbonyl-1,3,4,5-tetrahydro-2H-1,5-benzodiazepine, to thereby obtain the title compound.

Melting point: 209–211° C. (decomposition)

$^1$H-NMR($CDCl_3$) δ: 2.26(3H, s), 2.52(3H, s), 3.06(3H, s), 4.10–4.25(2H, m), 4.62(1H, d), 4.80–4.93(1H, m), 5.49(1H, d), 6.08(1H, d), 6.73–7.74(13H, m)

MS(FAB)m/z: 521(MH)$^+$

Example 48

Preparation of 1-[1-(2-toluoylmethyl)-2-oxo-5-(pyridin-2-yl)carbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-(pyridin-2-yl)carbonyl-1,3,4,5-tetrahydro-2H-1,5-benzodiazepine Step 1 of Example 3 was repeated except that 2-pyridylcarbonyl chloride was used instead of 1-adamantylcarbonyl chloride, to thereby obtain the title compound.

$^1$H-NMR(DMSO-$d_6$) δ: 1.37(9H, s), 3.75(1H, dd), 4.22–4.37(1H, m), 4.59(1H, t), 6.80–6.88(2H, m), 7.08(1H, d), 7.13–7.28 (2H, m), 7.30–7.43(2H, m), 7.71(1H, d), 10.12(1H, brs)

Step 2

Preparation of 1-(2-toluoylmethyl)-2-oxo-3-tert-butoxycarbonylamino-5-(pyridin-2-yl)carbonyl-1,3,4,5-tetrahydro-2H-1,5-benzodiazepine Step 2 of Example 3 was repeated except that 2-oxo-3-tert-butoxycarbonylamino-5-(pyridin-2-yl)carbonyl-1,3,4,5-tetrahydro-2H-1,5-benzodiazepine was used instead of 2-oxo-3-tert-butoxycarbonylamino-5-(adamantan-1-yl) carbonyl-1,3,4,5-tetrahydro-2H-1,5-benzodiazepine, to thereby obtain the title compound.

$^1$H-NMR($CDCl_3$) δ: 1.42(9H, s), 2.59(3H, s), 4.10–4.23 (1H, m), 4.47(1H, t), 4.61(1H, d), 4.69–4.85(1H, m), 5.60–5.74(2H, m), 6.76(1H, d), 6.90–7.00(1H, m), 7.08–7.48(6H, m), 7.58–7.72(2H, m), 7.82(1H, d), 8.14(1H, d)

Step 3

Preparation of 1-[1-(2-toluoylmethyl)-2-oxo-5-(pyridin-2-yl)carbonyl-1,3,4,5-tetrahydro-2H-1,5-benzodiazepin-3-yl]-3-(3-methylphenyl)urea Step 3 of Example 3 was repeated except that 1-(2-toluoylmethyl)-2-oxo-3-tert-butoxycarbonylamino-5-(pyridin-2-yl)carbonyl-1,3,4,5-tetrahydro-2H-1,5-benzodiazepine was used instead of 1-(2-toluoylmethyl)-2-oxo-3-tert-butoxycarbonylamino-5-(adamantan-1-yl) carbonyl-1,3,4,5-tetrahydro-2H-1,5-benzodiazepine, to thereby obtain the title compound.

Melting point: 238–240° C. (decomposition)

$^1$H-NMR($CDCl_3$) δ: 2.26(3H, s), 2.55(3H, s), 4.20(1H, dd), 4.56(1H, t), 4.67(1H, d), 5.65(1H, d), 6.15(1H, d), 6.73–7.87(16H, m), 8.15(1H, d)

MS(FAB)m/z: 548(MH)$^+$

Example 49

Preparation of 1-[1-(2-toluoylmethyl)-2-oxo-5-methoxycarbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-methoxycarbonyl-1,3,4,5-tetrahydro-2H-1,5-benzodiazepine Step 1 of Example 3 was repeated except that methyl chloroformate was used instead of 1-adamantylcarbonyl chloride, to thereby obtain the title compound.

$^1$H-NMR(DMSO-$d_6$) δ: 1.34(9H, s), 3.45–3.75(4H, m), 4.05–4.42(2H, m), 7.12(1H, d), 7.16–7.28(2H, m), 7.30–7.40(2H, m), 9.89(1H, brs)

Step 2

Preparation of 1-(2-toluoylmethyl)-2-oxo-3-tert-butoxycarbonylamino-5-methoxycarbonyl-1,3,4,5-tetrahydro-2H-1,5-benzodiazepine Step 2 of Example 3 was repeated except that 2-oxo-3-tert-butoxycarbonylamino-5-methoxycarbonyl-1,3,4,5-tetrahydro-2H-1,5-benzodiazepine was used instead of 2-oxo-3-tert-butoxycarbonylamino-5-(adamantan-1-yl) carbonyl-1,3,4,5-tetrahydro-2H-1,5-benzodiazepine, to thereby obtain the title compound.

$^1$H-NMR(DMSO-$d_6$) δ: 1.33(9H, s), 2.35(3H, s), 3.50–3.76(4H, m), 4.17–4.53(2H, m), 5.04–5.25( 2H, m), 7.26–7.52(8H, m), 7.80–7.90(1H, m)

Step 3

Preparation of 1-[1-(2-toluoylmethyl)-2-oxo-5-methoxycarbonyl-1,3,4,5-tetrahydro-2H-1,5-benzodiazepin-3-yl]-3-(3-methylphenyl)urea Step 3 of Example 3 was repeated except that 1-(2-toluoylmethyl)-2-oxo-3-tert-butoxycarbonylamino-5-methoxycarbonyl-1,3,4,5-tetrahydro-2H-1,5-benzodiazepine was used instead of 1-(2-toluoylmethyl)-2-oxo-3-tert-butoxycarbonylamino-5-(adamantan-1-yl) carbonyl-1,3,4,5-tetrahydro-2H-1,5-benzodiazepine, to thereby obtain the title compound.

$^1$H-NMR(DMSO-$d_6$, 100° C.) δ: 2.21(3H, s), 2.38(3H, s), 3.61(3H, s), 3.81(1H, dd), 4.12(1H, dd), 4.54(1H, ddd), 5.04(1H, d), 5.14(1H, d), 6.50(1H, d), 6.71(1H, m), 7.00–7.18(3H, m), 7.24–7.48(7H, m), 7.74–7.81(1H, m), 8.48(1H, brs)

MS(FAB)m/z: 501(MH)$^+$

Example 50

Preparation of 1-(1-tert-butoxycarbonylmethyl)-2-oxo-5-cyclohexylcarbonyl-1,3,4,5-tetrahydro-2H-1,5-benzodiazepin-3-yl)-3-(3-methylphenyl)urea Step 1

Preparation of 2-oxo-3-benzyloxycarbonylamino-5-cyclohexylcarbonyl-1,3,4,5-tetrahydro-2H-1,5-benzodiazepine 4N HCl-dioxane (10 ml) was added to a solution of 2-oxo-3-tert-butoxycarbonylamino-5-cyclohexylcarbonyl-1,3,4,5-tetrahydro-2H-1,5-benzodiazepine (1.0 g) obtained from Step 1 of Example 14 in ethanol (30 m1), the mixture was stirred at 50° C. for one hour. The reaction mixture was concentrated under reduced pressure, saturated aqueous sodium bicarbonate was added to the residue and extracted with chloroform. After the organic layer was dried over anhydrous sodiun sulfate, the solvent was evaporated under reduced pressure. The residue was dissolved in tetrahydrofuran (10 ml), a solution of sodium carbonate (274 mg) in water (10 ml) and a solution of benzyl chloroformate (440 mg) in tetrahydrofuran (10 ml) were added, and the mixture was stirred at room temperature for one hour. This solution was extracted with ethyl acetate, washed with saturated brine, dried over anhydrous sodiun sulfate, and the solvent was evaporated under reduced pressure. Isopropyl ether was added to the obtained solid for trituration and filtrated, to thereby obtain 890 mg of the title compound (Yield: 82.0%).

$^1$H-NMR($CDCl_3$) δ: 0.75–2.05(11H, m), 3.80–3.89(1H, m), 4.51–4.67(2H, m), 5.06(2H, s), 5.69(1H, br), 7.14–7.47 (9H, m), 7.75(1H, s)

Step 2

Preparation of 1-tert-butoxycarbonylmethyl-2-oxo-3-benzyloxycarbonylamino-5-cyclohexylcarbonyl-1,3,4,5-tetrahydro-2H-1,5-benzodiazepine Under ice-cooling, 2-oxo-3-benzyloxycarbonylamino-5-cyclohexylcarbonyl-1,3,4,5-tetrahydro-2H-1,5-benzodiazepine (800 mg) was added to a suspension of 60% sodium hydride (152 mg) in tetrahydrofuran (50 ml), the mixture was stirred at room temperature for one hour. Subsequently, tert-butyl bromoacetate (390 mg) was added and stirred at room temperature for one hour. The reaction mixture was concentrated under reduced pressure, Water was added to the residue and extracted with methylene chloride. The organic layer was washed with saturated brine, dried over anhydrous sodiun sulfate, and the mixture was purified by silica gel column chromatography (n-hexane:ethyl acetate=2:1), to thereby obtain 640 mg of the title compound (Yield: 63%).

$^1$H-NMR($CDCl_3$) δ: 0.98(9H, s), 1.50(9H, s), 3.84(1H, d), 3.91(1H, dd), 4.27(1H, t), 4.46–4.56(1H, m), 4.78(1H, d), 5.05(2H, s), 5.74(1H, d), 7.21–7.48(9H, m)

Step 3

Preparation of 1-tert-butoxycarbonylmethyl-2-oxo-3-amino-5-cyclohexylcarbonyl-1,3,4,5-tetrahydro-2H-1,5-benzodiazepine Step 2 of Example 16 was repeated except that 1-tert-butoxycarbonylmethyl-2-oxo-3-benzyloxycarbonylamino-5-cyclohexylcarbonyl-1,3,4,5-tetrahydro-2H-1,5-benzodiazepine was used instead of 1-tert-butoxycarbonylmethyl-2-oxo-3-benzyloxycarbonylamino-5-phenyl-1,3,4,5-tetrahydro-2H-1,5-benzodiazepine, to thereby obtain the title compound.

$^1$H-NMR($CDCl_3$) δ: 0.90–2.20(20H, m), 2.29(3H, s), 3.85(1H, dd), 4.03(1H, d), 4.51(1H, t), 4.71–4.92(2H, m), 6.19(1H, d), 6.82(1H, brs), 7.06–7.55(7H, m), 7.61(1H, s)

Step 4

Preparation of 1-(1-tert-butoxycarbonylmethyl-2-oxo-5-cyclohexylcarbonyl-1,3,4,5-tetrahydro-2H-1,5-benzodiazepin-3-yl)-3-(3-methylphenyl)urea Step 4 of Example 1 was repeated except that 1-tert-butoxycarbonylmethyl-2-oxo-3-amino-5-cyclohexylcarbonyl-1,3,4,5-tetrahydro- 2H-1,5-benzodiazepine was used instead of 1-(2-toluoylmethyl)-2-oxo-3-amino-5-pivaloyl-1,3,4,5-tetrahydro-2H-1,5-benzodiazepine, to thereby obtain the title compound.

Melting point: 143–145° C.

$^1$H-NMR($CDCl_3$) δ: 0.90–2.20(20H, m), 2.29(3H, s), 3.85(1H, dd), 4.03(1H, d), 4.51(1H, t), 4.71–4.92(2H, m), 6.19(1H, d), 6.82(1H, brs), 7.06–7.55(7H, m), 7.61(1H, s)

MS(FAB)m/z: 535(MH$^+$)

Example 51

Preparation of 1-(1-tert-butylcarbonylmethyl)-2-oxo-5-pivaloyl-1,3,4,5-tetrahydro-2H-1,5-benzodiazepin-3-yl)-3-(3-methylsulfonylaminocarbonylphenyl)urea Step 3 of Example 15 was repeated except that 1-tert-butylcarbonylmethyl-2-oxo-3-amino-5-pivaloyl-1,3,4,5-tetrahydro-2H-1,5-benzodiazepine obtained from Step 2 of Example 10 was used instead of 1-(N-phenyl-N-methylcarbamoylmethyl)-2-oxo-3-amino-5-phenyl-1,3,4,5-tetrahydro-2H-1,5-benzodiazepine, to thereby obtain the title compound.

Melting point: 216–220° C. (decomposition)

$^1$H-NMR(DMSO-$d_6$) δ: 0.93(9H, s), 1.20(3H, s), 2.87 (3H, s), 3.68(1H, dd), 4.19(1H, t), 4.41(1H, d), 4.37–4.51 (1H, m), 5.17(1H, d), 6.50–6.62(1H, m), 7.12–7.26(2H, m), 7.36–7.58(6H, m), 7.77(1H, brs), 8.85(1H, brs)

MS(FAB) m/z: 600(MH)$^+$

Example 52

Preparation of 1-[1-(N,N-dimethyl)carbamoylmethyl-2-oxo-5-pivaloyl-1,3,4,5-tetrahydro-2H-1,5-benzodiazepin-3-yl]-3-(3-methylphenyl)urea Step 1

Preparation of 1-(N,N-dimethylcarbamoylmethyl)-2-oxo-3-tert-butoxycarbonylamino-5-pivaloyl-1,3,4,5-tetrahydro-2H-1,5-benzodiazepine Step 2 of Example 1 was repeated except that 2-bromo-N-methyl-N-phenylacetamide was used instead of 2-bromo-2'-methylacetophenone, to thereby obtain the title compound.

$^1$H-NMR($CDCl_3$) δ: 1.01(9H, s), 1.39(9H, s), 3.05(3H, s), 3.10(3H, s), 3.83(1H, d), 3.90–4.03(1H, m), 4.21(1H, t), 4.41–4.56(1H, m), 5.14(1H, d), 5.55(1H, d), 7.17–7.51(4H, m)

Step 2

Preparation of 1-[1-(N,N-dimethylcarbamoylmethyl)-2-oxo-5-pivaloyl-1,3,4,5-tetrahydro-2H-1,5-benzodiazepin-3-yl]-3-(3-methylphenyl)urea Step 3 of Example 1 was repeated except that 1-(N,N-dimethylcarbamoylmethyl)-2-oxo-3-tert-butoxycarbonylamino-5-pivaloyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, the title compound was obtained.

Melting point: 252–254° C.

$^1$H-NMR($CDCl_3$) δ: 1.03(9H, s), 2.23(3H, s), 3.00(3H, s), 3.08(3H, s), 3.90(1H, d), 3.99(1H, dd), 4.35(1H, t), 4.76(1H, ddd), 5.16(1H, d), 6.14(1H, d), 6.77(1H, d), 6.97–7.50(8H, m)

MS(FAB)m/z: 480(MH)$^+$

Example 53

Preparation of 1-[1-(pyrrolidin-1-yl)carbonylmethyl-2-oxo-5-pivaloyl-1,3,4,5-tetrahydro-2H-1,5-benzodiazepin-3-yl]-3-(3-methylphenyl)urea Step 1

Preparation of 1-(pyrrolidin-1-yl)carbonylmethyl-2-oxo-3-tert-butoxycarbonylamino-5-pivaloyl-1,3,4,5-tetrahydro-2H-1,5-benzodiazepine Step 2 of Example 1 was repeated except that 1-bromo acetylpyrrolidine was used instead of 2-bromo-2'-methylacetophenone, to thereby obtain the title compound.

$^1$H-NMR($CDCl_3$) δ: 1.01(9H, s), 1.39(9H, s), 1.82–2.12 (4H, m), 3.36–3.72(4H, m), 3.77(1H, d), 3.89–4.00(1H, m), 4.21(1H, t), 4.40–4.54(1H, m), 5.01(1H, d), 5.47–5.58(1H, m), 7.16–7.45(3H, m), 7.59(1H, d)

Step 2

Preparation of 1-[1-(pyrrolidin-1-yl)carbonylmethyl-2-oxo-5-pivaloyl-1,3,4,5-tetrahydro-2H-1,5-benzodiazepin-3-yl]-3-(3-methylphenyl)urea Step 3 of Example 1 was repeated except that 1-(pyrrolidin-1-yl)carbonylmethyl-2-oxo-3-tert-butoxycarbonylamino-5-pivaloyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, the title compound was obtained.

Melting point: 246–248° C. (decomposition)

$^1$H-NMR($CDCl_3$) δ: 1.03(9H, s), 1.80–2.08(4H, m), 2.24 (3H, s), 3.36–3.70(4H, m), 3.85(1H, d), 3.98(1H, dd), 4.35 (1H, t), 4.76(1H, ddd), 5.03(1H, d), 6.08(1H, d), 6.78(111, m), 6.98–7.61(8H, m)

MS(FAB)m/z: 506(MH)$^+$

Example 54

Preparation of 1-[1-[N-(2-dimethylaminoethyl)-N-methylcarbamoylmethyl]-2-oxo-5-pivaloyl-1,3,4,5-tetrahydro-2H-1,5-benzodiazepin-3-yl]-3-(3-methylphenyl) urea Step 1

Preparation of 1-benzyloxycarbonylmethyl-2-oxo-3-tert-butoxycarbonylamino-5-pivaloyl-1,3,4,5-tetrahydro-2H-1,5-benzodiazepine Step 2 of Example 1 was repeated except that benzyl bromoacetate was used instead of 2-bromo-2'-methylacetophenone, to thereby obtain the title compound.

$^1$H-NMR($CDCl_3$) δ: 0.98(9H, s), 1.40(9H, s), 3.91(1H, dd), 4.02(1H, d), 4.24(1H, t), 4.41–4.56(1H, m), 4.91(1H, d), 5.26(2H, s), 5.48(1H, d), 7.20–7.44(9H, m)

Step 2

Preparation of 2-oxo-3-tert-butoxycarbonylamino-5-pivaloyl-1,3,4,5-tetrahydro-2H-1,5-benzodiazepin-1-yl-acetic acid 10% Palladium carbon (300 mg) was added to a suspension of 1-benzyloxycarbonylmethyl-2-oxo-3-tert-butoxycarbonylamino-5-pivaloyl-1,3,4,5-tetrahydro-2H-1,5-benzodiazepine (3.0 g) in methanol (100 ml), the mixture was stirred for 30 minutes under hydrogen atmosphere. The reaction mixture was filtrated and the filtrate was concentrated under reduced pressure. Isopropyl ether was added to the residue for trituration and filtrated, to thereby obtain 2.46 g of the title compound (Yield: 99.6%) as pale yellow powder.

$^1$H-NMR(DMSO-$d_6$) δ: 0.92(9H, s), 1.34(9H, s), 3.47 (1H, dd), 4.00–4.24(2H, m), 4.38(1H, t), 4.52(1H, d), 7.28 (1H, d), 7.34–7.58(4H, m), 12.0–13.0(1, br)

Step 3

Preparation of 1-[N-(2-dimethylaminoethyl)-N-methylcarbamoylmethyl]-2-6xo-3-tert-butoxycarbonylamino-5-pivaloyl-1,3,4,5-tetrahydro-2H-1,5-benzodiazepine 4-Dimethylaminopyridine (426 mg), 1-ethyl-3-(3-dimethylaminopropyl)carbodiimide hydrochloride (728 mg) and N,N,N'-trimethylethylenediamine (419 mg) was added to a suspension of 2-oxo- 3-tert-butoxycarbonylamino-5-pivaloyl-1,3,4,5-tetrahydro-2H-1,5-benzodiazepin-1-yl-acetic acid (1.01 g) in anhydrous methylene chloride (50 ml), the mixture was stirred for one hour at room temperature. The reaction mixture was concentrated under reduced pressure, ethyl acetate (100 ml) was added to the residue, washed with water and dried over anhydrous sodiun sulfate. The solvent was evaporated under reduced pressure, purified by silica gel column chromatography (chloroform:methanol=10: l), Ether was added to the residue for trituration, to thereby obtain 383 mg of the title compound as pale yellow powder.

Step 4

Preparation of 1-[1-[N-(2-dimethylaminoethyl)-N-methylcarbamoylmethyl]-2-oxo-5-pivaloyl-1,3,4,5-tetrahydro-2H-1,5-benzodiazepin-3-yl]-3-(3-methylphenyl) urea Step 3 of Example 1 was repeated except that 1-[N-(2-dimethylaminoethyl)-N-methylcarbamoylmethyl]-2-oxo-3-tert-butoxycarbonylamino-5-pivaloyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 216–218° C. (decomposition)

$^1$H-NMR($CDCl_3$) δ: 1.01 and 1.02(9H, each s), 2.23 and 2.25(9H, each s), 2.33–2.58(2H, m), 2.99 and 3.09(3H, each s), 3.21–3.54(2H, m), 3.84–4.16(2H, m), 4.26–4.40(1H, m), 4.69–4.82(1H, m), 5.14 and 5.18(1H, each d), 6.12(1H, d), 6.72–7.49(9H, m)

MS(FAB)m/z: 537(MH)$^+$

Example 55

Preparation of 1-[1-(4-methylpiperazin-1-yl) carbonylmethyl-2-oxo-5-pivaloyl-1,3,4,5-tetrahydro-2H-1,5-benzodiazepin-3-yl]-3-(3-methylphenyl)urea Step 3 of Example 54 was repeated except that 1-methylpiperazine was used instead of N,N,N'-trimethylethylenediamine, subsequently, in a similar manner to Step 3 and 4 of Example 1, to thereby obtain the title compound.

Melting point: 233–234° C. (decomposition)

$^1$H-NMR($CDCl_3$) δ: 1.03(9H, s), 2.19–2.52(4H, m), 2.24 (3H, s), 2.30(3H, s), 3.36–3.80(4H, m), 3.88(1H, d), 3.99 (1H, dd), 4.36(1H, t), 4.79(1H, dt), 5.19(1H, d), 6.12(1H, d), 6.73–7.46(9H, m)

MS(FAB)m/z: 535(MH)$^+$

Example 56

Preparation of sodium (+)-3-[3-[1-(2-toluoylmethyl)-2-oxo-5-pivaloyl-1,3,4,5-tetrahydro-2H-1,5-benzodiazepin-3-yl]ureido]benzoate Step 1

Preparation of (+)-1-(2-toluoylmethyl)-2-oxo-3-amino-5-pivaloyl-1,3,4,5-tetrahydro-2H-1,5-benzodiazepine (+)-Dibenzoyltartaric acid (5.19 g) was added to a solution of 1-(2-toluoylmethyl)-2-oxo-3-amino-5-pivaloyl-1,3,4,5-tetrahydro-2H-1,5-benzodiazepine (5.48 g) obtained from Step 3 of Example 1 in ethyl acetate (150 ml) under agitation, crystals so precipitated were collected by filtration. Saturated aqueous sodium bicarbonate was added this crystals, extracted with chloroform, dried over anhydrous sodiun sulfate, and the solvent was evaporated under reduced pressure, to thereby obtain crude (+)-1-(2-toluoylmethyl)-2-oxo-3-amino-5-pivaloyl-1,3,4,5-tetrahydro-2H-1,5-benzodiazepine. This crude compound was dissolved in ethyl acetate (150 ml) again, (+)-dibenzoyltartaric acid (2.60 g) was added under agitation and crystals so precipitated were collected by filtration. Saturated aqueous sodium bicarbonate was added this crystals, extracted with chloroform, dried over anhydrous sodiun sulfate, and the solvent was evaporated under reduced pressure, to thereby obtain 2.55 g of the title compound.

[α] $D^{25}$ (C=0.60, $CHCl_3$): +84.3°

Step 2

Preparation of (−)-1-(2-toluoylmethyl)-2-oxo-3-amino-5-pivaloyl-1,3,4,5-tetrahydro-2H-1,5-benzodiazepine Saturated aqueous sodium bicarbonate was added the filtrate obtained from Step 1, extracted with chloroform, dried over anhydrous sodiun sulfate, the solvent was evaporated, (−)-dibenzoyltartaric acid was added to the obtained residue, and in a similar manner to Step 1, to thereby obtain 2.44 g of the title compound.

[α] $D^{25}$ (C=1.00, $CHCl_3$): −84.0°

Step 3

Preparation of 1-[1-(2-toluoylmethyl)-2-oxo-5-pivaloyl-1,3,4,5-tetrahydro-2H-1,5-benzodiazepin-3-yl]-3-(3-benzyloxycarbonylphenyl)urea Diphenylphosphoryl azide (1.183 g) and triethylamine (455 mg) were added to a solution of isophthalic acid monobenzyl ester (1.073 g) in dioxane (50 ml), the mixture was stirred at 80° C. until bubbling was finished. The reaction mixture was allowed to cool at room temperature, (+)-1-(2-toluoylmethyl)-2-oxo-3-amino-5-pivaloyl-1,3,4,5-tetrahydro-2H-1,5-benzodiazepine (1.023 g) was added to this reaction mixture and then stirred for 30 minutes at room temperature. The resultant mixture was concentrated under reduced pressure, methylene chloride was added to the residue, successively washed with saturated aqueous sodium bicarbonate and saturated brine, dried over anhydrous sodiun sulfate. The mixture was purified by silica gel column chromatography (n-hexane:ethyl acetate=2:1), to thereby obtain 1.61 g of the title compound (Yield: 93.7%).

$^1$H-NMR($CDCl_3$) δ: 1.0(9H, s), 2.47(3H, s), 4.00(1H, dd), 4.38(1H, t), 4.39(1H, d), 4.77–4.89(1H, m), 5.32(2H, s), 5.50(1H, d), 6.32(1H, d), 7.12–7.46(13H, m), 7.57–7.67(4H, m), 7.92(1H, t)

Step 4

Preparation of sodium (+)-3-[3-[1-(2-toluoylmethyl)-2-oxo-5-pivaloyl-1,3,4,5-tetrahydro-2H-1,5-benzodiazepin-3-yl]ureido]benzoate 10% Palladium carbon (200 mg) was added to a solution of 1-[1-(2-toluoylmethyl)-2-oxo-5-pivaloyl-1,3,4,5-tetrahydro-2H-1,5-benzodiazepin-3-yl]-3-(3-benzyloxycarbonylphenyl)urea (1.4 g) obtained from Step 3 in ethanol (50 ml), stirred for 8 hours at room temperature under hydrogen atmosphere. The reaction mixture was filtrated and the filtrate was concentrated under reduced pressure, to thereby obtain 1.04 g of (+)-3-[3-[1-(2-toluoylmethyl)-2-oxo-5-pivaloyl-1,3,4,5-tetrahydro-2H-1,5-benzodiazepin-3-yl]ureido]benzoic acid (Yield: 86%).

[α] $D^{20}$ (C=0.45, $CHCl_3$): +15.8°

$^1$H-NMR($CDCl_3$) δ: 1.09(9H, s), 2.55(3H, s), 4.12(1H, dd), 4.45(1H, t), 4.59(1H, d), 4.77–4.89(1H, m), 5.51(1H, d), 7.17–7.75(13H, m), 8.18–8.38(2H, m)

Furthermore, the compound so obtained was converted into its sodium salt in a manner known per se in the art, to obtain the title compound.

Melting point: 210–212° C.

Example 57

Preparation of 1-[1-(2-toluoylmethyl)-2-oxo-5-pivaloyl-1,3,4,5-tetrahydro-2H-1,5-benzodiazepin-3-yl]-3-[3-(4-hydroxy-2-oxo-5H-thiolen-3-yl)carbonylphenyl]urea 2-Chloro-1,3-dimethylimidazoliniumchloride (355 mg) was added to a solution of 3-[3-[1-(2-toluoylmethyl)-2-oxo-5-pivaloyl-1,3,4,5-tetrahydro-2H-1,5-benzodiazepin-3-yl]ureido]benzoic acid (780 mg) in methylene chloride (20 ml), stirred at room temperature for 15 minutes, thiotetronic acid (198 mg) and triethyl amine (425 mg) were added, and the mixture was stirred for 30 minutes at room temperature. 1N hydrochloric acid (10 ml) was added to the reaction mixture and separated into organic layer and aqueous layer, the aqueous layer was extracted with methylene chloride. The organic layer was combined, and washed with the water, dried over anhydrous sodiun sulfate, and the solvent was evaporated under reduced pressure. The residue was purified by silica gel column chromatography (chloroform:methanol=20:1), and recrystallized from the mixed solvent of isopropyl ether and ethanol, to thereby obtain 660 mg of the title compound (Yield: 72.0%) as a light peach color solid.

Melting point: 206–208° C. (decomposition)

$^1$H-NMR($CDCl_3$) δ: 1.07(9H, s), 2.44(3H, s), 3.91(1H, dd), 4.18(2H, d), 4.44(1H, t), 4.48(1H, d), 4.86–5.03(1H, m), 5.68(1H, d), 6.54(1H, t), 6.73(1H, d), 7.13–7.58(11H, m), 7.73(1H, d), 8.02(1H, t)

MS(FAB)m/z: 655(MH)$^+$

Example 58

Preparation of 1-[1-(2-toluoylmethyl)-2-oxo-5-pivaloyl-1,3,4,5-tetrahydro-2H-1,5-benzodiazepin-3-yl]-3-[3-(4-hydroxy-2-oxo-5H-oxolen-3-yl)carbonylphenyl]urea Example 57 was repeated except that tetronic acid was used instead of thiotetronic acid, to thereby obtain the title compound.

Melting point: 208–209° C. (decomposition)

$^1$H-NMR(DMSO-$d_6$) δ: 0.96(9H, s), 2.45(3H, s), 3.72 (1H, dd), 4.29(1H, t), 4.45–4.60(1H, m), 4.90(2H, d), 5.16 (2H, d), 5.47(2H, d), 6.13(1H, t), 6.77(1H, d), 7.30–7.67 (10H, m), 7.97(1H, d), 8.21(1H, brs), 9.21(1H, brs)

MS(FAB)m/z: 639(MH)$^+$

Example 59

Preparation of 1-[1-(2-toluoylmethyl)-2-oxo-5-pivaloyl-1,3,4,5-tetrahydro-2H-1,5-benzodiazepin-3-yl]-3-[3-(N,N-dimethylamino)phenyl]urea 1,1'-Carbonyldiimidazole (244 mg) was added to a solution of 1-(2-toluoylmethyl)-2-oxo-3-amino-5-pivaloyl-1,3,4,5-tetrahydro-2H-1,5-benzodiazepine (393 mg) in anhydrous tetrahydrofuran (5 ml), stirred for 30 minutes at room temperature,N,N-dimethyl-m-phenylenediamine dihydrochloride (335 mg) and triethylamine (0.67 ml) was added, and the mixture was refluxed overnight. The reaction mixture was concentrated under reduced pressure, appeared insoluble material was removed and purified by silica gel column chromatography (n-hexane:ethyl acetate=1:1). Etanol was added to the residue for crystallization and filtrated, to thereby obtain 224 mg of the title compound (Yield: 40.3%) as white solid.

Melting point: 219–221° C. (decomposition)

$^1$H-NMR($CDCl_3$) δ: 1.03(9H, s), 2.53(3H, s), 2.91(6H, s), 4.04(1H, dd), 4.31(1H, t), 4.44(1H, d), 4.76–4.89(1H, m), 5.49(1H, d), 6.03(1H, d), 6.40–6.52(2H, m), 6.66(1H, brs), 6.76–6.83(1H, m), 7.11(1H, t), 7.20–7.47(7H, m), 7.69(1H, d)

MS(FAB)m/z: 556(MH)$^+$

Example 60

Preparation of 1-[1-(2-toluoylmethyl)-2-oxo-5-(piperidin-2-yl)carbonyl-1,3,4,5-tetrahydro-2H-1,5-benzodiazepin-3-yl]-3-(3-methylphenyl)urea Step 1

Preparation of 2-oxo-3-tert-butoxycarbonylamino-5-[(N-benzyloxycarbonyl)piperidin-2-yl]carbonyl-1,3,4,5-tetrahydro-2H-1,5-benzodiazepine Isobutyl chloroformate (983 mg) and N-methylmorpholine (728 mg) were added to a solution of (N-benzyloxycarbonyl)pipecolinic acid (1.90 g) in anhydrous 1,2-dichloroethane (50 ml) at 0° C., stirred at room temperature for 15 minutes. 2-Oxo-3-tert-butoxycarbonylamino-1,3,4,5-tetrahydro-2H-1,5-benzodiazepine (1.0 g) was added thereto, the mixture was refluxed for 5 hours. The reaction mixture was allowed to cool, methylene chloride was added and successively washed with water and saturated brine. The extract was dried over anhydrous sodiun sulfate, the solvent was evaporated under reduced pressure, and the residue was purified by silica gel column chromatography (n-hexane:ethyl acetate=1:1), to thereby obtain 802 mg of the title compound (Yield: 42.6%) as colorless amorphous.

$^1$H-NMR($CDCl_3$) δ: 1.10–2.10(15H, m), 3.00–4.20(3H, m), 4.35–4.75(3H, m), 4.82–4.95(1H, m), 5.04–5.18(1H, m), 5.33–5.53(1H, m), 6.60–7.80(9H, m)

Step 2

Preparation of 1-(2-toluoylmethyl)-2-oxo-3-tert-butoxycarbonylamino-5-[(N-benzyloxycarbonyl)piperidin-2-yl]carbonyl-1,3,4,5-tetrahydro-2H-1,5-benzodiazepine Step 2 of Example 1 was repeated except that 2-oxo-3-tert-butoxycarbonylamino-5-[(N-benzyloxycarbonyl) piperidin-2-yl]carbonyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.20–2.20(15H, m), 2.50–2.60(3H, m), 3.10–5.60(11H, m), 6.60–7.90(13H, m)

Step 3

Preparation of 1-[1-(2-toluoylmethyl)-2-oxo-5-(piperidin-2-yl)carbonyl-1,3,4,5-tetrahydro-2H-1,5-benzodiazepin-3-yl]-3-(3-methylphenyl)urea 4N HCl-dioxane (10 ml) was added to a solution of 1-(2-toluoylmethyl)-2-oxo-3-tert-butoxycarbonylamino-5-[(N-benzyloxycarbonyl)piperidin-2-yl]carbonyl-1,3,4,5-tetrahydro-2H-1,5-benzodiazepine (845 mg) in ethanol (30 ml), then stirred at 50 ° C. for 15 minutes. The reaction mixture was concentrated under reduced pressure, saturated aqueous sodium bicarbonate was added and extracted with chloroform. After the organic layer was dried over anhydrous sodium sulfate, the solvent was evaporated under reduced pressure, the residue was dissolved in tetrahydrofuran (20 ml), m-tolylisocyanate (0.18 ml) was added to the solution, and the mixture was stirred at room temperature for 15 minutes. This resultant mixture was concentrated under reduced pressure, purified by silica gel column chromatography (chloroform:methanol=20:1), and isopropyl ether was added to the residue for trituration and collected by filtration. 25% hydrobromic acid-acetic acid solution (10 ml) was added to the collection, then stirred at room temperature for 30 minutes, ether was added to reaction mixture. Solid so precipitated was collected by filtration, saturated aqueous sodium bicarbonate was added and extracted with chloroform. After the organic layer was dried over anhydrous sodium sulfate, the solvent was evaporated under reduced pressure, purified by silica gel column chromatography (chloroform: methanol=20:1), separated into first eluent that was compound A and second eluent that was compound B.

Ethanol was added to the (A) and solidified, to thereby obtain 22 mg of the title compound(A'). The mixed solvent of isopropyl ether and ethanol was added to the (B) and solidified, to thereby obtain 42 mg of the title compound(B').

Physicochemical data of (A')

Melting point: 207–210° C. (decomposition)

$^1$H-NMR(DMSO-$d_6$, 25° C.) δ: 1.00–1.80(6H, m), 2.22 (3H, s), 2.41(3H, s), 2.70–3.40(3H, m), 3.53–3.65(1H, m), 4.38–4.60(2H, m), 4.96(1H, d), 5.42(1H, d), 6.66–6.80(2H, m), 7.03–7.20(2H, m), 7.30–7.62(8H, m), 7.93(1H, d), 8.71 (1H, s), 8.86(1H, s)

MS(FAB)m/z: 554(MH)$^+$

Physicochemical data of (B')

Melting point: 202–204° C. (decomposition)

$^1$H-NMR(DMSO-$d_6$, 25° C.) δ: 1.00–1.73(6H, m), 2.90–3.40(3H, m), 2.22(3H, s), 2.37(3H, s), 3.66(1H, dd), 4.32(1H, t), 4.48–4.64(1H, m), 5.23(1H, d), 5.34(1H, d), 6.64–6.77(2H, m), 7.03–7.19(3H, m), 7.29–7.68(8H, m), 7.95(1H, d), 8.72(1H, brs)

MS(FAB)m/z: 554(MH)$^+$

Example 61

Preparation of 1-[1-(2-toluoylmethyl)-2-oxo-5-pivaloyl-1,3,4,5-tetrahydro-2H-1,5-benzodiazepin-3-yl]-3-[3-(tetrazol-5-yl)phenyl]urea Triethylamine (0.44 ml) was added to a suspension of 5-(3-aminophenyl)tetrazole hydrochloride (prepared according to International Publication WO93/17011) (316 mg) in anhydrous tetrahydrofuran (10 ml). After cooled at 0° C., triphosgene (157 mg) was added, and the mixture was adjusted to pH 8 with triethylamine (0.22 ml). After returned at room temperature, stirred for 30 minutes, 1-(2- toluoylmethyl)-2-oxo-3-amino-5-pivaloyl-1,3,4,5-tetrahydro-2H-1,5-benzodiazepine (472 mg) obtained from Step 3 of Example 1 in anhydrous tetrahydrofuran (10 ml) was added to the reaction mixture, and then stirred at room temperature for one hour. Ethyl acetate (20 ml) was added to the resultant mixture, 10% acetic acid (20 ml) was added thereto and separated into organic layer and aqueous layer. After the organic layer was dried over anhydrous sodium sulfate, the solvent was evaporated under reduced pressure. The residue was purified by silica gel column chromatography (chloroform:methanol=5:1) and the mixed solvent of isopropyl ether and ethanol was added to the residue for trituration, collected by filtration, to thereby obtain 443 mg of the title compound (Yield: 63.6%) as white powder.

Melting point: 187–203° C.

$^1$H-NMR(DMSO-$d_6$) δ: 0.96(9H, s), 2.45(3H, s), 3.73 (1H, dd), 4.30(1H, t), 4.48–4.62(1H, m), 4.92(1H, d), 5.47 (1H, d), 6.78(1H, d), 7.32–7.62(11H, m), 7.98(1H, d), 8.10 (1H, brs), 9.09(1H, brs)

MS(FAB)m/z: 581(MH)$^+$

Example 62

Preparation of 1-[1-(2-toluoylmethyl)-2-oxo-5-pivaloyl-1,3,4,5-tetrahydro-2H-1,5-benzodiazepin-3-yl]-3-[3-(5-oxo-4H-1,2,4-oxadiazolin-3-yl)phenyl]urea Example 61 was repeated except that 3-(3-aminophenyl)-5-oxo-4H-1,2,4-oxadiazoline hydrochloride (prepared according to Japanese Patent publication (Kohyo) Hei.7-504908) was used instead of 5-(3-aminophenyl) tetrazole hydrochloride, to thereby obtain the title compound.

Melting point: 179–182° C.

$^1$H-NMR($CDCl_3$) δ: 1.10(9H, s), 2.03(3H, s), 3.86(1H, dd), 4.52(1H, t), 4.56(1H, d), 5.04–5.20(1H, m), 5.75(1H, d), 6.62(1H, brs), 6.87(1H, d), 7.0–7.54(11H, m), 7.78(1H, dd), 10.75(1H, br)

MS(FAB)m/z: 597(MH)$^+$

Example 63

Preparation of 1-[1-(2-toluoylmethyl)-2-oxo-5-pivaloyl-1,3,4,5-tetrahydro-2H-1,5-benzodiazepin-3-yl]-3-[3-(N-hydroxycarbamoyl)phenyl]urea Step 1

Preparation of 1-[1-(2-toluoylmethyl)-2-oxo-5-pivaloyl-1,3,4,5-tetrahydro-2H-1,5-benzodiazepin-3-yl]-3-[3-(N-benzyloxycarbamoyl)phenyl]urea Triethylamine (0.28 ml) was added to a suspension of o-benzylhydroxylamine hydrochloride (319 mg) in anhydrous methylene chloride (10 ml) at 0° C., 3-[3-[1-(2-toluoylmethyl)-2-oxo-5-pivaloyl-1,3,4,5-tetrahydro-2H-1,5-benzodiazepin-3-yl]ureido]benzoic acid (557 mg) obtained from Example 37, 1-ethyl-3-(3-dimethylaminopropyl)carbodiimide hydrochloride (383 mg) and triethylamine (0.56 ml) were added, the mixture was stirred for at room temperature 2 hours. Methylene chloride (50 ml) was added to the reaction mixture, successively washed with 1N hydrochloric acid, saturated brine, and dried over anhydrous sodium sulfate. The solvent was evaporated under reduced pressure, the residue was purified by silica gel column chromatography (chloroform:methanol=20:1), to thereby obtain 420 mg of the title compound (Yield: 63.5%) as colorless oil.

$^1$H-NMR($CDCl_3$) δ: 1.09(9H, s), 2.26(3H, s), 3.86(1H, dd), 4.46(1H, t), 4.55(1H, d), 4.95(2H, ABq), 5.02–5.14(1H, m), 5.70(1H, d), 6.71(1H, d), 6.93(1H, t), 7.02(1H, brs), 7.11–7.47(15H, m), 7.76(1H, d), 10.10(1H, brs)

Step 2

Preparation of 1-[1-(2-toluoylmethyl)-2-oxo-5-pivaloyl-1,3,4,5-tetrahydro-2H-1,5-benzodiazepin-3-yl]-3-[3-(N-hydroxycarbamoyl)phenyl]urea Step 5 of Example 31 was repeated except that 1-[1-(2-toluoylmethyl)-2-oxo-5-pivaloyl-1,3,4,5-tetrahydro-2H-1,5-benzodiazepin-3-yl]-3-[3-(N-benzyloxycarbamoyl) phenyl]urea was used instead of 1-[1-[N-(1-methylpiperidin- 4-yl)]carbamoylmethyl-2-oxo-5-pivaloyl-1,3,4,5-tetrahydro-2H-1,5-benzodiazepin-3-yl]-3-(3-benzyloxycarbonylphenyl)urea hydrochloride, to thereby obtain the title compound.

Melting point: 192–196° C.

$^1$H-NMR(DMSO-$d_6$) δ: 0.95(9H, s), 2.45(3H, s), 3.71 (1H, dd), 4.27(1H, t), 4.44–4.60(1H, m), 4.90(1H, d), 5.46 (1H, d), 6.71(1H;d), 7.20–7.61(10H, m), 7.70(1H, brs), 7.97(1H, d), 8.95(2H, brs), 11.09(1H, brs)

MS(FAB)m/z: 572(MH)$^+$

Example 64

Preparation of N-[3-[3-[1-(2-toluoylmethyl)-2-oxo-5-pivaloyl-1,3,4,5-tetrahydro-2H-1,5-benzodiazepin-3-yl] ureido]benzoyl]glycine Step 1

Preparation of 1-[1-(2-toluoylmethyl)-2-oxo-5-pivaloyl-1,3,4,5-tetrahydro-2H-1,5-benzodiazepin-3-yl]-3-[3-(N-ethoxycarbonylmethyl)carbamoylphenyl]urea Step 1 of Example 63 was repeated except that glycine ethylester was used instead of o-benzylhydroxylamine hydrochloride, to thereby obtain the title compound.

$^1$H-NMR($CDCl_3$) δ: 1.08(9H, s), 1.27(3H, t), 2.40(3H, s), 3.88(1H, d), 4.03(1H, dd), 4.14–4.28(3H, m), 4.42(1H, t), 4.54(1H, d), 4.90–5.05(1H, m), 5.64(1H, d), 6.56(1H, d), 7.07(1H, t), 7.20–7.52(12H, m), 7.75(1H, d)

Step 2

Preparation of N-[3-[3-[1-(2-toluoylmethyl)-2-oxo-5-pivaloyl-1,3,4,5-tetrahydro-2H-1,5-benzodiazepin-3-yl] ureido]benzoyl]glycine Lithium hydroxide (151 mg) in water (1 0 ml) was added to a solution of 1-[L-(2-toluoylmethyl)-2-oxo-5-pivaloyl-1,3,4,5-tetrahydro-2H-1,5-benzodiazepin-3-yl]-3-[3-(N-ethoxycarbonylmethyl)carbamoylphenyl]urea (465 mg) in methanol (30 ml), the mixture was stirred at room temperature for one hour. The reaction mixture was concentrated under reduced pressure, adjusted to pH 2 with 1N hydrochloric acid and extracted with methylene chloride. The organic layer was washed with saturated brine, dried over anhydrous magnesium sulfate and the solvent was evaporated under reduced pressure. The mixed solvent of isopropyl ether and ethanol was added to the obtained compound and solidified and collected by filtration, to thereby obtain 320 mg of the title compound (Yield: 72.4%).

Melting point: 180–187° C.

$^1$H-NMR($CDCl_3$) δ: 1.04(9H, s), 2.40(3H, s), 3.50–5.00 (1H, br), 3.77–3.89(1H, m), 3.95–4.16(2H, m), 4.47(1H, t), 4.61(1H, d), 4.69–4.95(1H, m), 5.49(1H, d), 6.75(1H, d), 7.05(1H, t), 7.17–7.52(11H, m), 7.58–7.82(2H, m)

MS(FAB)m/z: 614(MH)$^+$

Example 65

Preparation of 1-[1-(2-toluoylmethyl)-2-oxo-5-pivaloyl-1,3,4,5-tetrahydro-2H-1,5-benzodiazepin-3-yl]-3-(3-methoxycarbonylphenyl)urea Step 3 of Example 10 was repeated except that methyl 3-amino benzoate was used instead of ethyl 3-amino benzoate and that 1-(2-toluoylmethyl)-2-oxo-3-amino-5-pivaloyl-1,3,4,5-tetrahydro-2H-1,5-benzodiazepine obtained from Step 3 of Example 1 was used instead of 1-tert-butylcarbonylmethyl-2-oxo-3-amino-5-pivaloyl-1,3,4,5-tetrahydro-2H-1,5-benzodiazepine, to thereby obtain the title compound.

Melting point: 201–207° C. (decomposition)

$^{1}$H-NMR($CDCl_3$) δ: 1.05(9H, s), 2.49(3H, s), 3.85(3H, s), 4.00(1H, dd), 4.39(1H, t), 4.42(1H, d), 4.87(1H, d t), 5.54 (1H, d), 6.30(1H, d), 7.16–7.69(12H, m), 7.93–7.99(1H, m)

MS(FAB)m/z: 571(MH)$^+$

Example 66

Preparation of 3-[3-[1-(2-toluoylmethyl)-2-oxo-5-(piperidin-2-yl)carbonyl-1,3,4,5-tetrahydro-2H-1,5-benzodiazepin-3-yl]ureido]benzoic acid hydrochloride Step 1

Preparation of 1-[1-(2-toluoylmethyl)-2-oxo-5-(1-benzyloxycarbonylpiperidin-2-yl)carbonyl-1,3,4,5-tetrahydro-2H-1,5-benzodiazepin-3-yl]-3-(3-benzyloxycarbonylphenyl)urea Step 2 of Example 10 was repeated except that 1-(2-toluoylmethyl)-2-oxo-3-tert-butoxycarbonylamino-5-(1-benzyloxycarbonylpiperidin-2-yl)carbonyl-1,3,4,5-tetrahydro-2H-1,5-benzodiazepine obtained from Step 2 of Example 60 was used instead of 1-tert-butylcarbonylmethyl-2-oxo-3-tert-butoxycarbonylamino-5-pivaloyl-1,3,4,5-tetrahydro-2H-1,5-benzodiazepine, subsequently, in a similar manner to Step 3 of Example 56, to thereby obtain the compound. The compound was purified by silica gel column chromatography (methylene chloride:ethyl acetate=20:1), was separated into 1.26 g of first eluent that was yellow oily title compound A and 0.93 of second eluent that was yellow oily title compound B.

Physicochemical data of (A)

$^{1}$H-NMR(DMSO-$d_6$, 100° C.) δ: 1.20–2.10(6H, m), 2.45 (3H, s), 3.00–3.20(1H, m), 3.70–3.88(2H, m), 4.34(1H, t), 4.47–4.65(2H, m), 4.67–4.83(2H, m), 4.90(1H, d), 5.32(2H, s), 6.54(1H, d), 7.15–7.62(20H, m), 7.71(1H, d), 8.00(1H, t), 8.91(1H, brs)

Physicochemical data of (B)

$^{1}$H-NMR($CDCl_3$) δ: 1.20–1.80(6H, m), 2.48(3H, s), 3.40–3.68(1H, m), 3.80–4.20(2H, m), 4.40–4.60(2H, m), 4.70–5.25(4H, m), 5.30(2H, s), 5.35–5.60(1H, m), 6.22(1H, d), 6.78(1H, br), 7.05–7.83(21H, m), 7.94(1H, d)

Step 2

Preparation of 3-[3-[1-(2-toluoylmethyl)-2-oxo-5-(piperidin-2-yl)carbonyl-1,3,4,5-tetrahydro-2H-1,5-benzodiazepin-3-yl]ureido]benzoic acid hydrochloride Compound(B) (860 mg) obtained from Step 1 was dissolved in methanol (20 ml), palladium hydroxide (86 mg) and 1N hydrochloric acid (1.2 m) were added, and then stirred at room temperature for 3 hours under hydrogen atmosphere. After the reaction mixture was filtrated and the filtrate was concentrated under reduced pressure, toluene was added and azeotropic distilled. The mixed solvent of isopropyl ether and ethanol was added to the obtained compound and solidified and collected by filtration, to thereby obtain 600 mg of the title compound(B1) (Yield: 91.3%).

Melting point: 221–226° C. (decomposition)

$^{1}$H-NMR(DMSO-$d_6$) δ: 1.00–1.85(6H, m), 2.70–4.00 (4H, m), 4.36(1H, t), 4.54–4.68(1H, m), 5.11(1H, d), 5.39 (1H, d), 6.93(1H, d), 7.28–8.05(12H, m), 8.74(1H, br), 9.31(1H, brs), 9.48(1H, br), 12.80(1H, br)

MS(FAB)m/z: 584(MH)$^+$

Furthermore, same procedure was carried out for compound(A), to thereby title compound(A1).

Melting point: 222–226° C. (decomposition)

$^{1}$H-NMR(DMSO-$d_6$) δ: 1.00–2.30(6H, m), 2.37(3H, s), 2.80–3.60(3H, m), 3.68–3.85(1H, m), 4.48–4.68(2H, m), 5.31(1H, d), 5.58(1H, d), 7.01(1H, d), 7.28–7.75(10H, m), 7.85–8.04(2H, m), 8.70–9.30(3H, m), 12.80(1H, br)

MS(FAB)m/z: 584(MH)$^+$

Example 67

Preparation of 3-[3-[1-(2-toluoylmethyl)-2-oxo-5-(pyrrolidin-2-yl)carbonyl-1,3,4,5-tetrahydro-2H-1,5-benzodiazepin-3-yl]ureido]benzoic acid hydrochloride Step 1

Preparation of 2-oxo-3-tert-butoxycarbonylamino-5-[(N-benzyloxycarbonyl)pyrrolidin-2-yl]carbonyl-1,3,4,5-tetrahydro-2H-1,5-benzodiazepine Step 1 of Example 60 was repeated except that (N-benzyloxycarbonyl)proline was used instead of (N-benzyloxycarbonyl)pipecholinic acid. The resultant product was purified by silica gel column chromatography (n-hexane:ethyl acetate=1:1), to thereby obtain 1.68 g of first eluent that was colorless oily title compound(A) and 1.34 g of second eluent that was colorless solid title compound (B).

Physicochemical data of (A)

$^{1}$H-NMR(DMSO-$d_6$, 100° C.) δ: 1.37(9H, m), 1.65–2.15 (4H, m), 3.30–3.47(2H, m), 3.50–4.04(2H, m), 4.15–4.30 (11H, m), 4.46–4.70(11H, m), 4.92–5.12(2H, m)), 6.68(11H, d), 7.18–7.48(9H, m), 9.65(1H, brs)

Physiochemical data of (B)

$^{1}$H-NMR(DMSO-$d_6$, 100° C.) δ: 1.34(9H, s), 1.45–1.90 (4H, m), 3.28–3.60(3H, m), 4.08–4.26(2H, m), 4.50–4.68 (1H, m), 5.06(2H, s), 6.60–6.72(1H, m), 6.80–7.50(9H, m), 9.76(1H, brs)

Step 2

Preparation of 1-(2-toluoylmethyl)-2-oxo-3-tert-butoxycarbonylamino-5-[(N-benzyloxycarbonyl)pyrrolidin-2-yl]carbonyl-1,3,4,5-tetrahydro-2H-1,5-benzodiazepine Step 2 of Example 1 was repeated except that the compound(A) obtained from Step 1 was used instead of 2-oxo-3-tert-butoxycarbonylamino-5-pivaloyl-1,3,4,5-tetrahydro-1,5-benzodiazepine, to thereby obtain the title compound(A1).

$^{1}$H-NMR($CDCl_3$) δ: 1.40(9H, s), 1.70–2.30(4H, m), 2.61 (3H, s), 3.36–3.50(1H, m), 3.56–3.68(1H, m), 3.80–3.98 (2H, m), 4.47(1H, d), 4.55–4.72(2H, m), 4.95(1H, d), 5.15 (1H, d), 5.63(1H, d), 5.86(1H, d), 7.06–7.50(12H, m), 7.84(1H, d)

Furthermore, the title compound(B1) was obtained, by using the compound (B) obtained from Step 1, in a similar manner as above.

$^{1}$H-NMR(DMSO-$d_6$) δ: 1.34(9H, s), 1.50–1.95(4H, m), 2.42(3H, s), 3.26–3.62(3H, m), 4.12–4.40(2H, m), 4.47–4.64(1H, m), 4.78–5.00(1H, m), 5.08(2H, d), 5.37(1H, d), 6.85(1H, d), 7.04–7.16(1H, m), 7.22–7.60(10H, m), 7.73(1H, d), 7.93(1H, d)

Step 3

Preparation of 1-[1-(2-toluoylmethyl)-2-oxo-5-[(N-benzyloxycarbonyl)pyrrolidin-2-yl]carbonyl-1,3,4,5-tetrahydro-2H-1,5-benzodiazepin-3-yl]-3-(3-benzyloxycarbonylphenyl)urea Step 2 of Example 10 was repeated except that the compound(A1) obtained from Step 2 was used instead of 1-tert-butylcarbonylmethyl-2-oxo-3-tert-butoxycarbonylamino-5-pivaloyl-1,3,4,5-tetrahydro-2H-1,5-benzodiazepine. Subsequently, in a similar manner to Step 3 of Example 56, to thereby obtain the title compound(A2).

$^1$H-NMR(DMSO-$d_6$, 100° C.) δ: 1.70–2.13(4H, m), 2.45 (3H, s), 3.36–3.49(2H, m), 3.64–4.12(2H, m), 4.30–4.70 (3H, m), 4.92–5.10(2H, m), 5.32(2H, s), 5.40–5.70(1H, br), 6.56(1H, d), 7.20–7.80(21H, m), 8.00(1H, brs), 8.90(1H, brs)

Furthermore, the title compound (B2) was obtained, by using the compound (B1) obtained from Step 2, in a similar manner as above.

$^1$H-NMR(DMSO-$d_6$) δ: 1.53–1.95(4H, m), 2.44(3H, s), 3.25–3.77(3H, m), 4.17–4.65(3H, m), 4.86–5.13(3H, m), 5.32(2H, s), 5.47(1H, d), 6.72(1H, d), 6.86(1H, d), 7.15(1H, t), 7.28–7.63(17H, m), 7.75(1H, d), 7.93–8.00(1H, m), 8.03–8.07(1H, m), 9.11(1H, d)

Step 4

Preparation of 3-[3-[1-(2-toluoylmethyl)-2-oxo-5-(pyrrolidin-2-yl)carbonyl-1,3,4,5-tetrahydro-2H-1,5-benzodiazepin-3-yl]ureido]benzoic acid Step 5 of Example 31 was repeated except that the compound(A2) obtained from Step 3 was used instead of 1-[1-[N-(1-methylpiperidin-4-yl)]carbamoylmethyl-2-oxo-5-pivaloyl-1,3,4,5-tetrahydro-2H-1,5-benzodiazepin-3-yl]-3-(3-benzyloxycarbonylphenyl)urea, to thereby obtain the title compound(A3).

Melting point: 225–230° C. (decomposition)

$^1$H-NMR(DMSO-$d_6$) δ: 1.75–2.40(5H, m), 2.44(3H, s), 3.05–3.50(1H, m), 3.66–3.83(2H, m), 4.53–4.73(2H, m), 5.27(1H, d), 5.36(1H, d), 6.98(1H, d), 7.28–7.74(10H, m), 7.90–8.05(2H, m), 8.83(1H, br), 9.24(1H, brs), 9.48(1H, br), 12.80(1H, br)

MS(FAB)m/z: 570(MH)$^+$

Furthermore, the title compound(B3) was obtained, by using the compound (B2) obtained from Step 3, in a similar manner as above.

Melting point: 219–224° C. (decomposition)

$^1$H-NMR(DMSO-$d_6$) δ: 1.43–1.91(4H, m), 2.43(3H, s), 3.10–3.20(2H, m), 3.84(1H, dd), 4.27(1H, t), 4.42(1H, t), 4.56–4.70(1H, m), 5.07(1H, d), 5.42(1H, d), 6.92(1H, d), 7.27–7.78(10H, m), 7.91–8.04(2H, m), 9.00–10.00(3H, br), 11.50–12.50(1H, br)

MS(FAB)m/z: 570(MH)$^+$

Example 68

Preparation of 1-[1-[N-(tetrazol-5-yl)carbamoylmethyl]-2-oxo-5-pivaloyl-1,3,4,5-tetrahydro-2H-1,5-benzodiazepin-3-yl]-3-(3-methylphenyl)urea Step 1

Preparation of 1-[1-benzyloxycarbonylmethyl-2-oxo-5-pivaloyl-1,3,4,5-tetrahydro-2H-1,5-benzodiazepin-3-yl]-3-(3-methylphenyl)urea Step 3 of Example 1 was repeated except that the 1-benzyloxycarbonylmethyl-2-oxo-3-tert-butoxycarbonylamino-5-pivaloyl-1,3,4,5-tetrahydro-2H-1,5-benzodiazepine obtained from Step 1 of Example 54 was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 4 of Example 1, to thereby obtain the title compound.

Melting point: 136–140° C.

$^1$H-NMR(CDCl$_3$) δ: 1.00(9H, s), 2.30(3H, s), 3.91(1H, d), 3.95(1H, dd), 4.34(1H, t), 4.65–4.78(1H, m), 5.03(1H, d), 5.21(2H, s), 6.06(1H, d), 6.83(1H, d), 7.04–7.47(13H, m)

MS(FAB)m/z: 543(MH)$^+$

Step 2

Preparation of [3-(3-methylphenyl)ureido-2-oxo-5-pivaloyl-1,3,4,5-tetrahydro-2H-1,5-benzodiazepin-1-yl] acetic acid Step 4 of Example 30 was repeated except that the 1-[-1-benzyloxycarbonylmethyl-2-oxo-5-pivaloyl-1,3,4,5-tetrahydro-2H--1,5-benzodiazepin-3-yl]-3-(3-methylphenyl)urea was used instead of 1-[1-(N-phenyl-N-benzyloxyethylcarbamoylmethyl)-2-oxo-5-pivaloyl-1,3,4,5-tetrahydro-2H-1,5-benzodiazepin-3-yl]-3-(3-carboxypbenyl)urea, to thereby obtain the title compound.

$^1$H-NMR(CDCl$_3$) δ: 0.98(9H, s), 2.22(3H, s), 3.85(1H, dd), 4.35(2H, dd), 4.53(1H, t), 4.70–4.84(1H, m), 6.33–6.45 (1H, m), 6.72–6.82(1H, m), 7.00–7.16(3H, m), 7.23–7.36 (4H, m), 7.40– 7.50(1H, m), 7.80(1H, brs)

Step 3

Preparation of 1-[]-[N-(tetrazol-5-yl)carbamoylmethyl]-2-oxo-5-pivaloyl-1,3,4,5-tetrahydro-2H-1,5-benzodiazepin-3-yl]-3-(3-methylphenyl)urea 5-Aminotetrazole (104 mg) and 1-ethyl-3-(3-dimethylaminopropyl)carbodiimide hydrochloride (194 mg) were added to a solution of [3-(3-methylphenyl)ureido-2-oxo-5-pivaloyl-1,3,4,5-tetrahydro-2H-1,5-benzodiazepin-1-yl]acetic acid (306 mg) in anhydrous methylene chloride (20 ml), the mixture was stirred at room temperature overnight. The reaction mixture was concentrated under reduced pressure, the residue was purified by silica gel column chromatography (chloroform:methanol=l0:1), the mixed solvent of isopropylether and ethanol was added, solidified, and filtrated, to obtain 115 mg of the title compound as a white solid.

$^1$H-NMR(DMSO-$d_6$, 100° C.) δ: 0.97(9H, s), 2.21(3H, s), 3.71(1H, dd), 4.19(1H, d), 4.20(1H, dd), 4.50(1H, ddd), 5.08(1H, d), 6.49(1H, d), 6.66–6.73(1H, m), 7.00–7.17(3H, m), 7.33–7.58(4H, m), 8.53(1H, brs MS(FAB)m/z: 558(M+K)$^+$

Example 69

Preparation of 3-[3-(1-phenacyl-2-oxo-5-pivaloyl-1,3,4,5-tetrahydro-2H-1,5-benzodiazepin-3-yl)ureido]benzoic acid Step 1

Preparation of 1-phenacyl-2-oxo-3-tert-butoxycarbonylamino-5-pivaloyl-1,3,4,5-tetrahydro-2H-1,5-benzodiazepine Step 2 of Example 1 was repeated except that 2-bromoacetophenone was used instead of 2-bromo-2'-methylacetophenone, to thereby obtain the title compound.

$^1$H-NMR(CDCl$_3$) δ: 1.04(9H, s), 1.40(9H, s), 3.98(1H, dd), 4.27(1H, dd), 4.56(1H, d), 4.56–4.61(1H, m), 5.52(1H, d), 5.74(1H, d), 7.22–7.43(4H, m), 7.49–7.55(2H, m), 7.61–7.67(1H, m), 8.01–8.05(2H, m)

Step 2

Preparation of 1-(1-phenacyl-2-oxo-5-pivaloyl-1,3,4,5-tetrahydro-2H-1,5-benzodiazepin-3-yl)-3-(3-ethoxycarbonylphenyl)urea Step 2 of Example 10 was repeated except that 1-phenacyl-2-oxo-3-tert-butoxycarbonylamino-5-pivaloyl-1,3,4,5-tetrahydro-2H-1,5-benzodiazepine was used instead of 1-tert-butylcarbonylmethyl-2-oxo-3-tert-butoxycarbonylamino-5-pivaloyl-1,3,4,5-tetrahydro-2H-1,5-benzodiazepine. Subsequently, in a similar manner to Step 3 of Example 10, to thereby obtain the title compound.

$^1$H-NMR(CDCl$_3$) δ: 1.06(9H, s), 1.35(3H, t), 3.98(1H, dd), 4.29–4.43(1H, m), 4.59(1H, d), 4.88(1H, ddd), 5.75(1H, d), 6.22(1H, d), 7.20–7.66(1H, m), 7.91(1H, s), 7.98(2H, d)

Step 3

Preparation of 3-[3-(1-phenacyl-2-oxo-5-pivaloyl-1,3,4,5-tetrahydro-2H-1,5-benzodiazepin-3-yl)ureido]benzoic acid Step 4 of Example 10 was repeated except that 1-(1-phenacyl-2-oxo-5-pivaloyl-1,3,4,5-tetrahydro-2H-1,5-benzodiazepin-3-yl)-3-(3-ethoxycarbonylphenyl)urea was used instead of 1-(1-tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

$^1$H-NMR($CDCl_3$) δ: 1.10(9H, s), 4.17(1H, dd), 4.43(1H, dd), 4.67(1H, d), 4.80–4.84(1H, m), 5.71(1H, d), 7.23–8.33 (16H, m)

MS(FAB)m/z: 543(MH)$^+$

Example 70

Preparation of (−)-3-[3-(1-tert-butylcarbonylmethyl-2-oxo-5-phenyl-1,3,4,5-tetrahydro-2H-1,5-benzodiazepin-3-yl)ureido]benzoic acid Step 1

Preparation of 1-(1-tert-butylcarbonylmethyl-2-oxo-5-phenyl-1,3,4,5-tetrahydro-2H-1,5-benzodiazepin-3-yl)-3-(3-benzyloxycarbonylphenyl)urea Diphenylphosphoryl azide (1.1 g) and triethylamine (0.62 ml) were added to a solution of isophthalic acid monobenzyl ester (792 mg) in dioxane (20 ml), the mixture was stirred internal temperature at 60° C. for 20 minutes and internal temperature at 80° C. for 2 hours. After the reaction mixture was allowed to cool to room temperature, a solution of 1-tert-butylcarbonylmethyl-2-oxo-3-amino-5-phenyl-1,3,4,5-tetrahydro-2H-1,5-benzodiazepine (723 mg) obtained from Step 1 of Example 33 in dioxane (5 ml) was added to the reaction mixture. The reaction mixture was stirred at room temperature for 30 minutes. The mixture was concentrated under reduced pressure, chloroform (50 ml) was added to the resultant residue, and washed with saturated aqueous sodium bicarbonate. After dried over anhydrous sodium sulfate, the solvent was evaporated under reduced pressure, the mixed solvent of isopropyl ether and ethyl acetate was added to the residue for trituration, to thereby obtain 674 mg of the title compound as a colorless solid (Yield: 54%).

$^1$H-NMR($CDCl_3$) δ: 1.22(9H, s), 3.77(1H, dd), 4.19(1H, dd), 4.50(1H, d), 4.85–4.95(1H, m), 5.07(1H, d), 5.32(2H, s), 6.26(1H, d), 6.76–7.67(18H, m), 7.93(1H, s)

Step 2

Preparation of 3-[3-(1-tert-butylcarbonylmethyl-2-oxo-5-phenyl-1,3,4,5-tetrahydro-2H-1,5-benzodiazepin-3-yl) ureido]benzoic acid Methanol (20 ml) and 10% palladium carbon (68 mg) were added to 1-(1-tert-butylcarbonylmethyl-2-oxo-5-phenyl-1,3,4,5-tetrahydro-2H-1,5-benzodiazepin-3-yl)-3-(3-benzyloxycarbonylphenyl)urea (635 mg), the mixture was stirred at 50° C. under hydrogen atmosphere for 2 hours. The reaction mixture was filtrated, the filtrate was concentrated under reduced pressure. The residue was dissolved in 2 N aqueous sodium hydroxide, washed with ether, adjusted to pH 2 with concentrated hydrochloric acid, and extracted with chloroform. The organic layer was dried over anhydrous magnesium sulfate. The solvent was evaporated under the pressure, the mixed solvent of isopropyl ether and ethyl acetate was added to the residue for trituration, and collected by filtration, to thereby obtain 144 mg of the title compound as a colorless solid.

Melting point: 237° C. (decomposition)

$^1$H-NMR($CDCl_3$) δ: 1.29(9H, s), 3.72(1H, dd), 4.32(1H, d), 4.43(1H, dd), 4.81–4.90(1H, m), 5.23(1H, d), 7.13–8.41 (13H, m), 7.50(1H, d), 8.29(1H, s), 10.71–10.77(1H, br)

MS(FAB)m/z: 515(MH)$^+$

Step 3

Preparation of 1-tert-butylcarbonylmethyl-2-oxo-3-[(2S)-(2-tert-butoxycarbonylamino-3-phenylpropionyl)amino]-5-phenyl-1,3,4,5-tetrahydro-2H-1,5-benzodiazepine 1-tert-Butylcarbonylmethyl-2-oxo-3-amino-5-phenyl-1,3,4,5-tetrahydro-2H-1,5-benzodiazepine (3.62 g) was dissolved in anhydrous N,N-dimethyl formamide (30 ml) under argon atmosphere, N-tert-butoxycarbonyl-L-phenylalanine (3.00 g), 1-hydroxybenzotriazole (1.73 g), 1-ethyl-3-(3-dimethylaminopropyl)carbodiimide hydrochloride (2.17 g) and triethylamine (2.08 g) were added at ice-cooling, thereto the mixture was stirred for 5 minutes under ice-cooling, and stirred at room temperature for one hour. Water and ethyl acetate were added to the reaction mixture, separated, the organic layer was successively washed with water and saturated brine, dried over anhydrous sodium sulfate, and the solvent was evaporated under reduced pressure. The residue was purified by silica gel column chromatography (n-hexane:ethyl acetate=2:1), to thereby obtain 6.17 g of the title compound.

$^1$H-NMR($CDCl_3$) δ: 1.25 and 1.26(9H, each s), 1.41(9H, s), 3.03(2H, br), 3.14–3.22 and 3.43–3.50(1H, each m), 4.00–4.50(4H, m), 4.73–4.82(1H, m), 4.98(1H, br), 5.10 (1H, d), 6.65–6.95(4H, m), 7.06–7.37(10H, m)

Step 4

Preparation of 1-tert-butylcarbonylmethyl-2-oxo-3-[(2S)-(2-amino-3-phenylpropionylamino]-5-phenyl-1,3,4,5-tetrahydro-2H-1,5-benzodiazepine 1-tert-butylcarbonylmethyl-2-oxo-3-[(2S)-2-tert-butoxycarbonylamino-3-phenylpropionylamino]-5-phenyl-1,3,4,5-tetrahydro-2H-1,5-benzodiazepine (6.17 g) was dissolved in 4N HCl-dioxane (30 ml), the mixture was stirred at room temperature for 3 hours. The reaction mixture was concentrated under reduced pressure, saturated aqueous sodium bicarbonate and ethyl acetate were added to the residue, separated, the organic layer was successively washed with water and saturated brine, dried over anhydrous sodium sulfate, and the solvent was evaporated under reduced pressure. The residue was purified by silica gel column chromatography (ethyl acetate saturated with water), separated into compound(A) of first eluent and compound (B) of second eluent and purified, to thereby obtain 2.29 g of the title compound(A) and 2.48 g of title compound (B).

Physiochemical data of (A)

$^1$H-NMR($CDCl_3$) δ: 1.25(9H, s), 1.53(2H, br), 2.78(1H, dd), 3.20(1H, dd), 3.48(1H, dd), 3.62(1H, dd), 4.19(1H, dd), 4.32(1H, d), 4.81–4.91(1H, m), 5.13(1H, d), 6.77(2H, d), 6.87(1H, t), 7.09–7.38(11H, m), 8.14(1H, d)

Physiochemical data of (B)

$^1$H-NMR($CDCl_3$) δ: 1.26(9H, s), 1.63(2H, br), 2.67(1H, dd), 3.21(1H, dd), 3.43(1H, dd), 3.58(1H, dd), 4.23(1H, m), 4.33(1H, d), 4.79–4.89(1H, m), 5.13(1H, d), 6.76(2H, d), 6.87(1H, t), 7.09–7.36(11H, m), 7.87(1H, d)

Step 5

Preparation of 1-tert-butylcarbonylmethyl-2-oxo-3-[(2S)-2-(N-phenylthioureido)-3-phenylpropionylamino]-5-phenyl-1,3,4,5-tetrahydro-2H-1,5-benzodiazepine The compound (A, 2.29 g) obtained from Step 4 was dissolved in anhydrous methylene chloride (20 ml), phenyl isothiocyanate (1.21 g) was added dropwise, the mixture was stirred at room temperature for 2 hours. The reaction mixture was concentrated under reduced pressure, the residue was purified by silica gel column chromatography (n-hexane:ethyl acetate=2:1), to thereby obtain 2.91 g of the title compound(A1).

$^1$H-NMR($CDCl_3$) δ: 1.27(9H, s), 3.17(2H, d), 3.55(1H, dd), 4.16–4.29(2H, m), 4.71–4.77(1H, m), 5.12–5.22(2H, m), 6.68–6.89(5H, m), 7.04–7.36(18H, m), 7.83(1H, s)

Furthermore, the title compound (B1) was obtained, by using the compound (B) obtained from Step 4, in a similar manner as above.

$^1$H-NMR($CDCl_3$) δ: 1.23(9H, s), 2.95(1H, dd), 3.14(1H, dd), 3.41(1H, dd), 3.97(1H, dd), 4.25(1H, d), 4.67–4.77(1H, m), 5.08(1H, d), 5.15–5.23(1H, m), 6.45(1H, d), 6.68–6.76 (4H, m), 6.88(1H, t), 7.04–7.40(18H, m), 7.78(1H, s)

Step 6

Preparation of (+)-1-tert-butylcarbonylmethyl-2-oxo-3-amino-5-phenyl-1,3,4,5-tetrahydro-2H-1,5-benzodiazepine The compound (A1, 2.91 g) obtained from Step 5 was dissolved in trifluoroacetic acid (30 ml), and stirred at 50–60 ° C. for 30 minutes. The reaction mixture was concentrated under reduced pressure, saturated aqueous sodium bicarbonate and ethyl acetate were added to the residue, separated, and extracted with ethyl acetate. The organic layer was successively washed with water and saturated brine and dried over anhydrous sodium sulfate. The solvent was evaporated under reduced pressure, the residue was purified by silica gel column chromatography (chloroform:methanol=20:1), to thereby obtain 0.85 g of the title compound. Optical purity was 99%ee by HPLC analysis.

[α] $D^{25}$ (C=1, MeOH): +87°

Step 7

Preparation of (−)-1-tert-butylcarbonylmethyl-2-oxo-3-amino-5-phenyl-1,3,4,5-tetrahydro-2H-1,5-benzodiazepine The compound (B1, 3.15 g) obtained from Step 5 was dissolved in trifluoroacetic acid (30 ml), stirred at 50–60° C. for 30 minutes. The reaction mixture was concentrated under reduced pressure, saturated aqueous sodium bicarbonate and ethyl acetate were added to the residue, separated, the organic layer was washed with water and saturated brine, and dried over anhydrous sodium sulfate. The solvent was evaporated under reduced pressure, the residue was purified by silica gel column chromatography (chloroform:methanol=20:1), to thereby obtain 0.83 g of the title compound. Optical purity was 99%ee by HPLC analysis.

[α] $D^{25}$ (C=1, MeOH): −89°

Step 8

Preparation of (+)-3-[3-(1-tert-butylcarbonylmethyl-2-oxo-5-phenyl-1,3,4,5-tetrahydro-2H-1,5-benzodiazepin-3-yl)ureido]benzoic acid Step 1 was repeated by using (+)-1-tert-butylcarbonylmethyl-2-oxo-3-amino-5-phenyl-1,3,4,5-tetrahydro-2H-1,5-benzodiazepine obtained from Step 6. Subsequently, the resultant compound was dissolved in tetrahydrofuran, palladium carbon was added, the mixture was stirred at room temperature under hydrogen atmosphere for 8 hours. Palladium carbon was removed by filtration, the filtrate was concentrated under reduced pressure, and the residue was purified by silica gel column chromatography (chloroform:methanol=20:1), to thereby obtain the title compound. Optical purity was 99.4%ee by HPLC analysis.

[α] $D^{25}$ (C=1, MeOH): +147.1°

Step 9

Preparation of (−)-3-[3-(1-tert-butylcarbonylmethyl-2-oxo-5-phenyl-1,3,4,5-tetrahydro-2H-1,5-benzodiazepin-3-yl)ureido]benzoic acid Step 8 was repeated by using (−)-1-tert-butylcarbonylmethyl-2-oxo-3-amino-5-phenyl-1,3,4,5-tetrahydro-2H-1,5-benzodiazepine obtained from Step 7, to thereby obtain the title compound. Optical purity was 99%ee by HPLC analysis.

[] $D^{25}$ (C=1, MeOH): −134.8°

Example 71

Preparation of 1-(1-tert-butylcarbonylmethyl-2-oxo-5-phenyl-1,3,4,5-tetrahydro-2H-1,5-benzodiazepin-3-yl)-3-(3-methylphenyl)urea Step 1 of Example 43 was repeated except that 1-tert-butylcarbonylmethyl-2-oxo-3-amino-5-phenyl-1,3,4,5-tetrahydro-2H-1,5-benzodiazepine obtained from Step 1 of Example 33 was used instead of 1-(2-toluoylmethyl)-2-oxo-3-amino-5-phenyl-1,3,4,5-tetrahydro-2H-1,5-benzodiazepine, to thereby obtain the title compound.

Melting point: 266–267° C. (decomposition)

$^1$H-NMR($CDCl_3$) δ: 1.24(9H, s), 2.28(3H, s), 3.65(1H, dd), 4.27(1H, dd), 4.40(1H, d), 4.88(1H, dt), 5.11(1H, d), 6.07(1H, d), 6.63(1H, s), 6.77–7.25(13H, m)

IR(KBr)$cm^{-1}$: 3372, 2971, 1717, 1684, 1659, 1593, 1553, 1497, 1426, 1296, 1237, 776, 760, 747, 691

MS(FAB)m/z: 485$(MH)^+$

Example 72

Preparation of 3-[3-[1-(2-toluoylmethyl)-2-oxo-5-pivaloyl- 1,3,4,5-tetrahydro-2H-1,5-benzodiazepin-3-yl]ureido]phenylacetic acid Step 1

Preparation of 1-[1-(2-toluoylmethyl)-2-oxo-5-pivaloyl-1,3,4,5-tetrahydro-2H-1,5-benzodiazepin-3-yl]-3-(3-methoxycarbonylmethylphenyl)urea Step 3 of Example 10 was repeated except that methyl (3-aminophenyl)acetate was used instead of ethyl 3-aminobenzoate, and that 1-(2-toluoylmethyl)-2-oxo-3-amino-5-pivaloyl-1,3,4,5-tetrahydro-2H-1,5-benzodiazepine obtained from Step 2 of Example 56 was used instead of 1-tert-butylcarbonylmethyl-2-oxo-3-amino-5-pivaloyl-1,3,4,5-tetrahydro-2H-1,5-benzodiazepine, to thereby obtain the title compound.

$^1$H-NMR($CDCl_3$) δ: 1.04(9H, s), 2.51(3H, s), 3.53(2H, s), 3.65(3H, s), 4.01(1H, dd), 4.36(1H, dd), 4.43(1H, d), 4.77–4.84(1H, m), 5.50(1H, d), 6.09(1H, brs), 6.88–7.68 (13H, m)

Step 2

Preparation of 3-[3-[1-(2-toluoylmethyl)-2-oxo-5-pivaloyl-1,3,4,5-tetrahydro-2H-1,5-benzodiazepin-3-yl]ureido]phenylacetic acid Step 4 of Example 10 was repeated except that 1-[1-(2-toluoylmethyl-2-oxo-5-pivaloyl-1,3,4,5-tetrahydro-2H-1,5-benzodiazepin-3-yl]-3-(3-methoxycarbonylmethylphenyl) urea was used instead of 1-(1-tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

$^1$H-NMR($CDCl_3$) δ: 1.04(9H, s), 2.50(3H, s), 3.56(2H, s), 3.98(1H, dd), 4.34(1H, dd), 4.53(1H, d), 4.82(1H, dt), 5.43(1H, d), 6.52–7.69(14H, m), 12.00–13.00(1H, br)

IR(KBr)$cm^{-1}$:2971, 1700-1620, 1597, 1561, 1499, 1458, 1397, 1320, 1223, 758

MS(FAB)m/z: 571$(MH)^+$

Example 73

Preparation of 4-[3-[1-(2-toluoylmethyl)-2-oxo-5-pivaloyl-1,3,4,5-tetrahydro-2H-1,5-benzodiazepin-3-yl]ureido]benzoic acid Step 1

Preparation of 1-[1-(2-toluoylmethyl)-2-oxo-5-pivaloyl-1,3,4,5-tetrahydro-2H-1,5-benzodiazepin-3-yl]-3-(4-methoxycarbonylphenyl)urea Step 3 of Example 10 was repeated except that methyl 4-aminobenzoate was used instead of ethyl 3-aminobenzoate and that 1-(2-toluoylmethyl)-2-oxo-3-amino-5-pivaloyl-1,3,4,5-tetrahydro-2H-1,5-benzodiazepine obtained from Step 2 of Example 56 was used instead of 1-tert-butylcarbonylmethyl-2-oxo-3-amino- 5-pivaloyl-1,3,4,5-tetrahydro-2H-1,5-benzodiazepine, to thereby obtain the title compound.

$^1$H-NMR($CDCl_3$) δ: 1.05(9H, s), 2.48(3H, s), 3.85(3H, s), 3.98(1H, dd), 4.38(1H, dd), 4.39(1H, d), 4.83–4.87(1H, m), 5.55(1H, d), 6.45(1H, d), 7.16–7.49(9H, m), 7.63(1H, d), 7.69(1H, brs), 7.84(2H, d)

Step 2

Preparation of 4-[3-[1-(2-toluoylmethyl)-2-oxo-5-pivaloyl-1,3,4,5-tetrahydro-2H-1,5-benzodiazepin-3-yl]ureido]benzoic acid Step 4 of Example 10 was repeated except that 1-[1-(2-toluoylmethyl)-2-oxo-5-pivaloyl-1,3,4,5-tetrahydro-2H-1,5-benzodiazepin-3-yl]-3-(4-methoxycarbonylphenyl)urea was used instead of 1-(tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

Melting point: 231–233° C. (decomposition)

$^1$H-NMR(DMSO-$d_6$) δ: 0.95(9H, s), 2.44(3H, s), 3.72 (1H, dd), 4.28(1H, dd), 4.50–4.54(1H, m), 4.90(1H, d), 5.46(1H, d), 6.82(1H, d), 7.33–7.60(9H, m), 7.79(2H, d), 7.88(1H, d), 9.19(1H, s), 12.51(1H, brs)

IR(KBr)$cm^{-1}$:3355, 1719, 1671, 1617, 1597, 1541, 1499, 1418, 1325, 1291, 1219, 1173, 774, 752

MS(FAB)m/z: 557$(MH)^+$

Example 74

Preparation of 3-[3-(1-tert-butoxycarbonylmethyl-2-oxo-5-pivaloyl-1,3,4,5-tetrahydro-2H-1,5-benzodiazepin-3-yl)ureido]benzoic acid Step 1

Preparation of 1-tert-butoxycarbonylmethyl-2-oxo-3-benzyloxycarbonylamino-5-pivaloyl-1,3,4,5-tetrahydro-2H-1,5-benzodiazepine Step 1 of Example 50 was repeated except that 2-oxo-3-tert-butoxycarbonylamino-5-pivaloyl-1,3,4,5-tetrahydro-2H-1,5-benzodiazepine was used instead of 2-oxo-3-tert-butoxycarbonylamino-5-cyclohexylcarbonyl-1,3,4,5-tetrahydro-2H-1,5-benzodiazepine. Subsequently, in a similar manner to Step 2 of Example 50, to thereby obtain the title compound.

Step 2

Preparation of 1-tert-butoxycarbonylmethyl-2-oxo-3-amino-5-pivaloyl-1,3,4,5-tetrahydro-2H-1,5-benzodiazepine Step 2 of Example 16 was repeated except that 1-tert-butoxycarbonylmethyl-2-oxo-3-benzyloxycarbonylamino-5-pivaloyl- 1,3,4,5-tetrahydro-2H-1,5-benzodiazepine was used instead of 1-tert-butoxycarbonylmethyl-2-oxo-3-benzyloxycarbonylamino-5-phenyl-1,3,4,5-tetrahydro-2H-1,5-benzodiazepine, to thereby obtain the title compound.

Step 3

Preparation of 1-(1-tert-butoxycarbonylmethyl-2-oxo-5-pivaloyl-1,3,4,5-tetrahydro-2H-1,5-benzodiazepin-3-yl)-3-(3-benzyloxycarbonylphenyl)urea Step 1 of Example 70 was repeated except that 1-tert-butoxycarbonylmethyl-2-oxo-3-amino-5-pivaloyl-1,3,4,5-tetrahydro-2H-1,5-benzodiazepine was used instead of 1-tert-butylcarbonylmethyl-2-oxo-3-amino-5-phenyl-1,3,4,5-tetrahydro-2H-1,5-benzodiazepine, to thereby obtain the title compound.

$^1$H-NMR($CDCl_3$) δ: 1.04(9H, s), 1.46(9H, s), 3.80(1H, d), 3.97(1H, dd), 4.37(1H, t), 4.65–4.73(1H, m), 5.14(1H, d), 5.40(2H, s), 6.30(1H, d), 7.25–7.53(10H, m), 7.64–7.76(2H, m), 7.95–7.97(1H, m), 8.09(1H, s)

Step 4

Preparation of 3-[3-(1-tert-butoxycarbonylmethyl-2-oxo-5-pivaloyl-1,3,4,5-tetrahydro-2H-1,5-benzodiazepin-3-yl)ureido]benzoic acid Methanol (20 ml) and 10% palladium carbon (57 mg) were added to 1-(1-tert-butoxycarbonylmethyl-2-oxo-5-pivaloyl-1,3,4,5-tetrahydro-2H-1,5-benzodiazepin-3-yl)-3-(3-benzyloxycarbonylphenyl)urea (550 mg), the mixture was stirred at room temperature under hydrogen atmosphere for one hour. The reaction mixture was filtrated and the filtrate was concentrated under reduced pressure. Isopropyl ether was added to the residue for trituration and collected by filtration, to thereby obtain 420 mg of the title compound as a colorless solid.

Melting point: 175° C. (decomposition)

$^1$H-NMR($CDCl_3$) δ: 1.03(9H, s), 1.51(9H, s), 3.93(1H, d), 4.11(1H, dd), 4.41(1H, dd), 4.66–4.73(1H, m), 4.77(1H, d), 7.24–8.34(10H, m), 10.00–11.00(1H, br)

IR(KBr)$cm^{-1}$:2980, 1676, 1617, 1595, 1557, 1501, 1395, 1368, 1321, 1225, 1156, 754

MS(FAB)nm/z: 539$(MH)^+$

Example 75

Preparation of 3-[3-[1-(N-methyl-N-phenylcarbamoylmethyl)-2-oxo-5-pivaloyl-1,3,4,5-tetrahydro-2H-1,5-benzodiazepin-3-yl]ureido]benzoic acid Step 1

Preparation of 1-(N-methyl-N-phenylcarbamoylmethyl)-2-oxo- 3-tert-butoxycarbonylamino-5-pivaloyl-1,3,4,5-tetrahydro-2H-1,5-benzodiazepine Step 2 of Example 1 was repeated except that 2-bromo-N-phenyl-N-methylacetamide was used instead of 2-bromo-2'-methyl acetophenone, to thereby obtain the title compound.

$^1$H-NMR($CDCl_3$) δ: 0.90(9H, s), 1.39(9H, s), 3.36(3H, s), 3.60(1H, d), 3.93(1H, dd), 4.15(1H, dd), 4.70(1H, d), 5.53 (1H, d), 6.68–7.54(9H, m)

Step 2

Preparation of 1-[1-(N-methyl-N-phenylcarbamoylmethyl)-2-oxo-5-pivaloyl-1,3,4,5-tetrahydro-2H-1,5-benzodiazepin-3-yl]-3-(3-etboxycarbonylphenyl)urea Step 2 of Example 10 was repeated except that 1-(N-methyl-N-phenylcarbamoylmethyl)-2-oxo-3-tert-butoxycarbonylamino-5-pivaloyl-1,3,4,5-tetrahydro-2H-1,5-benzodiazepine was used instead of 1-tert-butylcarbonylmethyl-2-oxo-3-tert-butoxycarbonylamino-5-pivaloyl-1,3,4,5-tetrahydro-2H-1,5-benzodiazepine. Subsequently, in a similar manner to Step 3 of Example 10, to thereby obtain the title compound.

$^1$H-NMR($CDCl_3$) δ: 1.35(3H, t), 3.31(3H, s), 3.70(1H, d), 3.96(1H, dd), 4.31(2H, q), 4.34(1H, dd), 4.72–4.81(2H, m), 6.27(1H, d), 7.21–7.94(14H, m)

Step 3

Preparation of 3-[3-[1-(N-methyl-N-phenylcarbamoylmethyl)-2-oxo-5-pivaloyl-1,3,4,5-tetrahydro-2H-1,5-benzodiazepin-3-yl]ureido]benzoic acid Step 4 of Example 10 was repeated except that 1-[1-(N-methyl-N-phenylcarbamoylmethyl)-2-oxo-5-pivaloyl-1,3,4,5-tetrahydro-2H-1,5-benzodiazepin-3-yl]-3-(3-ethoxycarbonylphenyl)urea was used instead of 1-(tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

Melting point: 233–237° C. (decomposition)

H-NMR(DMSO-$d_6$) δ: 0.83(9H, s), 3.24(3H, s), 3.65(1H, dd), 3.90–4.53(3H, m), 4.16(1H, dd), 6.66(1H, d), 7.28–7.56 (12H, m), 7.96(1H, s), 9.03(1, s), 12.35–12.90(1H, br)

IR (KBr)$cm^{-1}$:3366, 1684,1647, 1595, 1565, 1497, 1399, 1323, 1248, 1229, 772, 758, 702

MS(FAB) m/z: 572$(MH)^+$

Example 76

Preparation of 3-[3-(1-methyl-2-oxo-5-pivaloyl-1,3,4,5-tetrahydro-2H- 1,5-benzodiazepin-3-yl)ureido]benzoic acid Step 1

Preparation of 1-methyl-2-oxo-3-tert-butoxycarbonylamino-5-pivaloyl-1,3,4,5-tetrahydro-2H-1,5-benzodiazepine Step 2 of Example 1 was repeated except that methyl iodide was used instead of 2-bromo-2'-methylacetophenone, to thereby obtain the title compound.

$^1$H-NMR($CDCl_3$) δ: 0.99(9H, s), 1.40(9H, s), 3.40(3H, s), 3.83(1H, dd), 4.22(1H, dd), 4.36–4.46(1H, m), 5.45(1H, d), 7.20–7.47(4H, m)

Step 2

Preparation of 1-(1-methyl-2-oxo-5-pivaloyl-1,3,4,5-tetrahydro-2H-1,5-benzodiazepin-3-yl)-3-(3-ethoxycarbonylphenyl)urea Step 2 of Example 10 was repeated except that 1-methyl-2-oxo-3-tert-butoxycarbonylamino-5-pivaloyl-1,3,4,5-tetrahydro-2H-1,5-benzodiazepine was used instead of 1-tert-butylcarbonylmethyl-2-oxo-3-tert-butoxycarbonyl-amino-5-pivaloyl-1,3,4,5-tetrahydro-2H-1,5-benzodiazepine. Subsequently, in a similar manner to Step 3 of Example 10, to thereby obtain the title compound.

$^1$H-NMR($CDCl_3$) δ: 1.05(9H, s), 1.37(3H, t), 3.45(3H, s), 3.93(1H, dd), 4.30–4.39(3H, m), 4.65–4.75(1H, m), 6.18 (1H, d), 7.26–7.92(9H, m)

Step 3

Preparation of 3-[3-[1-methyl-2-oxo-5-pivaloyl-1,3,4,5-tetrahydro-2H-1,5-benzodiazepin-3-yl]ureido]benzoic acid Step 4 of Example 10 was repeated except that 1-(1-methyl-2-oxo-5-pivaloyl-1,3,4,5-tetrahydro-2H-1,5-benzodiazepin-3-yl)-3-(3-ethoxycarbonylphenyl)urea was used instead of 1-(tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

Melting point: 246° C. (decomposition)

$^1$H-NMR(DMSO-$d_6$) δ: 0.92(9H, s), 3.33(3H, s), 3.63 (1H, dd), 4.23(1H, dd), 4.32–4.39(1H, m), 6.69(1H, d), 7.31(1H, t), 7.38–7.51(4H, m), 7.58(2H, d), 7.99(1H, s), 9.00(1H, s), 12.78(1H, brs)

MS(FAB)m/z: 439(MH)$^+$

Example 77

Preparation of 3-[3-[1-(2-aminophenacyl)-2-oxo-5-pivaloyl-1,3,4,5-tetrahydro-2H-1,5-benzodiazepin-3-yl] ureido]benzoic acid Step 1

Preparation of 1-(2-nitrophenacyl)-2-oxo-3-tert-butoxycarbonylamino-5-pivaloyl-1,3,4,5-tetrahydro-2H-1,5-benzodiazepine 2-Oxo-3-tert-butoxycarbonylamino-5-pivaloyl-1,3,4,5-tetrahydro-2H-1,5-benzodiazepine (100 mg) was added to a suspension of 60% sodium hydride (22 mg) in N,N-dimethylformamide (5 ml), the mixture was stirred at room temperature for 15 minutes. Subsequently, 2-bromo-2'-nitroacetophenone (102 mg) was added thereto, and stirred at room temperature for one hour. Water was added to the reaction mixture, extracted with ethyl acetate. The organic layer was washed with saturated brine, dried over anhydrous magnesium sulfate, and the solvent was evaporated under reduced pressure. Isopropyl ether was added to the residue for trituration and collected by filtration, to thereby to obtain 76 mg of the title compound as a light yellow solid (Yield: 52%).

$^1$H-NMR($CDCl_3$) δ: 0.98(9H, s), 1.41(9H, s), 3.95(1H, dd), 4.29(1H, dd), 4.57(1H, d), 4.52–4.63(1H, m), 5.28(1H, d), 5.46(1H, brd), 7.26–8.23(8H, m)

Step 2

Preparation of 1-[1-(2-nitrophenacyl)-2-oxo-5-pivaloyl-1,3,4,5-tetrahydro-2H-1,5-benzodiazepin-3-yl]-3-(3-ethoxycarbonylphenyl)urea Step 2 of Example 10 was repeated except that 1-(2-nitro) phenacyl-2-oxo-3-tert-butoxycarbonylamino-5-pivaloyl-1,3,4,5-tetrahydro-2H-1,5-benzodiazepine was used instead of 1-tert-butylcarbonylmethyl-2-oxo-3-tert-butoxycarbonyl-amino-5-pivaloyl-1,3,4,5-tetrahydro-2H-1,5-benzodiazepine. Subsequently, in a similar manner to Step 3 of Example 10, to thereby obtain the title compound.

$^1$H-NMR($CDCl_3$) δ: 1.07(9H, s), 1.36(3H, t), 4.02(1H, dd), 4.30–4.49(4H, m), 4.80–4.90(1H, m), 5.19(1H, d), 6.14(1H, brd), 7.26–7.68(11H, m), 7.91(1H, s), 8.12(1H, d)

Step 3

Preparation of 1-[1-(2-aminophenacyl)-2-oxo-5-pivaloyl-1,3,4,5-tetrahydro-2H-1,5-benzodiazepin-3-yl]-3-(3-ethoxycarbonylphenyl)urea Etanol (20 ml) and 10% palladium carbon (70 mg) were added to 1-[1-(2-nitrophenacyl)-2-oxo-5-pivaloyl-1,3,4,5-tetrahydro-2H-1,5-benzodiazepin-3-yl]-3-(3-ethoxycarbonylphenyl)urea (700 mg), the mixture was stirred at room temperature under hydrogen atmosphere for 3 hours. The reaction mixture was filtrated and the filtrate was concentrated under reduced pressure, to thereby to obtain 280 mg of the title compound as colorless oil.

$^1$H-NMR($CDCl_3$) δ: 1.05(9H, s), 1.35(3H, t), 3.98(1H, dd), 4.32(2H, q), 4.39(1H, dd), 4.57(1H, d), 4.86–4.96(1H, m), 5.75(1H, d), 6.26(2H, brs), 6.30(1H, brd), 6.62–6.68 (2H, m), 7.12(1H, s), 7.16–7.91(10H, m)

Step 4

Preparation of 3-[3-[1-(2-aminophenacyl)-2-oxo-5-pivaloyl-1,3,4,5-tetrahydro-2H-1,5-benzodiazepin-3-yl] ureido]benzoic acid Step 4 of Example 10 was repeated except that 1-[1-(2-aminophenacyl)-2-oxo-5-pivaloyl-1,3,4,5-tetrahydro-2H-1,5-benzodiazepin-3-yl]-3-(3-ethoxycarbonylphenyl)urea was used instead of 1-(tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

$^1$H-NMR($CDCl_3$) δ: 1.08(9H, s), 4.16(1H, dd), 4.43(1H, dd), 4.65(1H, d), 4.79–4.89(1H, m), 5.70(1H, d), 6.67–6.73 (2H, m), 7.19–7.70(10H, m), 8.15(1H, s), 8.29(1H, d)

MS(FAB)m/z: 558(MH)$^+$

Example 78

Preparation of 3-[3-[1-(2-toluoylmethyl)-2-oxo-5-pivaloyl-1,3,4,5-tetrahydro-2H-1,5-benzodiazepin-3-yl] ureido]phenylthioacetic acid Step 1

Preparation of 1-[1-(2-toluoylmethyl)-2-oxo-5-pivaloyl-1,3,4,5-tetrahydro-2H-1,5-benzodiazepin-3-yl)-3-(3-ethoxycarbonylmethylthiophenyl)urea Step 2 of Example 33 was repeated except that 1-(2-toluoylmethyl)-2-oxo-3-amino-5-pivaloyl-1,3,4,5-tetrahydro-2H-1,5-benzodiazepine obtained from Step 2 of Example 56 was used instead of 1-tert-butylcarbonylmethyl-2-oxo-3-amino-5-phenyl-1,3,4,5-tetrahydro-2H-1,5-benzodiazepine, to thereby obtain the title compound.

$^1$H-NMR($CDCl_3$) δ: 1.04(9H, s), 1.93(3H, t), 2.49(3H, s), 3.61(2H, s), 3.99(1H, dd), 4.13(2H, q), 4.37(1H, t), 4.40(1H, d), 4.79–4.87(1H, m), 5.51(1H, d), 6.28(1H, d), 6.96–7.48 (12H, m), 7.64(1H, d)

Step 2

Preparation of 3-[3-(1-(2-toluoylmethyl)-2-oxo-5-pivaloyl-1,3,4,5-tetrahydro-2H-1,5-benzodiazepin-3-yl]ureido]phenylthioacetic acid Step 3 of Example 33 was repeated except that 1-[1-(2-toluoylmethyl)-2-oxo-5-pivaloyl-1,3,4,5-tetrahydro-2H-1,5-benzodiazepin-3-yl]-3-(3-ethoxycarbonylmethylthiophenyl)urea was used instead of 1-(1-tert-butylcarbonylmethyl-2-oxo-5-phenyl-1,3,4,5-tetrahydro-2H-1,5-benzodiazepin-3-yl)-3-(3-ethoxycarbonylmethylthiophenyl)urea, to thereby obtain the title compound.

Melting point: 127–130° C.

$^1$H-NMR($CDCl_3$) δ: 1.03(9H, s), 2.47(3H, s), 3.52(2H, ABq), 3.89(1H, dd), 4.41(1H, t), 4.53(1H, d), 4.77–4.88(1H, m), 5.06(1H, brs), 5.51(1H, d), 6.52(1H, d), 6.91–7.74(13H, m)

MS(FAB)m/z: 603(MH$^+$)

Example 79

Preparation of 3-[3-[1-(2-methoxyphenacyl)-2-oxo-5-pivaloyl-1,3,4,5-tetrahydro-2H-1,5-benzodiazepin-3-yl]ureido]benzoic acid Step 1

Preparation of 1-(2methoxyphenacyl)-2-oxo-3-tert-butoxycarbonylamino-5-pivaloyl-1,3,4,5-tetrahydro-2H-1,5-benzodiazepine Step 2 of Example 1 was repeated except that 2-bromo-2'-methoxyacetophenone was used instead of 2-bromo-2'-methylacetophenone, to thereby obtain the title compound.

$^1$H-NMR($CDCl_3$) δ: 1.04(9H, s), 1.40(9H, s), 3.92(3H, s), 3.93–4.02(1H, m), 4.26(1H, dd), 4.57(1H, d), 4.50–4.58(1H, m), 5.56(1H, d), 5.52–5.56(1H, brs), 6.99–7.58(7H, m), 7.98(11H, dd)

Step 2

Preparation of 1-[1-(2-methoxyphenacyl)-2-oxo-5-pivaloyl-1,3,4,5-tetrahydro-2H-1,5-benzodiazepin-3-yl]-3-(3-ethoxycarbonylphenyl)urea Step 2 of Example 10 was repeated except that 1-(2-methoxyphenacyl)-2-oxo-3-tert-butoxycarbonylamino-5-pivaloyl-1,3,4,5-tetrahydro-2H-1,5-benzodiazepine was used instead of 1-tert-butylcarbonylmethyl-2-oxo-3-tert-butoxycarbonylamino-5-pivaloyl-1,3,4,5-tetrahydro-2H-1,5-benzodiazepine. Subsequently, in a similar manner to Step 3 of Example 10, to thereby obtain the title compound.

$^1$H-NMR($CDCl_3$) δ: 1.06(9H, s), 1.35(3H, t), 3.87(3H, s), 4.33(2H, q), 4.32(1H, dd), 4.38(1H, dd), 4.61(1H, d), 4.58–4.89(1H, m), 5.59(1H, d), 6.31(1H, d), 6.95(1H, d), 6.99–7.94(12H, m)

Step 3

Preparation of 3-[3-[1-(2-methoxyphenacyl)-2-oxo-5-pivaloyl-1,3,4,5-tetrahydro-2H-1,5-benzodiazepin-3-yl]ureido]benzoic acid Step 4 of Example 10 was repeated except that 3-[3-[1-(2-methoxyphenacyl)-2-oxo-5-pivaloyl-1,3,4,5-tetrahydro-2H-1,5-benzodiazepin-3-yl]ureido]benzoic acid was used instead of 1-(tert-butylcarbonylmethyl-2-oxo-5-pivaloyl-1,3,4,5-tetrahydro-2H-1,5-benzodiazepin-3-yl)-3-(3-ethoxycarbonylphenyl)urea, to thereby obtain the title compound.

$^1$H-NMR(DMSO-$d_6$) δ: 0.96(9H, s), 3.67–3.75(1H, m), 4.27(1H, dd), 4.48–4.57(1H, m), 4.71(1H, d), 5.40(1H, d), 6.67(1H, d), 7.06–7.12(1H, m), 7.23(1H, d), 7.28–7.65(8H, m), 7.77(1H, dd), 7.99(1H, s), 9.00(1H, s), 12.70(1H, brs)

MS(FAB)m/z: 573(MH)$^+$

Example 80

Preparation of 3-[3-[1-tert-butoxycarbonylmethyl-2-oxo-5-phenyl-1,3,4,5-tetrahydro-2H-1,5-benzodiazepin-3-yl]ureido]benzoic acid Step 1

Preparation of 1-[1-tert-butoxycarbonylmethyl-2-oxo-5-phenyl-1,3,4,5-tetrahydro-2H-1,5-benzodiazepin-3-yl]-3-(3-benzyloxycarbonylphenyl)urea Step 3 of Example 56 was repeated except that 1-tert-butoxycarbonylmethyl-2-oxo-3-amino-5-phenyl-1,3,4,5-tetrahydro-2H-1,5-benzodiazepine obtained from Step 2 of Example 16 was used instead of 1-(2-toluoylmethyl)-2-oxo-3-amino-5-pivaloyl-1,3,4,5-tetrahydro-2H-1,5-benzodiazepine, to thereby obtain the title compound.

$^1$H-NMR(DMSO-$d_6$) δ: 1.36(9H, s), 3.61(1H, dd), 3.96–4.08(1H, m), 4.39–4.63(3H, m), 5.32(2H, s), 6.66–6.87(4H, m), 7.13–7.61(14H, m), 8.04–8.08(1H, m), 9.17(1H, s)

Step 2

Preparation of 3-[3-[1-tert-butoxycarbonylmethyl-2-oxo-5-phenyl-1,3,4,5-tetrahydro-2H-1,5-benzodiazepin-3-yl]ureido]benzoic acid Step 5 of Example 31 was repeated except that 1-[1-tert-butoxycarbonylmethyl-2-oxo-5-phenyl-1,3,4,5-tetrahydro-2H-1,5-benzodiazepin-3-yl]-3-(3-benzyloxycarbonylphenyl)urea was used instead of 1-[1-(1-methylpiperidin-4-yl)carbamoylmethyl-2-oxo-5-pivaloyl-1,3,4,5-tetrahydro-2H-1,5-benzodiazepin-3-yl]-3-(3-benzyloxycarbonylphenyl)urea, to thereby obtain the title compound.

Melting point: 215–216° C. (decomposition)

$^1$H-NMR(DMSO-$d_6$) δ: 1.36(9H, s), 3.63(1H, dd), 4.01 (1H, dd), 4.40–4.64(3H, m), 6.70–6.88(4H, m), 7.13– 7.57 (9H, m), 8.02(1H, d), 9.12(1H, s), 12.50–13.20(1H, br)

MS(FAB)m/z: 531(MH)$^+$

Example 81

Preparation of 3-[3-[1-tert-butoxycarbonylmethyl-2-oxo-5-phenyl-1,3,4,5-tetrahydro-2H-1,5-benzodiazepin-3-yl]ureido]phenylthioacetic acid Step 1

Preparation of 1-[1-tert-butoxycarbonylmethyl-2-oxo-5-phenyl-1,3,4,5-tetrahydro-2H-1,5-benzodiazepin-3-yl]-3-(3-benzyloxycarbonylmethylthiophenyl)urea Triphosgene (1.06 g) was added to a solution of benzyl 3-aminophenylthioacetate (2.06 g) in anhydrous tetrahydrofuran (100 ml) at 0° C., triethylamine (0.45 ml) was added thereto, and the mixture was stirred at same temperature for 10 minutes. A solution of 1-tert-butoxycarbonylmethyl-2-oxo-3-amino-5-phenyl-1,3,4,5-tetrahydro-2H-1,5-benzodiazepine (3.92 g) obtained from Step 2 of Example 16 in anhydrous tetrahydrofuran (50 ml) was added, the mixture was stirred at room temperature for one hour. The reaction mixture was concentrated under reduced pressure, water (200 ml) was added to the residue, and the resultant mixture was extracted with methylene chloride. The organic layer was washed with saturated brine and dried over anhydrous magnesium sulfate, and the solvent was evaporated under reduced pressure. The residue was purified by silica gel column chromatography (n-hexane:ethyl acetate=2:1), isopropyl ether was added to the solid so precipitated for trituration, collected by filtration, to thereby obtain 4.60 g of the title compound as a white solid (Yield: 84.4%).

$^1$H-NMR($CDCl_3$) δ: 1.43(9H, s), 3.66(2H, s), 3.63–3.74 (1H, m), 4.21(1H, d), 4.22(1H, d), 4.64(1H, d), 4.86(1H, ddd), 5.12(2H, s), 6.19(1H, d), 6.72–7.40(19H, m)

MS(FAB)m/z: 667(MH)$^+$

Step 2

Preparation of 3-[3-[1-tert-butoxycarbonylmethyl-2-oxo-5-phenyl-1,3,4,5-tetrahydro-2H-1,5-benzodiazepin-3-yl]ureido]phenylthioacetic acid Aqueous solution (15 ml) of lithium hydroxide (57 mg) was added to a solution of 1-[1-tert-butoxycarbonylmethyl-2-oxo-5-phenyl-1,3,4,5-tetrahydro-2H-1,5-benzodiazepin-3-yl]-3-(3-benzyloxycarbonylmethylthiophenyl)urea (864 mg) in tetrahydrofuran (45 ml), the mixture was stirred at room temperature for 5 hours. The reaction mixture was concentrated under reduced pressure, the residue was adjusted to pH 2 with 1N hydrochloric acid, and extracted with methylene chloride. The organic layer was dried over anhydrous magnesium sulfate, the solvent was evaporated under reduced pressure, the residue was purified by silica gel column chromatography (chloroform:methanol=5:1), the mixed solvent of isopropyl ether and ethanol was added to the solid so precipitated for trituration, collected by filtration, to thereby obtain 177 mg of the title compound as white powder.

$^1$H-NMR(DMSO-$d_6$) δ: 1.36(9H, s), 3.53(2H, s), 3.55–3.68(1H, m), 3.97(1H, dd), 4.43(1H, d), 4.52(1H, d), 4.52–4.62(1H, m), 6.73–6.87(4H, m), 6.92(1H, d), 7.02–7.46(9H, m), 9.11(1H, s)

MS(FAB) m/z : 559(MH-$H_2O$)$^+$

Example 82

Preparation of (−)-3-[3-[1-tert-butylcarbonylmethyl-2-oxo-5-[(2S)-pyrrolidin-2-yl]carbonyl-1,3,4,5-tetrahydro-2H-1,5-benzodiazepin-3-yl]ureido]benzoic acid hydrochloride and (+)-3-[3-[1-tert-butylcarbonylmethyl-2-oxo-5-[(2S)-pyrrolidin-2-yl]carbonyl-1,3,4,5-tetrahydro-2H-1,5-benzodiazepin-3-yl]ureido]benzoic acid hydrochloride Step 1

Preparation of (−)-2-oxo-3-tert-butoxycarbonylamino-5-[(2S)-(N-benzyloxycarbonyl)pyrrolidin-2-yl]carbonyl-1,3,4,5-tetrahydro-2H-1,5-benzodiazepine and (+)-2-oxo-3-tert-butoxycarbonylamino-5-[(2S)-(N-benzyloxycarbonyl)pyrrolidin-2-yl]carbonyl-1,3,4,5-tetrahydro-2H-1,5-benzodiazepine Step 1 of Example 60 was repeated except that (N-benzyloxycarbonyl)-L-proline was used instead of (N-benzyloxycarbonyl)pipecholinic acid. The resultant crude product was purified by silica gel column chromatography (n-hexane:ethyl acetate=1:1), to thereby obtain (−)-2-oxo-3-tert-butoxycarbonylamino-5-[(2S)-(N-benzyloxycarbonyl)pyrrolidin-2-yl]carbonyl-1,3,4,5-tetrahydro-2H-1,5-benzodiazepine(A) of first eluent and (+)-2-oxo-3-tert-butoxycarbonylamino-5-[(2S)-(N-benzyloxycarbonyl)pyrrolidin-2-yl]carbonyl-1,3,4,5-tetrahydro-2H-1,5-benzodiazepine(B) of second eluent.

Physiochemical data of (A)

[α] $D^{24}$ (C=0.40, $CHCl_3$): −65.6°

Physiochemical data of (B)

[α] $D^{24}$ (C=0.42, $CHCl_3$): +113.9°

Step 2

Preparation of (+)-1-tert-butylcarbonylmethyl-2-oxo-3-tert-butoxycarbonylamino-5-[(2S)-(N-benzyloxycarbonyl)pyrrolidin-2-yl]carbonyl-1,3,4,5-tetrahydro-2H-1,5-benzodiazepine Step 1 of Example 10 was repeated except that the compound(A) obtained from Step 1 was used instead of 2-oxo-3-tert-butoxycarbonylamino-5-pivaloyl-1,3,4,5-tetrahydro-1,5-benzodiazepine, to thereby obtain (+)-1-tert-butylcarbonylmethyl-2-oxo-3-tert-butoxycarbonylamino-5-[(2S)-(N-benzytoxycarbonyl)pyrrolidin-2-yl]carbonyl-1,3,4,5-tetrahydro-2H-1,5-benzodiazepine(A1).

$^1$H-NMR(DMSO-$d_6$, 100° C.) δ: 1.50–1.70(9H, m), 1.78 (9H, s), 2.10–2.55(4H, m), 3.80–4.05(3H, m), 4.24–4.82 (3H, m), 4.90–5.10(1H, m), 5.40–5.80(3H, m), 6.98(1H, d), 7.60–8.00(9H, m)

[α] $D^{23}$ (C=0.50, $CHCl_3$): +9.3°

Furthermore, (+)-1-tert-butylcarbonylmethyl-2-oxo-3-tert-butoxycarbonylamino-5-[(2S)-(N-benzyloxycarbonyl)pyrrolidin-2-yl]carbonyl-1,3,4,5-tetrahydro-2H-1,5-benzodiazepine(B1) was obtained, by using the compound (B) obtained from Step 1, in a similar manner as above.

$^1$H-NMR(DMSO-$d_6$) δ: 1.18(9H, s), 1.34(9H, s), 1.50–1.94(4H, m), 3.33–3.53(3H, m), 4.14–4.54(4H, m), 5.00–5.13(3H, m), 6.50–6.65(1H, m), 7.16–7.52(9H, m)

[α] $D^{25}$ (C=0.50, $CHCl_3$): +71.5°

Step 3

Preparation of (−)-1-[1-tert-butylcarbonylmethyl-2-oxo-5-[(2S)-(N-benzyloxycarbonyl)pyrrolidin-2-yl]carbonyl-1,3,4,5-tetrahydro-2H-1,5-benzodiazepin-3-yl]-3-(3-benzyloxycarbonylphenyl)urea and (+)-1-[1-tert-butylcarbonylmethyl-2-oxo-5-[(2S)-(N-benzyloxycarbonyl)pyrrolidin-2-yl]carbonyl-1,3,4,5-tetrahydro-2H-1,5-benzodiazepin-3-yl]-3-(3-benzyloxycarbonylphenyl)urea Step 2 of Example 10 was repeated except that the compound(A1) obtained from Step 2 was used instead of 1-tert-butylcarbonylmethyl-2-oxo-3-tert-butoxycarbonylamino-5-pivaloyl-1,3,4t5-tetrahydro-2H-1,5-benzodiazepine to thereby obtain 1-tert-butylcarbonylmethyl-2-oxo-3-amino-5-[(2S)-(N-benzyloxycarbonyl)pyrrolidin-2-yl]carbonyl-1,3,4,5-tetrahydro-2H-1,5-benzodiazepine. Subsequently, Step 3 of Example 56 was repeated except that 1-tert-butylcarbonylmethyl-2-oxo-3-amino-5-[(2S)-(N-benzyloxycarbonyl)pyrrolidin-2-yl]carbonyl-1,3,4,5-tetrahydro-2H-1,5-benzodiazepine was used instead of (+)-1-(2-toluoylmethyl)-2-oxo-3-amino-5-pivaloyl-1,3,4,5-tetrahydro-2H-1,5-benzodiazepine and that benzyl isophtalate was used instead of 3-aminobenzoic acid, to thereby obtain (−)-1-[1-tert-butylcarbonylmethyl-2-oxo-5-[(2S)-pyrrolidin-2-yl]carbonyl-1,3,4,5-tetrahydro-2H-1,5-benzodiazepin-3-yl]-3-(3-benzyloxycarbonylphenyl)urea (A2).

$^1$H-NMR(DMSO-$d_6$, 100° C.) δ: 1.16(9H, brs), 1.70–2.10 (4H, m), 3.37–3.48(2H, m), 3.65–4.62(5H, m), 5.04(1H, d), 5.08(1H, d), 5.20–5.40(1H, br), 5.32(2H, s), 6.52(1H, d) 7.15–7.60(17H, m), 7.99(1H, t), 8.89(1H, s)

[α] $D^{27}$ (C=0.51, $CHCl_3$): −22.0°

Furthermore, (+)-1-[1-tert-butylcarbonylmethyl-2-oxo-5-[(2S)-pyrrolidin-2-yl]carbonyl-1,3,4,5-tetrahydro-2H-1,5-benzodiazepin-3-yl]-3-(3-benzyloxycarbonylphenyl)urea (B2) was obtained, by using the compound (B1) obtained from Step 2, in a similar manner as above.

$^1$H-NMR(DMSO-$d_6$, 100° C.) δ: 1.20(9H, s), 1.55–1.94 (4H, m), 3.35–3.48(2H, m), 3.60–3.74(1H, m), 4.24–4.36 (2H, m), 4.42–4.55(2H, m), 5.09(2H, s), 5.10(1H, d), 5.32 (2H, s), 6.51(1H, d), 7.16–7.60(17H, m), 7.99(1H, t), 8.86 (1H, s)

[α] $D^{27}$ (C=0.52, $CHCl_3$): +72.4°

Step 4

Preparation of (−)-3-[3-[1-tert-butylcarbonylmethyl-2-oxo-5-[(2S)-pyrrolidin-2-yl]carbonyl-1,3,4,5-tetrahydro-2H-1,5-benzodiazepin-3-yl]ureido]benzoic acid hydrochloride and (+)-3-[3-[1-tert-butylcarbonylmethyl-2-oxo-5-[(2S)-pyrrolidin-2-yl]carbonyl-1,3,4,5-tetrahydro-2H-1,5-benzodiazepin-3-yl]ureido]benzoic acid hydrochloride Step 5 of Example 31 was repeated except that the compound(A2) obtained from Step 3 was used instead of 1-[1-N-(1-methylpiperidin-4-yl)]carbamoylmethyl-2-oxo-5-pivaloyl-1,3,4,5-tetrahydro-2H-1,5-benzodiazepin-3-yl]-3-(3-benzyloxycarbonylphenyl)urea, to thereby obtain (−)-1-[1-tert-butylcarbonylmethyl-2-oxo-5-[(2S)-pyrrolidin-2-yl]carbonyl-1,3,4,5-tetrahydro-2H-1,5-benzodiazepin-3-yl]-3-(3-carboxyphenyl)urea hydrochloride(A3).

$^1$H-NMR(DMSO-$d_6$) δ: 1.17(9H, s), 1.74–2.20(4H, m), 3.00–3.78(4H, m), 4.46–4.66(2H, m), 4.88(1H, d), 5.02(1H, d), 6.89(1H, d), 7.28–7.37(1H, m), 7.40–7.69(6H, m), 8.00 (1H, t), 8.60–9.80(2H, br), 9.16(1H, brs)

[α] $D^{24}$ (C=0.50, MeOH): −10.7°

MS(FAB)m/z: 536(MH)$^+$

Furthermore, (+)-3-[3-[1-tert-butylcarbonylmethyl-2-oxo-5-[( 2S)-pyrrolidin-2-yl]carbonyl-1,3,4,5-tetrahydro-2H-1,5-benzodiazepin-3-yl]ureido]benzoic acid hydrochloride(B3) was obtained, by using the compound (B2) obtained from Step 3, in a similar manner as above.

$^1$H-NMR(DMSO-$d_6$) δ: 1.19(9H, s), 1.40–1.91(4H, m), 3.10–3.20(2H, m), 3.80(1H, dd), 4.23(1H, t), 4.36(1H, t), 4.48–4.64(1H, m), 4.66(1H, d), 5.09(1H, d), 6.86(1H, d), 7.28–7.37(2H, m), 7.45–7.55(3H, m), 7.58–7.74(2H, m), 8.01(1H, t), 8.70–9.80(2H, br), 9.23(1H, brs), 12.00–13.00 (1H, br)

[α] $D^{24}$ (C=0.50, MeOH): +18.9°

MS(FAB)m/z: 536(MH)$^+$

Example 83

Preparation of 4-[3-[1-(furan-2-yl)carbonylmethyl-2-oxo-5-phenyl-1,3,4,5-tetrahydro-2H-1,5-benzodiazepin-3-yl] ureido]benzoic acid Step 1

Preparation of 1-(furan-2-yl)carbonylmethyl-2-oxo-3-benzyloxycarbonylamino-5-phenyl-1,3,4,5-tetrahydro-2H-1,5-benzodiazepine Step 1 of Example 15 was repeated except that 2-bromoacetylfuran was used instead of 2-bromo-(N-phenyl-N-methyl)acetamide, to thereby obtain the title compound.

$^1$H-NMR($CDCl_3$) δ: 3.60–3.70(1H, m), 4.25(1H, dd), 4.63–4.78(1H, m), 4.84(1H, d), 5.08(2H, s), 5.34(1H, d), 5.88(1H, d), 6.53(1H, dd), 6.76(2H, d), 6.87(1H, t), 7.15–7.40(12H, m), 7.56(1H, d)

Step 2

Preparation of 1-(furan-2-yl)carbonylmethyl-2-oxo-3-amino-5-phenyl-1,3,4,5-tetrahydro-2H-1,5-benzodiazepine Step 2 of Example 15 was repeated except that 1-(furan-2-yl)carbonylmethyl-2-oxo-3-benzyloxycarbonylamino-5-phenyl-1,3,4,5-tetrahydro-2H-1,5-benzodiazepine was used instead of 1-(N-phenyl-N-methylcarbamoylmethyl)-2-oxo-3-benzyloxycarbonylamino-5-phenyl-1,3,4,5-tetrahydro-2H-1,5-benzodiazepine, to thereby obtain the title compound.

Step 3

Preparation of 1-[1-(furan-2-y1)carbonylmethyl-2-oxo-5-phenyl-1,3,4,5-tetrahydro-2H-1,5-benzodiazepin-3-yl]-3-(4-ethoxycarbonylphenyl)urea Step 1 of Example 81 was repeated except that 1-(furan-2-yl)carbonylmethyl-2-oxo-3-amino-5-phenyl-1,3,4,5-tetrahydro-2H-1,5-benzodiazepine was used instead of 1-tert-butoxycarbonylmethyl-2-oxo-3-amino-5-phenyl-1,3,4,5-tetrahydro-2H-1,5-benzodiazepine and that ethyl 4-aminobenzoate was used instead of ethyl 3-aminophenylthioacetate, to thereby obtain the title compound.

$^1$H-NMR($CDCl_3$) δ: 1.37(3H, t), 3.73(1H, dd), 4.19(1H, dd), 4.32(2H, q), 4.93(1H, d), 4.91–5.03(1H, m), 5.35(1H, d), 6.48–6.56(2H, m), 6.74–6.90(3H, m), 7.12–7.37(9H, m), 7.55–7.65(2H, m), 7.78–7.90(2H, m)

Step 4

Preparation of 4-[3-[1-(furan-2-yl)carbonylmethyl-2-oxo-5-phenyl-1,3,4,5-tetrahydro-2H-1,5-benzodiazepin-3-yl] ureido]benzoic acid Step 4 of Example 10 was repeated except that 1-[1-(furan-2-yl)carbonylmethyl-2-oxo-5-phenyl-1,3,4,5-tetrahydro-2H-1,5-benzodiazepin-3-yl]-3-(4-ethoxycarbonylphenyl)urea was used instead of 1-(tert-butylcarbonylmethyl-2-oxo-5-pivaloyl-1,3,4,5-tetrahydro-2H-1,5-benzodiazepin-3-yl)-3-(3-ethoxycarbonylphenyl) urea, to thereby obtain the title compound.

$^1$H-NMR(DMSO-$d_6$) δ: 3.63(1H, dd), 4.04(1H, dd), 4.63 (1H, ddd), 5.10(1H, d), 5.36(1H, d), 6.73(1H, dd), 6.78–6.90 (4H, m), 7.13–7.37(5H, m), 7.40–7.49(3H, m), 7.61(1H, d), 7.80(2H, d), 8.03(1H, d), 9.27(1H, s), 12.40–12.60(1H, br)

MS(FAB)m/z: 525(MH)$^+$

Example 84

Preparation of 3-[3-[1-(2-toluoylmethyl)-2-oxo-5-(piperidin-4-yl)carbonyl-1,3,4,5-tetrahydro-2H-1,5-benzodiazepin-3-yl]ureido]benzoic acid hydrochloride Step 1

Preparation of 2-oxo-3-tert-butoxycarbonylamino-5-(N-benzyloxycarbonylpiperidin-4-yl)carbonyl-1,3,4,5-tetrahydro-2H-1,5-benzodiazepine Step 1 of Example 60 was repeated except that (N-benzyloxycarbonyl)isonipecotic acid was used instead of (N-benzyloxycarbonyl)pipecolinic acid, to thereby obtain the title compound.

$^1$H-NMR($CDCl_3$) δ: 1.23–1.95(6H, m), 1.40(9H, s), 2.11–2.68(3H, m), 3.80–4.30(3H, m), 4.40–4.63(2H, m), 5.08(2H, s), 5.40–5.48(1H, m), 7.13–7.54(9H, m), 7.60–7.73(1H, br)

Step 2

Preparation of 1-(2-toluoylmethyl)-2-oxo-3-tert-butoxycarbonylamino-5-(N-benzyloxycarbonylpiperidin-4-yl)carbonyl-1,3,4,5-tetrahydro-2H-1,5-benzodiazepine Step 2 of Example 1 was repeated except that 2-oxo-3-tert-butoxycarbonylamino-5-(N-benzyloxycarbonyl-piperidin-4-yl)carbonyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.40(9H, s), 1.60–1.90(4H, m), 2.32–2.70(3H, m), 2.44(3H, s), 3.85(1H, dd), 4.00–4.27(2H, br), 4.43–4.66(2H, m), 5.05–5.23(2H, m), 5.10(2H, s), 5.47 (1H, d), 7.22–7.49(12H, m)

Step 3

Preparation of 1-[1-(2-toluoylmethyl)-2-oxo-5-(N-benzyloxycarbonylpiperidin-4-yl)carbonyl-1,3,4,5-tetrahydro-2H-1,5-benzodiazepin-3-yl]-3-(3-benzyloxycarbonylphenyl)urea Step 3 of Example 1 was repeated except that 1-(2-toluoylmethyl)-2-oxo-3-tert-butoxycarbonylamino-5-(N-benzyloxycarbonylpiperidin-4-yl)carbonyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine. Subsequently, in a similar manner to Step 3 of Example 56, to thereby obtain the title compound.

$^1$H-NMR(DMSO-$d_6$) δ: 1.40–1.90(4H, m), 2.25–2.70 (3H, m), 2.37(3H, s), 3.65(1H, dd), 3.86–4.06(2H, m), 4.37–4.62(2H, m), 5.04(2H, s), 5.26(1H, d), 5.32(2H, s), 5.37(1H, d), 6.72(1H, d), 7.26–7.62(20H, m), 7.97(1H, d), 8.04(1H, brs), 9.09(1H, s)

Step 4

Preparation of 3-[3-[1-(2-toluoylmethyl)-2-oxo-5-(piperidin-4-yl)carbonyl-1,3,4,5-tetrahydro-2H-1,5-benzodiazepin-3-yl]ureido]benzoic acid hydrochloride Step 5 of Example 31 was repeated except that 1-[1-(2-toluoylmethyl)-2-oxo-5-(N-benzyloxycarbonylpiperidin-4-yl)carbonyl-1,3,4,5-tetrahydro-2H-1,5-benzodiazepin-3-yl]-

3-(3-benzyloxycarbonylphenyl)urea was used instead of -[1-(1-methylpiperidin-4-yl)carbamoylmethyl-2-oxo-5-pivaolyl-1,3,4,5-tetrahydro-2H-1,5-benzodiazepin-3-yl]-3-(3-benzyloxycarbonylphenyl)urea, to thereby obtain the title compound.

Melting point: 216–226° C. (decomposition)

$^1$H-NMR(DMSO-$d_6$) δ: 1.70–2.05(4H, m), 2.37(3H, s), 2.33–2.74(3H, m), 3.12–3.38(2H, m), 4.37–4.63(2H, m), 5.33(2H, s), 6.85(1H, d), 7.28–7.64(11H, m), 7.96(1H, d), 8.01(1H, t), 8.50–9.00(2H, br), 9.20(1H, brs), 12.60–13.00 (1H, br)

MS(FAB)m/z: 584(MH)$^+$

Example 85

Preparation of 4-[3-[1-(2-toluoylmethyl)-2-oxo-5-benzoyl-8-methyl-1,3,4,5-tetrahydro-2H-1,5-benzodiazepin-3-yl]ureido]benzoic acid Step 1

Preparation of 2-oxo-3-tert-butoxycarbonylamino-5-benzoyl-8-methyl-1,3,4,5-tetrahydro-2H-1,5-benzodiazepine Step 1 of Example 1 was repeated except that benzoyl chloride was used instead of pivaloyl chloride and that 2-oxo-3-tert-butoxycarbonylamino-8-methyl-1,3,4,5-tetrahydro-2H-1,5-benzodiazepine obtained from Referential Example 4 was used instead of 2-oxo-3-tert-butoxycarbonylamino-1,3,4,5-tetrahydro-2H-1,5-benzodiazepine, to thereby obtain the title compound.

$^1$H-NMR($CDCl_3$) δ: 1.43(9H, s), 2.27(3H, s), 4.15(1H, dd), 4.32–4.50(1H, m), 4.60–4.73(1H, m), 5.54(1H, d), 6.57–6.80(2H, m), 6.92(1H, s), 7.08–7.32(5H, m), 8.08(1H, brs)

Step 2

Preparation of 1-(2-toluoylmethyl)-2-oxo-3-tert-butoxycarbonylamino-5-benzoyl-8-methyl-1,3,4,5-tetrahydro-2H-1,5-benzodiazepine Step 2 of Example 1 was repeated except that 2-oxo-3-tert-butoxycarbonylamino-5-benzoyl1–8-methyl-1,3,4,5-tetrahydro-2H-1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.41(9H, s), 2.27(3H, s), 2.57(3H, s), 4.16(1H, dd), 4.28–4.44(1H, m), 4.64–4.86(2H, m), 5.42–5.64(2H, m), 6.58–6.80(2H, m), 7.01(1H, s), 7.10–7.52(8H, m), 7.83(1H, d)

Step 3

Preparation of 1-[1-(2-toluoylmethyl)-2-oxo-5-benzoyl-8-methyl-1,3,4,5-tetrahydro-2H-1,5-benzodiazepin-3-yl]-3-(4-ethoxycarbonylphenyl)urea Step 2 of Example 10 was repeated except that 1-(2-toluoylmethyl)-2-oxo-3-tert-butoxycarbonylamino-5-benzoyl-8-methyl-1,3,4,5-tetrahydro-2H-1,5-benzodiazepine was used instead of 1-tert-butylcarbonylmethyl-2-oxo- 3-tert-butoxycarbonylamino-5-pivaloyl-1,3,4,5-tetrahydro-2H-1,5-benzodiazepine. Subsequently, Step 3 of Example 10 was repeated except that ethyl 4-aminobenzoate was used instead of ethyl 3-aminobenzoate, to thereby obtain the title compound.

$^1$H-NMR(DMSO-$d_6$) δ: 1.29(3H, t), 2.27(3H, s), 2.45(3H, s), 3.87–3.98(1H, m), 4.20–4.37(1H, m), 4.25(2H, q), 4.60–4.73(1H, m), 5.18(1H, d), 5.52(1H, d), 6.77–7.00(3H, m), 7.15–7.63(11H, m), 7.83(2H, d), 8.03(1H, d), 9.28(1H, brs)

Step 4

Preparation of 4-[3-[1-(2-toluoylmethyl)-2-oxo-5-benzoyl-8-methyl-1,3,4,5-tetrahydro-2H-1,5-benzodiazepin-3-yl]ureido]benzoic acid Step 4 of Example 10 was repeated except that 1-[1-(2-toluoylmethyl)-2-oxo-5-benzoyl-8-methyl-1,3,4,5-tetrahydro-2H-1,5-benzodiazepin-3-yl]-3-(4-ethoxycarbonylphenyl)urea was used instead of 1-(1-tertbutylcarbonylmethyl-2-oxo-5-pivaloyl-1,3,4,5-tetrahydro-2H-1,5-benzodiazepin-3-yl]-3-(3-ethoxycarbonylphenyl)urea, to thereby obtain the title compound.

Melting point: 210–222° C. (decomposition)

$^1$H-NMR(DMSO-$d_6$) δ: 2.28(3H, s), 2.45(3H, s), 3.85–3.98(1H, m), 4.22–4.37(1H, m), 4.67(1H, ddd), 5.18 (1H, d), 5.51(1H, d), 6.78–6.92(2H, m), 6.99(1H, d), 7.15–7.56(11H, m), 7.81(2H, d), 8.03(1H, d), 9.28(1H, s), 11.50–12.80(1H, br)

MS(FAB)m/z: 591(MH)$^+$

Example 86

Preparation of 3-[3-[1-(2-toluoylmethyl)-2-oxo-5-benzoyl-8-methyl-1,3,4,5-tetrahydro-2H-1,5-benzodiazepin-3-yl]ureido]benzoic acid Step 1

Preparation of 1-[1-(2-toluoylmethyl)-2-oxo-5-benzoyl-8-methyl-1,3,4,5-tetrahydro-2H-1,5-benzodiazepin-3-yl]-3-(3-ethoxycarbonylphenyl)urea Step 2 of Example 10 was repeated except that 1-(2-toluoylmethyl)-2-oxo-3-tert-butoxycarbonylamino-5-benzoyl-8-methyl-1,3,4,5-tetrahydro-2H-1,5-benzodiazepine obtained from Step 2 of Example 85 was used instead of 1-tert-butylcarbonylmethyl-2-oxo-3-tert-butoxycarbonylamino-5-pivaloyl-1,3,4,5-tetrahydro-2H-1,5-benzodiazepine. Subsequently, in a similar manner to Step 3 of Example 10, to thereby obtain the title compound.

$^1$H-NMR(DMSO-$d_6$) δ: 1.30(3H, t), 2.28(3H, s), 2.46(3H, s), 3.86–3.98(1H, m), 4.22– 4.38(1H, m), 4.28(2H, q), 4.60–4.74(1H, m), 5.18(1H, d), 5.51(11H, d), 6. 75–6.93 (3H, m), 7.16–7.57(12H, m), 8.03(1H, d)

Step 2

Preparation of 3-[3-[1-(2-toluoylmethyl)-2-oxo-5-benzoyl-8-methyl-1,3,4,5-tetrahydro-2H-1,5-benzodiazepin-3-yl]ureido]benzoic acid Step 4 of Example 10 was repeated except that 1-[1-(2-toluoylmethyl)-2-oxo-5-benzoyl-8-methyl-1,3,4,5-tetrahydro-2H-1,5-benzodiazepin-3-yl]-3-(3-ethoxycarbonylphenyl)urea was used instead of 1-(1-tert-butylcarbonylmethyl-2-oxo-5-pivaloyl-1,3,4,5-tetrahydro-2H-1,5-benzodiazepin-3-yl)-3-(3-ethoxycarbonylphenyl) urea, to thereby obtain the title compound.

Melting point: 250–251° C. (decomposition)

$^1$H-NMR(DMSO-$d_6$) δ: 2.28(3H, s), 2.46(3H, s), 3.85–3.98(1H, m), 4.22–4.38(1H, m), 4.67(1H, dt), 5.18(1H, d), 5.51(1H, d), 6.76–6.92(3H, m), 7.15–7.56(12H, m), 7.99–8.07(2H, m), 9.07(1H, s), 12.50–13.00(1H, br)

MS(FAB)m/z: 591(MH)$^+$

Example 87

Preparation of 3-[3-[1-(2-toluoylmethyl)-2-oxo-5-cyclopentylcarbonyl-8-methyl-1,3,4,5-tetrahydro-2H-1,5-benzodiazepin-3-yl]ureido]benzoic acid Step 1

Preparation of 2-oxo-3-tert-butoxycarbonylamino-5-cyclopentylcarbonyl-8-methyl-1,3,4,5-tetrahydro-2H-1,5-benzodiazepine Step 1 of Example 1 was repeated except that cyclopentylcarbonyl chloride was used instead of pivaloyl chloride, and that 2-oxo-3-tert-butoxycarbonylamino-8-methyl-1,3,4,5-tetrahydro-2H-1,5-benzodiazepine obtained from Referential Example 4 was used instead of 2-oxo-3-tert-butoxycarbonylamino-1,3,4,5-tetrahydro-2H-1,5-benzodiazepine, to thereby obtain the title compound.

$^1$H-NMR($CDCl_3$) δ: 1.25–1.48(4H, m), 1.41(9H, s), 1.52–1.75(3H, m), 1.80–1.95(1H, m), 2.32–2.47(1H, m), 2.39(3H, s), 3.75–3.84(1H, m), 4.46–4.65(2H, m), 5.42(1H, d), 6.96(1H, s), 7.05–7.15(2H, m), 7.67(1H, s)

Step 2

Preparation of 1-(2-toluoylmethyl)-2-oxo-3-tert-butoxycarbonylamino-5-cyclopentylcarbonyl-8-methyl-1,3,4,5-tetrahydro-2H-1,5-benzodiazepine Step 2 of Example 1 was repeated except that 2-oxo-3-tert-butoxycarbonylamino-5-cyclopentylcarbony1–8-methyl-1,3,4,5-tetrahydro-2H- 1,5-benzodiazepine was used instead of 2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 1.30–1.95(8H, m), 1.40(9H, s), 2.38 (3H, s), 2.45–2.60(1H, m), 2.51(3H, s), 3.75–1 3.85(1H, m), 4.47–4.67(2H, m), 4.86(1H, d), 5.21(1H, d), 5.48(1H, d), 7.06(1H, s), 7.08–7.17(2H, m), 7.25–7.35(2H, m), 7.39–7.47(1H, m), 7.72–7.77(1H, m)

Step 3

Preparation of 1-[1-(2-toluoylmethyl)-2-oxo-5-cyclopentylcarbonyl-8-methyl-1,3,4,5-tetrahydro-2H-1,5-benzodiazepin-3-yl]-3-(3-ethoxycarbonylphenyl)urea Step 2 of Example 10 was repeated except that 1-(2-toluoylmethyl)-2-oxo-3-tert-butoxycarbonylamino-5-cyclopentylcarbonyl-8-methyl-1,3,4,5-tetrahydro-2H-1,5-benzodiazepine was used instead of 1-tert-butylcarbonylmethyl-2-oxo-3-tert-butoxycarbonylamino-5-pivaloyl-1,3,4,5-tetrahydro-2H-1,5-benzodiazepine. Subsequently, in a similar manner to Step 3 of Example 10, to thereby obtain the title compound.

$^1$H-NMR(DMSO-$d_6$) δ: 1.25–1.48(2H, m), 1.30(3H, t), 1.53–1.77(6H, m), 2.35–2.53(1H, m), 2.40(6H, s), 3.60(1H, dd), 4.28(2H, q), 4.40–4.63(2H, m), 5.18(1H, d), 5.31(1H, d), 6.72(11H, d), 7.21–7.27(1H, m), 7.30–7.41(5H, m), 7.45–7.54(3H, m), 7.95(1H, d), 8.05(1H, t), 9.06(1H, s)

Step 4

Preparation of 3-[3-[1-(2-toluoylmethyl)-2-oxo-5-cyclopentylcarbonyl-8-methyl-1,3,4,5-tetrahydro-2H-1,5-benzodiazepin-3-yl]ureido]benzoic acid Step 4 of Example 10 was repeated except that 1-[1-(2-toluoylmethyl)-2-oxo-5-cyclopentylcarbonyl-8-methyl-1,3,4,5-tetrahydro-2H-1,5-benzodiazepin-3-yl]-3-(3-ethoxycarbonylphenyl)urea was used instead of 1-(1-tert-butylcarbonylmethyl-2-oxo-5-pivaloyl-1,3,4,5-tetrahydro-2H-1,5-benzodiazepin-3-yl)-3-(3-ethoxycarbonylphenyl) urea, to thereby obtain the title compound.

Melting point: 166–183° C. (decomposition)

$^1$H-NMR(DMSO-$d_6$) δ: 1.22–1.78(8H, m), 2.30–2.55 (1H, m), 2.39(6H, s), 3.55–3.65(1H, m), 4.40–4.63(2H, m), 5.18(1H, d), 5.31(1H, d), 6.72(1H, d), 7.21–7.41(6H, m), 7.45–7.54(3H, m), 7.96(1H, d), 8.01(1H, t), 9.01(1H, s), 12.60–13.00(1H, br)

MS(FAB)m/z: 583$(MH)^+$

Example 88

Preparation of (+)-3-[3-(1-tert-butylcarbonylmethyl-2-oxo-5-phenyl-1,3,4,5-tetrahydro-2H-1,5-benzodiazepin-3-yl)]ureido]phenylthioacetic acid and (−)-3-[3-(1-tert-butylcarbonylmethyl-2-oxo-5-phenyl-1,3,4,5-tetrahydro-2H-1,5-benzodiazepin-3-yl)]ureido]phenylthioacetic acid Step 1

Preparation of (−)-1-(1-tert-butylcarbonylmethyl-2-oxo-5-phenyl-1,3,4,5-tetrahydro-2H-1,5-benzodiazepin-3-yl)-3-(3-tert-butoxycarbonylmethylthiophenyl)urea Triphosgene (592 mg) was added to a solution of tert-butyl 3-aminophenylthioacetate (1.27 g) in tetrahydrofuran (100 ml) under ice-cooling, triethylamine (2.5 ml) was added thereto five times each 0.5 ml over 15 minutes, and the mixture was stirred at room temperature for 5 minutes. A solution of (−)-1-tert-butylcarbonylmethyl-2-oxo-3-amino-5-phenyl-1,3,4,5-tetrahydro-2H-1,5-benzodiazepine (1.7 g) obtained from Step 7 of Example 70 in tetrahydrofuran (20 ml) was added to the mixture, stirred at room temperature for one hour. The reaction mixture was concentrated under reduced pressure, water was added to the residue, extracted with methylene chloride. The organic layer was dried over anhydrous sodium sulfate, the mixture was purified by silica gel column chromatography (n-hexane:ethyl acetate=2:1), to thereby obtain 2.75 g of the title compound.

[α] $D^{20}$ (C=1.05, $CHCl_3$): −94.7°

$^1$H-NMR($CDCl_3$) δ: 1.24(9H, s), 1.38(9H, s), 3.54(2H, s), 3.68(1H, dd), 4.18(1H, dd), 4.40(1H, d), 4.85–4.94(1H, m), 5.17(1H, d), 6.36(1H, d), 6.76–7.22(13H, m), 7.44(1H, s)

Step 2

Preparation of (+)-1-(1-tert-butylcarbonylmethyl-2-oxo-5-phenyl-1,3,4,5-tetrahydro-2H-1,5-benzodiazepin-3-yl)-3-(3-tert-butoxycarbonylmethylthiophenyl)urea Step 1 was repeated except that (+)-1-tert-butylcarbonylmethyl-2-oxo-3-amino-5-phenyl-1,3,4,5-tetrahydro-2H-1,5-benzodiazepine was used instead of (−)-1-tert-butylcarbonylmethyl-2-oxo-3-amino-5-phenyl-1,3,4,5-tetrahydro-2H-1,5-benzodiazepine, to thereby obtain the title compound.

[α] $D^{25}$ (C=1.03, $CHCl_3$): +95.8°

Step 3

Preparation of (−)-3-[3-(1-tert-butylcarbonylmethyl-2-oxo-5-phenyl-1,3,4,5-tetrahydro-2H-1,5-benzodiazepin-3-yl)]ureido]phenylthioacetic acid Trifluoroacetic acid (20 ml) was added to a solution of (−)-1-( 1-tert-butylcarbonylmethyl-2-oxo-5-phenyl-1,3,4,5-tetrahydro-2H-1,5-benzodiazepin-3-yl)-3-(3-tert-butoxycarbonylmethylthiophenyl)urea (2.75 g) in methylene chloride (20 ml), the mixture was stirred at room temperature for 3 hours. The reaction mixture was concentrated under reduced pressure and the resultant residue was purified by silica gel column chromatography (chloroform:methanol=5:1), to thereby obtain 2.5 g of the title compound.

[α] $D^{20}$ (C=0.62, $CHCl_3$): −45.8°

Step 4

Preparation of (+)-3-[3-(1-tert-butylcarbonylmethyl-2-oxo-5-phenyl-1,3,4,5-tetrahydro-2H-1,5-benzodiazepin-3-yl) ]ureido]phenylthioacetic acid Step 3 was repeated except that (+)-1-(1-tert-butylcarbonylmethyl-2-oxo-5-phenyl-1,3,4,5-tetrahydro-2H-1,5-benzodiazepin-3-yl)-3-(3-tert-butoxycarbonylmethylthiophenyl)urea was used instead of (−)-1-(1-tert-butylcarbonylmethyl-2-oxo-5-phenyl-1,3,4,5-tetrahydro-2H-1,5-benzodiazepin-3-yl)-3-(3-tert-butoxycarbonylmethylthiophenyl)urea, to thereby obtain the title compound.

[α] $D^{25}$ (C=0.50, $CHCl_3$): +44.0°

The structure of these compounds obtained from Examples 1–88 was shown in Tables 1–12.

TABLE 1
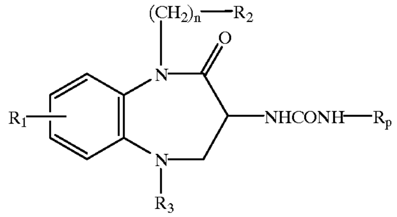
| Example | $R_1$ | $R_2$ | $R_3$ | $R_p$ | n |
|---|---|---|---|---|---|
| 1 | H | 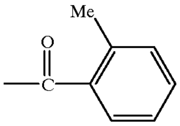 | 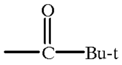 | 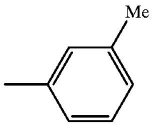 | 1 |
| 2 | H | 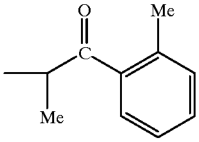 | 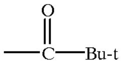 | 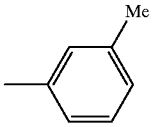 | 0 |
| 3 | H | 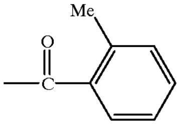 | 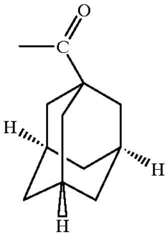 | 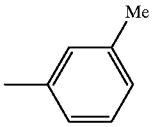 | 1 |
| 4 | 8-Me | 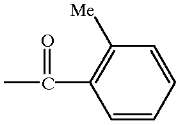 | 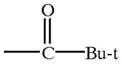 | 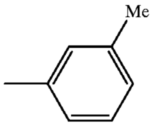 | 1 |
| 5 | 8-F | 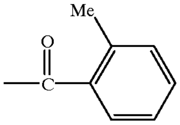 | 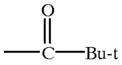 | 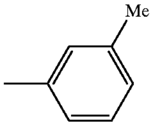 | 1 |
| 6 | H | 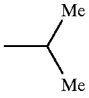 | 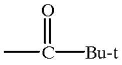 | 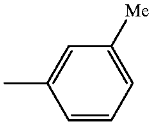 | 1 |
| 7 | H | 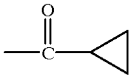 | 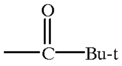 | 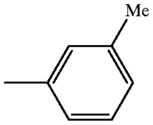 | 1 |

TABLE 2
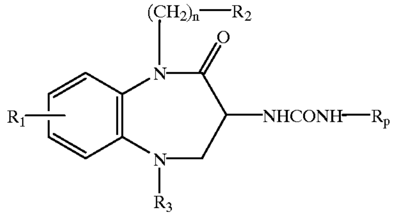
| Example | $R_1$ | $R_2$ | $R_3$ | $R_p$ | n |
|---|---|---|---|---|---|
| 8 | H | 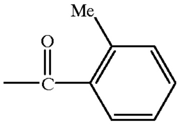 | 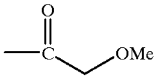 | 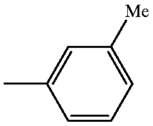 | 1 |
| 9 | H | 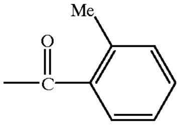 | 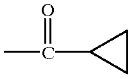 | 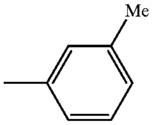 | 1 |
| 10 | H | 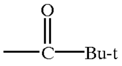 | 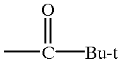 | 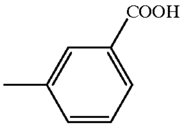 | 1 |
| 11 | H | 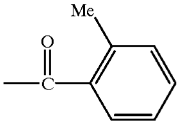 | 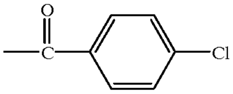 | 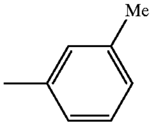 | 1 |
| 12 | H | 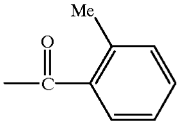 | 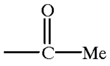 | 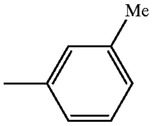 | 1 |
| 13 | 8-Me | 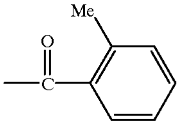 | 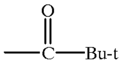 | 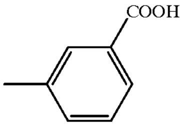 | 1 |
| 14 | H | 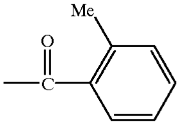 | 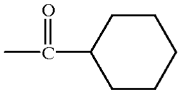 | 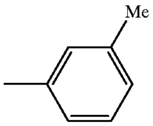 | 1 |

TABLE 3
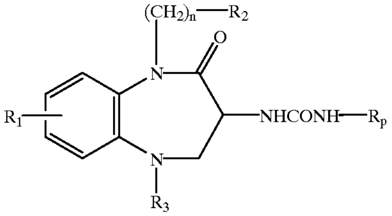
| Example | $R_1$ | $R_2$ | $R_3$ | $R_p$ | n |
|---|---|---|---|---|---|
| 15 | H | 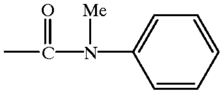 | 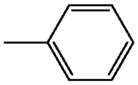 | 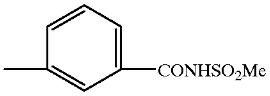 | 1 |
| 16 | H | 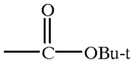 | 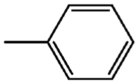 | 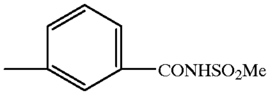 | 1 |
| 17 | H | $—CF_3$ | 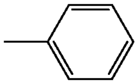 | 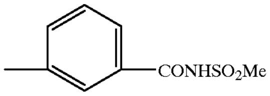 | 1 |
| 18 | H | 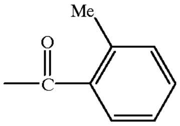 | 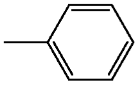 | 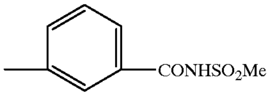 | 1 |
| 19 | H | $—CH_2OMe$ | 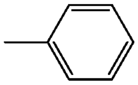 | 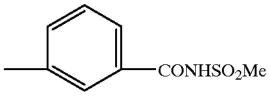 | 0 |
| 20 | H | H | 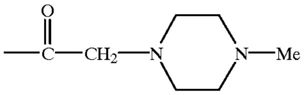 | 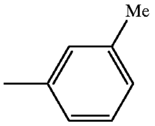 | 0 |
| 21 | H | 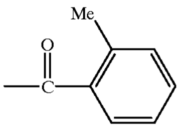 | 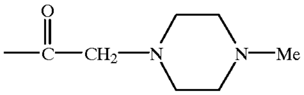 | 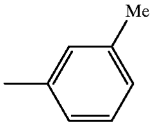 | 1 |
| 22 | H | 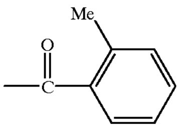 | 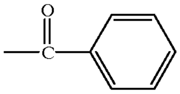 | 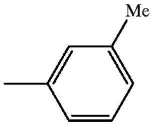 | 1 |

TABLE 4
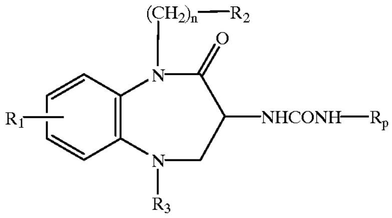
| Example | $R_1$ | $R_2$ | $R_3$ | $R_p$ | n |
|---|---|---|---|---|---|
| 23 | H | 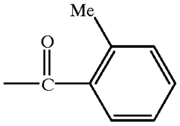 | 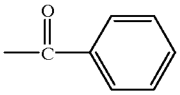 | 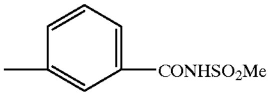 | 1 |
| 24 | H | 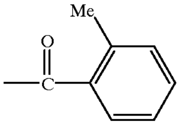 | 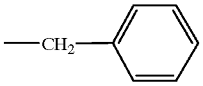 | 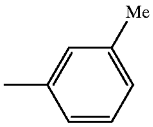 | 1 |
| 25 | H | 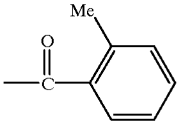 | 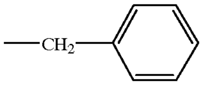 | 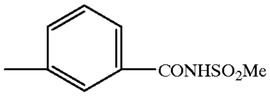 | 1 |
| 26 | H | 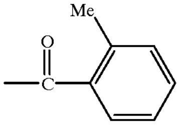 | 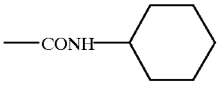 | 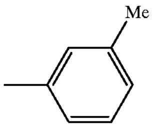 | 1 |
| 27 | H | 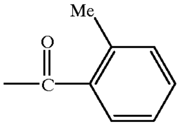 | $-CONMe_2$ | 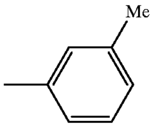 | 1 |
| 28 | H | 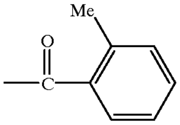 | 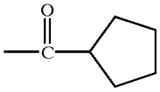 | 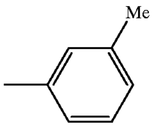 | 1 |
| 29 | H | 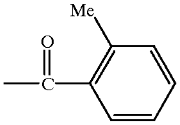 | 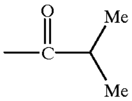 | 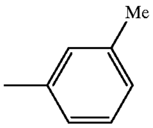 | 1 |
| 30 | H | 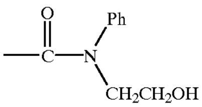 | 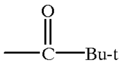 | 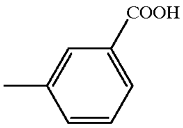 | 1 |

TABLE 5
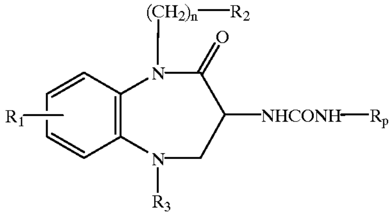
| Example | $R_1$ | $R_2$ | $R_3$ | $R_p$ | n |
|---|---|---|---|---|---|
| 31 ※ | H | 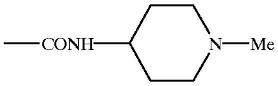 | 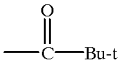 | 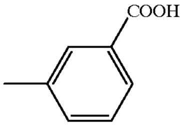 | 1 |
| 32 | H | 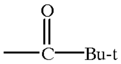 | 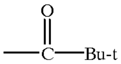 | 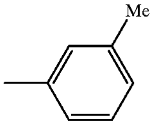 | 1 |
| 33 | H | 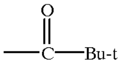 | 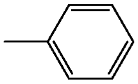 | 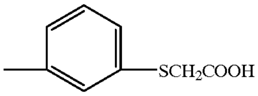 | 1 |
| 34 | H | 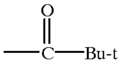 | 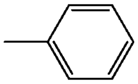 | 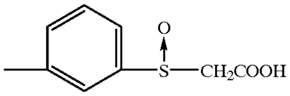 | 1 |
| 35 | H | 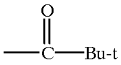 | 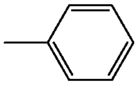 | 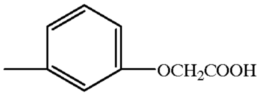 | 1 |
| 36 | H | 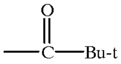 | 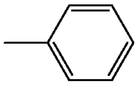 | 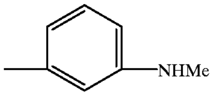 | 1 |
| 37 | H | 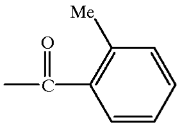 | 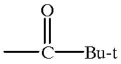 | 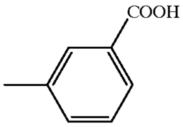 | 1 |
※: monohydrochloride TABLE 6
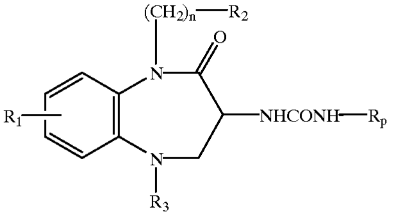
| Example | $R_1$ | $R_2$ | $R_3$ | $R_p$ | n |
|---|---|---|---|---|---|
| 38 | H | 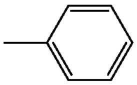 | 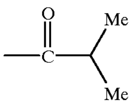 | 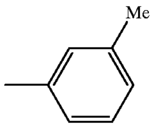 | 0 |
| 39 | H | 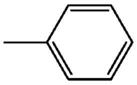 | 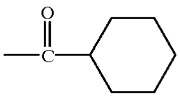 | 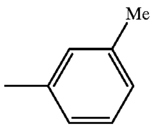 | 0 |
| 40 | H | —CONH—Bu-t | 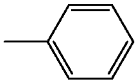 | 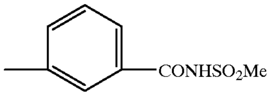 | 1 |
| 41 | H | 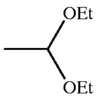 | 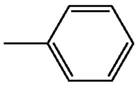 | 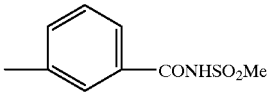 | 1 |
| 42 | H | —COOH | 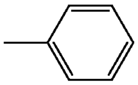 | 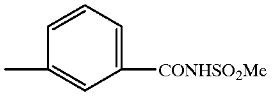 | 1 |
| 43 | H | 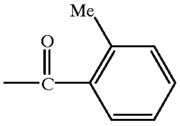 | 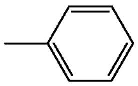 | 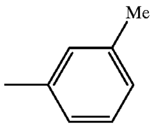 | 1 |
| 44 | H | 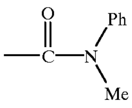 | Me | 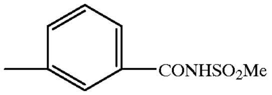 | 1 |
| 45 | H | 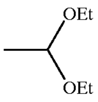 | 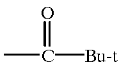 | 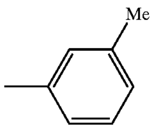 | 1 |

TABLE 7
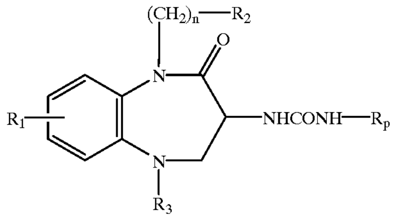
| Example | $R_1$ | $R_2$ | $R_3$ | $R_p$ | n |
|---|---|---|---|---|---|
| 46 | H | 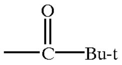 | 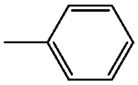 | 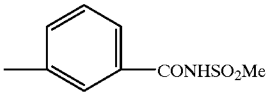 | 1 |
| 47 | H | 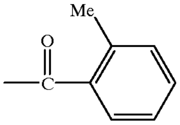 | $—SO_2Me$ | 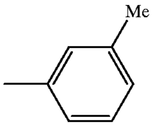 | 1 |
| 48 | H | 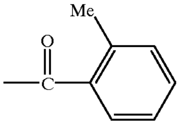 | 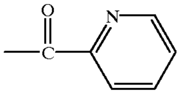 | 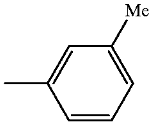 | 1 |
| 49 | H | 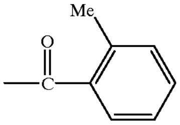 | —COOMe | 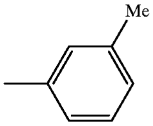 | 1 |
| 50 | H | 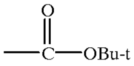 | 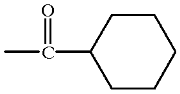 | 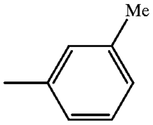 | 1 |
| 51 | H | 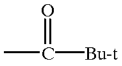 | 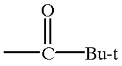 | 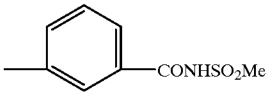 | 1 |
| 52 | H | $—CONMe_2$ | 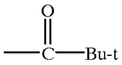 | 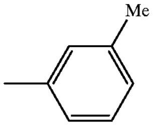 | 1 |
| 53 | H | 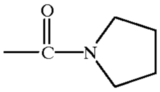 | 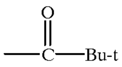 | 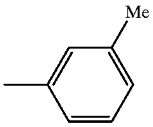 | 1 |

TABLE 8
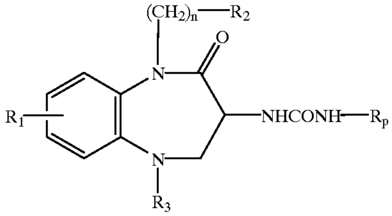
| Example | $R_1$ | $R_2$ | $R_3$ | $R_p$ | n |
|---|---|---|---|---|---|
| 54 | H | 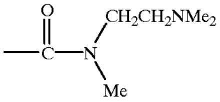 | 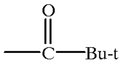 | 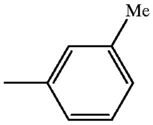 | 1 |
| 55 | H | 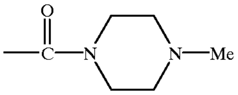 | 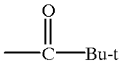 | 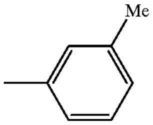 | 1 |
| 56 (*) | H | 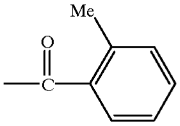 | 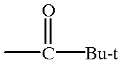 | 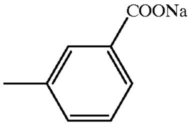 | 1 |
| 57 | H | 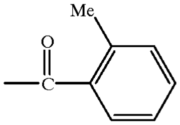 | 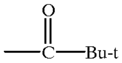 | 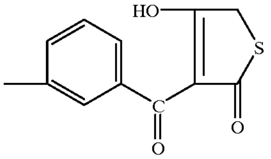 | 1 |
| 58 | H | 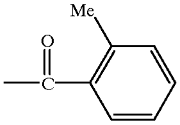 | 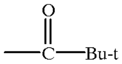 | 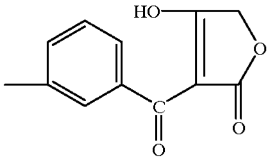 | 1 |
| 59 | H | 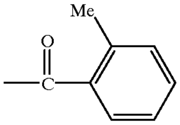 | 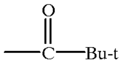 | 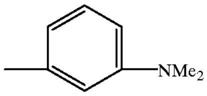 | 1 |
| 60 | H | 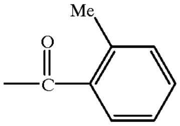 | 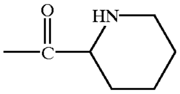 | 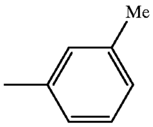 | 1 |
(*): optically active compound TABLE 9
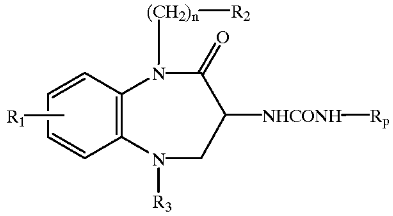
| Example | $R_1$ | $R_2$ | $R_3$ | $R_p$ | n |
|---|---|---|---|---|---|
| 61 | H | 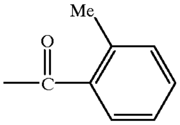 | 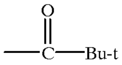 | 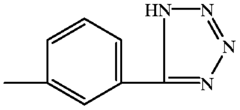 | 1 |
| 62 | H | 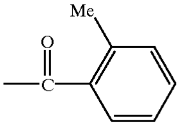 | 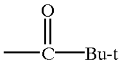 | 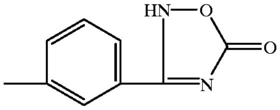 | 1 |
| 63 | H | 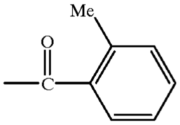 | 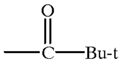 | 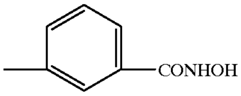 | 1 |
| 64 | H | 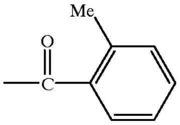 | 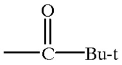 | 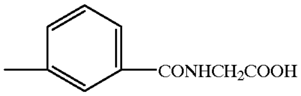 | 1 |
| 65 | H | 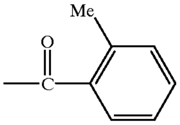 | 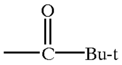 | 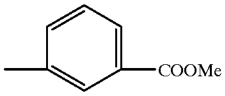 | 1 |
| 66 ·X· | H | 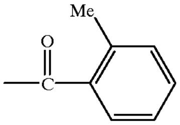 | 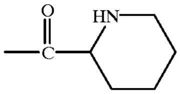 | 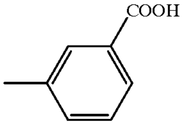 | 1 |
| 67 ·X· | H | 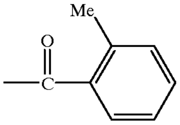 | 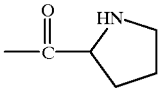 | 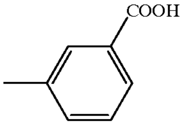 | 1 |
·X·: monohydrochloride TABLE 10
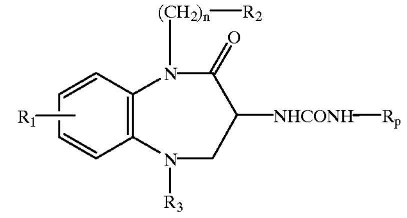
| Example | $R_1$ | $R_2$ | $R_3$ | $R_p$ | n |
|---|---|---|---|---|---|
| 68 | H | 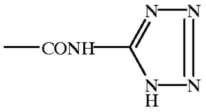 | 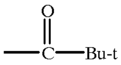 | 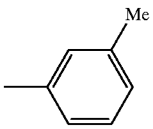 | 1 |
| 69 | H | 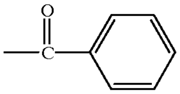 | 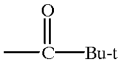 | 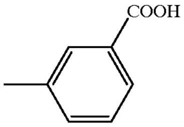 | 1 |
| 70 (*) | H | 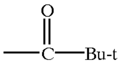 | 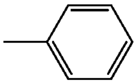 | 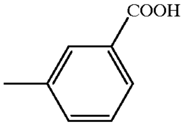 | 1 |
| 71 | H | 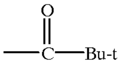 | 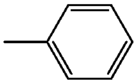 | 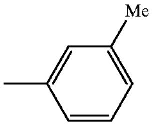 | 1 |
| 72 | H | 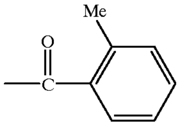 | 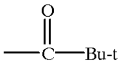 | 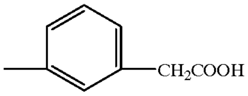 | 1 |
| 73 | H | 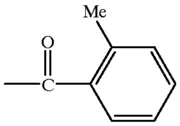 | 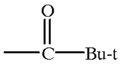 | 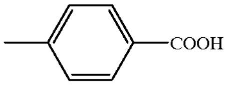 | 1 |
| 74 | H | 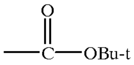 | 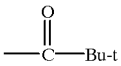 | 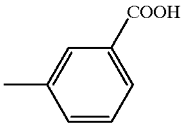 | 1 |
| 75 | H | 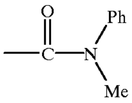 | 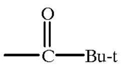 | 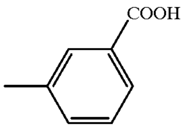 | 1 |
(*): optically active compound TABLE 11
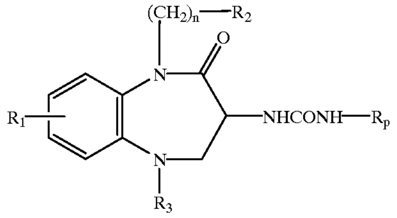
| Example | $R_1$ | $R_2$ | $R_3$ | $R_p$ | n |
|---|---|---|---|---|---|
| 76 | H | Me | 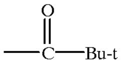 | 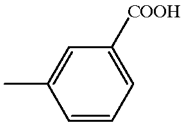 | 0 |
| 77 | H | 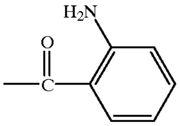 | 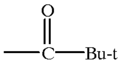 | 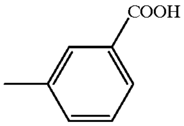 | 1 |
| 78 | H | 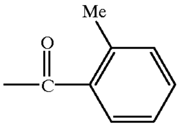 | 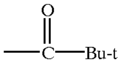 | 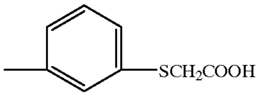 | 1 |
| 79 | H | 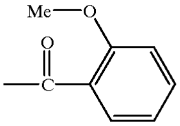 | 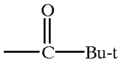 | 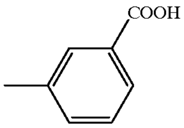 | 1 |
| 80 | H | 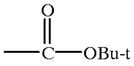 | 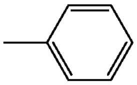 | 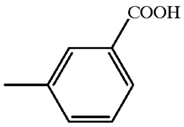 | 1 |
| 81 | H | 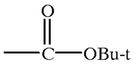 | 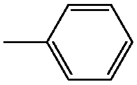 | 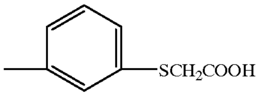 | 1 |
| 82 ※(*) | H | 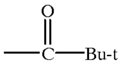 | 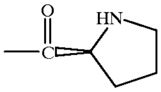 | 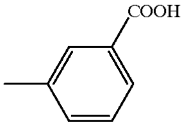 | 1 |
※: monohydrochloride
(*): optically active compound

TABLE 12

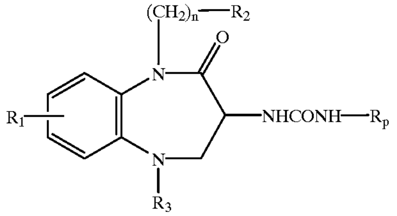

| Example | $R_1$ | $R_2$ | $R_3$ | $R_p$ | n |
| --- | --- | --- | --- | --- | --- |
| 83 | H | 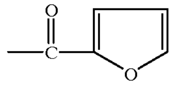 | 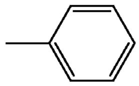 | 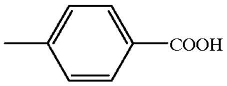 | 1 |
| 84 ※ | H | 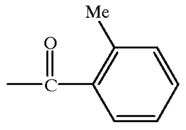 | 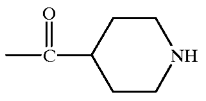 | 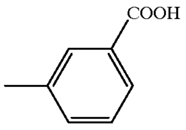 | 1 |
| 85 | 8-Me | 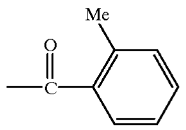 | 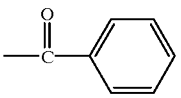 | 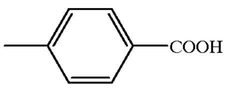 | 1 |
| 86 | 8-Me | 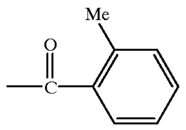 | 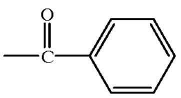 | 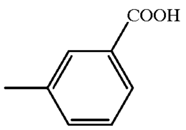 | 1 |
| 87 | 8-Me | 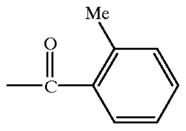 | 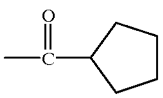 | 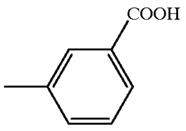 | 1 |
| 88 (*) | H | 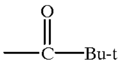 | 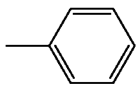 | 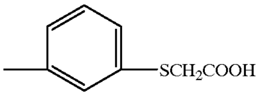 | 1 |

※: monohydrochloride
(*): optically active compound

Referential Example 7

Preparation of 2-oxo-3-tert-butoxycarbonylamino-8-methyl-1,3,4,5-tetrahydro-2H-1,5-benzodiazepine Potassium carbonate (6.91 g) was added to a solution of 3-amino-2-(tert-butoxycarbonyl)aminopropionic acid (5.11 g) obtained from Step 2 of Referential Example 1 and 4-fluoro-3-nitrotoluene (3.88 g) in ethanol (100 ml), the mixture was refluxed overnight. The reaction mixture was allowed to cool, filtrated, and the filtrate was concentrated under reduced pressure, to thereby obtain 3-(2-nitro-4-methyl)anilino-2-tert-butoxycarbonylaminopropionic acid.

$^1$H-NMR($CDCl_3$) δ: 1.43(9H, s), 2.26(3H, s), 3.55–3.89 (2H, m), 4.45–4.63(1H, m), 5.44(1H, d), 6.91(1H, d), 7.27 (1H, d), 7.94(1H, s), 8.14(1H, brs), 11.50(1H, brs)

This obtained compound was dissolved in water (200 ml), washed with diethyl ether, then adjusted to pH 3 with 1N hydrochloric acid, and extracted with methylene chloride. The organic layer was washed with saturated brine, dried over anhydrous sodium sulfate, and the solvent was evaporated. The residue was dissolved in ethanol (200 ml), 10% palladium carbon (1 g) was added, and the mixture was stirred for 5 hours under hydrogen atmosphere, under ambient pressure. The reaction mixture was filtrated, the filtrate was concentrated under reduced pressure, toluene was added and crystals so precipitated were collected by filtration, to thereby obtain 3-(2-amino-4-methylanilino)-2-tert-butoxycarbonylaminopropionic acid. This compound was suspended in toluene (100 ml), the mixture was refluxed overnight while water was removed by use of a Dean-Stark condenser. The reaction mixture was allowed to cool, crystals so precipitated were collected by filtration, and washed with isopropyl ether, subsequently, dried, to thereby obtain 1.66 g of the titled compound (Yield: 40%).

$^1$H-NMR(DMSO-$d_6$) δ: 1.36(9H, s), 2.17(3H, s), 3.25–3.32(1H, m), 3.43–3.49(1H, m), 4.07–4.18(1H, m), 5.30(1H, d), 6.70–6.76(3H, m), 6.83(1H, d), 9.61(1H, s)

Referential Example 8

Preparation of 2-oxo-3-benzyloxycarbonylamino-5-phenyl-8-methoxy-1,3,4,5-tetrahydro-2H-1,5-benzodiazepine Step 1

Preparation of N-phenyl-2-nitro-4-methoxyaniline

2-Nitro-4-methoxyaniline (75 g), bromobenzene (270 ml), potassium carbonate (31 g), copper powder (5.0 g) and potassium iodide (2.1 g) were mixed, the mixture was refluxed for 24 hours. The reaction mixture was allowed to cool. Insoluble products were removed by filtration. The filtrate was concentrated under reduced pressure, and the residue was purified by silica gel column chromatography (n-hexane:ethyl acetate=10:1), to thereby obtain 51 g of the titled compound as dark red crystals.

$^1$H-NMR($CDCl_3$) δ: 3.82(3H, s), 7.04–7.64(8H, m), 9.33 (1H, brs)

Step 2

Preparation of N-phenyl-N-(2-cyanoethyl)-2-nitro-4-methoxyaniline

N-phenyl-2-nitro-4-methoxyaniline (51 g) was dissolved in acrylonitrile (250 ml), triton B (40% benzyltrimethylammonium hydroxide in methanol solution) (1.0 ml) was added, and the mixture was stirred for 5 hours at room temperature. The reaction mixture was concentrated, the residue was purified by silica gel column chromatography (n-hexane:ethyl acetate=4:1), to thereby 39.5 g of the titled compound as orange-yellow crystals.

$^1$H-NMR($CDCl_3$) δ: 2.77(2H, t), 3.90(3H, s), 4.00(2H, t), 6.51–7.46(8H, m)

Step 3

Preparation of N-phenyl-N-(2-cyanoethyl)-2-amino-4-methoxyaniline

N-Phenyl-N-(2-cyanoethyl)-2-nitro-4-methoxyaniline (39.5 g) was dissolved in tetrahydrofuran (200 ml), 10% palladium carbon (4.0 g) was added, the mixture was stirred for 9 hours under hydrogen atmosphere. Palladium carbon was removed by filtration, the filtrate was concentrated under reduced pressure, to thereby obtain 35.6 g of the titled compound (Yield: 100%).

$^1$H-NMR($CDCl_3$) δ: 2.67(2H, t), 3.79(3H, s), 3.81(2H, brs), 3.92(3H, t), 6.34–7.24(8H, m)

Step 4

Preparation of 3-[N-(2-amino-4-methoxyphenyl)-N-phenyl]aminopropionic acid

N-Phenyl-N-(2-cyanoethyl)-2-amino-4-methoxyaniline (35.6 g) was dissolved in ethanol (200 ml), a solution (400 ml) of aqueous potassium hydroxide (71g) was added, the mixture was refluxed for 4 hours. The reaction mixture was allowed to cool, adjusted to pH 2 with concentrated hydrochloric acid, and extracted with chloroform. The organic layer was successively washed with water and saturated brine, dried over anhydrous sodium sulfate, and the solvent was evaporated under reduced pressure, to thereby obtain 38.1 g of the titled compound (Yield: 100%).

$^1$H-NMR($CDCl_3$) δ: 2.70(2H, t), 3.78(3H, s), 3.90(2H, t), 5.00(3H, br), 6.33–7.21(8H, m)

Step 5

Preparation of 2-oxo-5-phenyl-8-methoxy-1,3,4,5-tetrahydro-2H-1,5-benzodiazepine 3-[N-(2-Amino-4-methoxyphenyl)-N-phenyl]aminopropionic acid (38.1 g) was dissolved in xylene (500 ml), the solution was refluxed for 20 hours while water was removed by use of a Dean-Stark condenser. The reaction mixture was allowed to cool to room temperature, crystals so precipitated were collected by filtration, to thereby obtain 29.7 g of the titled compound (Yield: 83%).

$^1$H-NMR($CDCl_3$) δ: 2.65(2H, t), 3.82(3H, s), 4.00(2H, t), 6.61–6.83(5H, m), 7.13–7.22(2H, m), 7.34(1H, brs)

Step 6

Preparation of 1-methoxymethyl-2-oxo-5-phenyl-8-methoxy-1,3,4,5-tetrahydro-2H-1,5-benzodiazepine Under argon atmosphere, 60% sodium hydride (1.12 g) was suspended in tetrahydrofuran (10 ml), a solution of 2-oxo-5-phenyl-8-methoxy-1,3,4,5-tetrahydro-2H-1,5-benzodiazepine (5.0 g) in tetrahydrofuran (50 ml) was added thereto under ice-cooling, and the mixture was stirred for 40 minutes at same temperature. After ice bath was removeded, methoxymethyl chloride (2.25 g) was added, the mixture was stirred for 2 hours at room temperature. The reaction mixture was poured into ice-water, extracted with methylene chloride. The organic layer was successively washed with water and saturated brine, dried over anhydrous magnesium sulfate, and the solvent was evaporated under reduced pressure. The residue was purified by silica gel column chromatography (n-hexane:ethyl acetate=2:1), to thereby obtain 5.05 g of the titled compound as yellow-brown crystals (Yield: 87%).

$^1$H-NMR($CDCl_3$) δ: 2.64(2H, br), 3.34(3H, s), 3.83(3H, s), 3.93(2H, br), 5.19(2H, brs), 6.73–7.22(8H, m)

Step 7

Preparation of 1-methoxymethyl-2-oxo-3-hydroxyimino-5-phenyl-8-methoxy-1,3,4,5-hexahydro-2H-1,5-benzodiazepine Under argon atmosphere, 1-methoxymethyl-2-oxo-5-phenyl-8-methoxy-1,3,4,5-tetrahydro-2H-1,5-benzodiazepine (5.05 g) was dissolved in toluene (60 ml), under cooling potassium tert-butoxide (9.09 g) was added, stirred for 30 minutes at same temperature, tert-butyl nitrite (4.64g) was added thereto, and the mixture was stirred for 2 hours and 30 minutes at room temperature. Saturated brine was added to the reaction mixture, extracted with ethyl acetate. The organic layer was succesively washed with water and saturated brine, dried over anhydrous sodium sulfate, and the solvent was evaporated under reduced pressure. The residue was purified by silica gel column chromatography (chloroform:methanol=50:1), to thereby obtain 3.52 g of the titled compound as pale brown amorphous.

$^1$H-NMR($CDCl_3$) δ: 3.43(3H, s), 3.82(3H, s), 4.60(2H, br), 5.20(2H, br), 6.73–7.29(9H, m)

Step 8

Preparation of 1-methoxymethyl-2-oxo-3-propylaminocarbonyloxyimino-5-phenyl-8-methoxy-1,3,4,5-tetrahydro-2H-1,5-benzodiazepine 1-Methoxymethyl-2-oxo-3-hydroxyimino-5-phenyl-8-methoxy-1,3,4,5-tetrahydro-2H-1,5-benzodiazepine (1.0 g) was dissolved in tetrahydrofuran (10 ml), propyl isocyanate (0.62 g) and triethylamine (0.74 g) were added thereto, the mixture was refluxed for 2 hours and 30 minutes. The reaction mixture was allowed to cool to room temperature, crystals so precipitated were collected by filtration, and the crystals were washed with diisopropyl ether, to thereby obtain 0.78 g of the titled compound as white crystals.

$^1$H-NMR($CDCl_3$) δ: 0.91(3H, t), 1.47–1.60(2H, m), 3.15–3.20(2H, m), 3.42(3H, s), 3.82(3H, s), 4.43(1H, br), 4.91(1H, br), 5.21(1H, br), 5.32–5.65(1H, br), 6.23–7.27 (8H, m)

Step 9

Preparation of 1-methoxymethyl-2-oxo-3-amino-5-phenyl-8-methoxy-1,3,4,5-tetrahydro-2H-1,5-benzodiazepine 1-Methoxymethyl-2-oxo-3-propylaminocarbonyloxyimino-5-phenyl-8-methoxy-1,3,4,5-tetrahydro-2H-1,5-benzodiazepine (0.78 g) was suspended in methanol (20 ml), 10% palladium carbon (0.20 g)

was added thereto, the mixture was swung for 2 hours and 30 minutes under hydrogen atmosphere (3.5–3.0 kg/$cm^2$). The palladium carbon was removed by filtration, the filtrate was concentrated under reduced pressure. The residue was purified by silica gel column chromatography (chloroform:methanol=20:1), to thereby obtain 0.63 g of the titled compound.

$^1$H-NMR($CDCl_3$) δ: 1.73(2H, brs), 3.34(3H, s), 3.49–3.81 (2H, m), 3.83(3H, s), 3.87–3.92(1H, m), 5.15(1H, d), 5.31 (1H, d), 6.70–7.22(8H, m)

Step 10

Preparation of 2-oxo-3-benzyloxycarbonylamino-5-phenyl-8-methoxy-1,3,4,5-tetrahydro-2H-1,5-benzodiazepine 1-Methoxymethyl-2-oxo-3-amino-5-phenyl-8-methoxy-1,3,4,5-tetrahydro-2H-1,5-benzodiazepine (200 mg) was dissolved in 25% hydrobromic acid-acetic acid solution (1 ml), the solution was stirred for 2 hours. The reaction mixture was concentrated under reduced pressure, diisopropyl ether was added, the solid so precipitated was collected by filtration. The solid was dissolved in water (3 ml), a solution of benzyl chloroformate (140 mg) in tetrahydrofuran (3 ml) and 1N aqueous sodium hydroxide (2.8 ml) were successively added, and the mixture was stirred for one hours. Water was added to the resultant mixture, extracted with methylene chloride. The organic layer was successively washed with water and saturated brine, dried over anhydrous sodium sulfate. The solvent was evaporated under reduced pressure, the residue was purified by silica gel column chromatography (n-hexane:ethyl acetate=2:1), to thereby obtain 107 mg of the titled compound as colorless amorphous.

$^1$H-NMR($CDCl_3$) δ: 3.65(1H, m), 3.81(3H, s), 4.16–4.28 (1H, m), 4.61–4.70(1H, m), 5.09(2H, s), 5.83(1H, brd), 6.63–7.35(13H, m), 7.55(1H, brs)

Referential Example 9

Preparation of 2-oxo-3-benzyloxycarbonylamino-5-(2-fluorophenyl)-1,3,4,5-tetrahydro-2H-1,5-benzodiazepine Step 1

Preparation of N-(2-nitrophenyl)-2-fluoroaniline

2-Nitroaniline (14.9 g), 2-fluoronitrobenzene (29 g), potassium carbonate (14.9 g), copper powder (6.9 g) and xylene (100 ml) was mixed, the mixture was refluxed for 39 hours under argon atmosphere. The reaction mixture was allowed to cool, filtrated, and the filtrate was concentrated under reduced pressure. The residue was dissolved ethyl acetate, successively washed with water and saturated brine, dried over anhydrous sodium sulfate, and the solvent was evaporated under reduced pressure. The residue was purified by silica gel column chromatography (n-hexane:ethyl acetate=10:1), to thereby obtain 18.0 g of the titled compound as orange color crystals (Yield: 72%).

$^1$H-NMR($CDCl_3$) δ: 6.80–6.86(1H, m), 7.05–7.44(6H, m), 8.22(1H, dd), 9.30(1H, brs)

Step 2

Preparation of N-(2-nitrophenyl)-N-(2-cyanoethyl)-2-fluoroaniline

N-(2-Nitrophenyl)-2-fluoroaniline (17.8 g) was dissolved in acrylonitrile (100 ml), triton B (40% benzyltrimethylammonium hydroxide in methanol) (1.0 ml) was added, the mixture was stirred at 50–60° C. for 3 hours. The reaction mixture was concentrated under reduced pressure, the residue was purified by silica gel column chromatography (n-hexane:ethyl acetate=4:1), to thereby obtain 6.37 g of the titled compound as a orange color crystal.

$^1$H-NMR($CDCl_3$) δ: 3.81(2H, brs), 5.36(1H, brs), 6.64–7.13(8H, m)

Step 3

Preparation of N-(2-aminophenyl)-N-(2-cyanoethyl)-2-fluoroaniline

N-(2-Nitrophenyl)-N-(2-cyanoethyl)-2-fluoroaniline (6.37 g) was dissolved in methanol (60 ml), 10% palladium carbon (0.60 g) was added, the mixture was stirred for 3 hours under hydrogen atmosphere. Palladium carbon was removed by filtration, the filtrate was concentrated under reduced pressure, to thereby obtain 6.17 g of the titled compound (Yield: 100%).

$^1$H-NMR($CDCl_3$) δ: 2.73(2H, t), 4.08(2H, t), 6.87–7.77 (8H, m)

Step 4

Preparation of 3-[N-(2-aminophenyl)-N-(2-fluorophenyl) 3aminopropionic acid

N-(2-Aminophenyl)-N-(2-cyanoethyl)-2-fluoroaniline (6.18 g) was dissolved in ethanol (40 ml), aqueous potassium hydroxide (12.5 g) solution (80 ml) was added, the mixture was refluxed for 3 hours. The reaction mixture was allowed to cool, adjusted to pH 3 with concentrated hydrochloric acid, and extracted with methylene chloride. The organic layer was successively washed with water and saturated brine, dried over anhydrous sodium sulfate, and the solvent was evaporated under reduced pressure, to thereby obtain 5.6 g of the titled compound as brown amorphous (Yield: 86%).

$^1$H-NMR($CDCl_3$) δ: 2.68(2H, t), 3.86(2H, t), 6.70–7.10 (8H, m)

Step 5

Preparation of 2-oxo-5-(2-fluorophenyl)-1,3,4,5-tetrahydro-2H-1,5-benzodiazepine 3-[N-(2-Aminophenyl)-N-(2-fluorophenyl)] aminopropionic acid (5.6 g) was dissolved in xylene (60 ml), the solution was refluxed for 3 hours while water was removed by use of a Dean-Stark condenser. The reaction mixture was concentrated under reduced pressure, the residue was suspended in diisopropyl ether and collected by filtration, to thereby obtain 4.60 g of the titled compound as a pale brown crystal (Yield: 88%).

$^1$H-NMR($CDCl_3$) δ: 2.70(2H, t), 4.04(2H, t), 6.87–7.12 (8H, m), 8.00(1H, brs)

Step 6

Preparation of 1-methoxymethyl-2-oxo-5-(2-fluorophenyl)-1,3,4,5-tetrahydro-2H-1,5-benzodiazepine Under argon atmosphere, 60% sodium hydride (0.38 g) was suspended in N,N-dimethylformamide (5 ml), a solution of 2-oxo-5-(2-fluorophenyl)-1,3,4,5-tetrahydro-2H-1,5-benzodiazepine (1.89 g) in N,N-dimethylformamide (15 ml) was added dropwise over 15 minutes under ice-cooling, the mixture was stirred for one hour at same temperature. Chloromethylmethyl ether (0.89 g) was added thereto, the resultant mixture was stirred at room temperature for 2 hours. Water was added to the reaction mixture, extracted with chloroform, the organic layer was successively washed with water and saturated brine, and dried over anhydrous magnesium sulfate. The solvent was evaporated under reduced pressure, the residue was purified by silica gel column chromatography (n-hexane:ethyl acetate=2:1), to thereby obtain 5.26 g of the titled compound as colorless amorphous (Yield: 98.4%).

$^1$H-NMR($CDCl_3$) δ: 2.67(2H, t), 3.44(3H, s), 3.96(2H, t), 5.19(2H, s), 6.90–7.23(7H, m), 7.48(1H, dd)

Step 7

Preparation of 1-methoxymethyl-2-oxo-3-hydroxyimino-5-(2-fluorophenyl)-1,3,4,5-tetrahydro-2H-1,5-benzodiazepine Under argon atmosphere, 1-methoxymethyl-2-oxo-5-(2-fluorophenyl)-1,3,4,5-tetrahydro-2H-1,5-benzodiazepine (5.26 g) was dissolved in toluene (50 ml), the mixture was cooled on ice, potassium tert-butoxide (9.8 g) was added thereto at internal temperature 10° C., and stirred for 30 minutes under ice-cooling. tert-Butyl nitrite (5.0 g) was added thereto, the mixture was allowed to room temperature, and stirred for one hour and 30 minutes. Saturated brine was added to the reaction mixture, extracted with ethyl acetate. The organic layer was successively washed with water and saturated brine, dried over anhydrous sodium sulfate, and the solvent was evaporated under reduced pressure. The residue was purified by silica gel column chromatography (silica gel NH-DM1020, produced by Fujisilicia Co. Ltd., chloroform:methanol=20:1), to thereby obtain 2.35 g of the titled compound as pale brown amorphous.

$^1$H-NMR($CDCl_3$) δ: 3.51 and 3.53(3H, each s), 4.58 and 4.75(2H, each s), 5.27 and 5.29(2H, each s), 6.89–7.23(7H, m), 7.53(1H, m)

Step 8

Preparation of 1-methoxymethyl-2-oxo-3-propylaminocarbonyloxyimino-5-(2-fluorophenyl)-1,3,4,5-tetrahydro-2H-1,5-benzodiazepine 1-Methoxymethyl-2-oxo-3-hydroxyimino-5-(2-fluorophenyl)-1,3,4,5-tetrahydro-2H-1,5-benzodiazepine (2.35 g) was dissolved in tetrahydrofuran (25 ml), propyl isocyanate (1.52 g) and triethylamine (1.81 g) were added thereto, and the mixture was refluxed for 3 hours. The reaction mixture was concentrated under reduced pressure, the residue was purified by silica gel column chromatography (silica gel NH-DM1020, produced by Fujisilicia Co. Ltd., chloroform), to thereby obtain 2.52 g of the titled compound as brown amorphous (Yield: 85%).

$^1$H-NMR($CDCl_3$) δ: 0.87–0.97(3H, m), 1.46–1.57(2H, m), 3.14–3.23(2H, m), 3.53(3H, s), 4.71(2H, brs), 5.00–5.60 (3H, m), 6.93–7.28(7H, m), 7.53–7.56(1H, m)

Step 9

Preparation of 1-methoxymethyl-2-oxo-3-amino-5-(2-fluorophenyl)-1,3,4,5-tetrahydro-2H-1,5-benzodiazepine 1-Methoxymethyl-2-oxo-3-propylaminocarbonyloxyimino-5-(2-fluorophenyl)-1,3,4,5-tetrahydro-2H-1,5-benzodiazepine (2.52 g) was dissolved in methanol (30 ml), 10% palladium carbon (0.60 g) was added thereto, the mixture was swung for 4 hours under hydrogen atmosphere (3.5–3.0 kg/$cm^2$). Palladium carbon was removed by filtration, the filtrate was concentrated under reduced pressure, and the residue was purified by silica gel column chromatography (chloroform:methanol=20:1), to thereby obtain 0.48 g of the titled compound as yellow-brown amorphous.

$^1$H-NMR($CDCl_3$) δ: 3.45(3H, s), 3.70–3.77(1H, m), 4.06–4.12(1H, m), 4.23(2H, brs), 4.96(1H, d), 5.50(1H, d), 6.91–7.49(8H, m)

Step 10

Preparation of 2-oxo-3-benzyloxycarbonylamino-5-(2-fluorophenyl)-1,3,4,5-tetrahydro-2H-1,5-benzodiazepine 1-Methoxymethyl-2-oxo-3-amino-5-(2-fluorophenyl)-1,3,4,5-tetrahydro-2H-1,5-benzodiazepine (0.94 g) was dissolved in 25% hydrobromic acid-acetic acid solution (18 ml), the mixture was stirred for one hour. The reaction mixture was concentrated under reduced pressure, diethyl ether was add, the solid so precipitated was collected by filtration to give pale brown crystals. This crystals were suspended in water (5 ml), 1N aqueous sodium hydroxide (4.5 ml) and a solution of benzyl chloroformate (301 mg) in tetrahydrofuran (7 ml) were added thereto, the resultant mixture was stirred for one hour. Water was added to the reaction mixture, extracted with methylene chloride, the organic layer was successively washed with water and saturated brine, dried over anhydrous magnesium sulfate, and the solvent was evaporated under reduced pressure. The residue was purified by silica gel column chromatography (n-hexane:ethyl acetate=2:1), to thereby obtain 291 mg of the titled compound as amorphous.

$^1$H-NMR($CDCl_3$) δ: 3.49–3.60(1H, m), 4.35–4.50(1H, m), 4.63–4.70(1H, m), 5.08(2H, s), 5.89(1H, brd), 6.88–7.46 (13H, m), 7.76(1H, s)

Referential Example 10

Preparation of 2-oxo-3-tert-butoxycarbonylamino-5-phenyl-8-methyl-1,3,4,5-tetrahydro-2H-1,5-benzodiazepine Step 1

Preparation of 2-oxo-3-tert-butoxycarbonylamino-5-(2-cyclohexene-1-yl)-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (3.00 g) obtained from Referential Example 7 was suspended in methanol (30 ml), 90% 3-bromocyclohexene (6.08 g) and sodium bicarbonate (2.85 g) were added, and the mixture was stirred for 5 hours at room temperature. The reaction mixture was concentrated under reduced pressure, water (100 ml) was added to the residue, extracted with chloroform. The organic layer was dried over anhydrous sodium sulfate, the solvent was evaporated under reduced pressure, and the residue was purified by silica gel column chromatography (n-hexane:ethyl acetate=2:1), to thereby obtain 1.36 g of the titled compound.

$^1$H-NMR($CDCl_3$) δ: 1.41(9H, s), 1.44–2.05(6H, m), 2.27 (3H, s), 3.19–3.33(1H, m), 3.66–4.05(1H, m), 4.40–4.52 (1H, m), 5.48(1H, d), 5.63–5.93(2H, m), 6.75(1H, d), 6.91–7.11(2H1 m), 7.33(1H, brs)

MS(EI)m/z: 371($M^+$)

Step 2

Preparation of 2-oxo-3-tert-butoxycarbonylamino-5-phenyl-8-methyl-1,3,4,5-tetrahydro-2H-1,5-benzodiazepine 2-Oxo-3-tert-butoxycarbonylamino-5-(2-cyclohexen-1-yl)-8-methyl- 1,3,4,5-tetrahydro-2H-1,5-benzodiazepine (500 mg) was suspended in xylene (20 ml), nitrobenzene (831 mg) and 10% palladium carbon (250 mg) were added therto, and the mixture was refluxed for 2 hours. The reaction mixture was allowed to cool, filtrated, and the filtrate was concentrated under reduced pressure. Diisopropyl ether was added to the residue, crystals so precipitated were collected by filtration, to thereby obtain 413 mg of the titled compound (Yield: 83%).

$^1$H-NMR($CDCl_3$) δ: 1.43(9H, s), 2.34(3H, s), 3.65(1H, dd), 4.22(1H, dd), 4.57–4.64(1H, m), 5.58(1H, d), 6.69–6.72 (2H, m), 6.83(1H, t), 6.92–6.99(2H, m), 7.08–7.20(3H, m), 7.74(1H, s)

The production methods of the compound (1) of the present invention will hereinafter be described.

Example 89

Preparation of 3-[3-[1-(2-thienylmethyl)-2-oxo-5-pivaloyl-8-methyl-1,3,4,5-tetrahydro-2H-1,5-benzodiazepin-3-yl]ureido]benzoic acid Step 1

Preparation of 2-oxo-3-tert-butoxycarbonylamino-5-pivaloyl-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (30.0 g) obtained from Referential Example 7 was dissolved in methylene chloride (300 ml), pivaloyl chloride (15.0 g) and pyridine (9.8 g)

were added thereto, the mixture was refluxed for 2 hours and 30 minutes. The reaction mixture was allowed to cool, Water was added, and extracted with chloroform. The organic layer was successively washed with saturated aqueous sodium bicarbonate, water, and saturated brine, dried over anhydrous sodium sulfate. The solvent was evaporated under reduced pressure, to thereby obtain the 21.5 g of titled compound as white crystals.

$^1$H-NMR($CDCl_3$) δ: 0.97(9H, s), 1.40(9H, s), 2.39(3H, s), 3.87(1H, dd), 4.35(1H, t), 4.43–4.50(1H, m), 5.40(1H, d), 6.95(1H, s), 7.06(1H, d), 7.14(1H, d), 7.93(1H, s)

Step 2

Preparation of 1-(2-thenoylmethyl)-2-oxo-3-tert-butoxycarbonylamino-5-pivaloyl-8-methyl-1,3,4,5-tetrahydro-2H-1,5-benzodiazepine 2-Oxo-3-tert-butoxycarbonylamino-5-pivaloyl-8-methyl-1,3,4,5-tetrahydro-2H-1,5-benzodiazepine (1.0 g) was dissolved in tetrahydrofuran (10 ml), 60% sodium hydride (0.16 g) was added thereto under argon atmosphere, and the mixture was stirred for 30 minutes at room temperature. A solution of 2-bromoacetylthiophene (0.99 g) in tetrahydrofuran (1 ml) was added to the resultant mixture, stirred for 2 hours. The reaction mixture was poured into ice-water, extracted with ethyl acetate, the organic layer was washed succesively with water and saturated brine, and dried over anhydrous sodium sulfate. The solvent was evaporated under reduced pressure, the residue was purified by silica gel column chromatography (n-hexane:ethyl acetate=2:1), to thereby obtain 1.01 g of the titled compound (Yield: 76%).

$^1$H-NMR($CDCl_3$) δ: 1.03(9H, s), 1.39(9H, s), 2.37(3H, s), 3.88–3.95(1H, m), 4.20–4.28(1H, m), 4.43(1H, d), 4.53–4.57(1H, m), 5.48(1H, brd), 5.62(1H, d), 7.10–7.22 (4H, m), 7.74–7.87(2H, m)

Step 3

Preparation of 1-(2-thenoylmethyl)-2-oxo-3-amino-5-pivaloyl-8-methyl-1,3,4,5-tetrahydro-2H-1,5-benzodiazepine 1-(2-Thenoylmethyl)-2-oxo-3-tert-butoxycarbonyl-amino-5-pivaloyl-8-methyl-1,3,4,5-tetrahydro-2H-1,5-benzodiazepine (1.00 g) was dissolved in 4N HCl-dioxane (10 ml), the solution was stirred for one hour at 55° C. The reaction mixture was concentrated under reduced pressure. The residue was neutralized with saturated aqueous sodium bicarbonate, extracted with methylene chloride. The organic layer was successively washed with water and saturated brine, dried over anhydrous sodium sulfate, and the solvent was evaporated under reduced pressure, to thereby obtain 0.74 g of the titled compound as brown crystals (Yield: 92%).

$^1$H-NMR($CDCl_3$) δ: 1.03(9H, s), 2.37(3H, s), 3.64–3.78 (2H, m), 4.20–4.27(1H, m), 4.36(1H, d), 5.75(1H, d), 7.07–7.22(4H, m), 7.74–7.89(2H, m)

Step 4

Preparation of 1-[1-(2-thenoylmethyl)-2-oxo-5-pivaloyl-8-methyl-1,3,4,5-tetrahydro-2H-1,5-benzodiazepin-3-yl]-3-(3-ethoxycarbonylphenyl)urea Ethyl 3-aminobenzoate (0.23 g) was dissolved in tetrahydrofuran (10 ml), and the solution was cooled on ice-water. Triphosgene (0.15 g) was added thereto at internal temperature 7° C., triethylamine (0.53 g) was added dropwise thereto over 10 minutes period, the mixture was allowed to come to room temperature, and stirred for 10 minutes. Subsequently, a suspension of 1-(2-thenoylmethyl)-2-oxo-3-amino-5-pivaloyl-8-methyl-1,3,4,5-tetrahydro-2H-1,5-benzodiazepine (0.52 g) in tetrahydrofuran (10 ml ) was added, and the resultant mixture was stirred for one hour. Water was added to the reaction mixture, extracted with methylene chloride, the organic layer was successively washed with water and saturated brine, and dried over anhydrous magnesium sulfate. The solvent was evaporated under reduced pressure. The residue was purified by silica gel column chromatography(n-hexane:ethyl acetate=1:1), to thereby obtain 0.70 g of the titled compound as white crystals (Yield: 88%).

$^1$H-NMR($CDCl_3$) δ: 1.04(9H, s), 1.35(3H, t), 2.38(3H, s), 3.88–3.95(1H, m), 4.29–4.40(3H, m), 4.48(1H, d), 4.79–4.89(1H, m), 5.65(1H, d), 6.10–6.22(1H, m), 7.10–7.27 (6H, m), 7.55–7.91 (5H, m)

Step 5

Preparation of 3-[3-[1-(2-Thenoylmethyl)-2-oxo-5-pivaloyl-8-methyl-1,3,4,5-tetrahydro-2H-1,5-benzodiazepin-3-yl]ureido]benzoic acid 1-[1-(2-Thenoylmethyl)-2-oxo-5-pivaloyl-8-methyl-1,3,4,5-tetrahydro-2H-1,5-benzodiazepin-3-yl]-3-(3-ethoxycarbonylphenyl)urea (0.67 g) was suspended in a mixed solvent of ethanol (10 ml) and tetrahydrofuran (10 ml), aqueous lithiumhydroxide monohydrate (0.24 g) solution (10 ml) was added, and the mixture was stirred for 3 hours at room temperature. The reaction mixture was concentrated under reduced pressure, weakly acidified with 1N hydrochloric acid, extracted with methylene chloride. The organic layer was successively washed with water and saturated brine, and dried over anhydrous magnesium sulfate. The solvent was evaporated under reduced pressure, the residue was suspended in a mixed solvent of methanol and ethyl acetate, crystals so precipitated were collected by filtration, to thereby obtain 0.48 g of the titled compound as white crystals (Yield: 78%).

Melting point: 198–206° C.

$^1$H-NMR(DMSO-$d_6$) δ: 0.96(9H, s), 2.38(3H, s), 3.61–3.68 (1H, m), 4.21–4.30(1H, m), 4.46–4.53(1H, m), 4.86 (1H, d), 5.61 (1H, d), 6.65( (1H, brd), 7.20–7.52 (7H, m), 8.00–8.20 (3H, m), 9.00(1H, brs), 12.83(1H, brs)

Example 90

Preparation of 3-[3-(1-tert-butylcarbonylmethyl-2-oxo-5-phenyl-8-methoxy-1,3,4,5-tetrahydro-2H-1,5-benzodiazepin-3-yl)ureido]benzoic acid Step 1

Preparation of 1-tert-butylcarbonylmethyl-2-oxo-3-benzyloxycarbonylamino-5-phenyl-8-methoxy-1,3,4,5-tetrahydro-2H-1,5-benzodiazepine 2-Oxo-3-benzyloxycarbonylamino-5-phenyl-8-methoxy-1,3,4,5-tetrahydro-2H-1,5-benzodiazepine (2.0 g) obtained from Referential Example 8,bromomethyl-tert-butylketone ( 0.94 g), toluene (30 ml), 1N aqueous sodium hydroxide (15 ml) and tetra n-butylammonium bromide (20 mg) were mixed, the mixture was stirred for 20 hours. The reaction mixture was separated into aqueous layer and organic layer, the aqueous layer was extracted with ethyl acetate, the extract was combined with the former organic layer. The combined organic layer was successively washed with water and saturated brine, dried over anhydrous magnesium sulfate. The solvent was evaporated under reduced pressure, the residue was purified by silica gel column chromatography (n-hexane:ethyl acetate=2:1), to thereby obtain 1.12 g of the titled compound as colorless crystals (Yield: 45%).

$^1$H-NMR($CDCl_3$) δ: 1.26(9H, s), 3.57–3.65(1H, m), 3.79 (3H, s), 4.11–4.21 (1H, m), 4.26(1H, d), 4.63–4.72(1H, m), 5.08(2H, s), 5.14(1H, d), 5.85(1H,brd), 6.41–6.85(5H, m), 7.12–7.34(8H, m)

Step 2

Preparation of 1-tert-butylcarbonylmethyl-2-oxo-3-amino-5-phenyl-8-methoxy-1,3,4,5-tetrahydro-2H-1,5-benzodiazepine 1-tert-Butylcarbonylmethyl-2-oxo-3-benzyloxycarbonylamino-5-phenyl-8-methoxy-1,3,4,5-tetrahydro-2H-1,5-benzodiazepine (1.11 g) was dissolved in methanol (20 ml), 10% palladium carbon (220 mg) was added, and the mixture was stirred for 2 hours under hydrogen atmosphere. Palladium carbon was removed by filtration, the filtrate was concentrated under reduced pressure, to thereby obtain 0.82 g of the titled compound as colorless amorphous(Yield: 100%).

$^1$H-NMR($CDCl_3$) δ: 1.28(9H, s), 3.52–3.60(1H, m), 3.74–3.80(1H, m), 3.78(3H, s), 3.90–3.96(1H, m), 4.16(1H, d), 5.26(1H, d), 6.63–6.84(5H, m), 7.11–7.22(3H, m)

Step 3

Preparation of 1-(1-tert-butylcarbonylmethyl-2-oxo-5-phenyl-8-methoxy-1,3,4,5-tetrahydro-2H-1,5-benzodiazepin-3-yl)-3-(3-ethoxycarbonylphenyl)urea Ethyl 3-aminobenzoate (373 mg) was dissolved in tetrahydrofuran (20 ml), the solution was cooled on ice-water. Triphosgene (252 mg) was added at internal temperature 5° C., triethylamine (870 mg) was added dropwise thereto over 15 minutes period, the mixture was allowed to come to room temperature, and stirred for 10 minutes. Furthermore, a solution of 1-tert-butylcarbonylmethyl-2-oxo-3-amino-5-phenyl-8-methoxy-1,3,4,5-tetrahydro-2H-1,5-benzodiazepine (820 mg) in tetrahydrofuran (20 ml), the resultant mixture was stirred for one hour at room temperature. Water was added to the reaction mixture, extracted with methylene chloride, the organic layer was successively washed with water and saturated brine, and dried over anhydrous magnesium sulfate. The solvent was evaporated under reduced pressure, the residue was purified by silica gel column chromatography(n-hexane:ethyl amorphous(Yield: 95%).

$^1$H-NMR($CDCl_3$) δ: 1.20(9H, s), 1.38(3H, t), 3.71–3.75 (1H, m), 3.80(3H, s), 4.11–4.16(1H, m), 4.33 (2H, q), 4.44(1H, d), 4.91–4.95(1H, m), 5.11(1H, d), 6.27(1H, br), 6.67–7.65(12H, m), 7.94(1H, brs)

Step 4

Preparation of 3-[3-(1-tert-butylcarbonylmethyl-2-oxo-5-phenyl-8-methoxy-1,3,4,5-tetrahydro-2H-1,5-benzodiazepin-3-yl)ureido]benzoic acid 1-(1-tert-Butylcarbonylmethyl-2-oxo-5-phenyl-8-methoxy-1,3,4,5-tetrahydro-2H-1,5-benzodiazepin-3-yl)-3-(3-ethoxycarbonylphenyl)urea (1.17 g) was dissolved in a mixed solvent of tetrahydrofuran (20 ml) and ethanol (20 ml), aqueous lithium hydroxide monohydrate (428 mg) solution (10 ml) was added, and the mixture was stirred for 7 hours at room temperature. The reaction mixture was concentrated under reduced pressure, the residue was weakly acidified with 1N hydrochloric acid, extracted with chloroform. The organic layer was successively washed with water and saturated brine, and dried over anhydrous magnesium sulfate. The solvent was evaporated under reduced pressure, the residue was suspended in ethyl acetate for trituration, collected by filtration, to thereby obtain 616 mg of the titled compound.

Melting point: 202–203° C.

$^1$H-NMR(DMSO-$d_6$) δ: 1.17(9H, s), 3.55–3.63(1H, m), 3.78(3H, s), 3.92–3.99(1H, m), 4.54–4.64(1H, m), 4.79(1H, d), 5.12(1H, d), 6.69–7.54(12H, m), 8.01–8.03(1H, m), 9.10(1H, brs), 12.81(1H, br)

Example 91

Preparation of 3-[3-[1-(2-toluoylmethyl)-2-oxo-5-benzyloxycarbonyl-8-methyl-1,3,4,5-tetrahydro-2H-1,5-benzodiazepin-3-yl]ureido]benzoic acid Step 1

Preparation of 2-oxo-3-tert-butoxycarbonylamino-5-benzyloxycarbonyl-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) obtained from Referential Example 7 and potassium carbonate (1.10 g) were suspended in a mixed solvent of methylene chloride (30 ml) and water (20 ml). A solution of benzyl chloroformate (1.35 g) in methylene chloride (10 ml) was added thereto under ice-cooling, and the mixture was stirred for 2 hours at same temperature and then stirred overnight at room temperature. The reaction mixture was separated into organic layer and aqueous layer, the organic layer was successively washed with aqueous 10% oxalic acid solution, water, and saturated brine, dried over anhydrous magnesium sulfate, and the solvent was evaporated under reduced pressure, to thereby obtain the 2.61 g of titled compound.

$^1$H-NMR($CDCl_3$) δ: 1.40(9H, s), 2.34(3H, s), 4.02(1H, br), 4.28(1H, br), 4.46–4.51(1H, m), 4.99–5.17(2H, br), 5.48(1H, d), 6.87(1H, s), 7.05–7.35(7H, br), 7.65(1H, brs)

Step 2

Preparation of 1-(2-toluoylmethyl)-2-oxo-3-tert-butoxycarbonylamino-5-benzyloxycarbonyl-8-methyl-1,3,4,5-tetrahydro-2H-1,5-benzodiazepine 2-Oxo-3-tert-butoxycarbonylamino-5-benzyloxycarbonyl-8-methyl-1,3,4,5-tetrahydro-2H-1,5-benzodiazepine (23.1 g) was suspended in toluene (320 ml), 2-bromo-2'-methylacetophenone (13.9 g), 1N aqueous sodium hydroxide (160 ml) and tetra-n-butylammonium bromide (400 mg) were added thereto, the mixture was stirred for 2 hours at room temperature. After reaction, the reaction mixture was separated, the organic layer was washed with saturated brine, and dried over anhydrous sodium sulfate. The solvent was evaporated under reduced pressure, the residue was purified by silica gel column chromatography(n-hexane:ethyl acetate=4:1), to thereby obtain 12.9 g of the titled compound.

$^1$H-NMR($CDCl_3$) δ: 1.39(9H, s), 2.34(3H, s), 2.46–2.52 (3H, br), 3.98(1H, br), 4.29(1H, br), 4.53–4.62(1H, m), 4.75(1H, d), 5.01–5.18(3H, br), 5.52(1H, d), 7.00(1H, s), 7.12–7.43(10H, br), 7.65(1H, br)

Step 3

Preparation of 1-(2-toluoylmethyl)-2-oxo-3-amino-5-benzyloxycarbonyl-8-methyl-1,3,4,5-tetrahydro-2H-1,5-benzodiazepine 1-(2-Toluoylmethyl)-2-oxo-3-tert-butoxycarbonylamino-5-benzyloxycarbonyl-8-methyl-1,3,4,5-tetrahydro-2H-1,5-benzodiazepine (12.9 g) was suspended in 4N HCl-dioxane (100 ml), the suspension was stirred for one hour at 50° C. The reaction mixture was concentrated under reduced pressure, the residue was neutralized with saturated aqueous sodium bicarbonate, extracted with methylene chloride, dried over anhydrous sodium sulfate, and the solvent was evaporated under reduced pressure, to thereby obtain 9.78 g of the titled compound (Yield: 100%).

$^1$H-NMR($CDCl_3$) δ: 1.57(2H, br), 2.34(3H, s), 2.49(3H, s), 3.68– 3.78(2H, m), 4.19(1H, br), 4.56(1H, d), 5.13–5.25 (3H, br), 6.99(1H, s), 7.05(1H, d), 7.25–7.41 (9H, br), 7.64(1H, d)

Step 4

Preparation of 1-[1-(2-toluoylmethyl)-2-oxo-5-benzyloxycarbonyl-8-methyl-1,3,4,5-tetrahydro-2H-1,5-benzodiazepin-3-yl]-3-(3-ethoxycarbonylphenyl)urea Ethyl 3-aminobenzoate (4.29 g) was dissolved in tetrahydrofuran (600 ml), triphosgene (2.54 g) was added under ice-cooling, triethylamine (2.19 ml) was added thereto five times every 3 minutes after divided into five portions. A solution of 1-(2-toluoylmethyl)-2-oxo-3-amino-5-benzyloxycarbonyl-8-methyl-1,3,4,5-tetrahydro-2H-1,5-benzodiazepine (9.78 g) in tetrahydrofuran (200 ml) was added, the mixture was stirred for 30 minutes, subsequently, stirred overnight at room temperature. The reaction mixture was poured into water (3 L), acidified with 1N hydrochloric acid, extracted with methylene chloride. The organic layer was washed with saturated aqueous sodium bicarbonate, and dried over anhydrous sodium sulfate. The solvent was evaporated under reduced pressure. The residue was purified by silica gel column chromatography(chloroform:ethyl acetate=2:1), to thereby obtain 13.3 g of the titled compound.

$^1$H-NMR($CDCl_3$) δ: 1.34(3H, t), 2.35(3H, brs), 2.39–2.47 (3H, br), 4.01(1H, br), 4.33(2H, q), 4.41(1H, br), 4.81–4.87 (2H, br), 5.00–5.21(3H, br), 6.18(1H, br), 7.01(1H, brs), 7.11–7.41(12H, m), 7.53(1H, d), 7.59–7.66(2H, m), 7.87 (1H, brs)

MS(FAB)m/z: 649 ($MH^+$)

Step 5

Preparation of 3-[3-[1-(2-toluoylmethyl)-2-oxo-5-benzyloxycarbonyl-8-methyl-1,3,4,5-tetrahydro-2H-1,5-benzodiazepin-3-yl]ureido]benzoic acid 1-[1-(2-Toluoylmethyl)-2-oxo-5-benzyloxycarbonyl-8-methyl-1,3,4,5-tetrahydro-2H-1,5-benzodiazepin-3-yl]-3-(3-ethoxycarbonylphenyl)urea (435 mg) was dissolved in methanol (20 ml), aqueous lithium hydroxide monohydrate (141 mg) solution (10 ml) and tetrahydrofuran (10 ml) were added, the mixture was refluxed for 2 hours. The reaction mixture was concentrated under reduced pressure, the residue was dissolved in water (150 ml), washed with diethyl ether (100 ml), acidified with 1N hydrochloric acid, and extracted with methylene chloride. The organic layer was dried over anhydrous magnesium sulfate, the solvent was evaporated under reduced pressure, n-hexane was added to the residue for trituration, and collected by filtration, to thereby obtain 301 mg of the titled compound (Yield: 72.5%).

Melting point: 144–147° C.

$^1$H-NMR($CDCl_3$) δ: 2.36(3H, s), 2.47–2.51(3H, br), 4.22–4.44(3H, br), 4.79–4.85(2H, m), 5.03–5.23(3H, m), 7.01(1H, s), 7.17–7.47(11H, m), 7.57–7.60(2H, m), 7.72 (1H, s), 8.22 (1H, s), 8.35 (1H, dd), 10.60( (1H, br)

MS(FAB)m/z: 621 ($MH^+$)

Example 92

Preparation of 3-[3-[1-(thiophen-3-yl)carbonylmethyl-2-oxo-5-pivaloyl-8-methyl-1,3,4,5-tetrahydro-2H-1,5-benzodiazepin-3-yl]ureido]benzoic acid Step 1

Preparation of 1-(thiophen-3-yl)carbonylmethyl-2-oxo-3-tert-butoxycarbonylamino-5-pivaloyl-8-methyl-1,3,4,5-tetrahydro-2H-1,5-benzodiazepine 2-Oxo-3-tert-butoxycarbonylamino-5-pivaloyl-8-methyl-1,3,4,5-tetrahydro-2H-1,5-benzodiazepine (1.0 g) obtained from Step 1 of Example 89 was dissolved in tetrahydrofuran (10 ml), 60% sodium hydride (0.16 g) was added under argon atmosphere, the mixture was stirred for 30 minutes at room temperature. A solution of 3-bromoacetylthiophene (0.90 g) in tetrahydrofuran (5 ml) was added,stirred for one hour. The reaction mixture was poured into ice-water, extracted with ethyl acetate, the organic layer was successively washed with water and saturated brine, and dried over anhydrous sodium sulfate. The solvent was evaporated under reduced pressure, the residue was purified by silica gel column chromatography(n-hexane:ethyl acetate=2:1), to thereby obtain 0.94 g of the titled compound (Yield: 71%).

$^1$H-NMR($CDCl_3$) δ: 1.03(9H, s), 1.40(9H, s), 2.36(3H, s), 3.91–3.96(1H, m), 4.20–4.29(1H, m), 4.42(1H, d), 4.50–4.60(1H, m), 5.48(1H, brd), 5.59(1H, d), 7.05–7.14 (3H, m), 7.39–7.65(2H, m), 8.21–8.23(1H, m)

Step 2

Preparation of 1-(thiophen-3-yl)carbonylmethyl-2-oxo-3-amino-5-pivaloyl-8-methyl-1,3,4,5-tetrahydro-2H-1,5-benzodiazepine 1-(Thiophen-3-yl)carbonylmethyl-2-oxo-3-tert-butoxycarbonylamino-5-pivaloyl-8-methyl-1,3,4,5-tetrahydro-2H-1,5-benzodiazepine (0.94 g) was dissolved in 4N HCl-dioxane (10 ml), the solution was stirred for one hour at 55–60° C. The react ion mixture was concentrated under reduced pressure, the residue was neutralized with saturated aqueous sodium bicarbonate, and extracted with methylene chloride. The organic layer was successively washed with water and saturated brine, dried over anhydrous sodium sulfate, and the solvent was evaporated under reduced pressure, to thereby obtain 0.69 g of the titled compound as a brown solid(Yield: 100%).

$^1$H-NMR($CDCl_3$) δ: 1.03(9H, s), 1.61(2H, brs), 2.36(3H, s), 3.71–3.78(2H, m), 4.23–4.37(2H, m), 5.72(1H, d), 7.01–7.14(3H, m), 7.40–7.66(2H, m), 8.22–8.24(1H, m)

Step 3

Preparation of 1-[1-(thiophen-3-yl)carbonylmethyl-2-oxo-5-pivaloyl-8-methyl-1,3,4,5-tetrahydro-2H-1,5-benzodiazepin-3-yl]-3-(3-ethoxycarbonylphenyl)urea Ethyl 3-aminobenzoate (0.33 g) was dissolved in tetrahydrofuran (20 ml) and cooled on ice. Triphosgene (0.22 g) was added at internal temperature 5° C., triethylamine (0.76 g) was added dropwise thereto over 10 minutes period, the mixture was allowed to come to room temperature,stirred for 10 minutes. A solution of 1-(thiophen-3-yl)carbonylmethyl-2-oxo-3-amino-5-pivaloyl-8-methyl-1,3,4,5-tetrahydro-2H-1,5-benzodiazepine (0.69 g) in tetrahydrofuran (10 ml) was added, the resultant mixture was stirred for one hour. Water was added to the reaction mixture, extracted with methylene chloride, the organic layer was successively washed with water and saturated brine, and dried over anhydrous magnesium sulfate. The solvent was evaporated under reduced pressure, the residue was purified by silica gel column chromatography(n-hexane:ethyl acetate=1:1), to thereby obtain 0.86 g of the titled compound as pale brown crystals (Yield: 75%).

$^1$H-NMR($CDCl_3$) δ: 1.04(9H, s), 2.37(3H, s), 3.89–3.97 (1H, m), 4.29–4.49(4H, m), 4.80–4.87(1H, m), 5.62(1H, d), 6.10(1H,brd), 7.04–7.67(9H, m), 7.89–7.91(1H, m), 8.20–8.22(1H, m)

Step 4

Preparation of 3-[3-[1-(thiophen-3-yl)carbonylmethyl-2-oxo-5-pivaloyl-8-methyl-1,3,4,5-tetrahydro-2H-1,5-benzodiazepin-3-yl]ureido]benzoic acid 1-[1-(Thiophen-3-yl)carbonylmethyl-2-oxo-5-pivaloyl-8-methyl-1,3,4,5-1,3,4,5-tetrahydro-2H-1,5-benzodiazepin-3-yl]-3-(3-ethoxycarbonylphenyl)urea (0.85 g) was suspended in tetrahydrofuran (20 ml). Aqueous lithium hydroxide monohydrate (0.29 g) solution (10 ml) was added, and the mixture was stirred for 4 hours at room temperature. The reaction mixture was concentrated under reduced pressure, weakly acidified with 1N hydrochloric acid, and concentrated under reduced pressure. The residue was collected by filtration, the resultant solid was successively washed with water and ethyl acetate, to thereby obtain 0.65 g of the titled compound as colorless crystals (Yield: 82%).

Melting point: 215–216° C.

$^1$H-NMR(DMSO-$d_6$) δ: 0.96(9H, s), 2.37(3H, s), 3.62–3.69(1H, m), 4.22–4.30(1H, m), 4.47–4.54(1H, m), 4.80(1H, d), 5.58(1H, d), 6.64(1H,brd), 7.16–8.00(10H, m), 8.71–8.73( (1H, m), 9.01( (1H, brs), 12.84(1H, brs)

Example 93

Preparation of 3-[3-[1-(2-toluoylmethyl)-2-oxo-5-(2,2-dimethylbutanoyl)-8-methyl-1,3,4,5-tetrahydro-2H-1,5-benzodiazepin-3-yl]ureido]benzoic acid Step 1

Preparation of 1-[1-(2-toluoylmethyl)-2-oxo-8-methyl-1,3,4,5-tetrahydro-2H-1,5-benzodiazepin-3-yl]-3-(3-ethoxycarbonylphenyl)urea 1-[1-(2-Toluoylmethyl)-2-oxo-5-benzyloxycarbonyl-8-methyl-1,3,4,5-tetrahydro-2H-1,5-benzodiazepin-3-yl]-3-(3-ethoxycarbonylphenyl)urea (1.00 g) obtained from Step 4 of Example 91 was dissolved in ethanol (20 ml), 10% palladium carbon (200 mg) was added, and under hydrogen atmosphere the mixture was stirred for 2 hours and addtionally stirred for one hour at 50° C. The reaction mixture was filtrated through a pad of Celite, the filtrate was concentrated under reduced pressure, to thereby obtain 500 mg of the titled compound.

$^1$H-NMR($CDCl_3$) δ: 1.33(3H, t), 1.70(1H, br), 2.27(3H, s), 2.42(3H, s), 3.46( (1H, t), 3.93(1H, dd), 3.41(2H, q), 4.90–4.99(1H, m), 5.03(1H, d), 5.20(1H, d), 6.45(1H, d), 6.84–6.96(3H, m), 7.18–7.26(3H, m), 7.37(1H, t), 7.43(1H, s), 7.54–7.67(3H, m), 7.91(1H, s)

Step 2

Preparation of 1-[1-(2-toluoylmethyl)-2-oxo-5-(2,2-dimethylbutanoyl)-8-methyl-1,3,4,5-tetrahydro-2H-1,5-benzodiazepin-3-yl]-3-(3-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea (500 mg) was suspended in 1,2-dichloroethane (10 ml), 2,2-dimethylbutyryl chloride (144 mg) and pyridine (86 μl ) were added, and the mixture was refluxed for one hour and 30 minutes. Water (100 ml) and ethyl acetate (100 ml) were added to the reaction mixture, separated, the organic layer was washed with 1N hydrochloric acid, and dried over anhydrous sodium sulfate. The solvent was evaporated under reduced pressure, the residue was purified by silica gel column chromatography(n-hexane:ethyl acetate=2:1), to thereby obtain 248 mg of the titled compound.

$^1$H-NMR($CDCl_3$) δ: 0.88(3H, t), 0.93(3H, s), 0.97(3H, s), 1.29–1.37(1H, m), 1.34(3H, t), 1.61–1.70(1H, m), 2.39(3H, s), 2.51(3H, s), 3.94(1H, dd), 4.32(2H, q), 4.33–4.44(2H, m), 4.81–4.91(1H, m), 5.55(1H, d), 6.30(1H, d), 7.03(1H, s), 7.05–7.29(5H, m), 7.39–7.43(2H, m), 7.56–7.60(2H, m), 7.67(1H, t), 7.90(1H, t)

Step 3

Preparation of 3-[3-[1-(2-toluoylmethyl)-2-oxo-5-(2,2-dimethylbutanoyl)-8-methyl-1,3,4,5-tetrahydro-2H-1,5-benzodiazepin-3-yl]ureidolbenzoic acid 1-[1-(2-Toluoylmethyl)-2-oxo-5-(2,2-dimethylbutanoyl)-8-methyl-1,3,4,5-tetrahydro-2H-1,5-benzodiazepin-3-yl]-3-(3-ethoxycarbonylphenyl)urea (239 mg) was dissolved in methanol (20 ml), aqueous lithium hydroxide monohydrate (82 mg) solution (10 ml) and tetrahydrofuran (10 ml) was added, and the mixture was refluxed for one hour. The reaction mixture was concentrated under reduced pressure, 1N hydrochloric acid was added, and extracted with methylene chloride. The organic layer was dried over anhydrous sodium sulfate, the solvent was evaporated under reduced pressure, and isopropyl ether was added to the residue for trituration, and collected by filtration, to thereby obtain 130 mg of the titled compound.

Melting point: 153–155° C.

$^1$H-NMR(DMSO-$d_6$) δ: 0.78(3H, t), 0.82(3H, s), 0.88(3H, s), 1.20–1.28(1H, m), 1.50–1.60(1H, m), 2.39(3H, s), 2.46 (3H, s), 3.69(1H, dd), 4.24(1H, t), 4.47–4.55(1H, m), 4.89 (1H, d), 5.42(1H, d), 6.72(1H, d), 7.17(1H, s), 7.23(1H, d), 7.30–7.40(4H, m), 7.47–7.53(3H, m), 7.97–8.00(2H, m), 9.01(1H, s), 12.80(1H, br) MS(FAB)m/z: 585($MH^+$)

Example 94

Preparation of 3-[3-[1-(2-toluoylmethyl)-2-oxo-5-(3-chloro-2,2-dimethylpropionyl)-8-methyl-1,3,4,5-tetrahydro-2H-1,5-benzodiazepin-3-yl]ureido]benzoic acid Step 1

Preparation of 1-[1-(2-toluoylmethyl)-2-oxo-5-(3-chloro-2,2-dimethylpropionyl)-8-methyl-1,3,4,5-tetrahydro-2H-1,5-benzodiazepin-3-yl]-3-(3-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea (500 mg) obtained from Step 1 of Example 93 was suspended in 1,2-dichloroethane (10 ml), chloropivaloyl chloride (166 mg) and pyridine (86 μl) were added, and the mixture was refluxed for 2 hours 30 minutes. The reaction mixture was successively washed with water, 1N hydrochloric acid, and saturated aqueous sodium bicarbonate, dried over anhydrous sodium sulfate. The solvent was evaporated under reduced pressure, the residue was purified by silica gel column chromatography(n-hexane:ethyl acetate=2:1), to thereby obtain 509 mg of the titled compound (Yield: 81%).

$^1$H-NMR($CDCl_3$) δ: 0.96(3H, s), 1.16(3H, s), 1.35(3H, t), 2.39(3H, s), 2.52(3H, s), 3.42(1H, d), 3.70(1H, d), 3.98(1H, dd), 4.33(2H, q), 4.39(1H, t), 4.50(1H, d), 4.83–4.93(1H, m), 5.56(1H, d), 6.21(1H, d), 7.06(1H, s), 7.12–7.14(2H, m), 7.21–7.30(4H, m), 7.43(1H, t), 7.54(1H, dd), 7.64(1H,dt), 7.74(1H, d), 7.90(1H, t)

Step 2

Preparation of 3-[3-[1-(2-toluoylmethyl)-2-oxo-5-(3-chloro-2,2-dimethylpropionyl)-8-methyl-1,3,4,5-tetrahydro-2H-1,5-benzodiazepin-3-yl]ureido]benzoic acid -[1-(2-Toluoylmethyl)-2-oxo-5-(3-chloro-2,2-dimethylpropionyl)-8-methyl-1,3,4,5-tetrahydro-2H-1,5-benzodiazepin-3-yl]-3-(3-ethoxycarbonylphenyl)urea (491 mg) was dissolved in methanol (24 ml), aqueous lithium hydroxide monohydrate (159 mg) solution (12 ml) was added, the mixture was refluxed for 30 minutes. The reaction mixture was concentrated under reduced pressure,1N hydrochloric acid was added, and extracted with ethyl acetate. The organic layer was washed with saturated brine, dried over anhydrous magnesium sulfate, the solvent was evaporated under reduced pressure, diisopropyl ether was added to the residue for trituration, collected by filtration,to thereby obtain 320 mg of the titled compound.

Melting point: 224–226° C.

$^1$H-NMR(DMSO-$d_6$) δ: 0.86(3H, s), 1.06(3H, s), 2.40 (3H, s), 2.45(3H, s), 3.52(1H, d), 3.70–3.75(2H, m), 4.24 (1H, t), 4.49–4.59(1H, m), 4.92(1H, d), 5.41(1H, d), 6.73 (1H, d), 7.21(1H, s), 7.27(1H, t), 7.33–7.42(4H, m), 7.47–7.53(3H, m), 7.96(1H, d), 8.01(1H, s), 9.02(1H, s), 12.84(1H, s) MS(FAB)m/z: 605($MH^+$)

Example 95

Preparation of 3-[3-(1-tert-butylcarbonylmethyl-2-oxo-5-phenyl-8-methyl-1,3,4,5-tetrahydro-2H-1,5-benzodiazepin-3-yl]ureido]benzoic acid Step 1

Preparation of 1-tert-butylcarbonylmethyl-2-oxo-3-tert-butoxycarbonylamino-5-phenyl-8-methyl-1,3,4,5-tetrahydro-2H-1,5-benzodiazepine 60% Sodium hydride (33 mg) was suspended in anhydrous N,N-dimethylformamide (10 ml), under ice-cooling 2-oxo-3-tert-butoxycarbonylamino-5-phenyl-8-methyl-1,3,4,5-tetrahydro-2H-1,5-benzodiazepine (200 mg) obtained from Referentioal Example 5, and the mixture was stirred for one hour at room temperature. Subsequently, bromomethyl-tert-butylketone (147 mg) was added, stirred for one hour at room temperature. Ice-water was added to the reaction mixture, extracted with ethyl acetate, the organic layer was washed with saturated brine and dried over anhydrous magnesium sulfate. The solvent was evaporated under reduced pressure, diisopropyl ether was added to the residue for crystallization, crystals so precipitated were collected by filtration, to thereby obtain 140 mg of the titled compound.

$^1$H-NMR($CDCl_3$) δ: 1.27(9H, s), 1.42(9H, s), 2.32(3H, s), 3.58(1H, dd), 4.17(1H, dd), 4.25(1H, d), 4.55–4.65(1H, m), 5.13(1H, d), 5.62(1H, d), 6.73–6.91(4H, m), 6.97–7.22(4H, m)

Step 2

Preparation of 1-tert-butylcarbonylmethyl-2-oxo-3-amino-5-phenyl-8-methyl-1,3,4,5-tetrahydro-2H-1,5-benzodiazepine 4N HCl-dioxane (5 ml) was added to a solution of 1-tert-butylcarbonylmethyl-2-oxo-3-tert-butoxycarbonylamino-5-phenyl-8-methyl-1,3,4,5-tetrahydro-2H-1,5-benzodiazepine (100 mg) in ethanol (5 ml ), the mixture was stirred at 50° C. for 30 minutes. The reaction mixture was concentrated under reduced pressure, the residue was neutralized with saturated aqueous sodium bicarbonate, extracted with ethyl acetate. The organic layer was dried over anhydrous sodium sulfate, the solvent was evaporated under reduced pressure, to thereby obtain 78 mg of the titled compound (Yield: 100%).

$^1$H-NMR($CDCl_3$) δ: 1.29(9H, s), 1.66 (2H, brs), 2.33 (3H, s), 3.55 (1H, dd), 3.75 (1H, dd), 3.94(1H, dd), 4.16(1H, d), 5.24(1H, d), 6.71–6.91 (4H, m), 6.95–7.03(1H, m), 7.09 (1H, d), 7.14–7.24 (2H, m)

Step 3

Preparation of 1-(1-tert-butylcarbonylmethyl-2-oxo-5-phenyl-8-methyl-1,3,4,5-tetrahydro-2H-1,5-benzodiazepin-3-yl)-3-(3-ethoxycarbonylphenyl)urea Ethyl 3-aminobenzoate (14 mg) was dissolved in anhydrous tetrahydrofuran (10 ml), under ice-cooling triphosgene (68 mg) was added and triethylamine (60 μl ) was added thereto five times. The mixture was stirred for 30 minutes at same temperature. A solution of 1-tert-butylcarbonylmethyl-2-oxo-3-amino-5-phenyl-8-methyl-1,3,4,5-tetrahydro-2H-1,5-benzodiazepine (227 mg) in anhydrous tetrahydrofuran (10 ml) was added, the resultant mixture was allowed to come to room temperature, and stirred for 30 minutes. The reaction mixture was concentrated under reduced pressure, Water (50 ml) was added, and extracted with methylene chloride. The organic layer was dried over anhydrous sodium sulfate, the solvent was evaporated under reduced pressure, and diethyl ether was added to the residue for trituration, collected by filtration, to thereby obtain 280 mg of the titled compound (Yield: 81.1%).

$^1$H-NMR($CDCl_3$) δ: 1.23(9H, s), 1.35(3H, t), 2.34(3H, s), 3.76(1H, dd), 4.13(1H, dd), 4.33(2H, q), 4.48 (1H, d), 4.93(1H, ddd), 5.07(1H, d), 6.38(1H, d), 6.72–6.83(3H, m), 6.93–7.28(8H, m), 7.32–7.39(1H, m), 7.61(1H, dt), 7.96(1H, t)

Step 4

Preparation of 3-[3-(1-tert-butylcarbonylmethyl-2-oxo-5-phenyl-8-methyl-1,3,4,5-tetrahydro-2H-1,5-benzodiazepin-3-yl]ureido]benzoic acid 1-(1-tert-Butylcarbonylmethyl-2-oxo-5-phenyl-8-methyl-1,3,4,5-tetrahydro-2H-1,5-benzodiazepin-3-yl)-3-(3-ethoxycarbonylphenyl)urea (280 mg) was dissolved in a mixed solvent of methanol (20 ml) and tetrahydrofuran (10 ml), aqueous lithium hydroxide monohydrate (106 mg) solution (10 ml) was added, and the mixture was refluxed for one hour. The reaction mixture was concentrated under reduced pressure, adjusted to pH 1–2 with 1N hydrochloric acid, and extracted with methylene chloride. The organic layer was washed with saturated brine, dried over anhydrous sodium sulfate, the solvent was evaporated under reduced pressure, diisopropyl ether was added to the residue for trituration and collected by filtration, to thereby obtain 200 mg of the titled compound.

Melting point: 240–243° C.(decomposition)

$^1$H-NMR($CDCl_3$) δ: 1.30(9H, s), 2.35(3H, s), 3.70(1H, dd), 4.27(1H, d), 4.38(1H, dd), 4.85(1H, ddd), 5.21(1H, d), 6.79(2H, d), 6.86(1H, t), 6.96(1H, brs), 7.05(1H, dd), 7.12–7.27(4H, m), 7.38(1H, t), 7.52(1H, d), 7.61(1H, d), 7.72–7.78(1H, m), 8.30(1H, brs), 8.40(1H, dd), 10.70–10.90 (1H, br)

MS(FAB)m/z: 529($MH^+$)

Example 96

Preparation of (+)-3-[3-(1-tert-butylcarbonylmethyl-2-oxo-5-phenyl-8-methyl-1,3,4,5-tetrahydro-2H-1,5-benzodiazepin-3-yl]ureidozbenzoic acid Step 1

Preparation of 1-tert-butylcarbonylmethyl-2-oxo-3-[(2S)-(2-tert-butoxycarbonylamino-3-phenylpropionyl)amino]-5-phenyl-8-methyl-1,3,4,5 -tetrahydro-2H-1,5-benzodiazepine Under argon atmosphere, 1-tert-butylcarbonylmethyl-2-oxo-3-amino-5-phenyl-8-methyl-1,3,4,5-tetrahydro-2H-1,5-benzodiazepine (4.75 g) obtained from Step 2 of Example 95 was dissolved in anhydrous N,N-dimethylformamide (40 ml), N-tert-butoxycarbonyl-L-phenylalanine (3.80 g), 1-hydroxybenzotriazole (1.93 g), 1-ethyl-3-(3-dimethylaminopropyl)carbodiimide hydrochloride (2.74 g) and triethylamine (3.65 ml) were added under ice-cooling, the mixture was stirred for 5 minutes at same temperature, and subsequently the resultant mixture was allowed to come to room temperature, stirred for 2 hours. Ice-water was added to the reaction mixture, extracted with ethyl acetate, the organic layer was washed with saturated brine, and dried over anhydrous sodium sulfate. The solvent was evaporated under reduced pressure, the residue was purified by silica gel column chromatography(n-hexane:ethyl acetate=2:1), to thereby obtain 8.06 g of the titled compound (Yield: 100%).

$^1$H-NMR($CDCl_3$) δ: 1.25 and 1.26(9H, each s), 1.41(9H, s), 2.32 and 2.34(3H, each s), 3.00–3.08(2H, m), 3.16 and 3.45(1H, each dd), 3.96–4.45(4H, m), 4.77(1H, ddd), 4.95–5.04(1H, br), 5.08(1H, d), 6.70(2H,dt), 6.80–6.94(2H, m), 6.97–7.05(1H, m), 7.06–7.12(1H, m), 7.14–7.38(7H, m)

Step 2

Preparation of (+)-1-tert-butylcarbonylmethyl-2-oxo-3-[(2S)-(2-amino-3-phenylpropionyl)amino]-5-phenyl-8-methyl-1,3,4,5-tetrahydro-2H-1,5-benzodiazepine and (−)-1-tert-butylcarbonylmethyl-2-oxo-3-[(2S)-(2-amino-3-phenylpropionyl)amino]-5-phenyl-8-methyl-1,3,4,5-tetrahydro-2H-1,5-benzodiazepine 1-tert-Butylcarbonylmethyl-2-oxo-3-[(2S)-(2-tert-butoxycarbonylamino-3-phenylpropionyl)amino]-5-phenyl-8-methyl-1,3,4,5-tetrahydro-2H-1,5-benzodiazepine (8.06 g) was dissolved in 4N HCl-dioxane (40 ml), the solution was stirred for one hour at room temperature. The reaction mixture was concentrated under reduced pressure, neutralized with saturated aqueous sodium bicarbonate, and extracted with methylene chloride. The organic layer was dried over anhydrous sodium sulfate, the solvent was evaporated under reduced pressure. The residue was purified by silica gel column chromatography(ethyl acetate contained water), to thereby obtain 3.01 g of (+)-1-tert-butylcarbonylmethyl-2-oxo-3-[(2S)-(2-amino-3-phenylpropionyl)amino]-5-phenyl-8-methyl-1,3,4,5-tetrahydro-2H-1,5-benzodiazepine of first eluent and 3.17 g of (−)-1-tert-butylcarbonylmethyl-2 -oxo-3-[(2S)-(2-amino-3-phenylpropionyl)amino]-5-phenyl-8-methyl-1,3,4,5-tetrahydro-2H-1,5-benzodiazepine of second eluent.

Data of (+)-1-tert-butylcarbonylmethyl-2-oxo-3-[(2S)-(2-amino-3-phenylpropionyl)amino]-5-phenyl-8-methyl-1,3,4,5-tetrahydro-2H-1,5-benzodiazepine

[α]D$^{27}$(C=1.007, $CHCl_3$): +31.5°

$^1$H-NMR($CDCl_3$) δ: 1.26(9H, s), 1.53(2H, brs), 2.34(3H, s), 2.77(1H, dd), 3.20(1H, dd), 3.47(1H, dd), 3.62(1H, dd), 4.07–4.18(1H, m), 4.28(1H, d), 4.85(1H,dt), 5.11(1H, d), 6.74(2H,dq), 6.85(1H, tt), 6.91 (1H, q), 7.01(1H, dd), 7.11 (1H, d), 7.15–7.38(7H, m), 8.13(1H, d)

Data of (−)-1-tert-butylcarbonylmethyl-2-oxo-3-[(2S)-(2-amino-3-phenylpropionyl)amino]-5-phenyl-8-methyl-1,3,4,5-tetrahydro-2H-1,5-benzodiazepine

[α]D$^{25}$(C=1.027, $CHCl_3$): −111.7°

$^1$H-NMR($CDCl_3$) δ: 1.27(9H, s), 1.53(2H, brs), 2.33(3H, s), 2.67(1H, dd), 3.21 (1H, dd), 3.42(1H, dd), 3.58 (1H, dd), 4.07–4.18(1H, m), 4.29(1H, d), 4.83(1H,dt), 5.11(1H, d), 6.73(2H,dq), 6.84(1H, tt), 6.91 (1H, q), 7.01(1H, dd), 7.08–7.37(8H, m), 7.86(1H, d)

Step 3

Preparation of (+)-1-tert-butylcarbonylmethyl-2-oxo-3-[(2S)-[2-(N-phenylthioureido)-3-phenylpropionyl]amino]-5-phenyl-8-1,3,4,5-tetrahydro-2H-1,5-benzodiazepine (+)-1-tert-Butylcarbonylmethyl-2-oxo-3-[(2S)-(2-amino-3-phenylpropionyl)amino]-5-phenyl-8-methyl-1,3,4,5-tetrahydro-2H-1,5-benzodiazepine (2.94 g) was dissolved in anhydrous methylene chloride (30 ml), phenyl isothiocyanate (1.55 g) was added, and the mixture was stirred at room temperature for 2 hours and 30 minutes. The reaction mixture was concentrated under reduced pressure, the residue was purified by silica gel column chromatography(n-hexane:ethyl acetate=2:1), to thereby obtain 3.50 g of the titled compound (Yield: 94.3%).

[α]D$^{25}$(C=1.001, $CHCl_3$): +71.7°

$^1$H-NMR($CDCl_3$) δ: 1.28(9H, s), 2.33(3H, s), 3.17(2H, d), 3.52(1H, dd), 4.07–4.19(1H, m), 4.20(1H, d), 4.75(1H,dt), 5.14(1H, d), 5.20(1H, q), 6.66–6.77(4H, m), 6.84(1H,tt), 6.90(1H, q), 6.95–7.38(13H, m), 7.74(1H, s)

Step 4

Preparation of (+)-1-tert-butylcarbonylmethyl-2-oxo-3-amino-5-phenyl-8-methyl-1,3,4,5-tetrahydro-2H-1,5-benzodiazepine (+)-1-tert-Butylcarbonylmethyl-2-oxo-3-[(2S)-[2-(N-phenylthioureido)-3-phenylpropionyl]amino]-5-phenyl-8-methyl-1,3,4,5-tetrahydro-2H-1,5-benzodiazepine (3.24 g) was dissolved in trifluoroacetic acid (40 ml), the solution was stirred for one hour at 50° C. The reaction mixture was concentrated under reduced pressure, neutralized with saturated aqueous sodium bicarbonate, and extracted with methylene chloride. The organic layer was dried over anhydrous sodium sulfate, the solvent was evaporated under reduced pressure, and the residue was purified by silica gel column chromatography(chloroform:methanol=20:1), to thereby obtain 1.44 g of the titled compound.

Optical purity: 99%ee (the ee value was determined by High Performance Liquid Chromatography)

[α]D$^{27}$(C=1.04, $CHCl_3$): +22.1°

Step 5

Preparation of (+)-1-(1-tert-butylcarbonylmethyl-2-oxo-5-phenyl-8-methyl-1,3,4,5-tetrahydro-2H-1,5-benzodiazepin-3-yl)-3-(3-benzyloxycarbonylphenyl)urea Diphenylphosphoryl azide (1.38 g) and triethylamine (0.77 ml) were added to a solution of isophthalic acid benzyl ester (1.15 g) in anhydrous dioxane (20 ml), the mixture was stirred at 60° C. for 30 minutes and subsequently stirred at internal temperature 80° C. for one hour. The reaction mixture was allowed to come to room temperature, a solution of (+)-1-tert-butylcarbonylmethyl-2-oxo-3-amino-5-phenyl-8-methyl-1,3,4,5-tetrahydro-2H-1,5-benzodiazepine (1.1 g) in anhydrous dioxane (20 ml) was added thereto, the mixture was stirred for 2 hours at room temperature. The resultant mixture was concentrated under reduced pressure, chloroform was added, the mixture was washed succesively with saturated aqueous sodium bicarbonate and saturated brine, and dried over anhydrous sodium sulfate. The solvent was evaporated under reduced pressure, the residue was purified by silica gel column chromatography(n-hexane:ethyl acetate=2:1), to thereby obtain 622 mg of the titled compound.

[α]D$^{27}$ (C=1.028, $CHCl_3$): +47.2°

$^1$H-NMR($CDCl_3$) δ: 1.23(9H, s), 2.34(3H, s), 3.72(1H, dd), 4.10(1H, dd), 4.40(1H, d), 4.95(1H, dt), 5.15(1H, d), 5.31(1H, d), 5.32(1H, d), 6.57(1H, d), 6.75(2H, d), 6.83(1H, t), 6.93(1H, brs), 7.0 1(1H,d d), 7.06–7.52(11H, m), 7.60 (1H, dt), 8.02(1H, t)

Step 6

Preparation of (+)-3-[3-(1-tert-butylcarbonylmethyl-2-oxo-5-phenyl-8-methyl-1,3,4,5-tetrahydro-2H-1,5-benzodiazepin-3-yl)]ureido]benzoic acid Ethanol (20 ml) and 10% palladium carbon (100 mg) were added to (+)-1-(1-tert-butylcarbonylmethyl-2-oxo-5-phenyl-8-methyl-1,3,4,5-tetrahydro-2H-1,5-benzodiazepin-3-yl)-3-(3-benzyloxycarbonylphenyl)urea (840 mg), under hydrogen atmosphere the mixture was stirred at room temperature for 4 hours. The reaction mixture was filtrated, the filtrate was concentrated under reduced pressure. The residue was purified by silica gel column chromatography (chloroform:methanol=10:1), a mixed solvent of ethyl acetate and diisopropyl ether was added to the compound so precipitated for trituration, collected by filtration, to thereby obtain 360 mg of the titled compound.

Optical purity: 99%ee (the ee value was determined by High Performance Liquid Chromatography)

[α]D$^{27}$(C=1.005, MeOH): +108.1°

Example 97

Preparation of (−)-3-[3-(1-tert-butylcarbonylmethyl-2-oxo-5-phenyl-8-methyl-1,3,4,5-tetrahydro-2H-1,5-benzodiazepin-3-yl)]ureidolbenzoic acid Step 1

Preparation of (−)-1-tert-butylcarbonylmethyl-2-oxo-3-[(2S)-[2-(N-phenylthioureido)-3-phenylpropionyl]amino]-5-phenyl-8-methyl-1,3,4,5-tetrahydro-2H-1,5-benzodiazepine Step 3 of Example 96 was repeated except that (−)-1-tert-butylcarbonylmethyl-2-oxo-3-[(2S)-(2-amino-3-phenylpropionyl)amino]-5-phenyl-8-methyl-1,3,4,5-tetrahydro-2H-1,5-benzodiazepine (2.2 g) obtained from Step 2 of Example 96 was used instead of (+)-1-tert-butylcarbonylmethyl-2-oxo-3-[(2S)-(2-amino-3-phenylpropionyl)amino]-5-phenyl-8-methyl-1,3,4,5-tetrahydro-2H-1,5-benzodiazepine (2.94 g), to thereby obtain 2.68 g of the titled compound(Yield: 96.2%).

[α]D$^{26}$(C=1.043, $CHCl_3$): −19.3°

$^1$H-NMR($CDCl_3$) δ: 1.24(9H, s), 2.30(3H, s), 2.94(1H, dd), 3.10(1H, dd), 3.43(1H, dd), 3.91(1H, dd), 4.20(1H, d), 4.71(1H, dt), 5.06(1H, d), 5.12–5.22(1H, m), 6.38(1H, d), 6.66(2H,dq), 6.75(1H, d), 6.85(2H, tt), 6.95–7.43(12H, m), 7.71(1H, s)

Step 2

Preparation of (−)-1-tert-butylcarbonylmethyl-2-oxo-3-amino-5-phenyl-8-methyl-1,3,4,5-tetrahydro-2H-1,5-benzodiazepine (−)-1-tert-Butylcarbonylmethyl-2-oxo-3-[(2S)-[2-(N-phenylthioureido)-3-phenylpropionyl]amino]-5-phenyl-8-methyl-1,3,4,5-tetrahydro-2H-1,5-benzodiazepine (2.50 g) was dissolved in trifluoroacetic acid (30 ml), the solution was stirred at 50° C. for one hour. The reaction mixture was concentrated under reduced pressure, the residue was dissolved in methanol (50 ml), concentrated hydrochloric acid (20 ml) was added, and refluxed for one hour. The resultant mixture was concentrated under reduced pressure, neutralized with saturated aqueous sodium bicarbonate, and extracted with methylene chloride. The organic layer was dried over anhydrous sodium sulfate, the solvent was evaporated under reduced pressure, and the residue was purified by silica gel column chromatography(chloroform:ethyl acetate=20:1), to thereby obtain 1.40 g of the titled compound.

Optical purity: 99%ee (the ee value was determined by High Performance Liquid Chromatography)

[α]D$^{27}$(C=1.03, $CHCl_3$): −21.4°

Step 3

Preparation of (−)-1-(1-tert-butylcarbonylmethyl-2-oxo-5-phenyl-8-methyl-1,3,4,5-tetrahydro-2H-1,5-benzodiazepin-3-yl)-3-(3-benzyloxycarbonylphenyl)urea Step 5 of Example 96 was repeated except that (−)-1-tert-butylcarbonylmethyl-2-oxo-3-amino-5-phenyl-8-methyl-1,3,4,5-tetrahydro-2H-1,5-benzodiazepine was used instead of (+)-1-tert-butylcarbonylmethyl-2-oxo-3-amino-5-phenyl-8-methyl-1,3,4,5-tetrahydro-2H-1,5-benzodiazepine, to thereby obtain the titled compound.

[α]D$^{27}$(C=1.035, $CHCl_3$): −48.0°

Step 4

Preparation of (−)-3-[3-(1-tert-butylcarbonylmethyl-2-oxo-5-phenyl-8-methyl-1,3,4,5-tetrahydro-2H-1,5-benzodiazepin-3-yl)ureido]benzoic acid Step 6 of Example 96 was repeated except that (−)-1-(1-tert-butylcarbonylmethyl-2-oxo-5-phenyl-8-methyl-1,3,4,5-tetrahydro-2H-1,5-benzodiazepin-3-yl)-3-(3-benzyloxycarbonylphenyl)urea was used instead of (+)-1-(1-tert-butylcarbonylmethyl-2-oxo-5-phenyl-8-methyl-1,3,4,5-tetrahydro-2H-1,5-benzodiazepin-3-yl)-3-(3-benzyloxycarbonylphenyl)urea, to thereby obtain the titled compound.

Optical purity: 99%ee (the ee value was determined by High Performance Liquid Chromatography)

[α]D$^{27}$(C=1.04, MeOH ): −111.3°

Example 98

Preparation of 3-[3-[1-(2-toluoylmethyl)-2-oxo-5-isobutyryl-8-methyl-1,3,4,5-tetrahydro-2H-1,5-benzodiazepin-3-yl]ureido]benzoic acid Step 1

Preparation of 1-[1-(2-toluoylmethyl)-2-oxo-5-isobutyryl-8-methyl-1,3,4,5-tetrahydro-2H-1,5-benzodiazepin-3-yl]-3-(3-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea (500 mg) obtained from Step 1 of Example 93 was suspended in 1,2-dichloroethane (10 ml), isobutyryl chloride (114 mg) and pyridine (86 μl) were added thereto at room temperature, and the mixture was refluxed for 2 hours and 30 minutes. The reaction mixture was allowed to cool, washed with saturated aqueous sodium bicarbonate, dried over anhydrous sodium sulfate, and the solvent was evaporated under reduced pressure. The residue was purified by silica gel column chromatography(n-hexane:ethyl acetate=2:1), to thereby obtain 647 mg of the titled compound (Yield: 100%).

$^1$H-NMR($CDCl_3$) δ: H, tt), 3.86(1H, d d), 4.33(2H, q), 4.61(1H, t), 4.78(1H, d), 4.86–4.96(1H, m), 5.31(1H, d), 6.36(1H, d), 7.06(1H, s), 7.11–7.31(5H, m), 7.38(1H, t), 7.63–7.70(3H, m), 7.79(1H, br s), 7.91(1H, t)

Step 2

Preparation of 3-[3-[1-(2-toluoylmethyl)-2-oxo-5-isobutyryl-8-methyl-1,3,4,5-tetrahydro-2H-1,5-benzodiazepin-3-yl]ureido]benzoic acid 1-[1-(2-Toluoylmethyl)-2-oxo-5-isobutyryl-8-methyl-1,3,4,5-tetrahydro-2H-1,5-benzodiazepin-3-yl]-3-(3-ethoxycarbonylphenyl)urea (560 mg) was dissolved in methanol (28 ml), aqueous lithium hydroxide monohydrate (201 mg) solution (14 ml) and tetrahydrofuran (14 ml) were added, the mixture was refluxed for one hours. The reaction mixture was concentrated under reduced pressure, 1N hydrochloric acid was added, and extracted with ethyl acetate. The organic layer was dried over anhydrous magnesium sulfate, the solvent was evaporated under reduced pressure, and diisopropyl ether was added to the residue for trituration, collected by filtration, to thereby obtain 360 mg of the titled compound (Yield: 67.4%).

Melting point: 162–165° C.

$^1$H-NMR(DMSO-$d_6$) δ: 0.93(3H, d), 1.04(3H, d), 2.32–2.41(1H, m), 2.39(3H, s), 2.41(3H, s), 3.60(1H, dd), 4.43(1H, t), 4.52–4.62(1H, m), 5.11(1H, d), 5.36(1H, d), 6.75(1H, d), 7.24–7.42(6H, m), 7.46–7.53(3H, m), 7.96(1H, d), 8.01(1H, t), 9.06(1H, s), 12.82(1H, brs)

MS (FAB) m/z: 579 ($M^+$+Na)

Example 99

Preparation of 3-[3-[1-(2-toluoylmethyl)-2-oxo-5-(2-propylpentanoyl)-8-methyl-1,3,4,5-tetrahydro-2H-1,5-benzodiazepin-3-yllureidolbenzoic acid Step 1

Preparation of 1-[1-(2-toluoylmethyl)-2-oxo-5-(2-propylpentanoyl)-8-methyl-1,3,4,5-tetrahydro-2H-1,5-benzodiazepin-3-yl]-3-($^3$-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea($^{500}$ mg) obtained from Step 1 of Example 93 was suspended in 1,2-dichloroethane (10 ml), 2-n-propylpentanoyl chloride (174 mg) and pyridine (87 μl) were added, the mixture was refluxed for 2 hours. The reaction mixture was allowed to cool, successively washed with 1N hydrochloric acid and saturated aqueous sodium bicarbonate, dried over anhydrous sodium sulfate, the solvent was evaporated under reduced pressure, and the residue was purified by silica gel column chromatography(n-hexane:ethyl acetate=2:1), to thereby obtain 625 mg of the titled compound (Yield: 100%).

$^1$H-NMR($CDCl_3$) δ: 0.69(3H, t), 0.89(3H, t), 0.92–1.68 (8H, m), 1.35(3H, t), 2.25–2.38(1H, m), 2.38(3H, s), 2.54 (3H, s), 3.88(1H, dd), 4.32(2H, q), 4.33(1H, d), 4.90–5.00 (1H, m), 5.60(1H, d), 6.37(1H, br), 7.00(1H, s), 7.13–7.30 (5H, m), 7.42(1H, t), 7.58–7.69(4H, m), 7.95(1H, s)

Step 2

Preparation of 3-[3-[1-(2-toluoylmethyl)-2-oxo-5-(2-propylpentanoyl)-8-methyl-1,3,4,5-tetrahydro-2H-1,5-benzodiazepin-3-yllureido]benzoic acid 1-[1-(2-Toluoylmethyl)-2-oxo-5-(2-propylpentanoyl)-8-methyl-1,3,4,5-tetrahydro-2H-1,5-benzodiazepin-3-yl]-3-(3-ethoxycarbonylphenyl)urea (540 mg) was dissolved in methanol (28 ml). Aqueous lithium hydroxide monohydrate (177 mg) solution (14 ml) and tetrahydrofuran (14 ml) were added, the mixture was refluxed for 45 minutes. The reaction mixture was concentrated under reduced pressure, 1N hydrochloric acid was added to the residue, extracted with methylene chloride. The organic layer was washed with saturated brine, dried over anhydrous magnesium sulfate, the solvent was evaporated under reduced pressure, and diisopropyl ether was added to the residue for trituration, collected by filtration, to thereby obtain 408 mg of the titled compound (Yield: 79.3%).

Melting point: 232–234° C.

$^1$H-NMR(DMSO-$d_6$) δ: 0.70(3H, t), 0.82(3H, t), 0.92–1.60(8H, m), 2.14–2.19 (1H, m), 2.39 (3H, s), 2.46 (3H, s), 3.60–3.67(1H, m), 4.43(1H, t), 4.56–4.66(1H, m), 4.88(1H, d), 5.35(1H, d), 6.73(1H, d), 7.16(1H, s), 7.25–7.41(5H, m) 7.467–7.54(3H, m), 7.92(1H, d), 8.01(1H, t), 9.04(1H, s), 12.84(1H, brs)

MS (FAB)m/z: 613 (MH$^+$)

Example 100

Preparation of 2-fluoro-5-[3-[1-(2-toluoylmethyl)-2-oxo-5-pivaloyl-8-methyl-1,3,4,5-tetrahydro-2H-1,5-benzodiazepin-3-yl]ureido]benzoic acid Step 1

Preparation of 1-(2-toluoylmethyl)-2-oxo-3-tert-butoxycarbonylamino-5-pivaloyl-8-methyl-1,3,4,5-tetrahydro-2H-1,5-benzodiazepine 2-Oxo-3-tert-butoxycarbonylamino-5-pivaloyl-8-methyl-1,3,4,5-tetrahydro-2H-1,5-benzodiazepine (4.00 g) obtained from Step 1 of Example 89 was suspended in toluene (56 ml), 2-bromo-2'-methylacetophenone (2.72 g), 1N aqueous sodium hydroxide (28 ml) and tetra n-butylammonium bromide (40 mg) were added, and the mixture was stirred overnight at room temperature. The reaction mixture was weakly acidified with 1N hydrochloric acid, extracted with methylene chloride. The organic layer was washed with saturated aqueous sodium bicarbonate, dried over anhydrous sodium sulfate, and the solvent was evaporated under reduced pressure. Diisopropyl ether was added to the residue for trituration, collected by filtration, to thereby obtain 4.54 g of the titled compound.

$^1$H-NMR($CDCl_3$) δ: 1.03(9H, s), 1.40(9H, s), 2.37(3H, s), 2.57(3H, s), 3.93(1H, dd), 4.26(1H, t), 4.45(1H, d), 4.53–4.59(1H, m), 5.49(1H, d), 5.51 (1H, d), 7.04–7.15 (3H, m), 7.28–7.34(2H, m), 7.42–7.48(1H, m), 7.75–7.78(1H, m)

Step 2

Preparation of 1-(2-toluoylmethyl)-2-oxo-3-amino-5-pivaloyl-8-methyl-1,3,4,5-tetrahydro-2H-1,5-benzodiazepine 1-(2-Toluoylmethyl)-2-oxo-3-tert-butoxycarbonylamino-5-pivaloyl-8-methyl-1,3,4,5-tetrahydro-2H-1,5-benzodiazepine (1.00 g) was suspended in 4N HCl-dioxane (10 ml), the suspension was stirred at 50° C. for one hour. The reaction mixture was concentrated under reduced pressure, the residue was dissolved in water, the solution was washed with diethyl ether, alkaline with saturated aqueous sodium bicarbonate, and extracted with methylene chloride. The organic layer was dried over anhydrous sodium sulfate, the solvent was evaporated under reduced pressure, the residue was purified by silica gel column chromatography (ethyl acetate), to thereby obtain 538 mg of the titled compound.

$^1$H-NMR($CDCl_3$) δ: 1.02(9H, s), 1.66(2H, br), 2.38(3H, s), 2.59(3H, s), 3.66–3.78(2H, m), 4.19–4.28(1H, m), 4.36 (1H, d), 5.65(1H, d), 7.01(1H, s), 7.07–7.12(2H, m), 7.29–7.49(3H, m), 7.81(1H, m)

Step 3

Preparation of 1-[1-(2-toluoylmethyl)-2-oxo-5-pivaloyl-8-methyl-1,3,4,5-tetrahydro-2H-1,5-benzodiazepin-3-yl]-3-(3-methoxycarbonyl-4-fluorophenyl)urea Methyl 5-amino-2-fluorobenzoate (241 mg) was dissolved in tetrahydrofuran (43 ml), under ice-cooling triphosgene (142 mg) was added and triethylamine (123 μl) were added five times every 3 minutes, a solution of 1-(2-toluoylmethyl)-2-oxo-3-amino-5-pivaloyl-8-methyl-1,3,4,5-tetrahydro-2H-1,5-benzodiazepine (528 mg) in tetrahydrofuran (20 ml) was added thereto, and the mixture was allowed to come to room temperature and stirred at room temperature for 2 hours. The reaction mixture was concentrated under reduced pressure, water (50 ml) was added, and extracted with methylene chloride. The organic layer was washed with saturated brine, dried over anhydrous sodium sulfate, the solvent was evaporated under reduced pressure, and the residue was purified by silica gel column chromatography(n-hexane:ethyl acetate=2:1), to thereby obtain 543 mg of the titled compound (Yield: 69.3%).

$^1$H-NMR($CDCl_3$) δ: 1.05(9H, s), 2.39(3H, s), 2.47(3H, s), 3.84(3H, s), 3.84–3.39(1H, m), 4.39(1H, t), 4.45(1H, d), 4.84–4.92(1H, m), 5.55(1H, d), 6.57(1H, d), 6.91(1H, dd), 7.02(1H, s), 7.11–7.29(4H, m), 7.38–7.45(3H, m), 7.68(1H, d), 7.86(1H, dd)

Step 4

Preparation of 2-fluoro-5-[3-[1-(2-toluoylmethyl)-2-oxo-5-pivaloyl-8-methyl-1,3,4,5-tetrahydro-2H-1,5-benzodiazepin-3-yl]ureido]benzoic acid 1-[1-(2-Toluoylmethyl)-2-oxo-5-pivaloyl-8-methyl-1,3,4,5-tetrahydro-2H-1,5-benzodiazepin-3-yl]-3-(3-methoxycarbonyl-4-fluorophenyl)urea (510 mg) was dissolved in methanol (24 ml), aqueous lithium hydroxide monohydrate (178 mg) solution (12 ml) and tetrahydrofuran (12 ml) was added, and the mixture was refluxed for one hour. The reaction mixture was concentrated under reduced pressure, 1N hydrochloric acid was added, and extracted with methylene chloride. The organic layer was washed with saturated brine, dried over anhydrous magnesium sulfate, the solvent was evaporated under reduced pressure, and diisopropyl ether was added to the residue for trituration, collected by filtration, to thereby obtain 320 mg of the titled compound.

Melting point: 225–228° C.

$^1$H-NMR($CDCl_3$) δ: 1.07(9H, s), 2.39(3H, s), 2.55(3H, s), 4.10(1H, dd), 4.40(1H, t), 4.57(1H, d), 4.75–4.81(1H, m), 5.50(1H, d), 7.04–7.35(7H, m), 7.48(1H, t), 7.56(1H, dd), 7.71(1H, d), 8.05(1H, s), 8.31–8.34(1H, m), 11.00(1H, br)

MS(FAB)m/z: 589(MH$^+$)

Example 101

Preparation of 3-[3-[1-tert-butylcarbonylmethyl-2-oxo-5-(2-fluorophenyl)-1,3,4,5-tetrahydro-2H-1,5-benzodiazepin-3-yl]ureido]benzoic acid Step 1

Preparation of 1-tert-butylcarbonylmethyl-2-oxo-3-benzyloxycarbonylamino-5-(2-fluorophenyl)-1,3,4,5-tetrahydro-2H-1,5-benzodiazepine 2-Oxo-3-benzyloxycarbonylamino-5-(2-fluorophenyl)-1,3,4,5-tetrahydro-2H-1,5-benzodiazepine (291 mg) obtained from Referential Example 9,bromomethyl-tert-butylketone (171 mg), toluene (5 ml), 1N aqueous sodium hydroxide (5 ml) and tetra n-butylammonium bromide (28 mg) were mixed, the mixture was stirred for 20 hours. The reaction mixture was separated into aqueous layer and organic layer, the aqueous layer was extracted with ethyl acetate, the extract was combined with the former organic layer. The combined organic layer was successively washed with water and saturated brine, dried over anhydrous magnesium sulfate, and the solvent was evaporated under reduced pressure. The residue was purified by silica gel column chromatography(n-hexane:ethyl acetate=3:1), to thereby obtain 205 mg of the titled compound as colorless amorphous.

$^1$H-NMR(CDCl$_3$) δ: 1.28(9H, s), 3.43–3.51(1H, m), 4.11 (1H, d), 4.39–4.45(1H, m), 4.68–4.72(1H, m), 5.07(2H, s), 5.33(1H, d), 5.88(1H, brd), 6.87–7.34(13H, m)

Step 2

Preparation of 1-tert-butylcarbonylmethyl-2-oxo-3-amino-5-(2 -fluorophenyl)-1,3,4,5-tetrahydro-2H-1,5-benzodiazepine 1-tert-Butylcarbonylmethyl-2-oxo-3-benzyloxycarbonylamino-5-(2-fluorophenyl)-1,3,4,5-tetrahydro-2H-1,5-benzodiazepine (205 mg) was dissolved in methanol (10 ml), 10% palladium carbon (30 mg) was added, under hydrogen atmosphere the filtration, the filtrate was concentrated under reduced pressure, to thereby obtain 150 mg of the titled compound (Yield: 100%).

$^1$H-NMR(CDCl$_3$) δ: 1.19(9H, s), 3.48(2H, s), 4.01–4.09 (1H, m), 4.26(1H, d), 4.30–4.39(1H, m), 4.61–4.65(1H, m), 5.20(1H, d), 6.84–7.23(8H, m)

Step 3

Preparation of 1-[1-tert-butylcarbonylmethyl-2-oxo-5-(2-fluorophenyl)-1,3,4,5-tetrahydro-2H-1,5-benzodiazepin-3-yl]-3-(3-ethoxycarbonylphenyl)urea Ethyl 3-aminobenzoate (69 mg) was dissolved in tetrahydrofuran (10 ml), the solution was cooled on ice-water. Triphosgene (45 mg) was added at internal temperature 5° C., triethylamine (162 mg) was added thereto over 10 minutes period, the mixture was allowed to come to room temperature and stirred for 10 minutes. A solution of 1-tert-butylcarbonylmethyl-2-oxo-3-amino-5-(2-fluorophenyl)-1,3,4,5-tetrahydro-2H-1,5-benzodiazepine (150 mg) in tetrahydrofuran (5 ml), the mixture was additionally chloride. The organic layer was successively washed with water and saturated brine, dried over anhydrous sodium sulfate, the solvent was evaporated under reduced pressure, and the residue was purified by silica gel column chromatography (n-hexane:ethyl acetate=3:1), to thereby obtain 190 mg of the title compound as colorless crystals (Yield: 83%).

$^1$H-NMR(CDCl$_3$) δ: 1.27(9H, s), 1.37(3H, t), 3.50–3.57 (1H, m), 4.20(1H, d), 4.35(2H, q), 4.39–4.49(1H, m), 4.90–4.94(1H, m), 5.31(1H, d), 6.05(1H, brd), 6.64(1H, brs), 6.87–7.93(12H, m)

Step 4

Preparation of 3-[3-[1-tert-butylcarbonylmethyl-2-oxo-5-(2-fluorophenyl)-1,3,4,5-tetrahydro-2H-1,5-benzodiazepin-3-yl]ureidolbenzoic acid 1-[1-tert-butylcarbonylmethyl-2-oxo-5-(2-fluorophenyl)-1,3,4,5-tetrahydro-2H-1,5-benzodiazepin-3-yl]-3-(3-ethoxycarbonylphenyl)urea (190 mg) was dissolved in a mixed solvent of tetrahydrofuran (10 ml) and ethanol (10 ml), aqueous lithium hydroxide monohydrate (210 mg) solution (10 ml) was added, and the mixture was stirred at room temperature for 7 hours. The reaction mixture was concentrated under reduced pressure, weakly acidified with 1N hydrochloric acid, and extracted with chloroform. The organic layer was successively washed with water and saturated brine, the solvent was evaporated under reduced pressure. The residue was purified by silica gel column chromatography(chloroform:methanol=10:1), to thereby obtain 140 mg of the titled compound (Yield: 78%).

Melting point: 226–227° C.

$^1$H-NMR(CDCl$_3$) δ: 1.31(9H, s), 1.56(3H, brs), 3.49–3.62 (1H, m), 4.14(1H, d), 4.57–4.63(1H, m), 4.87–4.91 (1H, m), 5.41 (1H, d), 6.79–7.74(10H, m), 8.29–8.41 (2H, m)

Example 102

Preparation of 3-[3-[1-(2-toluoylmethyl)-2-oxo-5-(2-ethylbutanoyl)-8-methyl-1,3,4,5-tetrahydro-2H-1,5-benzodiazepin-3-yl]ureido]benzoic acid Step 1

Preparation of 1-[1-(2-toluoylmethyl)-2-oxo-5-(2-ethylbutanoyl)-8-methyl-1,3,4,5-tetrahydro-2H-1,5-benzodiazepin-3-yl]-3-(3-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea (500 mg) obtained from Step 1 of Example 93 was suspended in 1,2-dichloroethane (10 ml), 2-ethyl-n-butanoyl chloride (144 mg) and pyridine (87 μl) were added thereto, the mixture was refluxed for 2 hours. Water (100 ml) and ethyl acetate (100 ml) were added to the reaction mixture, and separated. The organic layer was washed with 1N hydrochloric acid, dried over anhydrous sodium sulfate, the solvent was evaporated under reduced pressure, and the residue was purified by silica gel column chromatography(n-hexane:ethyl acetate=2:1), to thereby obtain 666 mg of the titled compound (Yield: 100%).

$^1$H-NMR(CDCl$_3$) δ: 0.71(3H, t), 0.93(3H, t), 1.29–1.38 (1H, m), 1.35(3H, t), 1.41–1.57(2H, m), 1.63–1.76(1H, m), 2.10–2.20(1H, m), 2.39(3H, s), 2.52(3H, s), 3.90(1H, dd), 4.31(2H, d), 4.33(2H, q), 4.66(1H, t), 4.89–4.96 (1H, m), 5.55 (1H, d), 6.34 (1H, d), 7.03 (1H, s), 7.15–7.30 (5H, m), 7.40 (1H, t), 7.58–7.68(4H, m), 7.91(1H, t)

Step 2

Preparation of 3-[3-[1-(2-toluoylmethyl)-2-oxo-5-(2-ethylbutanoyl)-8-methyl-1,3,4,5-tetrahydro-2H-1,5-benzodiazepin-3-yl]ureido]benzoic acid 1-[1-(2-Toluoylmethyl)-2-oxo-5-(2-ethylbutanoyl)-8-methyl-1,3,4,5-tetrahydro-2H-1,5-benzodiazepin-3-yl]-3-(3-ethoxycarbonylphenyl)urea (510 mg) was dissolved in methanol (24 ml), aqueous lithium hydroxide monohydrate (175 mg) solution (12 ml) and tetrahydrofuran (12 ml) were added, and the mixture was refluxed for one hour. The reaction mixture was concentrated under reduced pressure, 1N hydrochloric acid was added to the residue, and extracted with ethyl acetate. The organic layer was dried over anhydrous magnesium sulfate, the solvent was evaporated under reduced pressure, isopropyl ether was added to the residue for trituration, collected by filtration, to thereby obtain 339 mg of the titled compound.

Melting point: 244–246° C.

$^1$H-NMR(DMSO-d$_6$) δ: 0.64(3H, t), 0.82(3H, t), 1.23–1.42(3H, m), 1.56–1.67(1H, m), 1.95–2.03(1H, m), 2.40(3H, s), 2.46(3H, s), 3.65(1H, dd), 4.44(1H, t), 4.56–4.66(1H, m), 4.91 (1H, d), 5.33 (1H, d), 6.74 (1H, d), 7.15 (1H, s), 7.25–7.40(5H, m), 7.47–7.53(3H, m), 7.92(1H, d), 8.01(1H, t), 9.02(1H, s), 12.82(1H, brs)

MS(FAB)m/z: 585(MH$^+$)

Example 103

Preparation of 3-[3-[1-(2-toluoylmethyl)-2-oxo-5-(2-methylpentanoyl)-8-methyl-1,3,4,5-tetrahydro-2H-1,5-benzodiazepin-3-yl]ureido]benzoic acid Step 1

Preparation of 1-[1-(2-toluoylmethyl)-2-oxo-5-(2-methylpentanoyl)-8methyl-1,3,4,5-tetrahydro-2H-1,5-benzodiazepin-3-yl]-3-(3-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea (500 mg) obtained from Step 1of Example 93 was suspended in 1,2-dichloroethane (10 ml), 2-methyl-n-pentanoyl chloride (144 mg) and pyridine (87 μl) were added, the mixture was refluxed for 3 hours. Water (100 ml) and ethyl acetate (100 ml) were added to the reaction mixture, separated, the organic layer was washed with 1N hydrochloric acid, and dried over anhydrous sodium sulfate. The solvent was evaporated under reduced pressure, the residue was purified by silica gel column chromatography(n-hexane:ethyl acetate=2:1), to thereby obtain 569 mg of the titled compound (Yield: 95.7%).

$^1$H-NMR($CDCl_3$) δ: 0.70 and 0.87(3H, respectively t), 0.97 and 1.16(3H, respectively d), 1.16–1.80(4H, m), 1.35 (3H, t), 2.29–2.45(1H, m), 2.38(3H, s), 2.48–2.53(3H, s), 3.8–3.90(1H, m), 4.33(2H, q), 4.41–4.70(2H, m), 4.87–4.97 (1H, m), 5.48(1H, t), 6.30(1H, d), 7.04(1H, s), 7.15–7.31 (5H, m), 7.36–7.41(1H, m), 7.55(1H, s), 7.63–7.69(3H, m), 7.92(1H, s)

Step 2

Preparation of 3-[3-[1-(2-toluoylmethyl)-2-oxo-5-(2-methylpentanoyl)-8-methyl-1,3,4,5-tetrahydro-2H-1,5-benzodiazepin-3-yl]ureido]benzoic acid 1-[1-(2-Toluoylmethyl)-2-oxo-5-(2-methylpentanoyl)-8-methyl-1,3,4,5-tetrahydro-2H-1,5-benzodiazepin-3-yl]-3-(3-ethoxycarbonylphenyl)urea (560 mg) was dissolved in methanol (26 ml), aqueous lithium hydroxide monohydrate (192 mg) solution (13 ml) and tetrahydrofuran (13 ml) were added, and the mixture was refluxed for one hour. The reaction mixture was concentrated under reduced pressure, 1N hydrochloric acid was added, and extracted with ethyl acetate. The organic layer was dried over anhydrous magnesium sulfate, the solvent was evaporated under reduced pressure, and diisopropyl ether was added to the residue for trituration, collected by filtration, to thereby obtain 319 mg of the titled compound.

Melting point: 227–229° C.

$^1$H-NMR(DMSO-$d_6$) δ: 0.69 and 0.81(3H, respectively t), 0.87 and 1.02(3H, respectively d), 0.81–1.63(4H, m), 2.18–2.29(1H, m), 2.39(3H, s), 2.43 and 2.45(3H, s), 3.58–3.66(1H, m), 4.35–4.62(2H, m), 4.99(1H, dd), 5.36 (1H, dd), 6.73(1H, d), 7.20–7.41(6H, m), 7.47–7.53(3H, m), 7.95(1H, t), 8.01(1H, t), 9.03(1H, s), 12.83(1H, brs)

MS(FAB)m/z: 585$(MH)^+$

Example 104

Preparation of 3-[3-[1-(2-toluoylmethyl)-2-oxo-5-(2-thenoyl)-8-methyl-1,3,4,5-tetrahydro-2H-1,5-benzodiazepin-3-yl]ureido]benzoic acid Step 1

Preparation of 1-[1-(2-toluoylmethyl)-2-oxo-5-(2-thenoyl)-8-methyl-1,3,4,5-tetrahydro-2H-1,5-benzodiazepin-3-yl]-3-(3-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea (500 mg) obtained from Step 1 of Example 93 was suspended in 1,2-dichloroethane (10 ml), 2-thienylcarbonyl chloride (157 mg) and pyridine (87 μl) were added, and the mixture was refluxed for 2 hours. Water (100 ml) and ethyl acetate (100 ml) were added, separated, the organic layer was washed with 1N hydrochloric acid, and dried over anhydrous sodium sulfate. The solvent was evaporated under reduced pressure, the residue was washed with diethyl ether, to thereby obtain 553 mg of the titled compound (Yield: 91.3%).

$^1$H-NMR($CDCl_3$) δ: 1.34(3H, t), 2.39(3H, s), 2.42(3H, s), 4.12(1H, dd), 4.32(2H, q), 4.65(1H, t), 4.78(1H, d), 5.00–5.10(1H, m), 5.39(1H, d), 6.41(1H, d), 6.83(1H, dd), 7.02– 7.09(3H, m), 7.13(1H, s), 7.20–7.41(6H, m), 7.52(1H, ddd), 7.63(1H, dt), 7.71(1H, d), 7.91(1H, t)

Step 2

Preparation of 3-[3-[1-(2-toluoylmethyl)-2-oxo-5-(2-thenoyl)-8-methyl-1,3,4,5-tetrahydro-2H-1,5-benzodiazepin-3-yl]ureido]benzoic acid 1-[1-(2-Toluoylmethyl)-2-oxo-5-(2-thenoyl)-8-methyl-1,3,4,5-tetrahydro-2H-1,5-benzodiazepin-3-yl]-3-(3-ethoxycarbonylphenyl)urea (495 mg) was dissolved in methanol (24 ml), aqueous lithium hydroxide monohydrate (166 mg) solution (12 ml) and tetrahydrofuran (12 ml) were added, and the mixture was refluxed for one hour. The reaction mixture was concentrated under reduced pressure, 1N hydrochloric acid was added to the residue, and extracted with ethyl acetate. The organic layer was dried over anhydrous magnesium sulfate, the solvent was evaporated under reduced pressure, and diisopropyl ether was added to the residue for trituration, collected by filtration, to thereby obtain 289 mg of the titled compound.

Melting point: 219–222° C.

$^1$H-NMR(DMSO-$d_6$) δ: 2.35(3H, s), 2.39(3H, s), 3.89 (1H, dd), 4.36(1H, t), 4.63–4.73(1H, m), 5.15(1H, d), 5.40 (1H, d), 6.73(1H, brs), 6.81–6.89(2H, m), 7.10–7.19(2H, m), 7.31–7.37(4H, m), 7.45–7.55(3H, m), 7.65(1H, dd), 7.94 (1H, d), 8.03(1H, s), 9.06(1H, s), 12.84(1H, brs)

MS(FAB)m/z: 597$(MH^+)$

Example 105

Preparation of 3-[3-[1-(2-toluoylmethyl)-2-oxo-5-(2-pyridylcarbonyl)-8-methyl-1,3,4,5-tetrahydro-2H-1,5-benzodiazepin-3-yl]ureido]benzoic acid Step 1

Preparation of 2-oxo-3-tert-butoxycarbonylamino-5-(2-pyridylcarbonyl)-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) obtained from Referential Example 7 was suspended in 1,2-dichloroethane (40 ml), picolinoyl chloride hydrochloride (1.41 g) and pyridine (1.28 ml) were added, and the mixture was refluxed for 1 hour and 30 minutes. The reaction mixture was concentrated under reduced pressure, the residue was dissolved in ethyl acetate (150 ml), successively washed with water and saturated aqueous sodium bicarbonate, and dried over anhydrous sodium sulfate. The solvent was evaporated under reduced pressure, diethyl ether was added to the residue for trituration, collected by filtration, to thereby obtain 1.75 g of the titled compound.

$^1$H-NMR($CDCl_3$) δ: 1.43(9H, s), 2.25(3H, s), 4.15(1H, dd), 4.50(1H, t), 4.64–4.71(1H, m), 5.59(1H, d), 6.61–6.69 (2H, m), 6.89(1H, s), 7.12(1H, dd), 7.38(1H, d), 7.56(1H, dt), 8.26–8.28(2H, m)

Step 2

Preparation of 1-(2-toluoylmethyl)-2-oxo-3-tert-butoxycarbonylamino-5-(2-pyridylcarbonyl)-8-methyl-1,3,4,5-tetrahydro-2H-1,5-benzodiazepine 2-Oxo-3-tert-butoxycarbonylamino-5-(2-pyridylcarbonyl)-8-methyl-1,3,4,5-tetrahydro-2H-1,5-benzodiazepine (1.74 g) was suspended in toluene (24 ml), 2-bromo-2'-methylacetophenone (1.12 g), 1N aqueous sodium hydroxide (12 ml) and tetra n-butylammonium bromide (20 mg) were added, the mixture was stirred for one day at room temperature. The reaction mixture was weakly acidified with 1N hydrochloric acid, extracted with methylene chloride. The organic layer was washed with saturated aqueous sodium bicarbonate, dried over anhydrous sodium sulfate, and the solvent was evaporated under reduced pressure. The residue was purified by silica gel column chromatography(chloroform:ethyl acetate=9:1), to thereby obtain 1.25 g of the titled compound.

$^1$H-NMR($CDCl_3$) δ: 1.42(9H, s), 2.25(3H, s), 2.60(3H, s), 4.12(1H, dd), 4.44(1H, t), 4.62(1H, d), 4.71–4.78(1H, m), 5.60–5.67(2H, m), 6.63(1H, d), 6.74(1H, d), 7.05(1H, s), 7.09–7.14(1H, m), 7.29–7.34(2H, m), 7.45(1H, t), 7.61–7.63 (2H, m), 7.82(1H, d), 8.20(1H, d)

Step 3

Preparation of 1-(2-toluoylmethyl)-2-oxo-3-amino-5-(2-pyridylcarbonyl)-8-methyl-1,3,4,5-tetrahydro-2H-1,5-benzodiazepine 1-(2-Toluoylmethyl)-2-oxo-3-tert-butoxycarbonylamino-5-(2-pyridylcarbonyl)-8-methyl-1,3,4,5-tetrahydro-2H-1,5-benzodiazepine (1.00 g) was suspended in 4N HCl-dioxane (10 ml), the suspension was stirred for one hour at 50° C. The reaction mixture was concentrated under reduced pressure, the residue was dissolved in water, the solution was washed with diethyl ether, alkaline with saturated aqueous sodium bicarbonate,and extracted with methylene chloride. The organic layer was dried over anhydrous sodium sulfate, the solvent was evaporated under reduced pressure, to thereby obtain 886 mg of the titled compound (Yield: 100%).

$^1$H-NMR($CDCl_3$) δ: 1.69(2H, brs), 2.26(3H, s), 2.61(3H, s), 3.91(2H, q), 4.46(1H, t), 4.53(1H, d), 5.76(1H, d), 6.64(1H, d), 6.73(1H, d), 7.02(1H, s), 7.12(1H, dd), 7.30–7.35(2H, m), 7.46(1H, t), 7.60–7.65(2H, m), 7.85(1H, d), 8.19(1H, d)

Step 4

Preparation of 1-[1-(2-toluoylmethy)-2-oxo-5-(2-pyridylcarbonyl)-8-methyl-1,3,4,5-tetrahydro-2H-1,5-benzodiazepin-3-yl]-3-(3-ethoxycarbonylphenyl)urea Ethyl 3-aminobenzoate (310 mg) was dissolved in tetrahydrofuran (50 ml), triphosgene (187 mg) was added under ice-cooling, triethylamine (161 μl) was added five times every 3 minutes,a solution of 1-(2-toluoylmethyl)-2-oxo-3-amino-5-(2-pyridylcarbonyl)-8-methyl-1,3,4,5-tetrahydro-2H-1,5-benzodiazepine (730 mg) in tetrahydrofuran (23 ml) was added thereto, and the reaction mixture was allowed to come to room temperature, stirred for 2 hours. The reaction mixture was concentrated under reduced pressure, water (50 ml) was added, extracted with methylene chloride. The organic layer was washed with saturated brine, dried over anhydrous sodium sulfate, the solvent was evaporated under reduced pressure, and the residue was purified by silica gel column chromatography(chloroform:ethyl acetate=10:1), to thereby obtain 483 mg of the titled compound.

$^1$H-NMR($CDCl_3$) δ: 1.35(3H, t), 2.27(3H, s), 2.54(3H, s), 4.08–4.17(1H, m), 4.33(2H, q), 4.61(1H, t), 4.71(1H, d), 5.03–5.13(1H, m), 5.62(1H, d), 6.45(1H, d), 6.69(1H, d), 6.76(1H, d), 7.04(1H, s), 7.10–7.15(1H, m), 7.20–7.33(5H, m), 7.42(1H, t), 7.53–7.56(1H, m), 7.61–7.64(2H, m), 7.80 (1H, d), 7.91(1H, s), 8.22(1H, d)

Step 5

Preparation of 3-[3-[1-(2-toluoylmethyl)-2-oxo-5-(2-pyridylcarbonyl)-8-methyl-1,3,4,5-tetrahydro-2H-1,5-benzodiazepin-3-yl]ureido]benzoic acid 1-[1-(2-Toluoylmethy)-2-oxo-5-(2-pyridylcarbonyl)-8-methyl-1,3,4,5-tetrahydro-2H-1,5-benzodiazepin-3-yl]-3-(3-ethoxycarbonylphenyl)urea (466 mg) was dissolved in methanol (22 ml), aqueous lithium hydroxide monohydrate (158 mg) solution (11 mg) and tetrahydrofuran (11 ml) were added, and the mixture was refluxed for one hour. The reaction mixture was concentrated under reduced pressure, the residue was dissolved in water, the solution was washed with diethyl ether, acidified with 1N hydrochloric acid, and extracted with methylene chloride. The organic layer was washed with saturated brine, dried over anhydrous magnesium sulfate, and the solvent was evaporated under reduced pressure. Isopropyl ether was added to the residue for trituration, collected by filtration, to thereby obtain 203 mg of the titled compound.

Melting point: 163–166° C.

$^1$H-NMR($CDCl_3$) δ: 2.28(3H, s), 2.59(3H, s), 4.28(1H, dd), 4.60(1H, t), 4.70(1H, d), 4.98–5.07(1H, m), 5.68(1H, d), 6.70(1H, d), 6.81(1H, d), 7.06(1H, s), 7.11–7.16(1H, m), 7.33–7.39(3H, m), 7.46–7.51(2H, m), 7.57–7.81 (5H, m), 8.18(1H, d), 8.27(1H, s), 8.36(1H, d), 12.82(1H, br)

MS(FAB)m/z: 592(MH)$^+$

Example 106

Preparation of 2-methyl-5-[1-(2-toluoylmethyl)-2-oxo-5-pivaloyl-8-methyl-1,3,4,5-tetrahydro-2H-1,5-benzodiazepin-3-yl]ureido]benzoic acid Step 1

Preparation of 1-[1-(2-toluoylmethyl)-2-oxo-5-pivaloyl-8-methyl-1,3,4,5-tetrahydro-2H-1,5-benzodiazepin-3-yl]-3-(3-methoxycarbonyl-4-methylphenyl)urea Methyl 5-amino-2-methylbenzoate (223 mg) was dissolved in tetrahydrofuran (30 ml), under ice-cooling triphosgene (135 mg) was added, triethylamine (116 μl) was added thereto five times every 3 minutes, the mixture was stirred for 10 minutes at same temperature. Subsequently, a solution of 1-(2-toluoylmethyl)-2-oxo-3-amino-5-pivaloyl-8-methyl-1,3,4,5-tetrahydro-2H-1,5-benzodiazepine (500 mg) in tetrahydrofuran (20 ml) was added dropwise, stirred for 30 minutes at same temperature, and then stirred for 3 hours at room temperature. The reaction mixture was concentrated under reduced pressure, water (50 ml) was added, and extracted with methylene chloride. The organic layer was washed with saturated brine, dried over anhydrous sodium sulfate, and the solvent was evaporated under reduced pressure. The residue was purified by silica gel column chromatography(chloroform:ethyl acetate=10:1), to thereby obtain 271 mg of the titled compound.

$^1$H-NMR($CDCl_3$) δ: 1.04(9H, s), 2.39(3H, s), 2.50(3H, s), 2.52(3H, s), 3.83(3H, s), 3.96(1H, dd), 4.34(1H, t), 4.43(1H, d), 4.79–4.89(1H, m), 5.50(1H, d), 6.01(1H, d), 6.89(1H, brs), 7.03(1H, s), 7.03–7.35(6H, m), 7.43(1H, t), 7.69(1H, d), 7.88(1H, d)

Step 2

Preparation of 2-methyl-5-[1-(2-toluoylmethyl)-2-oxo-5-pivaloyl-8-methyl-1,3,4,5-tetrahydro-2H-1,5-benzodiazepin-3-yl]ureido]benzoic acid 1-[1-(2-Toluoylmethyl-2-oxo-5-pivaloyl-8-methyl-1,3,4,5-tetrahydro-2H-1,5-benzodiazepin-3-yl]-3-(3-methoxycarbonyl-1-4-methylphenyl)urea (259 mg) was dissolved in methanol (14 ml), aqueous lithium hydroxide monohydrate (91 mg) solution (7 ml) and tetrahydrofuran (7 ml) were added, the mixture was refluxed for one hour. The reaction mixture was concentrated under reduced pressure, 1N hydrochloric acid was added, and extracted with methylene chloride. The organic layer was dried over anhydrous magnesium sulfate, the solvent was evaporated under reduced pressure, and a mixed solvent of diisopropyl ether and n-hexane was added to the residue for trituration, collected by filtration, to thereby obtain 180 mg of the titled compound (Yield: 73.4%).

Melting point: 174–177° C.

$^1$H-NMR($CDCl_3$) δ: 1.08(9H, s), 2.40(3H, s), 2.50(3H, s), 2.53(3H, s), 4.11(1H, dd), 4.41(1H, t), 4.54(1H, d), 4.78–4.84(1H, m), 5.47(1H, d), 7.07(1H, s), 7.14–7.35(6H, m), 7.46(1H, t), 7.67–7.74(2H, m), 8.01(1H, s), 8.17(1H, dd), 10.80(1H, br)

MS(FAB)m/z: 585($MH^+$)

Example 107

Preparation of 3-[3-[1-(2-toluoylmethyl)-2-oxo-5-(3-methyl-2-butenyl)-8-methyl-1,3,4,5-tetrahydro-2H-1,5-benzodiazepin-3-yl]ureido]benzoic acid Step 1

Preparation of 2-oxo-3-tert-butoxycarbonylamino-5-(3-methyl-2-butenyl)-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) obtained from Referential Example 7 was suspended in methanol (20 ml), 1-bromo-3-methyl-2-butene (1.18 g) and potassium carbonate (997 mg) were added, the mixture was stirred for 2 hours at room temperature. The reaction mixture was concentrated under reduced pressure, water (100 ml) was added, and extracted with methylene chloride. The organic layer was washed with saturated aqueous sodium bicarbonate, dried over anhydrous sodium sulfate, and the solvent was evaporated under reduced pressure, to thereby obtain 1.85 g of the titled compound (Yield: 71.4%).

$^1H$-NMR($CDCl_3$) δ: 1.40(9H, s), 1.68(3H, s), 1.71(3H, s), 2.28(3H, s), 3.29–3.44(2H, m), 3.61–3.63(2H, m), 4.38–4.47(1H, m), 5.15 (1H, br), 5.48(1H, d), 6.78(1H, s), 6.91(1H, d), 6.97(1H, d), 7.29(1H, brs)

MS (EI)m/z: 359($M^+$)

Step 2

Preparation of 1-(2-toluoylmethyl)-2-oxo-3-tert-butoxycarbonylamino-5-(3-methyl-2-butenyl)-8-methyl-1,3,4,5-tetrahydro-2H-1,5-benzodiazepine 2-Oxo-3-tert-butoxycarbonylamino-5-(3-methyl-2-butenyl)-8-methyl-1,3,4,5-tetrahydro-2H-1,5-benzodiazepine (965 mg) was suspended in toluene (14 ml), 2-bromo-2'-methylacetophenone (686 mg), 1N aqueous sodium hydroxide (7 ml) and tetran-butylammonium bromide (20 mg) were added, and the mixture was stirred overnight at room temperature. The reaction mixture was weakly acidified with 1N hydrochloric acid, extracted with methylene chloride. The organic layer was washed with saturated aqueous sodium bicarbonate, dried over anhydrous sodium sulfate, the solvent was evaporated under reduced pressure, and the residue was purified by silica gel column chromatography(chloroform:ethyl acetate=10:1), to thereby obtain 782 mg of the titled compound.

$^1H$-NMR($CDCl_3$) δ: 1.39(9H, s), 1.67(3H, s), 1.70(3H, s), 2.27(3H, s), 2.48(3H, s), 3.20–3.36(2H, m), 3.49–3.52 (2H, m), 4.46–4.50 (1H, m), 4.67(1H, d), 5.05 (1H, br), 5.34(1H, d), 5.54 (1H, d), 6.86–6.92(2H, m), 6.98 (1H, d), 7.23–7.27 (2H, m), 7.40 (1H, t), 7.68–7.71 (1H, m)

MS(EI)m/z: 491($M^+$)

Step 3

Preparation of 1-(2-toluoylmethyl)-2-oxo-3-amino-5-(3-methyl-2-butenyl)-8-methyl-1,3,4,5-tetrahydro-2H-1,5-benzodiazepine 1-(2-Toluoylmethyl)-2-oxo-3-tert-butoxycarbonylamino-5-(3-methyl-2-butenyl)-8-methyl-1,3,4,5-tetrahydro-2H-1,5-benzodiazepine (780 mg) was suspended in 4N HCl-dioxane (10 ml), the suspension was stirred for one hour at 50° C. The reaction mixture was concentrated under reduced pressure, the residue was dissolved in water, washed with diethyl ether, alkalified with saturated aqueous sodium bicarbonate, and extracted with methylene chloride. The organic layer was dried over anhydrous sodium sulfate, the solvent was evaporated under reduced pressure, to thereby obtain 493 mg of the titled compound (Yield: 79.4%).

$^1H$-NMR($CDCl_3$) δ: 1.68(3H, s), 1.70(3H, s), 1.70(2H, br), 2.28(3H, s), 2.51(3H, s), 3.12–3.25(2H, m), 3.48–3.55 (2H, m), 3.62(1H, dd), 4.57(1H, d), 5.07(1H, m), 5.49(1H, d), 6.89–6.92(2H, m), 6.99(1H, d), 7.26–7.30(2H, m), 7.38–7.44(1H, m), 7.72–7.75(1H, m)

Step 4

Preparation of 1-[1-(2-toluoylmethyl)-2-oxo-5-(3-methyl-2-butenyl)-8-methyl-1,3,4,5-tetrahydro-2H-1,5-benzodiazepin-3-yl]-3-(3-ethoxycarbonylphenyl)urea Ethyl 3-aminobenzoate (221 mg) was dissolved in tetrahydrofuran (20 ml), under ice-cooling triphosgene (134 mg) was added, triethylamine (115 μl) was added thereto five times every 3 minutes,a solution of 1-(2-toluoylmethyl)-2-oxo-3-amino-5-(3-methyl-2-butenyl)-8-methyl-1,3,4,5-tetrahydro-2H-1,5-benzodiazepine (477 mg) in tetrahydrofuran (20 ml) was added dropwise thereto, and the mixture was stirred for 30 minutes at same temperature and subsequently stirred overnight at room temperature. The reaction mixture was concentrated under reduced pressure, water (50 ml) was added, and extracted with methylene chloride. The organic layer was washed with saturated aqueous sodium bicarbonate, dried over anhydrous sodium sulfate, the solvent was evaporated under reduced pressure, and the residue was purified by silica gel column chromatography (chloroform:ethyl acetate=10:1), to thereby obtain 316 mg of the titled compound.

$^1H$-NMR($CDCl_3$) δ: 1.34(3H, t), 1.66(3H, s), 1.68(3H, s), 2.28(3H, s), 2.44(3H, s), 3.30–3.45(2H, m), 3.53(2H, d), 4.31(2H, q), 4.75(1H, d), 4.74–4.84(1H, m), 5.07(1H, m), 5.39(1H, d), 6.28(1H, d), 6.91–6.94(2H, m), 7.02(1H, d), 7.14(1H, s), 7.18–7.26(3H, m), 7.37(1H, t), 7.52(1H, d), 7.61–7.66(2H, m), 7.92(1H, t)

Step 5

Preparation of 3-[3-[1-(2-toluoylmethyl)-2-oxo-5-(3-methyl-2-butenyl)-8-methyl-1,3,4,5-tetrahydro-2H-1,5-benzodiazepin-3-yl]ureido]benzoic acid 1-[1-(2-Toluoylmethyl)-2-oxo5-(3-methyl-2-butenyl)-8-methyl-1,3,4,5-tetrahydro-2H-1,5-benzodiazepin-3-yl]-3-(3-ethoxycarbonylphenyl)urea (310 mg) was dissolved in methanol (16 ml), aqueous lithium hydroxide monohydrate (112 mg) solution (8 ml) and tetrahydrofuran (8 ml) were added, and the mixture was refluxed for 50 minutes. The reaction mixture was concentrated under reduced pressure, the residue was dissolved in water (150 ml), washed with diethyl ether, acidified with 1N hydrochloric acid, and extracted with methylene chloride. The organic layer was dried over anhydrous magnesium sulfate, the solvent was evaporated under reduced pressure, and a mixed solvent of diisopropyl ether and n-hexane were added to the residue for trituration, collected by filtration, to thereby obtain 230 mg of the titled compound (Yield: 78.3%).

Melting point: 129–131° C.

$^1H$-NMR($CDCl_3$) δ: 1.68(3H, s), 1.71(3H, s), 2.29(3H, s), 2.50(3H, s), 3.36(1H, t), 3.55–3.60(3H, m), 4.69–4.76(2H, m), 5.11(1H, brs), 5.40(1H, d), 6.93–6.97(2H, m), 7.05(1H, d), 7.26–7.46(5H, m), 7.57(1H, d), 7.66(1H, d), 7.73(1H, s), 8.22(1H, s), 8.38(1H, d), 10.96(1H, br)

MS(FAB)m/z: 555$(MH)^+$

Example 108

Preparation of 3-[3-[1-(2-toluoylmethyl)-2-oxo-5-isovaleryl-8-methyl-1,3,4,5-tetrahydro-2H-1,5-benzodiazepin-3-yl]ureido]benzoic acid Step 1

Preparation of 1-(1-(2-toluoylmethyl)-2-oxo-5-isovaleryl-8-methyl-1,3,4,5-tetrahydro-2H-1,5-benzodiazepin-3-yl]-3-(3-ethoxycarbonylphenyl)urea 1-[1-(2-Toluoylmethyl)-2-oxo-8-methyl-1,3,4,5-tetrahydro-2H-1,5-benzodiazepin-3-yl]-3-(3-ethoxycarbonylphenyl)urea (400 mg) obtained from Step 1 of Example 93 was suspended in 1,2-dichloroethane (10 ml), isovaleryl chloride (104 $\mu$l) and pyridine (70 $\mu$l) were added, and the mixture was refluxed for 1 hour and 30 minutes. Water and methylene chloride were added to the reaction mixture, separated, and the organic layer was successively washed with 1N hydrochloric acid and saturated aqueous sodium bicarbonate, and dried over anhydrous sodium sulfate. The solvent was evaporated under reduced pressure, the residue was purified by silica gel column chromatography (n-hexane:ethyl acetate=2:1), to thereby obtain 296 mg of the titled compound.

$^1$H-NMR($CDCl_3$) δ: 0.80–0.94(7H, m), 1.35(3H, t), 2.32–2.42(2H, m), 2.39(3H, s), 2.44(3H, s), 4.32(2H, q), 4.73(1H, t), 4.88–4.94(2H, m), 5.20(1H, d), 6.39(1H, d), 7.00(1H, s), 7.10–7.30(5H, m), 7.39(1H, t), 7.63–7.68(4H, m), 7.77(1H, brs), 7.87(1H, s)

Step 2

Preparation of 3-[3-[1-(2-toluoylmethyl)-2-oxo-5-isovaleryl-8-methyl-1,3,4,5-tetrahydro-2H-1,5-benzodiazepin-3-yl]ureido]benzoic acid 1-[1-(2-Toluoylmethyl)-2-oxo-5-isovaleryl-8-methyl-1,3,4,5-tetrahydro-2H-1,5-benzodiazepin-3-yl]-3-(3-ethoxycarbonylphenyl)urea (296 mg) was dissolved in methanol (14 ml), aqueous lithium hydroxide monohydrate (62 mg) solution (7 ml) and tetrahydrofuran (7 ml) were added, and the mixture was refluxed for 45 minutes. The reaction mixture was concentrated under reduced pressure, 1N hydrochloric acid was added, and extracted with methylene chloride. The organic layer was washed with saturated brine, dried over anhydrous magnesium sulfate, and the solvent was evaporated under reduced pressure. Isopropyl ether was added to the residue for trituration, collected by filtration, to thereby obtain 160 mg of the titled compound.

Melting point: 202–205° C.

$^1$H-NMR(DMSO-$d_6$) δ: 0.79(3H, d), 0.84(3H, d), 1.86–2.09(3H, m), 2.39(3H, s), 2.50(3H, s), 3.58–3.60(1H, m), 4.46–4.56(2H, m), 5.18(1H, d), 5.26(1H, d), 6.74(1H, d), 7.16–7.39(6H, m), 7.47–7.53(3H, m), 7.94 (1H, d), 8.01(1H, t), 9.00(1H, s), 12.80(1H, brs)

Example 109

Preparation of 3-[3-[1-(2-toluoylmethyl)-2-oxo-5-(3,3-dimethylbutanoyl)-8-methyl-1,3,4,5-tetrahydro-2H-1,5-benzodiazepin-3-yl]ureido]benzoic acid Step 1

Preparation of 2-oxo-3-tert-butoxycarbonylamino-5-(3,3-dimethylbutanoyl)-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) obtained from Referential Example 7 was suspended in 1,2-dichloroethane (40 ml), 3,3-dimethylbutanoyl chloride (1.07 g) and pyridine (627 mg) were added, and the mixture was refluxed for 2 hours. Water was added to the reaction mixture, separated, the organic layer was washed with saturated aqueous sodium bicarbonate, dried over anhydrous sodium sulfate, and the solvent was evaporated under reduced pressure, to thereby obtain 2.53 g of the titled compound (Yield: 90.1%).

$^1$H-NMR($CDCl_3$) δ: 0.89(9H, s), 1.41(9H, s), 1.93(2H, s), 2.39(3H, s), 3.80–3.81(1H, m), 4.53–4.56(2H, m), 5.40(1H, br), 6.94(1H, s), 7.07–7.09(2H, brs), 7.60(1H, brs)

Step 2

Preparation of 1-(2-toluoylmethyl)-2-oxo-3-tert-butoxycarbonylamino-5-(3,3-dimethylbutanoyl)-8-methyl-1,3,4,5-tetrahydro-2H-1,5-benzodiazepine 2-Oxo-3-tert-butoxycarbonylamino-5-(3,3-dimethylbutanoyl)-8-methyl-1,3,4,5-tetrahydro-2H-1,5-benzodiazepine (2.52 g) was suspended in toluene (36 ml), 2-bromo-2'-methylacetophenone (1.65 g), 1N aqueous sodium hydroxide (18 ml) and tetra n-butylammonium bromide (40 mg) were added thereto, and the mixture was stirred for 1 hour and 50 minutes at room temperature. Methylene chloride (100 ml) was added to the reaction mixture, separated, the organic layer was washed with saturated brine, and dried over anhydrous sodium sulfate. The solvent was evaporated under reduced pressure, the residue was purified by silica gel column chromatography(chloroform:ethyl acetate=30:1), to thereby obtain 1.47 g of the titled compound.

$^1$H-NMR($CDCl_3$) δ: 0.95(9H, s), 1.40(9H, s), 2.01(1H, d), 2.10(1H, d), 2.37(3H, s), 2.53(3H, s), 3.82(1H, dd), 4.44–4.57(2H, m), 4.69(1H, d), 5.28(1H, d), 5.48(1H, d), 7.04–7.12(2H, m), 7.26–7.33(3H, m), 7.44(1H, t), 7.73(1H, d)

Step 3

Preparation of 1-(2-toluoylmethyl)-2-oxo-3-amino-5-(3,3-dimethylbutanoyl)-8-methyl-1,3,4,5-tetrahydro-2H-1,5-benzodiazepine 1-(2-toluoylmethyl)-2-oxo-3-tert-butoxycarbonylamino-5-(3,3 -dimethylbutanoyl)-8-methyl-1,3,4,5-tetrahydro-2H-1,5-benzodiazepine (1.00 g) was suspended in4N HCl-dioxane (10 ml), the suspension was stirred for one hour at 50° C. The reaction mixture was concentrated under reduced pressure, saturated aqueous sodium bicarbonate was added, and extracted with methylene chloride. The organic layer was dried over anhydrous sodium sulfate, the solvent was evaporated under reduced pressure, to thereby obtain 741 mg of the titled compound (Yield: 91.6%).

$^1$H-NMR($CDCl_3$) δ: 0.94(9H, s), 1.60 (2H, br), 1.98(1H, d), 2.06(1H, d), 2.38(3H, s), 2.56(3H, s), 3.63–3.70(2H, m), 4.40–4.54(1H, m), 4.51(1H, d), 5.46(1H, d), 7.01(1H, s), 7.05–7.12(2H, m), 7.25–7.34(2H, m), 7.45(1H, t), 7.76(1H, d)

Step 4

Preparation of 1-[1-(2-toluoylmethyl)-2-oxo-5-(3,3-dimethylbutanoyl)-8-methyl-1,3,4,5-tetrahydro-2H-1,5-benzodiazepin-3-yl]-3-(3-ethoxycarbonylphenyl)urea Ethyl 3-aminobenzoate (236 mg) was dissolved in tetrahydrofuran (40 ml), under ice-cooling triphosgene (140 mg) was added and triethylamine (120 $\mu$l) was added thereto five times every 3 minutes, a solution of 1-(2-toluoylmethyl)-2-oxo-3-amino-5-(3,3-dimethylbutanoyl)-8-methyl-1,3,4,5-tetrahydro-2H-1,5-benzodiazepine (536 mg) in tetrahydrofuran (10 ml) was subsequently added, the mixture was stirred for 30 minutes at same temperature,and additionally stirred for 2 hours at room temperature. The reaction mixture was poured into water (400 ml),extracted with methylene chloride (50 ml), and the organic layer was dried over anhydrous sodium sulfate. The solvent was evaporated under reduced pressure, the residue was purified by silica gel column chromatography(n-hexane:ethyl acetate=2:1), to thereby obtain 479 mg of the titled compound $^1$H-NMR($CDCl_3$) δ: 0.97(9H, s), 1.35(3H, t), 2.05(1H, d), 2.17(1H, d), 2.38(3H, s), 2.48(3H, s), 3.85(1H, dd), 4.32(2H, q), 4.63(1H, t), 4.71(1H, d), 4.84–4.91(1H, m), 5.32(1H, d), 6.31(1H, d), 7.04(1H, s), 7.13(2H, s), 7.21–7.28(3H, m), 7.37–7.43(2H, m), 7.58–7.71(3H, m), 7.89(1H, t)

Step 5

Preparation of 3-[3-[1-(2-toluoylmethyl)-2-oxo-5-(3,3-dimethylbutanoyl)-8-methyl-1,3,4,5-tetrahydro-2H-1,5-benzodiazepin-3-yl]ureido]benzoic acid 1-[1-(2-toluoylmethyl)-2-oxo-5-(3,3-dimethylbutanoyl)-8-methyl-1,3,4,5-tetrahydro-2H-1,5-benzodiazepin-3-yl]-3-(3-ethoxycarbonylphenyl)urea (442 mg) was dissolved in methanol (20 ml), aqueous lithium hydroxide monohydrate (151 mg) solution (10 ml) and tetrahydrofuran (10 ml) were added, and the mixture was refluxed for one hour. The reaction mixture was concentrated under reduced pressure, 1N hydrochloric acid was added to the residue, extracted with methylene chloride. The solvent was evaporated under reduced pressure, diisopropyl ether was added to the residue for trituration, collected by filtration, to thereby obtain 324 mg of the titled compound as colorless powder (Yield: 77.1%).

$^1$H-NMR($CDCl_3$) δ: 0.98(9H, s), 2.04(1H, d), 2.10(1H, d), 2.39(3H, s), 2.51(3H, s), 3.92(1H, dd), 4.65–4.80(3H, m), 5.29(1H, d), 7.05(1H, s), 7.16(2H, s), 7.26–7.36(4H, m), 7.47(1H, t), 7.57(1H, d), 7.70–7.72(2H, m), 8.21(1H, brs), 8.32(1H, d), 10.00(1H, br)

MS(FAB)m/z: 607(M+Na)$^+$

Example 110

Preparation of 2-chloro-5-[3-[1-(2-toluoylmethyl)-2-oxo-5-pivaloyl-8-methyl-1,3,4,5-tetrahydro-2H-1,5-benzodiazepin-3-yl]ureido]benzoic acid Step 1

Preparation of 1-[1-(2-toluoylmethyl)-2-oxo-5-pivaloyl-8-methyl-1,3,4,5-tetrahydro-2H-1,5-benzodiazepin-3-yl]-3-(3-methoxycarbonyl-4-chlorophenyl)urea Methyl 5-amino-2-chlorobenzoate (223 mg) was dissolved in tetrahydrofuran (50 ml), triphosgene (135 mg) was added under ice-cooling, triethylamine (116 μl) was added thereto five times every 3 minutes, the mixture was stirred for 10 minutes at same temperature. A solution of 1-(2-toluoylmethyl)-2-oxo-3-amino-5-pivaloyl-8-methyl-1,3,4,5-tetrahydro-2H-1,5-benzodiazepine (500 mg) in tetrahydrofuran (10 ml) was added dropwise, the resultant mixture was stirred for 30 minutes at same temperature and additionally stirred for 2 hours at room temperature. The reaction mixture was poured into water (400 ml), extracted with methylene chloride. The organic layer was washed with 1N hydrochloric acid, dried over anhydrous sodium sulfate, the solvent was evaporated under reduced pressure, and the residue was purified by silica gel column chromatography (n-hexane:ethyl acetate=2:1), to thereby obtain 756 mg of the titled compound.

$^1$H-NMR($CDCl_3$) δ: 1.05(9H, s), 2.40(3H, s), 2.54(3H, s), 3.84(3H, s), 3.84–3.90(1H, m), 4.34–4.45(2H, m), 4.84–4.94(1H, m), 5.56(1H, d), 6.65(1H, d), 7.01(1H, s), 7.12–7.31(6H, m), 7.43(1H, t), 7.49(1H, s), 7.67(1H, d), 7.90(1H, d)

Step 2

Preparation of 2-chloro-5-[3-[1-(2-toluoylmethyl)-2-oxo-5-pivaloyl-8 -methyl-1,3,4,5-tetrahydro-2H-1,5-benzodiazepin-3-yl]ureido]benzoic acid 1-[1-(2-Toluoylmethyl)-2-oxo-5-pivaloyl-8-methyl-1,3,4,5-tetrahydro-2H-1,5-benzodiazepin-3-yl]-3-(3-methoxycarbonyl-4-chlorophenyl)urea (691 mg) was dissolved in methanol (30 ml), aqueous lithium hydroxide monohydrate (234 mg) solution (15 ml) and tetrahydrofuran (15 ml) were added, the mixture was refluxed for one hour. The reaction mixture was concentrated under reduced pressure, 1N hydrochloric acid was added, and extracted with methylene chloride. The organic layer was dried over anhydrous magnesium sulfate, the solvent was evaporated under reduced pressure, and diisopropyl ether was added to the residue for trituration, collected by filtration, to thereby obtain 437 mg of the titled compound.

Melting point: 178–180° C.

$^1$H-NMR($CDCl_3$) δ: 1.07(9H, s), 2.39(3H, s), 2.53(3H, s), 4.03–4.10(1H, m), 4.41(1H, t), 4.55(1H, d), 4.78–4.85(1H, m), 5.51(1H, d), 7.06(1H, s), 7.14–7.35(6H, m), 7.46(1H, t), 7.62 (1H, d), 7.70–7.73(1H, m), 7.96(1H, s), 8.14(1H, dd), 11.00(1H, br)

MS(FAB)m/z: 605(MH$^+$)

Example 111

Preparation of 3-[3-[1-(2-toluoylmethyl)-2-oxo-5-acetyl-8-methyl-1,3,4,5-tetrahydro-2H-1,5-benzodiazepin-3-yl]ureido]benzoic acid Step 1

Preparation of 2-oxo-3-tert-butoxycarbonylamino-5-acetyl-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) obtained from Referential Example 7 was suspended in 1,2-dichloroethane (40 ml), acetyl chloride (0.56 ml) and pyridine (0.64 ml) were added thereto, the mixture was refluxed for 2 hours. Water (100 ml) was added, extracted with ethyl acetate. The organic layer was washed with saturated aqueous sodium bicarbonate, dried over anhydrous sodium sulfate, the solvent was evaporated under reduced pressure, and diisopropyl ether was added to the residue for trituration, collectedly filtration, to thereby obtain 1.33 g of the titled compound.

$^1$H-NMR($CDCl_3$) δ: 1.41(9H, s), 1.79(3H, s), 2.39(3H, s), 3.80–3.85(1H, m), 4.52–4.64(2H, m), 5.45(1H, d), 6.97(1H, s), 7.14(1H, d), 7.22(1H, d), 7.81(1H, s)

Step 2

Preparation of 1-(2-toluoylmethyl)-2-oxo-3-tert-butoxycarbonylamino-5-acetyl-8-methyl-1,3,4,5-tetrahydro-2H-1,5-benzodiazepine 2-Oxo-3-tert-butoxycarbonylamino-5-acetyl-8-methyl-1,3,4,5-tetrahydro-2H-1,5-benzodiazepine (1.30 g) was suspended in toluene (18 ml), 2-bromo-2'-methylacetophenone (1.00 g), 1N aqueous sodium hydroxide (9 ml) and tetra n-butylammonium bromide (20 mg) were added thereto, and the mixture was stirred for 2 hours at room temperature. The reaction mixture was weakly acidified with 1N hydrochloric acid, extracted with methylene chloride. The organic layer was washed with saturated aqueous sodium bicarbonate, dried over anhydrous sodium sulfate, the solvent was evaporated under reduced pressure. Diisopropyl ether was added to the residue for trituration, collected by filtration, to thereby obtain 1.45 g of the titled compound (Yield: 79.7%).

$^1$H-NMR($CDCl_3$) δ: 1.40(9H, s), 1.89(3H, s), 2.38(3H, s), 2.47(3H, s), 3.70–3.80(1H, m), 4.51–4.60(2H, m), 5.00 (1H, d), 5.20 (1H, d), 5.47(1H, brs), 7.06(1H, s), 7.12 (2H, s), 7.26–7.32(2H, m), 7.43(1H, t), 7.73 (1H, d)

Step 3

Preparation of 1-(2-toluoylmethyl)-2-oxo-3-amino-5-acetyl-8-methyl-1,3,4,5-tetrahydro-2H-1,5-benzodiazepine 1-(2-Toluoylmethyl)-2-oxo-3-tert-butoxycarbonylamino-5-acetyl-8-methyl-1,3,4,5-tetrahydro-2H-1,5-benzodiazepine (1.00 g) was suspended in 4N HCl-dioxane (10 ml), the suspension was stirred for one hour at 50° C. The reaction mixture was concentrated under reduced pressure, the residue was dissolved in water, washed with diethyl ether, alkalified with saturated aqueous sodium bicarbonate, and extracted with methylene chloride. The organic layer was dried over anhydrous sodium sulfate, the solvent was evaporated under reduced pressure, to thereby obtain 820 mg of the titled compound (Yield: 100%).

$^1$H-NMR($CDCl_3$) δ: 1.61(2H, brs), 1.85(3H, s), 2.39(3H, s), 2.50(3H, s), 3.60–3.76(2H, m), 4.54(1H, t), 4.97(1H, d), 5.21(1H, d), 7.04(1H, s), 7.09 (2H, s), 7.30(2H, t), 7.44(1H, t), 7.76(1H, d)

Step 4

Preparation of 1-[1-(2-toluoylmethyl)-2-oxo-5-acetyl-8-methyl-1,3,4,5-tetrahydro-2H-1,5-benzodiazepin-3-yl]-3-(3-ethoxycarbonylphenyl)urea Ethyl 3-aminobenzoate (386 mg) was dissolved in tetrahydrofuran (60 ml), under ice-cooling triphosgene (233 mg) was added, triethylamine (201 $\mu$l) was added thereto five times every 3 minutes, a solution of 1-(2-toluoylmethyl)-2-oxo-3-amino-5-acethyl-8-methyl-1,3,4,5-tetrahydro-2H-1,5-benzodiazepine (777 mg) in tetrahydrofuran (18 ml) was subsequently added, and the mixture was allowed to come to room temperature and stirred for 4 hours. The reaction mixture was concentrated under reduced pressure, water (50 ml) was added, and extracted with methylene chloride. The organic layer was successively washed with 1N hydrochloric acid and saturated aqueous sodium bicarbonate, dried over anhydrous sodium sulfate, and the solvent was evaporated under reduced pressure, to thereby obtain 670 mg of the titled compound.

$^1$H-NMR($CDCl_3$) δ: 1.34(3H, t), 2.00(3H, s), 2.33(3H, s), 2.40(3H, s), 3.83(1H, dd), 4.32(2H, q), 4.73–4.98(3H, m), 5.40(1H, d), 6.52(1H, d), 7.10–7.38(7H, m), 7.61–7.76(3H, m), 7.90(1H, t), 8.25(1H, s)

Step 5

Preparation of 3-[3-[1-(2-toluoylmethyl)-2-oxo-5-acetyl-8-methyl-1,3,4,5-tetrahydro-2H-1,5-benzodiazepin-3-yl]ureido]benzoic acid 1-[1-(2-Toluoylmethyl)-2-oxo-5-acetyl-8-methyl-1,3,4,5-tetrahydro-2H-1,5-benzodiazepin-3-yl]-3-(3-ethoxycarbonylphenyl)urea (670 mg) was dissolved in methanol (32 ml), aqueous lithium hydroxide monohydrate (253 mg) solution (16 ml) and tetrahydrofuran (16 ml) were added, and the mixture was refluxed for 45 minutes, the reaction mixture was concentrated under reduced pressure, the residue was dissolved in water (150 ml), the solution was washed with diethyl ether, acidified with 1N hydrochloric acid, and extracted with methylene chloride. The organic layer was washed with saturated brine, dried over anhydrous magnesium sulfate, the solvent was evaporated under reduced pressure, diisoproryl ether was added to the residue for trituration, collected by filtration, to thereby obtain 370 mg of the titled compound.

Melting point: 184–187° C.

$^1$H-NMR($CDCl_3$) δ: 1.92(3H, s), 2.40(3H, s), 2.44(3H, s), 3.76(1H, dd), 4.65(1H, t), 4.84(1H, dd), 4.93(1H, d), 5.30 (1H, d), 7.10–7.43(10H, m), 7.60(1H, d), 7.76(1H, m), 7.88(1H, s), 12.83(1H, br)

IR(KBr)cm$^{-1}$:3376, 1713, 1647, 1608, 1560, 1221, 756

MS(FAB)m/z: 529(MH$^+$)

Example 112

Preparation of 3-[3-[1-(2-toluoylmethyl)-2-oxo-5-(3-methyl-2-butenoyl)-8-methyl-1,3,4,5-tetrahydro-2H-1,5-benzodiazepin-3-yl]ureido]benzoic acid Step 1

Preparation of 2-oxo-3-tert-butoxycarbonylamino-5-(3-methyl-2-butenoyl)-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) obtained from Referential Example 7 was suspended in 1,2-dichloroethane (40 ml), 3,3-dimethylacryloyl chloride (941 mg) and pyridine (626 mg) were added, the mixture was refluxed for one hour. The reaction mixture was allowed to cool, water (100 ml) was added, and extracted with ethyl acetate. The organic layer was washed with saturated aqueous sodium bicarbonate, dried over anhydrous sodium sulfate, and the solvent was evaporated under reduced pressure. Isopropylether was added to the residue for trituration, collected by filtration, to thereby obtain 1.62 g of the titled compound.

$^1$H-NMR($CDCl_3$) δ: 1.41(9H, s), 1.67(3H, s), 2.10(3H, s), 2.39(3H, s), 3.99(1H, dd), 4.42–4.57(2H, m), 5.20(1H, brs), 5.47(1H, d), 6.96(1H, s), 7.03(2H, s), 8.27(1H, br)

Step 2

Preparation of 1-(2-toluoylmethyl)-2-oxo-3-tert-butoxycarbonylamino-5-(3-methyl-2-butenoyl)-8-methyl-1,3,4,5-tetrahydro-2H-1,5-benzodiazepine 2-Oxo-3-tert-butoxycarbonylamino-5-(3-methyl-2-butenoyl)-8-methyl-1,3,4,5-tetrahydro-2H-1,5-benzodiazepine (1.54 g) was suspended in toluene (22 ml), 2-bromo-2'-methylacetophenone (1.05 g), 1N aqueous sodium hydroxide (11 ml) and tetra n-butylammonium bromide (25 mg) were added, and the mixture was stirred for 4 hours at room temperature. The reaction mixture was acidified with 1N hydrochloric acid, extracted with methylene chloride. The organic layer was washed with saturated aqueous sodium bicarbonate, dried over anhydrous sodium sulfate, the solvent was evaporated under reduced pressure, and the residue was purified by silica gel column chromatography(chloroform:ethyl acetate=10:1), to thereby obtain 2.26 g of the titled compound (Yield: 100%).

$^1$H-NMR($CDCl_3$) δ: 1.40(9H, s), 1.68(3H, s), 2.13(3H, s), 2.36(3H, s), 2.49(3H, s), 3.86(1H, dd), 4.39(1H, t), 4.56–4.63(1H, m), 4.94(1H, d), 5.17(1H, d), 5.28(1H, brs), 5.50(1H, d), 7.01–7.04(3H, m), 7.26–7.31(2H, m), 7.42(1H, t), 7.72(1H, d)

Step 3

Preparation of 1-(2-toluoylmethyl)-2-oxo-3-amino-5-(3-methyl-2-butenoyl)-8-methyl-1,3,4,5-tetrahydro-2H-1,5-benzodiazepine 1-(2-Toluoylmethyl)-2-oxo-3-tert-butoxycarbonylamino-5-(3-methyl-2-butenoyl)-8-methyl-1,3,4,5-tetrahydro-2H-1,5-benzodiazepine (1.00 g) was suspended in 4N HCl-dioxane (10 ml), the suspension was stirred for one hour at 50° C. The reaction mixture was concentrated under reduced pressure, the residue was dissolved in water, the solution was washed with diethyl ether, alkalified with saturated aqueous sodium bicarbonate, and extracted with methylene chloride. The organic layer was dried over anhydrous sodium sulfate, and the solvent was evaporated under reduced pressure, to thereby obtain 694 mg of the titled compound (Yield: 86.5%).

$^1$H-NMR($CDCl_3$) δ: 1.68(3H, s), 1.89(2H, br), 2.13(3H, s), 2.37(3H, s), 2.52(3H, s), 3.68–3.78(2H, m), 4.42(1H, t), 4.77(1H, d), 5.25(1H, brs), 5.34(1H, d), 7.02–7.14(3H, m), 7.27–7.32(2H, m), 7.43(1H, t), 7.75(1H, d)

Step 4

Preparation of 1-[1-(2-toluoylmethyl)-2-oxo-5-(3-methyl-2-butenoyl)-8-methyl-1,3,4,5-tetrahydro-2H-1,5-benzodiazepin-3-yl]-3-(3-ethoxycarbonylphenyl)urea Ethyl 3-aminobenzoate (290 mg) was dissolved in tetrahydrofuran (60 m), under ice-cooling triphosgene (175 mg) was added, triethylamine (151 $\mu$l) was added thereto five times every 3 minutes,a solution of 1-(2-toluoylmethyl)-2-oxo-3-amino-5-(3-methyl-2-butenoyl)-8-methyl-1,3,4,5-tetrahydro-2H-1,5-benzodiazepine (647 mg) in tetrahydrofuran (5 ml) was subsequently added, and the mixture was allowed to come to room temperature and stirred for 2 hours and 40 minutes. The reaction mixture was concentrated under reduced pressure, water was added, and extracted with methylene chloride. The organic layer was successively washed with 1N hydrochloric acid and saturated aqueous sodium bicarbonate, dried over anhydrous sodium sulfate, the solvent was evaporated under reduced pressure, and the residue was purified by silica gel column chromatography (chloroform:ethyl acetate=5:1), to thereby obtain 373 mg of the titled compound.

Step 5

Preparation of 3-[3-[1-(2-toluoylmethyl)-2-oxo-5-(3-methyl-2-butenoyl)-8-methyl-1,3,4,5-tetrahydro-2H-1,5-benzodiazepin-3-yl]ureido]benzoic acid 1-[1-(2-Toluoylmethyl)-2-oxo-5-(3-methyl-2-butenoyl)-8-methyl-1,3,4,5-tetrahydro-2H-1,5-benzodiazepin-3-yl]-3-(3-ethoxycarbonylphenyl)urea (340 mg) was dissolved in methanol (16 ml), aqueous lithium hydroxide monohydrate (120 mg) solution (8 ml) and tetrahydrofuran (8 ml) were added, and the mixture was refluxed for 50 minutes. The reaction mixture was concentrated under reduced pressure, the residue was dissolved in water (150 ml), the solution was washed with diethyl ether, acidified with 1N hydrochloric acid, and extracted with methylene chloride. The organic layer was washed with saturated brine, dried over anhydrous magnesium sulfate, the solvent was evaporated under reduced pressure, and diisoproryl ether was added to the residue for trituration, collected by filtration, to thereby obtain 223 mg of the titled compound (Yield: 68.8%).

Melting point: 240–242° C.

$^1$H-NMR(DMSO-$d_6$) δ: 1.63(3H, s), 2.04(3H, s), 2.36 (3H, s), 2.37(3H, s), 3.64(1H, m), 4.34(1H, t), 4.55(1H, m), 5.26(1H, s), 5.35(1H, s), 6.78(1H, d), 7.14–7.18(2H, m), 7.31–7.37(4H, m), 7.45–7.53(4H, m), 7.91(1H, d), 8.01(1H, s), 9.03(1H, s), 12.80(1H, br)

MS(FAB)m/z: 569(MH$^+$)

Example 113

Preparation of 3-[3-[1-(2-toluoylmethyl)-2-oxo-5-(furan-2-ylcarbonyl)-8-methyl-1,3,4,5-tetrahydro-2H-1,5-benzodiazepin-3-yl]ureido]benzoic acid Step 1

Preparation of 2-oxo-3-tert-butoxycarbonylamino-5-(furan-2-ylcarbonyl)-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) obtained from Referential Example 7 was suspended in 1,2-dichloroethane (40 ml), 2-furancarbonyl chloride (1.05 g) and pyridine (626 mg) were added thereto, the mixture was refluxed for 2 hours. Water (100 ml) was added to the reaction mixture, extracted with ethyl acetate. The organic layer was washed with saturated aqueous sodium bicarbonate, dried over anhydrous sodium sulfate, the solvent was evaporated under reduced pressure, and diisopropyl ether was added to the residue for trituration, collected by filtration, to thereby obtain 2.15 g of the titled compound (Yield: 77,4%).

$^1$H-NMR($CDCl_3$) δ: 1.42(9H, s), 2.39(3H, s), 4.09(1H, dd), 4.46(1H, t), 4.60–4.68(1H, m), 5.49(1H, d), 5.99(1H, br), 6.23(1H, dd), 6.98–7.03(3H, m), 7.26(1H, m), 7.69(1H, s)

Step 2

Preparation of 1-(2-toluoylmethyl)-2-oxo-3-tert-butoxycarbonylamino-5-(furan-2-ylcarbonyl)-8-methyl-1,3,4,5-tetrahydro-2H-1,5-benzodiazepine 2-Oxo-3-tert-butoxycarbonylamino-5-(furan-2-ylcarbonyl)-8-methyl-1,3,4,5-tetrahydro-2H-1,5-benzodiazepine (1.50 g) was suspended in toluene (20 ml), 2-bromo-2'-methylacetophenone (995 mg), 1N aqueous sodium hydroxide (10 ml) and tetra n-butylammonium bromide (20 mg) were added, and the mixture was stirred for 2 hours at room temperature. The reaction mixture was weakly acidified with 1N hydrochloric acid, and extracted with methylene chloride. The organic layer was washed with saturated aqueous sodium bicarbonate, dried over anhydrous sodium sulfate, the solvent was evaporated under reduced pressure, and the residue was purified by silica gel column chromatography(chloroform:ethyl acetate=20:1), to thereby obtain 1.55 g of the titled compound (Yield: 76.9%).

$^1$H-NMR($CDCl_3$) δ: 1.41(9H, s), 2.38(3H, s), 2.51(3H, s), 4.05–4.14(1H, m), 4.18(1H, t), 4.65–4.77(2H, m), 5.38(1H, d), 5.57(1H, d), 6.12(1H, br), 6.24(1H, brs), 6.98(2H, s), 7.11(1H, s), 7.26–7.30(3H, s), 7.42(1H, t), 7.75(1H, d)

Step 3

Preparation of 1-(2-toluoylmethyl)-2-oxo-3-amino-5-(furan-2-ylcarbonyl)-8-methyl-1,3,4,5-tetrahydro-2H-1,5-benzodiazepine 1-(2-Toluoylmethyl)-2-oxo-3-tert-butoxycarbonylamino-5-(furan-2-ylcarbonyl)-8-methyl-1,3,4,5-tetrahydro-2H-1,5-benzodiazepine (1.00 g) was dissolved in 4N HCl-dioxane (10 ml), the solution was stirred for one hour at 50° C. The reaction mixture was concentrated under reduced pressure, the residue was dissolved in water, the solution was washed with diethyl ether, alkalified with saturated aqueous sodium bicarbonate, and extracted with methylene chloride. The organic layer was dried over anhydrous sodium sulfate, the solvent was evaporated under reduced pressure, to thereby obtain 875 mg of the titled compound (Yield: 100%).

$^1$H-NMR($CDCl_3$) δ: 2.20(3H, s), 2.27(3H, s), 2.30(2H, br), 4.40–4.47(1H, m), 4.52–4.58(1H, m), 5.02(1H, d), 5.14 (1H, t), 5.29(1H, d), 6.15(2H, brs), 6.84(1H, d), 6.94(1H, d), 7.06(1H, d), 7.16–7.25(4H, m), 7.75(1H, d)

Step 4

Preparation of 1-[1-(2-toluoylmethyl)-2-oxo-5-(furan-2-ylcarbonyl)-8-methyl-1,3,4,5-tetrahydro-2H-1,5-benzodiazepin-3-yl]-3-(3-ethoxycarbonylphenyl)urea Ethyl 3-aminobenzoate (373 mg) was dissolved in tetrahydrofuran (60 ml), under ice-cooling triphosgene (225 mg) was added, triethylamine (194 μl) was added thereto five times every 3 minutes, a solution of 1-(2-toluoylmethyl)-2-oxo-3-amino-5-(furan-2-ylcarbonyl)-8-methyl-1,3,4,5-tetrahydro-2H-1,5-benzodiazepine (856 mg) in tetrahydrofuran (15 ml) was added thereto, the mixture was allowed to come to room temperature and stirred overnight. The reaction mixture was concentrated under reduced pressure, water (50 ml) was added to the residue, extracted with methylene chloride. The organic layer was dried over anhydrous sodium sulfate, the solvent was evaporated under reduced pressure, and the residue was purified by silica gel column chromatography(chloroform:ethyl acetate=10:1), to thereby obtain 447 mg of the titled compound.

$^1$H-NMR($CDCl_3$) δ: 1.35(3H, t), 2.36(3H, s), 2.41(3H, s), 4.05–4.13(1H, m), 4.34(2H, d), 4.73(1H, t), 4.91(1H, d), 5.01–5.11(1H, m), 5.20(1H, d), 5.78(1H, brs), 6.19–6.21 (1H, m), 6.65(1H, d), 7.05–7.36(7H, m), 7.41(1H, d), 7.63–7.70(2H, m), 7.78(1H, d), 7.89(1H, brs), 7.94(1H, t)

Step 5

Preparation of 3-[3-[1-(2-toluoylmethyl)-2-oxo-5-(furan-2-ylcarbonyl)-8-methyl-1,3,4,5-tetrahydro-2H-1,5-benzodiazepin-3-yl]ureido]benzoic acid 1-[1-(2-Toluoylmethyl)-2-oxo-5-(furan-2-ylcarbonyl)-8-methyl-1,3,4,5-tetrahydro-2H-1,5-benzodiazepin-3-yl]-3-(3-ethoxycarbonylphenyl)urea (429 mg) was dissolved in methanol (22 ml), aqueous lithium hydroxide monohydrate (148 mg) solution (11 ml) and tetrahydrofuran (11 ml) were added, and the mixture was refluxed for one hour. The reaction mixture was concentrated under reduced pressure, the residue was dissolved in water (150 ml), the solution was washed with diethyl ether, acidified with 1N hydrochloric acid, and extracted with methylene chloride. The organic layer was washed with saturated brine, dried over anhydrous magnesium sulfate, and the solvent was evaporated under reduced pressure. Isoproryl ether was added to the residue for trituration,collected by filtration, to thereby obtain 237 mg of the titled compound.

Melting point: 219–221° C.

$^1$H-NMR($CDCl_3$) δ: 2.40(3H, s), 2.45(3H, s), 4.08(1H, m), 4.50(1H, t), 4.79(1H, d), 4.92–5.01(1H, m), 5.29(1H, d), 6.03(1H, br), 6.25(1H, brs), 6.76(1H, d), 7.04(2H, s), 7.13 (1H, s), 7.25–7.31(4H, m), 7.38–7.44(1H, m), 7.61(1H, d), 7.73–7.81(2H, m), 7.88(1H, t), 8.68(1H, s), 11.60(1H, br)

MS(FAB)m/z: 581(MH$^+$)

Example 114

Preparation of 3-[3-[1-(furan-2-yl)carbonylmethyl-2-oxo-5-pivaloyl-8-methyl-1,3,4,5-tetrahydro-2H-1,5-benzodiazepin-3-yl]ureido]benzoic acid Step 1

Preparation of 1-(furan-2-yl)carbonylmethyl-2-oxo-3-tert-butoxycarbonylamino-5-pivaloyl-8-methyl-1,3,4,5-tetrahydro-2H-1,5-benzodiazepine 60% Sodium hydride (320 mg) was suspended in tetrahydrofuran (30 ml), under ice-cooling 2-oxo-3-tert-butoxycarbonylamino-5-pivaloyl-8-methyl-1,3,4,5-tetrahydro-2H-1,5-benzodiazepine (2.00 g) obtained from Step I of Example 89, and the mixture was stirred for 30 minutes. Bromomethyl(furan-2-yl)ketone (1.89 g) was added dropwise thereto, stirred for 2 hours at room temperature. The reaction mixture was concentrated under reduced pressure, water (100 ml) and ethyl acetate (100 ml) were added, and separated into aqueous layer and organic layer. The aqueous layer was acidified with 1N hydrochloric acid, extracted with ethyl acetate. The extract was combined with the former organic layer. The combined extract was washed with saturated brine, dried over anhydrous magnesium sulfate, subsequently, purified by silica gel column chromatography(chloroform:ethyl acetate=10:1), to thereby obtain 550 mg of the titled compound.

$^1$H-NMR($CDCl_3$) δ: 1.03(9H, s), 1.39(9H, s), 2.36(3H, s), 3.90(1H, dd), 4.24(1H, t), 4.39(1H, d), 4.52(1H, m), 5.47 (1H, d), 5.56(1H, d), 6.62(1H, dd), 7.07–7.14(3H, m), 7.37(1H, d), 7.64(1H, d)

Step 2

Preparation of 1-(furan-2-yl)carbonylmethyl-2-oxo-3-amino-5-pivaloyl-8-methyl-1,3,4,5-tetrahydro-2H-1,5-benzodiazepine 1-(Furan-2-yl)carbonylmethyl-2-oxo-3-tert-butoxycarbonylamino-5-pivaloyl-8-methyl-1,3,4,5-tetrahydro-2H-1,5-benzodiazepine (1.00 g) was suspended in ethanol (10 ml), concentrated hydrochloric acid (2 ml) was added, and the mixture was stirred for one hour at 50° C. The reaction mixture was concentrated under reduced pressure, the residue was dissolved in etheyl acetate, successively washed with saturated aqueous sodium bicarbonate and saturated brine, and dried over anhydrous magnesium sulfate. The solvent was evaporated under reduced pressure, diethyl ether was added to the residue for trituration, collected by filtration, to thereby obtain 373 mg of the titled compound.

$^1$H-NMR($CDCl_3$) δ: 1.02(9H, s), 2.37(3H, s), 2.38(2H, br), 3.77(2H, m), 4.30–4.38(1H, m), 4.35(1H, d), 5.65(1H, d), 6.62(1H, dd), 7.04–7.15(3H, m), 7.38(1H, d), 7.65(1H, d)

Step 3

Preparation of 1-[1-(furan-2-yl)carbonylmethyl-2-oxo-5-pivaloyl-8-methyl-1,3,4,5-tetrahydro-2H-1,5-benzodiazepin-3-yl]-3-(3-ethoxycarbonylphenyl)urea Ethyl 3-aminobenzoate (171 mg) was dissolved in tetrahydrofuran (20 ml), under ice-cooling triphosgene (104 mg) was added, triethylamine (90 μl) was added thereto five times every 3 minutes,a suspension of 1-(furan-2-yl) carbonylmathyl-2-oxo-3-amino-5-pivaloyl-8-methyl-1,3,4,5-tetrahydro-2H-1,5-benzodiazepine (362 mg) in tetrahydrofuran (10 ml), and the mixture was allowed to come to room temperature and stirred for 2 hours. The reaction mixture was concentrated under reduced pressure, water (50 ml) was added to the residue, and extracted with methylene chloride. The organic layer was washed with saturated brine, dried over anhydrous sodium sulfate, the solvent was evaporated under reduced pressure, and the residue was purified by silica gel column chromatography(chloroform:ethyl acetate=9:1), to thereby obtain 192 mg of the titled compound.

$^1$H-NMR($CDCl_3$) δ: 1.04(9H, s), 1.36(3H, t), 2.38(3H, s), 3.94(1H, dd), 4.30–4.46(2H, m), 4.34(2H, q), 4.78–4.85(1H, m), 5.60(1H, d), 6.02(1H, d), 6.59(1H, dd), 7.02–7.19(4H, m), 7.26–7.33(1H, m), 7.36(1H, dd), 7.58–7.69(3H, m), 7.90(1H, t)

Step 4

Preparation of 3-[3-[1-(furan-2-yl)carbonylmethyl-2-oxo-5-pivaloyl-8-methyl-1,3,4,5-tetrahydro-2H-1,5-benzodiazepin-3-yl]ureido]benzoic acid 1-[1-(Furan-2-yl)carbonylmethyl-2-oxo-5-pivaloyl-8-methyl-1,3,4,5-tetrahydro-2H-1,5-benzodiazepin-3-yl]-3-(3-ethoxycarbonylphenyl)urea (187 mg) was dissolved in methanol (8.8 ml), aqueous lithium hydroxide monohydrate (68.3 mg) solution (4.4 ml) and tetrahydrofuran (4.4 ml) were added, the mixture was refluxed for one hour. The reaction mixture was concentrated under reduced pressure, the residue was dissolved in water (50 ml), the solution was washed with diethyl ether, acidified with 1N hydrochloric acid,and extracted with methylene chloride. The organic layer was dried over anhydrous magnesium sulfate, the solvent was evaporated under reduced pressure, and diisoproryl ether was added to the residue for trituration, collected by filtration, to thereby obtain 110 mg of the titled compound.

Melting point: 202–204° C.

$^1$H-NMR($CDCl_3$) δ: 1.04(9H, m), 2.37(3H, s), 3.90(1H, dd), 4.32(1H, t), 4.45(1H, d), 4.75–4.82(1H, m), 5.51(1H, d), 6.55(1H, d), 6.62(1H, dd), 7.06(1H, s), 7.09–7.18(2H, m), 7.27(1H, t), 7.33–7.35(2H, m), 7.61(1H, d), 7.65–7.66 (1H, m), 7.80(1H, d), 7.84(1H, m), 8.58(1H, s)

IR(KBr)cm$^{-1}$:3389, 1702, 1641, 1555

Example 115

Preparation of 3-[3-[1-(2-toluoylmethyl)-2-oxo-5-cyclohexylcarbonyl-8-methyl-1,3,4,5-tetrahydro-2H-1,5-benzodiazepin-3-yl]ureido]benzoic acid Step 1

Preparation of 2-oxo-3-tert-butoxycarbonylamino-5-cyclohexylcarbonyl-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (2.00 g) was suspended in 1,2-dichloroethane (20 ml), cyclohexylcarbonyl chloride (1.21 g) and pyridine (652 mg) were added, and the mixture was refluxed for 1 hour and 30 minutes. Water (100 ml) was added to the reaction mixture, extracted with methylene chloride. The organic layer was washed with water, dried over anhydrous magnesium sulfate, the solvent was evaporated under reduced pressure, and n-hexane was added to the residue for trituration, collected by filtration, to thereby obtain 2.04 g of the titled compound (Yield: 74.2%).

$^{1}$H-NMR($CDCl_3$) δ: 0.86–1.73(10H, m), 1.41(9H, s), 2.00(1H, m), 2.40(3H, s), 3.74–3.78(1H, m), 4.52–4.55(2H, m), 5.40(1H, m), 6.95(1H, s), 7.10(2H, s), 7.76(1H, d)

Step 2

Preparation of 1-(2-toluoylmethyl)-2-oxo-3-tert-butoxycarbonylamino-5-cyclohexylcarbonyl-8-methyl-1,3,4,5-tetrahydro-2H-1,5-benzodiazepine 2-Oxo-3-tert-butoxycarbonylamino-5-cyclohexylcarbonyl-8-methyl-1,3,4,5-tetrahydro-2H-1,5-benzodiazepine (2.00 g) was suspended in toluene (28 ml), 2-bromo-2'-methylacetophenone (1.28 g), 1N aqueous sodium hydroxide (14 ml) and tetra n-butylammonium bromide (20 mg) were added, and the mixture was stirred for 2 hours at room temperature. The reaction mixture was acidified with 1N hydrochloric acid, extracted with ethyl acetate. The organic layer was successively washed with saturated aqueous sodium bicarbonate and saturated brine, dried over anhydrous magnesium sulfate, the solvent was evaporated under reduced pressure, and diisopropyl was added to the residue for trituration, collected by filtration, to thereby obtain 2.15 g of the titled compound (Yield: 80.7%).

$^{1}$H-NMR($CDCl_3$) δ: 0.94–1.81(10H, m), 1.40(9H, s), 2.13–2.17(1H, m), 2.39(3H, s), 2.51(3H, s), 3.79(1H, dd), 4.48(1H, t), 4.52–4.61(1H, m), 4.81(1H, d), 5.27(1H, d), 5.48(1H, d), 7.07–7.34(5H, m), 7.44(1H, t), 7.76(1H, d)

Step 3

Preparation of 1-(2-toluoylmethyl)-2-oxo-3-amino-5-cyclohexylcarbonyl-8-methyl-1,3,4,5-tetrahydro-2H-1,5-benzodiazepine 1-(2-Toluoylmethyl)-2-oxo-3-tert-butoxycarbonylamino-5-cyclohexylcarbonyl-8-methyl-1,3,4,5-tetrahydro-2H-1,5-benzodiazepine (1.00 g) was suspended in 4N HCl-dioxane (10 ml), the suspension was stirred for one hour at 50° C. The reaction mixture was concentrated under reduced pressure, the residue was dissolved in methylene chloride (100 ml), the solution was successively washed with saturated aqueous sodium bicarbonate and saturated brine, and dried over anhydrous sodium sulfate. The solvent was evaporated under reduced pressure, a mixed solvent of n-hexane and diisopropyl ether was added to the residue for trituration, collected by filtration, to thereby obtain 700 mg of the titled compound (Yield: 86.2%).

$^{1}$H-NMR($CDCl_3$) δ: 0.88–1.73(12H, m), 2.13(1H, m), 2.40(3H, s), 2.55(3H, s), 3.60–3.67(2H, m), 4.48(1H, t), 4.59(1H, d), 5.45(1H, d), 7.04(1H, s), 7.10(1H, d), 7.12(1H, d), 7.32(2H, t), 7.45(1H, t), 7.79(1H, d)

Step 4

Preparation of 1-[1-(2-toluoylmethyl)-2-oxo-5-cyclohexylcarbonyl-8-methyl-1,3,4,5-tetrahydro-2H-1,5-benzodiazepin-3-yl]-3-(3-ethoxycarbonylphenyl)urea Ethyl 3-aminobenzoate (252 mg) was dissolved in tetrahydrofuran (40 ml), triphosgene (152 mg) was added under ice-cooling, subsequently, triethylamine (132 μl) was added five times every 3 minutes, a solution of 1-(2-toluoylmethyl)-2-oxo-3-amino-5-cyclohexylcarbonyl-8-methyl-1,3,4,5-tetrahydro-2H-1,5-benzodiazepine (600 mg) in tetrahydrofuran (20 ml), and the reaction mixture was allowed to come to room temperature and additionally stirred for 2 hours. The reaction mixture was concentrated under reduced pressure, water (50 ml) was added to the residue, extracted with methylene chloride. The organic layer was washed with saturated brine, dried over anhydrous sodium sulfate, the solvent was evaporated under reduced pressure, and the residue was purified by silica gel column chromatography(n-hexane:ethyl acetate=2:1), to thereby obtain 500 mg of the titled compound.

$^{1}$H-NMR($CDCl_3$) δ: 1.06–1.84(10H, m), 1.35(3H, t), 2.23 (1H, m), 2.39(3H, s), 2.44(3H, s), 3.84(1H, dd), 4.34(2H, dd), 4.59(1H, t), 4.84–4.91(1H, m), 4.88(1H, d), 5.26(1H, d), 6.34(1H, d), 7.06(1H, s), 7.14–7.31(5H, m), 7.38(1H, t), 7.67(3H, t), 7.79(1H, brs), 7.92(1H, s)

Step 5

Preparation of 3-[3-[1-(2-toluoylmethyl)-2-oxo-5-cyclohexylcarbonyl-8-methyl-1,3,4,5-tetrahydro-2H-1,5-benzodiazepin-3-yl]ureido]benzoic acid 1-[1-(2-Toluoylmethyl)-2-oxo-5-cyclohexylcarbonyl-8-methyl-1,3,4,5-tetrahydro-2H-1,5-benzodiazepin-3-yl]-3-(3-ethoxycarbonylphenyl)urea (500 mg) was dissolved in methanol (24 ml), aqueous lithium hydroxide monohydrate (168 mg) solution (12 ml) and tetrahydrofuran (12 ml) were added, and the mixture was refluxed for 30 minutes. The reaction mixture was concentrated under reduced pressure, the residue was dissolved in water (50 ml), the solution was washed with diethyl ether, acidified with 1N hydrochloric acid, and extracted with methylene chloride (50ml). The organic layer was washed with saturated brine, dried over anhydrous magnesium sulfate, the solvent was evaporated under reduced pressure, and isoproryl ether was added to the residue for trituration, collected by filtration, to thereby obtain 240 mg of the titled compound.

Melting point: 183–185° C.

$^{1}$H-NMR($CDCl_3$) δ: 0.97–1.79(10H, m), 2.10–2.30(1H, m), 2.41(3H, s), 2.48(3H, s), 2.59(1H, t), 3.77(1H, dd), 4.53(1H, t), 4.77–4.87(1H, m), 4.92(1H, d), 5.23(1H, d), 6.67(1H, d), 7.10(1H, s), 7.16(2H, s), 7.24–7.35(3H, m), 7.42–7.47(1H, m), 7.59(1H, d), 7.77(2H, t), 7.88(1H, s), 8.71(1H, s)

MS(FAB)m/z: 597($MH^+$)

Example 116

Preparation of 3-[3-[1-(2-toluoylmethyl)-2-oxo-5-cyclohexyl-8-methyl-1,3,4,5-tetrahydro-2H-1,5-benzodiazepin-3-yl]ureido]benzoic acid Step 1

Preparation of 1-(2-toluoylmethyl)-2-oxo-3-tert-butoxycarbonylamino-5-(2-cyclohexen-1-yl)-8-methyl-1,3,4,5-tetrahydro-2H-1,5-benzodiazepine 2-Oxo-3-tert-butoxycarbonylamino-5-(2-cyclohexen-1-yl)-8-methyl-1,3,4,5-tetrahydro-2H-1,5-benzodiazepine (1.05 g) obtained from Step 1 of Referential Example 10 was dissolved in toluene (14 ml), 2-bromo-2'-methylacetophenone (723 mg), 1N aqueous sodium hydroxide (7 ml) and tetra n-butylammonium bromide (20 mg) were added, and the mixture was stirred overnight at room temperature. The reaction mixture was separated into organic layer and aqueous layer, the organic layer was dried over anhydrous magnesium sulfate, the solvent was evaporated under reduced pressure, and the residue was purified by silica gel column chromatography(n-hexane:ethyl acetate=5:1), to thereby obtain 557 mg of the titled compound.

$^{1}$H-NMR($CDCl_3$) δ: 1.40(9H, s), 1.63–2.05(6H, m), 2.26 (3H, s), 2.50–2.52(3H, s), 3.13–3.26(1H, m), 3.63–3.75(1H, m), 3.73–3.96(1H, m), 4.47– 4.56(1H, m), 4.63(1H, dd), 5.32(1H, t), 5.54(1H, d), 5.61–5.90(2H, m), 6.91(1H, s), 6.93–7.13(2H, m), 7.23–7.29(2H, m), 7.37–7.43(1H, m), 7.68–7.71(1H, m)

Step 2

Preparation of 1-(2-toluoylmethyl)-2-oxo-3-tert-butoxycarbonylamino-5-cyclohexyl-8-methyl-1,3,4,5-tetrahydro-2H-1,5-benzodiazepine 1-(2-Toluoylmethyl)-2-oxo-3-tert-butoxycarbonylamino-5-(2-cyclohexen-1-yl)-8-methyl-1,3,4,5-tetrahydro-2H-1,5- benzodiazepine (0.30 g) was dissolved in methanol (10 ml), 10% palladium carbon (0.10 g) was added, the mixture was stirred for 2 hours under hydrogen atmosphere. Palladium carbon was removed by filtration, the filtrate was concentrated under reduced pressure, to thereby obtain 0.29 g of the titled compound (Yield 96%).

$^1$H-NMR(CDCl$_3$) δ: 1.21–2.09(19H, m), 2.27(3H, s), 2.52(3H, s), 3.11–3.29(2H, m), 3.50–3.58(1H, m), 4.44–4.61(2H, m), 5.37(1H, d), 5.56(1H, brd), 6.92–7.74 (7H, m)

Step 3

Preparation of 1-(2-toluoylmethyl)-2-oxo-3-amino-5-cyclohexyl-8-methyl-1,3,4,5-tetrahydro-2H-1,5-benzodiazepine 1-(2-Toluoylmethyl)-2-oxo-3-tert-butoxycarbonylamino-5-cyclohexyl-8-methyl-1,3,4,5-tetrahydro-2H-1,5-benzodiazepine (0.28 g) was dissolved in 4N HCl-dioxane (5 ml), the solution was stirred for one hour at 60° C. The reaction mixture was concentrated under reduced pressure, the residue was neutralized with saturated aqueous sodium bicarbonate, and extracted with methylene chloride. The organic layer was dried over anhydrous sodium sulfate, the solvent was evaporated under reduced pressure, to thereby obtain 0.22 g of the titled compound (Yield: 100%).

$^1$H-NMR(CDCl$_3$) δ: 1.22–2.09(10H, m), 2.28(3H, s), 2.55(3H, s), 3.12–3.39(3H, m), 3.62(3H, br), 4.47(1H, d), 5.51(1H, d), 6.91–7.77(7H, m)

Step 4

Preparation of 1-[1-(2-toluoylmethyl)-2-oxo-5-cyclohexyl-8-methyl-1,3,4,5-tetrahydro-2H-1,5-benzodiazepin-3-yl]-3-(3-ethoxycarbonylphenyl)urea Ethyl 3-aminobenzoate (100 mg) was dissolved in tetrahydrofuran (5 ml), the solution was cooled on ice, triphosgene (65 mg) was added thereto at internal temperature 5° C., triethylamine (220 mg) was added thereto at 3 minutes intervals, the mixture was allowed to come to room temperature and stirred for 10 minutes. A solution of 1-(2-toluoylmethyl)-2-oxo-3-amino-5-cyclohexyl-8-methyl-1,3,4,5-tetrahydro-2H-1,5-benzodiazepine (820 mg) in tetrahydrofuran (5 ml) was added, additionally stirred for one hour. Water was added to the reaction mixture, extracted with methylene chloride. The organic layer was successively washed with water and saturated brine, dried over anhydrous sodium sulfate, the solvent was evaporated under reduced pressure, the residue was purified by silica gel column chromatography(n-hexane:ethyl acetate=3:1), to thereby obtain 265 mg of the titled compound (Yield 81%).

$^1$H-NMR(CDCl$_3$) δ: 1.18–1.96 (13H, m), 2.28 (3H, s), 2.46 (3H, s), 3.09–3.18(1H, m), 3.34–3.41(1H, m), 3.55–3.61(1H, m), 4.30(2H, q), 4.72 (1H, d), 4.75–4.86 (1H, m), 5.39(1H, d), 6.51(1H, brd), 6.93–7.93(12H, m)

Step 5

Preparation of 3-[3-[1-(2-toluoylmethyl)-2-oxo-5-cyclohexyl-8-methyl-1,3,4,5-tetrahydro-2H-1,5-benzodiazepin-3-yl]ureido]benzoic acid 1-[1-(2-Toluoylmethyl)-2-oxo-5-cyclohexyl-8-methyl-1,3,4,5-tetrahydro-2H-1,5-benzodiazepin-3-yl]-3-(3-ethoxycarbonylphenyl)urea (0.26 g) was dissolved in a mixed solvent of tetrahydrofuran (5 ml) and ethanol (5 ml), aqueous lithium hydroxide monohydrate (0.18 g) solution (5 ml) was added, and the mixture was stirred at room temperature for 3 hour. The reaction mixture was concentrated under reduced pressure, the residue was weakly acidified with 1N hydrochloric acid, and extracted with chloroform. The organic layer was successively washed with water and saturated brine, the solvent was evaporated under reduced pressure, and diisoproryl ether was added to the residue for trituration, collected by filtration, to thereby obtain 0.20 g of the titled compound as yellow-white powder (Yield: 82%)

$^1$H-NMR(CDCl$_3$) δ: 1.19–2.05(10H, m), 2.29(3H, s), 2.53(3H, s), 3.10–3.20(1H, m), 3.34–3.42(1H, m), 3.75–3.81(1H, m), 4.59–4.75(2H, m), 5.41(1H, d), 6.92–7.75(11H, m), 8.24–8.41(2H, m), 11.02(1H, br)

Example 117

Preparation of 5-[3-[1-(2-toluoylmethyl)-2-oxo-5-(2-thenoyl)-8-methyl-1,3,4,5-tetrahydro-2H-1,5-benzodiazepin-3-yl]ureido]-2-methylbenzoic acid Step 1

Preparation of 2-oxo-3-tert-butoxycarbonylamino-5-(2-thenoyl)-8-methyl-1,3,4,5-tetrahydro-2H-1,5-benzodiazepine 2-oxo-3-tert-butoxycarbonylamino-8-methyl-1,3,4,5-tetrahydro-2H-1,5-benzodiazepine (2.0 g) obtained from Referential Example 7 was suspended in 1,2-dichloroethane (20 ml), 2-thiophencarbonyl chloride (1.11 g) and pyridine (0.60 g) were added to the suspension, and the mixture was refluxed for 3 hours. The reaction mixture was allowed to cool, water was added to the mixture, extracted with chloroform. The organic layer was washed with water and saturated brine, dried over anhydrous magnesium sulfate, the solvent was evaporated under reduced pressure. The residue was purified by silica gel column chromatography (n-hexane:ethyl acetate=2:1), to thereby obtain 1.30 g of the title compound as a light yellow crystal.

$^1$H-NMR(CDCl$_3$) δ: 1.42(9H, s), 2.40(3H, s), 4.06–4.14 (1H, m), 4.44–4.53(1H, m), 4.60–4.67(1H, m), 5.47(1H, brd), 6.79–7.03(5H, m), 7.30–7.32(1H, m), 7.48 (1H, brs)

Step 2

Preparation of 1-(2-toluoylmethyl)-2-oxo-3-tert-butoxycarbonylamino-5-(2-thenoyl)-8-methyl-1,3,4,5-tetrahydro-2H-1,5-benzodiazepine 2-Bromo-2'-methylacetophenone (0.51 g), 1N aqueous sodium hydroxide (20 ml), toluene (20 ml) and tetra n-butylammonium bromide (20 mg) were added to 2-Oxo-3-tert-butoxycarbonylamino-5-(2-thenoyl)-8-methyl-1,3,4,5-tetrahydro-2H-1,5-benzodiazepine (0.80 g), the mixture was stirred at room temperature for 4 hours. The reaction mixture was separated into organic layer and aqueous layer, the aqueous layer was extracted with ethyl acetate, the extract was combined with the former organic layer. The combined extract was successively washed with water and saturated brine, and dried over anhydrous magnesium sulfate, the solvent was evaporated under reduced pressure, and the residue was purified by silica gel column chromatography(n-hexane:ethyl acetate=2:1), to thereby obtain 1.02 g of the title compound as colorless amorphous (Yield: 96%).

$^1$H-NMR(CDCl$_3$) δ: 1.42(9H, s), 2.39(3H, s), 2.52(3H, s), 4.07–4.16(1H, m), 4.41–4.50(1H, m), 4.63–4.74(2H, m), 5.44(1H, d), 5.72(1H, brd), 6.82–7.77(10H, m)

Step 3

Preparation of 1-(2-toluoylmethyl)-2-oxo-3-amino-5-(2-thenoyl)-8-methyl-1,3,4,5-tetrahydro-2H-1,5-benzodiazepine 1-(2-Toluoylmethyl)-2-oxo-3-tert-butoxycarbonylamino-5-(2-thenoyl)-8-methyl-1,3,4,5-tetrahydro-2H-1,5-benzodiazepine(1.0 g) was dissolved in 4N HCl-dioxane (10 ml), the mixture was stirred at 60° C. for one hour. The reaction mixture was concentrated under reduced pressure, neutralized with saturated aqueous sodium bicarbonate, and extracted with methylene chloride. The organic layer was washed with water and saturated brine, and dried over anhydrous sodium sulfate, the solvent was evaporated under reduced pressure, to thereby obtain 0.81 g of the title compound as a light yellow crystal (Yield: 100%).

$^1$H-NMR($CDCl_3$) δ: 1.60(2H, brs), 2.39(3H, s), 2.57(3H, s), 3.85–3.95(2H, m), 4.45–4.56(2H, m), 5.60(1H, d), 6.83–7.80(10H, m)

Step 4

Preparation of 1-[1-(2-toluoylmethyl)-2-oxo-5-(2-thenoyl)-8-methyl-1,3,4,5-tetrahydro-2H-1,5-benzodiazepin-3-yl]-3-(3-methoxycarbonyl-4-methylphenyl)urea Methyl 2-methyl-5-aminobenzoate (0.37 g) was dissolved in tetrahydrofuran (10 ml), triphosgene (0.22 g) was added at internal temperature 5° C., triethylamine (0.95 g) was added thereto over 10 minutes, the mixture was stirred at room temperature for 10 minutes. A solution of 1-(2-toluoylmethyl)-2-oxo-3-amino-5-(2-thenoyl)-8-methyl-1,3,4,5-tetrahydro-2H-1,5-benzodiazepine (0.81 g) in tetrahydrofuran (10 ml) was added, the mixture was stirred at room temperature for one hour. Water was added to the reaction mixture, and extracted with chloroform. The organic layer was successively washed with water and saturated brine and dried over anhydrous magnesium sulfate, the solvent was evaporated under reduced pressure, and the residue was purified by silica gel column chromatography (chloroform:methanol=50:1), to thereby obtain 1.17 g of the title compound as light yellow amorphous (Yield: 100%).

$^1$H-NMR($CDCl_3$) δ: 2.39(3H, s), 2.43(3H, s), 2.49(3H, s), 3.82(3H, s), 4.10–4.17(1H, m), 4.55–4.65(1H, m), 4.75(1H, d), 4.97–5.07(1H, m), 5.39(1H, d), 6.16(1H, brd), 6.82–7.87 (13H, m)

Step 5

Preparation of 5-[3-[1-(2-toluoylmethyl)-2-oxo-5-(2-thenoyl)-8-methyl-1,3,4,5-tetrahydro-2H-1,5-benzodiazepin-3-yl]ureido]-2-methylbenzoic acid 1-[1-(2-toluoylmethyl)-2-oxo-5-(2-thenoyl)-8-methyl-1,3,4,5-tetrahydro-2H-1,5-benzodiazepin-3-yl]-3-(3-methoxycarbonyl-4-methylphenyl)urea (0.70 g) was dissolved in a mixed solvent of tetrahydrofuran (10 ml) and methanol (10 ml), aqueous lithium hydroxide hydrate (0.23 g) solution (10 ml) was added, and the mixture was stirred at room temperature for 3 hours. The reaction mixture was acidified with 1N HCl and extracted with chloroform. The organic layer was washed with water and saturated brine, dried over anhydrous sodium sulfate, and the solvent was evaporated under reduced pressure. The residue was purified by silica gel column chromatography (chloroform:methanol=30:1), to thereby obtain 224 mg of the title compound as a white crystal.

Melting point: 192–195° C.

$^1$H-NMR(DMSO-$d_6$) δ: 2.35(3H, s), 2.39(3H, s), 2.42 (3H, s), 3.85–3.92(1H, m), 4.32–4.41(1H, m), 4.63–4.73 (1H, m), 5.15(1H, d), 5.39(1H, d), 6.74–7.95(13H, m), 8.95(1H, brs), 12.40(1H, br)

Example 118

Preparation of 3-[3-(1-tert-butylcarbonylmethyl-2-oxo-5-cyclohexyl-8-methyl-1,3,4,5-tetrahydro-2H-1,5-benzodiazepin-3-yl)ureido]benzoic acid Step 1

Preparation of 2-oxo-3-tert-butoxycarbonylamino-5-cyclohexyl-8-methyl-1,3,4,5-tetrahydro-2H-1,5-benzodiazepine 10% palladium carbon (100 mg) was added to a solution of 2-oxo-3-tert-butoxycarbonylamino-5-(2-cyclohexen-1-yl)-8-methyl-1,3,4,5-tetrahydro-2H-1,5-benzodiazepine (500 mg) obtained from Step 1 of Referential Example 10 in ethanol (50 ml), under hydrogen atmosphere the mixture was stirred at room temperature for 3 hours. The reaction mixture was filtrated, the filtrate was concentrated under reduced pressure, to thereby obtain 450 mg of the title compound (Yield: 90%).

$^1$H-NMR($CDCl_3$) δ: 1.05–2.05(19H, m), 2.27(3H, m), 3.11–3.19(1H, m), 3.27–3.34(1H, m), 3.60–3.69(1H, m), 3.35–3.47(1H, m), 5.56(1H, d), 6.78(1H, brs), 6.92–7.04 (2H, m), 7.84(1H, brs)

Step 2

Preparation of 1-tert-butylcarbonylmethyl-2-oxo-3-tert-butoxycarbonylamino-5-cyclohexyl-8-methyl-1,3,4,5-tetrahydro-2H-1,5-benzodiazepine 60% Sodium hydride (53 mg) was suspended in anhydrous N,N-dimethylformamide (5 ml), under ice-cooling 2-oxo-3-tert-butoxycarbonylamino-5-cyclohexyl-8-methyl-1,3,4,5-tetrahydro-2H-1,5-benzodiazepine (410 mg) was added, and the mixture was stirred at room temperature for 30 minutes. Subsequently, bromomethyl-tert-butyl ketone (217 mg) was added to the mixture under ice-cooling, the mixture was stirred at room temperature for 30 minutes. Ice-water was added to the reaction mixture, extracted with ethyl acetate. The organic layer was washed with saturated brine and dried over anhydrous sodium sulfate, the solvent was evaporated under reduced pressure, to thereby 517 mg of the title compound (Yield: 100%).

$^1$H-NMR($CDCl_3$) δ: 1.05–2.07(28H, m), 2.25(3H, s), 3.07–3.26(2H, m), 3.52–3.58(1H, m), 4.08(1H, d), 4.33–4.48(1H, m), 5.16(1H, d), 5.55(1H, d), 6.77(1H, s), 6.95–7.05(2H, m)

Step 3

Preparation of 1-tert-butylcarbonylmethyl-2-oxo-3-amino-5-cyclohexyl-8 -methyl-1,3,4,5-tetrahydro-2H-1,5-benzodiazepine 4N HCl-dioxane (7 ml) was added to a solution of 1-tert-butylcarbonylmethyl-2-oxo-3-tert-butoxycarbonylamino-5-cyclohexyl-8-methyl-1,3,4,5-tetrahydro-2H-1,5-benzodiazepine (517 mg) in ethanol (20 ml), the mixture was stirred at 50° C. for one hour. The reaction mixture was concentrated under reduced pressure, neutralized with saturated aqueous sodium bicarbonate, and extracted with methylene chloride. The organic layer was washed with saturated brine, dried over anhydrous sodium sulfate, and purified by silica gel column chromatography(chloroform:methanol=20:1), to thereby obtain 400 mg of the title compound (Yield: 98%).

$^1$H-NMR($CDCl_3$) δ: 1.10–2.05(21H, m), 2.27(3H, s), 3.10–3.21(2H, m), 3.32–3.38(1H, m), 3.51–3.58(1H, m), 3.98(1H, d), 5.28(1H, d), 6.76(1H, s), 6.96–7.08(2H, m)

Step 4

Preparation of 1-(1-tert-butylcarbonylmethyl-2-oxo-5-cyclohexyl-8-methyl-1,3,4,5-tetrahydro-2H-1,5-benzodiazepin-3-yl)-3-(3-ethoxycarbonylphenyl)urea Triphosgene (122 mg) was added to a solution of ethyl 3-aminobenzoate (182 mg) in tetrahydrofuran (10 ml) under ice-cooling, triethylamine (98 μl) was added thereto five times (total: 490 μl), the mixture was stirred at room temperature for 5 minutes. A solution of 1-tert-butylcarbonylmethyl-2-oxo-3-amino-5-cyclohexyl-8-methyl-1,3,4,5-tetrahydro-2H-1,5-benzodiazepine (393 mg) in anhydrous tetrahydrofuran (5 ml) was added to the mixture under ice-cooling, stirred at room temperature for 30 minutes. Ice-water was added to the reaction mixture, extracted with methylene chloride. The organic layer was washed with saturated brine and dried over anhydrous sodium sulfate, the solvent was evaporated under reduced pressure, and a mixed solvent of n-hexane and ethyl acetate (n-hexane:ethyl acetate=1:1) was added to the residue for crystallization, collected by filtration, to thereby obtain 380 mg of the title compound.

$^1$H-NMR($CDCl_3$) δ: 1.05–2.05(22H, m), 2.28(3H, s), 3.10–3.22(1H, m), 3.34–3.42(1H, m), 3.54–3.61(1H, m), 4.25(1H, d), 4.32(2H, q), 4.60–4.76(1H, m), 5.11(1H, d), 6.19(1H, d), 6.80(1H, brs), 6.98–7.10(3H, m), 7.23–7.28 (1H, m), 7.52–7.65(2H, m), 7.93–7.95(1H, m)

Preparation of 3-[3-(1-tert-butylcarbonylmethyl-2-oxo-5-cyclohexyl-8 -methyl-1,3,4,5-tetrahydro-2H-1,5-benzodiazepin-3-yl)ureido]benzoic acid 1-(1-tert-Butylcarbonylmethyl-2-oxo-5-cyclohexyl-8-methyl-1,3,4,5-tetrahydro-2H-1,5-benzodiazepin-3-yl)-3-(3-ethoxycarbonylphenyl)urea (370 mg) was suspended in methanol (5 ml), aqueous lithium hydroxide monohydrate (142 mg) solution (5 ml) was added to the suspension, and the mixture was stirred at 50° C. for 2 hours. The reaction mixture was filtrated. The filtrate was acidified with 1N hydrochloric acid, and methanol was evaporated. The mixture was extracted with ethyl acetate, the organic layer was washed with saturated brine, and dried over anhydrous sodium sulfate, the solvent was evaporated under reduced pressure. The residue was recrystallized from isopropyl alcohol, to thereby obtain 300 mg of the title compound (Yield: 83%).

$^1$H-NMR(DMSO-$d_6$) δ: 1.18(9H, s), 1.10–2.05(10H, m), 2.26(3H, s), 3.16–3.24(2H, m), 3.34–3.40(1H, m), 4.34–4.40(2H, m), 5.10(1H, d), 6.59(1H, d), 6.83(1H, s), 7.06–7.51(5H, m), 7.98(1H, s), 9.03(1H, s), 11.50(1H, br)

IR(KBr)$cm^{-1}$:3359, 2932, 1719, 1684, 1659

MS(FAB)m/z: 535($MH^+$)

Example 119

Preparation of 3-[3-[1-(5-methylfuran-2-yl)carbonylmethyl-2-oxo-5-pivaloyl-8-methyl-1,3,4,5-tetrahydro-2H-1,5-benzodiazepin-3-yl]ureido]benzoic acid Step 1

Preparation of 1-(5-methylfuran-2-yl)carbonylmethyl-2-oxo-3-tert-butoxycarbonylamino-5-pivaloyl-8-methyl-1,3,4,5-tetrahydro-2H-1,5-benzodiazepine 2-Oxo-3-tert-butoxycarbonylamino-5-pivaloyl-8-methyl-1,3,4,5-tetrabydro-2H-1,5-benzodiazepine (1.0 g) obtained from Step 1 of Example 89 was dissolved in tetrahydrofuran (10 ml), under argon atmosphere 60% sodium hydride (0.16 g) was added, and the mixture was stirred at room temperature for 30 minutes. Subsequently, a solution of 5-methyl-2-bromoacetylfuran (1.23 g) in tetrahydrofuran (1 ml) was added to the mixture, stirred at room temperature for 30 minutes. The reaction mixture was poured into ice-water and extracted with ethyl acetate. The organic layer was washed with water and saturated brine, and dried over anhydrous sodium sulfate, the solvent was evaporated under reduced pressure, and the residue was purified by silica gel column chromatography(n-hexane:ethyl acetate=3:1), to thereby obtain 0.89 g of the title compound.

$^1$H-NMR($CDCl_3$) δ: 1.03(9H, s), 1.39(9H, s), 2.36(3H, s), 2.43(3H, s), 3.87–3.94(1H, m), 4.19–4.36 (2H, m), 4.51–4.55(1H, m), 5.50–5.60(2H, m), 6.23–6.24(1H, m), 7.10–7.29(4H, m)

Step 2

Preparation of 1-(5-methylfuran-2-yl)carbonylmethyl-2-oxo-3-amino-5-pivaloyl-8-methyl-1,3,4,5-tetrahydro-2H-1,5-benzodiazepine 1-(5-Methylfuran-2-yl)carbonylmethyl-2-oxo-3-tert-butoxycarbonylamino-5-pivaloyl-8-methyl-1,3,4,5-tetrahydro-2H-1,5-benzodiazepine (0.89 g) was dissolved in 4N HCl-dioxane (10 ml), the mixture was stirred at 40–50° C. for 20 minutes. The reaction mixture was concentrated under reduced pressure, the residue was neutralized with saturated aqueous sodium bicarbonate, extracted with ethyl acetate. The organic layer was washed with water and saturated brine, dried over anhydrous sodium sulfate, the solvent was evaporated under reduced pressure, to thereby obtain 0.71 g of title compound (Yield: 100%).

$^1$H-NMR($CDCl_3$) δ: 1.03(9H, s), 1.64(2H, brs), 2.36(3H, s), 2.43(3H, s), 3.63–3.77(2H, m), 4.19–4.28(2H, m), 5.65 (1H, d), 6.23–6.25(1H, m), 7.06–7.30(4H, m)

Step 3

Preparation of 1-[1-(5-methylfuran-2yl)carbonylmethyl-2-oxo-5-pivaloyl-8-methyl-1,3,4,5-tetrahydro-2H-1,5-benzodiazepin-3-yl]-3-(3-ethoxycarbonylphenyl)urea Ethyl 3-aminobenzoate (0.33 g) was dissolved in tetrahydrofuran (10 ml), the solution was cooled on ice, triphosgene (0.21 g) was added at internal temperature 8° C., triethylamine (0.72 g) was added thereto over 15 minutes interval, the mixture was stirred at room temperature for 10 minutes. Subsequently, a solution of 1-(5-methylfuran-2-yl)carbonylmethyl-2-oxo-3-amino-5-pivaloyl-8-methyl-1,3,4,5-tetrahydro-2H-1,5-benzodiazepine (0.71 g) in tetrahydrofuran (10 ml) was added to the mixture. The resultant mixture was stirred at room temperature for 3 hours. Water was added to the reaction mixture, extracted with chloroform. The organic layer was washed with water and saturated brine, dried over anhydrous magnesium sulfate, the solvent was evaporated under reduced pressure, and the residue was purified by silica gel column chromatography (n-hexane:ethyl acetate=1:1), to thereby obtain 0.82 g of the title compound as a light brown crystal (Yield: 78%).

$^1$H-NMR($CDCl_3$) δ: 1.05(9H, s ), 1.35(3H, t), 2.38(3H, s), 2.39(3H, s), 3.89–3.97(1H, m), 4.30–4.41(4H, m), 4.78–4.84(1H, m), 5.56(1H, d), 6.07(1H, brd), 6.19–6.21 (1H, m), 7.04–7.32(6H, m), 7.56–7.68(2H, m), 7.90–7.92 (1H, m)

Step 4

Preparation of 3-[3-[1-(5-methylfuran-2-yl)carbonylmethyl-2-oxo-5-pivaloyl-8-methyl-1,3,4,5-tetrahydro-2H-1,5-benzodiazepin-3-yl]ureido]benzoic acid 1-[1-(5-Methylfuran-2-yl)carbonylmethyl-2-oxo-5-pivaloyl-8-methyl-1,3,4,5-tetrahydro-2H-1,5-benzodiazepin-3-yl]-3-(3-ethoxycarbonylphenyl)urea (0.80 g) was dissolved in the mixed solvent of tetrahydrofuran (10 ml) and methanol (10 ml), aqueous lithium hydroxide monohydrate (0.29 g) solution (10 ml) was added, the mixture was stirred at room temperature for 14 hours. The reaction mixture was concentrated under reduced pressure, the residue was weakly acidified with 1N hydrochloric acid and extracted with chloroform. The organic layer was washed with water and saturated brine, dried over anhydrous magnesium sulfate, the solvent was evaporated under reduced pressure, and the residue was purified by silica gel column chromatography(chloroform:methanol=20:1), to thereby obtain 442 mg of the title compound as a light yellow crystal.

Melting point: 224–226° C.

$^1$H-NMR(DMSO-$d_6$) δ: 0.95(9H, s), 2.38(3H, s), 2.40 (3H, s), 3.60–3.67(1H, m), 4.20–4.29(1H, m), 4.47–4.51 (1H, m), 4.65(1H, d), 5.37(1H, d), 6.42–6.43 (1H, m), 6.70(1H, brd), 7.20–7.58 (7H, m), 7.96 (1H, s), 9.04(1H, brs)

Example 120

Preparation of 5-[3-[1-(2-toluoylmethyl)-2-oxo-5-(3,3-dimethylbutanoyl)-8-methyl-1,3,4,5-tetrahydro-2H-1,5-benzodiazepin-3-yl]ureido]-2-methylbenzoic acid Step 1

Preparation of 1-[1-(2-toluoylmethyl)-2-oxo-5-(3,3-dimethylbutanoyl)-8-methyl-1,3,4,5-tetrahydro-2H-1,5-benzodiazepin-3-yl]-3-(3-methoxycarbonyl-4-methylphenyl)urea Methyl 2-methyl-5-aminobenzoate (0.30 g) was dissolved in tetrahydrofuran (10 ml), the solution was cooled on ice, triphosgene (0.20 g) was added at internal temperature 50° C., triethylamine (0.77 g) was added thereto over 10 minutes interval, and the mixture was stirred at room temperature for 10 minutes. Subsequently, a solution of 1-(2-toluoylmethyl)-2-oxo-3-amino-5-(3,3-dimethylbutanoyl)-8-methyl1-1,3,4,5-tetrahydro-2H-1,5-benzodiazepine (0.64 g) in tetrahydrofuran (10 ml) was added to the mixture, the resultant mixture was stirred for one hour. Water was added to the reaction mixture, extracted with chloroform. The organic layer was washed with water and saturated brine, and dried over anhydrous magnesium sulfate, the solvent was evaporated under reduced pressure, and the residue was purified by silica gel column chromatography(n-hexane:ethyl acetate=3:2), to thereby obtain 0.94 g of the title compound as colorless powder (Yield: 100%).

$^1$H-NMR($CDCl_3$) δ: 0.96(9H, s), 1.57(9H, s), 2.03(1H, d), 2.14(1H, d), 2.38(3H, s), 2.49(3H, s), 2.50(3H, s), 3.83–3.89 (4H, m), 4.54–4.88(3H, m), 5.31(1H, d), 5.98(1H, brd), 6.82–7.86(1H, m)

Step 2

Preparation of 5-[3-[1-(2-toluoylmethyl)-2-oxo-5-(3,3-dimethylbutanoyl)-8-methyl-1,3,4,5-tetrahydro-2H-1,5-benzodiazepin-3-yl]ureido]-2-methylbenzoic acid 1-[1-(2-Toluoylmethyl)-2-oxo-5-(3,3-dimethylbutanoyl)-8-methyl-1,3,4,5-tetrahydro-2H-1,5-benzodiazepin-3-yl]-3-(3-methoxycarbonyl-4-methylphenyl)urea (0.94 g) was dissolved in tetrahydrofuran (20 ml), aqueous lithium hydroxide monohydrate (0.32 g) solution (10 ml) was added, the mixture was stirred at 40–50° C. for 4 hours. The reaction mixture was concentrated under reduced pressure, the residue was weakly acidified with 1N hydrochloric acid and extracted with chloroform. The organic layer was washed with water and saturated brine, dried over anhydrous magnesium sulfate, the solvent was evaporated under reduced pressure, and the residue was purified by silica gel column chromatography(chloroform:methanol=30:1), to thereby obtain 0.56 g of the title compound as colorless powder (Yield: 61%).

$^1$H-NMR(DMSO-$d_6$) δ: 0.94(9H, s), 2.00(1H, d), 2.07 (1H, d), 2.39(3H, s), 2.40(3H, s), 3.41–3.47(1H, m), 7.86–4.53(2H, m), 5.18(1H, d), 5.27(1H, d), 6.66(1H, brd), 7.11–7.52(8H, m), 7.86–7.96(2H, m), 8.87(1H, s), 12.67 (1H, br)

Example 121

Preparation of 3-[3-(1-tert-butylcarbonylmethyl-2-oxo-5-cyclohexyl-1,3,4,5-tetrahydro-2H-1,5-benzodiazepin-3-yl) ureido]benzoic acid Step 1

Preparation of 2-oxo-3-tert-butoxycarbonylamino-5-(2-cyclohexen-1-yl)-1,3,4,5-tetrahydro-2H-1,5-benzodiazepine Step 1 of Referential Example 10 was repeated except that 2-oxo-3-tert-butoxycarbonylamino-1,3,4,5-tetrahydro-2H-1,5-benzodiazepine obtained from Referential Example 1 was used instead of 2-oxo-3-tert-butoxycarbonylamino-8-methyl-1,3,4,5-tetrahydro-2H-1,5-benzodiazepine, to thereby obtain the title compound.

$^1$H-NMR($CDCl_3$) δ: 1.41(9H, s), 1.55–2.08(6H, m), 3.23–3.37(1H, m), 3.69–3.82(1H, m), 3.87–4.12(1H, m), 4.42–4.55(1H, m), 5.47–5.54(1H, m), 5.62–6.01(2H, m), 6.90–6.99(2H, m), 7.08–7.22(2H, m), 7.47(1H, brs)

Step 2

Preparation of 2-oxo-3-tert-butoxycarbonylamino-5-cyclohexyl-1,3,4,5-tetrahydro-2H-1,5-benzodiazepine Step 1 of Example 118 was repeated except that 2-oxo-3-tert-butoxycarbonylamino-5-(2-cyclohexen-1-yl)-1,3,4,5-tetrahydro-2H-1,5-benzodiazepine was used instead of 2-oxo-3-tert-butoxycarbonylamino-5-(2-cyclohexen-1-yl)-8-methyl-1,3,4,5-tetrahydro-2H-1,5-benzodiazepine, to thereby obtain the title compound.

$^1$H-NMR($CDCl_3$) δ: 1.11–2.07(19H, m), 3.15–3.27(1H, m), 3.33(1H, dd), 3.68(1H, dd), 4.38–4.49(1H, m), 5.53(1H, d), 6.91–6.96(2H, m), 7.11–7.16(2H, m), 7.45(1H, brs)

Step 3

Preparation of 1-tert-butylcarbonylmethyl-2-oxo-3-tert-butoxycarbonylamino-5-cyclohexyl-1,3,4,5-tetrahydro-2H-1,5-benzodiazepine Step 2 of Example 118 was repeated except that 2-oxo-3-tert-butoxycarbonylamino-5-cyclohexyl-1,3,4,5-tetrahydro-2H-1,5-benzodiazepine was used instead of 2-oxo-3-tert-butoxycarbonylamino-5-cyclohexyl-8-methyl-1,3,4,5-tetrahydro-2H-1,5-benzodiazepine, to thereby obtain the title compound.

$^1$H-NMR($CDCl_3$) δ: 1.15–2.07(28H, m), 3.13–3.24(1H, m), 3.26(1H, dd), 3.61(1H, dd), 4.11(1H, d), 4.39–4.50(1H, m), 5.17(1H, d), 5.57(1H, d), 6.92–7.03(2H, m), 7.12–7.20 (2H, m)

Step 4

Preparation of 1-tert-butylcarbonylmethyl-2-oxo-3-amino-5-cyclohexyl-1,3,4,5-tetrahydro-2H-1,5-benzodiazepine Step 3 of Example 118 was repeated except that 1-tert-butylcarbonylmethyl-2-oxo-3-tert-butoxycarbonylamino-5-cyclohexyl-1,3,4,5-tetrahydro-2H-1,5-benzodiazepine was used instead of 1-tert-butylcarbonylmethyl-2-oxo-3-tert-butoxycarbonylamino-5-cyclohexyl-8-methyl-1,3,4,5-tetrahydro-2H-1,5-benzodiazepine, to thereby obtain the title compound.

$^1$H-NMR($CDCl_3$) δ: 1.11–2.08(21H, m), 3.12–3.27(2H, m), 3.40(1H, dd), 3.53–3.62(1H, m), 4.01(1H, d), 5.29(1H, d), 6.92–7.04(2H, m), 7.15–7.19(2H, m)

Step 5

Preparation of 1-(1-tert-butylcarbonylmethyl-2-oxo-5-cyclohexyl-1,3,4,5-tetrahydro-2H-1,5-benzodiazepin-3-yl)-3-(3-ethoxycarbonylphenyl)urea Step 4 of Example 118 was repeated except that 1-tert-butylcarbonylmethyl-2-oxo-3-amino-5-cyclohexyl-1,3,4,5-tetrahydro-2H-1,5-benzodiazepine was used instead of 1-tert-butylcarbonylmethyl-2-oxo-3-amino-5-cyclohexyl-8-methyl-1,3,4,5-tetrahydro-2H-1,5-benzodiazepine, to thereby obtain the title compound.

$^1$H-NMR($CDCl_3$) δ: 1.08–2.09(22H, m), 3.15–3.26(1H, m), 3.41(1H, dd), 3.65(1H, dd), 4.29(1H, d), 4.33(2H, t), 4.67–4.79(1H, m), 5.11(1H, d), 6.17(1H, d), 6.97–7.07(3H, m), 7.17–7.30(3H, m), 7.53–7.56(1H, m), 7.62–7.66(1H, m), 7.92–7.94(1H, m)

Step 6

Preparation of 3-[3-(1-tert-butylcarbonylmethyl-2-oxo-5-cyclohexyl-1,3,4,5-tetrahydro-2H-1,5-benzodiazepin-3-yl) ureido]benzoic acid Step 5 of Example 118 was repeated except that 1-(1-tert-butylcarbonylmethyl-2-oxo-5-cyclohexyl-1,3,4,5-tetrahydro-2H-1,5-benzodiazepin-3-yl)-3-(3-ethoxycarbonylphenyl)urea was used instead of 1-(1-tert-butylcarbonylmethyl-2-oxo-5-cyclohexyl-8-methyl-1,3,4,5-tetrahydro-2H-1,5-benzodiazepin-3-yl)-3-(3-ethoxycarbonylphenyl) urea, to thereby obtain the title compound.

Melting point: 250–252° C. (decomposition)
$^1$H-NMR(DMSO-$d_6$) δ: 1.05–2.08(19H, m), 3.16–3.49 (3H, m), 4.33–4.40(1H, m), 4.39(1H, d), 5.12(1H, d), 6.62 (1H, d), 6.98–7.14(2H, m), 7.23–7.36(3H, m), 7.44–7.52 (2H, m), 7.99(1H, brs), 9.06(1H, brs), 11.50(1H, br)
IR(KBr)$cm^{-1}$:3360, 1721, 1686, 1655
MS(FAB)m/z: 521($MH^+$)
The structure of these compounds obtained from Example 89–121 was shown in Table 13–17.
TABLE 13
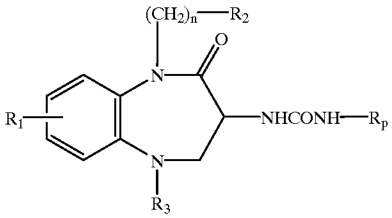
| Example | $R_1$ | $R_2$ | $R_3$ | $R_p$ | n |
|---|---|---|---|---|---|
| 89 | 8-$CH_3$ | 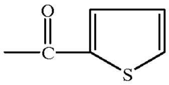 | 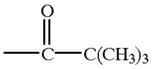 | 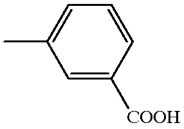 | 1 |
| 90 | 8-$CH_3O$ | 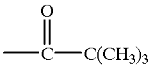 | 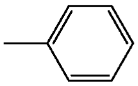 | 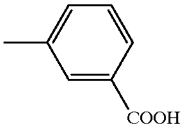 | 1 |
| 91 | 8-$CH_3$ | 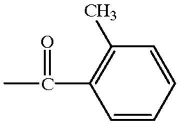 | 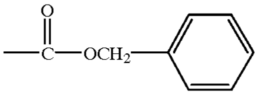 | 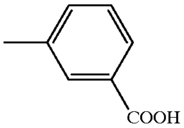 | 1 |
| 92 | 8-$CH_3$ | 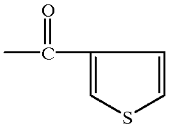 | 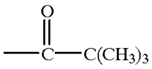 | 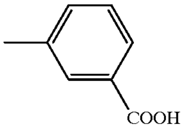 | 1 |
| 93 | 8-$CH_3$ | 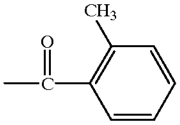 | 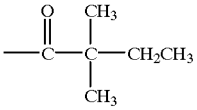 | 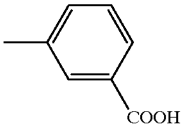 | 1 |
| 94 | 8-$CH_3$ | 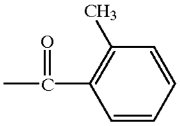 | 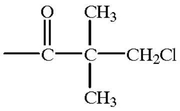 | 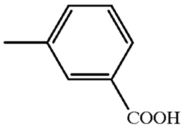 | 1 |
| 95 | 8-$CH_3$ | 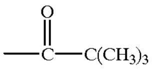 | 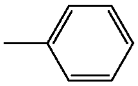 | 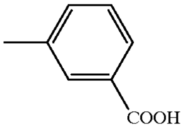 | 1 |

TABLE 14
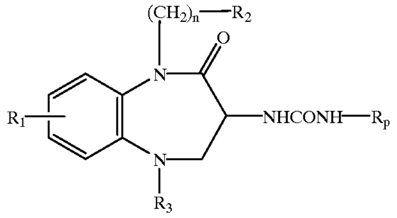
| Example | $R_1$ | $R_2$ | $R_3$ | $R_p$ | n |
|---|---|---|---|---|---|
| 96 (*) | 8-$CH_3$ | 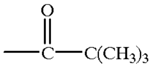 | 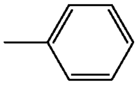 | 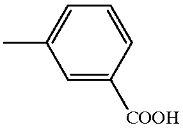 | 1 |
| 97 (*) | 8-$CH_3$ | 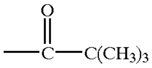 | 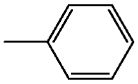 | 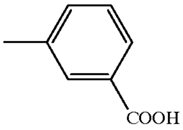 | 1 |
| 98 | 8-$CH_3$ | 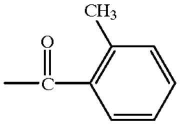 | 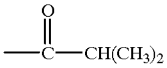 | 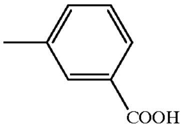 | 1 |
| 99 | 8-$CH_3$ | 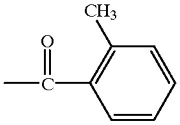 | 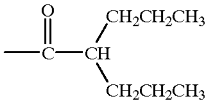 | 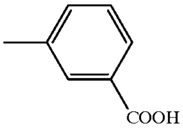 | 1 |
| 100 | 8-$CH_3$ | 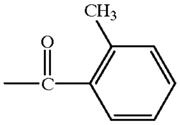 | 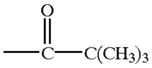 | 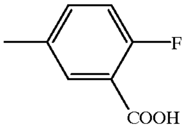 | 1 |
| 101 | H | 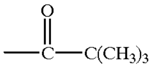 | 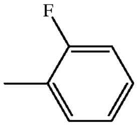 | 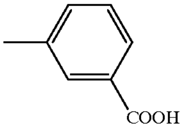 | 1 |
| 102 | 8-$CH_3$ | 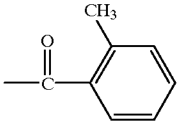 | 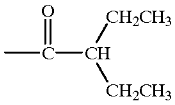 | 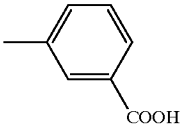 | 1 |
(*): optically active compound TABLE 15
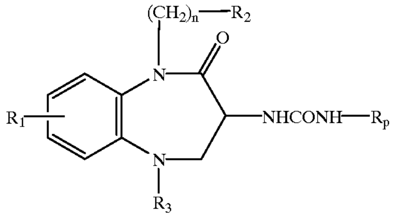
| Example | $R_1$ | $R_2$ | $R_3$ | $R_p$ | n |
|---|---|---|---|---|---|
| 103 | 8-$CH_3$ | 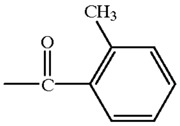 | 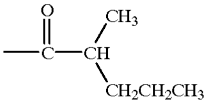 | 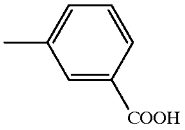 | 1 |
| 104 | 8-$CH_3$ | 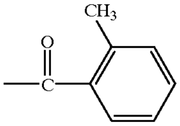 | 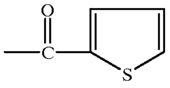 | 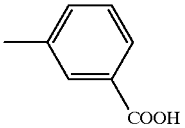 | 1 |
| 105 | 8-$CH_3$ | 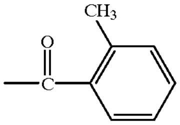 | 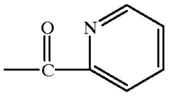 | 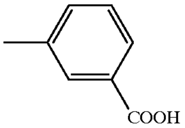 | 1 |
| 106 | 8-$CH_3$ | 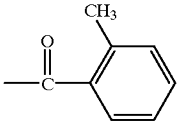 | 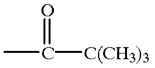 | 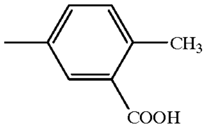 | 1 |
| 107 | 8-$CH_3$ | 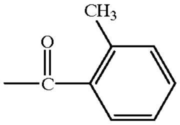 | 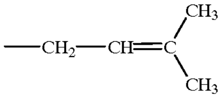 | 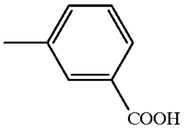 | 1 |
| 108 | 8-$CH_3$ | 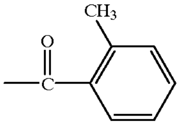 | 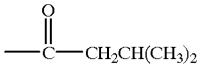 | 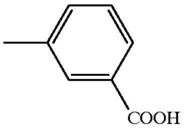 | 1 |
| 109 | 8-$CH_3$ | 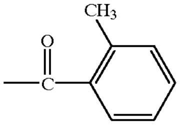 | 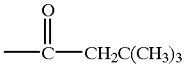 | 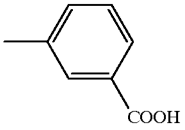 | 1 |

TABLE 16
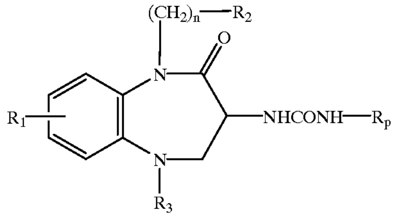
| Example | $R_1$ | $R_2$ | $R_3$ | $R_p$ | n |
|---|---|---|---|---|---|
| 110 | 8-$CH_3$ | 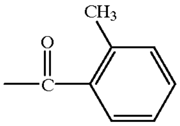 | 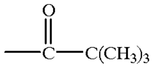 | 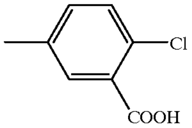 | 1 |
| 111 | 8-$CH_3$ | 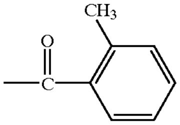 | 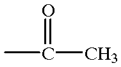 | 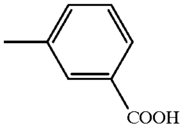 | 1 |
| 112 | 8-$CH_3$ | 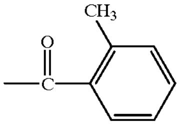 | 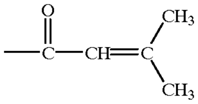 | 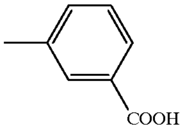 | 1 |
| 113 | 8-$CH_3$ | 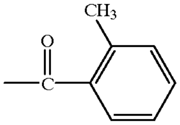 | 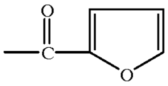 | 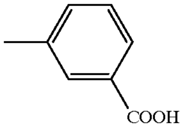 | 1 |
| 114 | 8-$CH_3$ | 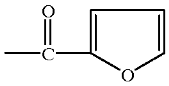 | 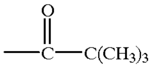 | 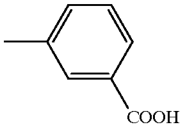 | 1 |
| 115 | 8-$CH_3$ | 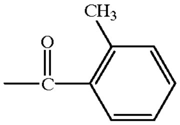 | 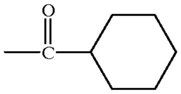 | 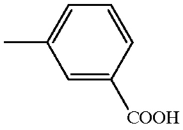 | 1 |
| 116 | 8-$CH_3$ | 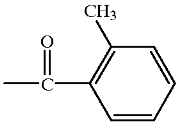 | 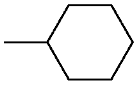 | 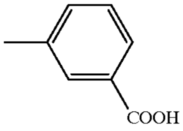 | 1 |

TABLE 17

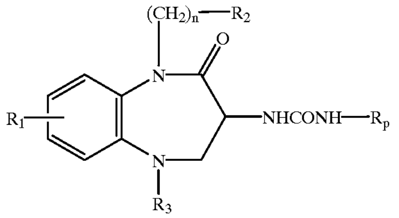

| Example | $R_1$ | $R_2$ | $R_3$ | $R_p$ | n |
|---|---|---|---|---|---|
| 117 | 8-$CH_3$ | 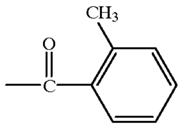 | 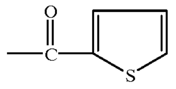 | 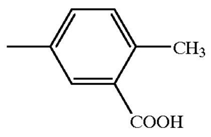 | 1 |
| 118 | 8-$CH_3$ | 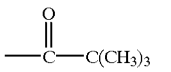 | 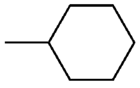 | 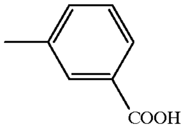 | 1 |
| 119 | 8-$CH_3$ | 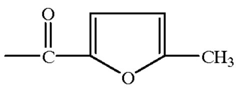 | 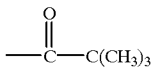 | 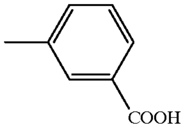 | 1 |
| 120 | 8-$CH_3$ | 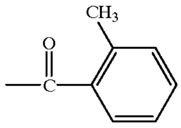 | 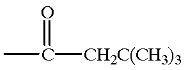 | 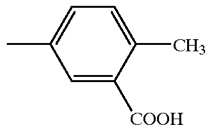 | 1 |
| 121 | H | 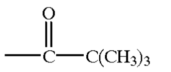 | 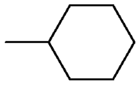 | 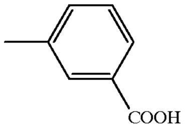 | 1 |

Example 122

Preparation of 3-[3-[1-(2-thenoylmethyl)-2-oxo-5-(2-thenoyl)-8-methyl-1,3,4,5-tetrahydro-2H-1,5-benzodiazepin-3-yl]ureido]benzoic acid Step 1

Preparation of 1-(2-thenoylmethyl)-2-oxo-3-(N-tert-butoxycarbonyl)amino-5-(2-thenoyl)-8-methyl-1,3,4,5-tetrahydro-2H-1,5-benzodiazepine 2-Oxo-3-(N-tert-butoxycarbonyl)amino-5-(2-thenoyl)-8-methyl-1,3,4,5-tetrahydro-2H-1,5-benzodiazepine (2.40 g) was dissolved in N,N-dimethylformamide (20 ml), the solution was cooled to internal temperature 5° C., 60% sodium hydride (0.29 g) was added under argon atmosphere, the mixture was stirred at internal temperature 5° C. for 30 minutes. Subsequently, 2-bromoacetylthiophene (1.47 g) was added to the mixture, stirred at internal temperature 5° C. for one hour and 30 minutes. The reaction mixture was poured into ice-water and extracted with ethyl acetate. The organic layer was washed with water and saturated brine, and dried over anhydrous sodium sulfate. The solvent was evaporated under reduced pressure, and the residue was purified by silica gel column chromatography(ethyl acetate:n-hexane=1:2), to thereby obtain 2.25 g of the title compound (Yield: 71.3%).

Melting point: 148–150° C.

$^1$H-NMR(DMSO-$d_6$) δ: 1.35(9H, s), 2.37(3H, s), 3.65–3.71(1H, m), 4.34–4.42(1H, m), 4.51(1H, q), 5.16(1H, d), 5.45(1H, d), 6.69(1H, brs), 6.87(1H, t-like), 7.02(2H, s), 7.26–7.30(1H, m), 7.36(1H, s), 7.42(1H, d), 7.63–7.65(1H, m), 8.06(1H, dd), 8.14(1H, d)

Step 2

Preparation of 1-(2-thenoylmethyl)-2-oxo-3-amino-5-(2-thenoyl)-8-methyl-1,3,4,5-tetrahydro-2H-1,5-benzodiazepine 1-(2-Thenoylmethyl)-2-oxo-3-(N-tert-butoxycarbonyl)amino-5-(2-thenoyl)-8-methyl-1,3,4,5-tetrahydro-2H-1,5-benzodiazepine (2.00 g) was dissolved in 4N HCl-dioxane (20 ml), the mixture was stirred at 60° C. for 30 minutes. The reaction mixture was concentrated under reduced pressure, saturated aqueous sodium bicarbonate and ethyl acetate were added to the residue, and extracted. The organic layer was washed with water and saturated brine, dried over anhydrous sodium sulfate. The solvent was evaporated under reduced pressure, the residue was purified by silica gel column chromatography(methanol:chloroform=1:20), to thereby obtain 1.36 g of title compound as amorphous (Yield: 84.1%).

$^1$H-NMR($CDCl_3$) δ: 2.39(3H, s), 3.71–3.94(2H, m), 4.44 (1H, m), 4.42(1H, d), 5.65(1H, d), 6.84–6.87(1H, m), 7.02–7.05(3H, m), 7.16–7.19(2H, m), 7.32(11H, dd), 7.72 (1H, dd), 7.85(1H, dd)

Step 3

Preparation of 1-[1-(2-thenoylmethyl)-2-oxo-5-(2-thenoyl)-8-methyl-1,3,4,5-tetrahydro-2H-1,5-benzodiazepin-3-yl]-3-(4-ethoxycarbonylphenyl)urea Ethyl 3-aminobenzoate (0.54 g) was dissolved in tetrahydrofuran (15 ml), the solution was cooled to internal temperature 5–8° C. Triphosgene (0.35 g) was added, the mixture was stirred for 5 minutes. Subsequently, triethylamine (1.20 g) was added to the mixture over 15 minutes interval, stirred at room temperature for 10 minutes, and a solution of 1-(2-thenoylmethyl)-2-oxo-3-amino-5-(2-thenoyl)-8-methyl-1,3,4,5-tetrahydro-2H-1,5-benzodiazepine (1.26 g) in tetrahydrofuran (15 ml) was added, stirred for one hour. Water and chloroform were added to the reaction mixture, and extracted. The organic layer was washed with saturated brine, and dried over anhydrous magnesium sulfate. The solvent was evaporated under reduced pressure, crystals so precipitated were collected by filtration with ether, to thereby obtain 1.46 g of the title compound (Yield: 79.8%).

Melting point: 244.5° C.

$^1$H-NMR(DMSO-$d_6$) δ: 1.32(3H, t), 2.40(3H, s), 3.85–3.92(1H, m), 4.25–4.37(3H, m), 4.62–4.69(1H, m), 5.11(1H, d), 5.54(1H, d), 6.72–6.75(2H, m), 6.85(1H, t), 7.04–7.14(2H, m), 7.24–7.35(3H, m), 7.49–7.51(2H, m), 7.60(1H, d), 8.01–8.04(2H, m), 8.12(1H, d), 9.04(1H, s)

Step 4

Preparation of 3-[3-[1-(2-thenoylmethyl)-2-oxo-5-(2-thenoyl)-8-methyl-1,3,4,5-tetrahydro-2H-1,5-benzodiazepin-3-yl]ureido]benzoic acid 1-[1-(2-Thenoylmethyl)-2-oxo-5-(2-thenoyl)-8-methyl-1,3,4,5-tetrahydro-2H-1,5-benzodiazepin-3-yl]-3-(4-ethoxycarbonylphenyl)urea (1.3 g) was suspended in tetrahydrofuran (30 ml), aqueous lithium hydroxide monohydrate (0.44 g) solution (15 ml) was added, the mixture was stirred at 40–50° C. for 6 hours. The solvent was concentrated under reduced pressure, 1N hydrochloric acid and chloroform were added to the residue, crystals so precipitated were collected by filtration, washed with a mixed solvent(chloroform:methanol=10:1), and filtrated by means of suction, to thereby obtain 102 mg of the title compound.

Melting point:over 290° C.

$^1$H-NMR(DMSO-$d_6$) δ: 2.39(3H, s), 3.84–3.91(1H, m), 4.34(1H, t), 4.62– 4.72(1H, m), 5.12(1H, d), 5.54(1H, d), 6.71–6.78(2H, m), 6.84–6.88(1H, m), 7.07–7.15 (2H, m), 7.25–7.33(3H, m), 7.46–7.53(2H, m), 7.61(1H, d), 7.99–8.04(2H, m), 8.12(1H, d), 9.02(1H, s)

MS(FAB)m/z: 589($MH^+$)

IR(KBr)$cm^{-1}$:3354, 1672, 1649, 1593, 1541, 1508, 1417, 1244

Example 123

Preparation of 3-[3-[1-(2-thenoylmethyl)-2-oxo-5-cyclohexyl-1,3,4,5-tetrahydro-2H-1,5-benzodiazepin-3-yl]ureido]benzoic acid Step 1

Preparation of 1-(2-thenoylmethyl)-2-oxo-3-(N-tert-butoxycarbonyl)amino-5-cyclohexyl-1,3,4,5-tetrahydro-2H-1,5-benzodiazepine 2-Oxo-3-(N-tert-butoxycarbonyl)amino-5-cyclohexyl-1,3,4,5-tetrahydro-2H-1,5-benzodiazepine (2.00 g) was dissolved in N,N-dimethylformamide (20 ml), the solution was cooled to internal temperature 5° C. Under argon atmosphere 60% sodium hydride (0.28 g) was added, the mixture was stirred at internal temperature 5° C. for 30 minutes. Subsequently, 2-bromoacetylthiophene (1.42 g) was added to the mixture, the resultant mixture was stirred at internal temperature 5° C. for 1 hour and 30 minutes. The reaction mixture was poured into ice-water and extracted with ethyl acetate. The organic layer was washed with water and saturated brine, and dried over anhydrous sodium sulfate. The solvent was evaporated under reduced pressure, and the residue was purified by silica gel column chromatography (ethyl acetate:n-hexane=1:2), to thereby obtain 1.49 g of the title compound.

Melting point: 166–168° C.

$^1$H-NMR($CDCl_3$) δ: 1.16–2.05(19H, m), 3.17–3.21(1H, m), 3.26–3.33(1H, m), 3.57–3.65(1H, m), 4.44–4.51(1H, m), 4.68(1H, d), 5.41(1H, d), 5.57(1H, d), 6.98–7.04(1H, m), 7.12–7.18(4H, m), 7.69(1H, dd), 7.84(1H, dd)

Step 2

Preparation of 1-(2-thenoylmethyl)-2-oxo-3-amino-5-cyclohexyl-1,3,4,5-tetrahydro-2H-1,5-benzodiazepine 1-(2-Thenoylmethyl)-2-oxo-3-(N-tert-butoxycarbonyl)amino-5-cyclohexyl-1,3,4,5-tetrahydro-2H-1,5-benzodiazepine (1.30 g) was dissolved in 4N HCl-dioxane (15 ml), the mixture was stirred at 60° C. for 30 minutes. The reaction mixture was concentrated under reduced pressure, methylene chloride and saturated aqueous sodium bicarbonate were added and extracted. The organic layer was washed with water and saturated brine, dried over anhydrous sodium sulfate. The solvent was evaporated under reduced pressure, the residue was purified by silica gel column chromatography(methanol:chloroform=1:20), to thereby obtain 0.99 g of title compound as amorphous (Yield: 94.3%).

$^1$H-NMR($CDCl_3$) δ: 1.17–2.00(10H, m), 3.17–3.73(4H, m), 4.58(1H, d), 5.54(1H, d), 6.99–7.05(1H, m), 7.14–7.19 (4H, m), 7.70(1H, dd), 7.86(1H, dd)

Step 3

Preparation of 1-[1-(2-thenoylmethyl)-2-oxo-5-cyclohexyl-1,3,4,5-tetrahydro-2H-1,5-benzodiazepin-3-yl]-3-(4-ethoxycarbonylphenyl)urea Ethyl 3-aminobenzoate (0.48 g) was dissolved in tetrahydrofuran (25 ml), the solution was cooled to internal temperature 5–8° C. Triphosgene (0.32 g) was added, and the mixture was stirred for 5 minutes. Subsequently, triethylamine (1.08 g) was added over 15 minutes interval. The resultant mixture was stirred at room temperature for 10 minutes,a solution of 1-(2-thenoylmethyl)-2-oxo-3-amino-5-cyclohexyl-1,3,4,5-tetrahydro-2H-1,5-benzodiazepine (0.99 g) in tetrahydrofuran (15 ml) was added and stirred for one hour. Water and chloroform were added to the reaction mixture and extracted. The organic layer was washed with saturated brine, and dried over anhydrous magnesium sulfate. The solvent was evaporated under reduced pressure, a mixed solvent of methylene chloride and ether (1:1) was added to crystals so precipitated for trituration, collected by filtration, to thereby obtain 1.07 g of the title compound.

Melting point: 219–220° C.

$^1$H-NMR(DMSO-$d_6$) δ: 1.22–1.99(13H, m), 3.25–3.45 (3H, m), 4.28(2H, q), 4.41–4.46(1H, m), 4.95(1H, d), 5.48 (1H, d), 6.61(1H, d), 7.11–7.19(2H, m), 7.28–7.38(4H, m), 7.50(2H, d-like), 8.05(1H, t), 8.08(1H, dd), 9.09(1H, s)

Step 4

Preparation of 3-[3-[1-(2-thenoylmethyl)-2-oxo-5-cyclohexyl-1,3,4,5-tetrahydro-2H-1,5-benzodiazepin-3-yl]ureido]benzoic acid 1-[1-(2-Thenoylmethyl)-2-oxo-5-cyclohexyl-1,3,4,5-tetrahydro-2H-1,5-benzodiazepin-3-yl]-3-(4- ethoxycarbonylphenyl)urea (0.70 g) was dissolved in tetrahydrofuran (19 ml), aqueous lithium hydroxide monohydrate (0.26 g) solution (15 ml) and methanol (7 ml) were added, the mixture was stirred at 40–50° C. for one hours. The reaction mixture was concentrated under reduced pressure, 1N hydrochloric acid and chloroform were added to the residue, and extracted. The organic layer was washed with water and saturated brine, and dried over anhydrous magnesium sulfate. The solvent was evaporated under reduced pressure, a mixed solvent of methylene chloride and ether (1:1) was added to powder so precipitated, and collected by filtration,to thereby obtain 0.61 g of the title compound (Yield: 92.4%).

$^1$H-NMR(DMSO-$d_6$) δ: 1.18–1.98(10H, m), 3.22–3.46(3H, m), 4.39–4.82(1H, m), 4.95(1H, d), 5.48(1H, d), 6.63(1H, d), 7.09–7.20(2H, m), 7.28–7.35 (4H, m), 7.46–7.52 (2H, m), 7.99 (1H, t), 8.08(1H, dd), 8.15(1H, dd), 9.05(1H, s)

MS (FAB) m/z: 547 ($MH^+$)

IR(KBr)$cm^{-1}$:3360, 2932, 1686, 1551, 1496, 1415, 1238

Example 124

Preparation of 3-[3-[1-(pyrrolidin-1-ylcarbonylmethyl)-2-oxo-5-cyclohexyl-1,3,4,5-tetrahydro-2H-1,5-benzodiazepin-3-yl]ureidolbenzoic acid Step 1

Preparation of 1-(pyrrolidin-1-ylcarbonylmethyl)-2-oxo-3-(N-tert-butoxycarbonyl)amino-5-cyclohexyl-1,3,4,5-tetrahydro-2H-1,5-benzodiazepine 2-Oxo-3-(N-tert-butoxycarbonyl)amino-5-cyclohexyl-1,3,4,5-tetrahydro-2H-1,5-benzodiazepine (1.75 g) was dissolved in N,N-dimethylformamide (20 ml), the solution was cooled to internal temperature 50° C. Under argon atmosphere 60% sodium hydride (0.28 g) was added,stirred at internal temperature 5° C. for 30 minutes. Subsequently, 1-bromoacetylpyrrolidine (1.33 g) was added to the mixture, stirred at internal temperature 50° C. for 1 hour and 30 minutes. The reaction mixture was poured into ice-water and extracted with ethyl acetate. The organic layer was washed with water and saturated brine, and dried over anhydrous magnesium sulfate. The solvent was evaporated under reduced pressure,and the residue was purified by silica gel column chromatography(ethyl acetate:n-hexane=1:2), to thereby obtain 1.25 g of the title compound (Yield: 54.5%).

Melting point: 159–161° C.

$^1$H-NMR($CDCl_3$) δ: 1.18–1.41(14H, m), 1.54–2.05(9H, m), 3.14–3.30(2H, m), 3.38–3.66(5H, m), 3.88(1H, d), 4.39–4.48(1H, m), 4.92(1H, d), 5.61(1H, d), 6.98–7.04(1H, m), 7.12–7.17(2H, m), 7.37(1H, d)

Step 2

Preparation of 1-(pyrrolidin-1-ylcarbonylmethyl)-2-oxo-3-amino-5-cyclohexyl-1,3,4,5-tetrahydro-2H-1,5-benzodiazepine 1-(Pyrrolidin-1-ylcarbonylmethyl)-2-oxo-3-(N-tert-butoxycarbonyl)amino-5-cyclohexyl-1,3,4,5-tetrahydro-2H-1,5-benzodiazepin (1.10 g) was dissolved in 4N HCl-dioxane (15 ml), the mixture was stirred at 60° C. for 30 minutes. After the reaction mixture was concentrated under reduced pressure, methylene chloride and saturated aqueous sodium bicarbonate was added to the residue, extracted. The organic layer was washed with water and saturated brine, and dried over anhydrous sodium sulfate. The solvent was evaporated under reduced pressure, and the residue was purified by silica gel column chromatography (methanol:chloroform=1:20), to thereby obtain 1.10 g of the title compound (Yield: 100%).

$^1$H-NMR($CDCl_3$) δ: 1.18–1.37(5H, m), 1.56–1.68(3H, m), 1.84–2.05(6H, m), 3.14–3.26(2H, m), 3.36–3.67(6H, m), 3.80(1H, d), 5.17(1H, d), 7.00–7.06(1H, m), 7.16–7.18 (2H, m), 7.39(1H, d-like)

Step 3

Preparation of 1-[1-(pyrrolidin-1-ylcarbonylmethyl)-2-oxo-5-cyclohexyl-1,3,4,5-tetrahydro-2H-1,5-benzodiazepin-3-yl]-3-(4-ethoxycarbonylphenyl)urea Ethyl 3-aminobenzoate (0.43 g) was dissolved in tetrahydrofuran (25 ml), the solution was cooled to internal temperature 5–8° C. Triphosgene (0.28 g) was added to the solution, and stirred for 5 minutes. Subsequently, triethylamine (0.95 g) was added dropwise over 15 minutes interval. The mixture was stirred at room temperature for 10 minutes, a solution of 1-(pyrrolidin-1-ylcarbonylmethyl)-2-oxo-3-amino-5-cyclohexyl-1,3,4,5-tetrahydro-2H-1,5-benzodiazepine (0.87 g) in tetrahydrofuran (15 ml) was added to the mixture, the resultant mixture was stirred for one hour. Water and chloroform were added to the reaction mixture and extracted. The organic layer was washed with saturated brine, and dried over anhydrous magnesium sulfate. The solvent was evaporated under reduced pressure, ether was added to crystals so precipitated for trituration, collected by filtration, to thereby obtain 1.20 g of the title compound (Yield: 91.3%).

Melting point: 240–243° C.

$^1$H-NMR($CDCl_3$) δ: 0.99–1.28(5H, m), 1.34(3H, t), 1.47–1.55(3H, m), 1.77–2.05(6H, m), 3.18–3.22(1H, m), 3.42–3.64(6H, m), 4.17(1H, d), 4.32(2H, q), 4.68–4.77(1H, m), 4.79(1H, d), 6.21(1H, d), 7.00–7.06(1H, m), 7.18–7.30 (4H, m), 7.60–7.68(2H, m), 7.72(1H, s), 7.98(1H, t)

Step 4

Preparation of 3-[3-[1-(pyrrolidin-1-ylcarbonylmethyl)-2-oxo-5-cyclohexyl-1,3,4,5-tetrahydro-2H-1,5-benzodiazepin-3-yl]ureido]benzoic acid 1-[1-(Pyrrolidin-1-ylcarbonylmethyl)-2-oxo-5-cyclohexyl-1,3,4,5-tetrahydro-2H-1,5-benzodiazepin-3-yl]-3-(4-ethoxycarbonylphenyl)urea was suspended in tetrahydrofuran (20 ml), aqueous lithium hydroxide (0.37 g) solution (10 ml) and methanol (20 ml) were added, the mixture was stirred at 40–50° C. for one hour. 1N hydrochloric acid and chloroform were added and extracted. The organic layer was washed with water and saturated brine, and dried over anhydrous magnesium sulfate. The solvent was evaporated under reduced pressure, isopropyl ether was added to crystals so precipitated for trituration, collected by filtration, to thereby obtain 0.81 g of the title compound (Yield: 85.1%).

Melting point: 223° C. (forming)

$^1$H-NMR(DMSO-$d_6$) δ: 1.17–1.35(4H, m), 1.51–1.60 (4H, m), 1.76–1.96(6H, m), 3.20–3.51(7H, m), 4.08(1H, d), 4.32–4.42(1H, m), 4.83(1H, d), 6.58(1H, d), 7.08–7.14 (1H, m), 7.23–7.35(4H, m), 7.46–7.52 (2H, m), 7.98(1H, t), 8.32(1H, s)

MS (FAB) m/z: 534($MH^+$)

IR(KBr)$cm^{-1}$:3324, 2930, 1686, 1660, 1595, 1556, 1496, 1448, 1219

Example 125

Preparation of (R)-(−)-2-methyl-2-[3-[3-(1-tert-butylcarbonylmethyl-2-oxo-5-cyclohexyl-1,3,4,5-tetrahydro-2H-1,5-benzodiazepin-3-yl)ureido]phenoxy] propionic acid Step 1

Preparation of 2-methyl-2-[3-(N-tert-butoxycarbonyl) aminophenoxy]propionic acid 3-(N-tert-Butoxycarbonyl)aminophenol (683 mg) was suspended in a solution of sodium hydroxide (1.70 g) in acetone (20 ml) under ice-cooling, chloroform (0.79 ml) was added, and then refluxed one hour. After the reaction mixture was allowed to cool, water and chloroform were added, extracted. The aqueous layer was acidified with 1N hydrochloric acid, and extracted with ethyl acetate. The ethyl acetate layer was washed with water and saturated brine, and dried over anhydrous magnesium sulfate. The solvent was evaporated under reduced pressure, to thereby obtain 675 mg of the title compound as pale yellow oil (Yield: 70.2%).

$^1$H-NMR($CDCl_3$) δ: 1.51(9H, s), 1.61(6H, s), 6.61(1H, ddd), 7.01(1H, d-like), 7.08(1H, brs), 7.17(1H, t)

Step 2

Preparation of benzyl 2-methyl-2-[3-(N-tert-butoxycarbonyl)aminophenoxy]propionate 2-Methyl-2-[3-(N-tert-butoxycarbonyl)aminophenoxy] propionic acid (675 mg) was dissolved in N,N-dimethylformamide (10 ml), benzyl bromide (0.30 ml) and potassium carbonate (633 mg) were added, and then stirred for one hour and 30 minutes at internal temperature 70° C. The reaction mixture was poured into ice-water and extracted with ethyl acetate. The organic layer was washed with saturated aqueous sodium bicarbonate, water and saturated brine, and dried over anhydrous magnesium sulfate. The solvent was evaporated under reduced pressure, to thereby obtain 882 mg of the title compound as pale yellow oil (Yield: 100%).

$^1$H-NMR($CDCl_3$) δ: 1.51(9H, s), 1.62(6H, s), 5.22(2H, s), 6.19(1H, brs), 6.42–6.46(1H, m), 6.71(1H, m), 7.00–7.10 (2H, m), 7.33(5H, s)

Step 3

Preparation of benzyl 2-methyl-2-(3-aminophenoxy) propionate

Benzyl 2-methyl-2-[3-(N-tert-butoxycarbonyl) aminophenoxy]propionate (882 mg) was dissolved in 4N HCl-dioxane (5.7 ml) and then stirred for 30 minutes at 50° C. After the solvent was evaporated under reduced pressure, methylene chloride and saturated aqueous sodium bicarbonate were added to the residue, and extracted. The organic layer was washed with water and saturated brine, and dried over anhydrous sodium sulfate. The solvent was evaporated under reduced pressure, the residue was purified by silica gel column chromatography(chloroform), to thereby obtain 270 mg of the title compound as oil.

$^1$H-NMR($CDCl_3$) δ: 1.60(6H, s), 3.50(2H, brs), 5.21(2H, s), 6.08(1H, t), 6.17(1H, ddd), 6.29(1H, ddd), 6.93(1H, t), 7.32(5H, s)

Step 4

Preparation of (R)-(−)-2-methyl-2-[3-[1-(1-tert-butylcarbonylmethyl-2-oxo-5-cyclohexyl-1,3,4,5-tetrahydro-2H-1,5-benzodiazepin-3-yl)ureido]phenoxy] propionic acid benzyl ester Benzyl 2-methyl-2-(3-aminophenoxy)propionate (200 mg) was dissolved in tetrahydrofuran (5 ml), the solution was cooled to internal temperature 5–8° C. Triphosgene (77 mg) was added, stirred for 5 minutes. Subsequently, triethylamine (0.36 g) was added every 5 minutes after divided into two portions. The mixture was stirred at room temperature for 10 minutes, a solution of (R)-1-tert-butylcarbonylmethyl-2-oxo-3-amino-5-cyclohexyl-1,3,4,5-tetrahydro-2H-1,5-benzodiazepine (230 mg) in tetrahydrofuran (5 ml) was added to the mixture, stirred for one hour. Water and chloroform were added to the reaction mixture, and extracted. The organic layer was washed with saturated brine, and dried over anhydrous magnesium sulfate. The solvent was evaporated under reduced pressure, the residue was purified by silica gel column chromatography (chloroform), to thereby obtain 310 mg of the title compound as pale yellow oil (Yield: 72.4%).

$^1$H-NMR($CDCl_3$) δ: 1.24(9H, s), 1.57(6H, s), 1.11–1.85 (9H, m), 2.00(1H, m), 3.20(1H, m), 3.26–3.31(1H, m), 3.69–3.73(1H, m), 4.18(1H, d), 4.64–4.68(1H, m), 5.14(1H, d), 5.20(2H, s), 5.81(1H, d), 6.16(1H, s), 6.42–6.46(1H, m), 6.66(1H, t), 6.90–7.06(4H, m), 7.17–7.19(2H, m), 7.32–7.35 (5H, m)

[α] $D^{25}$ (C=0.375, $CHCl_3$): −64.8°

Step 5

Preparation of (R)-(−)-2-methyl-2-[3-[3-(1-tert-butylcarbonylmethyl-2-oxo-5-cyclohexyl-1,3,4,5-tetrahydro-2H-1,5-benzodiazepin-3-yl)ureido]phenoxy] propionic acid (R)-(−)-2-Methyl-2-[3-[1-(1-tert-butylcarbonylmethyl-2-oxo-5-cyclohexyl-1,3,4,5-tetrahydro-2H-1,5-benzodiazepin-3-yl)ureido]phenoxy]propionic acid benzyl ester (210 mg) was dissolved in ethanol (5 ml), 10% palladium carbon (21 mg) was added, and the mixture was stirred for 2 hours at room temperature under hydrogen atmosphere. The reaction mixture was filtrated through a pad of Celite, the filtrate was concentrated under reduced pressure. n-Hexane was added to the residue, collected by filtration,to thereby obtain 170 mg of the title compound (97.2%).

$^1$H-NMR(DMSO-$d_6$) δ: 1.18(9H, s), 1.46(6H, s), 1.11–1.99(10H, m), 3.21–3.25(3H, m), 4.35–4.42(2H, m), 5.13(1H, d), 6.33–6.37(1H, m), 6.54(1H, d), 6.81(1H, m), 6.99–7.10(4H, m), 7.25–7.27(2H, m), 8.82(1H, s), 12.90 (1H, brs)

MS(FAB)m/z: 579($MH^-$)

IR(KBr)$cm^{-1}$:3370, 2934, 1724, 1647, 1597, 1551, 1496, 1153

[α] $D^{25}$ (C=0.8, $CHCl_3$): −60.1°

Example 126

Preparation of (−)-3-[3-[1-(2-toluoylmethyl)-2-oxo-5-(2-thenoyl)-8-methyl-1,3,4,5-tetrahydro-2H-1,5-benzodiazepin-3-yl]ureido]benzoic acid Step 1

Preparation of (−)-1-(2-toluoylmethyl)-2-oxo-3-amino-5-(2-thenoyl)-8-methyl-1,3,4,5-tetrahydro-2H-1,5-benzodiazepine 1-(2-toluoylmethyl)-2-oxo-3-amino-5-(2-thenoyl)-8-methyl-1,3,4,5-tetrahydro-2H-1,5-benzodiazepine (7.98 g) was dissolved in ethanol (100 ml), (+)-debenzoyl tartaric acid (3.96 g) was added under reflux, and then refluxed for 5 minutes, allowed to cool overnight,crystals so precipitated were collected by filtration, to thereby obtain (+)-dibenzoyl tartaric acid salt.

Melting point: 184–185° C.

The obtained (+)-dibenzoyl tartaric acid salt was suspended in saturated aqueous sodium bicarbonate and extracted with chloroform. The organic layer was washed with water and saturated brine, and dried over anhydrous sodium sulfate, the solvent was evaporated under reduced pressure, to thereby obtain 2.23 g of the title compound as colorless amorphous.

Optical purity: 98%ee (the ee value was determined by High Performance Liquid Chromatography)

[α] $D^{25}$ (C=1.00, $CH_2Cl_2$): −39.1°

Step 2

Preparation of 1-[1-(2-toluoylmethyl)-2-oxo-5-(2-thenoyl)-8-methyl-1,3,4,5-tetrahydro-2H-1,5-benzodiazepin-3-yl]-3-(3-tert-butoxycarbonylphenyl)urea Tert-butyl 3-aminobenzoate (1.09 g) was dissolved in tetrahydrofuran (20 ml), triphosgene (0.61 g) was added to a solution under ice-cooling. Subsequently, under ice-cooling triethylamine (2.12 g) was added dropwise, and the mixture was stirred at room temperature for one hour. A solution of 1-(2-toluoylmethyl)-2-oxo-3-amino-5-(2-thenoyl)-8-methyl-1,3,4,5-tetrahydro-2H-1,5-benzodiazepine (2.23 g) in tetrahydrofuran (20 ml) was added to the mixture, stirred at room temperature for one hour. The reaction mixture was concentrated under reduced pressure, 1N hydrochloric acid was added to the residue and extracted with chloroform. The organic layer was washed with water, saturated aqueous sodium bicarbonate and saturated brine, and dried over anhydrous magnesium sulfate. The solvent was evaporated under reduced pressure, the residue was purified by silica gel column chromatography (n-hexane:ethyl acetate=1:1), to thereby obtain 3.35 g of the title compound as colorless amorphous (Yield: 100%).

Step 3

Preparation of (−)-3-[3-[1-(2-toluoylmethyl)-2-oxo-5-(2-thenoyl)-8-methyl-1,3,4,5-tetrahydro-2H-1,5-benzodiazepin-3-yl]ureido]benzoic acid 1-[1-(2-Toluoylmethyl)-2-oxo-5-(2-thenoyl)-8-methyl-1,3,4,5-tetrahydro-2H-1,5-benzodiazepin-3-yl]-3-(3-tert-butoxycarbonylphenyl)urea (3.35 g) was dissolved in trifluoroacetic acid (30 ml), and then stirred for one hour at room temperature. The reaction mixture was concentrated under reduced pressure, hexane was added to the residue for trituration, and collected by filtration, to thereby obtain 3.04 g of the title compound as colorless powder (Yield: 99%).

Optical purity: 97.8%ee (the ee value was determined by High Performance Liquid Chromatography)

[α] D (C=1.017, $CHCl_3$): −59.6°

Example 127

Preparation of various salts of (−)-3-[3-(l-tert-butylcarbonylmethyl-2-oxo-5-phenyl-1,3,4,5-tetrahydro-2H-1,5-benzodiazepin-3-yl)ureido]benzoic acid (1) Preparation of (+)-phenethylamine salt (−)-3-[3-(1-tert-Butylcarbonylmethyl-2-oxo-5-phenyl-1,3,4,5-tetrahydro-2H-1,5-benzodiazepin-3-yl)ureido]benzoic acid (300 mg) was dissolved in methanol (3 ml), (+)-α-phenethylamine (71 mg) was added, the mixture was refluxed, and the reaction mixture was allowed to cool under agitation. Crystals so precipitated were collected by filtration and dried under reduced pressure, to thereby obtain 86 mg of the title salt as a colorless crystal.

Melting point: 176–177° C.

$^1$H-NMR(DMSO-$d_6$) δ: 1.17(9H, s), 1.34(3H, d), 3.46 (3H, br), 3.98–4.04(1H, m), 4.14(1H, q), 4.56–4.61(1H, m), 4.76(1H, d), 5.11(1H, d), 6.79–6.87(4H, m), 7.13–7.54(15H, m), 7.90(1H, s), 9.15(1H, s)

(2) Preparation of benzylamine salt

Free compound (100 mg) was dissolved in acetonitrile (1 ml), benzylamine (21 mg) was added, and the mixture was refluxed. The reaction mixture was allowed to cool under agitation, crystals so precipitated were collected by filtration and dried under reduced pressure, to thereby obtain 91 mg of benzylamine salt as a colorless crystal.

Melting point: 161–1630° C.

(3) Preparation of 4-methylbenzylamine salt

Free compound (100 mg) was dissolved in acetonitrile (1 ml), 4-methylbenzyl amine (24 mg) was added, the mixture was refluxed. The reaction mixture was allowed to cool, crystals so precipitated were collected by filtration and dried, to thereby obtain 92 mg of the title salt as a colorless crystal.

Melting point: 172–174° C.

Example 128

Preparation of (−)-3-[3-(1-tert-butylcarbonylmethyl-2-oxo-5-phenyl-8-methyl-1,3,4,5-tetrahydro-2H-1,5-benzodiazepin-3-yl)ureido]benzoic acid (−)-α-phenethylamine salt Free compound (300 mg) was dissolved in acetonitrile (2 ml), (−)-α-phenethylamine (69 mg) was added under heating and refluxed for 5 minutes. The reaction mixture was allowed to cool, crystals so precipitated were collected by filtration, and dried, to thereby obtain 327 mg of the title compound as a colorless crystal.

Melting point: 169–171° C.

Example 129

Preparation of (−)-3-[3-[1-(2-toluoylmethyl)-2-oxo-5-(2-thenoyl)-8-methyl-1,3,4,5-tetrahydro-2H-1,5-benzodiazepin-3-yl]ureido]benzoic acid (+)-α-phenethylamine salt Free compound (10 mg) was dissolved in acetonitrile (1 ml), (+)-α-phenethylamine was added, and stirred at room temperature. Crystals so precipitated were collected by filtration and dried, to thereby obtain 8.7 mg of the title compound as a colorless crystal.

Melting point: 178–181° C.

Example 130

Preparation of (+)-3-[3-[1-(2-thenoylmethyl)-2-oxo-5-(3,3-dimethylbutanoyl)-8-methyl-1,3,4,5-tetrahydro-2H-1,5-benzodiazepin-3-yl]ureido]benzoic acid (+)-α-phenethylamine salt Free compound (10 mg) was dissolved in acetonitrile (1 ml), (+)-α-phenethylamine (2 mg) was added, and stirred at room temperature. Crystals so precipitated were collected by filtration and dried, to thereby obtain 8.0 mg of the title compound as a colorless crystal.

Melting point: 156–160° C.

Example 131

Preparation of 3-[3-[1-(N-methyl-N-phenylcarbamoylmethyl)-2-oxo-5-cyclohexyl-1,3,4,5-tetrahydro-2H-1,5-benzodiazepin-3-yllureidolbenzoic acid Step 1

Preparation of 1-(N-methyl-N-phenylcarbamoylmethyl)-2-oxo-3-tert-butoxycarbonylamino-5-cyclohexyl-1,3,4,5-tetrahydro-2H-1,5-benzodiazepine Under argon atmosphere 2-oxo-3-tert-butoxycarbonylamino-5-cyclohexyl-1,3,4,5-tetrahydro-2H-1,5-benzodiazepine (1.0 g) was added to a suspension of 60% sodium hydride (222 mg) in anhydrous tetrahydrofuran (30 ml), and the mixture was stirred at room temperature for 30 minutes. Subsequently, 2-bromo-(N-methyl-N-phenyl) acetamide (951 mg) was added, and the mixture was stirred at room temperature for one hour. The reaction mixture was concentrated under reduced pressure, ice-water (50 ml) was added and extracted with ethyl acetate. The organic layer was washed with saturated brine, dried over anhydrous sodium sulfate. The solvent was concentrated under reduced pressure, the residue was purified by silica gel column chromatography(n-hexane:ethyl acetate=2:1), to thereby obtain 1.13 g of the title compound (Yield: 80.2%).

$^1$H-NMR($CDCl_3$) δ: 1.03–1.68(8H, m), 1.38(9H, s), 1.74–1.85(1H, m), 1.94–2.09(1H, m), 3.03–3.16(1H, m), 3.21(1H, dd), 3.35(3H, s), 3.55–3.70(2H, m), 4.42(1H, dt), 4.66(1H, d), 5.61(1H, d), 6.96–7.05(1H, m), 7.07–7.19(2H, m), 7.26–7.48(6H, m)

Step 2

Preparation of 1-(N-methyl-N-phenylcarbamoylmethyl)-2-oxo-3-amino-5-cyclohexyl-1,3,4,5-tetrahydro-2H-1,5-benzodiazepine 1-(N-Methyl-N-phenylcarbamoylmethyl)-2-oxo-3-tert-butoxycarbonylamino-5-cyclohexyl-1,3,4,5-tetrahydro-2H-1,5-benzodiazepine (1.13 g) was dissolved in ethanol (20 ml), 4N HCl-dioxane (10 ml) was added, and the mixture was stirred at 50° C. for 30 minutes. The reaction mixture was concentrated under reduced pressure, saturated aqueous sodium bicarbonate was added and extracted with methylene chloride. The organic layer was dried over anhydrous sodium sulfate, and the solvent was evaporated under reduced pressure, to thereby obtain 907 mg of the titled compound.

$^1$H-NMR($CDCl_3$) δ: 1.03–1.40(4H, m), 1.45–1.70(6H, m), 1.73–1.85(1H, m), 1.93–2.05(1H, m), 3.03–3.22(2H, m), 3.33–3.43(1H, m), 3.36(3H, s), 3.50–3.62(2H, m), 4.76 (1H, d), 6.98–7.07(1H, m), 7.10–7.17(2H, m), 7.25–7.49 (6H, m)

Step 3

Preparation of 1-[1-(N-methyl-N-phenylcarbamoylmethyl)-2-oxo-5-cyclohexyl-1,3,4,5-tetrahydro-2H-1,5-benzodiazepin-3-yl]-3-(3-ethoxycarbonylphenyl)urea Ethyl 3-aminobenzoate (406 mg) was dissolved in anhydrous tetrahydrofuran (20 ml), triphosgene (243 mg) was added under ice-cooling, triethylamine (0.21 ml) was added thereto five times every 3 minutes, and the mixture was stirred for one hour under ice-cooling. A solution of 1-(N-methyl-N-phenylcarbamoylmethyl)-2-oxo-3-amino-5-cyclohexyl-1,3,4,5-tetrahydro-2H-1,5-benzodiazepine (907 mg) in anhydrous tetrahydrofuran (20 ml) was added, the mixture was allowed to come to room temperature, and stirred for one hour. The reaction mixture was concentrated under reduced pressure, water (50 ml) was added and extracted with methylene chloride. The organic layer was dried over anhydrous sodium sulfate, the solvent was concentrated under reduced pressure, the residue was purified by silica gel column chromatography(n-hexane:ethyl acetate=4:3), and isopropyl ether was added to the residue for trituration, collected by filtration, to thereby obtain 1.10 g of the titled compound (Yield: 82.5%).

$^1$H-NMR(DMSO-$d_6$, 80° C.) δ: 1.03–1.35(4H, m), 1.30 (3H, t), 1.40–1.60(4H, m), 1.65–1.77(1H, m), 1.88–2.00(1H, m), 3.10–3.45(6H, m), 3.75–3.90(1H, m), 4.22–4.55(2H, m), 4.28(2H, q), 6.58(1H, d), 7.09–7.18(1H, m), 7.22–7.55 (11H, m), 8.03(1H, t), 9.09(1H, s)

Step 4

Preparation of 3-[3-[1-(N-methyl-N-phenylcarbamoylmethyl)-2-oxo-5-cyclohexyl-1,3,4,5-tetrahydro-2H-1,5-benzodiazepin-3-yl]ureido]benzoic acid 1-[1-(N-Methyl-N-phenylcarbamoylmethyl)-2-oxo-5-cyclohexyl-1,3,4,5-tetrahydro-2H-1,5-benzodiazepin-3-yl]-3-(3-ethoxycarbonylphenyl)urea (1.0 g) was dissolved in a mixed solvent of methanol (50 ml) and tetrahydrofuran (25 ml), aqueous lithium hydroxide monohydrate (350 mg) solution (25 ml) was added, and the mixture was refluxed for 30 minutes. The reaction mixture was concentrated under reduced pressure, the residue was acidified with 1N hydrochloric acid, extracted with methylene chloride. The organic layer was washed with saturated brine, dried over anhydrous sodium sulfate, the solvent was evaporated under reduced pressure, and isopropyl ether was added to the residue for trituration, collected by filtration, to thereby obtain 904 mg of the titled compound (Yield: 95.0%).

Melting point: 244–248° C. (decomposition)

$^1$H-NMR(DMSO-$d_6$, 80° C.) δ: 1.05–1.79(9H, m), 1.87–1.98(1H, m), 3.10–3.25(2H, m), 3.42(1H, dd), 3.87 (1H, d), 4.36(1H, dt), 4.55(1H, d), 6.46(1H, d), 7.05–7.15 (1H, m), 7.20–7.54(12H, m), 7.95(1H, t), 8.86(1H, s)

MS(FAB)m/z: 570($MH^+$) 133(base)

IR(KBr)$cm^{-1}$:3325, 2932, 1686, 1653, 1595, 1559, 1497, 1242, 758

Example 132

Preparation of 3-[3-[1-(N-tert-butyl)carbamoylmethyl-2-oxo-5-cyclohexyl-1,3,4,5-tetrahydro-2H-1,5-benzodiazepin-3-yl)ureido]benzoic acid Step 1

Preparation of 1-(N-tert-butyl)carbamoylmethyl-2-oxo-3-tert-butoxycarbonylamino-5-cyclohexyl-1,3,4,5-tetrahydro-2H-1,5-benzodiazepine 2-Oxo-3-tert-butoxycarbonylamino-5-cyclohexyl-1,3,4,5-tetrahydro-2H-1,5-benzodiazepine (1.0 g) was suspended in toluene (25 ml), N-tert-butyl-2-bromoacetamide (1.14 g), 1N aqueous sodium hydroxide (15 ml) and tetra n-butylammonium bromide (90 mg) were added thereto, and the mixture was stirred at room temperature overnight. Water and ethyl acetate were added to the reaction mixture, separated. The aqueous layer was extracted with ethyl acetate, the ethyl acetate extract was combined with the former organic layer, and the combined extract was washed with saturated brine, dried over anhydrous sodium sulfate. The solvent was evaporated under reduced pressure, ether was added to the residue for trituration, collected by filtration, to thereby obtain 1.09 g of the title compound (Yield: 83.0%).

$^1$H-NMR($CDCl_3$) δ: 1.10–1.90(9H, m), 1.31(9H, s), 1.40 (9H, s), 2.00–2.10(1H, m), 3.10–3.22(1H, m), 3.29(1H, dd), 3.48–3.57(1H, m), 4.20(1H, d), 4.31–4.42(1H, m), 4.45(1H, d), 5.41(1H, d), 6.11(1H, brs), 7.05–7.13(1H, m), 7.17–7.25 (3H, m)

Step 2

Preparation of 1-(N-tert-butyl)carbamoylmethyl-2-oxo-3-amino-5-cyclohexyl-1,3,4,5-tetrahydro-2H-1,5-benzodiazepine Step 2 of Example 131 was repeated except that 1-(N-tert-butyl)carbamoylmethyl-2-oxo-3-tert-butoxycarbonylamino-5-cyclohexyl-1,3,4,5-tetrahydro-2H-1,5-benzodiazepine was used instead of 1-(N-methyl-N-phenylcarbamoylmethyl)-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 1.10–1.90(11H, m), 1.30(9H, s), 2.01–2.13(1H, m), 3.08–3.21(1H, m), 3.24(1H, dd), 3.38 (1H, dd), 3.51(1H, dd), 4.30(1H, d), 4.39(1H, d), 6.10(1H, brs), 7.05–7.13(1H, m), 7.17–7.30(3H, m)

Step 3

Preparation of 1-[1-(N-tert-butyl)carbamoylmethyl-2-oxo-5-cyclohexyl-1,3,4,5-tetrahydro-2H-1,5-benzodiazepin-3-yl]-3-(3-ethoxycarbonylphenyl)urea Step 3 of Example 131 was repeated except that 1-(N-tert-butyl)carbamoylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, to thereby obtain the title compound.

$^1$H-NMR(DMSO-$d_6$) δ: 1.10–1.80(21H, m), 1.88–2.00 (1H, m), 3.17–3.44(3H, m), 3.75(1H, d), 4.28(2H, q), 4.22–4.39(1H, m), 4.64(1H, d), 6.64(1H, d), 7.10–7.18(1H, m), 7.23–7.38(4H, m), 7.46–7.56(3H, m), 8.04(1H, t), 9.12 (1H, s)

Step 4

Preparation of 3-[3-[1-(N-tert-butyl)carbamoylmethyl-2-oxo-5-cyclohexyl- 1,3,4,5-tetrahydro-2H-1,5-benzodiazepin-3-yl]ureido]benzoic acid Step 4 of Example 131 was repeated except that 1-[1-(N-tert-butyl)carbamoylmethyl-2-oxo-5-cyclohexyl-1,3,4,5- tetrahydro-2H-1,5-benzodiazepin-3-yl]-3-(3-ethoxycarbonylphenyl)urea was used instead of 1-[1-(N-methyl-N-phenylcarbamoylmethyl)-2-oxo-5-cyclohexyl-1,3,4,5-tetrahydro-2H-1,5-benzodiazepin-3-yl]-3-(3-ethoxycarbonylphenyl)urea, to thereby obtain the title compound.

Melting point: 230–234° C. (decomposition)

$^1$H-NMR(DMSO-$d_6$) δ: 1.10–1.80(18H, m), 1.88–2.00 (1H, m), 3.15–3.45(3H, m), 3.75(1H, d), 4.27–4.40(1H, m), 4.63(1H, d), 6.69(1H, d), 7.08–7.18(1H, m), 7.21–7.35(4H, m), 7.42–7.58(3H, m), 7.99(1H, t), 9.20(1H, s), 12.60–13.00 (1H, br)

MS(FAB)m/z: 536(MH$^+$)

IR(KBr)cm$^{-1}$:3316,2932, 1686, 1655, 1551, 756

Example 133

Preparation of 3-[3-[1-(2,5-dimethylthiophen-3-yl) carbonylmethyl-2-oxo-5-cyclohexyl-1,3,4,5-tetrahydro-2H-1,5-benzodiazepin-3-yl]ureido]benzoic acid Step 1

Preparation of 1-(2,5-dimethylthiophen-3-yl) carbonylmethyl-2-oxo-3-tert-butoxycarbonylamino-5-cyclohexyl-1,3,4,5-tetrahydro-2H-1,5-benzodiazepine Step 1 of Example 131 was repeated except that 3-bromoacetyl-2,5-dimethylthiophene was used instead of 2-bromo-(N-methyl-N-phenyl)acetamide, to thereby obtain the title compound.

$^1$H-NMR($CDCl_3$) δ: 1.17–1.88(9H, m), 1.39(9H, s), 1.96–2.08(1H, m), 2.41(3H, s), 2.71(3H, s), 3.12–3.25(1H, m), 3.29(1H, dd), 3.57–3.70(1H, m), 4.39(1H, d), 4.45–4.54 (1H, m), 5.37(1H, d), 5.56–5.64(1H, m), 6.94–7.18(5H, m)

Step 2

Preparation of 1-(2,5-dimethylthiophen-3-yl) carbonylmethyl-2-oxo-3-amino-5-cyclohexyl-1,3,4,5-tetrahydro-2H-1,5-benzodiazepine Step 2 of Example 131 was repeated except that 1-(2,5-dimethylthiophen-3-yl)carbonylmethyl-2-oxo-3-tert-butoxycarbonylamino-5-cyclohexyl-1,3,4,5-tetrahydro-2H-1,5-benzodiazepine was used instead of 1-(N-methyl-N-phenylcarbamoylmethyl)-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 1.10–2.15(12H, m), 2.41(3H, s), 2.72(3H, s), 3.12–3.33(2H, m), 3.39–3.47(1H, m), 3.61–3.72(1H, m), 4.32(1H, d), 5.48(1H, d), 6.92–7.22(5H, m)

Step 3

Preparation of 1-[1-(2,5-dimethylthiophen-3-yl) carbonylmethyl-2-oxo-5-cyclohexyl-1,3,4,5-tetrahydro-2H-1,5-benzodiazepin-3-yl]-3-(3-tert-butoxycarbonylphenyl) urea Step 3 of Example 131 was repeated except that 1-(2,5-dimethylthiophen-3-yl)carbonylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, and that tert-butyl 3-aminobenzoate was used instead of ethyl 3-aminobenzoate, to thereby obtain the title compound.

$^1$H-NMR($CDCl_3$) δ: 1.02–1.86(18H, m), 1.94–2.06(1H, m), 2.35(3H, s), 2.65(3H, s), 3.11–3.23(1H, m), 3.38(1H, dd), 3.67(1H, dd), 4.49(1H, d), 4.78(1H, dt), 5.38(1H, d), 6.23(1H, d), 6.93–7.37(7H, m), 7.53–7.62(1H, m), 7.65–7.72(1H, m), 7.80(1H, dt)

Step 4

Preparation of 3-[3-[1-(2,5-dimethylthiophen-3-yl) carbonylmethyl-2-oxo-5-cyclohexyl-1,3,4,5-tetrahydro-2H-1,5-benzodiazepin-3-yl]ureido]benzoic acid Trifluoroacetic acid (5 ml) was added to a solution of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea (450 mg) in anhydrous methylene chloride (10 ml), and the mixture was stirred at room temperature for 30 minutes. The reaction mixture was concentrated under reduced pressure, ethanol was added to the residue, crystals were collected by filtration, to thereby obtain 202 mg of the title compound.

Melting point: : 226–229° C. (decomposition)

$^1$H-NMR(DMSO-$d_6$) δ:

1.10–1.83(9H, m), 1.94–2.05(1H, m), 2.39(3H, s), 2.62 (3H, s), 3.15–3.38(2H, m), 3.44(1H, dd), 4.44(1H, dt), 4.67(1H, d), 5.32(1H, d), 6.61(1H, d), 7.07–7.12(2H, m), 7.22–7.37(4H, m), 7.49(2H, tq), 7.99(1H, t), 9.04(1H, s), 12.70–13.00(1H, br)

MS(FAB)m/z: 575(MH$^+$), 154(base)

IR(KBr)cm$^{-1}$:3337, 2934, 1692, 1670, 1661, 1557, 1238, 760

Example 134

Preparation of 2-methoxy-5-[3-(1-tert-butylcarbonylmethyl-2-oxo-5-cyclohexyl-1,3,4,5-tetrahydro-2H-1,5-benzodiazepin-3-yl)ureido]benzoic acid Step 1

Preparation of 1-(1-tert-butylcarbonylmethyl-2-oxo-5-cyclohexyl-1,3,4,5-tetrahydro-2H-1,5-benzodiazepin-3-yl)-3-(3-methoxycarbonyl-4-methoxyphenyl)urea Step 3 of Example 131 was repeated except that 1-tert-butylcarbonylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, and that methyl 5-amino-2-methoxybenzoate was used instead of ethyl 3-aminobenzoate, to thereby obtain the title compound.

$^1$H-NMR(DMSO-$d_6$) δ: 1.18(9H, s), 1.10–1.82(9H, m), 1.93–2.05(1H, m), 3.13–3.50(3H, m), 3.74(3H, s), 3.75(3H, s), 4.30–4.45(2H, m), 5.11(1H, d), 6.49(1H, d), 6.97–7.13 (3H, m), 7.20–7.30(2H, m), 7.38(1H, dd), 7.69(1H, d), 8.79(1H, s)

Step 2

Preparation of 2-methoxy-5-[3-[1-tert-butylcarbonylmethyl-2-oxo-5-cyclohexyl-1,3,4,5-tetrahydro-2H-1,5-benzodiazepin-3-yl]ureido]benzoic acid Step 4 of Example 131 was repeated except that 1-(1-tert-butylcarbonylmethyl-2-oxo-5-cyclohexyl-1,3,4,5-tetrahydro-2H-1,5-benzodiazepin-3-yl)-3-(3-methoxycarbonyl-4-methoxyphenyl)urea was used instead of 1-(1-(N-methyl-N-phenylcarbamoylmethyl)-2-oxo-5-cyclohexyl-1,3,4,5-tetrahydro-2H-1,5-benzodiazepin-3-yl]-3-(3-ethoxycarbonylphenyl)urea, to thereby obtain the title compound.

Melting point: 207~209° C. (decomposition)

$^1$H-NMR(DMSO-$d_6$) δ: 1.18(9H, s), 1.10~1.82(9H, m), 1.93~2.05(1H, m), 3.15~3.45(3H, m), 3.74(3H, s), 4.30~4.45(2H, m), 5.12(1H, d), 6.48(1H, d), 6.95~7.03(2H, m), 7.05~7.13(1H, m), 7.20~7.30(2H, m), 7.39(1H, dd), 7.63(1H, d), 8.76 (1H, s), 12.30~12.70(1H, br)

MS(FAB)m/z: 551(MH$^+$), 133(base)

IR(KBr)cm$^{-1}$:3386, 3340, 3289, 2934, 1742, 1686, 1661, 1553, 1497, 1221

Example 135

Preparation of 3-[3-[1-(2-thenoyl)methyl-2-oxo-5-(3,3-dimethylbutanoyl)-8-methyl-1,3,4,5-tetrahydro-2H-1,5-benzodiazepin-3-yl]ureido]benzoic acid Step 1

Preparation of 1-(2-thenoyl)methyl-2-oxo-3-tert-butoxycarbonylamino-5-(3,3-dimethylbutanoyl)-8-methyl-1,3,4,5-tetrahydro-2H-1,5-benzodiazepine Step 2 of Example 109 was repeated except that 2-bromoacetyl thiophene was used instead of 2-bromo-2'-methylacetophenone, to thereby obtain the title compound.

$^1$H-NMR($CDCl_3$) δ: 0.96(9H, s), 1.39(9H, s), 1.95~2.10 (2H, m), 2.37(3H, s), 3.80(1H, dd), 4.42~4.62(2H, m), 4.68(1H, d), 5.38(1H, d), 5.48(1H, d), 7.03~7.15(3H, m), 7.19(1H, dd), 7.73(1H, dd), 7.82(1H, dd)

Step 2

Preparation of 1-(2-thenoyl)methyl-2-oxo-3-amino-5-(3,3-dimethylbutanoyl)-8-methyl-1,3,4,5-tetrahydro-2H-1,5-benzodiazepine Step 2 of Example 131 was repeated except that 1-(2-thenoyl)methyl-2-oxo-3-tert-butoxycarbonylamino-5-(3,3-dimethylbutanoyl)-8-methyl-1,3,4,5-tetrahydro-2H-1,5-benzodiazepine was used instead of 1-(N-methyl-N-phenylcarbamoylmethyl)-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 0.95(9H, s), 1.53~1.72(2H, m), 1.94~2.08(2H, m), 2.38(3H, s), 3.58~3.80(2H, m), 4.48(1H, t), 4.51(1H, d), 5.54(1H, d), 7.03~7.13(3H, m), 7.20(1H, dd), 7.74(1H, dd), 7.84(1H, dd)

Step 3

Preparation of 1-[1-(2-thenoyl)methyl-2-oxo-5-(3,3-dimethylbutanoyl)-8-methyl-1,3,4,5-tetrahydro-2H-1,5-benzodiazepin-3-yl]-3-(3-tert-butoxycarbonylphenyl)urea Step 2 of Example 126 was repeated except that 1-(2-thenoyl)methyl-2-oxo-3-amino-5-(3,3-dimethylbutanoyl)-8-methyl-1,3,4,5-tetrahydro-2H-1,5-benzodiazepine was used instead of 1-(2-toluoylmethyl)-2-oxo-3-amino-5-(2-thenoyl)-8-methyl-1,3,4,5-tetrahydro-2H-1,5-benzodiazepine, to thereby obtain the title compound.

$^1$H-NMR($CDCl_3$) δ: 0.96(9H, s), 1.56(9H, s), 1.98~2.13 (2H, m), 2.37(3H, s), 3.87(1H, dd), 4.61(1H, t), 4.74(1H, d), 4.84(1H, dt), 5.37(1H, d), 6.15(1H, d), 7.07~7.16(4H, m), 7.22~7.34(2H, m), 7.58~7.71(3H, m), 7.75~7.82(2H, m)

Step 4

Preparation of 3-[3-[1-(2-thenoyl)methyl-2-oxo-5-(3,3-dimethylbutanoyl)-8-methyl-1,3,4,5-tetrahydro-2H-1,5-benzodiazepin-3-yl]ureidolbenzoic acid Step 4 of Example 133 was repeated except that 1-[1-(2-thenoyl)methyl-2-oxo-5-(3,3-dimethylbutanoyl)-8-methyl-1,3,4,5-tetrahydro-2H-1,5-benzodiazepin-3 -yl]-3-(3-tert-butoxycarbonylphenyl)urea was used instead of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound.

Melting point: 247–249° C. (decomposition)

$^1$H-NMR(DMSO-$d_6$) δ: 0.95(9H, s), 1.93(1H, d), 2.05 (1H, d), 2.38(3H, s), 3.52–3.60(1H, m), 4.41–4.60(2H, m), 5.20(1H, d), 5.41(1H, d), 6.71(1H, d), 7.20–7.38(5H, m), 7.45–7.55(2H, m), 8.02(1H, t), 8.08(1H, dd), 8.13(1H, dd), 9.00(1H, s), 12.80(1H, br)

MS(FAB)m/z: 577($MH^+$), 145(base)

IR(KBr)$cm^{-1}$:3392, 1702, 1649, 1632, 1561, 1233, 760

Example 136

Preparation of 2-methyl-5-(3-[1-(2-thenoyl)methyl-2-oxo-5-(3,3-dimethylbutanoyl)-8-methyl-1,3,4,5-tetrahydro-2H-1,5-benzodiazepin-3-yl]ureido]benzoic acid Step 1

Preparation of 1-[1-(2-thenoyl)methyl-2-oxo-5-(3,3-dimethylbutanoyl)-8-methyl-1,3,4,5-tetrahydro-2H-1,5-benzodiazepin-3-yl]-3-(3-tert-butoxycarbonyl-4-methylphenyl)urea Step 3 of Example 131 was repeated except that 1-(2-thenoyl)methyl-2-oxo-3-amino-5-(3,3-dimethylbutanoyl)-8-methyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, and that tert-butyl 5-amino-2-methylbenzoate was used instead of ethyl 3-aminobenzoate, to thereby obtain the title compound.

$^1$H-NMR(DMSO-$d_6$) δ: 0.94(9H, s), 1.52(9H, s), 1.92 (1H, d), 2.04(1H, d), 2.37(3H, s), 2.37(3H, s), 3.50–3.58(1H, m), 4.38–4.55(2H, m), 5.18(1H, d), 5.41(1H, d), 6.64(1H, d), 7.12(1H, d), 7.20–7.40(5H, m), 7.72(1H, d), 8.08(1H, dd), 8.13(1H, dd), 8.88(1H, s)

Step 2

Preparation of 2-methyl-5-[3-[1-(2-thenoyl)methyl-2-oxo-5-(3,3-dimethylbutanoyl)-8-methyl-1,3,4,5-tetrahydro-2H-1,5-benzodiazepin-3-yl]ureido]benzoic acid Step 4 of Example 133 was repeated except that 1-[1-(2-thenoyl)methyl-2-oxo-5-(3,3-dimethylbutanoyl)-8-methyl-1,3,4,5-tetrahydro-2H-1,5-benzodiazepin-3-yl]-3-(3-tert-butoxycarbonyl-4-methylphenyl)urea was used instead of 1-[1-(2,5 -dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound.

Melting point: 241–242° C. (decomposition)

$^1$H-NMR(DMSO-$d_6$) δ: 0.95(9H, s), 1.92(1H, d), 2.04 (1H, d), 2.37(3H, s), 2.41(3H, s), 3.50–3.58(1H, m), 4.40–4.58(2H, m), 5.19(1H, d), 5.40(1H, d), 6.64(1H, d), 7.13(1H, d), 7.20–7.40(5H, m), 7.87(1H, d), 8.08(1H, dd), 8.13(1H, dd), 8.86(1H, s), 12.70(1H, brs)

MS(FAB)m/z: 591($MH^+$), 136(base)

IR(KBr)$cm^{-1}$:3364, 3291, 1719, 1682, 1657, 1242, 737

Example 137

Preparation of 2-methyl-5-[1-(2-toluoylmethyl)-2-oxo-5-(2,2-dimethylbutanoyl)-8-methyl-1,3,4,5-tetrahydro-2H-1,5-benzodiazepin-3-yl]ureido]benzoic acid Step 1

Preparation of 2-oxo-3-tert-butoxycarbonylamino-5-(2,2-dimethylbutanoyl)-8-methyl-1,3,4,5-tetrahydro-2H-1,5-benzodiazepine 2-Oxo-3-tert-butoxycarbonylamino-8-methyl-1,3,4,5-tetrahydro-2H-1,5-benzodiazepine (1.0 g) was suspended in 1,2-dichloroethane (20 ml), and 2,2-dimethylbutanoyl chloride (538 mg) and pyridine (0.33 ml) were added thereto to the suspension, and the mixture was refluxed for 2 hours. Methylene chloride was added to the reaction mixture, washed with water and saturated aqueous sodium bicarbonate, dried over anhydrous sodium sulfate, the solvent was evaporated under reduced pressure, crystals so precipitate were washed with ether, to thereby obtain 1.20 g of the title compound (Yield 89.8%).

$^1$H-NMR($CDCl_3$) δ: 0.81(3H, t), 0.84(3H, s), 0.91(3H, s), 1.18–1.28(1H, m), 1.40(9H, s), 1.52–1.66(1H, m), 2.39(3H, s), 3.88(1H, dd), 4.30–4.53(2H, m), 5.39(1H, d), 6.95(1H, brs), 7.03–7.15(2H, m), 7.86(1H, s)

Step 2

Preparation of 1-(2-toluoylmethyl)-2-oxo-3-tert-butoxycarbonylamino-5-(2,2-dimethylbutanoyl)-8-methyl-1,3,4,5-tetrahydro-2H-1,5-benzodiazepine Step 2 of Example 1 was repeated except that 2-oxo-3-tert-butoxycarbonylamino-5-(2,2-dimethylbutanoyl)-8-methyl-1,3,4,5-tetrahydro-2H-1,5-benzodiazepine was used instead of 2-oxo-3-tert-butoxycarbonylamino-5-pivaloyl-1, 3,4,5-tetrahydro-2H-1,5-benzodiazepine, to thereby obtain the title compound.

$^1$H-NMR($CDCl_3$) δ: 0.84(3H, t), 0.90(3H, s), 0.96(3H, s), 1.15–1.45(1H, m), 1.40(9H, s), 1.57–1.75(1H, m), 2.37(3H, s), 2.60(3H, s), 3.95(1H, dd), 4.25(1H, t), 4.39(1H, d), 4.49–4.62(1H, m), 5.46–5.55(1H, m), 5.55(1H, d), 7.02–7.14(3H, m), 7.25–7.37(2H, m), 7.41–7.49(1H, m), 7.73–7.80(1H, m)

Step 3

Preparation of 1-(2-toluoylmethyl)-2-oxo-3-amino-5-(2,2-dimethylbutanoyl)-8-methyl-1,3,4,5-tetrahydro-2H-1,5-benzodiazepine Step 3 of Example 1 was repeated except that 1-(2-toluoylmethyl)-2-oxo-3-tert-butoxycarbonylamino-5-(2,2-dimethylbutanoyl)-8-methyl-1,3,4,5-tetrahydro-2H-1,5-benzodiazepine was used instead of 1-(2-toluoylmethyl)-2-oxo-3-tert-butoxycarbonylamino-5-pivaloyl-1,3,4,5-tetrahydro-2H-1,5-benzodiazepine, to thereby obtain the title compound.

$^1$H-NMR($CDCl_3$) δ: 0.83(3H, t), 0.87(3H, s), 0.97(3H, s), 1.20–1.35(1H, m), 1.58–1.75(3H, m), 2.37(3H, s), 2.59(3H, s), 3.61–3.81(2H, m), 4.25(1H, t), 4.33(1 H, d), 5.67(1H, d), 7.00(1H, brs), 7.05–7.14(2H, m), 7.28–7.37(2H, m), 7.42–7.50(1H, m), 7.76–7.82(1H, m)

Step 4

Preparation of 1-[1-(2-toluoylmethyl)-2-oxo-5-(2,2-dimethylbutanoyl)-8-methyl-1,3,4,5-tetrahydro-2H-1,5-benzodiazepin-3-yl]-3-(3-tert-butoxycarbonyl-4-methylphenyl)urea Step 3 of Example 131 was repeated except that 1-(2-toluoylmethyl)-2-oxo-3-amino-5-(2,2-dimethylbutanoyl)-8-methyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, and that tert-butyl 5-amino-2-methylbenzoate was used instead of ethyl 3-aminobenzoate, to thereby obtain the title compound.

$^1$H-NMR($CDCl_3$) δ: 0.86(3H, t), 0.93(3H, s), 0.94(3H, s), 1.22–1.37(1H, m), 1.56(9H, s), 1.52–1.71(1H, m), 2.37(3H, s), 2.46(3H, s), 2.52(3H, s), 3.98(1H, dd), 4.34(1H, t), 4.38(1H, d), 4.82(1H, dt), 5.52(1H, d), 6.03(1H, d), 6.98–7.32(7H, m), 7.37–7.46(2H, m), 7.60–7.72(2H, m)

Step 5

Preparation of 2-methyl-5-[1-(2-toluoylmethyl)-2-oxo-5-(2,2-dimethylbutanoyl)-8-methyl-1,3,4,5-tetrahydro-2H-1,5-benzodiazepin-3-yl]ureido]benzoic acid Step 4 of Example 133 was repeated except that 1-[1-(2-toluoylmethyl)-2-oxo-5-(2,2-dimethylbutanoyl)-8-methyl-1,3,4,5-tetrahydro-2H-1,5-benzodiazepin-3-yl]-3-(3-tert-butoxycarbonyl-4-methylphenyl)urea was used instead of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound.

Melting point: 234–236° (decomposition)

$^1$H-NMR (DMSO-$d_6$) δ: 0.77(3H, t), 0.82(3H, s), 0.88 (3H, s), 1.15–1.35(1H, m), 1.50–1.70(1H, m), 2.39(3H, s), 2.40(3H, s), 2.45(3H, s), 3.68(1H, dd), 4.24(1H, t), 4.52(1H, ddd), 4.89(1H, d), 5.41(1H, d), 6.66(1H, d), 7.10–7.42(7H, m), 7.46–7.55(1H, m), 7.87(1H, d), 7.98(1H, d), 8.87(1H, s), 12.70(1H, br)

MS(FAB)m/z: 599($MH^+$), 119(base)

IR(KBr)$cm^{-1}$:3413, 3343, 2967, 1719, 1692, 1655, 1632, 1545, 752

Example 138

Preparation of 3-[3-[1-(2,5-dimethylthiophen-3-yl)carbonylmethyl-2-oxo-5-(3,3-dimethylbutanoyl)-8-methyl-1,3,4,5-tetrahydro-2H-1,5-benzodiazepin-3-yl]ureido]benzoic acid Step 1

Preparation of 1-(2,5-dimethylthiophen-3-yl)carbonylmethyl-2-oxo-3-tert-butoxycarbonylamino-5-(3,3-dimethylbutanoyl)-8-methyl-1,3,4,5-tetrahydro-2H-1,5-benzodiazepine Step 2 of Example 109 was repeated except that 3-bromoacetyl-2,5-dimethylthiophene was used instead of 2-bromo-2'-methylacetophenone, to thereby obtain the title compound.

$^1$H-NMR($CDCl_3$) δ: 0.96(9H, s), 1.39(9H, s), 2.00(1H, d), 2.09(1H, d), 2.36(3H, s), 2.43(3H, s), 2.70(3H, s), 3.81(1H, dd), 4.40–4.62(3H, m), 5.21(1H, d), 5.50(1H, d), 6.98–7.13 (4H, m)

Step 2

Preparation of 1-(2,5-dimethylthiophen-3-yl)carbonylmethyl-2-oxo-3-amino-5-(3,3-dimethylbutanoyl)-8-methyl-1,3,4,5-tetrahydro-2H-1,5-benzodiazepine Step 2 of Example 131 was repeated except that 1-(2,5-dimethylthiophen-3-yl)carbonylmethyl-2-oxo-3-tert-butoxycarbonylamino-5-(3,3-dimethylbutanoyl)-8-methyl-1,3,4,5-tetrahydro-2H-1,5-benzodiazepine was used instead of 1-(N-methyl-N-phenylcarbamoylmethyl)-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 0.95(9H, s), 1.63(2H, s), 1.97(1H, d), 2.06(1H, d), 2.36(3H, s), 2.44(3H, s), 2.72(3H, s), 3.58–3.80 (2H, m), 4.37 (1H, d), 4.47(1H, t), 5.38(1H, d), 6.97(1H, brs), 7.02–7.13(3H, m)

Step 3

Preparation of 1-[1-(2,5-dimethylthiophen-3-yl)carbonylmethyl-2-oxo-5-(3,3-dimethylbutanoyl)-8-methyl-1,3,4,5-tetrahydro-2H-1,5-benzodiazepin-3-yl]-3-(3-tert-butoxycarbonylphenyl)urea Step 2 of Example 126 was repeated except that 1-(2,5-dimethylthiophen-3-yl)carbonylmethyl-2-oxo-3-amino-5-(3,3-dimethylbutanoyl)-8-methyl-1,3,4,5-tetrahydro-2H-1,5-benzodiazepine was used instead of 1-(2-toluoylmethyl)-2-oxo-3-amino-5-(2-thenoyl)-8-methyl-1,3,4,5-tetrahydro-1,5-benzodiazepine, to thereby obtain the title compound.

$^1$H-NMR($CDCl_3$) δ: 0.97(9H, s), 1.56(9H, s), 2.04(1H, d), 2.15(1H, d), 2.37(3H, s), 2.39(3H, s), 2.64(3H, s), 3.83(1H, dd), 4.59(1H, t), 4.62(1H, d), 4.85(1H, ddd), 5.24(1H, d), 6.15(1H, d), 7.01(2H, s), 7.07–7.15(3H, m), 7.19–7.28(11H, m), 7.60(11H, dd), 7.77(1H, t)

Step 4

Preparation of 3-[3-[1-(2,5-dimethylthiophen-3-yl)carbonylmethyl-2-oxo-5-(3,3-dimethylbutanoyl)-8-methyl-1,3,4,5-tetrahydro-2H-1,5-benzodiazepin-3-yl]ureido]benzoic acid Step 4 of Example 133 was repeated except that 1-[1-(2,5-dimethylthiophen-3-yl)carbonylmethyl-2-oxo-5-(3,3-dimethylbutanoyl)-8-methyl-1,3,4,5-tetrahydro-2H-1,5-benzodiazepin-3-yl]-3-(3-tert-butoxycarbonylphenyl)urea was used instead of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound.

Melting point: 231–233° C. (decomposition)

$^1$H-NMR(DMSO-$d_6$) δ: 0.95(9H, s), 1.97–2.11(2H, m), 2.37(3H, s), 2.41(3H, s), 2.59(3H, s), 3.52–3.60(1H, m), 4.40–4.60(2H, m), 5.05(1H, d), 5.21(1H, d), 6.70(1H, d), 7.18–7.37(5H, m), 7.46–7.55(2H, m), 8.02(1H, t), 9.02(1H, s), 12.80(1H, br)

MS(FAB)m/z: 605($MH^+$), 139(base)

IR(KBr)$cm^{-1}$:3420, 3333, 2955, 1688, 1653, 1555, 754

Example 139

Preparation of 2-methyl-5-[3-(1-tert-butylcarbonylmethyl-2-oxo-5-phenyl-8-methyl-1,3,4,5-tetrahydro-2H-1,5-benzodiazepin-3-yl)ureido]benzoic acid Step 1

Preparation of 1-(1-tert-butylcarbonylmethyl-2-oxo-5-phenyl-8-methyl-1,3,4,5-tetrahydro-2H-1,5-benzodiazepin-3-yl)-3-(3-tert-butoxycarbonylphenyl)urea Step 3 of Example 95 was repeated except that tert-butyl 5-amino-2-methylbenzoate was used instead of ethyl 3-aminobenzoate, to thereby obtain the title compound.

$^1$H-NMR(DMSO-$d_6$) δ: 1.17(9H, s), 1.52(9H, s), 2.33 (3H, s), 2.37(3H, s), 3.51–3.63(1H, m), 3.96(1H, dd), 4.57 (1H, ddd), 4.72(1H, d), 5.08(1H, d), 6.63–6.87(3H, m), 7.00–7.24(6H, m), 7.38(1H, dd), 7.74(1H, d)

Step 2

Preparation of 2-methyl-5-[3-(1-tert-butylcarbonylmethyl-2-oxo-5-phenyl-8-methyl-1,3,4,5-tetrahydro-2H-1,5-benzodiazepin-3-ylureido)benzoic acid Step 4 of Example 133 was repeated except that 1-(1-tert-butylcarbonylmethyl-2-oxo-5-phenyl-8-methyl-1,3,4,5-tetrahydro-2H-1,5-benzodiazepin-3-yl)-3-(3-tert-butoxycarbonylphenyl)urea was used instead of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound.

Melting point: 248–250° C. (decomposition)

$^1$H-NMR(DMSO-$d_6$) δ: 1.17(9H, s), 2.33(3H, s), 2.41 (3H, s), 3.57(1H, dd), 3.96(1H, dd), 4.57(1H, ddd), 4,72(1H, d), 5.08(1H, d), 6.65(1H, d), 6.73–6.87(3H, m), 7.00–7.24 (6H, m), 7.38(1H, dd), 7.87(1H, d), 9.97(1H, s), 12.50–12.90(1H, br)

MS(FAB)m/z: 543(MH$^+$), 154(base)

IR(KBr)cm$^{-1}$:3364, 3305, 2967, 1725, 1686, 1647, 1532, 1267, 760, 695

Example 140

Preparation of (+)-3-[1-(2-toluoylmethyl)-2-oxo-5-(3,3-dimethylbutanoyl)-8-methyl-1,3,4,5-tetrahydro-2H-1,5-benzodiazepin-3-yl]ureido]benzoic acid Step 1

Preparation of (+)-1-(2-toluoylmethyl)-2-oxo-3-amino-5-(3,3-dimethylbutanoyl)-8-methyl-1,3,4,5-tetrahydro-2H-1,5-benzodiazepine (±)-1-(2-toluoylmethyl)-2-oxo-3-amino-5-(3,3-dimethylbutanoyl)-8-methyl-1,3,4,5-tetrahydro-2H-1,5-benzodiazepine (10.0 g) was dissolved in ethyl acetate (150 ml), a solution (100 ml) of (+)-dibenzoyl-D-tartaric acid monohydrate (8.92 g) in ethyl acetate was added, and the mixture was stirred at room temperature overnight. Crystals so precipitated were collected by filtration, saturated aqueous sodium bicarbonate was added to the residue, and extracted with chloroform. The organic layer was dried over anhydrous sodium sulfate, the solvent was evaporated under reduced pressure, to thereby obtain 4.44 g of the title compound as light-yellow-color amorphous.

Optical purity: 95%ee (Mosher method)

[α] D$^{27}$ (C=1.03, $CHCl_3$): +75.5°

Step 2

Preparation of (+)-1-[1-(2-toluoylmethyl)-2-oxo-5-(3,3-dimethylbutanoyl)-8-methyl-1,3,4,5-tetrahydro-2H-1,5-benzodiazepin-3-yl]-3-(3-benzyloxycarbonylphenyl)urea Diphenylphosphoryl azide (6.60 g) and triethylamine (3.75 g) were added to a solution of isophthalic acid benzyl ester (5.38 g) in anhydrous dioxane (50 ml), and the mixture was stirred at internal temperature 60° for 30 minutes and stirred at internal temperature 80° for one hour. The reaction mixture was allowed to cool at room temperature,a solution of (+)-1-(2-toluoylmethyl)-2-oxo-3-amino-5-(3,3-dimethylbutanoyl)-8-methyl-1,3,4,5-tetrahydro-2H-1,5-benzodiazepine (3.0 g) in anhydrous dioxane (50 ml) was added thereto, and the mixture was stirred at room temperature for 15 minutes. The reaction mixture was concentrated under reduced pressure, chloroform (200 ml) was added to the residue, the organic layer was washed with saturated aqueous sodium bicarbonate and saturated brine, and dried over anhydrous sodium sulfate. The solvent was evaporated under reduced pressure, and the residue was purified by silica gel column chromatography(NH-DM1020, produced by Fujisilicia Co. Ltd., n-hexane:ethyl acetate=2:1), to thereby obtain 4.08 g of the title compound (Yield 85.2%).

$^1$H-NMR($CDCl_3$) δ: 0.96(9H, s), 2.04(1H, d), 2.17(1H, d), 2.37(3H, s), 2.47(3H, s), 3.84(1H, dd), 4.61(1H, t), 4.67(1H, d), 4.87(1H, dt), 5.32(1H, d), 6.36(1H, d), 7.02(1H, s), 7.11(2H, s), 7.17–7.45(9H, m), 7.49(1H, s), 7.60–7.72 (3H, m), 7.88–7.93(1H, m)

[α] D$^{27}$ (C=1.034, $CHCl_3$): +34.8°

Step 3

Preparation of (+)-3-[1-(2-toluoylmethyl)-2-oxo-5-(3,3-dimethylbutanoyl)-8-methyl-1,3,4,5-tetrahydro-2H-1,5-benzodiazepin-3-yl]ureido]benzoic acid (+)-1-[1-(2-Toluoylmethyl)-2-oxo-5-(3,3-dimethylbutanoyl)-8-methyl-1,3,4,5-tetrahydro-2H-1,5-benzodiazepin-3-yl]-3-(3-benzyloxycarbonylphenyl)urea (4.0 g) was dissolved in ethanol (50 ml), 10% palladium carbon (400 mg) was added thereto, the mixture was stirred for 2 hours and 30 minutes at room temperature under hydrogen atmosphere. The reaction mixture was filtrated, the filtrate was concentrated under reduced pressure. The residue was purified by silica gel column chromatography (chloroform:methanol=20:1), subsequently isopropyl ether was added to the residue for trituration, collected by filtration, to thereby obtain 2.82 g of the titled compound (Yield 81.5%).

Melting point: 174–179° C. (forming)

Optical purity: 97.6%ee (the ee value was determined by High Performance Liquid Chromatography)

MS(FAB)m/z: 585(MH$^+$), 133(base)

[α] D$^{27}$ (C=1.054, $CHCl_3$): +45.2°

Example 141

Preparation of (+)-2-methyl-5-[1-(2-toluoylmethyl)-2-oxo-5-(3,3-dimethylbutanoyl)-8-methyl-1,3,4,5-tetrahydro-2H-1,5-benzodiazepin-3-yl]ureido]benzoic acid Step 1

Preparation of (+)-1-[1-(2-toluoylmethyl)-2-oxo-5-(3,3-dimethylbutanoyl)-8-methyl-1,3,4,5-tetrahydro-2H-1,5-benzodiazepin-3-yl]-3-(3-benzyloxycarbonyl-4-methylphenyl)urea Step 4 of Example 109 was repeated except that (+)-1-(2-toluoylmethyl)-2-oxo-3-amino-5-(3,3-dimethylbutanoyl)-8-methyl-1,3,4,5-tetrahydro-2H-1,5-benzodiazepine was used instead of 1-(2-toluoylmethyl)-2-oxo-3-amino-5-(3,3-dimethylbutanoyl)-8-methyl-1,3,4,5-tetrahydro-2H-1,5-benzodiazepine, and that tert-butyl 5-amino-2-methylbenzoate was used instead of ethyl 3-aminobenzoate, to thereby obtain the title compound.

$^1$H-NMR($CDCl_3$) δ: 0.96(9H, s), 1.56(9H, s), 2.03(1H, d), 2.15(1H, d), 2.38(3H, s), 2.47(3H, s), 2.49(3H, s), 3.85(1H, dd), 4.57(1H, t), 4.70(1H, d), 4.85(1H, ddd), 5.29(1H, d), 6.05(1H, d), 7.00–7.13(5H, m), 7.20–7.30(2H, m), 7.37–7.45(2H, m), 7.62(1H, d), 7.69(1H, d)

[α] D (C=1.043, $CHCl_3$): +28.1°

Step 2

Preparation of (+)-2-methyl-5-[1-(2-toluoylmethyl)-2-oxo-5-(3,3-dimethylbutanoyl)-8-methyl-1,3,4,5-tetrahydro-2H-1,5-benzodiazepin-3-yl]ureido]benzoic acid Step 4 of Example 133 was repeated except that (+)-1-[1-(2-toluoylmethyl)-2-oxo-5-(3,3-dimethylbutanoyl)-8-methyl-1,3,4,5-tetrahydro-2H-1,5-benzodiazepin-3-yl]-3-(3-benzyloxycarbonyl-4-methylphenyl)urea was used instead of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound as amorphous.

Optical purity: 98.6%ee (the ee value was determined by High Performance Liquid Chromatography)

MS(FAB)m/z: 599($MH^+$), 119(base)

[α] D (C=1.01, MeOH): +39.6°

Example 142

Preparation of (+)-3-[3-[1-(2-thenoyl)methyl-2-oxo-5-(3,3-dimethylbutanoyl)-8-methyl-1,3,4,5-tetrahydro-2H-1,5-benzodiazepin-3-yl]ureido]benzoic acid Step 1

Preparation of (+)-1-(2-thenoyl)methyl-2-oxo-3-amino-5-(3,3-dimethylbutanoyl)-8-methyl-1,3,4,5-tetrahydro-2H-1,5-benzodiazepine Step 1 of Example 140 was repeated except that (±)-1-(2-thenoyl)methyl-2-oxo-3-amino-5-(3,3-dimethylbutanoyl)-8-methyl-1,3,4,5-tetrahydro-2H-1,5-benzodiazepine was used instead of (±)-1-(2-toluoylmethyl)-2-oxo-3-amino-5-(3,3-dimethylbutanoyl)-8-methyl-1,3,4,5-tetrahydro-2H-1,5-benzodiazepine, to thereby obtain the title compound.

Optical purity: 95%ee (the ee value was determined by $^1$H-NMR, after the title compound was converted into Mosher ester)

[α] D (C=1.02, $CHCl_3$): +106.6°

Step 2

Preparation of (+)-1-[1-(2-thenoyl)methyl-2-oxo-5-(3,3-dimethylbutanoyl)-8-methyl-1,3,4,5-tetrahydro-2H-1,5-benzodiazepin-3-yl]-3-(3-tert-butoxycarbonylphenyl)urea In a similar manner to Step 3 of Example 135, by use of (+)-1-(2-thenoyl)methyl-2-oxo-3-amino-5-(3,3-dimethylbutanoyl)-8-methyl-1,3,4,5-tetrahydro-2H-1,5-benzodiazepine, to thereby obtain the title compound.

[α] D (C=1.06, $CHCl_3$): +58.3°

Step 3

Preparation of (+)-3-[3-[1-(2-thenoyl)methyl-2-oxo-5-(3,3-dimethylbutanoyl)-8-methyl-1,3,4,5-tetrahydro-2H-1,5-benzodiazepin-3 -yl]ureido]benzoic acid In a similar manner to Step 4 of Example 135, by use of (+)-1-[1-(2-thenoyl)methyl-2-oxo-5-(3,3-dimethylbutanoyl)-8-methyl-1,3,4,5-tetrahydro-2H-1,5-benzodiazepin-3-yl]-3-(3-tert-butoxycarbonylphenyl)urea, to thereby obtain the title compound.

Melting point: 170–180° C. (forming)

Optical purity: 99.5%ee (the ee value was determined by High Performance Liquid Chromatography)

MS(FAB)m/z: 577($MH^+$), 154(base)

[α] D (C=1.07, $CHCl_3$): +65.40°

Example 143

Preparation of (R)-(−)-3-[3-(1-tert-butylcarbonylmethyl-2-oxo-5-cyclohexyl-1,3,4,5-tetrahydro-2H-1,5-benzodiazepin-3-yl]ureido]benzoic acid Step 1

Preparation of (R)-(−)-2-tert-butoxycarbonylamino-3-(2-nitrophenylamino)propionic acid (R)-2-tert-Butoxycarbonylamino-3-aminopropionic acid (5 g) and potassium carbonate (6.77 g) were added to a solution of 2-fluoronitrobenzene (3.45 g) in N,N-dimethylformamide (60 ml), and the mixture was stirred overnight at 70° C. After the reaction mixture was allowed to cool, the reaction mixture was poured into ice-water and washed with ethyl acetate. The water layer was adjusted to pH 3 with 1N hydrochloric acid, extracted with ethyl acetate. This organic layer was washed with saturated brine, dried over anhydrous sodium sulfate, and the solvent was evaporated under reduced pressure. Hexane was added to the residue for crystallization, collected by filtration,to thereby obtain 7.9 g of the title compound (Yield 99%).

[α] $D^{25}$ (C=1.00, $CHCl_3$): −145°

Step 2

Preparation of (R)-(+)-2-oxo-3-tert-butoxycarbonylamino-1,3,4,5-tetrahydro-2H-1,5-benzodiazepine 10% palladium carbon (1 g) was added to a solution of (R)-(−)-2-tert-butoxycarbonylamino-3-(2-nitrophenylamino)propionic acid (7.6 g) in tetrahydrofuran (100 ml), and the mixture was stirred under hydrogen atmosphere at room temperature for 3 hours. The reaction mixture was filtrated, and the filtrate was concentrated under reduced pressure, to thereby obtain (R)-2-tert-butoxycarbonylamino-3-(2-aminophenylamino)propionic acid. The residue was dissolved in toluene (100 ml), the solution was refluxed overnight. After allowed to cool, the reaction mixture was concentrated under reduced pressure, the residue was purified by silica gel column chromatography(ethyl acetate:n-hexane=1:1), to thereby obtain 5.16 g of the title compound (Yield 80%).

[α] $D^{25}$ (C=1.0, $CHCl_3$): +7.21°

Optical purity: 98%ee (the ee value was determined by High Performance Liquid Chromatography)

Step 3

Preparation of (3R)-(−)-2-oxo-3-tert-butoxycarbonylamino-5-(2-cyclohexen-1-yl)-1,3,4,5-tetrahydro-2H-1,5-benzodiazepine 3-Bromocyclohexene (7.06 g) and sodium bicarbonate (3.68 g) were added to a solution of (R)-(+)-2-oxo-3-tert-butoxycarbonylamino-1,3,4,5-tetrahydro-2H-1,5-benzodiazepine (6.08 g) in anhydrous N,N-dimethylformamide (50 ml), and the mixture was stirred at 50° C. for one hour. The reaction mixture was allowed to cool, ice-water was added, and extracted with ethyl acetate. The organic layer was washed with saturated brine, dried over anhydrous sodium sulfate. The solvent was evaporated under reduced pressure,the residue was purified by silica gel column chromatography(ethyl acetate:n-hexane=1:3), to thereby obtain 7.84 g of the titled compound.

[α] $D^{25}$ (C=1.00, $CHCl_3$): −179°

Step 4

Preparation of (R)-(−)-2-oxo-3-tert-butoxycarbonylamino-5-cyclohexyl-1,3,4,5-tetrahydro-2H-1,5-benzodiazepine Step 1 of Example 118 was repeated except that (3R)-(−)-2-oxo-3-tert-butoxycarbonylamino-5-(2-cyclohexen-1-yl)-1,3,4,5-tetrahydro-2H-1,5-benzodiazepine was used instead of 2-oxo-3-tert-butoxycarbonylamino-5-(2-cyclohexen-1-yl)-8-methyl-1,3,4,5-tetrahydro-2H-1,5-benzodiazepine, to thereby obtain the title compound.

[α] $D^{23}$ (C=1.02, $CHCl_3$): −188°

Step 5

Preparation of (R)-(−)-2-oxo-3-amino-5-cyclohexyl-1,3,4,5-tetrahydro-2H-1,5-benzodiazepine 4N HCl-dioxane (10 ml) was added to a solution of (R)-(−)-2-oxo-3-tert-butoxycarbonylamino-5-cyclohexyl-1,3,4,5-tetrahydro-2H-1,5-benzodiazepine (5.11 g) in ethanol (15 ml), and the mixture was stirred at 50: for one hour. After allowed to cool, the reaction mixture was concentrated under reduced pressure, the residue was neutralized with saturated aqueous sodium bicarbonate, and extracted with chloroform. The organic layer was washed with saturated brine, dried over anhydrous sodium sulfate. The solvent was evaporated under reduced pressure, diisopropyl ether was added to crystals so precipitated, washed, and collected by filtration. This was recrystallized from a mixed solvent of ethanol and diisopropyl ether, to thereby obtain 2.1 g of the titled compound.

Melting point: 180–182° C.

$^1$H-NMR($CDCl_3$) δ: 1.06–2.07(12H, m), 3.17–3.32(2H, m), 3.49–3.62(2H, m), 6.90–6.99(2H, m), 7.09–7.18(2H, m), 7.45(1H, s)

[α] $D^{25}$ (C=1.04, $CHCl_3$): −163°

Optical purity: 99%ee over (the ee value was determined by High Performance Liquid Chromatography)

Step 6

Preparation of (R)-(−)-1-(2-oxo-5-cyclohexyl-1,3,4,5-tetrahydro-2H-1,5-benzodiazepin-3-yl)-3-(3-tert-butoxycarbonylphenyl)urea Triphosgene (1.8 g) was added to a solution of tert-butyl 3-aminobenzoate (3.13 g) in anhydrous tetrahydrofuran (200 ml) under ice-cooling, and then triethylamine (7.25 ml) was added five times each 1.45 ml over 15 minutes, and the mixture was stirred at room temperature for 5 minutes. Subsequently (R)-(−)-2-oxo-3-amino-5-cyclohexyl-1,3,4,5-tetrahydro-2H-1,5-benzodiazepine (4 g) was added under ice-cooling. The mixture was stirred at room temperature for one hour, the reaction mixture was concentrated under reduced pressure. Ice-water was added to the residue, extracted with methylene chloride,the organic layer was washed with saturated brine. After dried over anhydrous sodium sulfate, the solvent was evaporated under reduced pressure. Diisopropyl ether was added to the residue, crystals were collected by filtration, to thereby obtain 7.38 g of the titled compound.

$^1$H-NMR(DMSO-$d_6$) δ: 1.10–2.03(19H, m), 3.18–3.36 (2H, m), 3.53(1H, dd), 4.27–4.36(1H, m), 6.59(1H, d), 6.97–7.03(2H, m), 7.10–7.22(2H, m), 7.32(1H, t), 7.41–7.47 (1H, m), 7.52–7.58(1H, m), 7.92(1H, t), 9.08(1H, s), 9.85 (1H, s)

[α] $D^{25}$ (C=0.91, MeOH): −148°

Step 7

Preparation of (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylphenyl)urea Bromomethyl tert-butylketone (2.95 g), potassium iodide (125 mg), tetra n-butylammonium bromide (145 mg) and potassium carbonate (2.07 g) were added to a solution of (R)-(−)-1-(2-oxo-5-cyclohexyl-1,3,4,5-tetrahydro-2H-1,5-benzodiazepin-3-yl)-3-(3-tert-butoxycarbonylphenyl)urea (7.18 g) in dimethylsulfoxide (100ml), the mixture was stirred for 2hours at room temperature. The reaction mixture was poured into ice-water, extracted with ethyl acetate. The organic layer was washed with saturated brine, dried over anhydrous sodium sulfate. The solvent was evaporated under reduced pressure, the residue was purified by silica gel column chromatography(ethyl acetate:n-hexane=1:2), to thereby obtain 8.22 g of the titled compound (Yield 95%).

$^1$H-NMR($CDCl_3$) δ: 1.00–2.04(28H, m), 3.16–3.28(1H, m), 3.89(1H, dd), 3.64(1H, dd), 4.28(1H, d), 4.67–4.78(1H, m), 5.14(1H, d), 6.33(1H, d), 6.97–7.06(2H, m), 7.14–7.27 (4H, m), 7.50–7.59(2H, m), 7.81(1H, t)

[α] $D^{25}$ (C=1.05, $CHCl_3$): −63.0°

Step 8

Preparation of (R)-(−)-3-[3-(1-tert-butylcarbonylmethyl-2-oxo-5-cyclohexyl-1,3,4,5-tetrahydro-2H-1,5-benzodiazepin-3-yl)ureido]benzoic acid Trifluoroacetic acid (40 ml) was added to a solution of (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylphenyl)urea (8 g) in methylene chloride (40 ml), the mixture was stirred for one hour at room temperature. The reaction mixture was concentrated under reduced pressure, a mixed solvent (32 ml) of diisopropyl ether and ethanol (15:1) was added to the residue for crystallization, collected by filtration, to thereby obtain 6.35 g of the title compound (Yield 88%).

Melting point: 159–161° C.

MS(FAB)m/z: 521($MH^+$), 543$(M+Na)^+$

IR(KBr)$cm^{-1}$:3370, 2932, 2855, 1727, 1644, 1561, 1497

[α] $D^{25}$ (C=1.01, $CHCl_3$): −148°

Optical purity: 99.0%ee over (the ee value was determined by High Performance Liquid Chromatography)

Example 144

Preparation of 1-(1-tert-butylcarbonylmethyl-2-oxo-5-cyclohexyl-1,3,4,5-tetrahydro-2H-1,5-benzodiazepin-3-yl)-3-phenylurea Step 1

Phenyl isocyanate (110 mg) was added to a solution of 1-tert-butylcarbonylmethyl-2-oxo-3-amino-5-cyclohexyl-1,3,4,5-tetrahydro-2H-1,5 -benzodiazepine (300 mg) in anhydrous tetrahydrofuran (10 ml), the mixture was stirred for 10 minutes at room temperature. The reaction mixture was concentrated under reduced pressure, etanol was added to the residue for crystallization, collected by filtration, to thereby obtain 336 mg of the title compound (Yield 83.9%).

Melting point: 247–251° C.

$^1$H-NMR(DMSO-$d_6$) δ: 1.18(9H, s), 1.10–1.82(9H, m), 1.93–2.05(1H, m), 3.15–3.47(3H, m), 4.31–4.45(1H, m), 4. 39(1H, d), 5.13(1H, d), 6.57(1H, d), 6.84–6.92(1H, m), 6.98–7.03(1H, m), 7.09(1H, ddd), 7.17–7.35(6H, m), 8.81 (1H, s)

MS(FAB)m/z: 477($MH^+$), 133(base)

IR(KBr)$cm^{-1}$:3378, 2936, 1717, 1684, 1657, 1597, 1547, 1499, 1219, 752, 691

Example 145

Preparation of 1-(1-tert-butylcarbonylmethyl-2-oxo-5-cyclohexyl-1,3,4,5-tetrahydro-2H-1,5-benzodiazepin-3-yl)-3-(1-naphthyl)urea Example 144 was repeated except that 1-naphthyl isocyanate was used instead of phenyl isocyanate, to thereby obtain the title compound.

Melting point: 200–203° C.

$^1$H-NMR(DMSO-$d_6$) δ: 1.19(9H, s), 1.10–1.83(9H, m), 1.93–2.07(1H, m), 3.15–3.54(3H, m), 4.40(1H, d), 4.39–4.51 (1H, m), 5. 16(1H, d), 6.99–7.14(2H, m), 7.17–7.32(3H, m), 7.38(11H, t), 7.58(3H, m), 7.84–7.97(2H, m), 8.08–8.17(1H, m), 8.87(1H, s)

MS(FAB)m/z: 527($MH^+$), 133(base)

IR(KBr)$cm^{-1}$:3389, 3343, 2936, 1717, 1667, 1545, 1499, 1215, 1080, 764

Example 146

Preparation of 1-(1-tert-butylcarbonylmethyl-2-oxo-5-cyclohexyl-1,3,4,5-tetrahydro-2H-1,5-benzodiazepin-3-yl)-3-(3-chlorophenyl)urea Example 144 was repeated except that m-chlorophenyl isocyanate was used instead of phenyl isocyanate, to thereby obtain the title compound.

Melting point: 245–248° (decomposition)

$^1$H-NMR(DMSO-$d_6$) δ: 1.18(9H, s), 1.12–1.82(9H, m), 1.93–2.05(1H, m), 3.15–3.50(3H, m), 4.30–4.45(1H, m), 4.39(1H, d), 5.12(1H, d), 6.65(1H, d), 6.90–7.04(2H, m), 7.06–7.14(2H, m), 7.18–7.32(3H, m), 7.58(1H, t), 9.47(1H, s)

MS(FAB)m/z: 511(MH$^+$), 133(base)

IR(KBr)cm$^{-1}$:3368, 2936, 1721, 1686, 1657, 1595, 1545, 1233, 860, 681

Example 147

Preparation of 1-(1-tert-butylcarbonylmethyl-2-oxo-5-cyclohexyl-1,3,4,5-tetrahydro-2H-1,5-benzodiazepin-3-yl)-3-(4-chlorophenyl)urea Example 144 was repeated except that p-chlorophenyl isocyanate was used instead of phenyl isocyanate, to thereby obtain the title compound.

Melting point: 258–260° C. (decomposition)

$^1$H-NMR(DMSO-$d_6$) δ: 1.18(9H, s), 1.10–1.82(9H, m), 1.92–2.05(1H, m), 3.15–3.46(3H, m), 4.30–4.44(1H, m), 4.39(1H, d), 5.12(1H, d), 6.60(1H, d), 6.98–7.03(1H, m), 7.09(1H, ddd), 7.20–7.38(6H, m), 8.96(1H, s)

MS(FAB)m/z: 511(MH$^+$), 133(base)

IR(KBr)cm$^{-1}$:3355, 2932, 1719, 1688, 1655, 1597, 1536, 1495, 1233, 830, 766

Example 148

Preparation of 1-(1-tert-butylcarbonylmethyl-2-oxo-5-cyclohexyl-1,3,4,5-tetrahydro-2H-1,5-benzodiazepin-3-yl)-3-(4-fluorophenyl)urea Example 144 was repeated except that p-fluorophenyl isocyanate was used instead of phenyl isocyanate, to thereby obtain the title compound.

Melting point: 236–238° C. (decomposition)

$^1$H-NMR(DMSO-$d_6$) δ: 1.18(9H, s), 1.12–1.82(9H, m), 1.93–2.05(1H, m), 3.15–3.46(3H, m), 4.30–4.45 (2H, m), 5.13(1H, d), 6.54(1H, d), 6.98–7.13(4H, m), 7.20–7.37(4H, m), 8.86(1H, s)

MS(FAB)m/z: 495(MH$^+$), 133(base)

IR(KBr)cm$^{-1}$:3368, 2936, 1719, 1686, 1655, 1549, 1507, 1217, 833

Example 149

Preparation of 1-(1-tert-butylcarbonylmethyl-2-oxo-5-cyclohexyl-1,3,4,5-tetrahydro-2H-1,5-benzodiazepin-3-yl)-3-(4-bromophenyl)urea Example 144 was repeated except that p-bromophenyl isocyanate was used instead of phenyl isocyanate,to thereby obtain the title compound.

Melting point: 264–266° C. (decomposition)

$^1$H-NMR(DMSO-d6) δ: 1.18(9H, s), 1.10–1.82(9H, m), 1.92–2.05(1H, m), 3.14–3.47(3H, m), 4.30–4.45(2H, m), 5.12(1H, d), 6.60(1H, d), 6.97–7.03(1H, m), 7.09(1H, ddd), 7.20–7.41(6H, m), 8.96(1H, s)

MS(FAB)m/z: 555(MH$^+$), 133(base)

IR(KBr)cm$^{-1}$:3366, 2932, 1719, 1686, 1655, 1534, 1491, 1247, 1076, 826

Example 150

Preparation of 1-(1-tert-butylcarbonylmethyl-2-oxo-5-cyclohexyl-1,3,4,5 -tetrahydro-2H-1,5-benzodiazepin-3-yl)-3-(3-trifluoromethylphenyl)urea Example 144 was repeated except that 3-trifluoromethylphenyl isocyanate was used instead of phenyl isocyanate, to thereby obtain the title compound.

Melting point: 245–247° C. (decomposition)

$^1$H-NMR(DMSO-$d_6$) δ: 1.18(9H, s), 1.10–1.82(9H, m), 1.93–2.06(1H, m), 3.15–3.48(3H, m), 4.31–4.47(2H, m), 5.13(1H, d), 6.70(1H, d), 6.98–7.04(1H, m), 7.10(1H, ddd), 7.20–7.32(3H, m), 7.35–7.49(2H, m), 7.92(1H, s), 9.21(1H, s)

MS(FAB)m/z: 545(MH$^+$), 133(base)

IR(KBr)cm$^{-1}$:3341, 2934, 1719, 1684, 1655, 1549, 1337, 1127, 695

Example 151

Preparation of 1-(1-tert-butylcarbonylmethyl-2-oxo-5-cyclohexyl-1,3,4,5-tetrahydro-2H-1,5-benzodiazepin-3-yl)-3-(3-methoxyphenyl)urea Step 3 of Example 131 was repeated except that 1-tert-butylcarbonylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, and that m-anisidine was used instead of ethyl 3-aminobenzoate, to thereby obtain the title compound. Melting point: 234–235° C.

$^1$H-NMR(DMSO-$d_6$) δ: 1.18(9H, s), 1.10–1.82(9H, m), 1.93–2.05(1H, m), 3.15–3.46(3H, m), 3.67(3H, s), 4.30–4.44(2H, m), 5.12(1H, d), 6.47(1H, dd), 6.55(1H, d), 6.72–6.79(1H, m), 6.97–7.14(4H, m), 7.21–7.32(2H, m), 8.82(1H, s)

MS(FAB)m/z: 507(MH$^+$), 154(base)

IR(KBr)cm$^{-1}$:3360, 2936, 1717, 1682, 1655, 1595, 1541, 1157, 864, 758

Example 152

Preparation of 1-(1-tert-butylcarbonylmethyl-2-oxo-5-cyclohexyl-1,3,4,5-tetrahydro-2H-1,5-benzodiazepin-3-yl)-3-(3-nitrophenyl)urea Step 3 of Example 131 was repeated except that 1-tert-butylcarbonylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine,and that m-nitroaniline was used instead of ethyl 3-aminobenzoate, to thereby obtain the title compound.

Melting point: 248–250° C. (decomposition)

$^1$H-NMR(DMSO-$d_6$) δ: 1.18(9H, s), 1.08–1.82(9H, m), 1.94–2.06(1H, m), 3.13–3.37(2H, m), 3.40–3.50(1H, m), 4.31–4.46(2H, m), 5.13(1H, d), 6.74(1H, d), 6.98–7.06(1H, m), 7.11(1H, ddd), 7.21–7.32(2H, m), 7.45–7.57(2H, m), 7.75(1H, dt), 8.44(1H, t), 9.36(1H, s)

MS(FAB)m/z: 522(MH$^+$), 133(base)

IR(KBr)cm$^{-1}$:3347, 1713, 1688, 1655, 1347, 1082

Example 153

Preparation of 1-(1-tert-butylcarbonylmethyl-2-oxo-5-cyclohexyl-1,3,4,5-tetrahydro-2H-1,5-benzodiazepin-3-yl)-3-[3-(tetrazol-5-yl)phenyl]urea Step 3 of Example 131 was repeated except that 1-tert-butylcarbonylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine,and that 5-(3-aminophenyl) tetrazole was used instead of ethyl 3-aminobenzoate, to thereby obtain the title compound.

Melting point: 224–226° C. (forming)

$^1$H-NMR(DMSO-d6) δ: 1.18(9H, s), 1.10–1.82(9H, m), 1.93–2.06(1H, m), 3.15–3.53(3H, m), 4.34–4.47(2H, m), 5.13(1H, d), 6.68(1H, d), 6.98–7.05(1H, m), 7.10(1H, ddd), 7.21–7.32(2H, m), 7.38–7.49(3H, m), 7.51–7.58(1H, m), 8.13(1H, s), 9.10(1H, s)

MS(FAB)m/z: 545(MH$^+$), 154(base)

IR(KBr)cm$^{-1}$:3332, 2932, 1716, 1644, 1539, 1252, 1080, 739

Example 154

Preparation of 1-(1-tert-butylcarbonylmethyl-2-oxo-5-cyclohexyl-1,3,4,5-tetrahydro-2H-1,5-benzodiazepin-3-yl)-3-(3-pyridyl)urea Step 3 of Example 131 was repeated except that 1-tert-butylcarbonylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, and that 3-aminopyridine was used instead of ethyl 3-aminobenzoate, to thereby obtain the title compound.

Melting point: 239–241° C. (decomposition)

$^1$H-NMR(DMSO-$d_6$) δ: 1.18(9H, s), 1.93–2.04(9H, m), 3.15–3.48(3H, m), 4.31–4.45(2H, m), 5.12(1H, d), 6.70(1H, d), 6.97–7.03(1H, m), 7.10(1H, ddd), 7.20–7.31(3H, m), 7.79(1H, dq), 8.11(1H, dd), 8.46(1H, d), 9.01(1H, s)

MS(FAB)m/z: 478(MH$^+$), 121(base)

IR(KBr)cm$^{-1}$:3337, 2934, 1717, 1686, 1597, 1221, 758, 708

Example 155

Preparation of 3-[3-(1-tert-butylcarbonylmethyl-2-oxo-5-cyclohexyl-1,3,4,5-tetrahydro-2H-1,5-benzodiazepin-3-yl) ureido]phenylacetic acid Step 1

Preparation of 1-(1-tert-butylcarbonylmethyl-2-oxo-5-cyclohexyl-1,3,4,5-tetrahydro-2H-1,5-benzodiazepin-3-yl)-3-(3-tert-butoxycarbonylphenylmethyl)urea Step 3 of Example 131 was repeated except that 1-tert-butylcarbonylmethyl-2-oxo-3-amino-5-cyclohexyl-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, and that tert-butyl 3-aminophenylacetate was used instead of ethyl 3-aminobenzoate, to thereby obtain the title compound.

$^1$H-NMR(DMSO-d6) δ: 1.18(9H, s), 1.38(9H, s), 1.08–1.82(9H, m), 1.92–2.05(1H, m), 3.15–3.48(5H, m), 4.31–4.45(2H, m), 5.12(1H, d), 6.56(1H, d), 6.76(1H, d), 6.98–7.30(7H, m), 8.80(1H, s)

Step 2

Preparation of 3-[3-(1-tert-butylcarbonylmethyl-2-oxo-5-cyclohexyl-1,3,4,5-tetrahydro-2H-1,5-benzodiazepin-3-yl) ureido]phenylacetic acid Step 4 of Example 133 was repeated except that 1-(1-tert-butylcarbonylmethyl-2-oxo-5-cyclohexyl-1,3,4,5-tetrahydro-2H-1,5-benzodiazepin-3-yl)-3-(3-tert-butoxycarbonylmethylphenyl)urea was used instead of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound.

Melting point: 184–190° C. (decomposition)

$^1$H-NMR(DMSO-$d_6$) δ: 1.18(9H, s), 1.12–1.82(9H, m), 1.93–2.05(1H, m), 3.13–3.46(5H, m), 4.30–4.45(2H, m), 5.11(1H, d), 6.55(1H, d), 6.78(1H, d), 6.98–7.30(7H, m), 8.80(1H, s), 12.2(1H, br)

MS(FAB)m/z: 535(MH$^+$), 133(base)

IR(KBr)cm$^{-1}$:3357, 2934, 1719, 1655, 1497, 1238, 760

Example 156

Preparation of 3-[3-[(3R)-1-tert-butylcarbonylmethyl-2-oxo-5-[(1S)-2-pinen-10-yl]-1,3,4,5-tetrahydro-2H-1,5-benzodiazepin-3-yl]ureido]benzoic acid Step 1

Preparation of (3R)-2-oxo-3-tert-butoxycarbonylamino-5-[(1S)-2-pinen-10-yl]-1,3,4,5-tetrahydro-2H-1,5-benzodiazepine Sodium bicarbonate (2.02 g) and (1s)-10-chloro-2-pinene (4.1 g) were added to a solution of (R)-2-oxo-3-tert-butoxycarbonylamino-1,3,4,5-tetrahydro-2H-1,5-benzodiazepine (2.22 g) in anhydrous methanol (40 ml), and the mixture was refluxed overnight. The reaction mixture was concentrated under reduced pressure, water (200 ml) was added, and extracted with ethyl acetate (200 ml) twice. The organic layer was washed with saturated brine, dried over anhydrous sodium sulfate. The solvent was evaporated under reduced pressure, the residue was purified by silica gel column chromatography(n-hexane:ethyl acetate=4:1), to thereby obtain 2.03 g of the titled compound.

$^1$H-NMR($CDCl_3$) δ: 0.82(3H, s), 0.80–0.92(1H, m), 1.18 (3H, s), 1.41(9H, s), 2.00–2.06(2H, m), 2.15–2.25(3H, m), 3.68–3.78(1H, m), 4.38–4.50(1H, m), 5.37–5.42(1H, m), 5.52(1H, d), 6.92–7.05(3H, m), 7.08–7.18(1H, m), 7.87(1H, brs)

Step 2

Preparation of (3R)-2-oxo-3-amino-5-[(1S)-2-pinen-10-yl]-1,3,4,5-tetrahydro-2H-1,5-benzodiazepine Step 2 of Example 131 was repeated except that (3R)-2-oxo-3-tert-butylcarbonylamino-5-[(1S)-2-pinen-10-yl]-1,3,4,5-tetrahydro-2H-1,5-benzodiazepine was used instead of 1-(N-methyl-N-phenylcarbamoylmethyl)-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 0.82(1H, d), 0.82(3H, s), 1.18(3H, s), 1.69(2H, brs), 1.98–2.08(2H, m), 2.15–2.25(3H, m), 3.28 (1H, dd), 3.38(1H, dd), 3.45(1H, dd), 3.56(1H, dd), 3.73(1H, dd), 5.36–5.43(1H, m), 6.92–7.18(4H, m), 7.79(1H, s)

Step 3

Preparation of (3R)-1-[2-oxo-5-[(1S)-2-pinen-10-yl]-1,3,4,5-tetrahydro-2H-1,5-benzodiazepin-3-yl]-3-(3-tert-butoxycarbonylphenyl)urea Step 3 of Example 131 was repeated except that (3R)-2-oxo-3-amino-5-[(1S)-2-pinen-10-yl]-1,3,4,5-tetrahydro-2H-1,5-benzodiazepine was used instead of 1-(N-methyl-N-phenylcarbamoylmethyl)-2-oxo-3-amino-5-cyclohexyl-1,3,4,5-tetrahydro-2H-1,5-benzodiazepine, to thereby obtain the title compound.

$^1$H-NMR($CDCl_3$) δ: 0.81(3H, s), 0.80–0.92(1H, m), 1.18 (3H, s), 1.56(9H, s), 2.00–2.08(2H, m), 2.15–2.25(3H, m), 3.37–3.52 (2H, m), 3.66 (1H, dd), 3.71–3.82 (1H, m), 4.74(1H, ddd), 5.38–5.44(1H, m), 6.18(1H, d), 6.94–7.10 (3H, m), 7.13–7.22(1H, m), 7.28–7.34(1H, m), 7.59(1H, dt), 7.77–7.92(4H, m)

Step 4

Preparation of 1-[(3R)-1-tert-butylcarbonylmethyl-2-oxo-5-[(1S)-2-pinen-10-yl]-1,3,4,5-tetrahydro-2H-1,5-benzodiazepin-3-yl]-3-(3-tert-butoxycarbonylphenyl)urea Step 2 of Example 1 was repeated except that 1-[(3R)-2-oxo-5-[(1S)-2-pinen-10-yl]-1,3,4,5-tetrahydro-2H-1,5-benzodiazepin-3-yl]-3-(3-tert-butoxycarbonylphenyl)urea was used instead of 2-oxo-3-tert-butoxycarbonylamino-5-pivaloyl-1,3,4,5-tetrahydro-2H-1,5-benzodiazepine, that bromomethyl-tert-butylketone was used instead of 2-bromo- 2'-methylacetophenone, and that N,N-dimethyl acetamide was used instead of tetrahydrofuran as solvent, to thereby obtain the title compound.

$^1$H-NMR(CDCl$_3$) δ: 0.75(1H, d), 0.83(3H, s), 1.23(9H, s), 1.25(3H, s), 1.56(9H, s), 2.00–2.25(5H, m), 3.30–3.55(3H, m), 3.71–3.81(1H, m), 4.15(1H, d), 4.74(1H, dt), 5.17(1H, d), 5.37–5.42(1H, m), 6.27(1H, d), 6.90(1H, s), 6.97–7.10 (3H, m), 7.15–7.28(2H, m), 7.52(1H, dq), 7.58(1H, dt), 7.80(1H, t)

Step 5

Preparation of 3-[3-[(3R)-1-tert-butylcarbonylmethyl-2-oxo-5-[(1S)-2-pinen-10-yl]-1,3,4,5-tetrahydro-2H-1,5-benzodiazepin-3-yl]ureido]benzoic acid Step 4 of Example 133 was repeated except that 1-[(3R)-1-tert-butylcarbonylmethyl-2-oxo-5-[(1S)-2-pinen-10-yl]-1,3,4,5-tetrahydro-2H-1,5-benzodiazepin-3-yl]-3-(3-tert-butoxycarbonylphenyl)urea was used instead of 1-[1-(2,5-dimethylthiophen-3-yl)carbonylmethyl-2-oxo-5-cyclohexyl-1,3,4,5-tetrahydro-2H-1,5-benzodiazepin-3-yl]-3-(3-tert-butoxycarbonylphenyl)urea, to thereby obtain the title compound as amorphous.

$^1$H-NMR(CDCl$_3$) δ: 0.78–0.92(1H, m), 0.84(3H, s), 1.27 (3H, s), 1.29(9H, s), 2.02–2.27(5H, m), 3.34–3.48(2H, m), 3.63(1H, dd), 3.70–3.80(1H, m), 4.10(1H, d), 4.69(1H, ddd), 5.22(1H, d), 5.38–5.44(1H, m), 7.00–7.12(3H, m), 7.18–7.26(1H, m), 7.31–7.43(2H, m), 7.60(1H, d), 7.71(1H, s), 8.19(1H, s), 8.34–8.41(1H, m), 10.80–11.20(1H, br)

MS(FAB)m/z: 573(MH$^+$), 79(base)

IR(KBr)cm$^{-1}$:3376, 2969, 1725, 1647, 1555, 1219, 758

Example 157

Preparation of 3-[3-[(3R)-1-tert-butylcarbonylmethyl-2-oxo-5-[(1S, 2R, 5S)-pinan-10-yl]-1,3,4,5-tetrahydro-2H-1,5-benzodiazepin-3-yl]ureido]benzoic acid Platinum oxide (8 mg) was added to a solution of 3-[3-(3R)-1-tert-butylcarbonylmethyl-2-oxo-5-[(1S)-2-pinen-10-yl]-1,3,4,5-tetrahydro-2H-1,5-benzodiazepin-3-yl]ureido] benzoic acid (80 mg) in anhydrous tetrahydrofuran (2 ml) was added, and the mixture was stirred for one hour and 30 minutes under hydrogen atmosphere, under ambient pressure. The reaction mixture was filtrated through a pad of Celite, the filtrate was concentrated under reduced pressure, n-hexane and isopropyl ether were added to the residue for trituration, collected by filtration, to thereby obtain 55 mg of the titled compound as amorphous.

$^1$H-NMR(CDCl$_3$) δ: 0.87(1H, d), 0.97(3H, s), 1.20(3H, s), 1.30(9H, s), 1.45–1.72(3H, m), 1.80–1.98(4H, m), 2.26–2.40(2H, m), 2.92(1H, dd), 3.21(1H, dd), 3.41(1H, dd), 3.60–3.70(1H, m), 4.07(1H, d), 4.69(1H, ddd), 5.29(1H, d), 6.98–7.12(3H, m), 7.20–7.28(1H, m), 7.30–7.42(2H, m), 7.60(1H, d), 7.71(1H, s), 8.21(1H, s), 8.37(1H, dd), 10.60–11.20(1H, br)

IR(KBr)cm$^{-1}$:3372, 2936, 1725, 1647, 1593, 1554, 1219, 756

Example 158

Preparation of 3-[3-(1-cyclohexylcarbonylmethyl-2-oxo-5-cyclohexyl-1,3,4,5-tetrahydro-2H-1,5-benzodiazepin-3-yl)ureido]benzoic acid Step 1

Preparation of 1-cyclohexylcarbonylmethyl-2-oxo-3-tert-butoxycarbonylamino-5-cyclohexyl-1,3,4,5-tetrahydro-2H-1,5-benzodiazepine Bromomethylcyclohexylketone (861 mg), potassium iodide (23 mg), tetra n-butylammonium bromide (27 mg) and potassium carbonate (464 mg) were added to a solution of 2-oxo-3-tert-butoxycarbonylamino-5-cyclohexyl-1,3,4,5-tetrahydro-2H-1,5-benzodiazepine (1 g) in dimethylsulfoxide (10 ml), the mixture was stirred overnight at room temperature. Ice-water was added to the reaction mixture, extracted with ethyl acetate. The organic layer was washed with saturated brine, dried over anhydrous sodium sulfate. The solvent was evaporated under reduced pressure, and the residue was purified by silica gel column chromatography (ethyl acetate:n-hexane=1:5) and subsequently purified by silica gel column chromatography(silica gel NH-DM1020, produced by Fujisilicia Co. Ltd., ethyl acetate:n-hexane=1:5), to thereby obtain 500 mg of the title compound.

$^1$H-NMR(CDCl$_3$) δ: 1.12–2.08(29H, m), 2.44–2.56(1H, m), 3.13–3.25(1H, m), 3.27(1H, dd), 3.59(1H, dd), 4.14(1H, d), 4.37–4.48(1H, m), 4.90(1H, d), 5.54(1H, d), 6.96–7.03 (2H, m), 7.12–7.19(2H, m)

Step 2

Preparation of 1-cyclohexylcarbonylmethyl-2-oxo-3-amino-5-cyclohexyl-1,3,4,5-tetrahydro-2H-1,5-benzodiazepine 4N HCl-dioxane (10 ml) was added to a solution of 1-cyclohexylcarbonylmethyl-2-oxo-3-tert-butoxycarbonylamino-5-cyclohexyl-1,3,4,5-tetrahydro-2H-1,5-benzodiazepine (500 mg) in ethanol (10 ml), and the mixture was stirred at 50° C. for one hour. The reaction mixture was concentrated under reduced pressure, the residue was neutralized with saturated aqueous sodium bicarbonate, extracted with methylene chloride. The organic layer was dried over anhydrous sodium sulfate, the solvent was evaporated under reduced pressure, to thereby obtain 400 mg of the title compound.

$^1$H-NMR(CDCl$_3$) δ: 1.11–1.90(20H, m), 1.94–2.07(2H, m), 2.46–2.58(1H, m), 3.12–3.21(1H, m), 3.22(1H, dd), 3.39(1H, dd), 3.51–3.60(1H, m), 4.05(1H, d), 5.02(1H, d), 6.97–7.05 (2H, m), 7.15–7.27(2H, m)

Step 3

Preparation of 1-(1-cyclohexylcarbonylmethyl-2-oxo-5-cyclohexyl-1,3,4,5-tetrahydro-2H-1,5-benzodiazepin-3-yl)-3-(3-tert-butoxycarbonylphenyl)urea Triphosgene (122 mg) was added to a solution of tert-butyl 3-aminobenzoate (213 mg) in anhydrous tetrahydrofuran (30 ml) at 0° C., triethylamine (0.49 ml) was added thereto at 0° C. five times each 98 μl over 15 minutes. After the mixture was stirred at room temperature for 5 minutes, a solution of 1-cyclohexylcarbonylmethyl-2-oxo-3-amino-5-cyclohexyl-1,3,4,5-tetrahydro-2H-1,5-benzodiazepine (395 mg) in anhydrous tetrahydrofuran (10 ml) was added at 0° C., the resultant mixture was stirred at room temperature for one hour. The reaction mixture was concentrated under reduced pressure, and water was added to the residue, extracted with ethyl acetate. The organic layer was washed with saturated brine, and dried over anhydrous sodium sulfate. The solvent was evaporated under reduced pressure, diisopropyl ether was added to the residue for crystallization, collected by filtration, to thereby obtain 570 mg of the title compound (Yield: 92%).

$^1$H-NMR(CDCl$_3$) δ: 1.07–1.93(28H, m), 1.97–2.08(1H, m), 2.46(1H, tt), 3.14– 3.25(1H, tt), 3.38(1H, dd), 3.66(1H, dd), 4.29(1H, d), 4.72(1H, dt), 4.88(1H, d), 6.13(1H, d), 6.97–7.06(3H, m), 7.15–7.21(2H, m), 7.24–7.31(1H, m), 7.60(1H, d), 7.63(1H, d), 7.78(1H, t)

Step 4

Preparation of 3-[3-(1-cyclohexylcarbonylmethyl-2-oxo-5-cyclohexyl-1,3,4,5-tetrahydro-2H-1,5-benzodiazepin-3-yl)ureido]benzoic acid Trifluoroacetic acid (5 ml) was added to a solution of 1-(1-cyclohexylcarbonylmethyl-2-oxo-5-cyclohexyl-1,3,4, 5-tetrahydro-2H-1,5-benzodiazepin-3-yl)-3-(3-tert-butoxycarbonylphenyl)urea (560 mg) in methylene chloride (5 ml), the mixture was stirred at room temperature for one hour. The reaction mixture was concentrated under reduced pressure, etanol was added to the residue for crystallization, collected by filtration, to thereby obtain 330 mg of the title compound.

Melting point: 220–222° C. (decomposition)

$^1$H-NMR(DMSO-$d_6$) δ: 1.05–2.05(20H, m), 2.50–2.63 (1H, m), 3.16–3.50(3H, m), 4.31–4.44(2H, m), 4.89(1H, d), 6.60(1H, d), 7.02–7.15(2H, m), 7.21–7.36(3H, m), 7.46–7.52(2H, m), 7.98(1H, t), 9.01(1H, s), 12.80(1H, brs)

MS(FAB)m/z: 547($MH^+$), $569(M+Ha)^+$

IR(KBr)$cm^{-1}$:3351, 3291, 2932, 2857, 1727, 1689, 1651, 1553

Example 159

Preparation of 3-[3-(1-tert-butylcarbonylmethyl-2-oxo-5-cyclopentyl-1,3,4,5-tetrahydro-2H-1,5-benzodiazepin-3-yl) ureido]benzoic acid Step 1

Preparation of 2-oxo-3-tert-butoxycarbonylamino-5-(2-cyclopentyl-1-yl)-1,3,4,5-tetrahydro-2H-1,5-benzodiazepine Sodium bicarbonate (1.68 g) and 3-bromocyclopentene (2.94 g) were added to a solution of 2-oxo-3-tert-butoxycarbonylamino-1,3,4,5-tetrahydro-2H-1,5-benzodiazepine (2.77 g) in dimethylformamide (20 ml), the mixture was stirred at 50° C. for one hour. After the reaction mixture was allowed to cool, ice-water was added thereto, extracted with ethyl acetate,the organic layer was washed with saturated brine. The resultant mixture was dried over anhydrous sodium sulfate, the solvent was evaporated under reduced pressure, and the residue was purified by silica gel column chromatography(ethyl acetate:n-hexane=1:2), diisopropyl ether was added to the residue for crystallization, collected by filtration, to thereby obtain 1.9 g of the title compound as the mixture of diastereomer compounds.

$^1$H-NMR($CDCl_3$) δ: 1.40(9H, s), 2.10–2.26(2H, m), 2.38–2.53(2H, m), 3.15–3. 26 (1H, m), 3.49–3.61(1H, m), 4.39–4.60(2H, m), 5.48(1H, d), 5.62–5.66(1H, m), 5.93–5.98(1H, m), 6.91–7.01(2H, m), 7.10–7.20(2H, m), 7.47(1H, s)

Step 2

Preparation of 2-oxo-3-tert-butoxycarbonylamino-5-cyclopentyl-1,3,4,5-tetrahydro-2H-1,5-benzodiazepine Platinum oxide (100 mg) was added to a solution of 2-oxo-3-tert-butoxycarbonylamino-5-(2-cyclopenten-1-yl)-1,3,4,5-tetrahydro-2H-1,5-benzodiazepine (1.8 g) in anhydrous tetrahydrofuran (20 ml), the mixture was stirred at room temperature under ambient pressure under hydrogen atmosphere for 2 hours. The reaction mixture was filtrated through a pad of Celite, the filtrate was concentrated under reduced pressure, and the residue was purified by silica gel column chromatography(ethyl acetate:n-hexane=1:2). Diisopropyl ether was added to the residue for crystallization, to thereby obtain 1.2 g of the title compound.

$^1$H-NMR($CDCl_3$) δ: 1.40(9H, s), 1.49–2.04(8H, m), 3.33 (1H, dd), 3.51(1H, dd), 3.59–3.70(1H, m), 4.30–4.42(1H, m), 5.51(1H, d), 6.94–7.04(2H, m), 7.10–7.21(2H, m), 7.50 (1H, s)

Step 3

Preparation of 1-tert-butylcarbonylmethyl-2-oxo-3-tert-butoxycarbonylamino-5-cyclopentyl-1,3,4,5-tetrahydro-2H-1,5-benzodiazepine Bromomethyl tert-butylketone (684 mg), potassium iodide (26.4 mg), tetra n-butylammonium bromide (30.8 mg) and potassium carbonate (528 mg) were added successively to a solution of 2-oxo-3-tert-butoxycarbonylamino-5-cyclopentyl-1,3,4,5-tetrahydro-2H-1,5-benzodiazepine (1.1 g) in N,N-dimethylformamide (30 ml), the mixture was stirred at room temperature for 2 hours. Ice-water was added to the reaction mixture, extracted with ethyl acetate, the organic layer was washed with saturated brine. The resultant mixture was dried over anhydrous sodium sulfate, the solvent was evaporated under reduced pressure, and n-hexane was added to the residue for crystallization, collected by filtration, to thereby obtain 1.07 g of the title compound.

$^1$H-NMR($CDCl_3$) δ: 1.26(9H, s), 1.38(9H, s), 1.49–2.03 (8H, m), 3.26(1H, dd), 3.45(1H, dd), 3.59(1H, q), 4.25(1H, d), 4.31–4.42(1H, m), 5.22(1H, d), 5.57(1H, d), 6.94–7.05 (2H, m), 7.09–7.21(2H, m)

Step 4

Preparation of 1-tert-butylcarbonylmethyl-2-oxo-3-amino-5-cyclopentyl- 1,3,4,5-tetrahydro-2H-1,5-benzodiazepine Step 2 of Example 158 was repeated except that 1-tert-butylcarbonylmethyl-2-oxo-3-tert-butoxycarbonylamino-5-cyclopentyl-1,3,4,5-tetrahydro-2H-1,5-benzodiazepine was used instead of 1-cyclohexylcarbonylmethyl-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 1.28(9H, s), 1.50–2.04(10H, m), 3.16–3.27(2H, m), 3.47–3.64(2H, m), 4.02(1H, d), 5.33(1H, d), 6.93–7.06(2H, m), 7.11–7.22(2H, m)

Step 5

Preparation of 1-(1-tert-butylcarbonylmethyl-2-oxo-5-cyclopentyl-1,3,4,5-tetrahydro-2H-1,5-benzodiazepin-3-yl)-3-(3-tert-butoxycarbonylphenyl)urea Step 3 of Example 158 was repeated except that 1-tert-butylcarbonylmethyl-2-oxo-3-amino-5-cyclopentyl-1,3,4,5-tetrahydro-2H-1,5benzodiazepine was used instead of 1-cyclohexylcarbonylmethyl-2-oxo-3-amino-5-cyclohexyl-1,3,4,5-tetrahydro-2H-1,5-benzodiazepine, to thereby obtain the title compound.

$^1$H-NMR($CDCl_3$) δ: 1.22(9H, s), 1.46–2.03(17H, m), 3.37–3.52(2H, m), 3.53–3.66(1H, m), 4.32(1H, d), 4.65(1H, dt), 5.13(1H, d), 6.13(1H, d), 6.97–7.12(3H, m) 7.29(3H, m), 7.56–7.63(2H, m), 7.80(1H, t)

Step 6

Preparation of 3-[3-(1-tert-butylcarbonylmethyl-2-oxo-5-cyclopentyl-1,3,4,5-tetrahydro-2H-1,5-benzodiazepin-3-yl) ureido]benzoic acid Step 4 of Example 158 was repeated except that 1-(1-tert-butylcarbonylmethyl-2-oxo-5-cyclopentyl-1,3,4,5-tetrahydro-2H-1,5-benzodiazepin-3-yl)-3-(3-tert-butoxycarbonylphenyl)urea was used instead of 1-(1-cyclohexylcarbonylmethyl-2-oxo-5-cyclohexyl-1,3,4,5-tetrahydro-2H-1,5-benzodiazepin-3-yl)-3-(3-tert-butoxycarbonylphenyl)urea, to thereby obtain the title compound.

$^1$H-NMR(DMSO-$d_6$) δ: 1.18(9H, s), 1.45–2.05(8H, m), 3.17–3.39(2H, m), 3.58–3.71(1H, m), 4.26–4.37(1H, m), 4.41(1H, d), 5. 18(1H, d), 6.62(1H, d), 7.01(1H, d), 7.08–7.18(1H, m), 7.25–7.35(3H, m), 7.44–7.53(2H, m), 7.96–8.00(1H, m), 9.01(1H, s), 12.5(1H, brs)

MS(FAB)m/z: 507($MH^+$), $529(M+Na)^+$

IR(KBr)$cm^{-1}$:3367, 2870, 1719, 1690, 1655, 1557

Example 160

Preparation of 3-[3-(1-tert-butylcarbonylmethyl-2-oxo-5-cycloheptyl-1,3,4,5-tetrahydro-2H-1,5-benzodiazepin-3-yl) ureido]benzoic acid Step 1

Preparation of 2-oxo-3-tert-butoxycarbonylamino-5-(2-cyclohepten-1-yl)-1,3,4,5-tetrahydro-2H-1,5-benzodiazepine Sodium bicarbonate (1.6 g) and 3-bromocycloheptene (3.33 g) were added to a solution of 2-oxo-3-tert-butoxycarbonylamino-1,3,4,5-tetrahydro-2H-1,5-benzodiazepine (2.77 g) in N,N-dimethylformamide (20 ml), the mixture was stirred at 50° C. for one hour. After the reaction mixture was allowed to cool, ice-water was added thereto, extracted with ethyl acetate, the organic layer was washed with saturated brine. The resultant mixture was dried over anhydrous sodium sulfate, the solvent was evaporated under reduced pressure, and the residue was purified by silica gel column chromatography(ethyl acetate:n-hexane=1:2), diisopropyl ether was added to the residue for crystallization, and collected by filtration, to thereby obtain 2.1 g of the title compound as the mixture of diastereomer compounds.

$^1$H-NMR($CDCl_3$) δ: 1.22–2.30(17H, m), 3.24–3.44(1H, m), 3.78–3.89(1H, m), 3.90–4.05(1H, m), 4.40–4.57(1H, m), 5.48–5.57(1H, m), 5.75–6.17(2H, m), 6.89–6.99(2H, m), 7.06–7.17(2H, m), 7.48–7.55(1H, m)

Step 2

Preparation of 2-oxo-3-tert-butoxycarbonylamino-5-cycloheptyl-1,3,4,5-tetrahydro-2H-1,5-benzodiazepine Step 2 of Example 159 was repeated except that 2-oxo-3-tert-butoxycarbonylamino-5-(2-cyclohepten-1-yl)-1,3,4,5-tetrahydro-2H-1,5-benzodiazepine was used instead of 2-oxo-3-tert-butoxycarbonylamino-5-(2-cyclopenten-1-yl)-1,3,4,5-tetrahydro-2H-1,5-benzodiazepine, to thereby obtain the title compound.

$^1$H-NMR($CDCl_3$) δ: 1.20–2.10(21H, m), 3.27–3.40(2H, m), 3.74(1H, dd), 4.39–4.50(1H, m), 5.53(1H, d), 6.90–7.18 (4H, m), 7.64(1H, s)

Step 3

Preparation of 1-tert-butylcarbonylamino-2-oxo-3-tert-butoxycarbonylamino-5-cycloheptyl-1,3,4,5-tetrahydro-2H-1,5-benzodiazepine Step 3 of Example 159 was repeated except that 2-oxo-3-tert-butoxycarbonylamino- 5-cycloheptyl-1,3,4,5-tetrahydro-2H-1,5-benzodiazepine was used instead of 2-oxo-3-tert-butoxycarbonylamino-5-cyclopentyl-1,3,4,5-tetrahydro-2H-1,5-benzodiazepine, to thereby obtain the title compound.

$^1$H-NMR($CDCl_3$) δ: 1.20–2.08(30H, m), 3.24(1H, dd), 3.26–3.39(1H, m), 3.68(1H, dd), 4.12(1H, d), 4.40–4.52(1H, m), 5.14(1H, d), 5.56(1H, d), 6.92–7.00(2H, m), 7.02–7.08 (1H, m), 7.11–7.19(1H, m)

Step 4

Preparation of 1-tert-butylcarbonylmethyl-2-oxo-3-amino-5-cycloheptyl-1,3,4,5-tetrahydro-2H-1,5-benzodiazepine Step 2 of Example 158 was repeated except that 1-tert-butylcarbonylamino-2-oxo-3-tert-butoxycarbonylamino-5-cycloheptyl-1,3,4,5-tetrahydro-2H-1,5-benzodiazepine was used instead of 1-cyclohexylcarbonylmethyl-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 1.27(9H, s), 1.32–2.06(14H, m), 3.18(1H, dd), 3.27–3.38(1H, m), 3.50(1H, dd), 3.55–3.65 (1H, m), 4.01 (1H, d), 5.27(1H, d), 6.90–7.01(2H, m), 7.04–7.09(1H, m), 7.13–7.20(1H, m)

Step 5

Preparation of 1-(1-tert-butylcarbonylmethyl-2-oxo-5-cycloheptyl-1,3,4,5-tetrahydro-2H-1,5-benzodiazepin-3-yl)-3-(3-tert-butoxycarbonylphenyl)urea Step 3 of Example 158 was repeated except that 1-tert-butoxycarbonylmethyl-2-oxo-3-amino-5-cycloheptyl-1,3,4,5-tetrahydro-2H-1,5-benzodiazepine was used instead of 1-cyclohexylcarbonylmethyl-2-oxo-3-amino-5-cyclohexyl-1,3,4,5-tetrahydro-2H-1,5-benzodiazepine, to thereby obtain the title compound.

$^1$H-NMR($CDCl_3$) δ: 1.21(9H, s), 1.30–2.08(21H, m), 3.30–3.41(2H, m), 3.74(1H, dd), 4.28(1H, d), 4.68–4.79(1H, m), 5.09(11H, d), 6.15(11H, d), 6.95–7.03(3H, m), 7.05–7.12(1H, m), 7.15–7.29(2H, m), 7.55–7.63(2H, m), 7.80(1H, t)

Step 6

Preparation of 3-[3-(1-tert-butylcarbonylmethyl-2-oxo-5-cycloheptyl-1,3,4,5-tetrahydro-2H-1,5-benzodiazepin-3-yl) ureido]benzoic acid Step 4 of Example 158 was repeated except that 1-(1-tert-butylcarbonylmethyl-2-oxo-5-cycloheptyl-1,3,4,5-tetrahydro-2H-1,5-benzodiazepin-3-yl)-3-(3-tert-butoxycarbonylphenyl)urea was used instead of 1-(1 -cyclohexylcarbonylmethyl-2-oxo-5-cyclohexyl-1,3,4,5-tetrahydro-2H-1,5-benzodiazepin-3-yl)-3-(3-tert-butoxycarbonylphenyl)urea, to thereby obtain the title compound.

Melting point: 253–255° C. (decomposition)

$^1$H-NMR(DMSO-$d_6$) δ: 1.18(9H, s), 1.28–2.03(12H, m), 3.17–3.45(2H, m), 3.48–3.56(1H, m), 4.34–4.45(2H, m), 5.10(1H, d), 6.61(1H, d), 6.97–7.17(3H, m), 7.21–7.36(2H, m), 7.45–7.52(2H, m), 7.99(1H, t), 9.03(1H, s), 12.80(1H, brs)

MS(FAB)m/z: 535($MH^+$), 557$(M+Na)^+$

IR(KBr)$cm^{-1}$:3357, 2934, 2859, 1721, 1688, 1655, 1595, 1557

Example 161

Preparation of 3-[3-(1-tert-butylcarbonylmethyl-2-oxo-5-cyclooctyl-1,3,4,5-tetrahydro-2H-1,5-benzodiazepin-3-yl) ureido]benzoic acid Step 1

Preparation of 2-oxo-3-tert-butoxycarbonylamino-5-(2-cycloocten-1-yl)-1,3,4,5-tetrahydro-2H-1,5-benzodiazepine Sodium bicarbonate (606 mg) and 3-bromocyclooctene (1.36 g) were added to a solution of 2-oxo-3-tert-butoxycarbonylamino-1,3,4,5-tetrahydro-2H-1,5-benzodiazepine (1 g) in N,N-dimethylformamide (20 ml), the mixture was stirred overnight at 80° C. After the reaction mixture was allowed to cool, ice-water was added thereto, extracted with ethyl acetate, the organic layer was washed with saturated brine. The resultant mixture was dried over anhydrous sodium sulfate, the solvent was evaporated under reduced pressure, and diisopropyl ether was added to the residue for crystallization, and collected by filtration, to thereby obtain 615 mg of the title compound as the mixture of diastereomer compounds.

$^1$H-NMR($CDCl_3$) δ: 1.24–2.32(19H, m), 3.30–3.45(1H, m), 3.59–3.81(1H, m), 4.13–4.30(1H, m), 4.32–4.52(1H, m), 5.23–6.02(3H, m), 6.91–7.26(4H, m), 7.41(1H, brs)

Step 2

Preparation of 2-oxo-3-tert-butoxycarbonylamino-5-cyclooctyl-1,3,4,5-tetrahydro-2H-1,5-benzodiazepine Step 2 of Example 159 was repeated except that 2-oxo-3-tert-butoxycarbonylamino-5-(2-cycloocten-1-yl)-1,3,4,5-tetrahydro-2H-1,5-benzodiazepine was used instead of 2-oxo-3-tert-butoxycarbonylamino-5-(3-cyclopentenyl)-1,3,4,5-tetrahydro-2H-1,5-benzodiazepine, to thereby obtain the title compound.

$^1$H-NMR($CDCl_3$) δ: 1.26–2.03(23H, m), 3.29(1H, dd), 3.32–3.46(1H, m), 3.75(1H, dd), 4.38–4.49(1H, m), 5.51 (1H, d), 6.90–6.96(2H, m), 7.03–7.18(2H, m), 7.29(1H, s)

Step 3

Preparation of 1-tert-butylcarbonylmethyl-2-oxo-3-tert-butoxycarbonylamino-5-cyclooctyl-1,3,4,5-tetrahydro-2H-1,5-benzodiazepine Step 3 of Example 159 was repeated except that 2-oxo-3-tert-butoxycarbonylamino-5-cyclooctyl-1,3,4,5-tetrahydro-2H-1,5-benzodiazepine was used instead of 2-oxo-3-tert-butoxycarbonylamino-5-cyclopentyl-1,3,4,5-tetrahydro-2H-1,5-benzodiazepine, to thereby obtain the title compound.

$^1$H-NMR($CDCl_3$) δ: 1.26(9H, s), 1.31–2.03(23H, m), 3.21(1H, dd), 3.31–3.42(1H, m), 3.65–3.74(1H, m), 4.12 (1H, d), 4.38–4.50(1H, m), 5.14(1H, d), 5.56(1H, d), 6.92–7.19(4H, m)

Step 4

Preparation of 1-tert-butylcarbonylmethyl-2-oxo-3-amino-5-cyclooctyl-1,3,4,5-tetrahydro-2H-1,5-benzodiazepine Step 2 of Example 158 was repeated except that 1-tert-butylcarbonylmethyl-2-oxo-3-tert-butoxycarbonylamino-5-cyclooctyl-1,3,4,5-tetrahydro-2H-1,5-benzodiazepine was used instead of 1-cyclohexylcarbonylmethyl-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 1.21–2.00(25H, m), 3.15(1H, dd), 3.31–3.42(1H, m), 3.49–3.67(2H, m), 4.01(1H, d), 5.27(1H, d), 6.91–7.19(4H, m)

Step 5

Preparation of 1-(1-tert-butylcarbonylmethyl-2-oxo-5-cyclooctyl-1,3,4,5-tetrahydro-2H-1,5-benzodiazepin-3-yl)-3-(3-tert-butoxycarbonylphenyl)urea Step 3 of Example 158 was repeated except that 1-tert-butylcarbonylmethyl-2-oxo-3-amino-5-cyclooctyl-1,3,4,5-tetrahydro-2H-1,5-benzodiazepine was used instead of 1-cyclohexylcarbonylmethyl-2-oxo-3-amino-5-cyclohexyl-1,3,4,5-tetrahydro-2H-1,5-benzodiazepine, to thereby obtain the title compound.

$^1$H-NMR($CDCl_3$) δ: 1.22(9H, s), 1.25–2.03(23H, m), 3.13(1H, dd), 3.33–3.45(1H, m), 3.76(1H, dd), 4.26(1H, d), 4.65–4.76(1H, m), 5.10(1H, d), 6.07(1H, d), 6.88(1H, s), 6.94–7.02(2H, m), 7.07– 7.13(1H, m), 7.15–7.22(1H, m), 7.24–7.32(1H, m), 7.56–7.65(2H, m), 7.78(1H, s)

Step 6

Preparation of 3-[3-(1-tert-butylcarbonylmethyl-2-oxo-5-cyclooctyl-1,3,4,5-tetrahydro-2H-1,5-benzodiazepin-3-yl) ureido]benzoic acid Step 4 of Example 158 was repeated except that 1-(1-tert-butylcarbonylmethyl-2-oxo-5-cyclooctyl-1,3,4,5-tetrahydro-2H-1,5-benzodiazepin-3-yl)-3-(3-tert-butoxycarbonylphenyl)urea was used instead of 1-(1-cyclohexylcarbonylmethyl-2-oxo-5-cyclohexyl-1,3,4,5-tetrahydro-2H-1,5-benzodiazepin-3-yl)-3-(3-tert-butoxycarbonylphenyl)urea, to thereby obtain the title compound.

Melting point: 215–217° C. (decomposition)

$^1$H-NMR(DMSO-$d_6$) δ: 1.18(9H, s), 1.30–1.98(14H, m), 3.14–3.40(2H, m), 3.49–3.59(1H, m), 4.32–4.46(2H, m), 5.10(1H, d), 6.60(1H, d), 6.97–7.19(3H, m), 7.20–7.37(2H, m), 7.43–7. 54(2H, m), 7.99(1H, s), 9.04(1H, s), 12.80(1H, brs)

MS(FAB)m/z: 549($MH^+$)

IR(KBr)$cm^{-1}$:3357, 2926, 1719, 1690, 1655, 1595, 1557

Example 162

Preparation of 5-[3-(1-tert-butylcarbonylmethyl-2-oxo-5-cyclohexyl-1,3,4,5-tetrahydro-2H-1,5-benzodiazepin-3-yl) ureido]isophthalic acid Step 1

Preparation of 1-(1-tert-butylcarbonylmethyl-2-oxo-5-cyclohexyl-1,3,4,5-tetrabydro-2H-1,5-benzodiazepin-3-yl)-3-[3,5-bis(metboxycarbonyl)phenyl]urea Under ice-cooling, triphosgene (147 mg) was added to a solution of dimethyl 5-aminoisophthalate (276 mg) in anhydrous tetrahydrofuran (30 ml), triethylamine (0.59 ml) was added thereto five times over 15 minutes after divided into five portions. After the mixture was stirred at room temperature for 5 minutes, a solution of 1-tert-butylcarbonylmethyl-2-oxo-3-amino-5-cyclohexyl-1,3,4,5-tetrahydro-2H-1,5-benzodiazepine (450 mg) in anhydrous tetrahydrofuran (10 ml) was added under ice-cooling. The resultant mixture was stirred at room temperature for one hour, the reaction mixture was concentrated under reduced pressure. Water was added to the residue, crystals so precipitated were collected by filtration and dried, to thereby obtain 700 mg of the title compound (Yield: 94%).

$^1$H-NMR(DMSO-$d_6$) δ: 1.10–1.82(18H, m), 1.95–2.05 (1H, m), 3.16–3.35(2H, m), 3.41–3.48(1H, m), 3.86(6H, s), 4.33–4.46(2H, m), 5.13(1H, d), 6.66(1H, d), 6.99– 7.04(1H, m), 7.07 –7.14(1H, m), 7.23–7.32(2H, m), 8.02(1H, t), 8.20(2H, d), 9.36(1H, s)

Step 2

Preparation of 5-[3-(1-tert-butylcarbonylmethyl-2-oxo-5-cyclohexyl-1,3,4,5-tetrahydro-2H-1,5-benzodiazepin-3-yl) ureido]isophthalic acid Aqueous lithium hydroxide monohydrate (420 mg) solution (20 ml) was added to a solution of 1-(1-tert-butylcarbonylmethyl-2-oxo-5-cyclohexyl-1,3,4,5-tetrahydro-2H-1,5-benzodiazepin-3-yl)-3-[3,5-bis (methoxycarbonyl)phenyl]urea (593 mg) in tetrahydrofuran (20 ml), the mixture was stirred at 50° C. for 2 hours. After allowed to cool, the reaction mixture was concentrated under reduced pressure, the residue was acidified with 1N hydrochloric acid, extracted with the mixed solvent of chloroform and methanol (5:1), and dried over anhydrous sodium sulfate. The solvent was evaporated under reduced pressure, Isopropyl alcohol was added to the residue, crystals so precipitated were collected by filtration, to thereby obtain 420 mg of the title compound (Yield: 74%).

$^1$H-NMR(DMSO-$d_6$) δ: 1.08–1.83(18H, m), 1.93–2.06 (1H, m), 3.35–3.47(1H, m), 3.73–3.83(1H, m), 4.31–4.46 (3H, m), 5.12(1H, d), 6.65(1H, d), 6.99–7.05(1H, m), 7.06–7.14(1H, m), 7.21–7.32(2H, m), 8.02(1H, t), 8.14(2H, d), 9.27(1H, s), 12.70(2H, brs)

MS(FAB)m/z: 565($MH^+$), 587($M+Na)^+$

IR(KBr)$cm^{-1}$:3347, 2936, 1717, 1692, 1649, 1609, 1561

Example 163

Preparation of 2-methyl-5-[3-(1-tert-butylcarbonylmethyl-2-oxo-5-cyclohexyl-1,3,4,5-tetrahydro-2H-1,5-benzodiazepin-3-yl)ureido]benzoic acid Step 1

Preparation of 1-(1-tert-butylcarbonylmethyl-2-oxo-5-cyclohexyl-1,3,4,5-tetrahydro-2H-1,5-benzodiazepin-3-yl)-3-(3-tert-butoxycarbonyl-4-methylphenyl)urea Under ice-cooling, triphosgene (205 mg) was added to a solution of tert-butyl 2-methyl-5-aminobenzoate (383 mg) in anhydrous tetrahydrofuran (40 ml), triethylamine (825 μl) was added thereto five times over 15 minutes after divided into five portions. After the mixture was stirred at room temperature for 5 minutes, a solution of 1-tert-butylcarbonylmethyl-2-oxo-3-amino-5-cyclohexyl-1,3,4,5-tetrahydro-2H-1,5-benzodiazepine (600 mg) in anhydrous tetrahydrofuran (10 ml) was added under ice-cooling. The resultant mixture was stirred at room temperature for one hour, the reaction mixture was poured into ice-water, extracted with ethyl acetate, and the organic layer was washed with saturated brine. After dried over anhydrous sodium sulfate, the solvent was evaporated under reduced pressure, diisopropyl ether was added to the residue for crystallization, and collected by filtration, to thereby obtain 960 mg of the title compound (Yield: 97%).

$^1$H-NMR(DMSO-$d_6$) δ: 1.10–2.04(28H, m), 2.36(3H, s), 3.15–3.31(2H, m), 3.42(1H, dd), 4.31–4.44(2H, m), 5.12 (1H, d), 6.54(1H, d), 6.98–7.03(1H, m), 7.05–7.14(2H, m), 7.21–7.30(2H, m), 7.36(1H, dd), 7.70(1H, d), 8.90(1H, s)

Step 2

Preparation of 2-methyl-5-[3-(1-tert-butylcarbonylmethyl-2-oxo-5-cyclohexyl-1,3,4,5-tetrahydro-2H-1,5-benzodiazepin-3-yl)ureido]benzoic acid Step 4 of Example 158 was repeated except that 1-(1-tert-butylcarbonylmethyl-2-oxo-5-cyclohexyl-1,3,4,5-tetrahydro-2H-1,5-benzodiazepin-3-yl)-3-(3-tert-butoxycarbonyl-4-methylphenyl)urea was used instead of 1-(1-cyclohexylcarbonylmethyl-2-oxo-5-cyclohexyl-1,3,4,5-tetrahydro-2H-1,5-benzodiazepin-3-yl)-3-(3-tert-butoxycarbonylphenyl)urea, to thereby obtain the title compound.

Melting point: 222–224° C. (decomposition)

$^1$H-NMR(DMSO-$d_6$) δ: 1.09–1.82(18H, m), 1.94–2.05 (1H, m), 2.40(3H, s), 3.15–3.29(2H, m), 3.37–3.48(1H, m), 4.31–4.45(2H, m), 5.12(1H, d), 6.54(1H, d), 6.98–7.15(3H, m), 7.21–7.37(3H, m), 7.84(1H, d), 8.89(1H, s), 12.71(1H, brs)

MS(FAB) 535(M+H), 557(M+Na)

IR(KBr)cm$^1$:3360, 2932, 1719, 1694, 1661, 1541, 1499

Example 164

Preparation of 3-[3-(1-tert-butoxycarbonylmethyl-2-oxo-5-cyclohexyl-1,3,4,5-tetrahydro-2H-1,5-benzodiazepin-3-yl)ureido]benzoic acid Step 1

Preparation of 1-(2-oxo-5-cyclohexyl-1,3,4,5-tetrahydro-2H-1,5-benzodiazepin-3-yl)-3-(3-benzyloxycarbonylphenyl)urea Diphenylphosphoryl azide (938 mg) and triethylamine (354 mg) were added to a solution of monobenzyl isophthalate (874 mg) in anhydrous tetrahydrofuran (30 ml), the mixture was stirred at 100° C. for one hour and 30 minutes. The resultant mixture was allowed to cool, 1-tert-butylcarbonylmethyl-2-oxo-3-amino-5-cyclohexyl-1,3,4,5-tetrahydro-2H-1,5-benzodiazepine (680 mg) was added thereto, the mixture was stirred at room temperature for one hour. The reaction mixture was concentrated under reduced pressure, the residue was purified by silica gel column chromatography (ethyl acetate:n-hexane=1:3), to thereby obtain 890 mg of the title compound.

$^1$H-NMR($CDCl_3$) δ: 1.04–2.03(10H, m), 3.14–3.25(1H, m)), 3.38(1H, dd), 3.80(1H, dd), 4.75(1H, dt), 5.31(2H, s), 6.33(1H, d), 6.93–7.00(2H, m), 7.13–7.21(2H, m), 7.28–7.41(6H, m), 7.63–7.67(1H, m), 7.87–7.92(2H, m), 8.00–8.04(2H, m)

Step 2

Preparation of 1-(1-tert-butoxycarbonylmethyl-2-oxo-5-cyclohexyl-1,3,4,5-tetrahydro-2H-1,5-benzodiazepin-3-yl)-3-(3-benzyloxycarbonylphenyl)urea Tert-butyl bromoacetate (503 mg), potassium iodide (23 ml), tetra n-butylammonium bromide (23 mg) and potassium carbonate (713 mg) were added to a solution of 1-(2-oxo-5-cyclohexyl-1,3,4,5-tetrahydro-2H-1,5-benzodiazepin-3-yl)-3-(3-benzyloxycarbonylphenyl)urea (800 mg) in dimethylsulfoxide (10 ml), the mixture was stirred at room temperature for one hour. Ice-water was added thereto, extracted with ethyl acetate. The organic layer was washed with saturated brine, dried over anhydrous sodium sulfate. The solvent was evaporated under reduced pressure, the residue was purified by silica gel column chromatography (ethyl acetate:n-hexane=1:2), to thereby obtain 970 mg of the titled compound (Yield: 90%).

$^1$H-NMR($CDCl_3$) δ: 1.05–2.04(19H, m), 3.11–3.23(1H, m), 3.38(1H, dd), 3.61(1H, dd), 3.92(1H, d), 4.63(1H, d), 4.69–4.79(1H, m), 5.31(2H, s), 6.42(1H, d), 7.02–7.42(11H, m), 7.63–7.69(2H, m), 7.90–7.94(1H, m)

Step 3

Preparation of 3-[3-(1-tert-butoxycarbonylmethyl-2-oxo-5-cyclohexyl-1,3,4,5-tetrahydro-2H-1,5-benzodiazepin-3-yl)ureido]benzoic acid 5% Palladium carbon (300 mg) was added to a solution of 1-(1-tert-butoxycarbonylmethyl-2-oxo-5-cyclohexyl-1,3,4,5-tetrahydro-2H-1,5-benzodiazepin-3-yl)-3-(3-benzyloxycarbonylphenyl)urea (960 mg) in ethanol (50 ml), the mixture was stirred at room temperature for 3 hours under hydrogen atmosphere. The reaction mixture was filtrated through a pad of Celite, and the filtrate was concentrated under reduced pressure. Isopropyl alcohol was added to the residue for crystallization, collected by filtrated, to thereby obtain 450 mg of the titled compound.

Melting point: 187–189° C. (decomposition)

$^1$H-NMR(DMSO-$d_6$) δ: 1.10–2.05(19H, m), 3.16–4.47 (3H, m), 4.17(1H, d), 4.31–4.43(1H, m), 4.51(1H, d), 6.63 (1H, d), 7.10–7.37(5H, m), 7.45–7.53(2H, m), 7.99(1H, t), 9.04(1H, s), 12.82(1H, brs)

MS(FAB)m/z: 537(MH'), 559(M+Na)$^+$

IR(KBr)cm$^{-1}$:3360, 1738, 1692, 1649, 1545

Example 165

Preparation of (R)-(−)-3-[3-[1-(2-thenoyl)methyl-2-oxo-5-cyclohexyl-1,3,4,5-tetrahydro-2H-1,5-benzodiazepin-3-yl]ureido]benzoic acid Step 1

Preparation of (R)-(+)-1-[1-(2-thenoyl)methyl-2-oxo-5-cyclohexyl-1,3,4,5-tetrahydro-2H-1,5-benzodiazepin-3-yl]-3-(3-tert-butoxycarbonylphenyl)urea Step 7 of Example 143 was repeated except that 2-bromoacetylthiophene was used instead of bromomethyl tert-butylketone, and that N,N-dimethylacetamide was used as a solvent, to thereby obtain the title compound.

$^1$H-NMR(DMSO-$d_6$) δ: 1.10–1.82(9H, m), 1.52(9H, s), 1.95–2.07(1H, m), 3.15–3.35(2H, m), 3.43(1H, dd), 4.43 (1H, ddd), 4.94(1H, d), 5.48(1H, d), 6.60(1H, d), 7.07–7.37 (6H, m), 7.44(1H, dt), 7.54(1H, dq), 7.90(1H, t), 8.08(1H, dd), 8.14(1H, dd), 9.04(1H, s)

[α] D (C=1.067, $CHCl_3$): +15.1°

Step 2

Preparation of (R)-(−)-3-[3-[1-(2-thenoyl)methyl-2-oxo-5-cyclohexyl-1,3,4,5-tetrahydro-2H-1,5-benzodiazepin-3-yl]ureido]benzoic acid Step 4 of Example 133 was repeated except that (R)-(+)-1-[1-(2-thenoyl)methyl-2-oxo-5-cyclohexyl-1,3,4,5-tetrahydro-2H-1,5-benzodiazepin-3-yl]-3-(3-tert-butoxycarbonylphenyl)urea was used instead of 1-[1-(2,5-dimethylthiophen-3-yl)carbonylmethyl-2-oxo-5-cyclohexyl-1,,3,4,5-tetrahydro-2H-1,5-benzodiazepin-3-yl]-3-(3-tert-butoxycarbonylphenyl)urea, to thereby obtain the title compound.

Optical purity: 99.0% ee (the ee value was determined by High Performance Liquid Chromatography)

MS(FAB)m/z: 547(MH$^+$), 136(base)

[α] D (C=1.01, $CHCl_3$): −14.1°

Example 166

Preparation of (R)-(−)-2-methyl-5-[3-(1-tert-butylcarbonylmethyl-2-oxo-5-cyclohexyl-1,3,4,5-tetrahydro-2H-1,5-benzodiazepin-3-yl)ureido]benzoic acid Step 1

Preparation of (R)-(−)-1-(2-oxo-5-cyclohexyl-1,3,4,5-tetrahydro-2H-1,5-benzodiazepin-3-yl)-3-(3-tert-butoxycarbonyl-4-methylphenyl)urea Under ice-cooling, triphosgene (456 mg) was added to a solution of tert-butyl 2-methyl-5-aminobenzoate (850 mg) in anhydrous tetrahydrofuran (50 ml), triethylamine (1.85 ml) was added thereto five times each 0.37 ml over a 15 minutes after divided into five portions. After the mixture was stirred at room temperature for 5 minutes, (R)-(−)-2-oxo-3-amino-5-cyclohexyl-1,3,4,5-tetrahydro-2H-1,5-benzodiazepine (1.04 g) was added under ice-cooling. The resultant mixture was stirred at room temperature for one hour, the reaction mixture was poured into ice-water, and extracted with ethyl acetate. The organic layer was washed with saturated brine, dried over anhydrous sodium sulfate. The solvent was evaporated under reduced pressure, crystals so precipitated were washed with diisopropyl ether, to thereby obtain 1.94 g of the title compound (Yield: 98%).

$^1$H-NMR(DMSO-$d_6$) δ: 1.10–2.03(19H, m), 2.37(3H, s), 3.16–3.35(2H, m), 3.51(1H, dd), 4.25–4.36(1H, m), 6.53 (1H, d), 6.96–7.02(2H, m), 7.09–7.21(3H, m), 7.38(1H, dd), 7.72(1H, d), 8.93(1H, s), 9.83(1H, s)

[α] $D^{28}$ (C=1.15, DMSO): −133°

Step 2

Preparation of (R)-(−)-1-(1-tert-butylcarbonylmethy-2-oxo-5-cyclohexyl-1,3,4,5-tetrahydro-2H-1,5-benzodiazepin-3-yl)-3-(3-tert-butoxycarbonyl-4-methylphenyl)urea Step 7 of Example 143 was repeated except that (R)-(−)-1-(2-oxo-5-cyclohexyl-1,3,4,5-tetrahydro-2H-1,5-benzodiazepin-3-yl)-3-(3-tert-butoxycarbonyl-4-methylphenyl)urea was used instead of (R)-(−)-1-(2-oxo-5-cyclohexyl-1,3,4,5-tetrahydro-2H-1,5-benzodiazepin-3-yl)-3-(3-tert-butoxycarbonylphenyl)urea, to thereby obtain the title compound.

[α] $D^{27}$ (C=1.08, $CHCl_3$): −64.1°

Step 3

Preparation of (R)-(−)-2-methyl-5-[3-(1-tert-butylcarbonylmethy-2-oxo-5-cyclohexyl-1,3,4,5-tetrahydro-2H-1,5-benzodiazepin-3-yl)ureido]benzoic acid Trifluoroacetic acid (10 ml) was added to (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonyl-4-methylphenyl)urea (1.9g) in methylene chloride (10 ml), the mixture was stirred at room temperature for one hour. The reaction mixture was concentrated under reduced pressure, the mixed solvent (100 ml) of diisopropyl ether and ethanol (40:1) was added to the residue for crystallization, collected by filtrated, to thereby obtain 1.47 g of the title compound (Yield: 86%).

MS(FAB)m/z: 535($MH^+$), 557$(M+Na)^+$

IR(KBr)$cm^{-1}$:3346, 2928, 2853, 1728, 1711, 1690, 1644, 1553, 1499

[α] $D^{23}$ (C=0.61, $CHCl_3$): −177°

Optical purity: 99.5% ee over (the ee value was determined by High Performance Liquid Chromatography)

Example 167

Preparation of (R)-(−)-3-[3-(1-tert-butylcarbonylmethyl-2-oxo-5-cyclopentyl-1,3,4,5-tetrahydro-2H-1,5-benzodiazepin-3-yl)ureido]benzoic acid Step 1

Preparation of (3R)-2-oxo-3-tert-butoxycarbonylamino-5-(2-cyclopenten-1-yl)-1,3,4,5-tetrahydro-2H-1,5-benzodiazepine In a similar manner to Step 1 of Example 159, by use of (R)-2-oxo-3-tert-butoxycarbonylamino-1,3,4,5-tetrahydro-2H-1,5-benzodiazepine, to thereby obtain the title compound.

Step 2

Preparation of (R)-(−)-2-oxo-3-tert-butoxycarbonylamino-5-cyclopentyl-1,3,4,5-tetrahydro-2H-1,5-benzodiazepine Step 2 of Example 159 was repeated except that (3R)-2-oxo-3-tert-butoxycarbonylamino-5-(2-cyclopenten-1-yl)-1,3,4,5-tetrahydro-2H-1,5-benzodiazepine was used instead of 2-oxo-3-tert-butoxycarbonylamino-5-(2-cyclopenten-1-yl)-1,3,4,5-tetrahydro-2H-1,5-benzodiazepine, to thereby obtain the title compound.

[α] $D^{25}$ (C=1.06, $CHCl_3$): −104°

Step 3

Preparation of (R)-(−)-2-oxo-3-amino-5-cyclopentyl-1,3,4,5-tetrahydro-2H-1,5-benzodiazepine Step 5 of Example 143 was repeated except that (R)-(−)-2-oxo-3-tert-butoxycarbonylamino-5-cyclopentyl-1,3,4,5-tetrahydro-2H-1,5-benzodiazepine was used instead of (R)-(−)-2-oxo-3-tert-butoxycarbonylamino-5-cyclohexyl-1,3,4,5-tetrahydro-2H-1,5-benzodiazepine, to thereby obtain the title compound.

$^1$H-NMR($CDCl_3$) δ: 1.19–1.34(1H, m), 1.50–2.05(9H, m), 3.22–3.39(2H, m), 3.45–3.53(1H, m), 3.59–3.71(1H, m), 6.92–7.04(2H, m), 7.10–7.21(2H, m), 7.29(1H, s)

[α] $D^{27}$ (C=1.09, $CHCl_3$): −59.3°

Step 4

Preparation of (R)-(−)-1-(2-oxo-5-cyclopentyl-1,3,4,5-tetrahydro-2H-1,5-benzodiazepin-3-yl)-3-(3-tert-butoxycarbonylphenyl)urea Step 6 of Example 143 was repeated except that (R)-(−)-2-oxo-3-amino-5-cyclopentyl-1,3,4,5-tetrahydro-2H-1,5-benzodiazepine was used instead of (R)-(−)-2-oxo-3-amino-5-cyclohexyl-1,3,4,5-tetrahydro-2H-1,5-benzodiazepine, to thereby obtain the title compound.

$^1$H-NMR(DMSO-$d_6$) δ: 1.07–1.20(1H, m), 1.35–2.05 (16H, m), 3.21–3.43(2H, m), 3.59–3.74(1H, m), 4.19–4.31 (1H, m), 6.59(1H, d), 6.97–7.08(2H, m), 7.13–7. 25(2H, m), 7.32(1H, t), 7.43(1H, d), 7.54(1H, d), 7.91(1H, s), 9.04(1H, s), 9.83(1H, s)

[α] $D^{26}$ (C=0.82, MeOH): −106°

Step 5

Preparation of (R)-(−)-1-(1-tert-butylcarbonylmethyl-2-oxo-5-cyclopentyl-1,3,4,5-tetrahydro-2H-1,5-benzodiazepin-3-yl)-3-(3-tert-butoxycarbonylphenyl)urea Step 7 of Example 143 was repeated except that (R)-(−)-1-(2-oxo-5-cyclopentyl-1,3,4,5-tetrahydro-2H-1,5-benzodiazepin-3-yl)-3-(3-tert-butoxycarbonylphenyl)urea was used instead of (R)-(−)-1-(2-oxo-5-cyclohexyl-1,3,4,5-tetrahydro-2H-1,5-benzodiazepin-3-yl)-3-(3-tert-butoxycarbonylphenyl)urea, to thereby obtain the title compound.

[α] $D^{25}$ (C=1.06, $CHCl_3$): −14.5°

Step 6

Preparation of (R)-(−)-3-[3-(1-tert-butylcarbonylmethyl-2-oxo-5-cyclopentyl-1,3,4,5-tetrahydro-2H-1,5-benzodiazepin-3-yl)ureido]benzoic acid Step 8 of Example 143 was repeated except that (R)-(−)-1-(1-tert-butylcarbonylmethyl-2-oxo-5-cyclopentyl-1,3,4,5-tetrahydro-2H-1,5-benzodiazepin-3-yl)-3-(3-tert-butoxycarbonylphenyl)urea was used instead of (R)-(−)-1-(1-tert-butylcarbonylmethyl-2-oxo-5-cyclopentyl-1,3,4,5-tetrahydro-2H-1,5-benzodiazepin-3-yl)-3-(3-tert-butoxycarbonylphenyl)urea, to thereby obtain the title compound.

MS(FAB)m/z: 507($MH^+$), 529$(M+Na)^+$

IR(KBr)$cm^{-1}$:3350, 2969, 2870, 1727, 1696, 1646, 1611, 1565, 1495

[α] $D^{26}$ (C=1.00, $CHCl_3$): −95.2°

Optical purity: 99% ee over (the ee value was determined by High Performance Liquid Chromatography)

Example 168

Preparation of (R)-(−)-1-(1-tert-butylcarbonylmethyl-2-oxo-5-cyclohexyl-1,3,4,5-tetrahydro-2H-1,5- benzodiazepin-3-yl)-3-(3-methylsulfonylamino-carbonylphenyl)urea

Step 1

Preparation of (R)-(−)-(1-tert-butylcarbonylmethyl-2-oxo-3-tert-butoxycarbonylamino-5-cyclohexyl-1,3,4,5-tetrahydro-2H-1,5-benzodiazepine Step 3 of Example 121 was repeated except that a optical active compound was used instead of the racemic mixture, to thereby obtain the title compound.

[ a] $D^{23}$ (C=1.05, $CHCl_3$): −73.9°

Step 2

Preparation of (R)-(−)-(1-tert-butylcarbonylmethyl-2-oxo-3-amino-5-cyclohexyl-1,3,4,5-tetrahydro-2H-1,5-benzodiazepine hydrochloride (R)-(−)-(1-tert-butylcarbonylmethyl-2-oxo-3-tert-butoxycarbonylamino-5-cyclohexyl-1,3,4,5-tetrahydro-2H-1,5-benzodiazepine (2 g) was suspended in ethanol (15 ml), 4N HCl-dioxane (10 ml) was added to the suspension, and the mixture was stirred at 50° C. for one hour. After allowed to cool, crystals so precipitated were collected by filtration, the crystals were washed with dioxane. The crystals were dried, to thereby obtain 1.6 g of the title compound (Yield: 93%).

[α] $D^{23}$ (C=1.12, MeOH): −10.4°

Step 3

Preparation of (R)-(−)-1-(1-tert-butylcarbonylmethyl-2-oxo-5-cyclohexyl-1,3,4,5-tetrahydro-2H-1,5-benzodiazepin-3-yl)-3-(3-methylsulfonylamino-carbonylphenyl)urea Step 3 of Example 15 was repeated except that (R)-(−)-(1-tert-butylcarbonylmethyl-2-oxo-3-amino-5-cyclohexyl-1,3,4,5-tetrahydro-2H-1,5-benzodiazepine was used instead of 1-(N-phenyl-N-methyl)carbamoylmethyl-2-oxo-3-amino-5-phenyl-1,3,4,5-tetrahydro-2H-1,5-benzodiazepine, to thereby obtain the title compound.

$^1$H-NMR(DMSO-$d_6$) δ: 1.10–1.83(18H, m), 1.94–2.05 (1H, m), 2.85(3H, s), 3.17–3.47(3H, m), 4.32–4.46(2H, m), 5.12(1H, d), 6.52(1H, d), 6.99–7.30(5H, m), 7.44–7.54(2H, m), 7.75(1H, t), 8.84(1H, s), 12.60(1H, brs)

MS(FAB) m/z : 636 $(M+K)^+$ IR(KBr)$cm^{-1}$:2934, 1725, 1660, 1545

[α] $D^{25}$ (C=0.82, $CHCl_3$): −91.0°

Example 169

Preparation of (R)-(−)-3-[3-(1-tert-butylcarbonylmethyl-2-oxo-5-cyclohexyl-1,3,4,5-tetrahydro-2H-1,5-benzodiazepin-3-yl)ureido]phenylthioacetic acid Step 1

Preparation of (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylmethyl-thiophenyl)urea Under ice-cooling, triphosgene (184 mg) was added to a solution of 3-aminophenylthioacetic acid (395 mg) in anhydrous tetrahydrofuran (50 ml), triethylamine (0. 75 ml) was added thereto five times each 0.15 ml over a 15 minutes after divided into five portions. After the mixture was stirred at room temperature for 5 minutes, a solution of (R)-1-tert-butylcarbonylmathyl-2-oxo-3-amino-5-cyclohexyl-1,3,4,5-tetrahydro-2H-1,5-benzodiazepine (570 mg) in tetrahydrofuran (10 ml) was added under ice-cooling, and the resultant mixture was stirred at room temperature for one hour. Water was added to the reaction mixture, and the resultant mixture was extracted with ethyl acetate. The organic layer was washed with saturated brine, dried over anhydrous sodium sulfate, and purified by silica gel column chromatography (n-hexane:ethyl acetate=2:1), to thereby obtain 1 g of the title compound.

$^1$H-NMR($CDCl_3$) δ: 1.12–1.89(27H, m), 1.97–2.08(1H, m), 3.16–3.27 (1H, m), 3.37(1H, dd), 3.53 (2H, s), 3.63 ( (1H, dd), 4.23 (1H, d), 4.66–4.77 (1H, m), 5.14 (1H, d), 6.30(1H, d), 6.94–7.13 (6H, m), 7.17–7.21 (2H, m), 7.42 (1H, t)

[α] $D^{24}$ (C=1.04, $CHCl_3$): −56.0°

Step 2

Preparation of (R)-(−)-3-[3-(1-tert-butylcarbonylmethyl-2-oxo-5-cyclohexyl-1,3,4,5-tetrahydro-2H-1,5-benzodiazepin-3-yl)ureido]phenylthioacetic acid Step 8 of Example 143 was repeated except that (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylmethylthiophenyl)urea was used instead of (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylphenyl)urea, to thereby obtain the title compound as amorphous.

$^1$H-NMR(DMSO-$d_6$) δ: 1.10–1.82(18H, m), 1.92–2.02 (1H, m), 3.15–3.45(3H, m), 3.49(2H, s), 4.31–4.43(2H, m), 5.11(1H, d), 6.74–6.82(2H, m), 6.98–7.13(4H, m), 7.20–7.34(3H, m), 9.05(1H, s), 12.50(1H, brs)

MS(FAB)m/z: 605$(M+K)^+$

IR(KBr)$cm^{-1}$:3370, 2932, 1725, 1655, 1593

[α] $D^{23}$ (C=1.00, $CHCl_3$): −29.7°

Example 170

Preparation of (R)-(−)-3-[3-(1-tert-butylcarbonylmethyl-2-oxo-5-cyclohexyl-1,3,4,5-tetrahydro-2H-1,5-benzodiazepin-3-yl-ureido]phenylacetic acid Step 1

Preparation of (R)-(−)-1-(2-oxo-5-cyclohexyl-1,3,4,5-tetrahydro-2H-1,5-benzodiazepin-3-yl)-3-(3-tert-butoxycarbonylmethylphenyl)urea Step 6 of Example 143 was repeated except that tert-butyl 3-aminophenylacetate was used instead of tert-butyl 3-aminobenzoate, to thereby obtain the title compound.

$^1$H-NMR($CDCl_3$) δ: 1.05–1.89(18H, m), 1.97–2.09(1H, m), 3.17–3.28(1H, m), 3.40(1H, dd), 3.47(2H, s), 3.85(1H, dd), 4.73(1H, dt), 6.33(1H, d), 6.82–7.06(3H, m), 7.13–7.28 (4H, m), 7.49–7.54(1H, m), 8.07(2H, s)

[α] $D^{21}$ (C=1.05, $CHCl_3$): −171°

Step 2

Preparation of (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylmethyl-phenyl)urea (R)-(−)-1-(2-oxo-5-cyclohexyl-1,3,4,5-tetrahydro-2H-1,5-benzodiazepin-3-yl)-3-(3-tert-butoxycarbonylmethyl-phenyl)urea (4.93 g) was added to a suspension of 60% sodium hydride (440 mg) in anhydrous N,N-dimethylformamide (50 ml) under ice-cooling, the mixture was stirred for one hour. Bromomethyl tert-butylketone (1.97 g) was added thereto, the resultant mixture was stirred at room temperature for one hour, the reaction mixture was poured into ice-water, extracted with ethyl acetate, and the organic layer was washed with saturated brine. After dried over anhydrous sodium sulfate, the mixture was purified by silica gel column chromatography (ethyl acetate:n-hexane= 1:3), to thereby obtain 5.07 g of the title compound (Yield: 86%).

$^1$H-NMR($CDCl_3$) δ: 1.06–1.89(27H, m), 1.97–2.09(1H, m), 3.15–3.27(1H, m), 3.34(1H, dd), 3.43(2H, s), 3.66(1H, dd), 4.23(1H, d), 4.70(1H, dt), 5.12(1H, d) 6.14(1H, d), 6.83(1H, s), 6.86–6.92(1H, m), 6.95–7.04(2H, m), 7.07–7.24(5H, m)

[α] $D^{24}$ (C=1.03, $CHCl_3$): −62.3°

Step 3

Preparation of (R)-(−)-3-[3-(1-tert-butylcarbonylmethyl-2-oxo-5-cyclohexyl-1,3,4,5-tetrahydro-2H-1,5-benzodiazepin-3-yl)ureido]phenylacetic acid Step 8 of Example 143 was repeated except that (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylmethylphenyl)urea was used instead of (R)-

(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylphenyl)urea, to thereby obtain the title compound.

$^1$H-NMR(DMSO-$d_6$) δ: 1.05–1.81(18H, m), 1.91–2.02 (1H, m), 3.13–3.42(5H, m), 4.31–4.43(2H, m), 5.11(1H, d), 6.69(1H, d), 6.78(1H, d), 6.98–7.28(7H, m), 8.92(1H, s), 12.50(1H, brs)

MS(FAB)m/z: 535($MH^+$), 557$(M+Na)^+$, 573$(M+K)^+$

IR(KBr)$cm^{-1}$:3370, 2932, 1725, 1655, 1559

[α] $D^{24}$ (C=1.05, MeOH): −64.6°

Example 171

Preparation of (R)-(−)-5-[3-(1-tert-butylcarbonylmethyl-2-oxo-5-cyclohexyl-1,3,4,5-tetrahydro-2H-1,5-benzodiazepin-3-yl)ureido]-2-methylbenzoic acid Step 1

Preparation of (3R)-(−)-2-oxo-3-amino-5-phenyl-1,3,4,5-tetrahydro-2H-1,5-benzodiazepine Nitrobenzene (22.16 g) and 10% palladium carbon (6 g) were added to a solution of (3R)-2-oxo-3-butoxycarbonylamino-5-(2-cyclohexen-1-yl)-1,3,4,5-tetrahydro-2H-1,5-benzodiazepine (12.87 g) in xylene (200 ml), the mixture was refluxed for one hour and 30 minutes. The reaction mixture was allowed to cool, filtered, and the filtrate was concentrated under reduced pressure. The residue was dissolved in ethanol (30 ml), 4N HCl-dioxane (20 ml) was added, the resultant mixture was stirred at 50° C. for one hour. After allowed to cool, crystals so precipitated were collected by filtration, the crystals were washed with 2-propanol, to thereby obtain hydrochloride of the title compound. The compound was dissolved under heating in the mixed solvent of methanol and water, allowed to cool, saturated sodium bicarbonate was added for neutralization, crystals so precipitated were collected be filtration, the crystals were washed with water and dried, to thereby obtain 5.55 g of the title compound (Yield: 86%).

$^1$H-NMR(DMSO-$d_6$) δ: 1.83(2H, brs), 3.41–3.53(2H, m), 3.89(1H, ABq), 6.62–6.68(2H, m), 6.74–6.81(1H, m), 7.08–7.25(6H, m), 9.87(1H, s)

[α] $D^{23}$ (C=1.00, DMSO): −66.0°

Step 2

Preparation of (R)-(−)-1-(2-oxo-5-phenyl-1,3,4,5-tetrahydro-2H-1,5-benzodiazepin-3-yl)-3-(3-tert-butoxycarbonyl-4-methylphenyl)urea Step 6 of Example 143 was repeated except that tert-butyl 5-amino-2-methylbenzoate was used instead of tert-butyl 3-aminobenzoate, to thereby obtain the title compound.

$^1$H-NMR(DMSO-$d_6$) δ: 1.52(9H, s), 2.37(3H, s), 3.64 (1H, dd), 4.08(1H, dd), 4.46–4.57(1H, m), 6.62(1H, d), 6.66–6.84(3H, m), 7.10–7.42(8H, m), 7.75(1H, d), 9.01(1H, s), 10.14(1H, s)

[α] $D^{22}$ (C=1.00, $CHCl_3$): −192°

Step 3

Preparation of (R)-(−)-1-(1-tert-butylcarbonylmethyl-2-oxo-5-phenyl-1,3,4,5-tetrahydro-2H-1,5-benzodiazepin-3-yl)-3-(3-tert-butoxycarbonyl-4-methylphenyl)urea Step 2 of Example 170 was repeated except that (R)-(−)-1-(2-oxo-5-phenyl-1,3,4,5-tetrahydro-2H-1,5-benzodiazepin-3-yl)-3-(3-tert-butoxycarbonyl-4-methylphenyl)urea was used instead of (R)-(−)-1-(2-oxo-5-cyclohexyl-1,3,4,5-tetrahydro-2H-1,5-benzodiazepin-3-yl)-3-(3-tert-butoxycarbonylmethylphenyl)urea, to thereby obtain the title compound.

$^1$H-NMR($CDCl_3$) δ: 1.23(9H, s), 1.57(9H, s), 2.47(3H, s), 3.65(1H, dd), 4.24(1H, dd), 4.42(1H, d), 4.84–4.95(1H, m), 5.13(1H, d), 6.14(1H, d), 6.76–6.89(4H, m), 7.05–7.25(7H, m), 7.37(1H, dd), 7.67(1H, d)

[α] $D^{23}$ (C=0.72, $CHCl_3$): −111°

Step 4

Preparation of (R)-(−)-5-[3-(1-tert-butylcarbonylmethyl-2-oxo-5-cyclohexyl-1,3,4,5-tetrahydro-2H-1,5-benzodiazepin-3-yl)ureido]-2-methylbenzoic acid Step 8 of Example 143 was repeated except that (R)-(−)-1-(1 -tert-butylcarbonylmethyl-2-oxo-5-phenyl-1,3,4,5-tetrahydro-2H-1,5-benzodiazepin-3-yl)-3-(3-tert-butoxycarbonyl-4-methylphenyl)urea was used instead of (R)-(−)-1-(1-tert-butylcarbonylmethyl-2-oxo-5-cyclohexyl-1,3,4,5-tetrahydro-2H-1,5-benzodiazepin-3-yl)-3-(3-tert-butoxycarbonylphenyl)urea, to thereby obtain the title compound.

$^1$H-NMR(DMSO-$d_6$) δ: 1.17(9H, s), 2.41(3H, s), 3.54–3.63(1H, m), 4.01(1H, dd), 4.52–4.63(1H, m), 4.74 (1H, d), 5.12(1H, d), 6.65(1H, d), 6.67–6.89(3H, m), 7.11–7.41(8H, m), 7.88(1H, d), 8.97(1H, s), 12.70(1H, brs)

MS(FAB)m/z: 529($MH^+$)

[a] $D^{22}$ (C=0.67, $CHCl_3$): −269°

The structure of these compounds obtained from Example 122–171 was shown in Table 18–24, except for the Examples for producing salt only.

TABLE 18

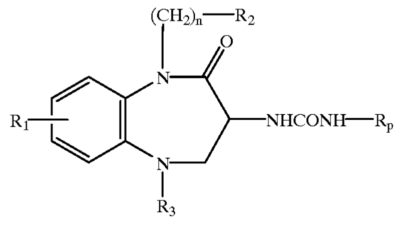

| Example | $R_1$ | $R_2$ | $R_3$ | $R_p$ | n |
|---|---|---|---|---|---|
| 122 | 8-$CH_3$ | 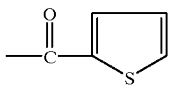 | 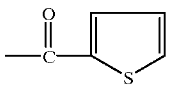 | 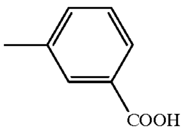 | 1 |

TABLE 18-continued
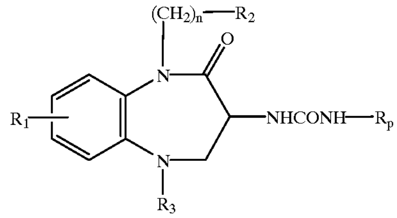
| Example | $R_1$ | $R_2$ | $R_3$ | $R_p$ | n |
|---|---|---|---|---|---|
| 123 | H | 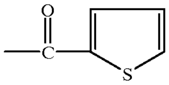 | 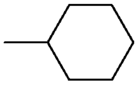 | 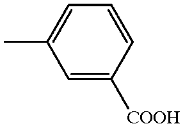 | 1 |
| 124 | H | 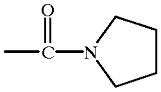 | 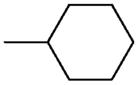 | 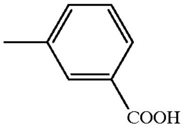 | 1 |
| 125 (*) | H | 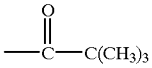 | 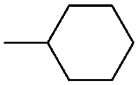 | 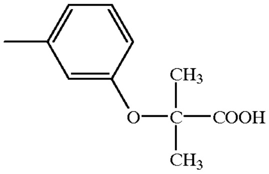 | 1 |
| 126 (*) | 8-$CH_3$ | 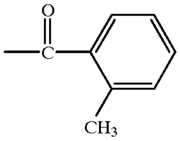 | 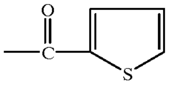 | 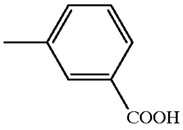 | 1 |
| 131 | H | 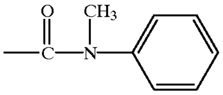 | 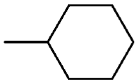 | 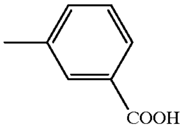 | 1 |
(*): optically active compound
TABLE 19
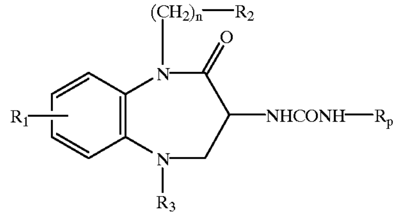
| Example | $R_1$ | $R_2$ | $R_3$ | $R_p$ | n |
|---|---|---|---|---|---|
| 132 | H | 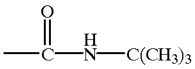 | 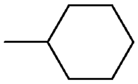 | 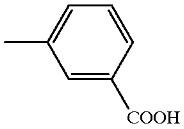 | 1 |

TABLE 19-continued
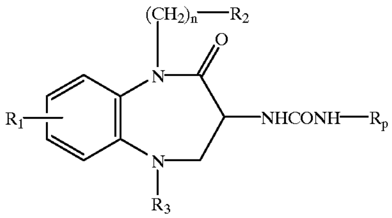
| Example | $R_1$ | $R_2$ | $R_3$ | $R_p$ | n |
|---|---|---|---|---|---|
| 133 | H | 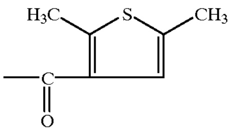 | 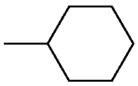 | 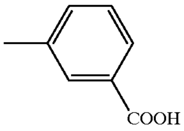 | 1 |
| 134 | H | 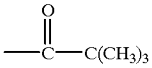 | 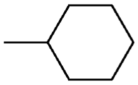 | 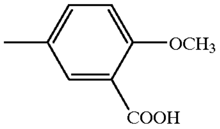 | 1 |
| 135 | 8-$CH_3$ | 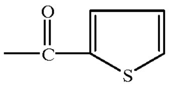 | 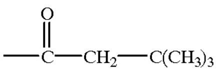 | 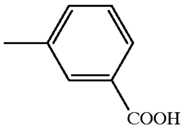 | 1 |
| 136 | 8-$CH_3$ | 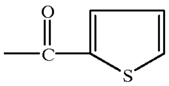 | 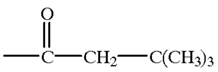 | 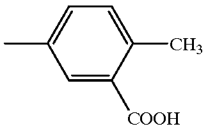 | 1 |
| 137 | 8-$CH_3$ | 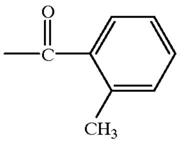 | 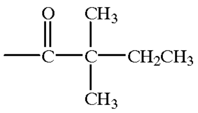 | 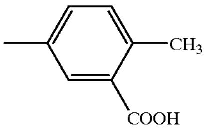 | 1 |
TABLE 20
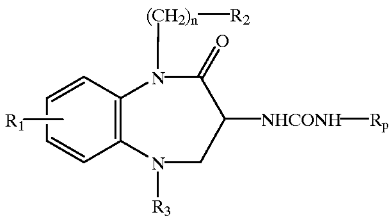
| Example | $R_1$ | $R_2$ | $R_3$ | $R_p$ | n |
|---|---|---|---|---|---|
| 138 | 8-$CH_3$ | 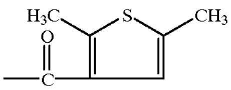 | 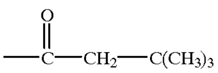 | 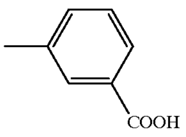 | 1 |

TABLE 20-continued
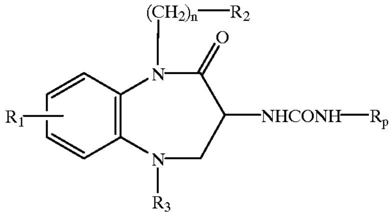
| Example | $R_1$ | $R_2$ | $R_3$ | $R_p$ | n |
|---|---|---|---|---|---|
| 139 | 8-$CH_3$ | 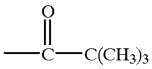 | 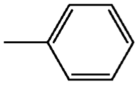 | 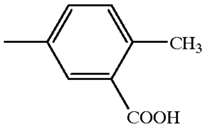 | 1 |
| 140 (*) | 8-$CH_3$ | 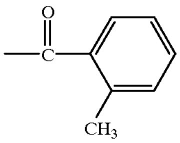 | 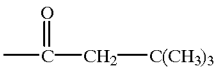 | 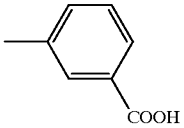 | 1 |
| 141 (*) | 8-$CH_3$ | 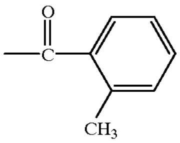 | 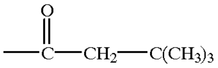 | 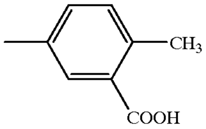 | 1 |
| 142 (*) | 8-$CH_3$ | 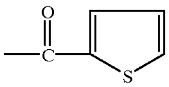 | 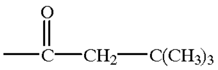 | 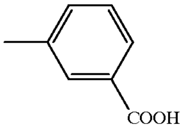 | 1 |
| 143 (*) | H | 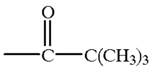 | 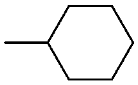 | 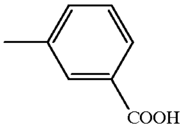 | 1 |
(*): optically active compound
TABLE 21
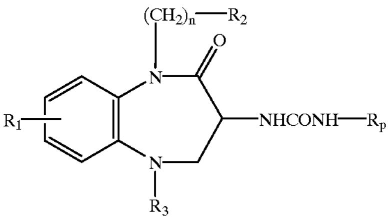
| Example | $R_1$ | $R_2$ | $R_3$ | $R_p$ | n |
|---|---|---|---|---|---|
| 144 | H | 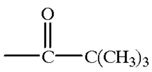 | 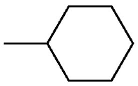 | 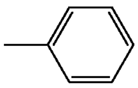 | 1 |

TABLE 21-continued
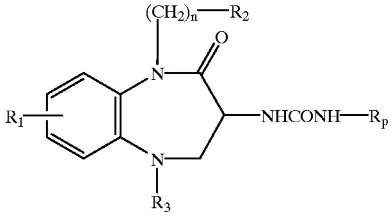
| Example | $R_1$ | $R_2$ | $R_3$ | $R_p$ | n |
|---|---|---|---|---|---|
| 145 | H | 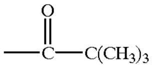 | 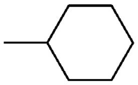 | 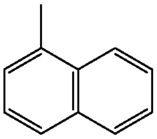 | 1 |
| 146 | H | 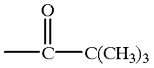 | 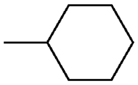 | 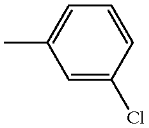 | 1 |
| 147 | H | 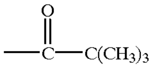 | 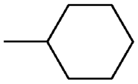 | 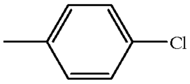 | 1 |
| 148 | H | 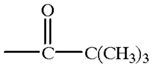 | 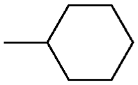 | 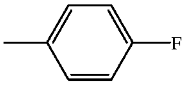 | 1 |
| 149 | H | 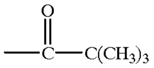 | 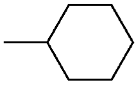 | 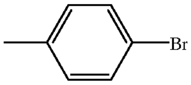 | 1 |
| 150 | H | 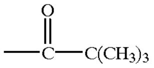 | 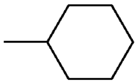 | 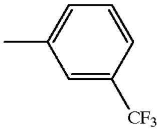 | 1 |
TABLE 22
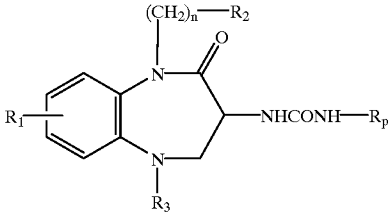
| Example | $R_1$ | $R_2$ | $R_3$ | $R_p$ | n |
|---|---|---|---|---|---|
| 151 | H | 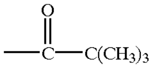 | 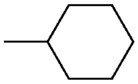 | 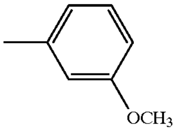 | 1 |

TABLE 22-continued
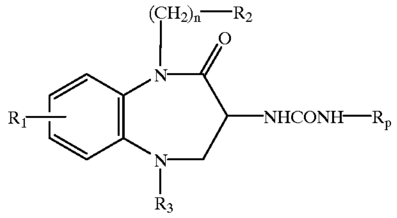
| Example | $R_1$ | $R_2$ | $R_3$ | $R_p$ | n |
|---|---|---|---|---|---|
| 152 | H | 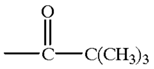 | 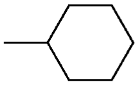 | 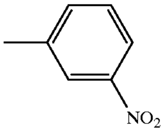 | 1 |
| 153 | H | 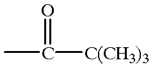 | 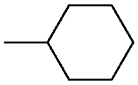 | 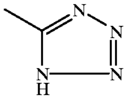 | 1 |
| 154 | H | 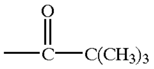 | 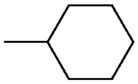 | 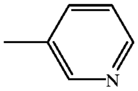 | 1 |
| 155 | H | 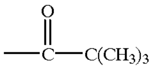 | 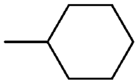 | 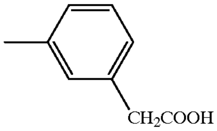 | 1 |
| 156 | H | 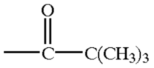 | 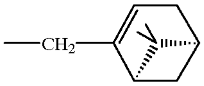 | 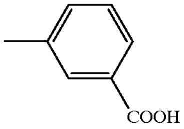 | 1 |
| 157 | H | 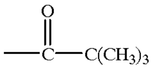 | 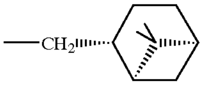 | 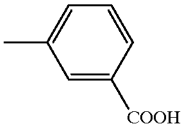 | 1 |

TABLE 23
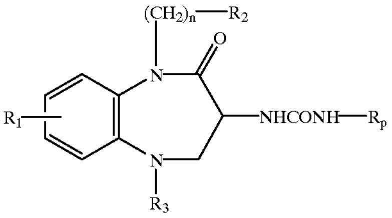
| Example | $R_1$ | $R_2$ | $R_3$ | $R_p$ | n |
|---|---|---|---|---|---|
| 158 | H | 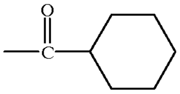 | 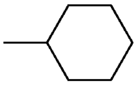 | 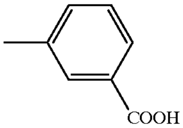 | 1 |
| 159 | H | 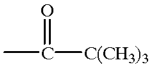 | 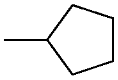 | 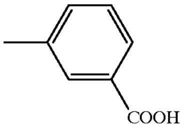 | 1 |
| 160 | H | 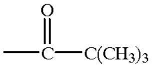 | 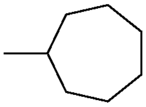 | 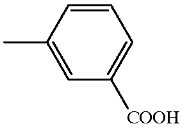 | 1 |
| 161 | H | 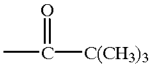 | 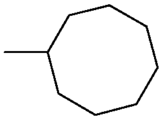 | 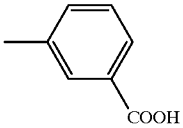 | 1 |
| 162 | H | 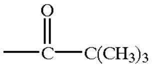 | 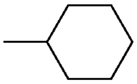 | 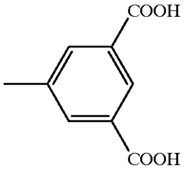 | 1 |
| 163 | H | 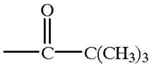 | 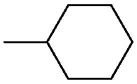 | 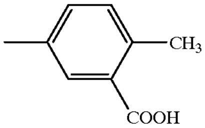 | 1 |
| 164 | H | 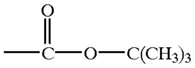 | 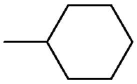 | 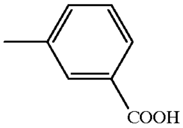 | 1 |

TABLE 24

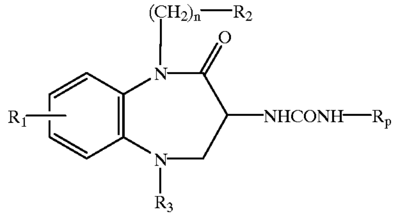

| Example | $R_1$ | $R_2$ | $R_3$ | $R_p$ | n |
|---|---|---|---|---|---|
| 165 (*) | H | 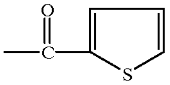 | 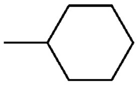 | 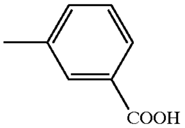 | 1 |
| 166 (*) | H | 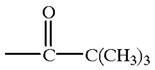 | 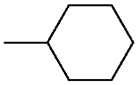 | 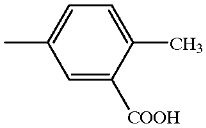 | 1 |
| 167 (*) | H | 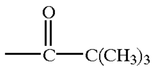 | 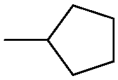 | 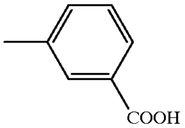 | 1 |
| 168 (*) | H | 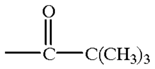 | 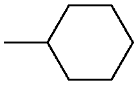 | 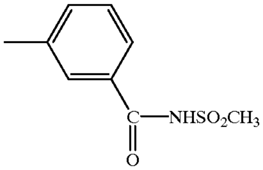 | 1 |
| 169 (*) | H | 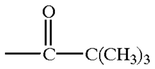 | 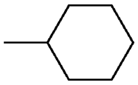 | 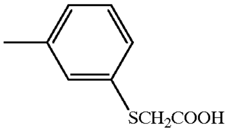 | 1 |
| 170 (*) | H | 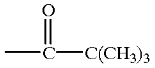 | 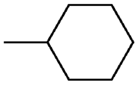 | 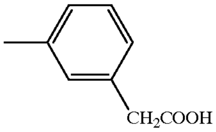 | 1 |
| 171 (*) | H | 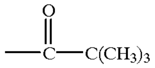 | 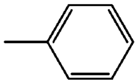 | 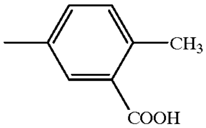 | 1 |

(*): optically active compound

Example 172

Preparation of (−)-3-[3-(1-tert-butylcarbonylmethyl-2-oxo-5-phenyl-1,3,4,5-tetrahydro-2H-1,5-benzodiazepin-3-yl)ureido]benzoic acid (R)-(+)-α-methylbenzylamine salt (R)-(+)-α-methylbenzylamine (242 mg) was added to a solution of (±)-3-[3-(1-tert-butylcarbonylmethyl-2-oxo-5-phenyl-1,3,4,5-tetrahydro-2H-1,5-benzodiazepin-3-yl)ureido]benzoic acid (1.03 g) in 2-propanol (20 ml), the mixture was stirred overnight. Crystals so precipitated were collected by filtration, the crystals were recrystallized from 2-propanol, to thereby obtain 220 mg of the title compound.

Optical purity: 99.7%ee over (After the compound was converted into free base, the ee value was determined by High Performance Liquid Chromatography)

Example 173

Preparation of (R)-(−)-3-[3-(1-tert-butylcarbonylmethyl-2-oxo-5-cyclohexyl-8-methyl-1,3,4,5-tetrahydro-2H-1,5-benzodiazepin-3-yl)ureido]benzoic acid Step 1

Preparation of (R)-2-oxo-3-amino-5-cyclohexyl-8-methyl-1,3,4,5-tetrahydro-2H-1,5-benzodiazepine (R)-2-oxo-3-(N-tert-butoxycarbonyl)amino-5-cyclohexyl-8-methyl-1,3,4,5-tetrahydro-2H-1,5-benzodiazepine (3.50 g) was dissolved in 4N HCl-dioxane (23.4 ml), stirred at 60° C. for one hour. After the reaction mixture was concentrated under reduced pressure, methylene chloride and saturated aqueous sodium bicarbonate were added to the residue, and extracted. The organic layer was successively washed with water and saturated brine, dried over anhydrous sodium sulfate. The solvent was evaporated under reduced pressure, to thereby obtain 2.20 g of the title compound as amorphous (Yield: 85.9%).

$^1$H-NMR(DMSO-$d_6$) δ: 1.12–1.94(10H, m), 2.24(1H, s), 3.19–3.77(4H, m), 6.83(1H, s), 6.96(1H, d), 7.12(1H, d), 10.12(1H, s)

Step 2

Preparation of (R)-1-(2-oxo-5-cyclohexyl-8-methyl-1,3,4,5-tetrahydro-2H-1,5-benzodiazepin-3-yl)-3-(4-tert-butoxycarbonylphenyl)urea Tert-butyl 3-aminobenzoate (1.63 g) was dissolved in tetrahydrofuran (30 ml), the solution was cooled to internal temperature 5–8° C. Triphosgene (0.91 g) was added to the solution, stirred for 5 minutes. Subsequently triethylamine (4.30 ml) was added thereto four times after divided into four portions. After the mixture was stirred at room temperature for 10 minutes, a solution of (R)-2-oxo-3-amino-5-cyclohexyl-8-methyl-1,3,4,5-tetrahydro-2H-1,5-benzodiazepine (2.10 g) in tetrahydrofuran (10 ml) was added, the resultant mixture was stirred for one hour. Water and ethyl acetate were added the reaction mixture, and extracted. The organic layer was successively washed with water and saturated brine, dried over anhydrous sodium sulfate. The solvent was evaporated under reduced pressure, to thereby obtain 3.28 g of the title compound as amorphous (Yield: 86.8%).

$^1$H-NMR(DMSO-$d_6$) δ: 1.18–1.99(19H, m), 2.24(3H, s), 3.20–3.49(3H, m), 4.26–4.31 (1H, m), 6.57(1H, d), 6.81(1H, s), 6.96(1H, d), 7.09(1H, d), 7.32(1H, t), 7.44(1H, d), 7.54(1H, d), 7.92(1H, s), 9.06(1H, s), 9.78(1H, s)

Step 3

Preparation of (R)-(−)-1-(1-tert-butylcarbonylmethyl-2-oxo-5-cyclohexyl-8-methyl-1,3,4,5-tetrahydro-2H-1,5-benzodiazepin-3-yl)-3-(4-tert-butoxycarbonylphenyl)urea (R)-1-(2-oxo-5-cyclohexyl-8-methyl-1,3,4,5-tetrahydro-2H-1,5-benzodiazepin-3-yl)-3-(4-tert-butoxycarbonylphenyl)urea (500 mg) was dissolved in N,N-dimethylformamide (5 ml), the solution was cooled to internal temperature 5° C. Under argon atmosphere, 60% sodium hydride (49 mg) was added, the mixture was stirred at internal temperature 5° C. for 30 minutes. Bromomethyl tert-butylketone (218 mg) was added thereto, stirred at internal temperature 5° C. for one hour. The reaction mixture was poured into ice-water, extracted with ethyl acetate. The organic layer was successively washed with water and saturated brine, dried over anhydrous magnesium sulfate. The solvent was evaporated under reduced pressure. The residue was purified by silica gel column chromatography (chloroform), to thereby obtain 200 mg of the title compound.

$^1$H-NMR(DMSO-$d_6$) δ: 0.83–1.99(28H, m), 2.27(3H, s), 3.16–3.31(3H, m), 4.34–4.40(2H, m), 5.10(1H, d), 6.58(1H, d), 6.83(1H, s), 7.06(1H, d), 7.17(1H, d), 7.32(1H, t), 7.43(1H, d), 7.53(1H, d), 7.90(1H, s), 9.03(1H, s)

[α] $D^{22}$ (C=1.3, $CHCl_3$): −27.0°

Step 4

Preparation of (R)-(−)-3-[3-(1-tert-butylcarbonylmethyl-2-oxo-5-cyclohexyl-8-methyl-1,3,4,5-tetrahydro-2H-1,5-benzodiazepin-3-yl)ureido]benzoic acid (R)-(−)-1-(1-tert-butylcarbonylmethyl-2-oxo-5-cyclohexyl-8-methyl- 1,3,4,5-tetrahydro-2H-1,5-benzodiazepin-3-yl)-3-(4-tert-butoxycarbonylphenyl)urea (100 mg) was dissolved in methylene chloride (1 ml), trifluoroacetic acid (1 ml) was added, the mixture was stirred at room temperature for 30 minutes. After the solvent was evaporated, isopropyl ether was added to the residue, powder so precipitated was collected by filtration, to thereby obtain 50 mg of the title compound.

[α] $D^{27}$ (C=0.26, $CHCl_3$): −64.0°

Test 1

Measurement of Binding Affinity for CCK-B Receptors

Cerebral cortices were removed from Hartley-strain guinea pigs, the cerebral cortices were homogenized in 50 volumes of 50 mM Tris-HCl buffer (pH7.4) and centrifuged at 50000×g for 10 minutes. The Tris-HCl buffer was added to the pellet and recentrifuged as above two times. The final pellet was rehomogenized in 10 mM HEPES buffer (pH 6.5, which hereinafter be abbreviated as "solvent") containing 5 mM $MgCl_2$, 1 mM EGTA, 0.25 mg/ml bacitracin and 130 mM NaCl, and used as the receptor preparation.

Binding assay was measured as follows. Fifty μl of [$^3$H]CCK-8 (at the final concentration of 1.0 nM) and 900 μl of the receptor preparation (800 μg protein/tube) were added to 50 μl of either solvent, CCK-8 (1 μM) or a test compound. These ware reacted at 25° C. for 2 hours. After the reaction, the mixture was filtrated through Whatman GF/B filter presoaked in 0.1% BSA. The filter was washed with 3 ml of ice-cold 50 mM Tris-HCl buffer (pH 7.4) four times, immediately after the filtration. The filter was soaked in the ACS-II scintillation cocktail for a day and radioactivity was measured using a liquid scintillation counter. Non-specific binding was defined as the radioactivity in the presence of 1 μM CCK-8. Specific binding was defined as the difference between total binding (used solvent without CCK-8) and non-specific binding. Inhibitor dissociation constant (Ki) of each test compound was determined from the inhibition of specific [$^3$H]CCK-8 binding.

Results are shown in Tables 25 and 26.

TABLE 25

Measurement of binding affinity for CCK-B receptors

| Test compound | Ki (nM) |
|---|---|
| Compound of Example 1 | 6.47 |
| Compound of Example 4 | 1.11 |
| Compound of Example 10 | 6.87 |
| Compound of Example 13 (racemate) | 3.16 |
| Compound of Example 13 (+form) | 1.16 |
| Compound of Example 15 | 0.99 |
| Compound of Example 16 | 2.14 |
| Compound of Example 33 | 0.14 |
| Compound of Example 35 | 0.61 |
| Compound of Example 46 | 0.70 |
| Compound of Example 49 | 5.02 |
| Compound of Example 56 | 1.42 |
| Compound of Example 61 | 0.98 |
| Compound of Example 62 | 0.79 |
| Compound of Example 70 (recemate) | 0.77 |
| Compound of Example 70 (−form) | 0.36 |
| Compound of Example 71 | 2.88 |

TABLE 25-continued

| Measurement of binding affinity for CCK-B receptors | |
|---|---|
| Test compound | Ki (nM) |
| Compound of Example 72 | 1.57 |
| Compound of Example 78 | 0.18 |
| Compound of Example 80 | 2.62 |
| Compound of Example 81 | 0.56 |
| Compound of Example 87 | 1.39 |
| Compound of Example 88 (−form) | 0.11 |

TABLE 26

| Measurement of binding affinity for CCK-B receptors | |
|---|---|
| Test compound | Ki (nM) |
| Compound of Example 93 | 1.29 |
| Compound of Example 94 | 1.62 |
| Compound of Example 95 | 2.26 |
| Compound of Example 97 | 1.59 |
| Compound of Example 101 | 1.13 |
| Compound of Example 104 | 0.59 |
| Compound of Example 105 | 1.33 |
| Compound of Example 109 | 1.81 |
| Compound of Example 114 | 9.43 |
| Compound of Example 120 | 0.75 |
| Compound of Example 121 | 1.20 |
| Compound of Example 125 | 0.43 |
| Compound of Example 143 | 0.63 |
| Compound of Example 151 | 2.86 |
| Compound of Example 157 | 1.97 |
| Compound of Example 168 | 0.21 |
| Compound of Example 169 | 0.1 |
| L-365, 260 | 24.6 |

Measurement of Inhibition of Pentagastrin-stimulated Acid Secretion

Male Sprague-Dawley (SD)-strain rats were used. Each rat was operated to ligate the pylorus, and equip with a duodenal catheter and gastric fistula under a ether anesthesia. After the operation, each rat was placed in a Bollman-type cage and continuously infused pentagastrin (15 μg/kg/hr) through the tail vein. Test compounds were suspended in 0.5% aqueous sodium carboxymethylcellulose (which hereinafter be abbreviated as "vehicle"). Vehicle or test compound was administered through the intraduodenal catheter 1 hour after the beginning of pentagastrin infusion. Acidity of the collected gastric juice was measured by an automatic titillation device. Acid output was determined by multiplying the volume by the acidity of gastric juice. Percent inhibition of acid output from 1 to 4 hours after administration of test compound was calculated by the following equation.

$$\%\,\text{inhibition} = \frac{\begin{array}{c}(\text{mean acid output of vehicle treated group} - \\ \text{mean acid output of test compound treated group})\end{array}}{\text{Mean acid output of vehicle treated group}} \times 100$$

Results are presented in Table 27.

TABLE 27

| Measurement of inhibition of pentagastrin-stimulated acid secretion | | |
|---|---|---|
| Test compound | Dose (mg/kg) | % Inhibition |
| Compound of Example 1 | 30 | 59.4 |
| Compound of Example 10 | 10 | 67.1 |
| Compound of Example 13 (racemate) | 3 | 80.9 |
| Compound of Example 13 (+form) | 1 | 81.5 |
| Compound of Example 33 | 3 | 77.2 |
| Compound of Example 56 | 10 | 69.8 |
| Compound of Example 70 (racemate) | 3 | 76.5 |
| Compound of Example 70 (−form) | 1 | 84.8 |
| Compound of Example 80 | 3 | 45.4 |
| Compound of Example 87 | 30 | 80.1 |
| Compound of Example 88 (−form) | 1 | 68.4 |
| Compound of Example 89 | 30 | 87.8 |
| Compound of Example 94 | 30 | 93.3 |
| Compound of Example 95 | 1 | 49.0 |
| Compound of Example 101 | 3 | 78.0 |
| Compound of Example 104 | 1 | 58.0 |
| Compound of Example 109 | 1 | 54.0 |
| Compound of Example 113 | 30 | 75.7 |
| Compound of Example 114 | 30 | 89.7 |
| Compound of Example 118 | 30 | 88.3 |
| Compound of Example 120 | 30 | 88.3 |
| Compound of Example 121 | 0.3 | 47.0 |
| Compound of Example 143 | 0.1 | 54.6 |
| Compound of Example 166 | 0.3 | 51.2 |
| Compound of Example 168 | 1 | 58.9 |
| Compound of Example 169 | 1 | 75.2 |
| L-365, 260 | 30 | 46.5 |

Test 3

Measurement of Binding Affinity for CCK-A Receptors

Pancreases were removed from Hartley-strain guinea pigs, the pancreases were homogenized in 40 volumes of 10 mM PIPES buffer (pH 6.5, which hereinafter be abbreviated as "solvent") containing 1 mM EGTA, 30 mM $MgCl_2$, 0.02% bacitracin, 0.02% soybean trypsin inhibitor and 0.3 M sucrose. The homogenate was filtrated through gauze and centrifuged at 50000×g for 10 minutes. Solvent was added to the pellet and recentrifuged as above. The final pellet thus obtained was homogenized in 40 volumes of solvent and used as the receptor preparation.

Binding assay was measured as follows. Fifty μl of [$^3$H]L-364, 718 (at the final concentration of 0.2 nM) and 900 μl of the receptor preparation (50 μg protein/tube) were added to 50 μl of solvent, or L-364, 718 (1 μM) or a test compound. This mixture was incubated at 25° C. for 2 hours. After the reaction, the mixture was filtrated through Whatman GF/B filter presoaked in 0.1% BSA (bovine serum albumin). The filter was washed with 3 ml of ice-cold 10 mM PIPES buffer (pH 6.5) three times, immediately after the filtration. The filter was soaked in the ACS-II scintillation cocktail for one day and radioactivity was measured using a liquid scintillation counter. Non-specific binding was defined as the radioactivity in the presence of 1 μM L-364, 718. Specific binding was defined as the difference between total binding (used solvent without L-364, 718) and non-specific binding. Inhibitor dissociation constant (Ki) of each test compound was determined from the inhibition of specific [$^3$H]L-364, 718 binding.

Results are shown in Table 28.

TABLE 28

| Measurement of Binding Affinity for CCK-A Receptors | |
|---|---|
| Test compound | Ki (nM) |
| Compound of Example 14 | 13.2 |
| Compound of Example 28 | 14.3 |

TABLE 28-continued

| Measurement of Binding Affinity for CCK-A Receptors | |
|---|---|
| Test compound | Ki (nM) |
| Compound of Example 33 | 244 |
| Compound of Example 70 (racemate) | 303 |
| Compound of Example 70 (−form) | 255 |
| Compound of Example 87 | 120 |
| Compound of Example 88 (-form) | 16.7 |
| Compound of Example 97 | 367 |
| Compound of Example 101 | 472 |
| Compound of Example 104 | 130 |
| Compound of Example 109 | 346 |
| Compound of Example 111 | 6.34 |
| Compound of Example 120 | 506 |
| L-365, 260 | 0.64 |

Test 4

Toxicity Test

Three male Sprague-Dawley (SD)-strain rats (5.5 weeks) were employed. Test compound suspended in aqueous 0.5% methylcellulose was orally administered at a dose of 1000 mg/kg. No case of death was observed in each group until one week after the administration.

| Formulation Example 1 | |
|---|---|
| Compound of Example 1 | 20 g |
| Lactose | 315 g |
| Corn Starch | 125 g |
| Crystalline cellulose | 25 g |

The above-described ingredients were uniformly mixed, followed by the addition of 200 ml of a 7.5% aqueous hydroxypropylcellulose solution. The mixture was pulverized into granules through a screen of 0.5 mm in diameter by an extruder. Immediately after that, the resultant granules were rounded by Marumerizer and then dried, whereby granules were obtained.

| Formulation Example 2 | |
|---|---|
| Compound of Example 15 | 20 g |
| Lactose | 100 g |
| Corn Starch | 36 g |
| Crystalline cellulose | 30 g |
| Carboxymethycellulose calcium | 10 g |
| Magnesium stearate | 4 g |

The above-described ingredients were uniformly mixed. The mixture was pressed into 200 mg tablets by a punch of 7.5 mm in diameter on a single punch tableting machine.

| Formulation Example 3 | |
|---|---|
| Compound of Example 54 | 100 mg |
| Sodium acetate | 2 mg |
| Acetic acid (for adjusting pH to 5.8) | q.s. |
| Distilled water | q.s. |
| Total | 10 ml/vial |

Accordingly to the above formulation, an injection was prepared in a manner known per se in the art.

| Formulation Example 4 | |
|---|---|
| Compound of Example 89 | 20 g |
| Lactose | 315 g |
| Corn Starch | 125 g |
| Crystalline cellulose | 25 g |

The above-described ingredients were uniformly mixed, followed by the addition of 200 ml of a 7.5% aqueous hydroxypropylcellulose solution. The mixture was pulverized into granules through a screen of 0.5 mm in diameter by an extruder. Immediately after that, the resultant granules were rounded by Marumerizer and then dried, whereby granules were obtained.

| Formulation Example 5 | |
|---|---|
| Compound of Example 93 | 20 g |
| Lactose | 100 g |
| Corn Starch | 36 g |
| Crystalline cellulose | 30 g |
| Carboxymethycellulose calcium | 10 g |
| Magnesium stearate | 4 g |

The above-described ingredients were uniformly mixed. The mixture was pressed into 200 mg tablets by a punch of 7.5 mm in diameter on a single punch tableting machine.

| Formulation Example 6 | |
|---|---|
| Compound of Example 98 | 100 mg |
| Sodium acetate | 2 mg |
| Acetic acid (for adjusting pH to 5.8) | q.s. |
| Distilled water | q.s. |
| Total | 10 ml/vial |

Accordingly to the above formulation, an injection was prepared in a manner known per se in the art.

CAPABILITY OF EXPLOITATION IN INDUSTRY

The compounds of the present invention exhibit excellent gastrin and/or CCK-B receptor antagonism as well as strong action of suppressing secretion dog gastric acid, and exhibit high safety. Therefore the compounds of the present invention are used widely in the medical field, that include gastric ulcer, duodenal ulcer, gastritis, reflux esophagitis, pancreatitis, Zolinger-Ellison syndrome, vacuolating G-cell hyperplasia, basal-mucous-membrane hyperplasia, inflammation of the gallbladder, attack of biliary colic, motor disorders of alimentary canal, irritable bowel syndrome, certain types of tumors, eating disorders, anxiety, panic disorder, depression, schizophrenia, Parkinson's disease, tardive dyskinesia, Gilles de la Tourette syndrome, drug dependence, and drug-withdrawal symptoms;and drug-withdrawal symptoms; and induction of pain relief or facilitation of induction of pain relief by use of an opioid drug.

What is claimed is:

1. A compound represented by the following formula (I) or a salt thereof:

(I)

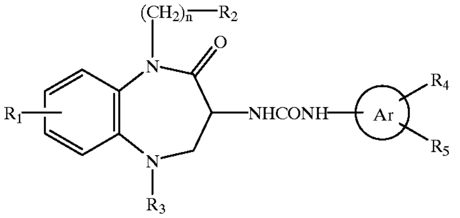

wherein $R_1$ represents a hydrogen atom, a lower alkyl group, a lower alkoxyl group, or a halogen atom;

each of $R_2$ and $R_3$, which may be the same or different, represents a hydrogen atom, a lower alkenyl group, a lower alkyl group which may be substituted by a halogen atom, a lower alkylsulfonyl group, a mono- or di-lower alkoxyalkyl group, a phenyl group which may have a substituent, a group represented by —$CH(R_6)R_7$ (wherein $R_6$ represents a lower alkyl group, a lower alkoxyl group, a mono- or di-lower alkoxyalkyl group, a saturated or unsaturated hydrocarbon group having a bicyclic or tricyclic C7–C10 condensed ring, or a phenyl or heterocyclic group which may have a substituent; and $R_7$ represents a hydrogen atom or a lower alkyl group), or a group represented by —CO—$R_8$ (wherein $R_8$ represents a lower alkyl group which may be substituted by a halogen atom; a lower alkenyl group; a lower alkoxyl group; a mono- or di-lower alkoxyalkyl group; an adamantyl group; a hydroxyl group; a benzyloxy group; a phenyl or heterocyclic group which may have a substituent; or a group represented by —$N(R_9)R_{10}$ (wherein $R_9$ and $R_{10}$ may be the same or different, and each represents a hydrogen atom, a lower alkyl group, a hydroxyalkyl group, a mono- or di-lower alkylaminoalkyl group, a phenyl group, or a heterocyclic group which may have a substituent));

each of $R_4$ and $R_5$, which may be identical to or different from each other, represents a hydrogen atom, a lower alkyl group which may be substituted by a halogen atom, a lower alkoxyl group, a halogen atom, a hydroxyalkyl group, an amino group, a nitro group, a mono- or di-lower alkylamino group, a lower alkylsulfonylaminocarbonyl group, a hydroxyaminocarbonyl group, a benzyloxyaminocarbonyl group, a tetrazolyl group, a 4-oxoxadiazolinyl group, a group represented by the following formula:

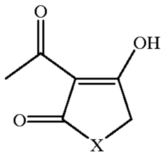

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R_{11}$ represents a hydrogen atom, a lower alkyl group or a benzyl group);

Ar represents a benzene or naphthalene ring, or an aromatic heterocyclic ring; and n represents an integer between 0 and 2 inclusive, wherein said heterocyclic group independently is selected from 5 and 6 membered rings containing at least one heteroatom selected from the group consisting of N, O and S;

wherein said substituent independently is selected from one or two substituents selected from the group consisting of a lower alkyl group, a lower alkoxy group, a halogen atom, an amino group and a nitro group; and wherein at least one of $R_2$, $R_3$, $R_4$ and $R_5$ contains a carbonyl group.

2. The compound according to claim 1, wherein $R_2$ is a group —$COR_8$.

3. The compound according to claim 1, wherein Ar is a benzene ring, and at least one of $R_4$ and $R_5$ is a group —Y—$COOR_{11}$.

4. The compound according to claim 2, wherein Ar is a benzene ring, and at least one of $R_4$ and $R_5$ is a group —Y—$COOR_{11}$.

5. A compound represented by the following formula (I) or a salt thereof:

(I)

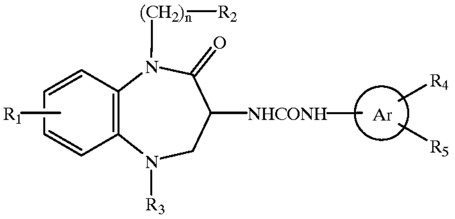

wherein $R^1$ represents a hydrogen atom, a lower alkyl group, a lower alkoxyl group, or a halogen atom;

$R_2$ represents —CO—$R_8$;

$R_3$ represents a hydrogen atom, a lower alkenyl group, a lower alkyl group which may be substituted by a halogen atom, a lower alkylsulfonyl group, a mono- or di-lower alkoxyalkyl group, a phenyl group which may have a substituent, a group represented by —$CH(R_6)R_7$ (wherein $R_6$ represents a lower alkyl group, a lower alkoxyl group, a mono- or di-lower alkoxyalkyl group, a saturated or unsaturated hydrocarbon group having a bicyclic or tricyclic C7–C10 condensed ring, or a phenyl or heterocyclic group which may have a substituent; and $R_7$ represents a hydrogen atom or a lower alkyl group), or a group represented by —CO—$R_8$ (wherein $R_8$ represents a lower alkyl group which may be substituted by a halogen atom; a lower alkenyl group; a lower alkoxyl group; a mono- or di-lower alkoxyalkyl group; an adamantyl group; a hydroxyl group; a benzyloxy group; a phenyl or heterocyclic group which may have a substituent; or a group represented by —$N(R_9)R_{10}$ (wherein $R_9$ and $R_{10}$ may be the same or different, and each represents a hydrogen atom, a lower alkyl group, a hydroxyalkyl group, a mono- or di-lower alkylaminoalkyl group, a phenyl group, or a heterocyclic group which may have a substituent));

each of $R_4$ and $R_5$, which may be identical to or different from each other, represents a hydrogen atom, a lower alkyl group which may be substituted by a halogen atom, a lower alkoxyl group, a halogen atom, a hydroxyalkyl group, an amino group, a nitro group, a mono- or di-lower alkylamino group, a lower alkylsulfonylaminocarbonyl group, a hydroxyaminocarbonyl group, a benzyloxyaminocarbonyl group, a tetrazolyl group, a 4-oxoxadiazolinyl group, a group represented by the following formula:

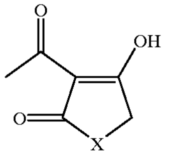

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R_{11}$ represents a hydrogen atom, a lower alkyl group or a benzyl group);

Ar represents a benzene or naphthalene ring, or an aromatic heterocyclic ring; and n represents an integer between 0 and 2 inclusive, wherein said heterocyclic group independently is selected from 5 and 6 membered rings containing at least one heteroatom selected from the group consisting of N, O and S; and wherein said substituent independently is selected from one or two substituents selected from the group consisting of a lower alkyl group, a lower alkoxy group, a halogen atom, an amino group and a nitro group.

6. A compound represented by the following formula (I) or a salt thereof:

(I)

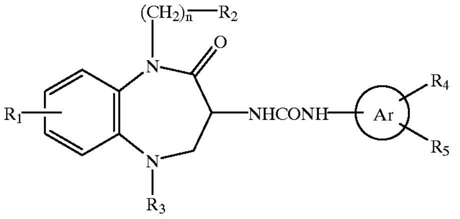

wherein $R_1$ represents a hydrogen atom, a lower alkyl group, a lower alkoxyl group, or a halogen atom;

$R_2$ represents a hydrogen atom, a lower alkenyl group, a lower alkyl group which may be substituted by a halogen atom, a lower alkylsulfonyl group, a mono- or di-lower alkoxyalkyl group, a phenyl group which may have a substituent, a group represented by —$CH(R_6)R_7$ (wherein $R_6$ represents a lower alkyl group, a lower alkoxyl group, a mono- or di-lower alkoxyalkyl group, a saturated or unsaturated hydrocarbon group having a bicyclic or tricyclic C7–C10 condensed ring, or a phenyl or heterocyclic group which may have a substituent; and $R_7$ represents a hydrogen atom or a lower alkyl group), or a group represented by —CO—$R_8$ (wherein $R_8$ represents a lower alkyl group which may be substituted by a halogen atom; a lower alkenyl group; a lower alkoxyl group; a mono- or di-lower alkoxyalkyl group; an adamantyl group; a hydroxyl group; a benzyloxy group; a phenyl or heterocyclic group which may have a substituent; or a group represented by —$N(R_9)R_{10}$ (wherein $R_9$ and $R_{10}$ may be the same or different, and each represents a hydrogen atom, a lower alkyl group, a hydroxyalkyl group, a mono- or di-lower alkylaminoalkyl group, a phenyl group, or a heterocyclic group which may have a substituent));

$R_3$ represents —CO—$R_8$;

each of $R_4$ and $R_5$, which may be identical to or different from each other, represents a hydrogen atom, a lower alkyl group which may be substituted by a halogen atom, a lower alkoxyl group, a halogen atom, a hydroxyalkyl group, an amino group, a nitro group, a mono- or di-lower alkylamino group, a lower alkylsulfonylaminocarbonyl group, a hydroxyaminocarbonyl group, a benzyloxyaminocarbonyl group, a tetrazolyl group, a 4-oxoxadiazolinyl group, a group represented by the following formula:

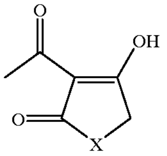

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R_{11}$ represents a hydrogen atom, a lower alkyl group or a benzyl group);

Ar represents a benzene or naphthalene ring, or an aromatic heterocyclic ring; and n represents an integer between 0 and 2 inclusive, wherein said heterocyclic group independently is selected from 5 and 6 membered rings containing at least one heteroatom selected from the group consisting of N, O and S; and wherein said substituent independently is selected from one or two substituents selected from the group consisting of a lower alkyl group, a lower alkoxy group, a halogen atom, an amino group and a nitro group.

7. A compound represented by the following formula (I) or a salt thereof:

(I)

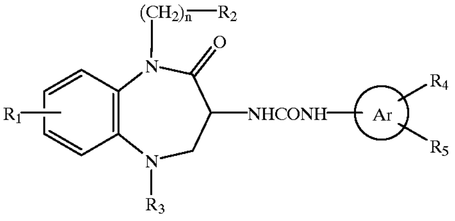

wherein $R_1$ represents a hydrogen atom, a lower alkyl group, a lower alkoxyl group, or a halogen atom;

each of $R_2$ and $R_3$, which may be the same or different, represents a hydrogen atom, a lower alkenyl group, a lower alkyl group which may be substituted by a halogen atom, a lower alkylsulfonyl group, a mono- or di-lower alkoxyalkyl group, a phenyl group which may have a substituent, a group represented by —$CH(R_6)R_7$ (wherein $R_6$ represents a lower alkyl group, a lower alkoxyl group, a mono- or di-lower alkoxyalkyl group, a saturated or unsaturated hydrocarbon group having a bicyclic or tricyclic C7–C10 condensed ring, or a phenyl or heterocyclic group which may have a substituent; and $R_7$ represents a hydrogen atom or a lower alkyl group), or a group represented by —CO—$R_8$ (wherein $R_8$ represents a lower alkyl group which may be substituted by a halogen atom; a lower alkenyl group; a lower alkoxyl group; a mono- or di-lower alkoxyalkyl group; an adamantyl group; a hydroxyl group; a benzyloxy group; a phenyl or heterocyclic group which may have a substituent; or a group represented by —N($R_9$)$R_{10}$ (wherein $R_9$ and $R_{10}$ may be the same or different, and each represents a hydrogen atom, a lower alkyl group, a hydroxyalkyl group, a mono- or di-lower alkylaminoalkyl group, a phenyl group, or a heterocyclic group which may have a substituent));

$R_4$ represents a lower alkylsulfonylaminocarbonyl group, a hydroxyaminocarbonyl group, a benzyloxyaminocarbonyl group, a group represented by the following formula:

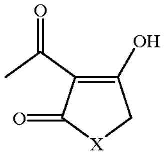

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R_{11}$ represents a hydrogen atom, a lower alkyl group or a benzyl group);

$R_5$ represents a hydrogen atom, a lower alkyl group which may be substituted by a halogen atom, a lower alkoxyl group, a halogen atom, a hydroxyalkyl group, an amino group, a nitro group, a mono- or di-lower alkylamino group, a lower alkylsulfonylaminocarbonyl group, a hydroxyaminocarbonyl group, a benzyloxyaminocarbonyl group, a tetrazolyl group, a 4-oxoxadiazolinyl group, a group represented by the following formula:

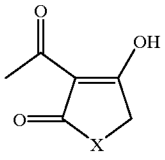

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R_{11}$ represents a hydrogen atom, a lower alkyl group or a benzyl group);

Ar represents a benzene or naphthalene ring, or an aromatic heterocyclic ring; and n represents an integer between 0 and 2 inclusive, wherein said heterocyclic group independently is selected from 5 and 6 membered rings containing at least one heteroatom selected from the group consisting of N, O and S; and wherein said substituent independently is selected from one or two substituents selected from the group consisting of a lower alkyl group, a lower alkoxy group, a halogen atom, an amino group and a nitro group.

8. A compound represented by the following formula (I) or a salt thereof:

(I)

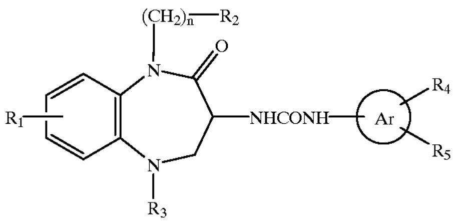

wherein $R_1$ represents a hydrogen atom, a lower alkyl group, a lower alkoxyl group, or a halogen atom;

each of $R_2$ and $R_3$, which may be the same or different, represents a hydrogen atom, a lower alkenyl group, a lower alkyl group which may be substituted by a halogen atom, a lower alkylsulfonyl group, a mono- or di-lower alkoxyalkyl group, a phenyl group which may have a substituent, a group represented by —CH($R_6$)$R_7$ (wherein $R_6$ represents a lower alkyl group, a lower alkoxyl group, a mono- or di-lower alkoxyalkyl group, a saturated or unsaturated hydrocarbon group having a bicyclic or tricyclic C7–C10 condensed ring, or a phenyl or heterocyclic group which may have a substituent; and $R_7$ represents a hydrogen atom or a lower alkyl group), or a group represented by —CO—$R_8$ (wherein $R_8$ represents a lower alkyl group which may be substituted by a halogen atom; a lower alkenyl group; a lower alkoxyl group; a mono- or di-lower alkoxyalkyl group; an adamantyl group; a hydroxyl group; a benzyloxy group; a phenyl or heterocyclic group which may have a substituent; or a group represented by —N($R_9$)$R_{10}$ (wherein $R_9$ and $R_{10}$ may be the same or different, and each represents a hydrogen atom, a lower alkyl group, a hydroxyalkyl group, a mono- or di-lower alkylaminoalkyl group, a phenyl group, or a heterocyclic group which may have a substituent));

$R_4$ represents a hydrogen atom, a lower alkyl group which may be substituted by a halogen atom, a lower alkoxyl group, a halogen atom, a hydroxyalkyl group, an amino group, a nitro group, a mono- or di-lower alkylamino group, a lower alkylsulfonylaminocarbonyl group, a hydroxyaminocarbonyl group, a benzyloxyaminocarbonyl group, a tetrazolyl group, a 4-oxoxadiazolinyl group, a group represented by the following formula:

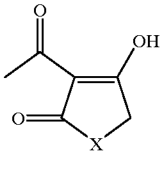

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R_{11}$ represents a hydrogen atom, a lower alkyl group or a benzyl group);

$R_5$ represents a lower alkylsulfonylaminocarbonyl group, a hydroxyaminocarbonyl group, a benzyloxyaminocarbonyl group, a group represented by the following formula:

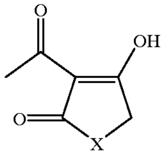

(wherein X represents an oxygen or sulfur atom), or a group represented by —Y—$COOR_{11}$ (wherein Y represents a single bond, alkylene, —O-alkylene, —S-alkylene, —SO-alkylene, —CONH— or CONH-alkylene; and $R_{11}$ represents a hydrogen atom, a lower alkyl group or a benzyl group);

Ar represents a benzene or naphthalene ring, or an aromatic heterocyclic ring; and n represents an integer between 0 and 2 inclusive, wherein said heterocyclic group independently is selected from 5 and 6 membered rings containing at least one heteroatom selected from the group consisting of N, O and S; and wherein said substituent independently is selected from one or two substituents selected from the group consisting of a lower alkyl group, a lower alkoxy group, a halogen atom, an amino group and a nitro group.

9. A pharmaceutical composition containing a compound as recited in claim 1 and a pharmaceutically acceptable carrier.

10. A pharmaceutical composition containing a compound as recited in claim 2 and a pharmaceutically acceptable carrier.

11. A pharmaceutical composition containing a compound as recited in claim 3 and a pharmaceutically acceptable carrier.

12. A pharmaceutical composition containing a compound as recited in claim 4 and a pharmaceutically acceptable carrier.

13. A method of suppressing the secretion of gastric acid, in a mammalian subject in need thereof, which comprises administration of an effective amount of a compound as recited in claim 1 to a mammal.

14. The method of claim 13, wherein the mammal is a human.

15. A method of treating a disease in which a gastrin receptor and/or cholecystokinin (CCK)-B receptor participates and selected from the group consisting of gastric ulcer, duodenal ulcer, gastritis, reflux esophagitis, and Zollinger-Ellison syndrome, comprising administration of a compound as recited in claim 1 to a mammal, in an amount effective for binding to said gastrin receptor and/or said cholecystokinin (CCK)-B receptor in said mammal.

16. The method of claim 15, wherein the mammal is a human.

* * * * *

UNITED STATES PATENT AND TRADEMARK OFFICE
CERTIFICATE OF CORRECTION

PATENT NO. : 6,239,131 B1
DATED : May 29, 2001
INVENTOR(S) : Shinozaki et al.

It is certified that error appears in the above-identified patent and that said Letters Patent is hereby corrected as shown below:

Title page, Item [54], Column 1, line 1,
Should read:
-- [54] 1,5-BENZODIAZEPINE DERIVATIVES --;

Title page,
Item [75], the inventors' information should read:
-- [75] Inventors: Katsuo Shinozaki; Tomoyuki Yoneta; Masakazu Murata; Naoyoshi Miura; Kiyoto Maeda, all of Osato-gun (JP) --;

Item [87], the PCT publication information should read:
-- (87) PCT Pub. No.: WO 98/25911
PCT Pub. Date: Jun. 18, 1998 --

Signed and Sealed this

Nineteenth Day of February, 2002

*Attest:*

JAMES E. ROGAN

*Attesting Officer*

*Director of the United States Patent and Trademark Office*